United States Patent
Patel et al.

(10) Patent No.: US 11,578,066 B1
(45) Date of Patent: Feb. 14, 2023

(54) FLUOROALKYL-OXADIAZOLES AND USES THEREOF

(71) Applicant: Tenaya Therapeutics, Inc., South San Francisco, CA (US)

(72) Inventors: Snahel Patel, South San Francisco, CA (US); Mohammad A. Mandegar, South San Francisco, CA (US); David Sperandio, South San Francisco, CA (US); Julio Medina, South San Francisco, CA (US); Ulhas Bhatt, South San Francisco, CA (US); Alok Nerurkar, South San Francisco, CA (US); Tien Widjaja, South San Francisco, CA (US)

(73) Assignee: Tenaya Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/731,949

(22) Filed: Apr. 28, 2022

Related U.S. Application Data

(63) Continuation of application No. PCT/US2020/066439, filed on Dec. 21, 2020.

(60) Provisional application No. 63/064,516, filed on Aug. 12, 2020, provisional application No. 63/027,602, filed on May 20, 2020, provisional application No. 62/951,853, filed on Dec. 20, 2019.

(51) Int. Cl.
*C07D 417/14* (2006.01)

(52) U.S. Cl.
CPC .................. *C07D 417/14* (2013.01)

(58) Field of Classification Search
CPC .................................................. C07D 417/14
USPC ......................................................... 514/342
See application file for complete search history.

(56) References Cited

U.S. PATENT DOCUMENTS

| | | |
|---|---|---|
| 6,509,110 B1 | 1/2003 | Salbeck et al. |
| 6,706,686 B2 | 3/2004 | Long et al. |
| 6,946,441 B2 | 9/2005 | Long et al. |
| 7,863,414 B2 | 1/2011 | Backs et al. |
| 8,889,742 B2 | 11/2014 | Gruber et al. |
| 9,884,031 B2 | 2/2018 | Patel et al. |
| 2004/0167188 A1 | 8/2004 | Xin et al. |
| 2004/0214870 A1 | 10/2004 | Xin et al. |
| 2008/0262028 A1 | 10/2008 | Kallus et al. |
| 2010/0069381 A1 | 3/2010 | Itoh |
| 2011/0171196 A1 | 7/2011 | Backs et al. |
| 2017/0182127 A1 | 6/2017 | Dschietzig |
| 2018/0028477 A1 | 2/2018 | Chen et al. |
| 2018/0243317 A1 | 8/2018 | Shuttleworth et al. |
| 2019/0135799 A1 | 5/2019 | Ito et al. |
| 2019/0169127 A1 | 6/2019 | Lin et al. |
| 2020/0179313 A1 | 6/2020 | Haidar et al. |
| 2021/0078999 A1 | 3/2021 | Papaioannou et al. |

FOREIGN PATENT DOCUMENTS

| | | |
|---|---|---|
| CN | 112794860 A | 5/2021 |
| EP | 625513 A1 | 11/1994 |
| EP | 826685 A1 | 3/1998 |
| EP | 950407 A1 | 10/1999 |
| EP | 1297851 B1 | 1/2005 |
| JP | 2011008205 A | 1/2011 |
| WO | WO 9740017 A2 | 10/1997 |
| WO | WO 2000021959 A1 | 4/2000 |
| WO | WO 2003074038 A1 | 9/2003 |
| WO | WO 2004016221 A2 | 2/2004 |
| WO | WO 2004069812 A1 | 8/2004 |
| WO | WO 2004074266 A1 | 9/2004 |
| WO | WO 2005000300 A1 | 1/2005 |
| WO | WO 2005090328 A1 | 9/2005 |
| WO | WO 2006044958 A1 | 4/2006 |
| WO | WO 2006057922 A2 | 6/2006 |
| WO | WO 2006129199 A1 | 12/2006 |
| WO | WO 2007034846 A1 | 3/2007 |
| WO | WO 2009151529 A1 | 12/2009 |
| WO | WO 2009156336 A1 | 12/2009 |
| WO | WO 2010089303 A1 | 8/2010 |
| WO | WO 2010091310 A1 | 8/2010 |
| WO | WO 2010122151 A1 | 10/2010 |
| WO | WO 2010139966 A1 | 12/2010 |
| WO | WO 2011038185 A2 | 3/2011 |
| WO | WO 2011132048 A1 | 10/2011 |
| WO | WO 2011143466 A1 | 11/2011 |
| WO | WO 2012045710 A1 | 4/2012 |
| WO | WO 2012054510 A1 | 4/2012 |

(Continued)

OTHER PUBLICATIONS

Brix, S., "HDAC6 controls the development and progression of cardiac mal-adaptive hypertrophy," Dissertation, submitted to the Department of Biology, Chemistry and Pharmacy of Freie Universität Berlin, 2017, 116 pages.

(Continued)

*Primary Examiner* — Kahsay Habte
(74) *Attorney, Agent, or Firm* — Cooley LLP

(57) ABSTRACT

Provided herein are compounds identified as inhibitors of HDAC6 activity having the formula:

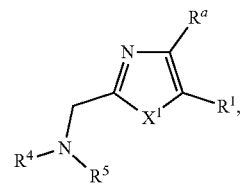

or a pharmaceutically acceptable salt thereof, that can be used to treat various diseases and disorders.

28 Claims, No Drawings

(56) References Cited

FOREIGN PATENT DOCUMENTS

| WO | WO2012066330 A1 | 5/2012 |
|---|---|---|
| WO | WO 2012076898 A1 | 6/2012 |
| WO | WO 2012170867 A1 | 12/2012 |
| WO | WO 2013066835 A2 | 5/2013 |
| WO | WO 2013068552 A1 | 5/2013 |
| WO | WO 2013068554 A1 | 5/2013 |
| WO | WO 2014047662 A2 | 3/2014 |
| WO | WO 2014179144 A1 | 11/2014 |
| WO | WO 2014202582 A1 | 12/2014 |
| WO | WO 2015031824 A1 | 3/2015 |
| WO | WO 2015/078081 A1 | 6/2015 |
| WO | WO 2015187088 A1 | 12/2015 |
| WO | WO 2015196071 A1 | 12/2015 |
| WO | WO 2016/004318 A1 | 1/2016 |
| WO | WO 2016055786 A1 | 4/2016 |
| WO | WO 2016113273 A1 | 7/2016 |
| WO | WO 2016174377 A1 | 11/2016 |
| WO | WO2017018805 A1 | 2/2017 |
| WO | WO2017023133 A2 | 2/2017 |
| WO | WO 2017027357 A1 | 2/2017 |
| WO | WO 2017049173 A1 | 3/2017 |
| WO | WO 2017049177 A1 | 3/2017 |
| WO | WO 2017053706 A1 | 3/2017 |
| WO | WO 2017065473 A1 | 4/2017 |
| WO | WO 2017193030 A1 | 11/2017 |
| WO | WO 2017222951 A1 | 12/2017 |
| WO | WO 2018029602 A1 | 2/2018 |
| WO | WO 2018222795 A1 | 12/2018 |
| WO | WO 2019067999 A1 | 4/2019 |
| WO | WO 2019118528 A1 | 6/2019 |
| WO | WO 2019/155066 A1 | 8/2019 |
| WO | WO 2019171234 A1 | 9/2019 |
| WO | WO 2019173790 A1 | 9/2019 |
| WO | WO 2019211463 A1 | 11/2019 |
| WO | WO 2019232103 A1 | 12/2019 |
| WO | WO 2020036979 A1 | 2/2020 |
| WO | WO 2022038500 A1 | 2/2020 |
| WO | WO 2020097511 A2 | 5/2020 |
| WO | WO 2020207941 A1 | 10/2020 |
| WO | WO 2020247445 A1 | 12/2020 |
| WO | WO 2020247447 A1 | 12/2020 |
| WO | WO 2021048242 A1 | 3/2021 |
| WO | WO 2021081337 A1 | 4/2021 |
| WO | WO 2021113401 A1 | 6/2021 |
| WO | WO 2021127643 A1 | 6/2021 |
| WO | WO 2021183796 A1 | 9/2021 |
| WO | WO 2021185256 A1 | 9/2021 |
| WO | WO 2021261562 A1 | 12/2021 |
| WO | WO 2021261563 A1 | 12/2021 |
| WO | WO 2022042591 A1 | 3/2022 |

OTHER PUBLICATIONS

International Search Report and Written Opinion, dated Apr. 27, 2021, for International Application No. PCT/US2020/066439 (12 pages).
International Search Report and Written Opinion, dated Oct. 8, 2020, for International Application No. PCT/US2020/032943 (12 total pages).
"Pubchem CID 50954356"; Create Date: Mar. 29, 2011 (Mar. 29, 2011); Date Accessed: Apr. 12, 2021 (Apr. 12, 2021).
"Pubchem CID 82008729"; Create Date: Oct. 20, 2014 (Oct. 20, 2014); Date Accessed: Apr. 12, 2021 (Apr. 12, 2021).

FLUOROALKYL-OXADIAZOLES AND USES THEREOF

CROSS-REFERENCE TO RELATED APPLICATIONS

This application is a continuation of International Application No. PCT/US2020/066439, filed Dec. 21, 2020, which claims the benefit of and priority to U.S. Provisional Application Ser. No. 63/064,516, filed Aug. 12, 2020, U.S. Provisional Application Ser. No. 63/027,602, filed May 20, 2020, and U.S. Provisional Application Ser. No. 62/951,853, filed Dec. 20, 2019, the contents of each of which are hereby incorporated by reference in their entirety for all purposes.

BACKGROUND

Histone deacetylase (HDAC) are a class of enzymes with deacetylase activity with a broad range of genomic and non-genomic substrates. There are eleven zinc-dependent HDAC enzymes classified based on sequence identity and catalytic activity.

Histone deacetylase inhibitors have been described and used in various therapeutic applications, including oncology, neurodegeneration, autoimmune disease, chemotherapy-induced peripheral neuropathy and cardiac indications. However, many HDAC inhibitors are non-specific (i.e., they inhibit the activity of more than one HDAC with more or less the same affinity). When administered to humans, these so-called pan-HDAC inhibitors (e.g., SAHA and Panabinostat) exhibit significant adverse effects such as fatigue, nausea, diarrhea and thrombocytopenia. Thus, there is a need for HDAC inhibitors that selectively target a particular HDAC, such as HDAC6.

SUMMARY

The present disclosure is directed to compounds that selectively inhibit HDAC6 activity and uses thereof in treating various diseases and disorders. For example, the present disclosure provides small molecules and compositions as well as therapeutic compositions and uses of specific small molecule compounds.

In one aspect, the present disclosure provides compound of Formula (I), or a pharmaceutically acceptable salt thereof:

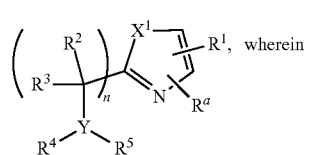

(I)

$R^1$ is selected from the group consisting of:

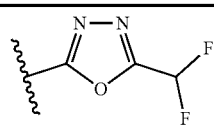

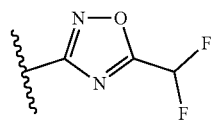 [SMILES: *c1noc(C(F)F)n1]

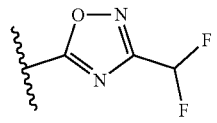

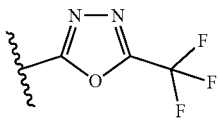 [SMILES: *c1nnc(C(F)(F)F)o1]

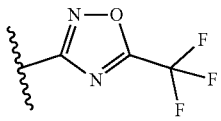 [SMILES: *c1noc(C(F)(F)F)n1]

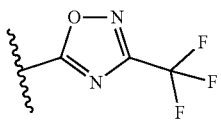 [SMILES: *c1nc(C(F)(F)F)no1]

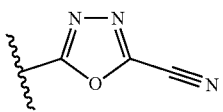 [SMILES: *c1nnc(C#N)o1]

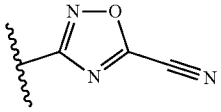 [SMILES: *c1noc(C#N)n1]

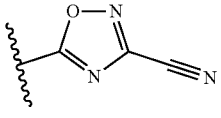 [SMILES: *c1nc(C#N)no1]

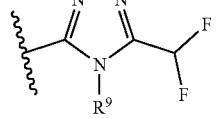

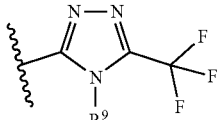

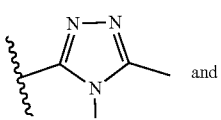

and

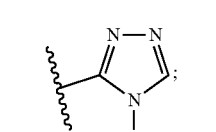

;

$R^a$ is selected from the group consisting of H, halo, $C_{1-3}$ alkyl, cycloalkyl, haloalkyl, and alkoxy;

$R^2$ and $R^3$ are independently selected from the group consisting of H, halogen, alkoxy, haloalkyl, aryl, heteroaryl, alkyl, and cycloalkyl, each of which is optionally substituted, or $R^2$ and $R^3$ together with the atom to which they are attached form a cycloalkyl or heterocyclyl;

$R^4$ and $R^5$ are independently selected from the group consisting of H, —($SO_2$)$R^2$, —($SO_2$)$NR^2R^3$, —(CO)$R^2$, —(CONR$^2R^3$), aryl, arylheteroaryl, alkylenearyl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl, each of which is optionally substituted; $X^1$ is selected from the group consisting of S, O, NH and $NR^6$, wherein $R^6$ is selected from the group consisting of $C_1$-$C_6$ allyl, alkoxy, haloalkyl, cycloalkyl and heterocyclyl;

$R^9$ is selected from the group consisting of H, $C_1$-$C_6$ alkyl, haloalkyl, cycloalkyl and heterocyclyl;

Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and n is selected from 0, 1, and 2.

In some embodiments, the present disclosure provides a compound of Formula (Ia) or pharmaceutically acceptable salt thereof:

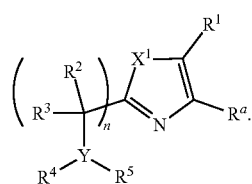

(Ia)

In some embodiments, the present disclosure provides a compound of Formula (Ib) or pharmaceutically acceptable salt thereof:

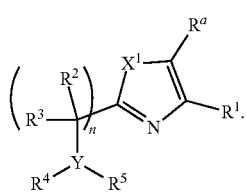

(Ib)

In some embodiments, the present disclosure provides a compound of Formula (Ic) or a pharmaceutically acceptable salt thereof:

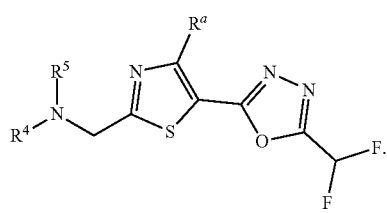

(Ic)

In another aspect, the present disclosure provides a compound of Formula (II) or pharmaceutically acceptable salt thereof:

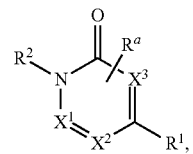

(II)

wherein
$R^1$ is selected from the group consisting of:

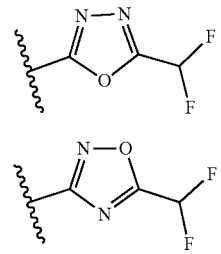

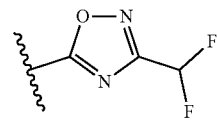 [SMILES: *c1nc(C(F)F)no1]

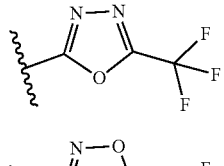

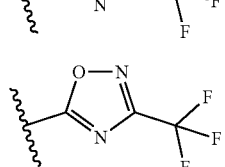

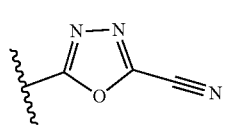 [SMILES: *c1nnc(C#N)o1]

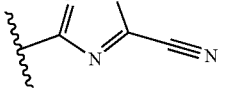 and $R^a$ is selected from the group consisting of H, halo, $C_{1-3}$ alkyl, cycloalkyl, haloalkyl, and alkoxy;

$R^2$ is selected from the group consisting of H, aryl, heteroaryl, cycloalkyl, heterocyclyl, haloalkyl, alkoxy, —$(CH_2)_m$aryl, —$(CH_2)_m$N($R^3$)aryl, —$(CH_2)_m$Oaryl, —$(CH_2)_m$($SO_2$)aryl, —$(CH_2)_m$heteroaryl, —$(CH_2)_m$N($R^3$)heteroaryl, —$(CH_2)_m$Oheteroaryl, —$(CH_2)_m$cycloalkyl, —$(CH_2)_m$heterocyclyl, —$(CH_2)_m$(COOH), —$(CH_2)_m$ $(COOR^3)$, $-(CH_2)_m(CONR^3R^4)$, $-(CH_2)_m(NR^3SO_2NR^3R^4)$, and $-(CH_2)_m(SO_2R^3)$, each of which is optionally substituted, wherein m is selected from 1, 2, or 3;

$R^3$ and $R^4$ are independently selected from the group consisting of H, aryl, heteroaryl, cycloalkyl, heterocyclyl, and alkyl each of which is optionally substituted, or $R^3$ and $R^4$ together with the atom to which they are attached form an optionally substituted heterocyclyl;

and $X^1$, $X^2$ and $X^3$ are independently selected from C and N, with the proviso that $X^1$ and $X^2$ cannot both be N.

In some embodiments, the present disclosure provides a compound of Formula (III) or pharmaceutically acceptable salt thereof:

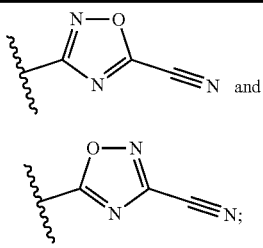

(III)

wherein
$R^1$ is selected from the group consisting of:

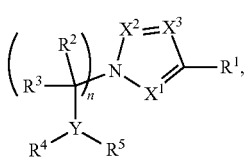

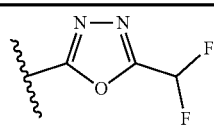

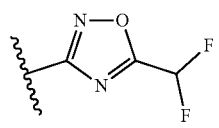 [SMILES: *c1noc(C(F)F)n1]

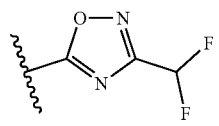 [SMILES: *c1nc(C(F)F)no1]

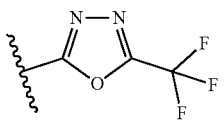

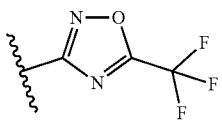 [SMILES: *c1noc(C(F)(F)F)n1]

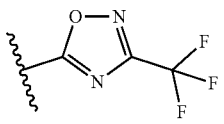 [SMILES: *c1nc(C(F)(F)F)no1]

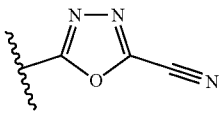 [SMILES: *c1nnc(C#N)o1]

-continued

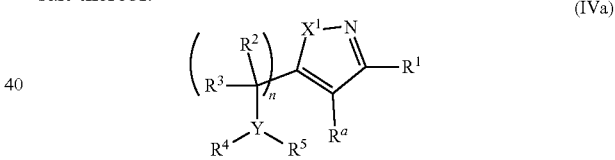

and $R^a$ is selected from the group consisting of H, halo, $C_{1-3}$ alkyl, cycloalkyl, haloalkyl, and alkoxy;

$R^2$ and $R^3$ are independently selected from the group consisting of H, halogen, alkoxy, haloalkyl, aryl, heteroaryl, alkyl, and cycloalkyl, or $R^2$ and $R^3$ together with the atom to which they are attached form a cycloalkyl or heterocyclyl;

$R^4$ and $R^5$ are selected from the group consisting of H, $-(SO_2)R^2$, $-(SO_2)NR^2R^3$, $-(CO)R^2$, $-(CONR^2R^3)$, aryl, arylheteroaryl, heteroaryl, cycloalkyl, heterocyclyl, alkyl, haloalkyl, and alkoxy, or $R^4$ and $R^5$ together with the atom to which they are attached form a cycloalkyl or heterocyclyl;

$X^1$, $X^2$, and $X^3$ are selected from the group consisting of: (1) $X^1$ is $CR^a$, $X^2$ is N, and $X^3$ is $CR^3$; (2) $X^1$ is N, $X^2$ is $CR^a$, and $X^3$ is $CR^a$; (3) $X^1$ is $CR^a$, $X^2$ is $CR^a$, and $X^3$ is N; (4) $X^1$ is N, $X^2$ is $CR^a$, and $X^3$ is N; (5) $X^1$ is $CR^a$, $X^2$ is N, and $X^3$ is N; and (6) $X^1$ is N, $X^2$ is N, and $X^3$ is $CR^a$;

Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and n is 1 or 2.

In some embodiments, the present disclosure provides a compound of Formula (IV) or pharmaceutically acceptable salt thereof:

(IVa)

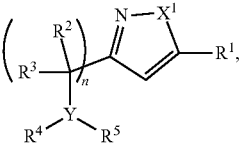

or (IVb)

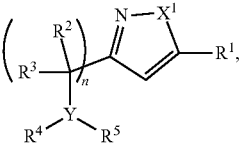

wherein
$R^1$ is selected from the group consisting of:

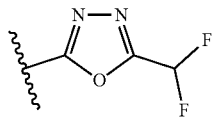 [SMILES: *c1nnc(C(F)F)o1]

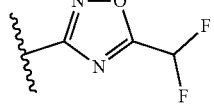

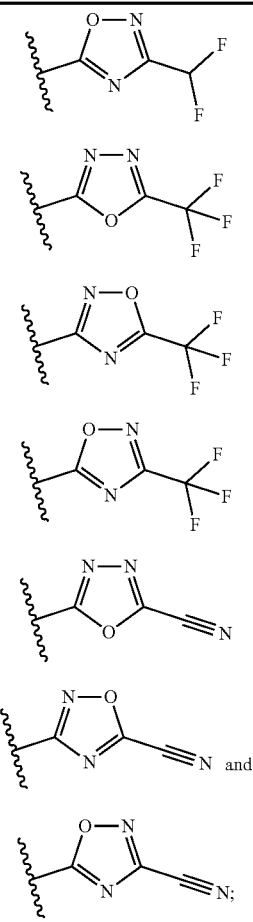

$R^a$ is selected from the group consisting of H, halo, $C_{1-3}$ alkyl, cycloalkyl, haloalkyl, and alkoxy;

$R^2$ and $R^3$ are independently selected from the group consisting of H, halogen, alkoxy, haloalkyl, aryl, heteroaryl, alkyl, and cycloalkyl, each of which is optionally substituted, or $R^2$ and $R^3$ together with the atom to which they are attached form a cycloalkyl or heterocyclyl;

$R^4$ and $R^5$ are independently selected from the group consisting of H, —(SO$_2$)R$^2$, —(SO$_2$)NR$^2$R$^3$, —(CO)R$^2$, —(CONR$^2$R$^3$), aryl, arylheteroaryl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl;

$X^1$ is selected from the group consisting of O, S, NH, or NR$^6$, wherein R$^6$ is selected from the group consisting of $C_1$-$C_6$ alkyl, alkoxy, haloalkyl, cycloalkyl and heterocyclyl; and Y is selected from the group consisting of CR$^2$, O, N, S, SO, and SO$_2$, wherein when Y is O, S, SO, or SO$_2$, R$^5$ is not present and when R$^4$ and R$^5$ together with the atom to which they are attached form a cycloalkyl or heterocyclyl, Y is CR$^2$ or N; and n is selected from 0, 1, or 2.

In some embodiments, the present disclosure provides therapeutic methods comprising use of the compounds disclosed herein (i.e., Formula (I), Formula (Ia), Formula (Ib), Formula (Ic), Formula (Id), Formula (Id-1), Formula (Id-2), Formula (Id-3), Formula (Id-4), Formula (Ie), Formula (Ie-1), Formula (If), Formula (If-1), Formula (Ig), Formula (Ig-1), Formula (Ih), Formula (Ih-1), Formula (Ii), Formula (Ii-1), Formula (Ij), Formula (Ij-1), Formula (Ik), Formula (Ik-1), Formula (Ik-2), Formula (Ik-3), Formula (II), Formula (III), Formula (IVa), and Formula (IVb)) in treating patients suffering from aberrant cell proliferative disorders, β-amyloid protein aggregation, polyglutamine protein aggregation, neurodegeneration, stroke, psychiatric disorders, depression, autoimmune disease, inflammatory diseases (e.g., inflammatory bowel disorder or disease (IBD), irritable bowel syndrome (IBS), Crohn's disease, ulcerative colitis (UC), glaucoma, psoriasis, pyoderma gangrenosum, psoriatic arthritis, rheumatoid arthritis, spondyloarthritis, juvenile idiopathic arthritis, and osteoarthritis, sepsis, acute kidney injury, lung injury, ischemia reperfusion injury' of solid organs), heart failure with preserved ejection fraction (HFpEF), indications including, but not limited to inflammasome formation leading to cell death and inflammation, chemotherapy-induced neuropathy, Charcot-Marie-Tooth disease, idiopathic pulmonary fibrosis, erectile dysfunction, hypertension, muscular dystrophy, and/or cardiac diseases or disorders. Proliferative disorders include, but are not limited to, malignant gliomas, breast cancer, basal cell carcinoma, medulloblastomas, neuroectodermal tumors, and ependymomas. Cardiac diseases or disorders that can be treated with the compounds of the present disclosure include, but art not limited to, coronary heart disease, cardiomyopathy, endocarditis, congenital cardiovascular defects, congestive heart failure, dilated cardiomyopathy, hypertrophic cardiomyopathy, valvular heart disease, myocardial infarction, congestive heart failure, long QT syndrome, atrial arrhythmia, ventricular arrhythmia, diastolic heart failure, systolic heart failure, cardiac valve disease, cardiac valve calcification, left ventricular non-compaction, ventricular septal defect, and ischemia.

DEFINITIONS

While the following terms are believed to be well understood by one of ordinary skill in the art, the following definitions are set forth to facilitate explanation of the presently disclosed subject matter.

The term "a" or "an" refers to one or more of that entity; for example, "an HDAC6 inhibitor" refers to one or more HDAC6 inhibitors or at least one HDAC6 inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, all alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to an unsaturated, straight or branched divalent hydrocarbon chain radical having one or more alkynes and from two to twelve carbon atoms. Non-limiting examples of $C_2$-$C_{12}$ alkynylene include ethynylene, propynylene, n-butynylene, and the like. The alkynylene chain is attached to the rest of the molecule through a single bond and to a radical group (e.g., those described herein) through a single bond. The points of attachment of the alkynylene chain to the rest of the molecule and to the radical group can be through any two carbons within the chain having a suitable valency. Unless stated otherwise specifically in the specification, an alkynylene chain can be optionally substituted.

"Alkoxy" refers to a group of the formula —O $R_a$ where $R_a$ is an alkyl, alkenyl or alknyl as defined above containing one to twelve carbon atoms. Unless stated otherwise specifically in the specification, an alkoxy group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indene, indene, naphthalene, phenalene, phenanthrene, pleiadene, pyrene, and triphenylene. Unless stated otherwise specifically in the specification, the "aryl" can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Carbocyclylalkyl" refers to a radical of the formula —$R_b$—$R_d$ where $R_b$ is an alkylene, alkenylene, or alkynylene group as defined above and $R_d$ is a carbocyclyl radical as defined above. Unless stated otherwise specifically in the specification, a carbocyclylalkyl group can be optionally substituted.

"Cycloalkyl" refers to a stable non-aromatic monocyclic or polycyclic fully saturated hydrocarbon consisting solely of carbon and hydrogen atoms, which can include fused or bridged ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cyclooctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl include, for example, cycloheptynyl, cyclooctynyl, and the like. Unless otherwise stated specifically in the specification, a cycloalkynyl group can be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclcl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, berizo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyiimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heterocyclylalkyl" refers to a radical of the formula —$R_b$—$R_e$ where $R_b$ is an alkylene, alkenylene, or alkynylene group as defined above and $R_e$ is a heterocyclyl radical as defined above. Unless stated otherwise specifically in the specification, a heterocycloalkylalkyl group can be optionally substituted.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amities, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SO_2R_g$, —$OSO_2R_g$, —$SO_2OR_g$, =$NSO_2R_g$, and —$SO2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, heterocyclyl, heterocyclylalkyl, heteroaryl, N-heteroaryl and/or heteroaryl alkyl group. In addition, each of the foregoing substituents can also be optionally substituted with one or more of the above substituents.

As used herein, the symbol "  " (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "  " indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or "  " infers that when $R^3$ is "XY", the point of attachment bond is the same bond as the bond by which $R^3$ is depicted as being bonded to $CH_3$.

DETAILED DESCRIPTION

Histone deacetylases ("HDAC") are a class of enzymes with deacetylase activity with a broad range of genomic and non-genomic substrates. There are eleven Zinc-dependent HDAC enzymes classified based on sequence identity and catalytic activity (Haberland et al., 2009).

Histone deacetylase inhibitors have been described as a therapeutic agents in oncology (Yoon and Eom, 2016), neurodegeneration (Butler et al., 2010) autoimmune disease (Choi et al., 2018), chemotherapy-induced peripheral neuropathy (Krukowski et al., 2017) and cardiac indications (Zhang et al., 2002). Given the role of nuclear HDACs on regulating gene transcription, inhibition of these class of targets is known to have pleiotropic effects in various cell types; most notably resulting in cell toxicities. Therefore, limiting the toxicity of pan-HDAC inhibitors has been a major obstacle in wide-spread utilization for this class of compounds. In addition, significant adverse effects of pan-HDAC inhibitors (e.g. SAHA and Panabinostat) has been observed in the clinic including fatigue, nausea, diarrhea and thrombocytopenia (Subramanian et al., 2010).

In the cardiac-indication space, most studies have utilized pan-HDAC inhibitors (e.g. SAHA, TSA and Givinostat) for the treatment of pressure-overload rodent models including transverse aortic constriction (TAC) (Cao et al., 2011), hypertension in Dahl salt-sensitive rats (Jeong et al., 2018) and myocardial infarction (Nagata et al., 2019). In addition, HDAC6-selective inhibitors have been used to ameliorate the effects of pressure overload in rodent models (Demos-Davies et al., 2014) and provide protection against proteotoxicity in a transgenic cardiomyopathy mouse model (McLendon et al., 2014).

HDAC6 belongs to the class IIb enzyme and contains two catalytic domains, a ubiquitin binding domain and a cytoplasmic retention domain (Haberland et al., 2009). HDAC6 is predominately a cytoplasmic enzyme and its best-characterized substrates include tubulin, HSP90 and cortactin (Brindisi et al., 2019).

Pharmacological inhibition of HDAC6 blocks its deacetylase activity, thus resulting in hyperacetylation of its substrates, most notably tubulin (Hubbert et al., 2002).

HDAC6-selective inhibitors are known to have reduced cytotoxicity due to the cytoplasmic nature of HDAC6 substrates and reduced effects on nuclear targets (including H3K9 and c-MYC) and on global transcription (Nebbioso et al., 2017).

Hydroxamic acids are zinc chelators and have been used extensively in the development of pan- and HDAC-selective inhibitors. However, most hydroxamic-acid based HDAC inhibitors either lack the desired selectivity or show poor bioavailability with a poor pharmacokinetic profile (Butler et al., 2010; Santo et al., 2012).

The present disclosure provides compounds that, in some embodiments, selectively inhibit HDAC6. In some embodiments, the selectivity ratio of HDAC6 over HDAC1 is from about 5 to about 30,0000, e.g., about 5, about 10, about 20, about 30, about 40, about 50, about 60, about 70, about 80, about 90, about 100, about 1000, about 2000, about 3000, about 4000, about 5000, about 6000, about 7000, about 8000, about 9000, about 10,000, about 15,000, about 20,000, about 25,000, or about 30,000, including all values and ranges therebetween.

Compounds of the Disclosure

In one aspect, the present disclosure provides a compound of Formula (A) or a pharmaceutically acceptable salt thereof:

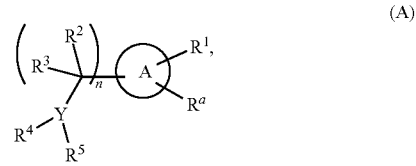

(A)

wherein:
Ⓐ is selected from the group consisting
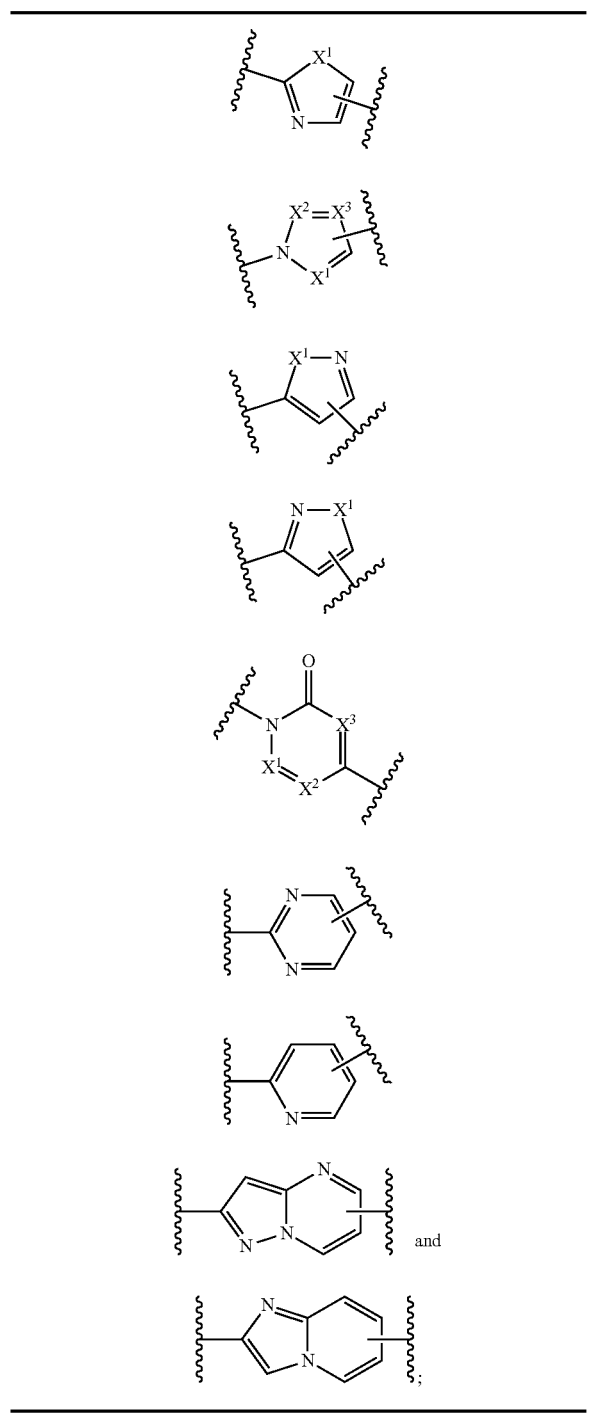
and
$R^1$ is selected from the group consisting of:
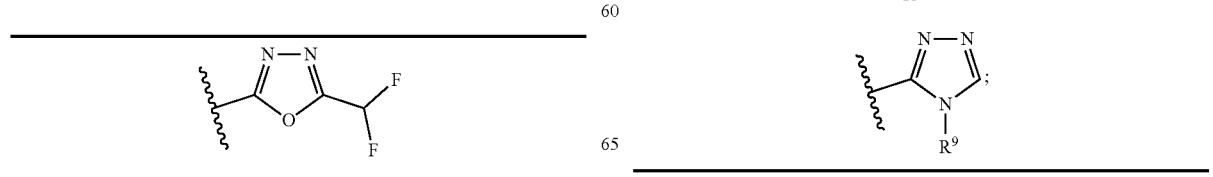

$R^2$ and $R^3$ are independently selected from the group consisting of H, halogen, alkoxy, haloalkyl, aryl, heteroaryl, alkyl, and cycloalkyl each of which is optionally substituted, or $R^2$ and $R^3$ together with the atom to which they are attached form a cycloalkyl or heterocyclyl;

$R^4$ and $R^5$ are independently selected from the group consisting of H, —$(SO_2)NR^2$, —$(SO_2)NR^2R^3$, —$(CO)R^2$, —$(CONR^2R^3)$, aryl, arylheteroaryl, alkylenearyl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl, each of which is optionally substituted;

$R^9$ is selected from the group consisting of H, $C_1$-$C_6$ alkyl, haloalkyl, cycloalkyl and heterocyclyl;

when (A) is

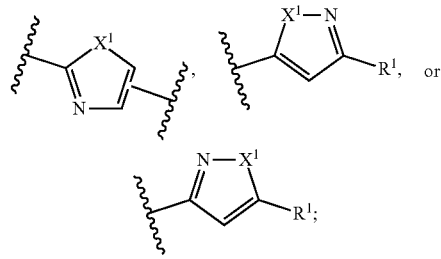

$X^1$ is selected from the group consisting of S, O, NH and $NR^6$, wherein $R^6$ is selected from the group consisting of $C_1$-$C_6$ alkyl alkoxy, haloalkyl, cycloalkyl and heterocyclyl;

when (A) is

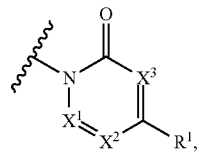

$X^1$, $X^2$ and $X^3$ are independently selected from C and N, with the proviso that $X^1$ and $X^2$ cannot both be N;

when (A)

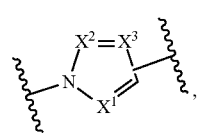

$X^1$, $X^2$, and $X^3$ are selected from the group consisting of: (1) $X^1$ is CH, $X^2$ is N, and $X^3$ is CH; (2) $X^1$ is N, $X^2$ is CH, and $X^3$ is CH; (3) $X^1$ is CH, $X^2$ is CH, and $X^3$ is N; (4) $X^1$ is N, $X^2$ is CH, and $X^3$ is N; (5) $X^1$ is CH, X is N, and $X^3$ is N; and (6) $X^1$ is N, $X^2$ is N, and $X^3$ is CH;

$R^a$ is selected from the group consisting of H, halo, $C_{1-3}$ alkyl, cycloalkyl, haloalkyl, and alkoxy;

Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and n is selected from 0, 1, and 2.

In some embodiments, the compound of Formula (A) is selected from the group consisting of:

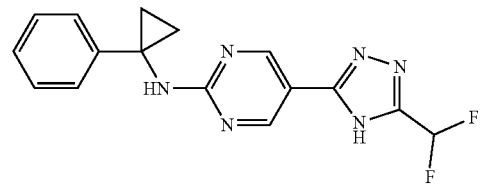 [SMILES: FC(F)c1nnc(-c2cnc(NC3(c4ccccc4)CC3)nc2)[nH]1]

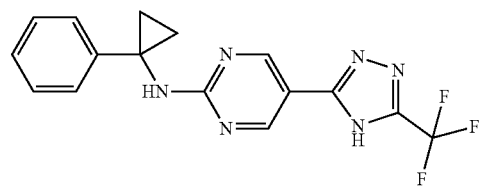 [SMILES: FC(F)(F)c1nnc(-c2cnc(NC3(c4ccccc4)CC3)nc2)[nH]1]

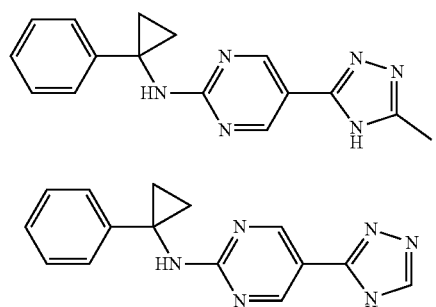

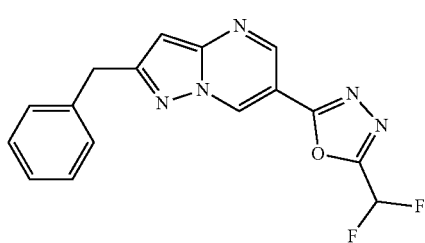 [SMILES: FC(F)c1nnc(-c2cnc3cc(Cc4ccccc4)nn3c2)o1]

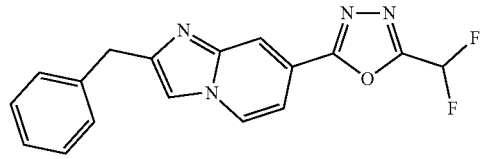 [SMILES: FC(F)c1nnc(-c2ccn3cc(Cc4ccccc4)nc3c2)o1]

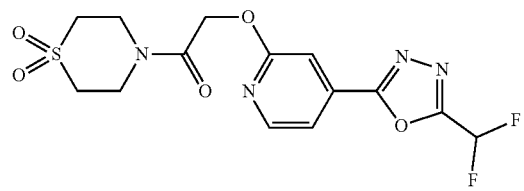 [SMILES: O=C(COc1cc(-c2nnc(C(F)F)o2)ccn1)N1CCS(=O)(=O)CC1]

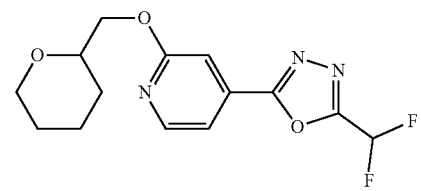 [SMILES: FC(F)c1nnc(-c2ccnc(OCC3CCCCO3)c2)o1]

Compounds of Formula (I)

In one aspect, the present disclosure provides a compound of Formula (I) or pharmaceutically acceptable salt thereof:

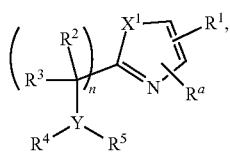

wherein
$R^1$ is selected from the group consisting of:

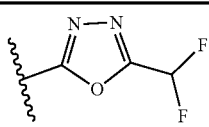

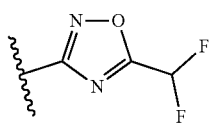 [SMILES: *c1noc(C(F)F)n1]

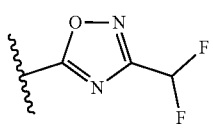 [SMILES: *c1nc(C(F)F)no1]

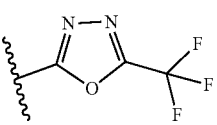 [SMILES: *c1nnc(C(F)(F)F)o1]

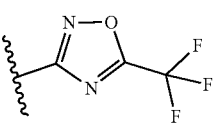 [SMILES: *c1noc(C(F)(F)F)n1]

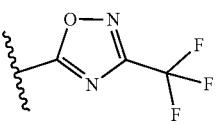 [SMILES: *c1nc(C(F)(F)F)no1]

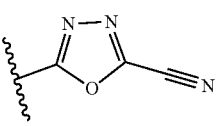 [SMILES: *c1nnc(C#N)o1]

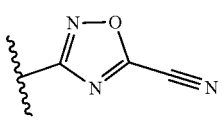 [SMILES: *c1noc(C#N)n1]

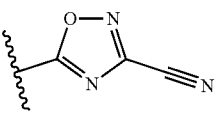

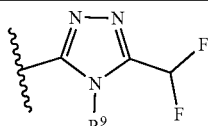

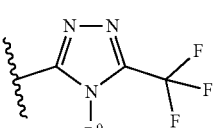

and

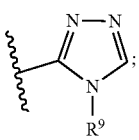

;

$R^a$ is selected from the group consisting of H, halo, $C_{1-3}$ alkyl, cycloalkyl, haloalkyl, and alkoxy;
$R^2$ and $R^3$ are independently selected from the group consisting of H, halogen, alkoxy, haloalkyl, aryl, heteroaryl, alkyl, and cycloalkyl, each of which is optionally substituted, or $R^2$ and $R^3$ together with the atom to which they are attached form a cycloalkyl or heterocyclyl;
$R^4$ and $R^5$ are independently selected from the group consisting of H, —$(SO_2)R^2$, —$(SO_2)NR^2R^3$, —$(CO)R^2$, —$(CONR^2R^3)$, aryl, arylheteroaryl, heteroaryl, alkylenearyl, cycloalkyl, heterocyclyl, alkyl haloalkyl, and alkoxy, each of which is optionally substituted, or $R^4$ and $R^5$ together with the atom to which they are attached form a cycloalkyl or heterocyclyl, each of which is optionally substituted;
$R^9$ is selected from the group consisting of $C_1$-$C_6$ alkyl, haloalkyl, cycloalkyl and heterocyclyl;
$X^1$ is selected from the group consisting of S, O, NH and $NR^6$, wherein $R^6$ is selected from the group consisting of $C_1$-$C_6$ alkyl, alkoxy, haloalkyl, cycloalkyl and heterocyclyl;
Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form an optionally substituted cycloalkyl or an optionally substituted heterocyclyl, Y is $CR^2$ or N; and
n is selected from 0, 1, and 2.

In some embodiments of Formula (I), n is 0. In some embodiments, n is 1. In some embodiments, n is 2. In some embodiments, n is 0 or 1. In some embodiments, n is 1 or 2. In some embodiments, n is 0 or 2.

In some embodiments of Formula (I), $X^1$ is O. In some embodiments, $X^1$ is S. In some embodiments, $X^1$ is NH. In some embodiments, $X^1$ is $NR^6$. In some embodiments, $X^1$ is selected from the group consisting of S, O, and $NR^6$. In some embodiments, $X^1$ is selected from the group consisting of S, O, and $NCH_3$. In some embodiments, $X^1$ is S or O. In some embodiments, $X^1$ is S or $NR^6$. In some embodiments, is $C_1$-$C_6$ alkyl.

In some embodiments of Formula (I), $R^2$ and $R^3$ are H.
In some embodiments of Formula (I), Y is N, $CR^2$, or O. In some embodiments, Y is N or O. In some embodiments, Y is N. In some embodiments, Y is $CR^2$. In some embodiments, Y is O.

In some embodiments, $R^4$ and $R^5$ are independently selected from the group consisting of H, —(SO$_2$)R$^2$, —(SO$_2$)NR$^2$R$^3$, —(CO)R$^2$, —(CONR$^2$R$^3$), aryl, arylheteroaryl, heteroaryl, alkylenearyl, cycloalkyl, alkylenecycloalkyl, heterocyclyl, alkyleneheterocyclyl, alkyl, haloalkyl, and alkoxy, each of which is optionally substituted, or $R^4$ and $R^5$ together with the atom to which they are attached form a cycloalkyl or heterocyclyl, each of which is optionally substituted In some embodiments of Formula (I), $R^4$ is selected from the group consisting of —C(O)-alkyl, —C(O)-cycloalkyl, —C(O)-aryl, —C(O)-heteroaryl, —(SO$_2$)NR2R$^3$, —SO$_2$-alkyl, and —SO$_2$-cycloalkyl, each of which is optionally substituted. In some embodiments, $R^4$ is selected from the group consisting of —C(O)-alkyl, —C(O)-cycloalkyl, —SO$_2$-alkyl, —SO$_2$-haloalkyl, —SO$_2$-cycloalkyl, and —(SO$_2$)NR$^2$R$^3$, each of which is optionally substituted. In some embodiments, aryl is optionally substituted with one or more halogens. In some embodiments of Formula (I), $R^4$ is selected from the group consisting of —SO$_2$alkyl, —SO$_2$haloalkyl, or —SO$_2$cycloalkyl. In some embodiments of Formula (I), $R^4$ is selected from the group consisting of —SO$_2$Me, —SO$_2$Et, and —SO$_2$-cPr. In some embodiments of Formula (I), $R^4$ is —SO$_2$Me or —SO$_2$Et. In some embodiments, $R^2$ and $R^3$ are each independently -C$_{1-5}$alkyl. In some embodiments, $R^2$ and $R^3$ taken together with the nitrogen atom to which they are attached form an optionally substituted heterocyclyl. In some embodiments, the optionally substituted heterocyclyl is morpholine, thiomorpholine, or thiomorpholine 1,1-dioxide.

In some embodiments of Formula (I), $R^5$ is aryl, heteroaryl, or cycloalkyl, each of which is optionally substituted.

In some embodiments, $R^5$ is aryl. In some embodiments, aryl is

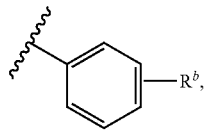

wherein $R^b$ is one or more selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, the haloalkyl is selected from CF$_3$, CF$_2$CH$_3$, CHF$_2$, or CH$_2$F. In some embodiments, the alkyl is a -C$_{1-5}$alkyl. In some embodiments, -C$_{1-5}$alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a C$_{3-6}$cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from OCF$_3$, OCHF$_2$, or OCH$_2$F. In some embodiments, the Oalkyl is O-methyl, O-ethyl, O-propyl, O-i-propyl, O-butyl, or O-t-butyl.

In some embodiments, $R^5$ is heteroaryl. In some embodiments, heteroaryl is an optionally substituted 5- to 14-membered heteroaryl. In some embodiments, heteroaryl is an optionally substituted 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzthiophenyl, imidazopyridinyl, imidazopyrazinyl, and benzimidazolyl. In some embodiments, the optionally substituted 5- to 14-membered heteroaryl is selected from the group consisting of pyrazolyl, pyridinyl, pyrimidinyl, pyrazinyl, pyridazinyl, benzoxazolyl, imidazopyridinyl, and imidazopyrazinyl. In some embodiments, $R^5$ is

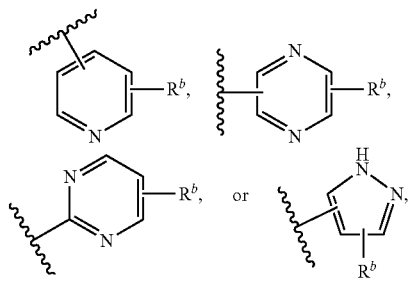

wherein $R^b$ is one or more selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, the haloalkyl is selected from CF$_3$, CF$_2$CH$_3$, CHF$_2$, or CH$_2$F. In some embodiments, the alkyl is a -C$_{1-5}$alkyl. In some embodiments, -C$_{1-5}$alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a C$_{3-6}$cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from OCF$_3$, OCHF$_2$, or OCH$_2$F. In some embodiments, the Oalkyl is O-methyl, O-ethyl, O-propyl, O-i-propyl, O-butyl, or O-t-butyl.

In some embodiments, $R^5$ is cycloalkyl. In some embodiments, cycloalkyl is a cyclopropyl, cyclobutyl, cyclopentyl, or cyclohexyl, each of which is optionally substituted. In some embodiments, the optionally substituted cycloalkyl is

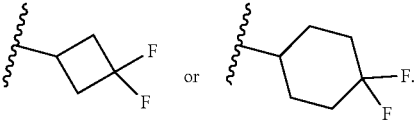 [SMILES: *C1CC(F)(F)C1 ; *C1CCC(F)(F)CC1]

In some embodiments, $R^5$ is selected from the group consisting of phenyl, 3-chlorophenyl, 3-chloro-4-fluorophenyl, 3-trifluoromethylphenyl, 3,4-difluorophenyl, and 2,6-difluorophenyl. In some embodiments, $R^5$ is cyclopropyl. In some embodiments, $R^5$ selected from the group consisting of pyridin-3-yl and 1-methylindazole-6-yl. In some embodiments, $R^5$ is selected from the group consisting of H, phenyl, 3-chlorophenyl, 3-chloro-4-fluorophenyl, 3-trifluoromethylphenyl, 3,4-difluorophenyl, cyclopropyl, pyridin-3-yl, 1-methylindazole-6-yl, 3,3-difluorocyclobutyl, and 4,4-difluorocyclohexyl. In some embodiments, $R^5$ is 3-chlorophenyl. In some embodiments $R^5$ is H. In some embodiments, $R^5$ is

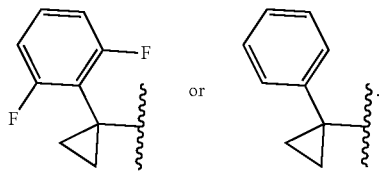 [SMILES: *C1(c2c(F)cccc2F)CC1 ; *C1(c2ccccc2)CC1]

In some embodiments, $R^5$ is —$CH_2CH_2Ph$. In some embodiments, $R^5$ is selected from the group consisting of H, aryl, heteroaryl, alkylenearyl, cycloalkyl, heterocyclyl, alkyl, and haloalkyl, each of which is optionally substituted, or $R^4$ and $R^5$ together with the atom to which they are attached form an optionally substituted heterocyclyl.

In some embodiments of Formula (I), $R^5$ is optionally substituted with one or more halogen, haloalkyl, alkyl, Oalkyl, Ohaloalkyl, cycloalkyl, heterocyclyl aryl, or heteroaryl. In some embodiments, the haloalkyl is selected from $CF_3$, $CHF_2$, or $CH_2F$. In some embodiments, the alkyl is a -$C_{1-5}$alkyl. In some embodiments, -$C_{1-5}$alkyl is methyl, ethyl, propyl, i-propyl, butyl, or t-butyl. In some embodiments, the cycloalkyl is a $C_{3-6}$cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is $OCF_3$, $OCHF_2$, or $OCH_2F$. In some embodiments, the Oalkyl is O-methyl, O-ethyl, O-propyl, O-i-propyl, O-butyl, or O-t-butyl.

In some embodiments of Formula (I), $R^4$ is H or -$C_{1-5}$alkyl and $R^5$ is aryl. In some embodiments, $R^4$ is H or -$C_{1-5}$alkyl and $R^5$ is heteroaryl. In some embodiments, $R^4$ is H or -$C_{1-5}$alkyl and $R^5$ is cycloalkyl. In some embodiments, the -$C_{1-5}$alkyl is methyl, ethyl, or propyl. In some embodiments, the -$C_{1-5}$alkyl is methyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzthiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, or oxazolyl. In some embodiments, the 6-membered heteroaryl is optionally substituted pyridinyl, pyrimidinyl, pyrazinyl, or pyridazinyl. In some embodiments, cycloalkyl is optionally substituted cyclopropyl, cyclobutyl, cyclopentyl, or cyclohexyl. In some embodiments, aryl is optionally substituted with one or more substituents selected from the group consisting of halogen, $C_{1-6}$haloalkyl, $C_{1-6}$alkyl, O-$C_{1-6}$haloalkyl, O-$C_{1-6}$haloalkyl, or $C_{3-6}$cycloalky. In some embodiments, heteroaryl is optionally substituted with one or more substituents selected from the group consisting of halogen, $C_{1-6}$haloalkyl, $C_{1-6}$alkyl, O-$C_{1-6}$alkyl, O-$C_{1-6}$haloalkyl, or $C_{3-6}$cycloalky.

In some embodiments of Formula (I), $R^4$ is —(CO)$R^2$ and $R^5$ is aryl. In some embodiments, $R^4$ is —(CO)$R^2$ and $R^5$ is heteroaryl. In some embodiments, $R^4$ is —(CO)$R^2$ and $R^5$ is cycloalkyl. In some embodiments, the aryl is optionally substituted phenyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzthiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, oxazolyl. In some embodiments, the 6-membered heteroaryl is optionally substituted pyridinyl, pyrazinyl, or pyridazinyl. In some embodiments, cycloalkyl is optionally substituted cyclopropyl, cyclobutyl, cyclopentyl, or cyclohexyl. In some embodiments, aryl is optionally substituted with one or more substituents selected from the group consisting of halogen, $C_{1-6}$haloalkyl, $C_{1-6}$alkyl, O-$C_{1-6}$alkyl, O-$C_{1-6}$haloalkyl, or $C_{3-6}$cycloalky. In some embodiments, heteroaryl is optionally substituted with one or more substituents selected from the group consisting of halogen, $C_{1-6}$haloalkyl, $C_{1-6}$alkyl, O-$C_{1-6}$alkyl, O-$C_{1-6}$haloalkyl, or $C_{3-6}$cycloalkyl.

In some embodiments of Formula (I), $R^4$ is —($SO_2$)$R^2$ and $R^5$ is aryl. In some embodiments, $R^4$ is —($SO_2$)$R^2$ and $R^5$ is heteroaryl. In some embodiments, $R^4$ is —($SO_2$)$R^2$ and $R^5$ is cycloalkyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzthiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, or oxazolyl. In some embodiments, the 6-membered heteroaryl is optionally substituted pyridinyl, pyrirnidinyl, pyrazinyl, or pyridazinyl. In some embodiments, cycloalkyl is optionally substituted cyclopropyl, cycloybutyl, cyclopentyl, or cyclohexyl. In some embodiments, aryl is optionally substituted with one or more substituents selected from the group consisting of halogen, $C_{1-6}$haloalkyl, $C_{1-6}$alkyl, O-$C_{1-6}$alkyl, O-$C_{1-6}$haloalkyl, or $C_{3-6}$cycloalkyl. In some embodiments, heteroaryl is optionally substituted with one or more substituents selected from the group consisting of halogen, $C_{1-6}$haloalkyl, $C_{1-6}$alkyl, O-$C_{1-6}$alkyl, O-$C_{1-6}$haloalkyl, or $C_{3-6}$cycloalkyl. In some embodiments, the $C_{1-6}$haloalkyl is $CF_3$, $CHF_2$, or $CH_2F$. In some embodiments, the O-$C_{1-6}$haloalkyl is $OCF_3$, $OCHF_2$, or $OCH_2F$. In some embodiments, cycloalkyl is optionally substituted with halogen, $C_{1-6}$alkyl, or O-$C_{1-6}$alkyl.

In some embodiments of Formula (I), $R^4$ and $R^5$ together with the atom to which they are attached form a cycloalkyl or heterocyclyl. In some embodiments, $R^4$ and $R^5$ together with the atom to which they are attached form a cycloalkyl or heterocyclyl, each of which is optionally substituted. In some embodiments, the cycloalkyl or heterocyclyl is optionally substituted with —NS($O_2$)(alkyl)(aryl). In some embodiments, the alkyl is $C_{1-5}$alkyl and the aryl is phenyl optionally substituted with one or more halogen atoms. In some embodiments, the heterocyclyl is a 4- to 10-membered heterocyclyl. In some embodiments the heterocyclyl is a saturated 4- to 7-membered heterocyclyl.

In some embodiments of Formula (I), n is 0 and $R^1$ and $R^5$ together with the atom to which they are attached form an optionally substituted heterocyclyl selected from the group consisting of:

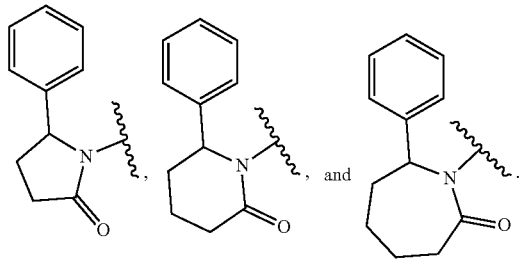

In some embodiments, the optionally substituted heterocyclyl is

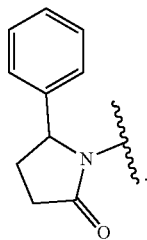 [SMILES: *N1C(=O)CCC1c1ccccc1]

In some embodiments, the optionally substituted heterocyclyl is

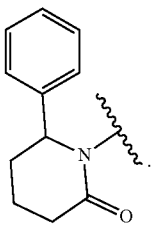 [SMILES: *N1C(=O)CCCC1c1ccccc1]

In some embodiments, the optionally substituted heterocyclyl is

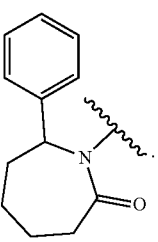 [SMILES: *N1C(=O)CCCCC1c1ccccc1]

In some embodiments, the optionally substituted heterocyclyl is selected from the group consisting of:

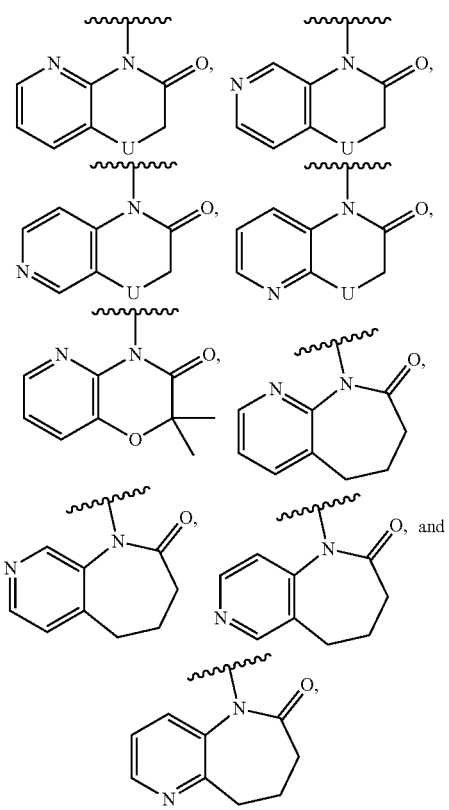

wherein U is O or $CH_2$. In some embodiments, the optional substituent is an alkyl group. In some embodiments, the optional substituent is an aryl group.

In some embodiments of Formula (I) $R^1$ is selected from the group consisting of

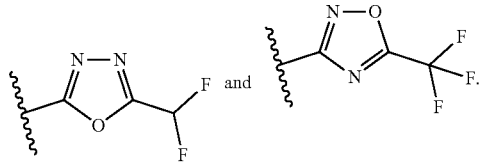 [SMILES: *c1nnc(C(F)F)o1 ; *c1noc(C(F)(F)F)n1]

In some embodiments of Formula (I), $R^1$ is

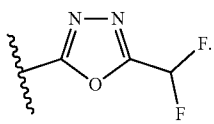 [SMILES: *c1nnc(C(F)F)o1]

In some embodiments, $R^1$ is

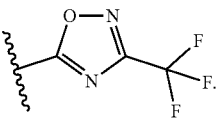 [SMILES: *c1nc(C(F)(F)F)no1]

In some embodiments, $R^1$ is

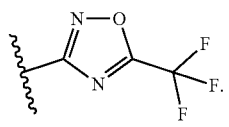

In some embodiments, $R^1$

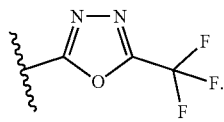 [SMILES: *c1nnc(C(F)(F)F)o1]

In some embodiments of Formula (I), $R^a$ is H, halo, $C_{1-3}$alkyl, or haloalkyl. In some embodiments, $R^1$ is H. In some embodiments, $R^a$ is $C_{1-3}$alkyl. In some embodiments, $R^a$ is haloalkyl. In some embodiments, halo is F. In some embodiments, the $C_{1-3}$alkyl alkyl is methyl, ethyl or isopropyl. In some embodiments, haloalkyl is $CF_3$, $CHF_2$, or $CH_2F$.

In some embodiments of Formula (I), Y is CH and $R^4$ and $R^5$ are H.

In some embodiments of Formula (I), Y is N, $R^4$ is H, and $R^5$ is ethyl optionally substituted with —N(S(O$_2$)alkyl)(aryl) or —N(S(O$_2$)cycloalkyl)(aryl). In some embodiments, alkyl is $C_{1-5}$alkyl, cycloalkyl is $C_{3-6}$cycloalkyl, and aryl is phenyl optionally substituted with one or more halogen atoms.

In some embodiments of Formula (I), n is 1, $X^1$ is O or N, Y is N, $R^1$ is

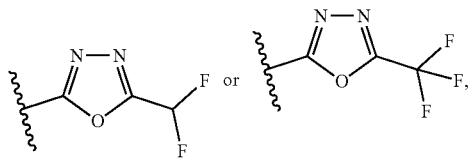 [SMILES: *c1nnc(C(F)F)o1 ; *c1nnc(C(F)(F)F)o1]

$R^2$ and $R^3$ are H, $R^4$ is H, -$C_{1-5}$alkyl, —C(O)alkyl, —C(O)cycloalkyl, —(SO$_2$)NR$^2$R$^3$, —SO$_2$alkyl, —SO$_2$haloalkyl and —SO$_2$cycloalkyl, each of which is optionally substituted, and $R^5$ is aryl, heteroaryl, or cycloalkyl, each of which is optionally substituted.

In some embodiments of Formula (I), n is 1, $X^1$ is O or N, Y is O, $R^1$ is

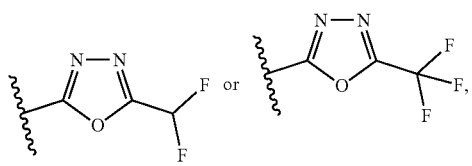 [SMILES: *c1nnc(C(F)F)o1 ; *c1nnc(C(F)(F)F)o1]

$R^2$ and $R^3$ are H, and. $R^5$ is aryl, heteroaryl, cycloalkyl, or alkylenecycloalkyl, each of which is optionally substituted.

In some embodiments of Formula (I), is 0, $X^1$ is O or N, Y is N, $R^1$ is

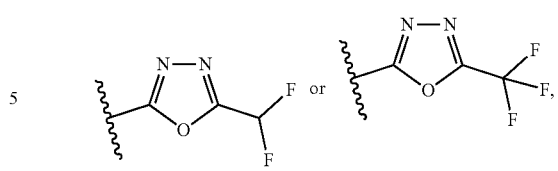

and $R^4$ and $R^5$ taken together with the atom to which they are attached form a cycloalkyl or heterocyclyl, each of which is optionally substituted.

In some embodiments, the present disclosure provides a compound of Formula (Ia) or a pharmaceutically acceptable salt thereof:

(Ia)

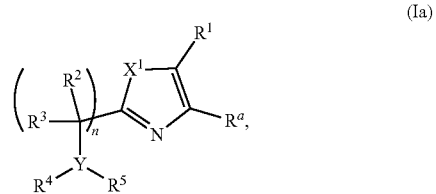

wherein:

$R^1$, $R^2$, $R^3$, $R^4$, $R^5$, $R^a$, $X^1$, n, and Y are as defined above for Formula (I).

In some embodiments of Formula (Ia), $R^1$ is

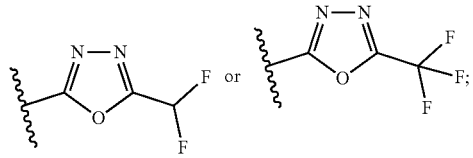 [SMILES: *c1nnc(C(F)F)o1 ; *c1nnc(C(F)(F)F)o1]

n is 1; Y is N; $X^1$ is S or O; and variables $R^2$, $R^3$, $R^4$, $R^5$, and $R^a$ are as defined above for Formula (I).

In some embodiments of Formula (Ia), n is 1, $X^1$ is S, Y is N, $R^1$ is

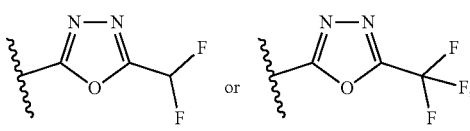

$R^2$ and $R^3$ are H, $R^4$ is —SO$_2$alkyl, —SO2haloalkyl, or —SO$_2$cycloalkyl, each of which is optionally substituted, $R^5$ is heteroaryl, each of which is optionally substituted, and $R^a$ is H or F. In some further embodiments, $R^4$ is —SO$_2$C$_{1-5}$alkyl, —SO$_2$cyclopropyl, —SO$_2$CF$_3$ or —SO$_2$CHF$_2$, and the heteroaryl is optionally substituted pyridine or pyrazine. In some further embodiments, the heteroaryl is optionally substituted pyridine.

In some embodiments of Formula (Ia), n is 1, $X^1$ is S, Y is N, $R^1$ is

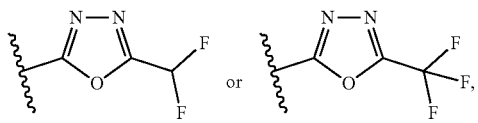 [SMILES: *c1nnc(C(F)F)o1 ; *c1nnc(C(F)(F)F)o1]

R² and R³ are H, R⁴ is —SO₂Me, —SO₂Et, or —SO₂cyclopropyl, each of which is optionally substituted, R⁵ is pyridine or pyrazine, each of which is optionally substituted, and $R^a$ is H. In some embodiments, R⁵ is optionally substituted pyridine.

In some embodiments of Formula (Ia), n is 1, X¹ is S, Y is N, R¹ is

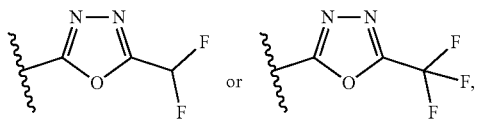 [SMILES: *c1nnc(C(F)F)o1 ; *c1nnc(C(F)(F)F)o1]

R² and R³ are H, R⁴ is —SO₂alkyl or —SO₂cycloalkyl, each of which is optionally substituted, R⁵

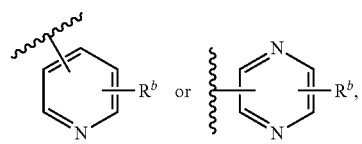

is wherein $R^b$ is selected from the group consisting of halogen, -C₁₋₅alkyl, haloalkyl, —OC₁₋₅alkyl, —Ohaloalkyl, —CH₂Ohaloalkyl, cyclopropyl, and CN, and $R^a$ is H. In some embodiments, the halogen is F or Cl. In some embodiments, the haloalkyl is CF₃, CHF₂, CH₂CF₃, or CF₂CH₃. In some embodiments, the -C₁₋₅alkyl is methyl.

In some embodiments of Formula (Ia), n is 1, X¹ is S, Y is N, R¹ is

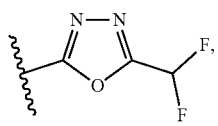

R² and R³ are H, R⁴ is —SO₂Me, —SO₂Et, or —SO₂cyclopropyl, each of which is optionally substituted, and R⁵ is

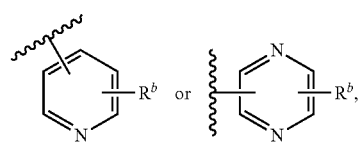

wherein $R^b$ is selected from the group consisting of halogen, -C₁₋₅alkyl, haloalkyl, —OC₁₋₅alkyl, —Ohaloalkyl, —CH₂Ohaloalkyl, cyclopropyl, or CN, and $R^a$ is H. In some embodiments, the halogen is F or Cl. In some embodiments, the haloalkyl is CF₃, CHF₂, CH₂CF₃, or CF₂CH₃. In some embodiments, the -C₁₋₅alkyl is methyl.

In some embodiments of Formula (Ia), n is 1, X¹ is S, Y is N, R¹ is

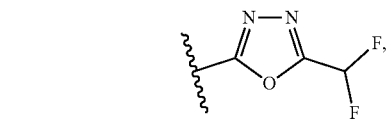 [SMILES: *c1nnc(C(F)F)o1]

R² and R³ are H, R⁴ is —SO₂Me, —SO₂Et, or —SO₂cyclopropyl, each of which is optionally substituted, and R⁵ is

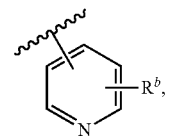

wherein $R^b$ is selected from the group consisting of Cl, F, Me, cyclopropyl, CF₃, CHF₂, CH₂CH₃, OCF₃, OCHF₂, OCH2CF2H and CN, and $R^a$ is H.

In some embodiments, the present disclosure provides a compound of Formula (Ib) or a pharmaceutically acceptable salt thereof:

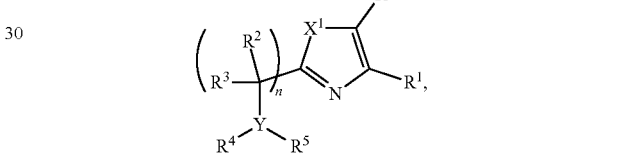

wherein:
R¹, R², R³, R⁴, R⁵, $R^a$, X¹, n, and Y are as defined above for Formula (I).

In some embodiments of Formulas (I)-(Ib), each optionally substituted alkyl is independently an optionally substituted C₁₋₆ alkyl. In some embodiments, the C₁₋₆ alkyl is Me or Et.

In some embodiments of Formulas (I)-(Ib), each optionally substituted haloalkyl is independently an optionally substituted C₁₋₆ haloalkyl. In some embodiments, the C₁₋₆ haloalkyl is CF₃, CHF₂, or CH₂F. In some embodiments, the C₁₋₆ haloalkyl is CF₃ or CHF₂.

In some embodiments of Formulas (I)-(Ib), each optionally substituted cycloalkyl is independently an optionally substituted C₃₋₁₂ cycloalkyl. In some embodiments, the cycloalkyl is a C₃₋₆ cycloalkyl. In some embodiments, the cycloalkyl is selected from the group consisting of cyclopropyl, cyclobutyl, cyclopentyl, and cyclohexyl.

In some embodiments of Formulas (I)-(Ib), each optionally substituted heterocyclyl is independently an optionally substituted 3-12 membered heterocycloalkyl having 1 or 2 heteroatoms independently selected from N, O, and S. In some embodiments, each optionally substituted heterocyclyl is independently an optionally substituted 3-6 membered heterocycloalkyl having 1 or 2 heteroatoms independently selected from N, O, and S. In further embodiments, the heterocycloalkyl is an optionally substituted 5-membered or 6-membered heterocycle having 1 or 2 heteroatoms independently selected from N, O, and S. In some embodiments, the heterocyclyl is selected from the group consisting of aziridinyl, azetidinyl, pyrrolidinyl, piperidinyl, and morpholinyl, and thiomorpholinyl.

In some embodiments of Formulas (I)-(Ib), each optionally substituted aryl is independently a $C_{6-12}$ aryl. In further embodiments, the $C_{6-12}$ aryl is an optionally substituted phenyl.

In some embodiments of Formulas (I)-(Ib), each optionally substituted heteroaryl is independently a 5-12 membered heteroaryl having 1, 2, or 3 heteroatoms independently selected from N, O, and S. In some embodiments, each optionally substituted heteroaryl is independently a 5-12 membered heteroaryl having 3 heteroatoms independently selected from N, O, and S. In some embodiments, each optionally substituted heteroaryl is independently a 5-12 membered heteroaryl having 2 heteroatoms independently selected from N, O, and S. In some embodiments, each optionally substituted heteroaryl is independently a 5-12 membered heteroaryl having 1 heteroatom independently selected from N, O, and S. In further embodiments, each optionally substituted heteroaryl is an optionally substituted 5-membered or 6-membered heteroaryl having 1 heteroatom independently from N, O, and S. In some embodiments, each heteroaryl is independently selected from the group consisting of tetrazole, oxadiazole, thiadiazole, imidazole, pyrazole, thiazole, or oxazole, each of which is optionally substituted.

In some embodiments, the compound of Formula (I) is a compound of Table 1.

TABLE 1

Compounds of Formula (I) of the Present Disclosure.

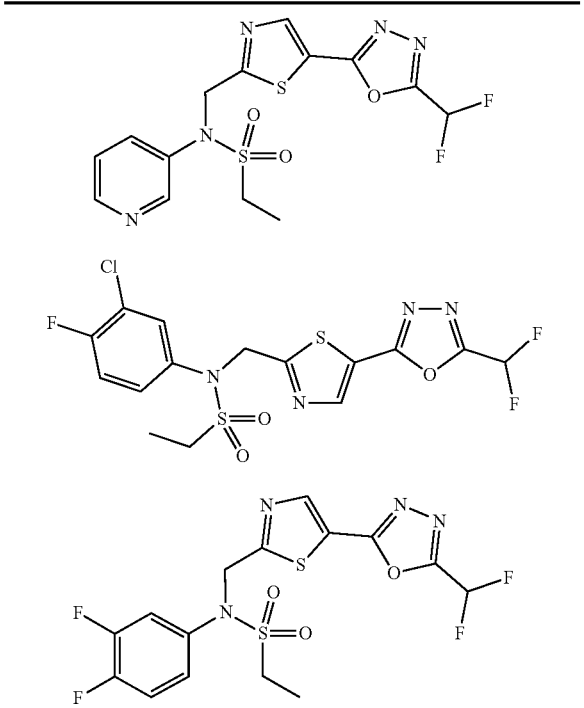

TABLE 1-continued

Compounds of Formula (I) of the Present Disclosure.

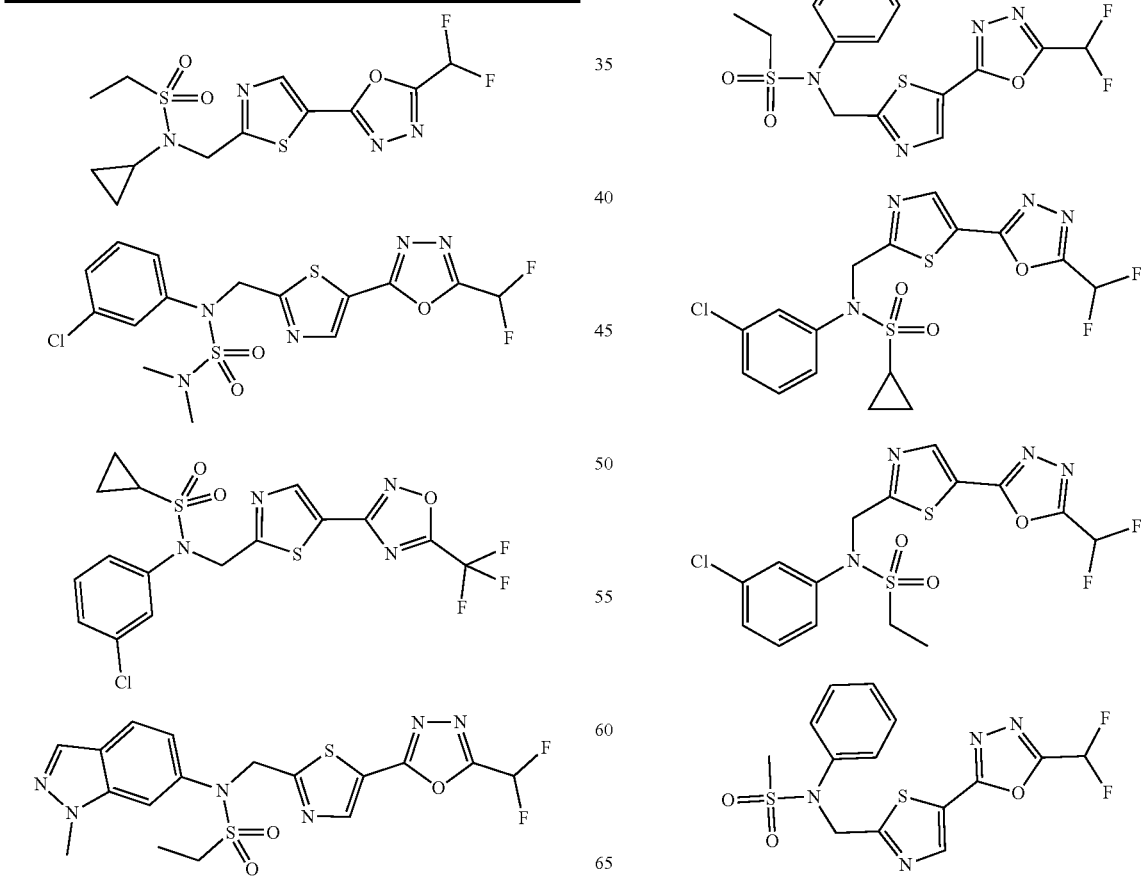

TABLE 1-continued
Compounds of Formula (I) of the Present Disclosure.
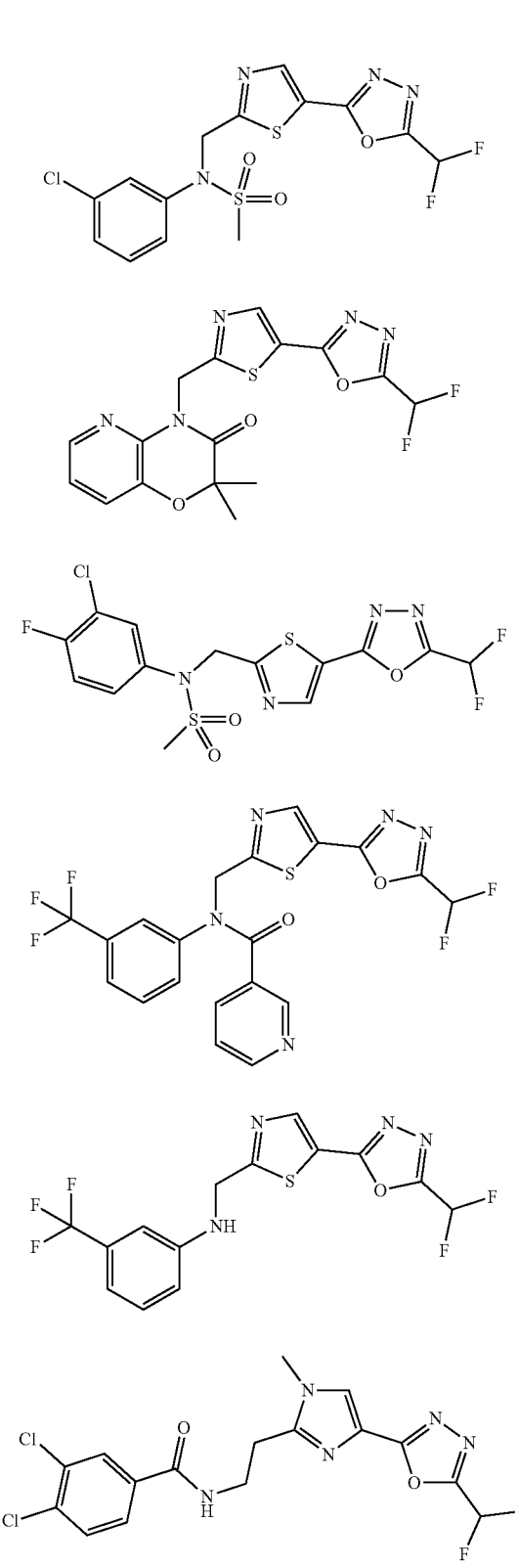
TABLE 1-continued
Compounds of Formula (I) of the Present Disclosure.
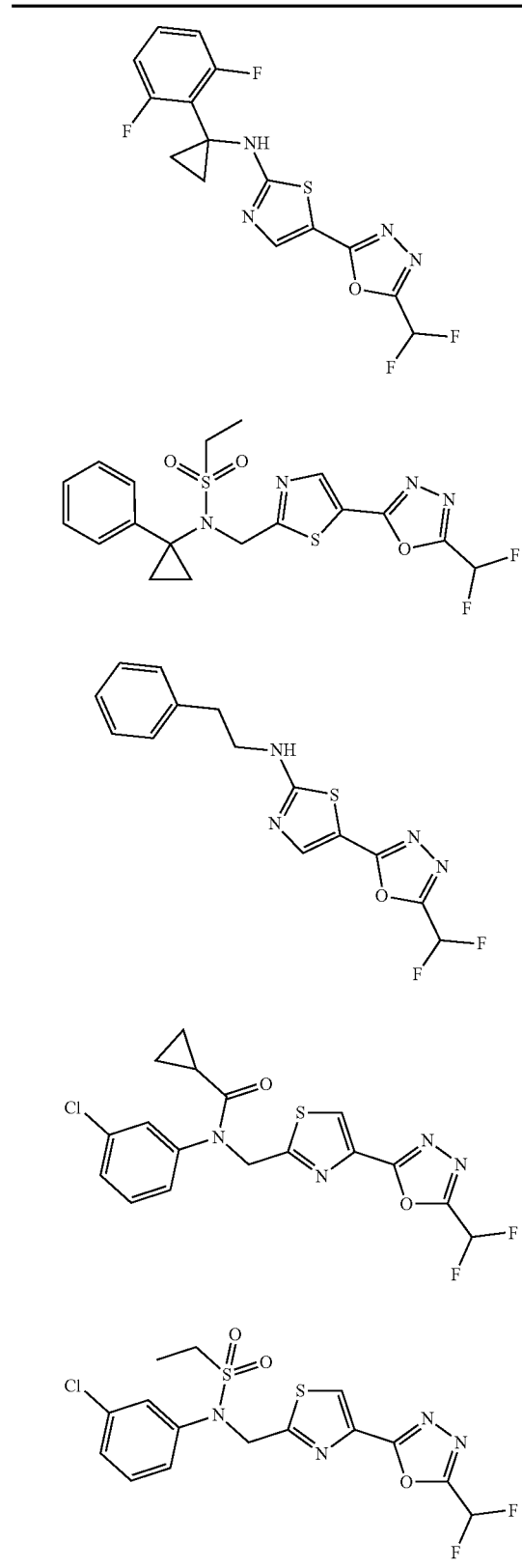

TABLE 1-continued
Compounds of Formula (I) of the Present Disclosure.
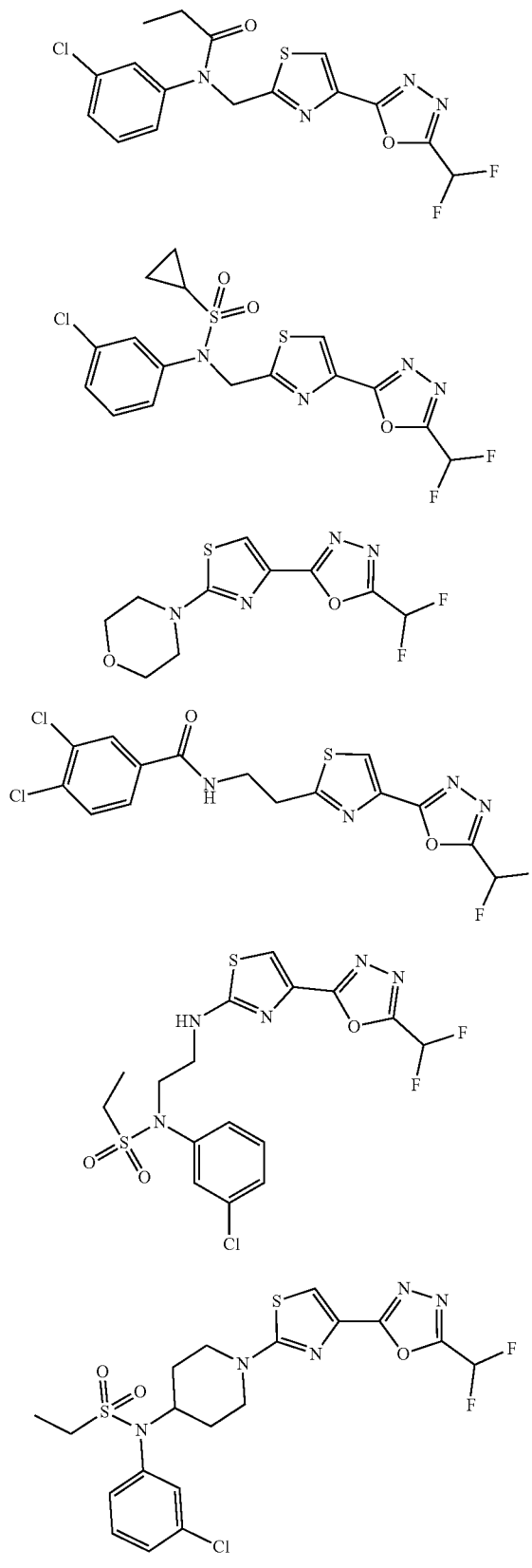

TABLE 1-continued
Compounds of Formula (I) of the Present Disclosure.
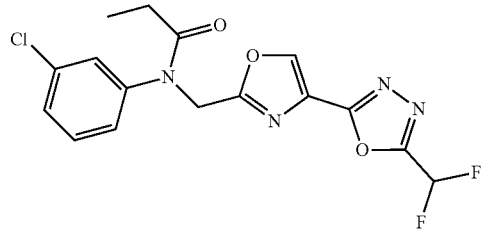 [SMILES: CCC(=O)N(Cc1nc(-c2nnc(C(F)F)o2)co1)c1cccc(Cl)c1]
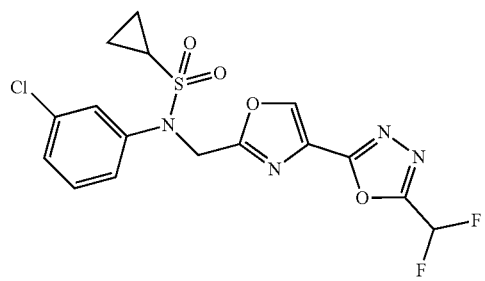 [SMILES: O=S(=O)(C1CC1)N(Cc1nc(-c2nnc(C(F)F)o2)co1)c1cccc(Cl)c1]
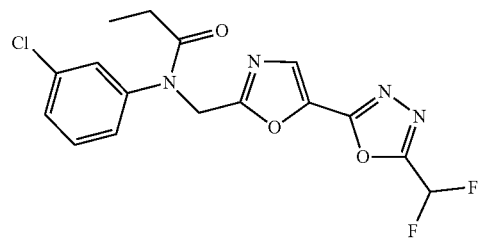 [SMILES: CCC(=O)N(Cc1ncc(-c2nnc(C(F)F)o2)o1)c1cccc(Cl)c1]
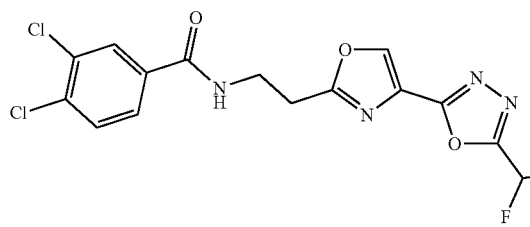
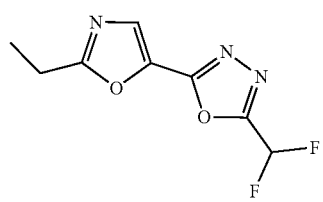
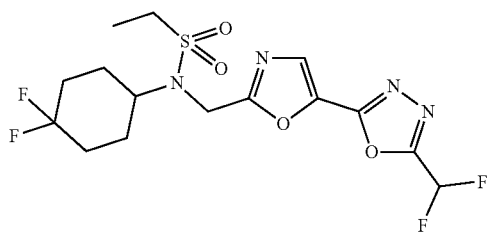 [SMILES: CCS(=O)(=O)N(Cc1ncc(-c2nnc(C(F)F)o2)o1)C1CCC(F)(F)CC1]
TABLE 1-continued
Compounds of Formula (I) of the Present Disclosure.
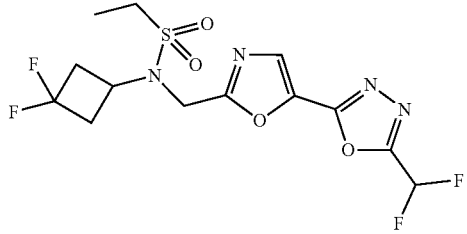 [SMILES: CCS(=O)(=O)N(Cc1ncc(-c2nnc(C(F)F)o2)o1)C1CC(F)(F)C1]
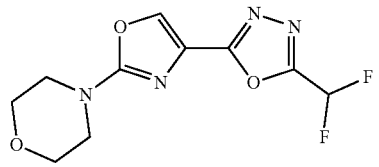 [SMILES: FC(F)c1nnc(-c2coc(N3CCOCC3)n2)o1]
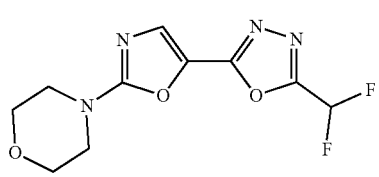 [SMILES: FC(F)c1nnc(-c2cnc(N3CCOCC3)o2)o1]
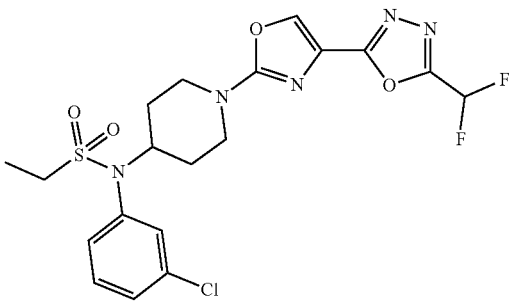 [SMILES: CCS(=O)(=O)N(c1cccc(Cl)c1)C1CCN(c2nc(-c3nnc(C(F)F)o3)co2)CC1]
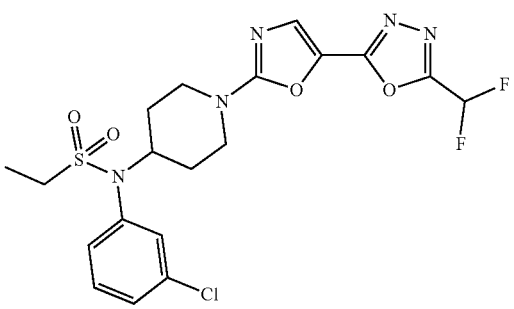 [SMILES: CCS(=O)(=O)N(c1cccc(Cl)c1)C1CCN(c2ncc(-c3nnc(C(F)F)o3)o2)CC1]
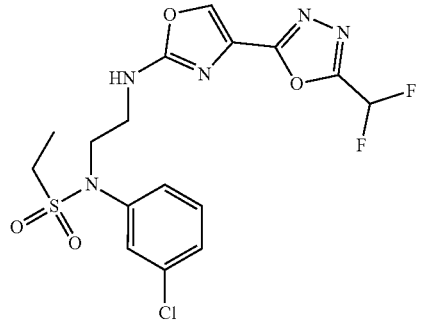 [SMILES: CCS(=O)(=O)N(CCNc1nc(-c2nnc(C(F)F)o2)co1)c1cccc(Cl)c1]

TABLE 1-continued
Compounds of Formula (I) of the Present Disclosure.
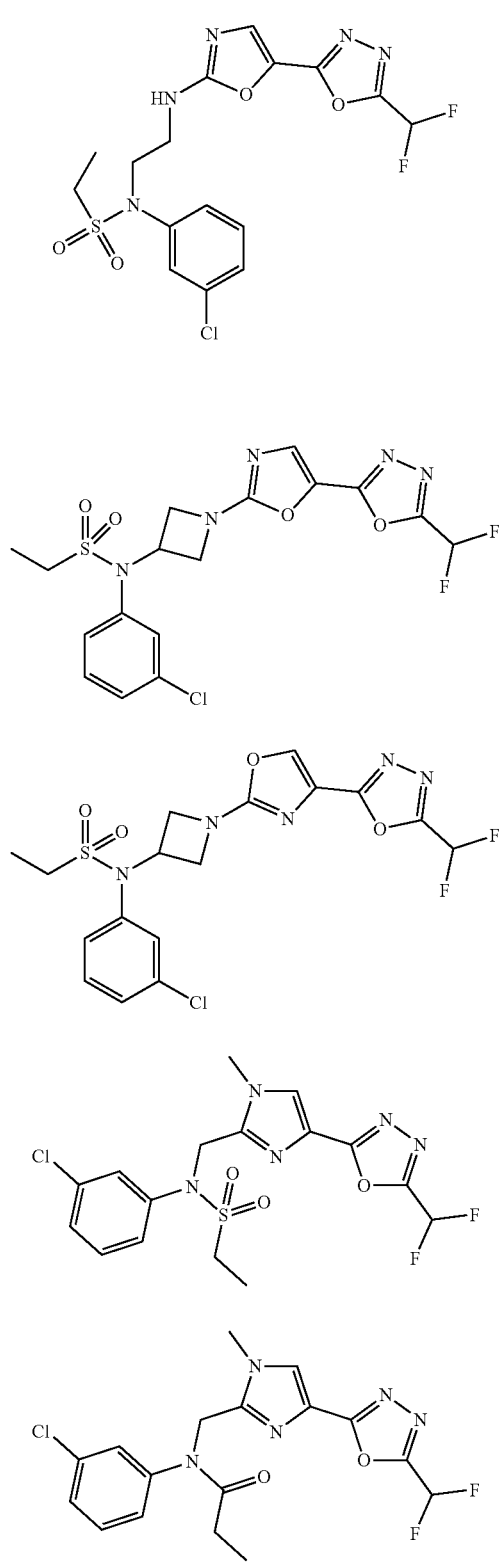
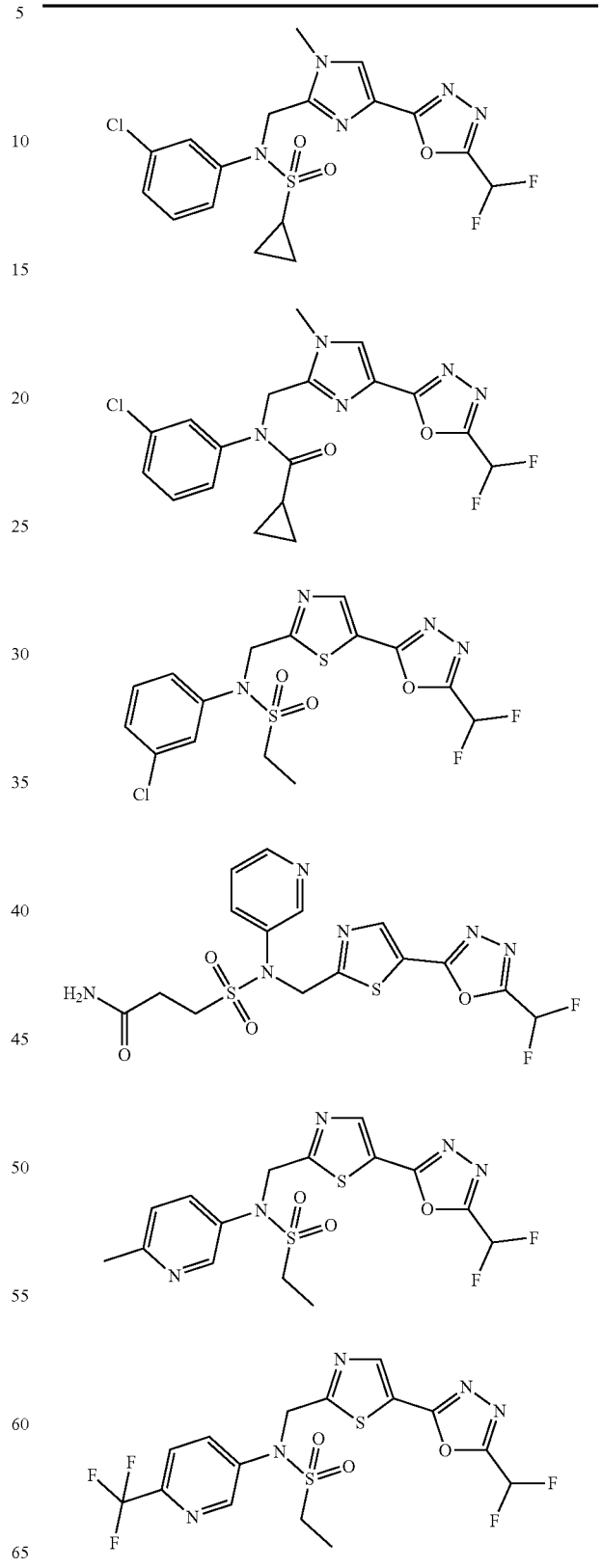

TABLE 1-continued
Compounds of Formula (I) of the Present Disclosure.
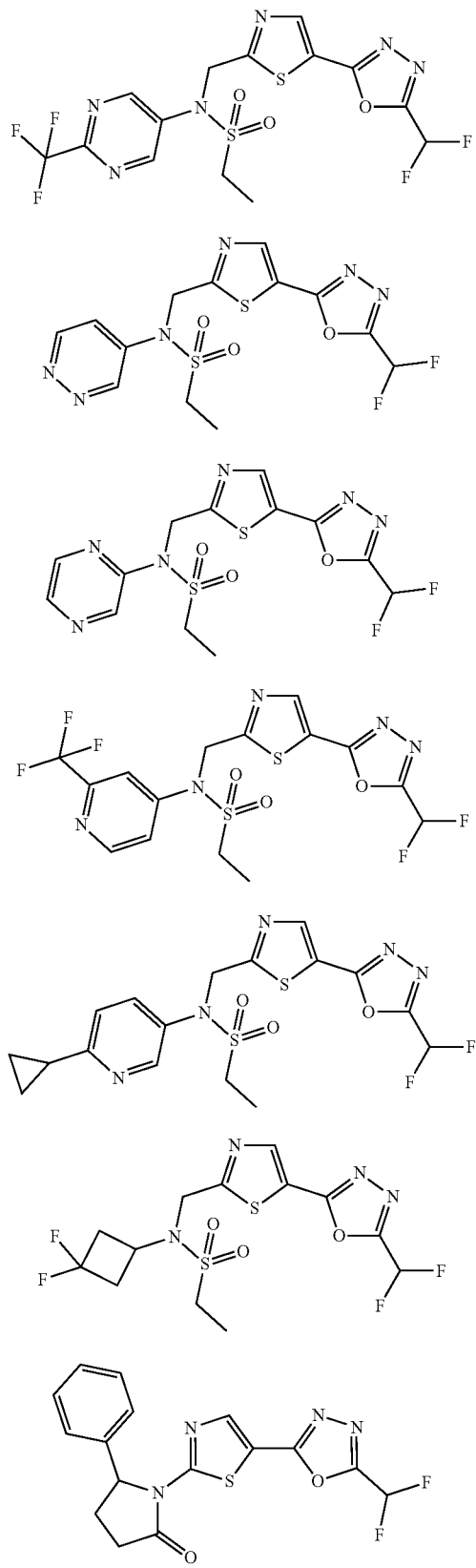
TABLE 1-continued
Compounds of Formula (I) of the Present Disclosure.
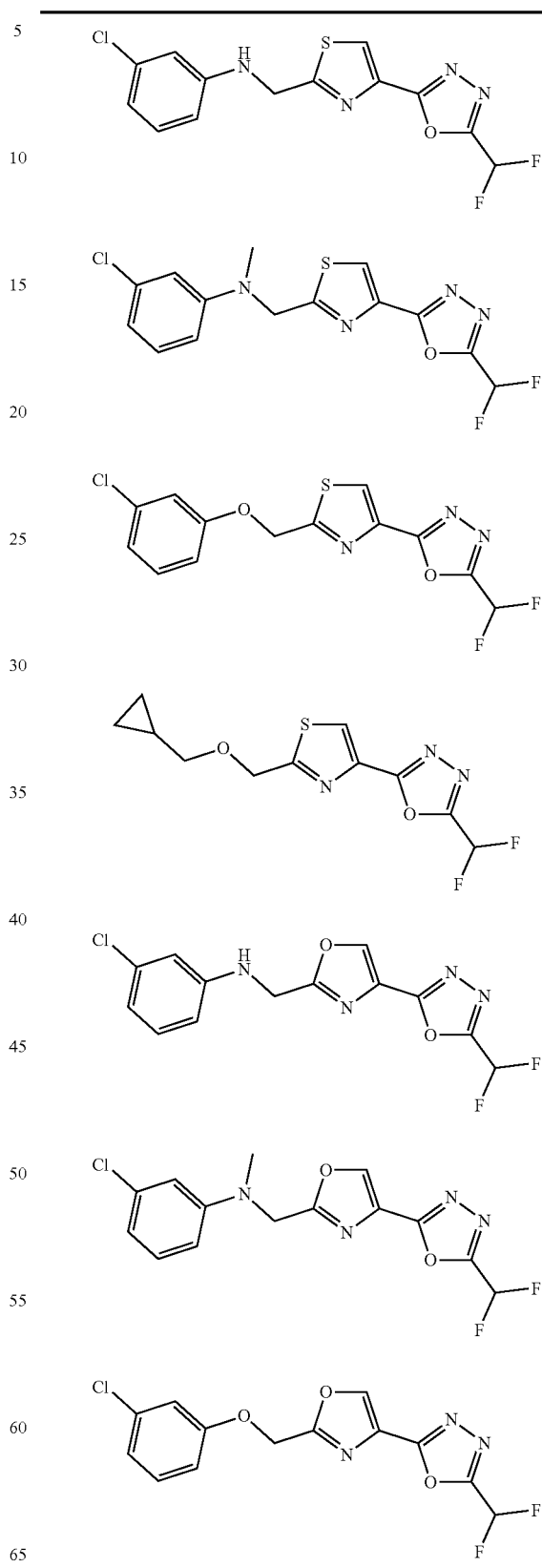

TABLE 1-continued
Compounds of Formula (I) of the Present Disclosure.
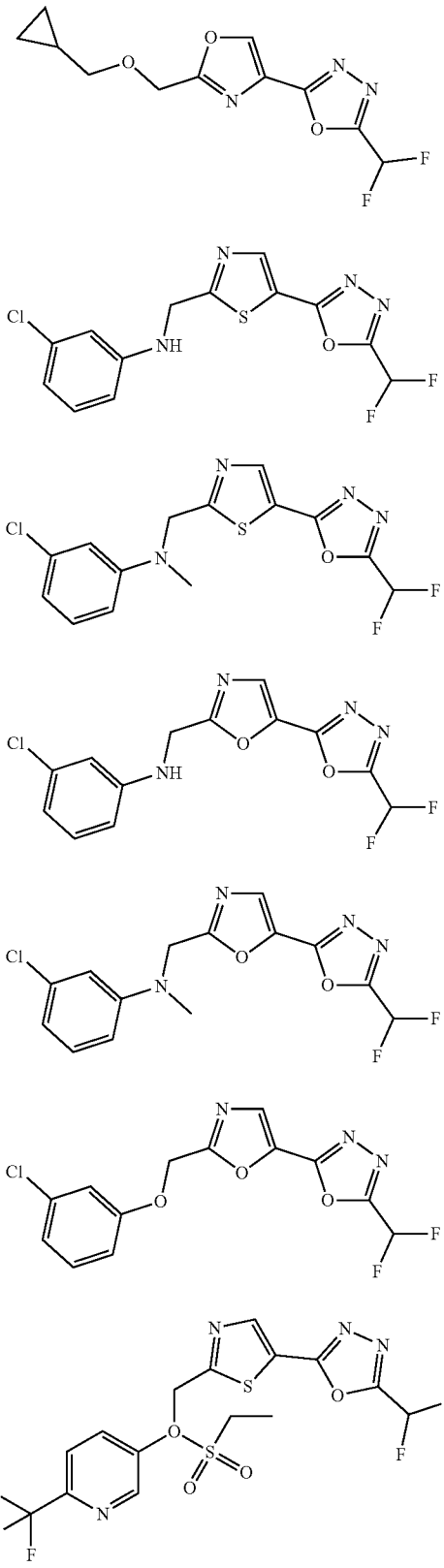
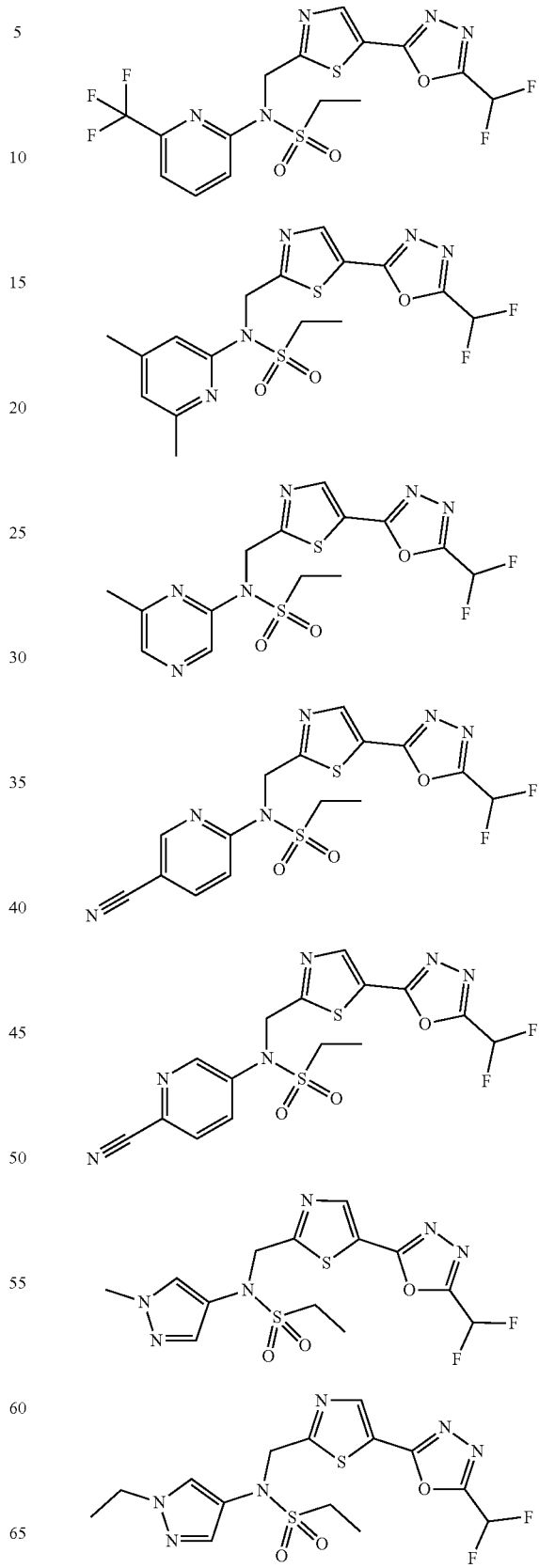

TABLE 1-continued
Compounds of Formula (I) of the Present Disclosure.
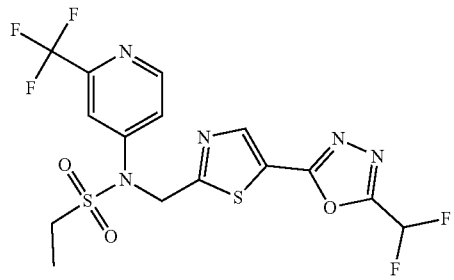 [SMILES: CCS(=O)(=O)N(Cc1ncc(-c2nnc(C(F)F)o2)s1)c1ccnc(C(F)(F)F)c1]
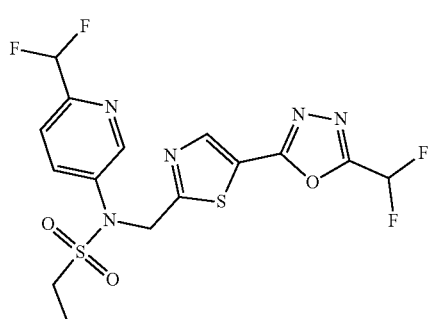
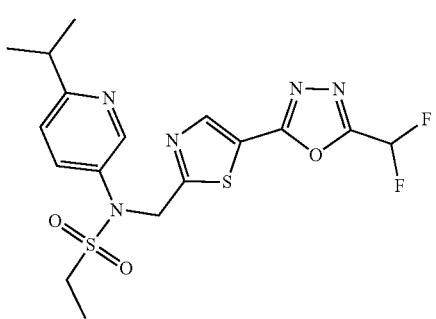 [SMILES: CCS(=O)(=O)N(Cc1ncc(-c2nnc(C(F)F)o2)s1)c1ccc(C(C)C)nc1]
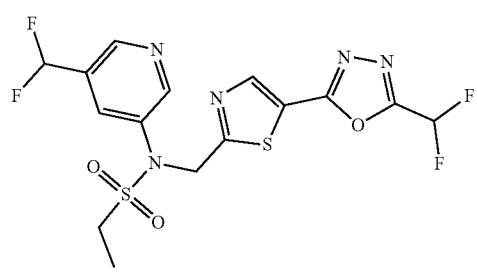 [SMILES: CCS(=O)(=O)N(Cc1ncc(-c2nnc(C(F)F)o2)s1)c1cncc(C(F)F)c1]
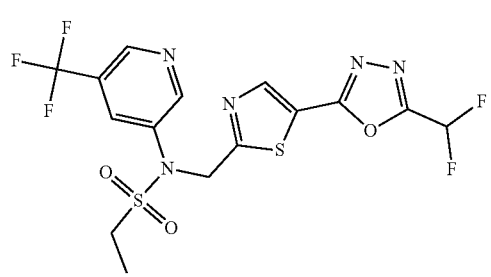 [SMILES: CCS(=O)(=O)N(Cc1ncc(-c2nnc(C(F)F)o2)s1)c1cncc(C(F)(F)F)c1]
TABLE 1-continued
Compounds of Formula (I) of the Present Disclosure.
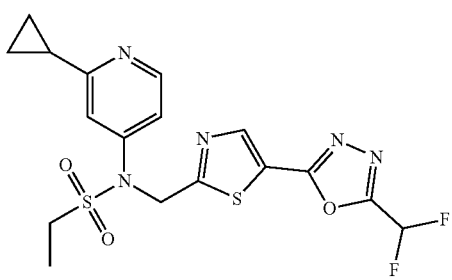 [SMILES: CCS(=O)(=O)N(Cc1ncc(-c2nnc(C(F)F)o2)s1)c1ccnc(C2CC2)c1]
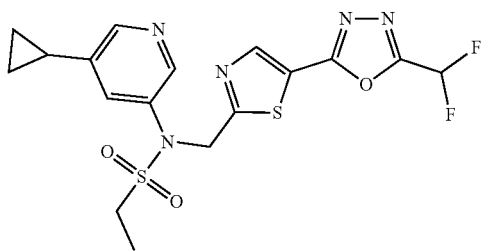 [SMILES: CCS(=O)(=O)N(Cc1ncc(-c2nnc(C(F)F)o2)s1)c1cncc(C2CC2)c1]
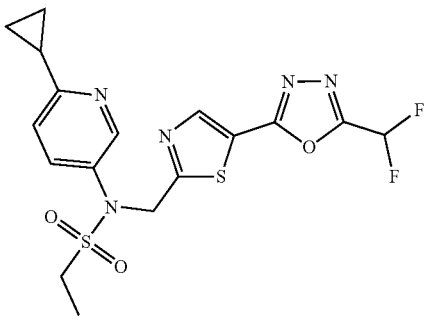 [SMILES: CCS(=O)(=O)N(Cc1ncc(-c2nnc(C(F)F)o2)s1)c1ccc(C2CC2)nc1]
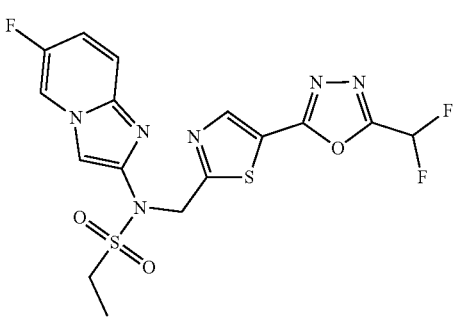 [SMILES: CCS(=O)(=O)N(Cc1ncc(-c2nnc(C(F)F)o2)s1)c1cn2cc(F)ccc2n1]
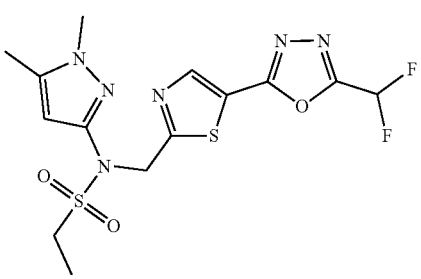 [SMILES: CCS(=O)(=O)N(Cc1ncc(-c2nnc(C(F)F)o2)s1)c1cc(C)n(C)n1]

TABLE 1-continued
Compounds of Formula (I) of the Present Disclosure.
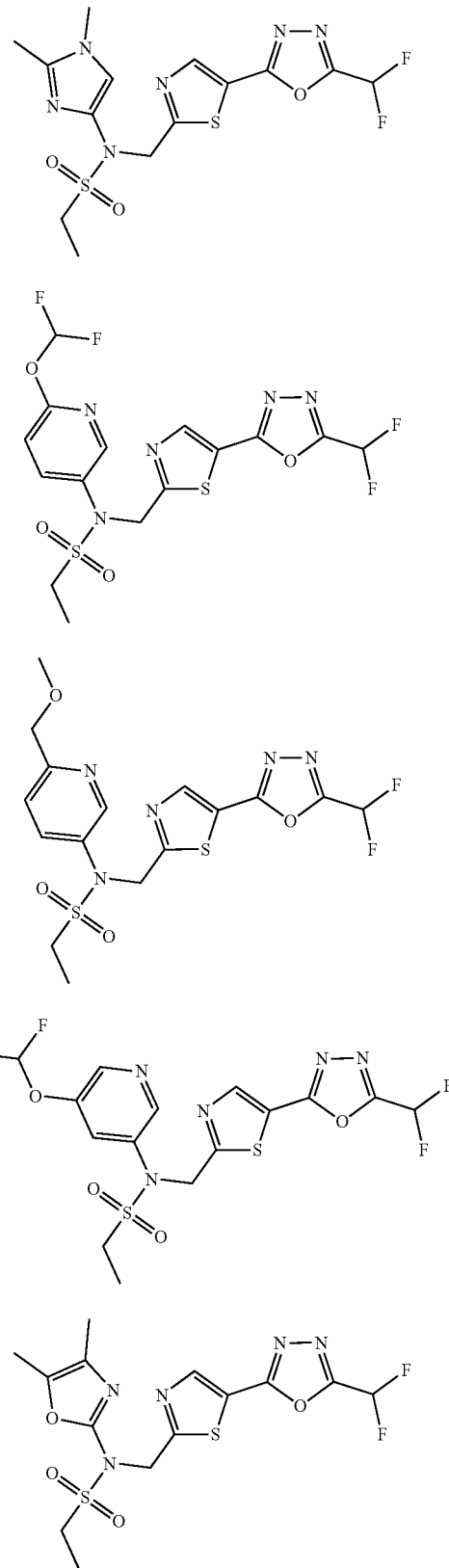
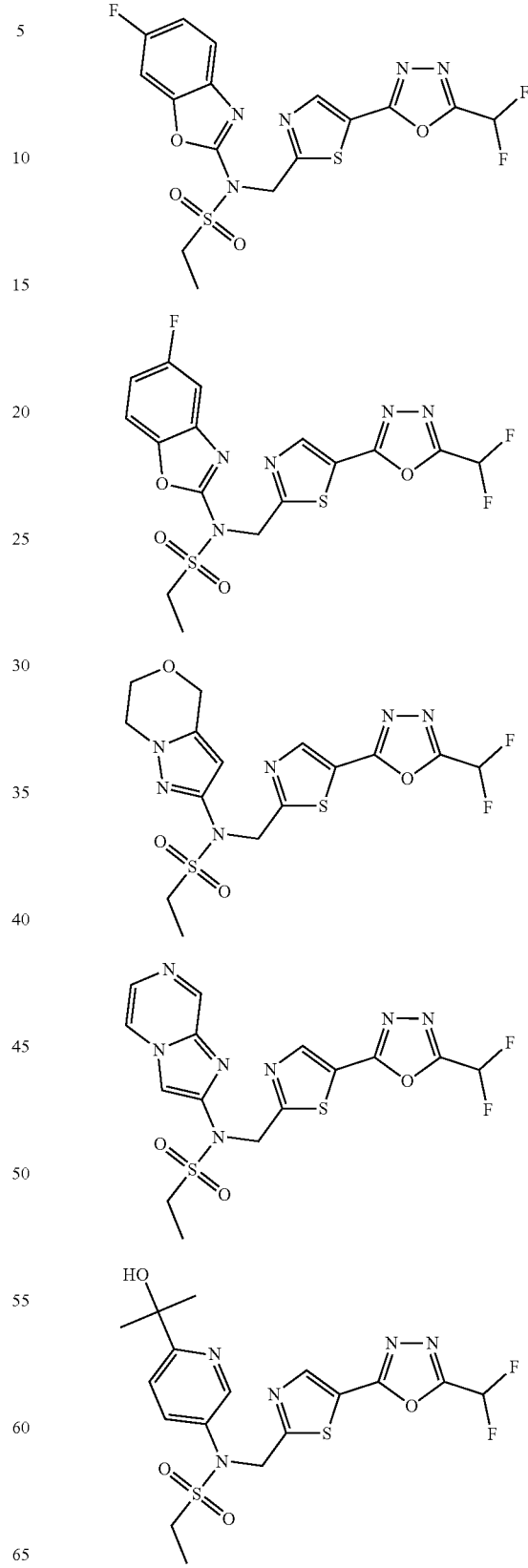

TABLE 1-continued
Compounds of Formula (I) of the Present Disclosure.
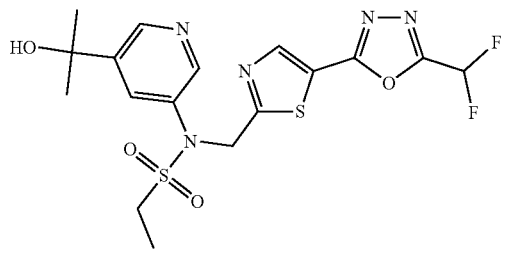 [SMILES: CCS(=O)(=O)N(Cc1ncc(-c2nnc(C(F)F)o2)s1)c1cncc(C(C)(C)O)c1]
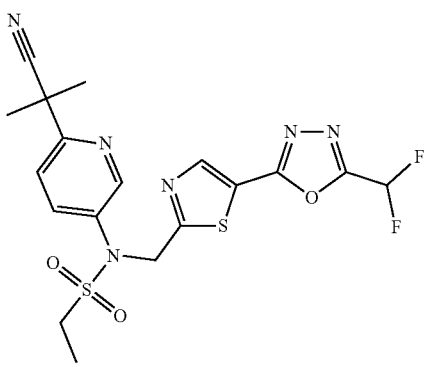 [SMILES: CCS(=O)(=O)N(Cc1ncc(-c2nnc(C(F)F)o2)s1)c1ccc(C(C)(C)C#N)nc1]
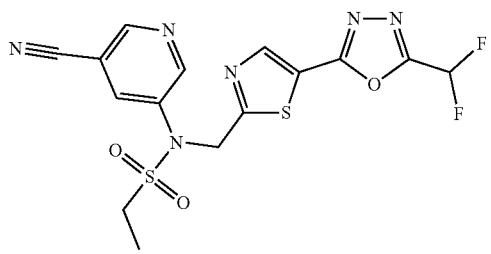 [SMILES: CCS(=O)(=O)N(Cc1ncc(-c2nnc(C(F)F)o2)s1)c1cncc(C#N)c1]
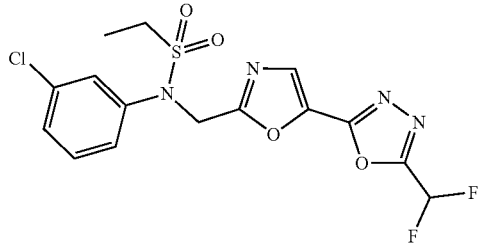 [SMILES: CCS(=O)(=O)N(Cc1ncc(-c2nnc(C(F)F)o2)o1)c1cccc(Cl)c1]
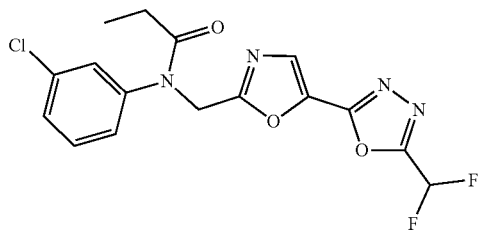 [SMILES: CCC(=O)N(Cc1ncc(-c2nnc(C(F)F)o2)o1)c1cccc(Cl)c1]
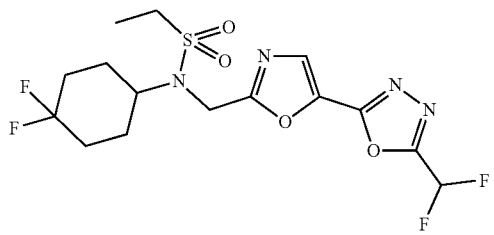 [SMILES: CCS(=O)(=O)N(Cc1ncc(-c2nnc(C(F)F)o2)o1)C1CCC(F)(F)CC1]
TABLE 1-continued
Compounds of Formula (I) of the Present Disclosure.
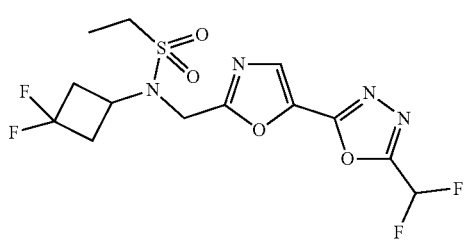 [SMILES: CCS(=O)(=O)N(Cc1ncc(-c2nnc(C(F)F)o2)o1)C1CC(F)(F)C1]
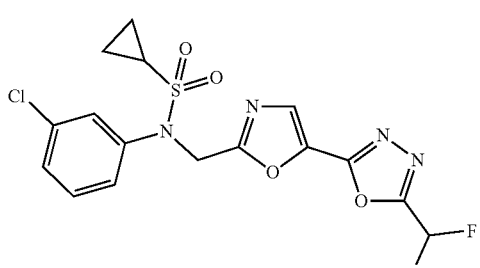
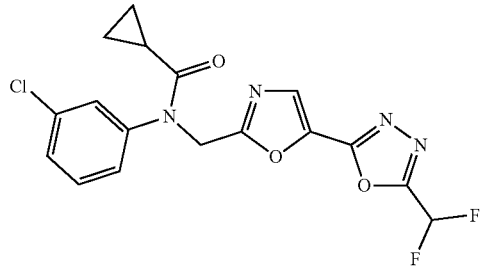 [SMILES: O=C(C1CC1)N(Cc1ncc(-c2nnc(C(F)F)o2)o1)c1cccc(Cl)c1]
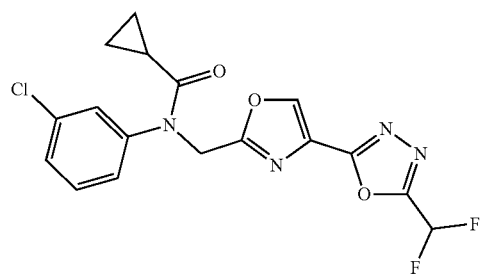 [SMILES: O=C(C1CC1)N(Cc1nc(-c2nnc(C(F)F)o2)co1)c1cccc(Cl)c1]
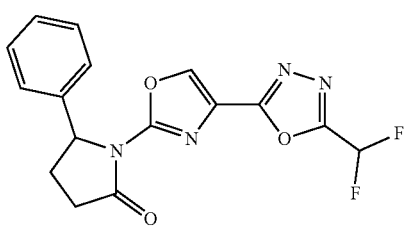 [SMILES: O=C1CCC(c2ccccc2)N1c1nc(-c2nnc(C(F)F)o2)co1]
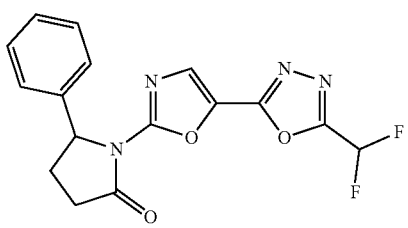 [SMILES: O=C1CCC(c2ccccc2)N1c1ncc(-c2nnc(C(F)F)o2)o1]

TABLE 1-continued
Compounds of Formula (I) of the Present Disclosure.
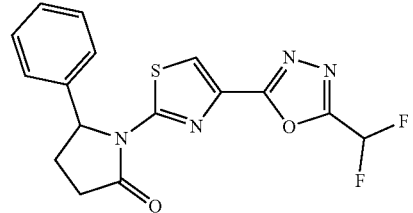
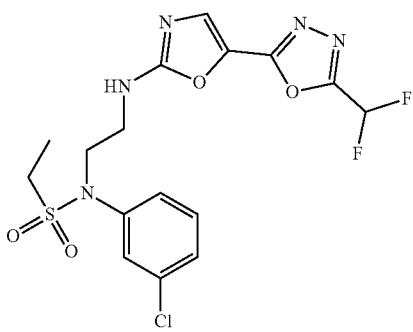 [SMILES: CCS(=O)(=O)N(CCNc1ncc(-c2nnc(C(F)F)o2)o1)c1cccc(Cl)c1]
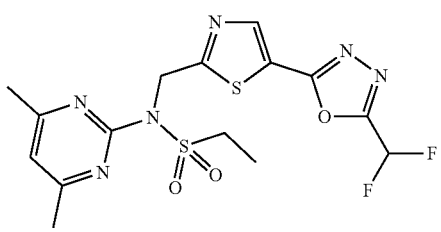 [SMILES: CCS(=O)(=O)N(Cc1ncc(-c2nnc(C(F)F)o2)s1)c1nc(C)cc(C)n1]
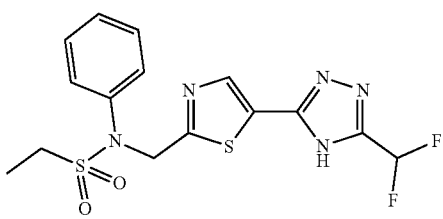 [SMILES: CCS(=O)(=O)N(Cc1ncc(-c2nnc(C(F)F)[nH]2)s1)c1ccccc1]
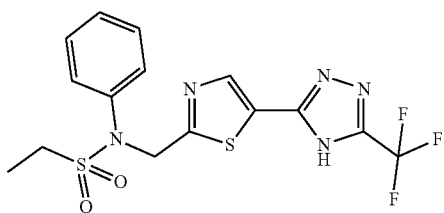 [SMILES: CCS(=O)(=O)N(Cc1ncc(-c2nnc(C(F)(F)F)[nH]2)s1)c1ccccc1]
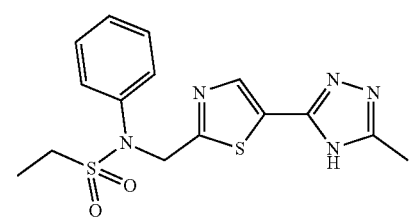 [SMILES: CCS(=O)(=O)N(Cc1ncc(-c2nnc(C)[nH]2)s1)c1ccccc1]
TABLE 1-continued
Compounds of Formula (I) of the Present Disclosure.
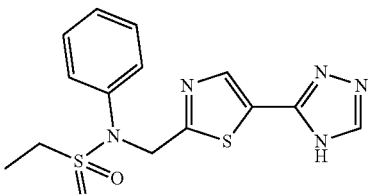
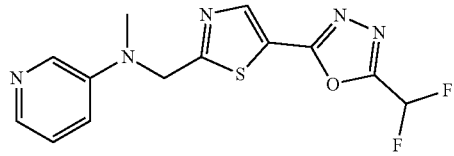 [SMILES: CN(Cc1ncc(-c2nnc(C(F)F)o2)s1)c1cccnc1]
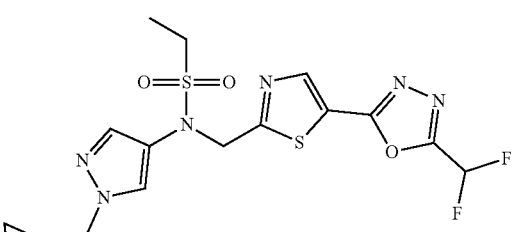
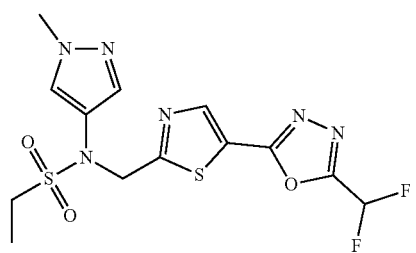 [SMILES: CCS(=O)(=O)N(Cc1ncc(-c2nnc(C(F)F)o2)s1)c1cnn(C)c1]
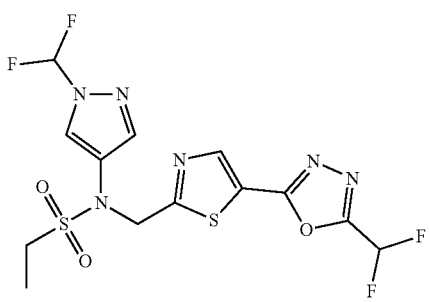 [SMILES: CCS(=O)(=O)N(Cc1ncc(-c2nnc(C(F)F)o2)s1)c1cnn(C(F)F)c1]
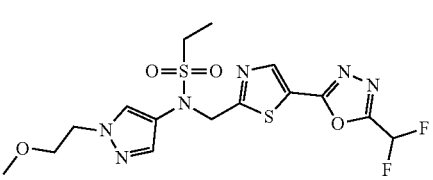 [SMILES: CCS(=O)(=O)N(Cc1ncc(-c2nnc(C(F)F)o2)s1)c1cnn(CCOC)c1]

TABLE 1-continued
Compounds of Formula (I) of the Present Disclosure.
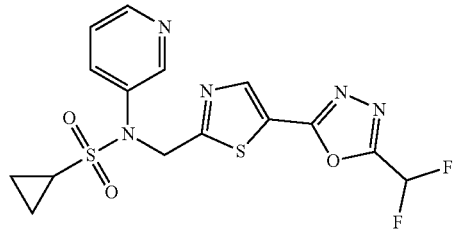 [SMILES: O=S(=O)(C1CC1)N(Cc1ncc(-c2nnc(C(F)F)o2)s1)c1cccnc1]
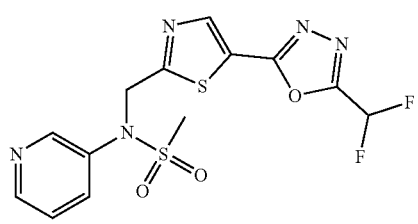 [SMILES: CS(=O)(=O)N(Cc1ncc(-c2nnc(C(F)F)o2)s1)c1cccnc1]
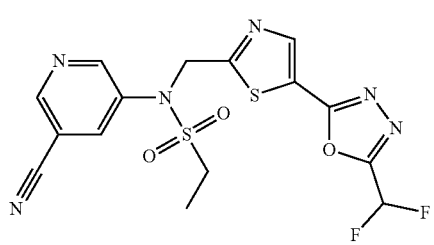 [SMILES: CCS(=O)(=O)N(Cc1ncc(-c2nnc(C(F)F)o2)s1)c1cncc(C#N)c1]
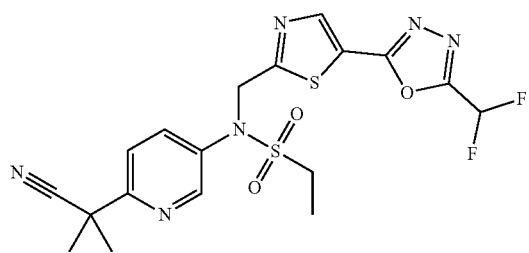 [SMILES: CCS(=O)(=O)N(Cc1ncc(-c2nnc(C(F)F)o2)s1)c1ccc(C(C)(C)C#N)nc1]
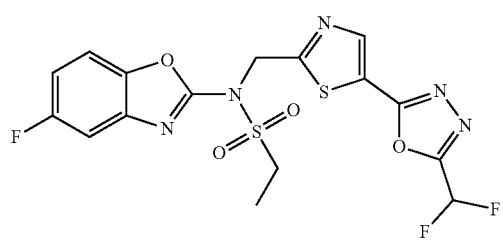 [SMILES: CCS(=O)(=O)N(Cc1ncc(-c2nnc(C(F)F)o2)s1)c1nc2cc(F)ccc2o1]
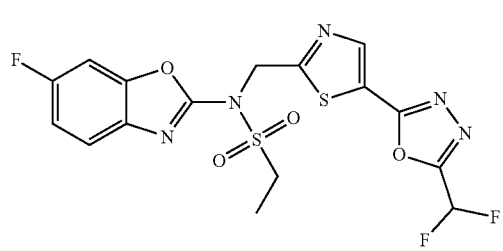 [SMILES: CCS(=O)(=O)N(Cc1ncc(-c2nnc(C(F)F)o2)s1)c1nc2ccc(F)cc2o1]
TABLE 1-continued
Compounds of Formula (I) of the Present Disclosure.
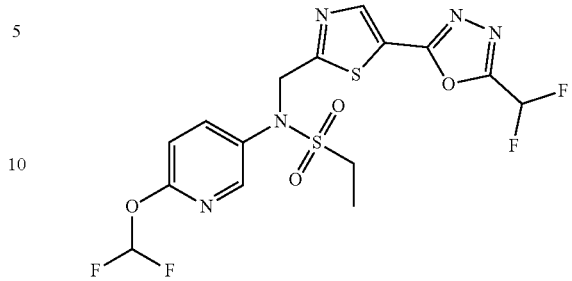
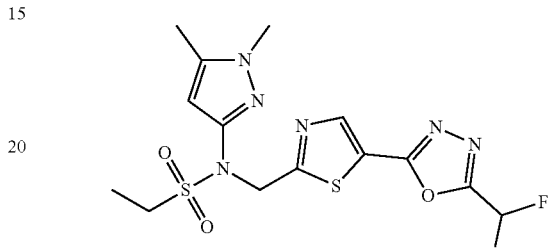
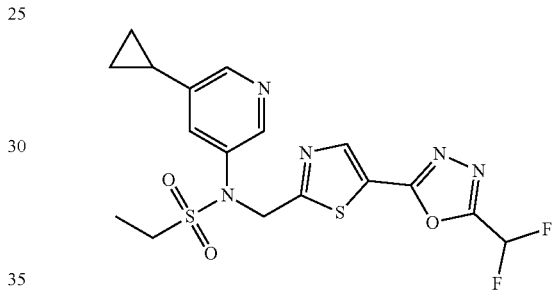
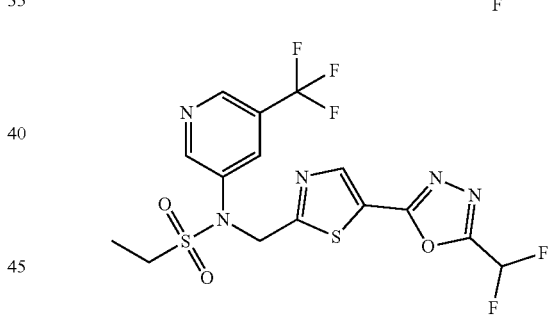
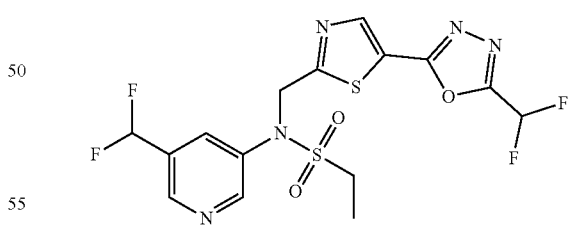
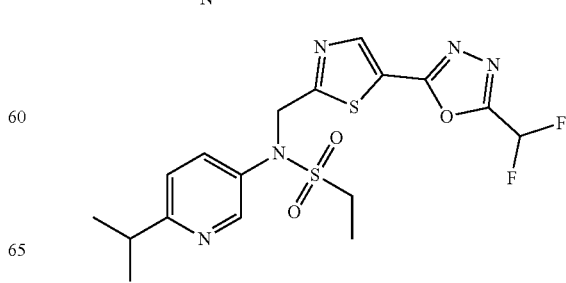

TABLE 1-continued
Compounds of Formula (I) of the Present Disclosure.
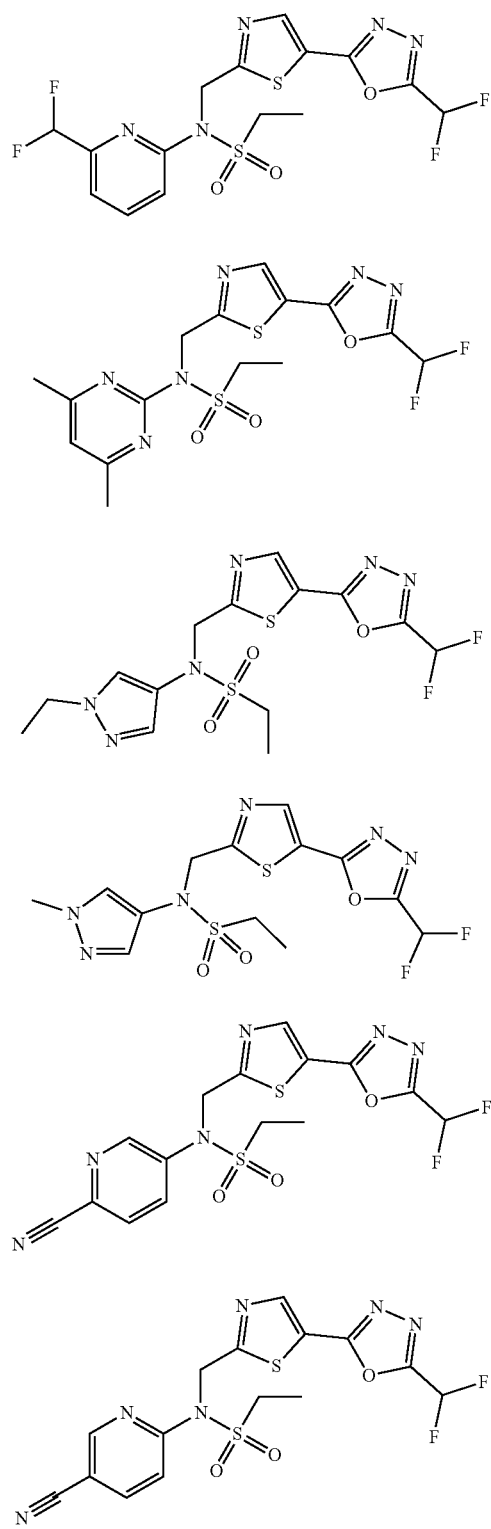
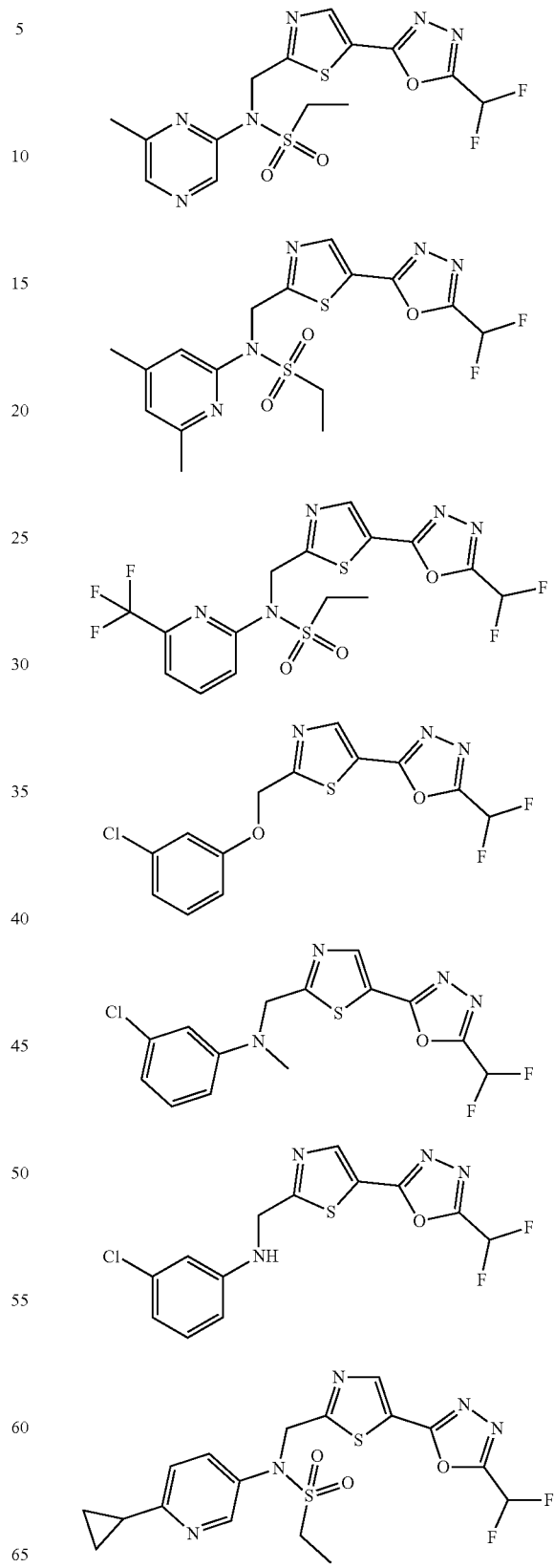

TABLE 1-continued
Compounds of Formula (I) of the Present Disclosure.
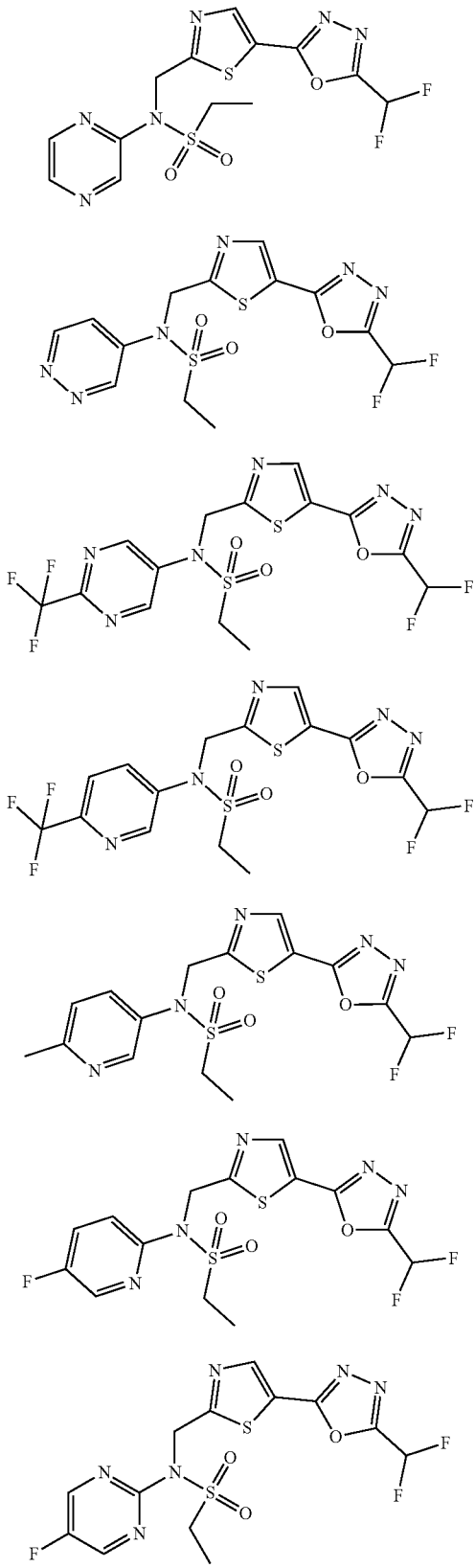
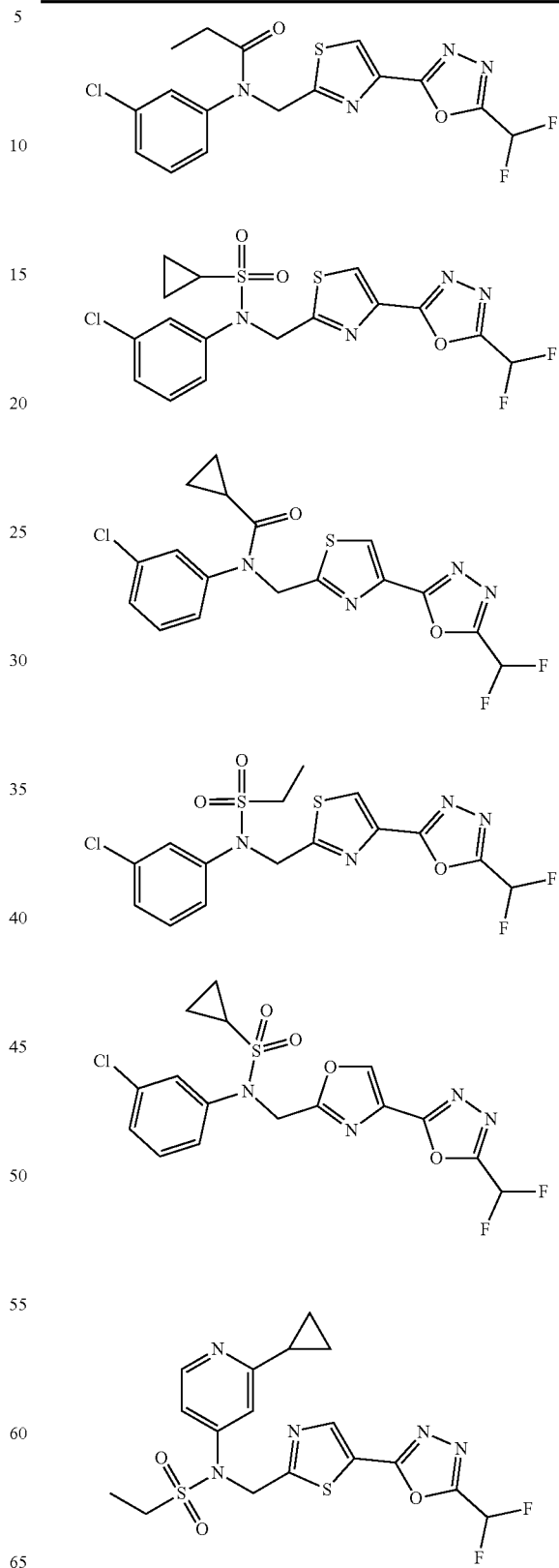

TABLE 1-continued
Compounds of Formula (I) of the Present Disclosure.
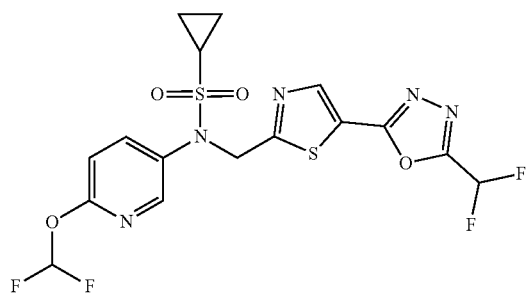 [SMILES: O=S(=O)(C1CC1)N(Cc1ncc(-c2nnc(C(F)F)o2)s1)c1ccc(OC(F)F)nc1]
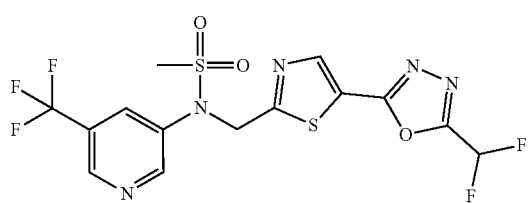 [SMILES: CS(=O)(=O)N(Cc1ncc(-c2nnc(C(F)F)o2)s1)c1cncc(C(F)(F)F)c1]
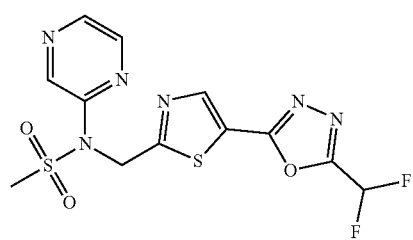 [SMILES: CS(=O)(=O)N(Cc1ncc(-c2nnc(C(F)F)o2)s1)c1cnccn1]
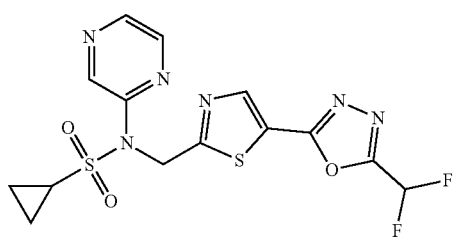 [SMILES: O=S(=O)(C1CC1)N(Cc1ncc(-c2nnc(C(F)F)o2)s1)c1cnccn1]
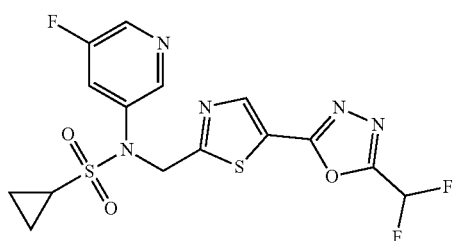
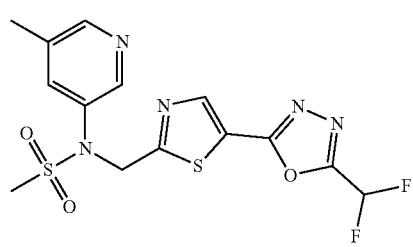 [SMILES: Cc1cncc(N(Cc2ncc(-c3nnc(C(F)F)o3)s2)S(C)(=O)=O)c1]
TABLE 1-continued
Compounds of Formula (I) of the Present Disclosure.
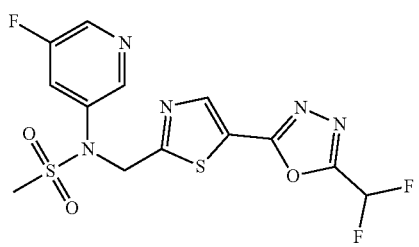 [SMILES: CS(=O)(=O)N(Cc1ncc(-c2nnc(C(F)F)o2)s1)c1cncc(F)c1]
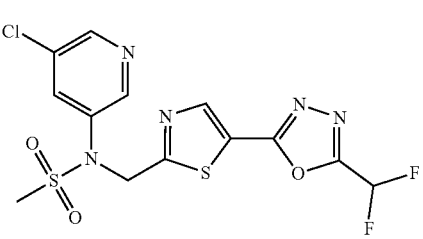 [SMILES: CS(=O)(=O)N(Cc1ncc(-c2nnc(C(F)F)o2)s1)c1cncc(Cl)c1]
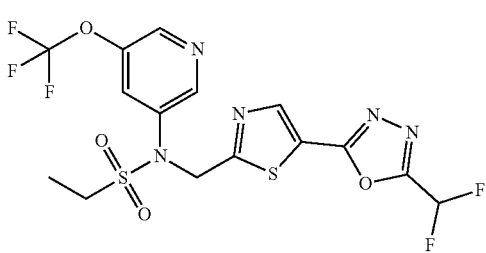 [SMILES: CCS(=O)(=O)N(Cc1ncc(-c2nnc(C(F)F)o2)s1)c1cncc(OC(F)(F)F)c1]
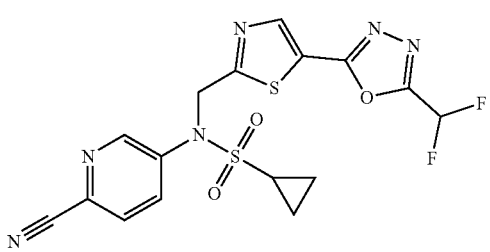 [SMILES: N#Cc1ccc(N(Cc2ncc(-c3nnc(C(F)F)o3)s2)S(=O)(=O)C2CC2)cn1]
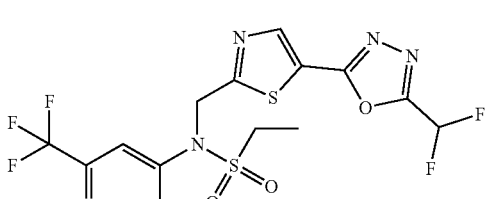
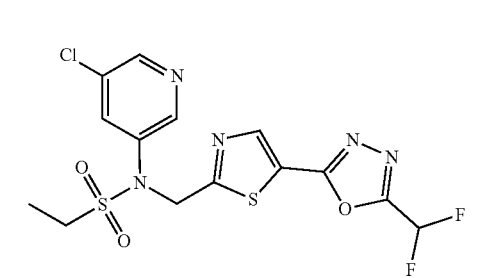 [SMILES: CCS(=O)(=O)N(Cc1ncc(-c2nnc(C(F)F)o2)s1)c1cncc(Cl)c1]

TABLE 1-continued
Compounds of Formula (I) of the Present Disclosure.
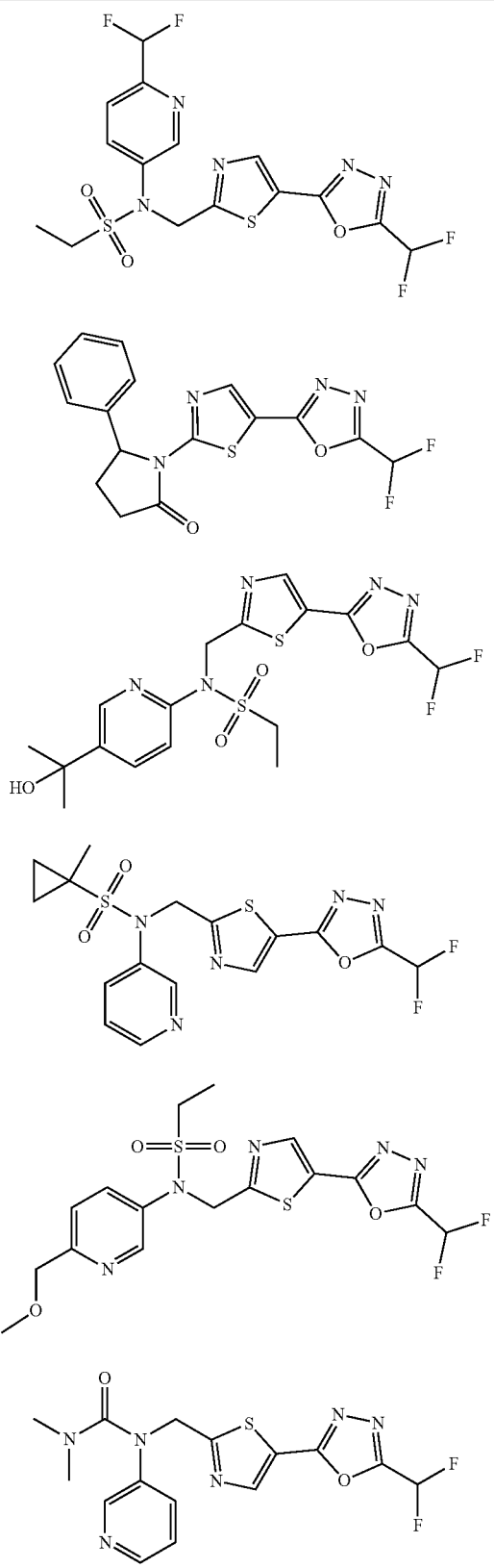
TABLE 1-continued
Compounds of Formula (I) of the Present Disclosure.
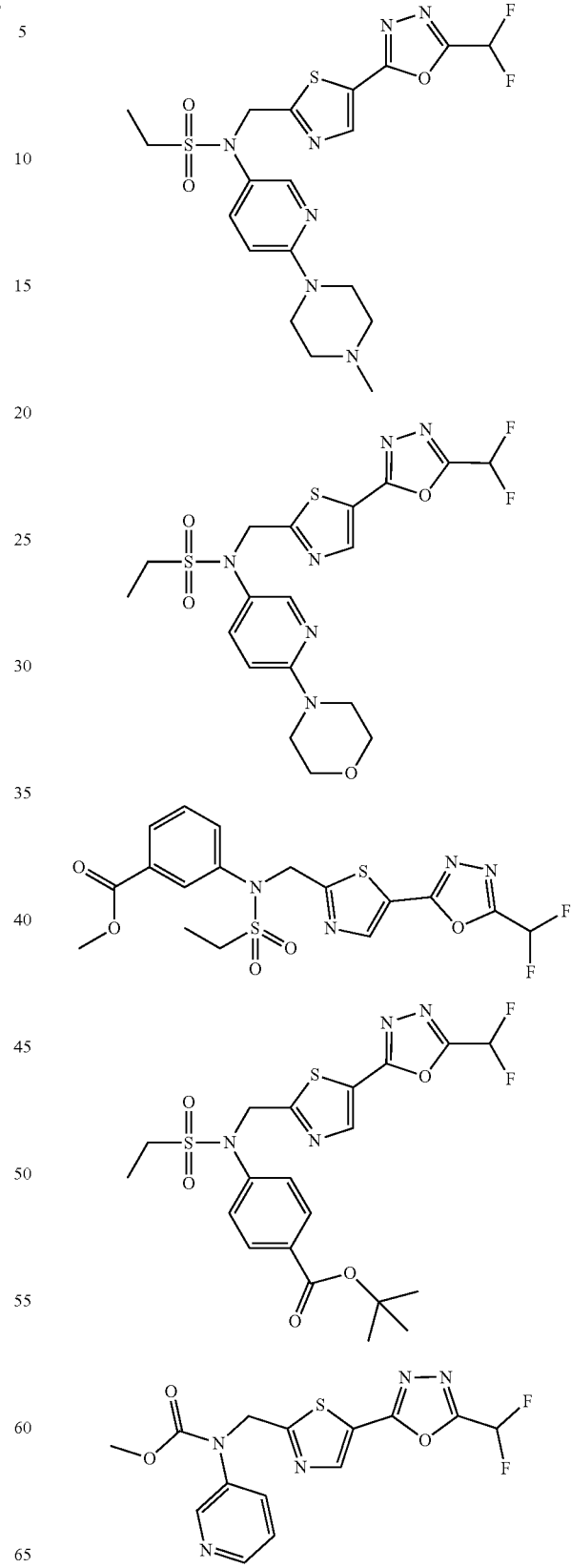

TABLE 1-continued
Compounds of Formula (I) of the Present Disclosure.
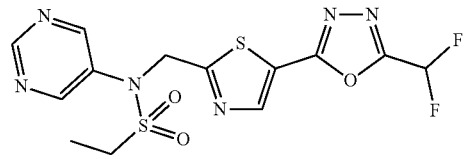 [SMILES: CCS(=O)(=O)N(Cc1ncc(-c2nnc(C(F)F)o2)s1)c1cncnc1]
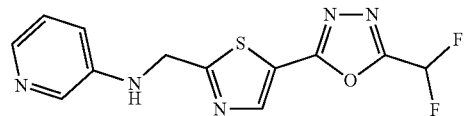 [SMILES: FC(F)c1nnc(-c2cnc(CNc3cccnc3)s2)o1]
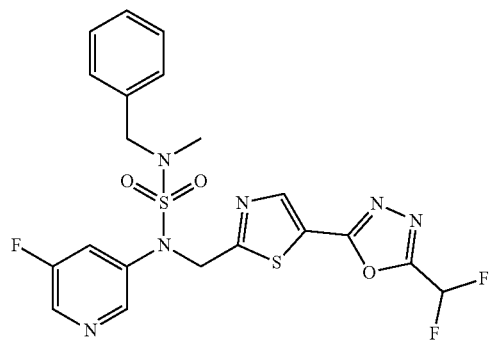 [SMILES: CN(Cc1ccccc1)S(=O)(=O)N(Cc1ncc(-c2nnc(C(F)F)o2)s1)c1cncc(F)c1]
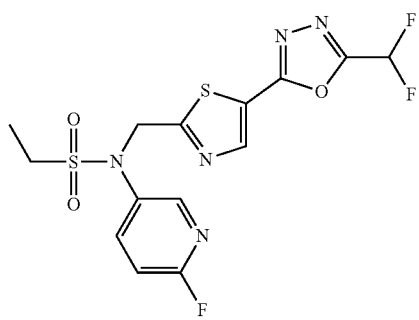 [SMILES: CCS(=O)(=O)N(Cc1ncc(-c2nnc(C(F)F)o2)s1)c1ccc(F)nc1]
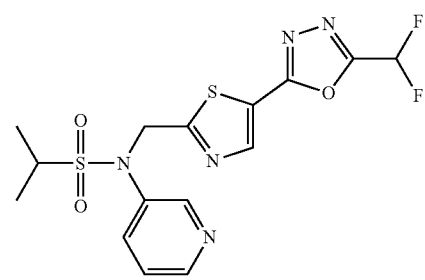 [SMILES: CC(C)S(=O)(=O)N(Cc1ncc(-c2nnc(C(F)F)o2)s1)c1cccnc1]
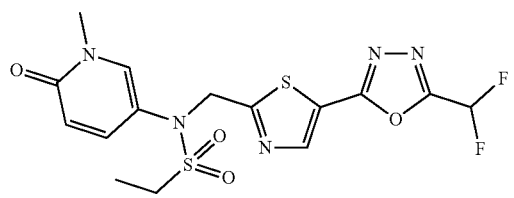 [SMILES: CCS(=O)(=O)N(Cc1ncc(-c2nnc(C(F)F)o2)s1)c1ccc(=O)n(C)c1]
TABLE 1-continued
Compounds of Formula (I) of the Present Disclosure.
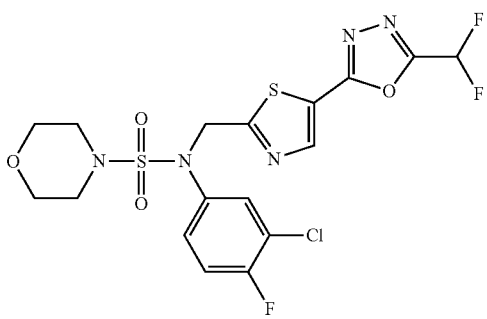 [SMILES: O=S(=O)(N1CCOCC1)N(Cc1ncc(-c2nnc(C(F)F)o2)s1)c1ccc(F)c(Cl)c1]
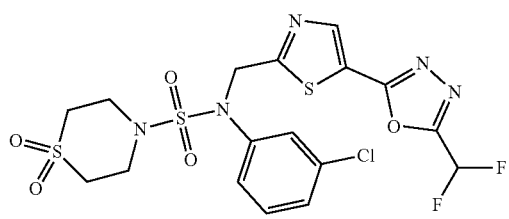 [SMILES: O=S1(=O)CCN(S(=O)(=O)N(Cc2ncc(-c3nnc(C(F)F)o3)s2)c2cccc(Cl)c2)CC1]
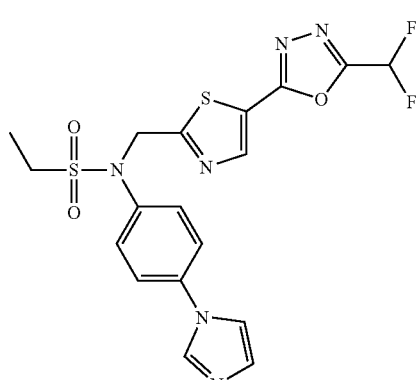
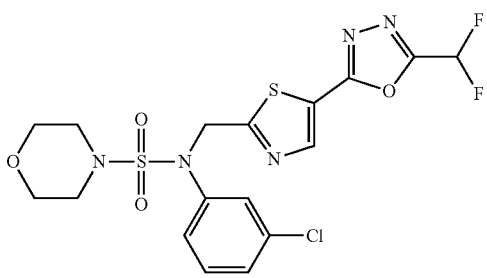 [SMILES: O=S(=O)(N1CCOCC1)N(Cc1ncc(-c2nnc(C(F)F)o2)s1)c1cccc(Cl)c1]
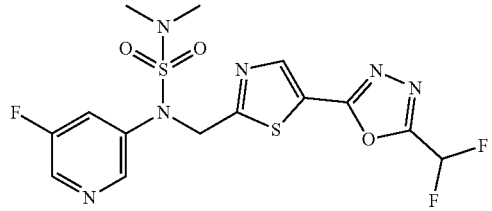 [SMILES: CN(C)S(=O)(=O)N(Cc1ncc(-c2nnc(C(F)F)o2)s1)c1cncc(F)c1]

TABLE 1-continued
Compounds of Formula (I) of the Present Disclosure.
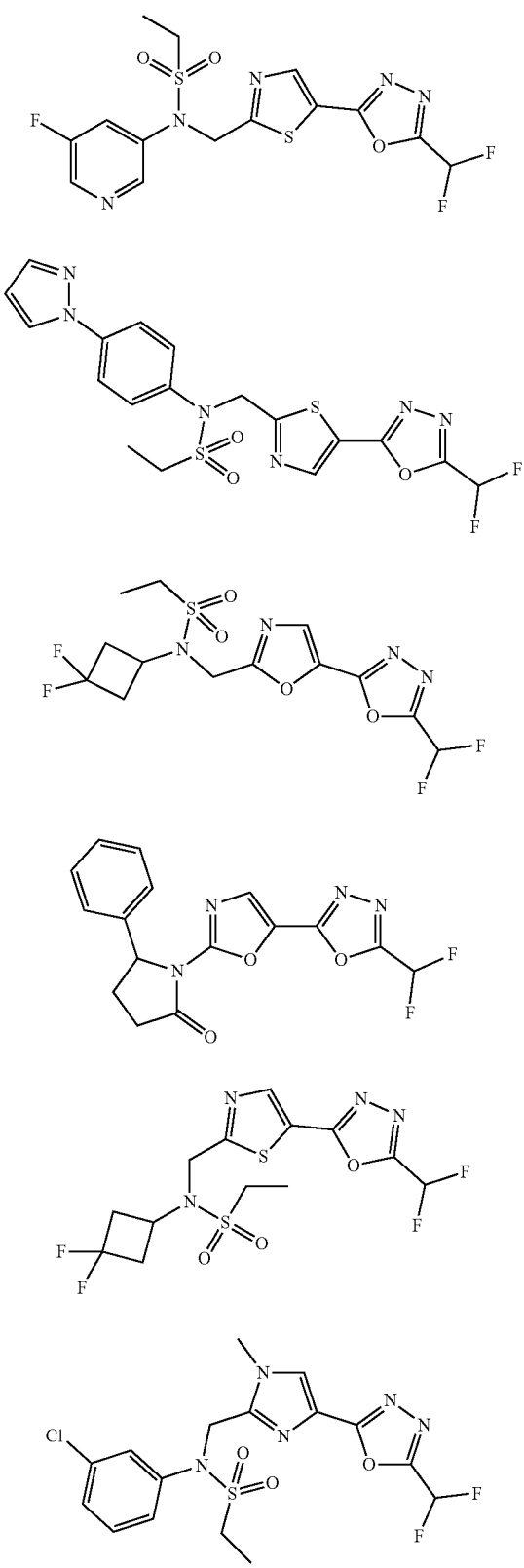
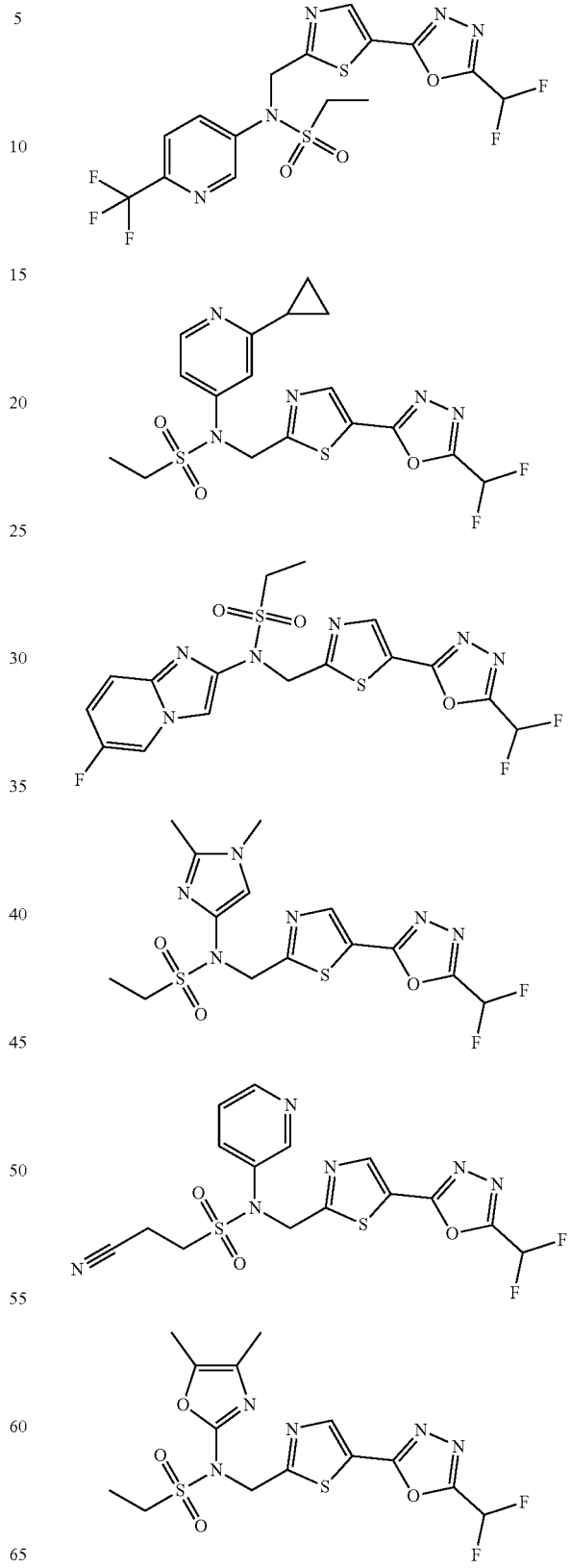

TABLE 1-continued
Compounds of Formula (I) of the Present Disclosure.
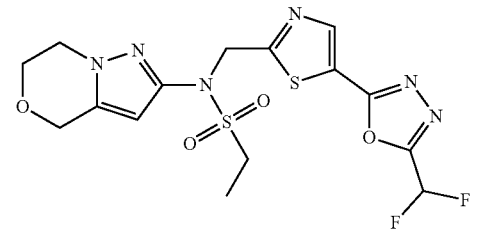 [SMILES: CCS(=O)(=O)N(Cc1ncc(-c2nnc(C(F)F)o2)s1)c1cc2n(n1)CCOC2]
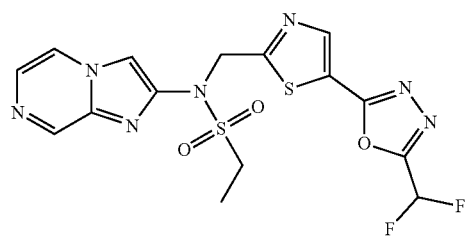 [SMILES: CCS(=O)(=O)N(Cc1ncc(-c2nnc(C(F)F)o2)s1)c1cn2ccncc2n1]
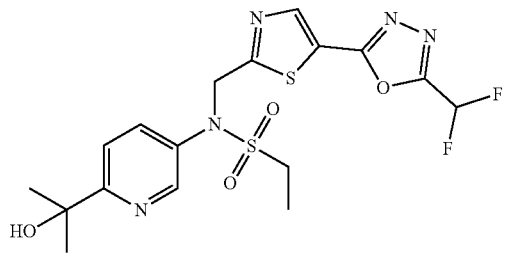 [SMILES: CCS(=O)(=O)N(Cc1ncc(-c2nnc(C(F)F)o2)s1)c1ccc(C(C)(C)O)nc1]
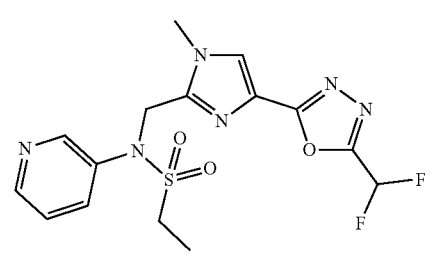 [SMILES: CCS(=O)(=O)N(Cc1nc(-c2nnc(C(F)F)o2)cn1C)c1cccnc1]
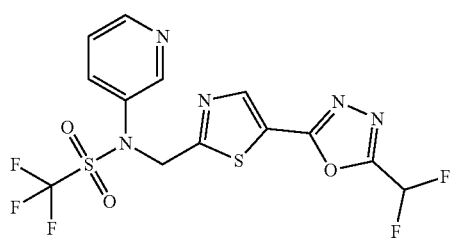 [SMILES: O=S(=O)(N(Cc1ncc(-c2nnc(C(F)F)o2)s1)c1cccnc1)C(F)(F)F]
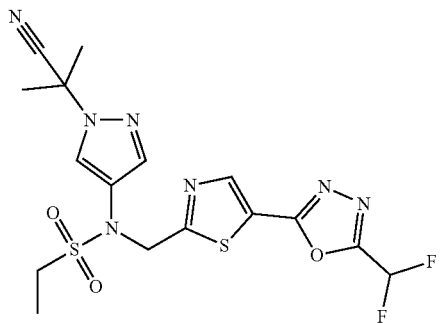 [SMILES: CCS(=O)(=O)N(Cc1ncc(-c2nnc(C(F)F)o2)s1)c1cnn(C(C)(C)C#N)c1]
TABLE 1-continued
Compounds of Formula (I) of the Present Disclosure.
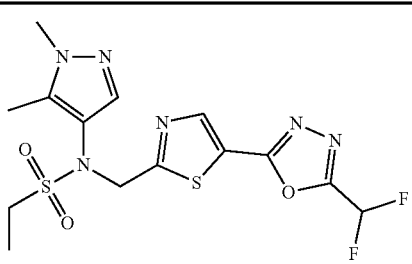
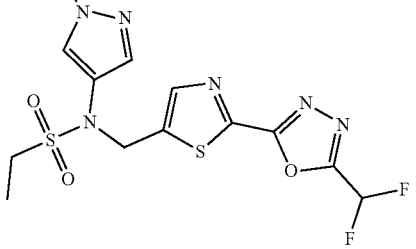
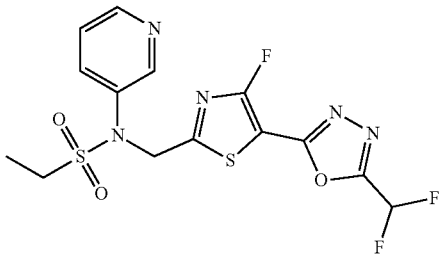 [SMILES: CCS(=O)(=O)N(Cc1nc(F)c(-c2nnc(C(F)F)o2)s1)c1cccnc1]
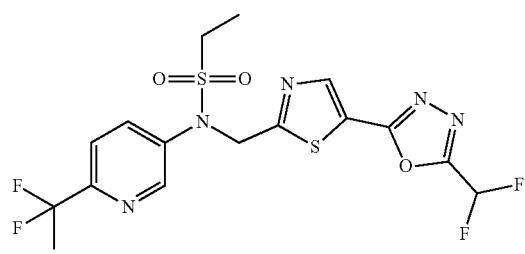 [SMILES: CCS(=O)(=O)N(Cc1ncc(-c2nnc(C(F)F)o2)s1)c1ccc(C(C)(F)F)nc1]
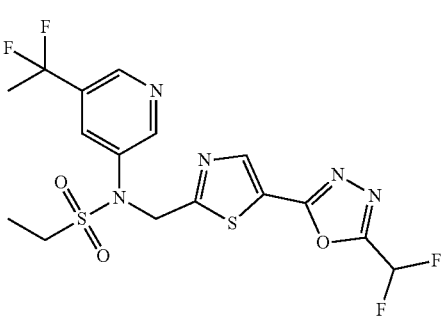 [SMILES: CCS(=O)(=O)N(Cc1ncc(-c2nnc(C(F)F)o2)s1)c1cncc(C(C)(F)F)c1]

TABLE 1-continued
Compounds of Formula (I) of the Present Disclosure.
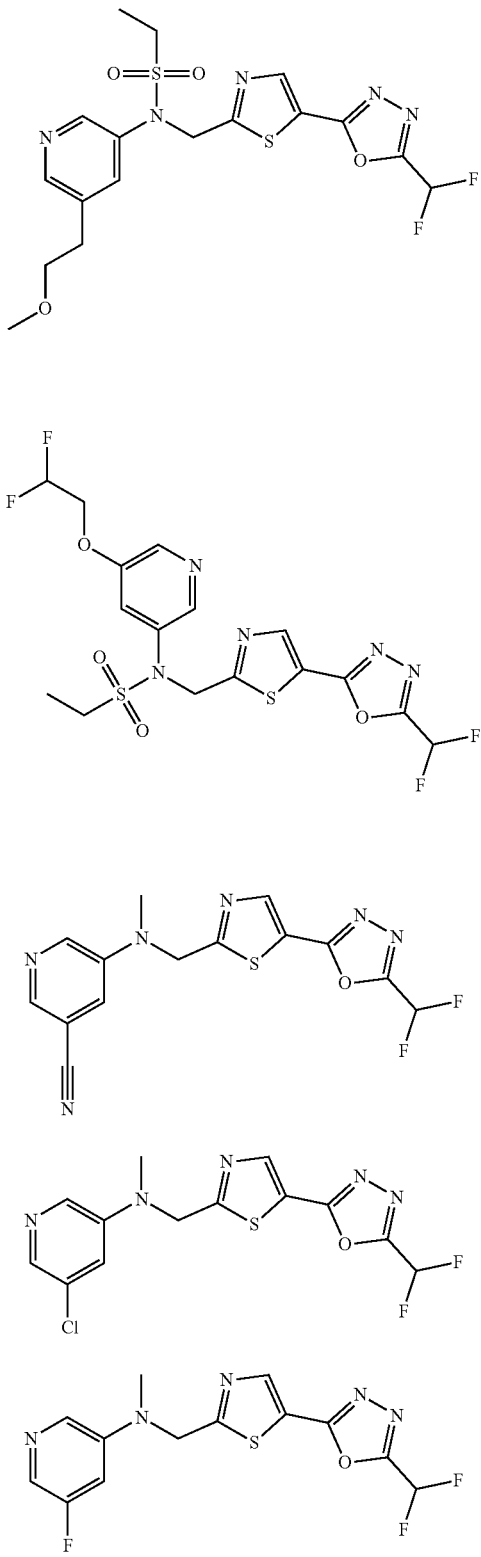
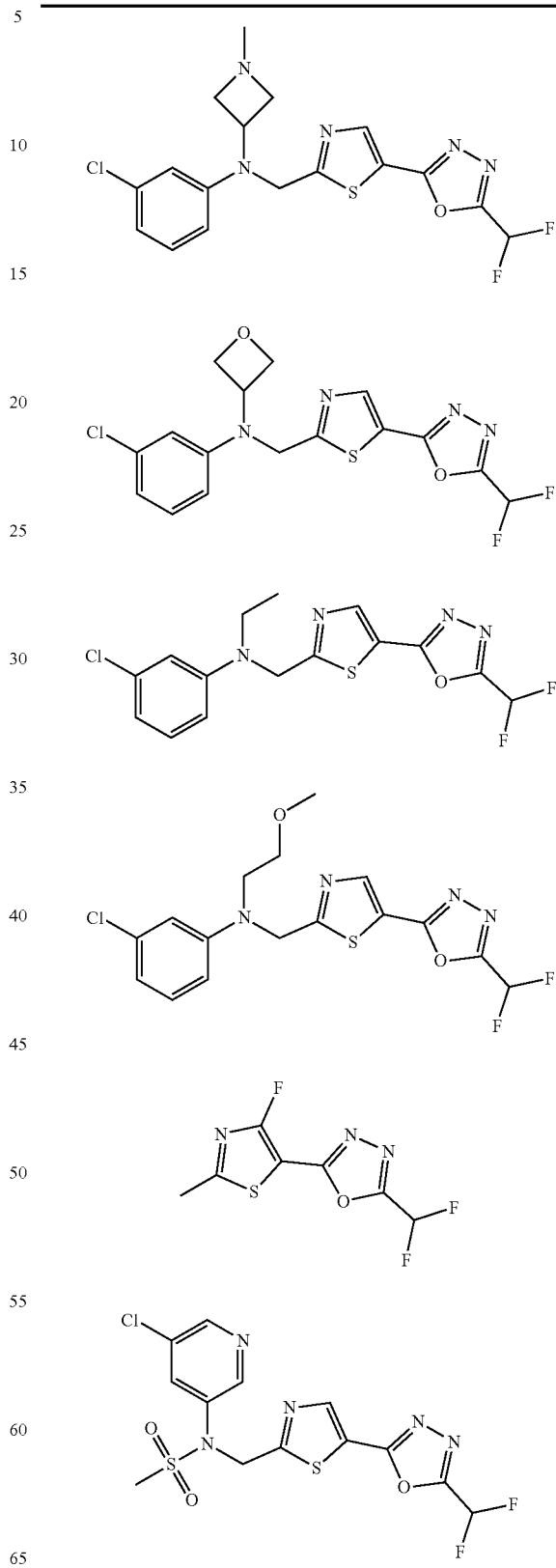

TABLE 1-continued
Compounds of Formula (I) of the Present Disclosure.
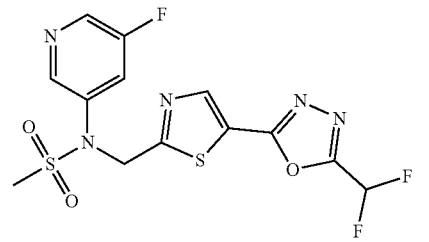 [SMILES: CS(=O)(=O)N(Cc1ncc(-c2nnc(C(F)F)o2)s1)c1cncc(F)c1]
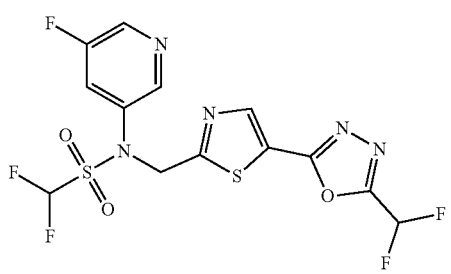 [SMILES: O=S(=O)(C(F)F)N(Cc1ncc(-c2nnc(C(F)F)o2)s1)c1cncc(F)c1]
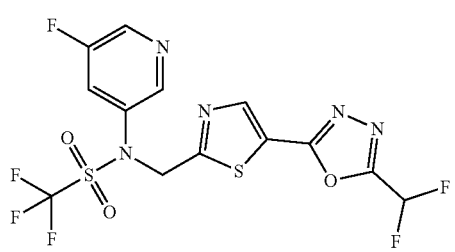 [SMILES: O=S(=O)(N(Cc1ncc(-c2nnc(C(F)F)o2)s1)c1cncc(F)c1)C(F)(F)F]
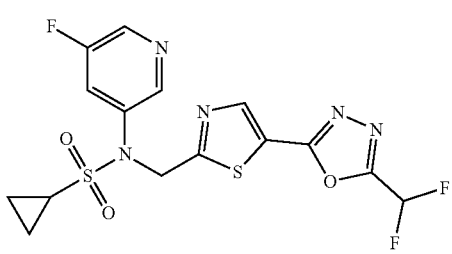 [SMILES: O=S(=O)(C1CC1)N(Cc1ncc(-c2nnc(C(F)F)o2)s1)c1cncc(F)c1]
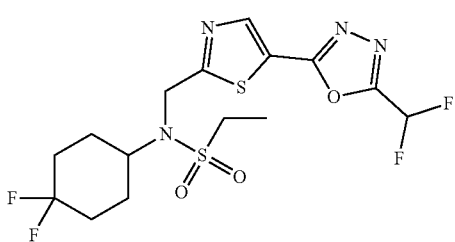 [SMILES: CCS(=O)(=O)N(Cc1ncc(-c2nnc(C(F)F)o2)s1)C1CCC(F)(F)CC1]
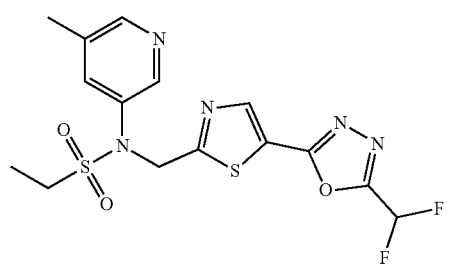 [SMILES: CCS(=O)(=O)N(Cc1ncc(-c2nnc(C(F)F)o2)s1)c1cncc(C)c1]
TABLE 1-continued
Compounds of Formula (I) of the Present Disclosure.
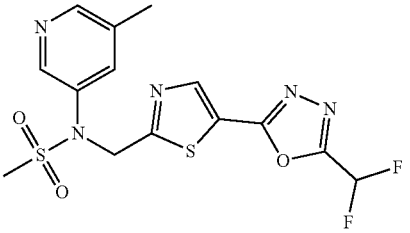 [SMILES: Cc1cncc(N(Cc2ncc(-c3nnc(C(F)F)o3)s2)S(C)(=O)=O)c1]
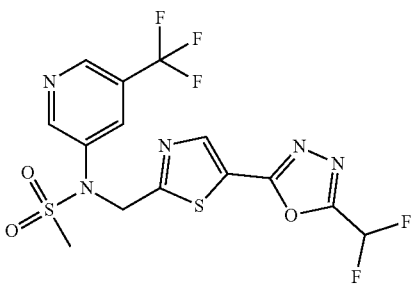 [SMILES: CS(=O)(=O)N(Cc1ncc(-c2nnc(C(F)F)o2)s1)c1cncc(C(F)(F)F)c1]
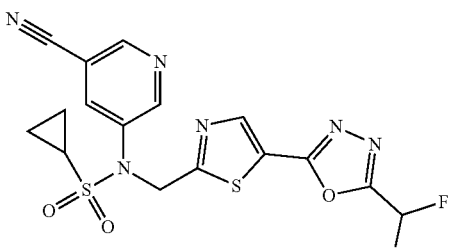
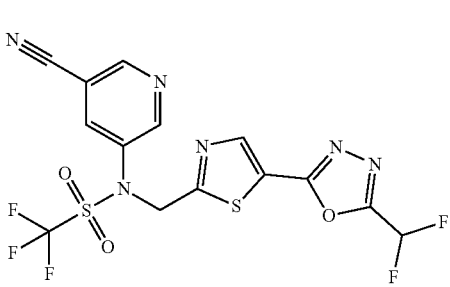 [SMILES: N#Cc1cncc(N(Cc2ncc(-c3nnc(C(F)F)o3)s2)S(=O)(=O)C(F)(F)F)c1]
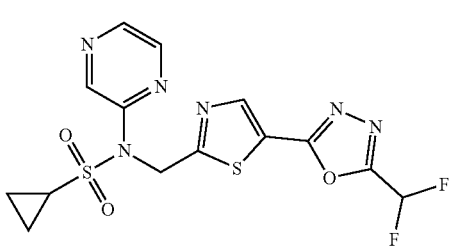 [SMILES: O=S(=O)(C1CC1)N(Cc1ncc(-c2nnc(C(F)F)o2)s1)c1cnccn1]
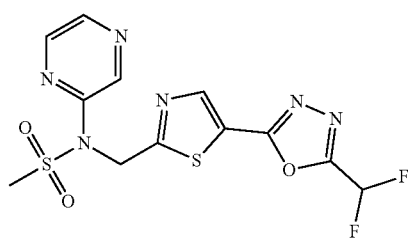 [SMILES: CS(=O)(=O)N(Cc1ncc(-c2nnc(C(F)F)o2)s1)c1cnccn1]

TABLE 1-continued
Compounds of Formula (I) of the Present Disclosure.
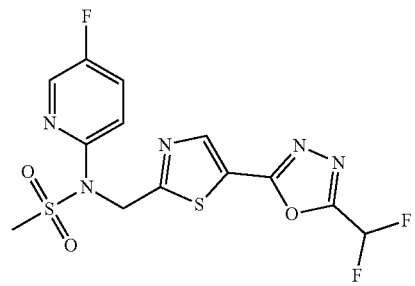 [SMILES: CS(=O)(=O)N(Cc1ncc(-c2nnc(C(F)F)o2)s1)c1ccc(F)cn1]
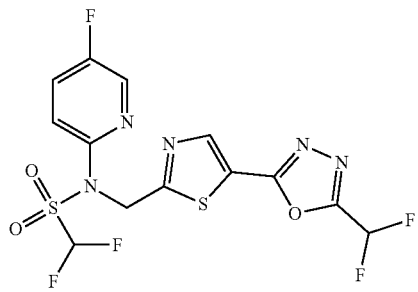 [SMILES: O=S(=O)(C(F)F)N(Cc1ncc(-c2nnc(C(F)F)o2)s1)c1ccc(F)cn1]
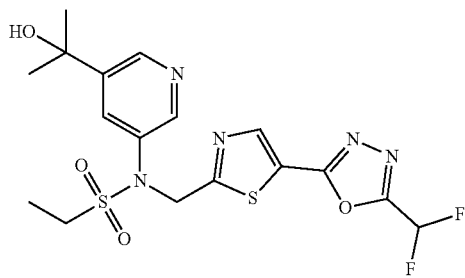 [SMILES: CCS(=O)(=O)N(Cc1ncc(-c2nnc(C(F)F)o2)s1)c1cncc(C(C)(C)O)c1]
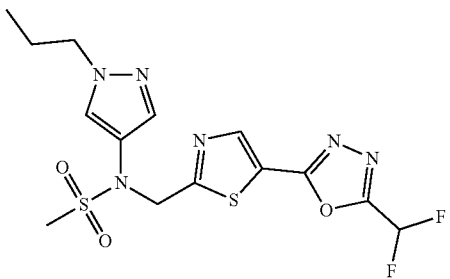 [SMILES: CCCn1cc(N(Cc2ncc(-c3nnc(C(F)F)o3)s2)S(C)(=O)=O)cn1]
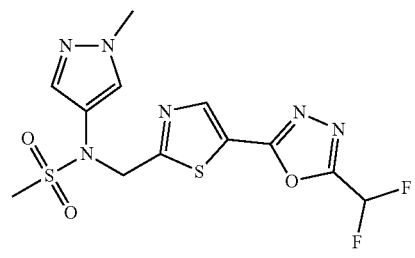 [SMILES: Cn1cc(N(Cc2ncc(-c3nnc(C(F)F)o3)s2)S(C)(=O)=O)cn1]
TABLE 1-continued
Compounds of Formula (I) of the Present Disclosure.
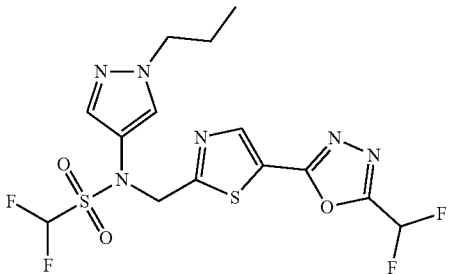 [SMILES: CCCn1cc(N(Cc2ncc(-c3nnc(C(F)F)o3)s2)S(=O)(=O)C(F)F)cn1]
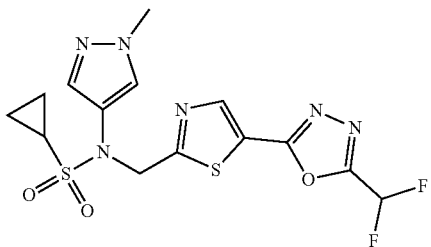 [SMILES: Cn1cc(N(Cc2ncc(-c3nnc(C(F)F)o3)s2)S(=O)(=O)C2CC2)cn1]
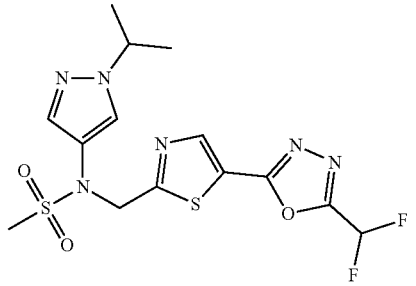 [SMILES: CC(C)n1cc(N(Cc2ncc(-c3nnc(C(F)F)o3)s2)S(C)(=O)=O)cn1]
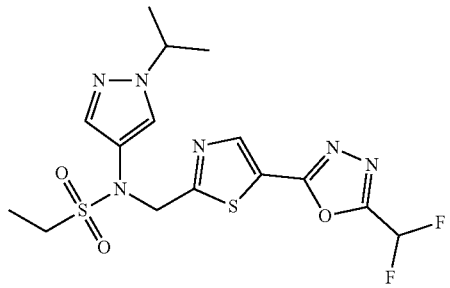 [SMILES: CCS(=O)(=O)N(Cc1ncc(-c2nnc(C(F)F)o2)s1)c1cnn(C(C)C)c1]
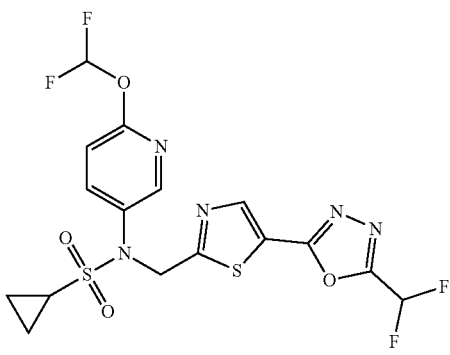 [SMILES: O=S(=O)(C1CC1)N(Cc1ncc(-c2nnc(C(F)F)o2)s1)c1ccc(OC(F)F)nc1]

TABLE 1-continued
Compounds of Formula (I) of the Present Disclosure.
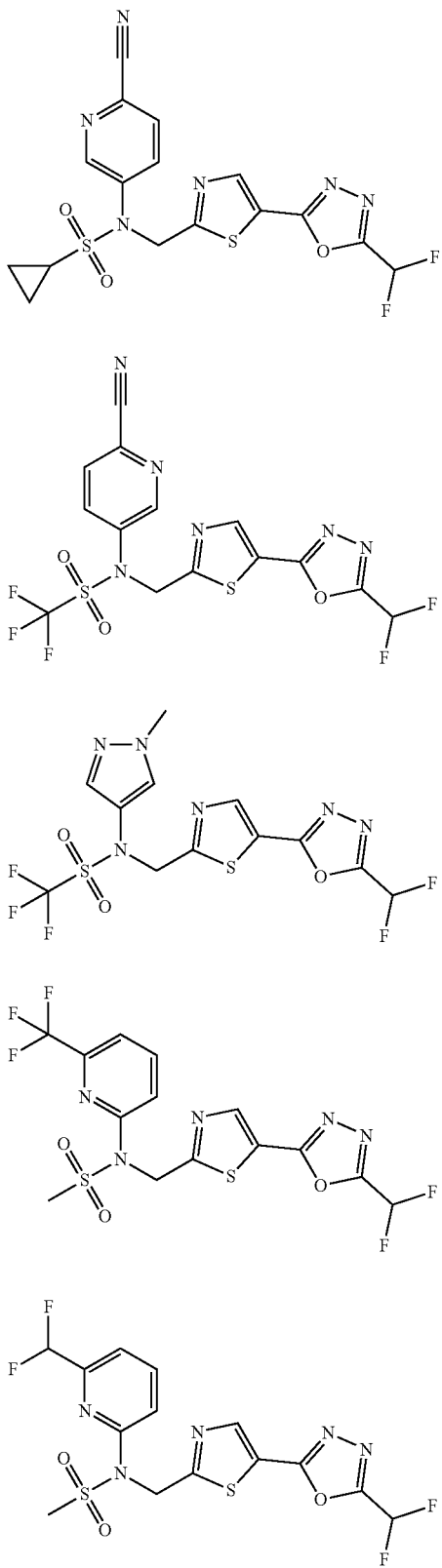
TABLE 1-continued
Compounds of Formula (I) of the Present Disclosure.
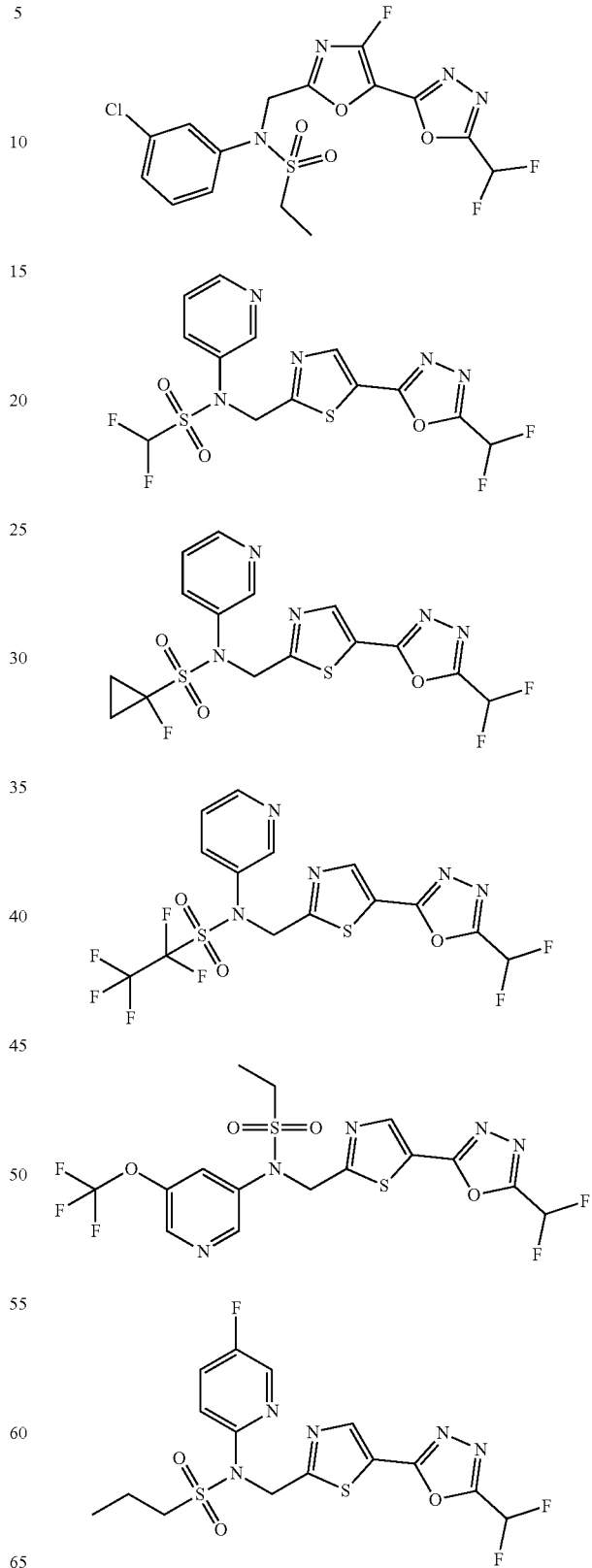

TABLE 1-continued
Compounds of Formula (I) of the Present Disclosure.
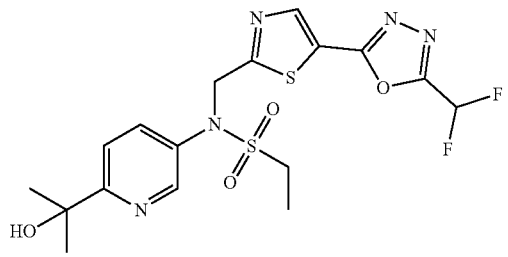 [SMILES: CCS(=O)(=O)N(Cc1ncc(-c2nnc(C(F)F)o2)s1)c1ccc(C(C)(C)O)nc1]
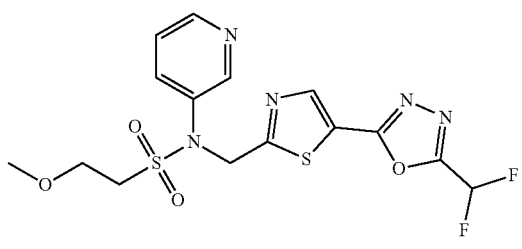 [SMILES: COCCS(=O)(=O)N(Cc1ncc(-c2nnc(C(F)F)o2)s1)c1cccnc1]
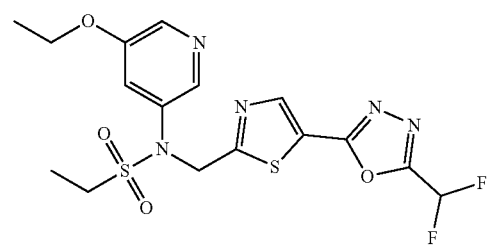
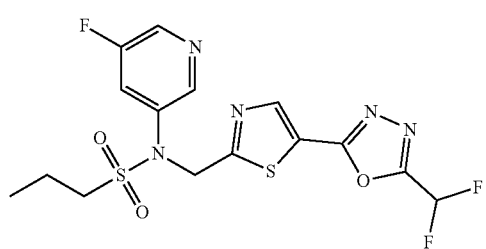 [SMILES: CCCS(=O)(=O)N(Cc1ncc(-c2nnc(C(F)F)o2)s1)c1cncc(F)c1]
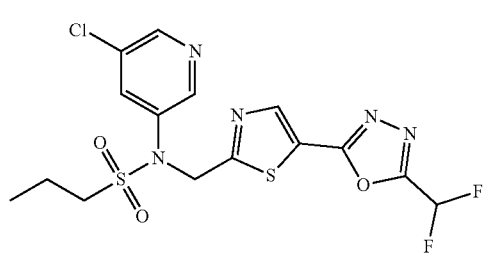
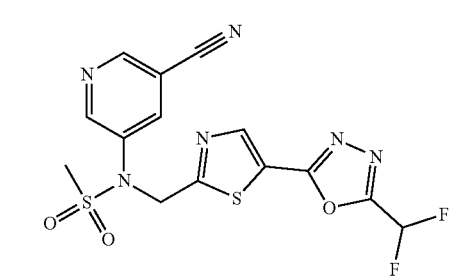 [SMILES: CS(=O)(=O)N(Cc1ncc(-c2nnc(C(F)F)o2)s1)c1cncc(C#N)c1]
TABLE 1-continued
Compounds of Formula (I) of the Present Disclosure.
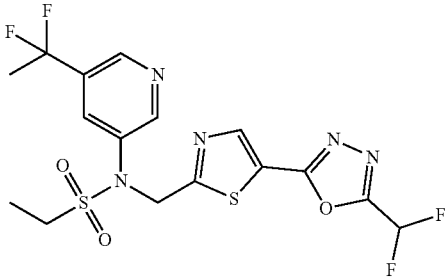 [SMILES: CCS(=O)(=O)N(Cc1ncc(-c2nnc(C(F)F)o2)s1)c1cncc(C(C)(F)F)c1]
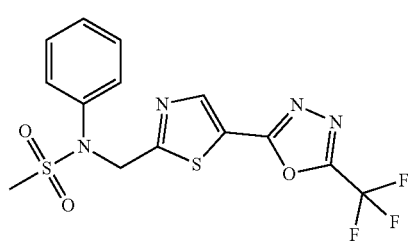 [SMILES: CS(=O)(=O)N(Cc1ncc(-c2nnc(C(F)(F)F)o2)s1)c1ccccc1]
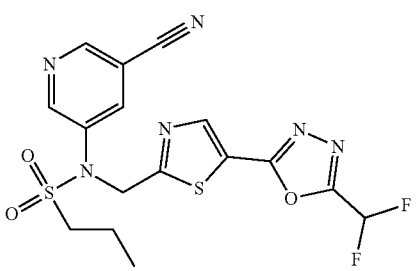 [SMILES: CCCS(=O)(=O)N(Cc1ncc(-c2nnc(C(F)F)o2)s1)c1cncc(C#N)c1]
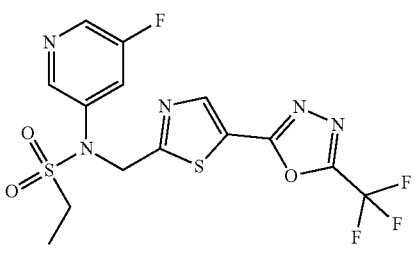 [SMILES: CCS(=O)(=O)N(Cc1ncc(-c2nnc(C(F)(F)F)o2)s1)c1cncc(F)c1]
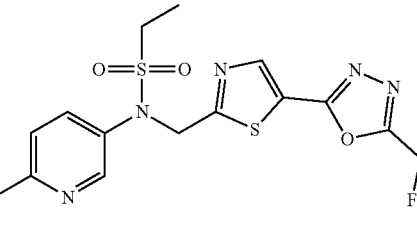
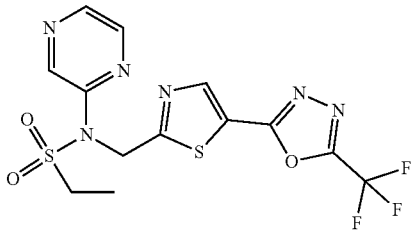 [SMILES: CCS(=O)(=O)N(Cc1ncc(-c2nnc(C(F)(F)F)o2)s1)c1cnccn1]

TABLE 1-continued
Compounds of Formula (I) of the Present Disclosure.
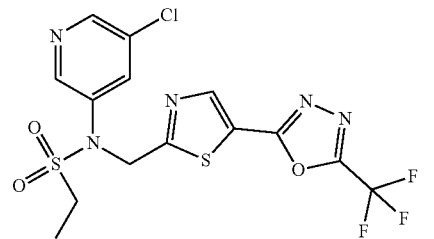
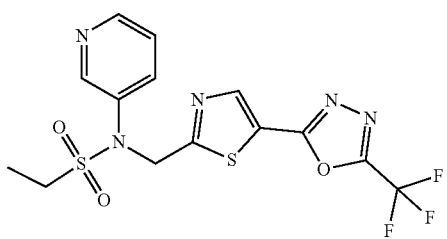 [SMILES: CCS(=O)(=O)N(Cc1ncc(-c2nnc(C(F)(F)F)o2)s1)c1cccnc1]
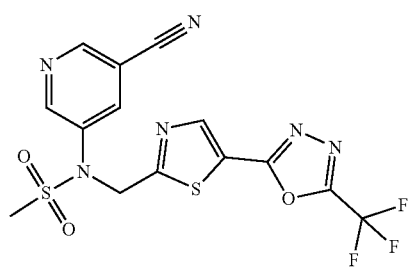
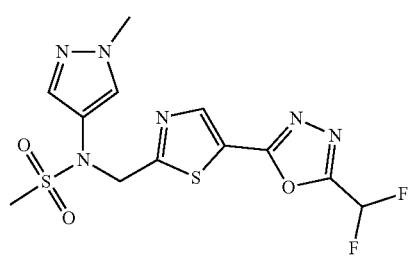 [SMILES: Cn1cc(N(Cc2ncc(-c3nnc(C(F)F)o3)s2)S(C)(=O)=O)cn1]
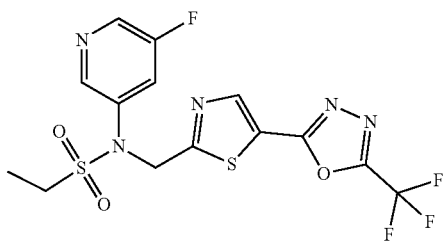 [SMILES: CCS(=O)(=O)N(Cc1ncc(-c2nnc(C(F)(F)F)o2)s1)c1cncc(F)c1]
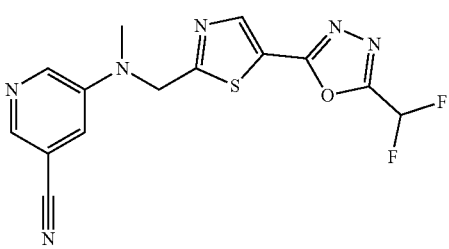 [SMILES: CN(Cc1ncc(-c2nnc(C(F)F)o2)s1)c1cncc(C#N)c1]
TABLE 1-continued
Compounds of Formula (I) of the Present Disclosure.
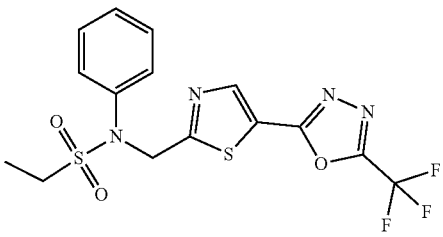 [SMILES: CCS(=O)(=O)N(Cc1ncc(-c2nnc(C(F)(F)F)o2)s1)c1ccccc1]
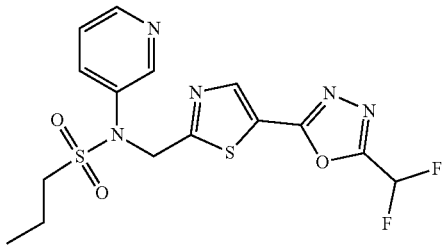 [SMILES: CCCS(=O)(=O)N(Cc1ncc(-c2nnc(C(F)F)o2)s1)c1cccnc1]
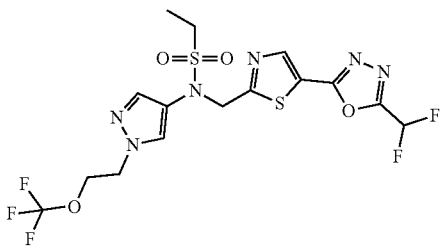 [SMILES: CCS(=O)(=O)N(Cc1ncc(-c2nnc(C(F)F)o2)s1)c1cnn(CCOC(F)(F)F)c1]
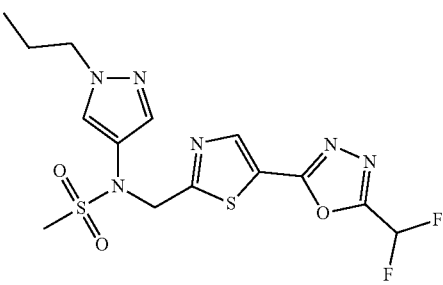 [SMILES: CCCn1cc(N(Cc2ncc(-c3nnc(C(F)F)o3)s2)S(C)(=O)=O)cn1]
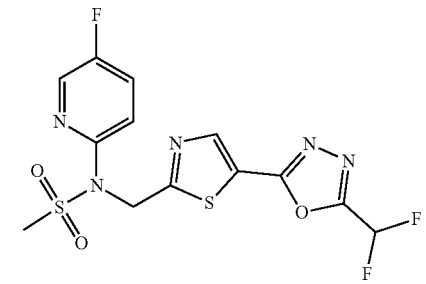 [SMILES: CS(=O)(=O)N(Cc1ncc(-c2nnc(C(F)F)o2)s1)c1ccc(F)cn1]
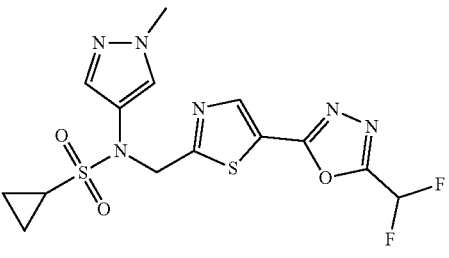 [SMILES: Cn1cc(N(Cc2ncc(-c3nnc(C(F)F)o3)s2)S(=O)(=O)C2CC2)cn1]

TABLE 1-continued

Compounds of Formula (I) of the Present Disclosure.

TABLE 1-continued
Compounds of Formula (I) of the Present Disclosure.
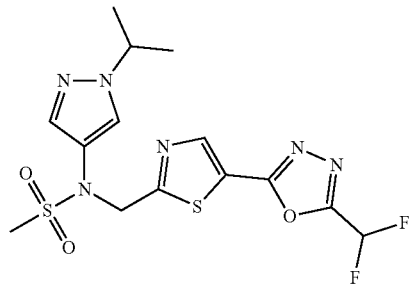 [SMILES: CC(C)n1cc(N(Cc2ncc(-c3nnc(C(F)F)o3)s2)S(C)(=O)=O)cn1]
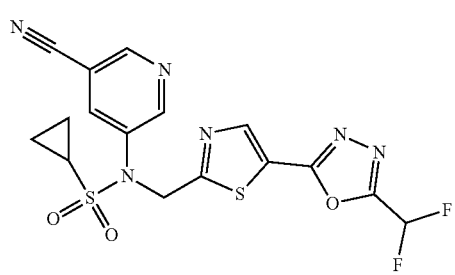 [SMILES: N#Cc1cncc(N(Cc2ncc(-c3nnc(C(F)F)o3)s2)S(=O)(=O)C2CC2)c1]
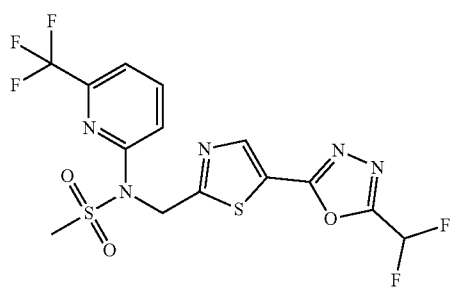 [SMILES: CS(=O)(=O)N(Cc1ncc(-c2nnc(C(F)F)o2)s1)c1cccc(C(F)(F)F)n1]
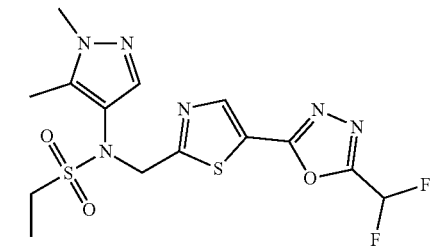 [SMILES: CCS(=O)(=O)N(Cc1ncc(-c2nnc(C(F)F)o2)s1)c1cnn(C)c1C]
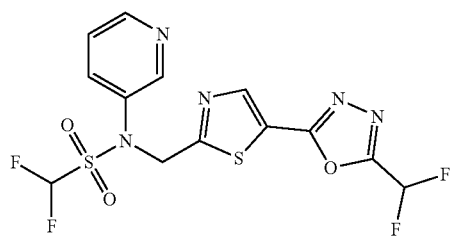
TABLE 1-continued
Compounds of Formula (I) of the Present Disclosure.
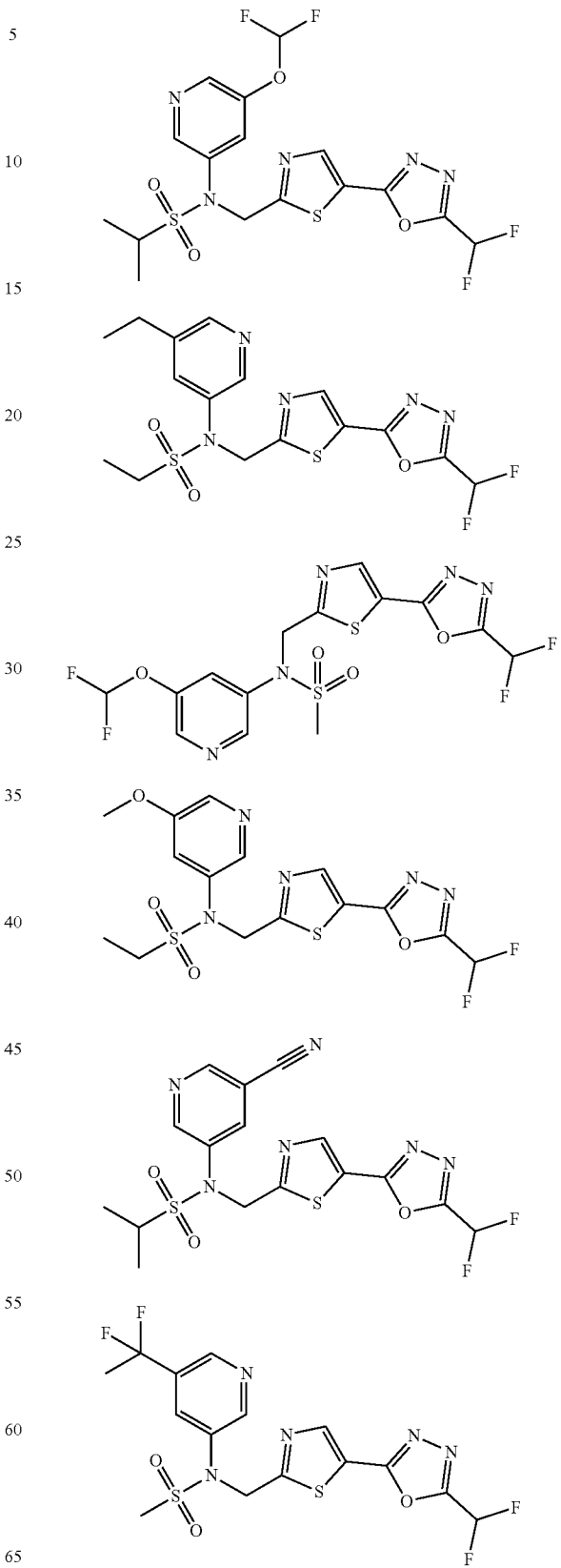

TABLE 1-continued
Compounds of Formula (I) of the Present Disclosure.
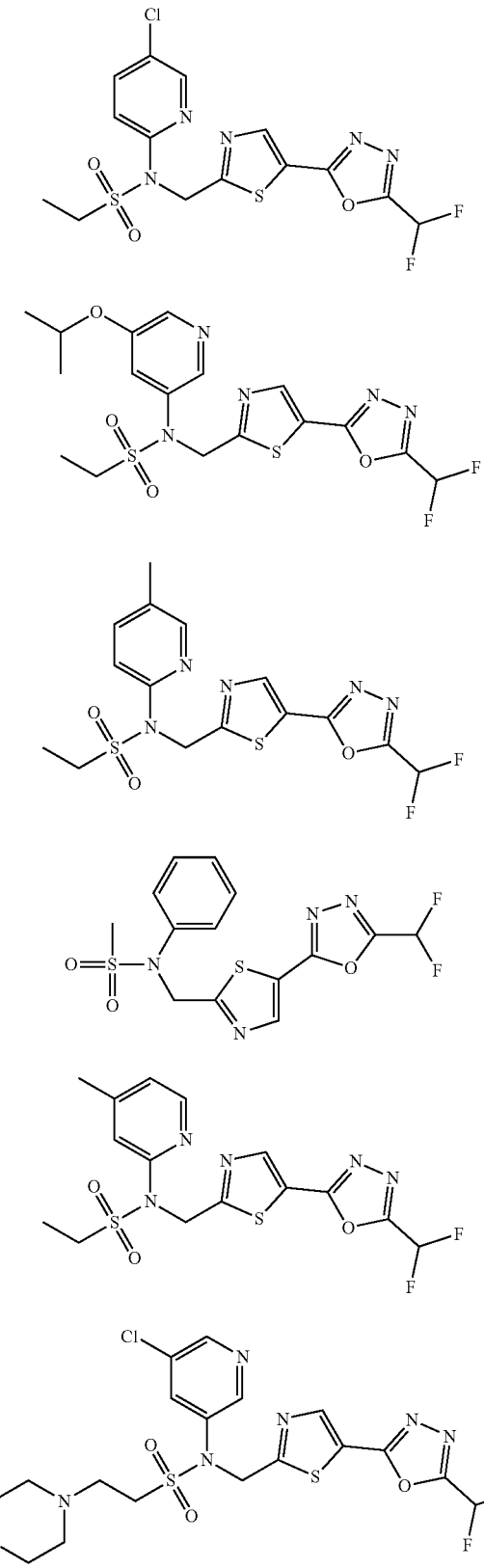
TABLE 1-continued
Compounds of Formula (I) of the Present Disclosure.
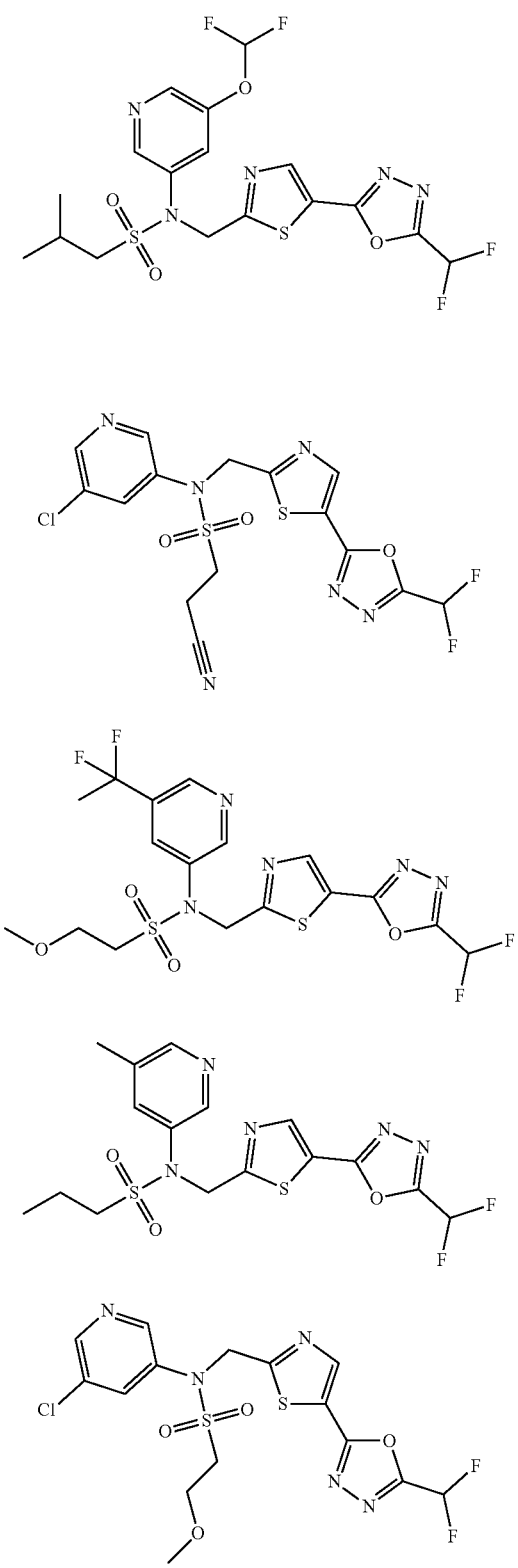

TABLE 1-continued
Compounds of Formula (I) of the Present Disclosure.
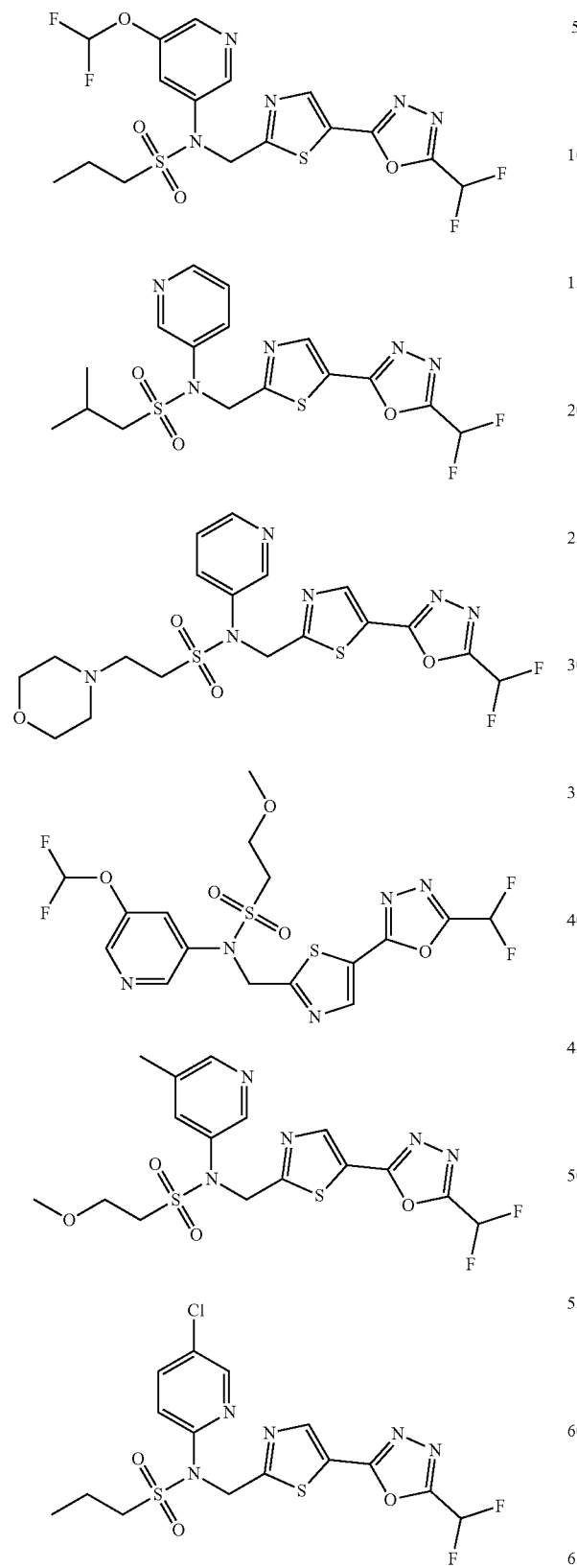
TABLE 1-continued
Compounds of Formula (I) of the Present Disclosure.
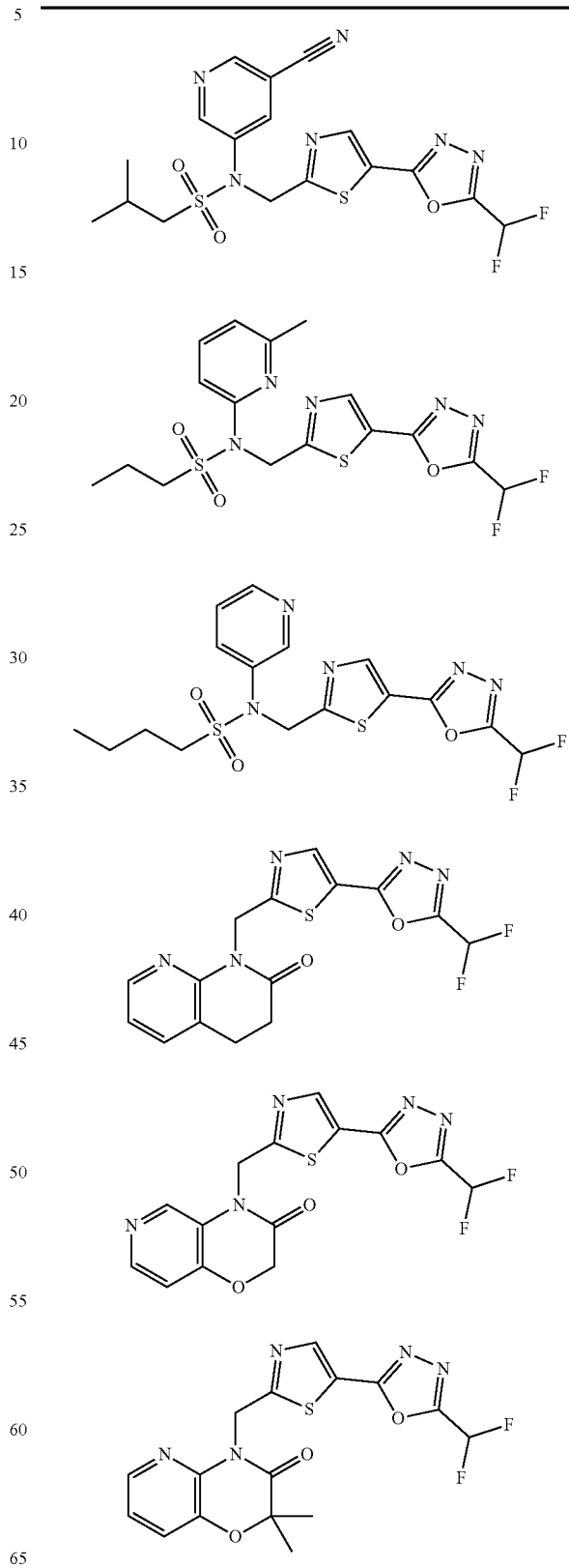

TABLE 1-continued
Compounds of Formula (I) of the Present Disclosure.
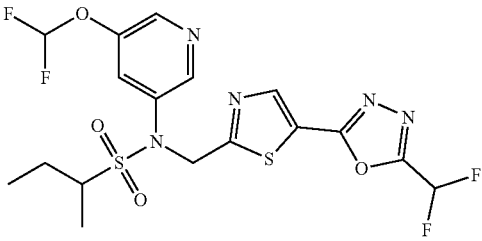 [SMILES: CCC(C)S(=O)(=O)N(Cc1ncc(-c2nnc(C(F)F)o2)s1)c1cncc(OC(F)F)c1]
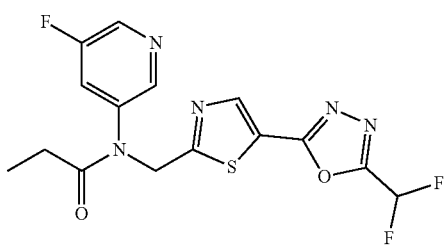
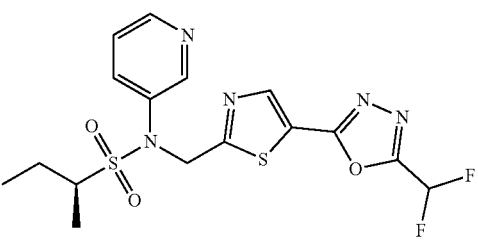 [SMILES: CC[C@H](C)S(=O)(=O)N(Cc1ncc(-c2nnc(C(F)F)o2)s1)c1cccnc1]
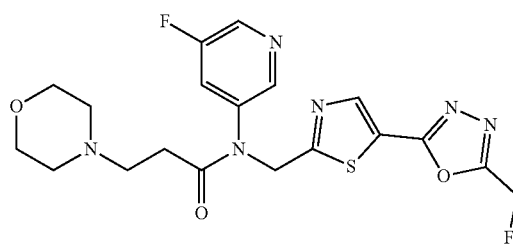
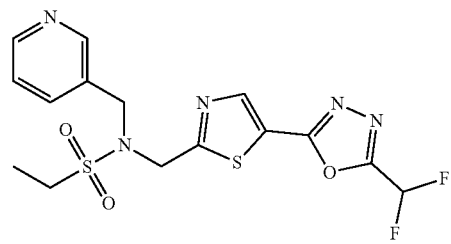 [SMILES: CCS(=O)(=O)N(Cc1cccnc1)Cc1ncc(-c2nnc(C(F)F)o2)s1]
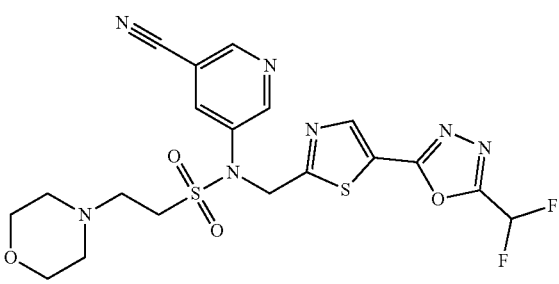 [SMILES: N#Cc1cncc(N(Cc2ncc(-c3nnc(C(F)F)o3)s2)S(=O)(=O)CCN2CCOCC2)c1]
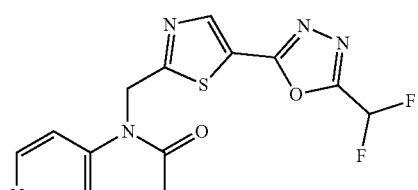
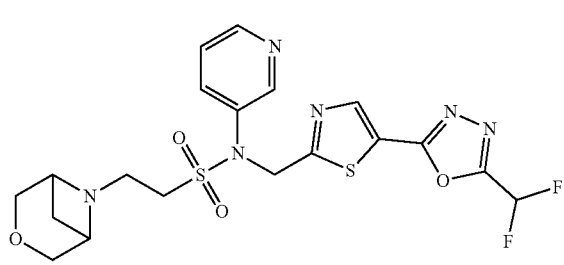 [SMILES: O=S(=O)(CCN1C2COCC1C2)N(Cc1ncc(-c2nnc(C(F)F)o2)s1)c1cccnc1]
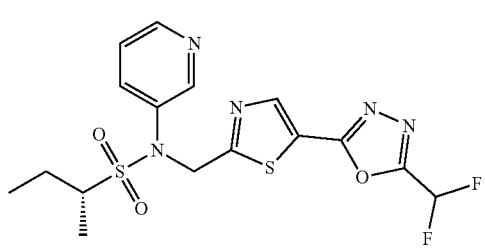
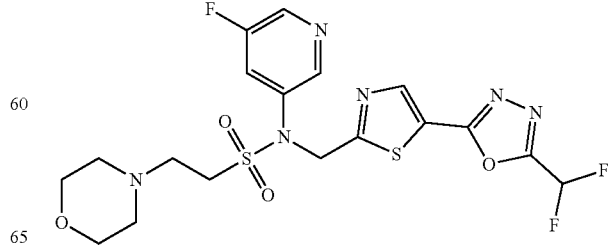

TABLE 1-continued
Compounds of Formula (I) of the Present Disclosure.
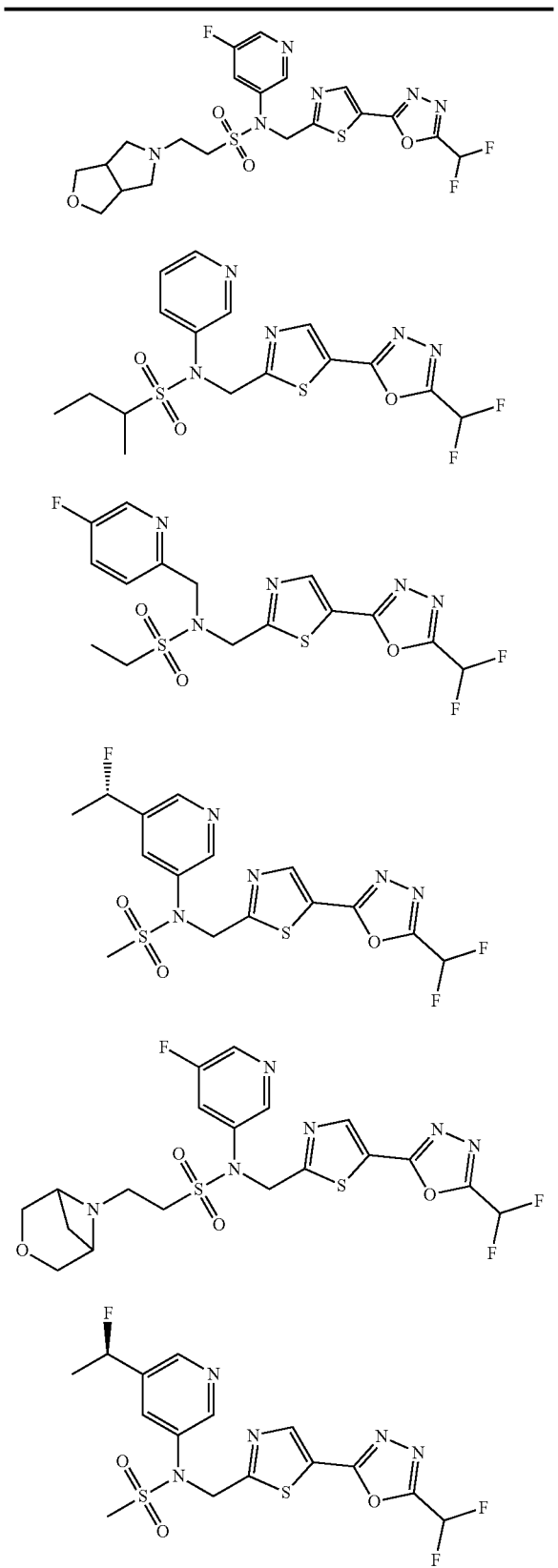
TABLE 1-continued
Compounds of Formula (I) of the Present Disclosure.
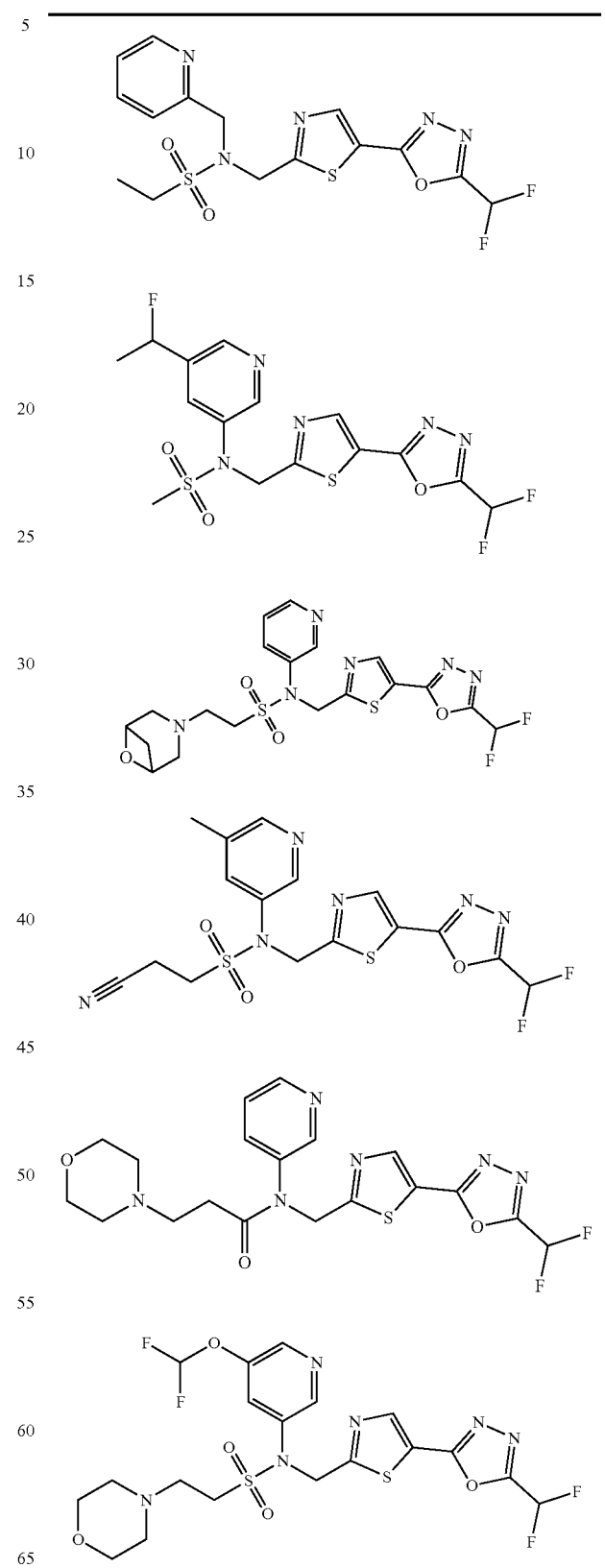

US 11,578,066 B1
TABLE 1-continued
Compounds of Formula (I) of the Present Disclosure.
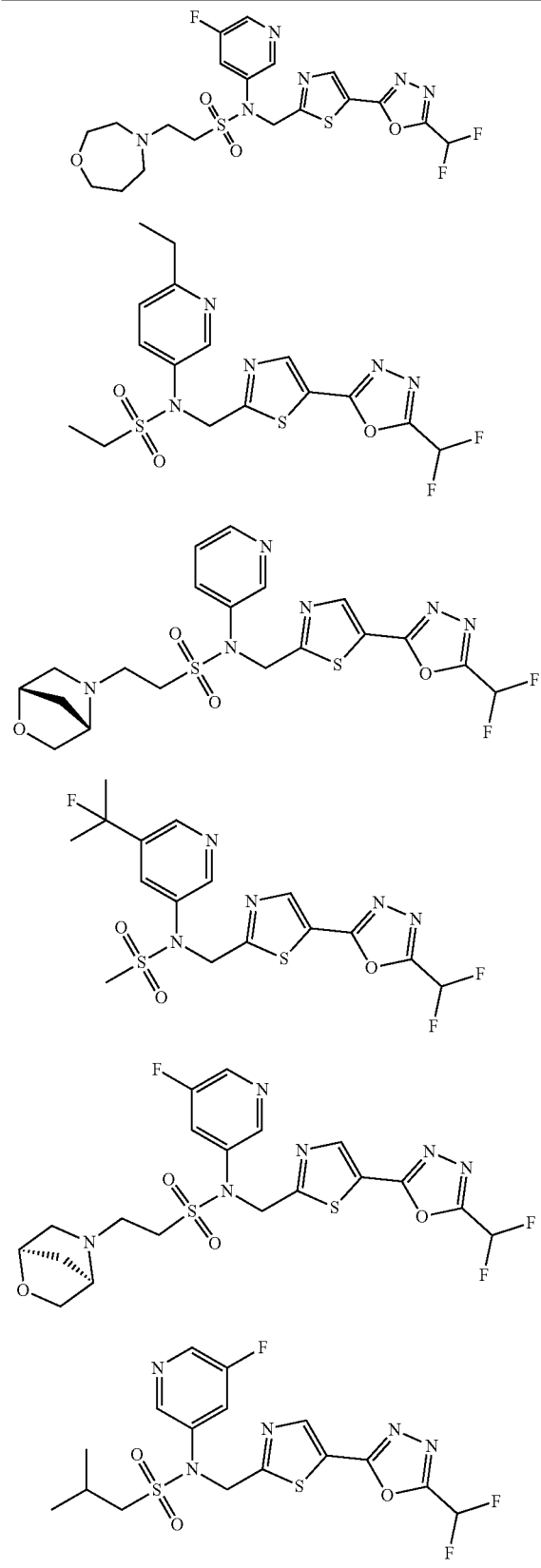
TABLE 1-continued
Compounds of Formula (I) of the Present Disclosure.
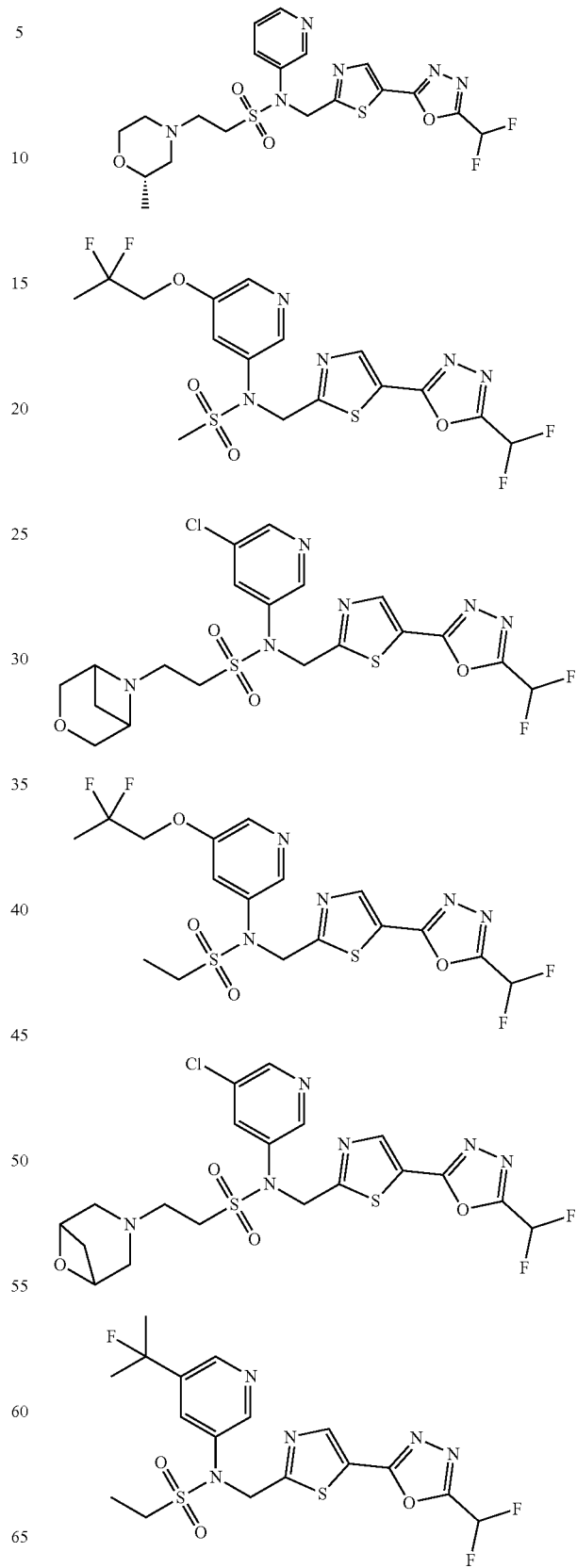

TABLE 1-continued
Compounds of Formula (I) of the Present Disclosure.
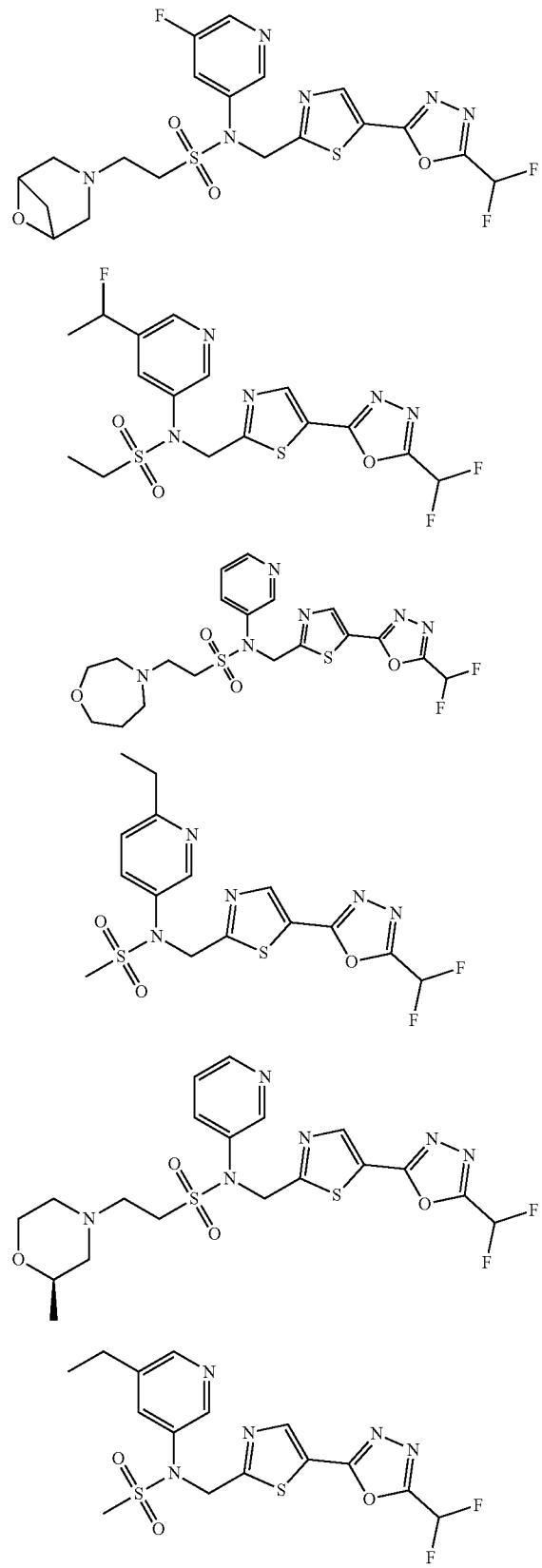
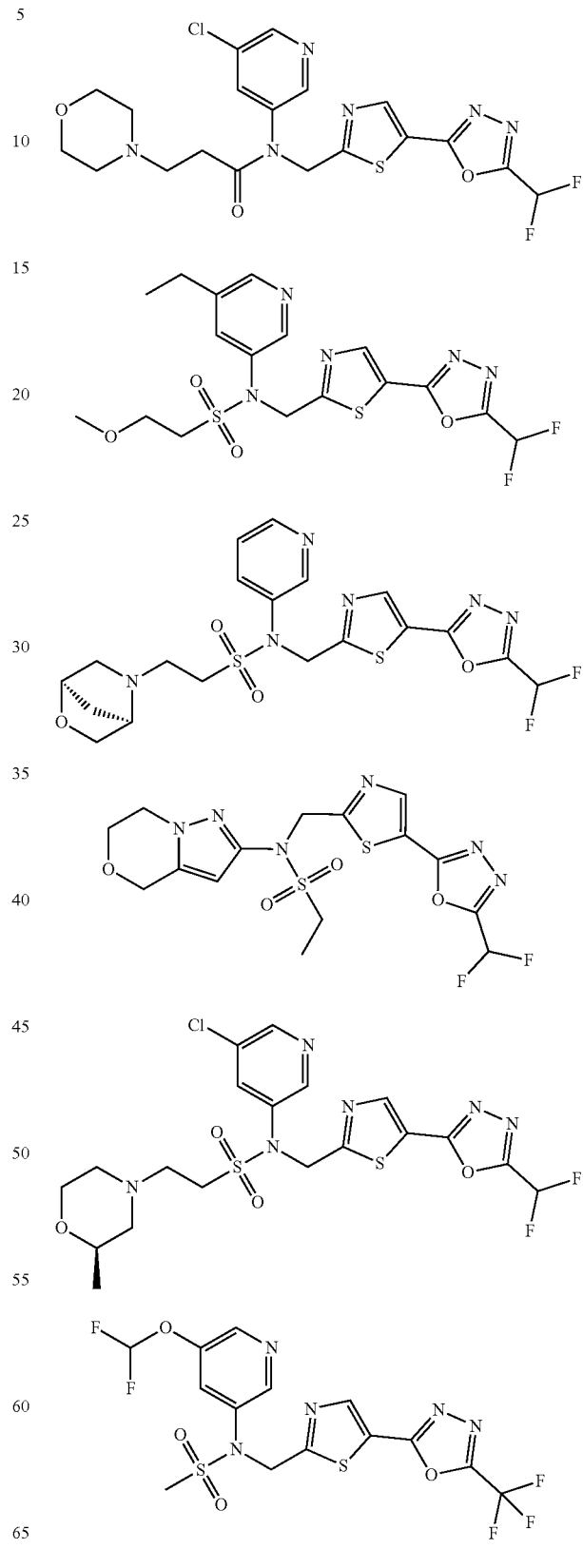

TABLE 1-continued
Compounds of Formula (I) of the Present Disclosure.
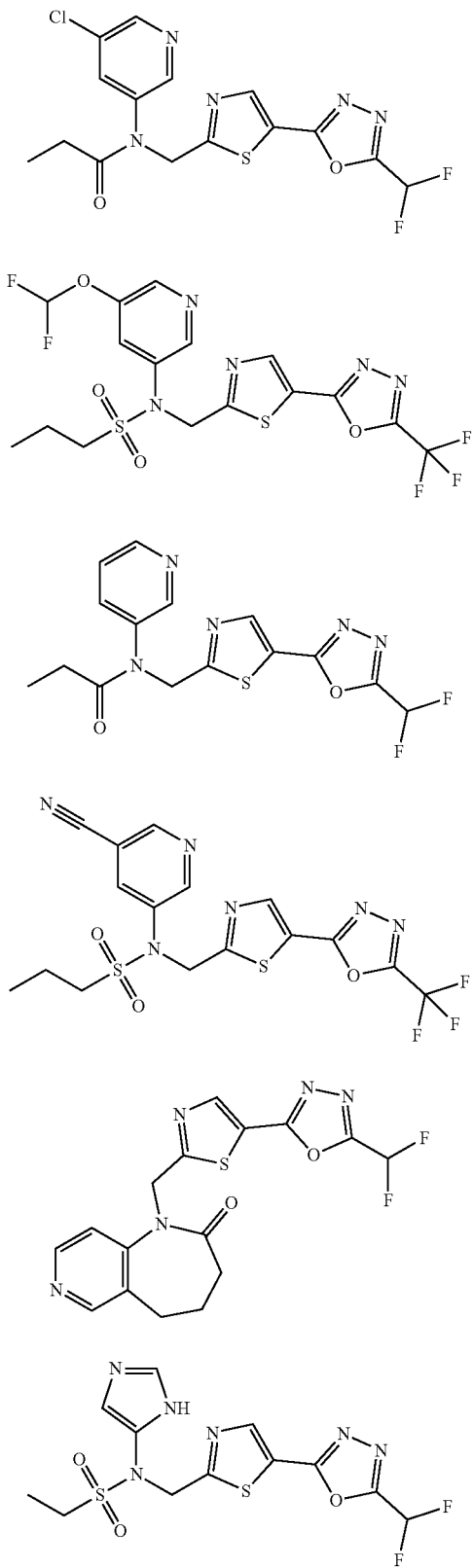
TABLE 1-continued
Compounds of Formula (I) of the Present Disclosure.
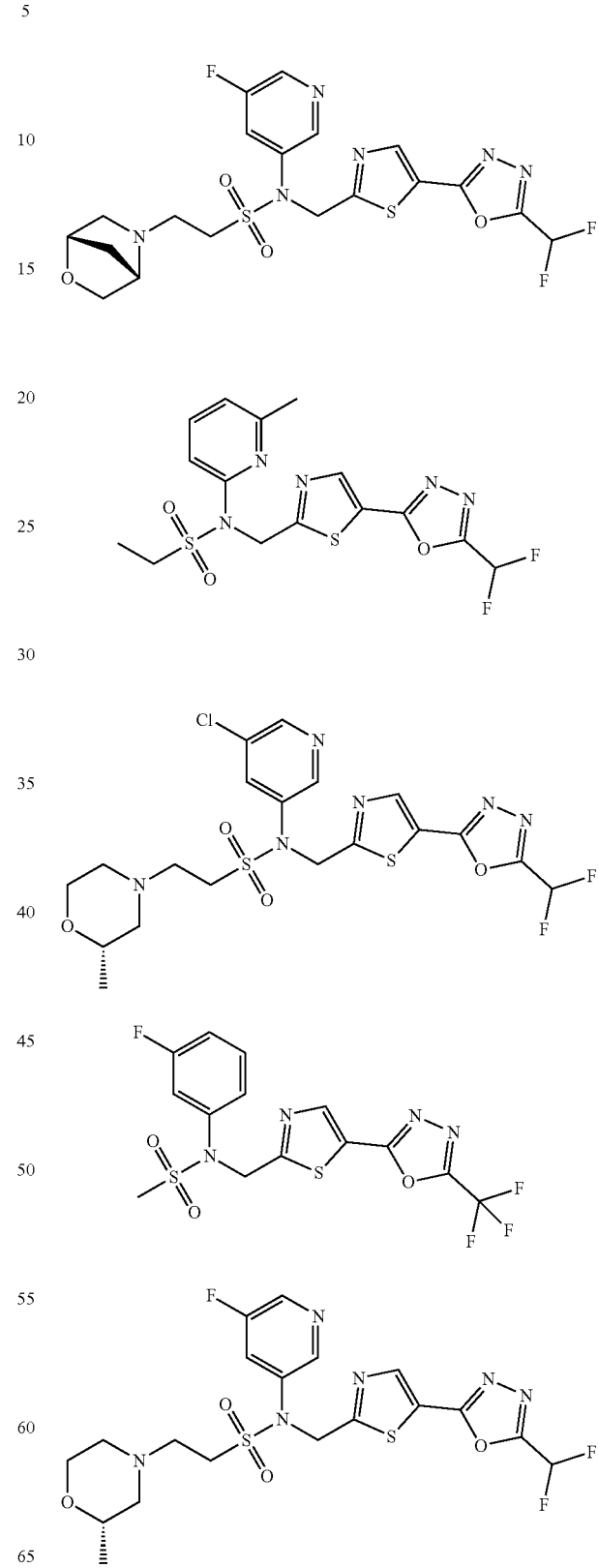

TABLE 1-continued
Compounds of Formula (I) of the Present Disclosure.
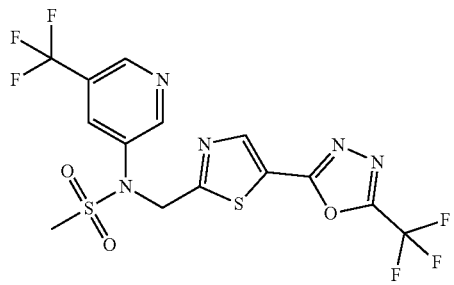 [SMILES: CS(=O)(=O)N(Cc1ncc(-c2nnc(C(F)(F)F)o2)s1)c1cncc(C(F)(F)F)c1]
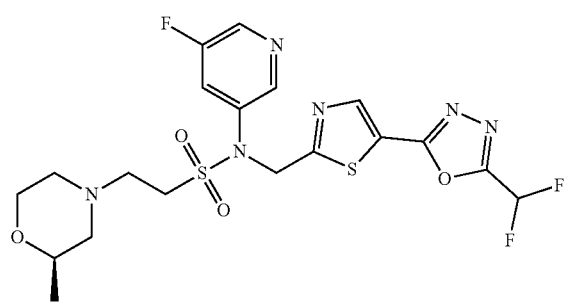 [SMILES: C[C@@H]1CN(CCS(=O)(=O)N(Cc2ncc(-c3nnc(C(F)F)o3)s2)c2cncc(F)c2)CCO1]
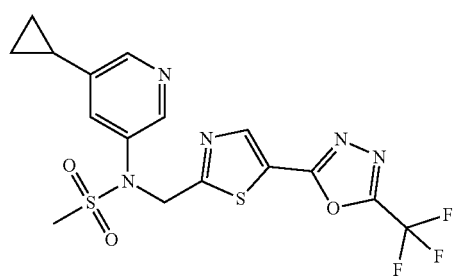 [SMILES: CS(=O)(=O)N(Cc1ncc(-c2nnc(C(F)(F)F)o2)s1)c1cncc(C2CC2)c1]
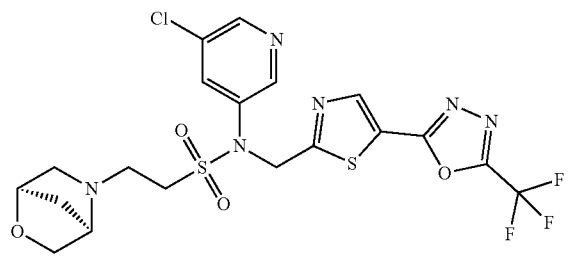 [SMILES: O=S(=O)(CCN1C[C@H]2C[C@@H]1CO2)N(Cc1ncc(-c2nnc(C(F)(F)F)o2)s1)c1cncc(Cl)c1]
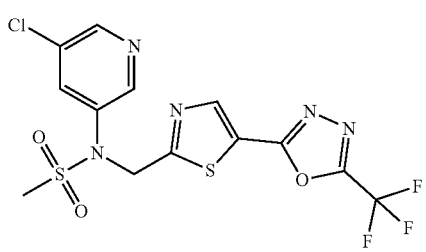
TABLE 1-continued
Compounds of Formula (I) of the Present Disclosure.
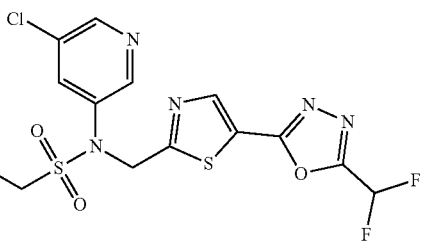
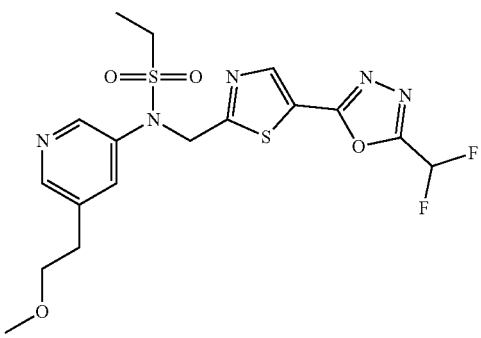 [SMILES: CCS(=O)(=O)N(Cc1ncc(-c2nnc(C(F)F)o2)s1)c1cncc(CCOC)c1]
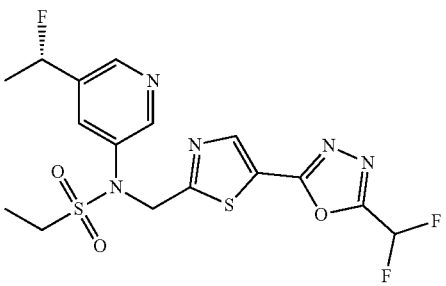
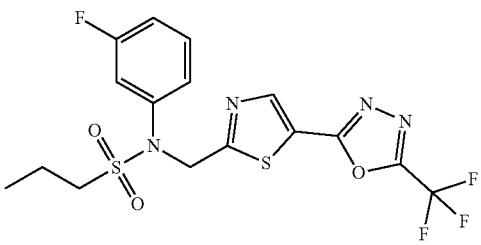 [SMILES: CCCS(=O)(=O)N(Cc1ncc(-c2nnc(C(F)(F)F)o2)s1)c1cccc(F)c1]
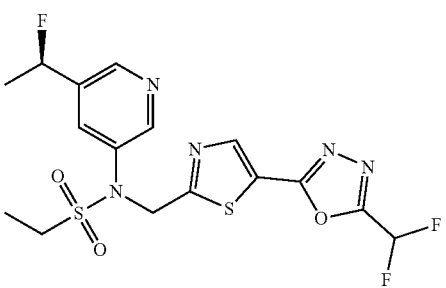 [SMILES: CCS(=O)(=O)N(Cc1ncc(-c2nnc(C(F)F)o2)s1)c1cncc([C@@H](C)F)c1]

TABLE 1-continued
Compounds of Formula (I) of the Present Disclosure.
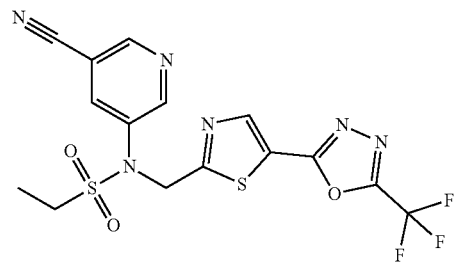 [SMILES: CCS(=O)(=O)N(Cc1ncc(-c2nnc(C(F)(F)F)o2)s1)c1cncc(C#N)c1]
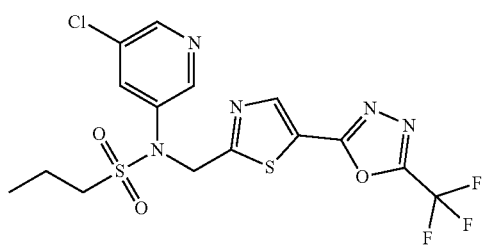 [SMILES: CCCS(=O)(=O)N(Cc1ncc(-c2nnc(C(F)(F)F)o2)s1)c1cncc(Cl)c1]
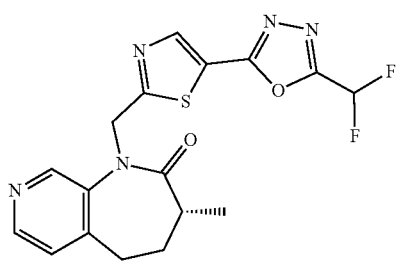 [SMILES: C[C@@H]1CCc2ccncc2N(Cc2ncc(-c3nnc(C(F)F)o3)s2)C1=O]
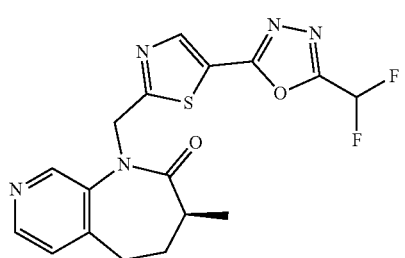
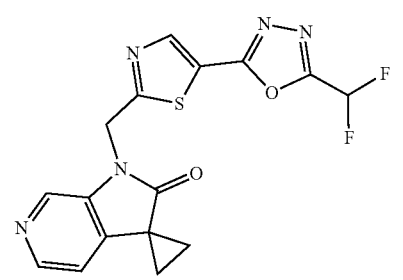 [SMILES: O=C1N(Cc2ncc(-c3nnc(C(F)F)o3)s2)c2cnccc2C12CC2]
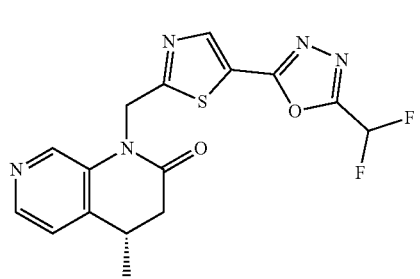 [SMILES: C[C@H]1CC(=O)N(Cc2ncc(-c3nnc(C(F)F)o3)s2)c2cnccc21]
TABLE 1-continued
Compounds of Formula (I) of the Present Disclosure.
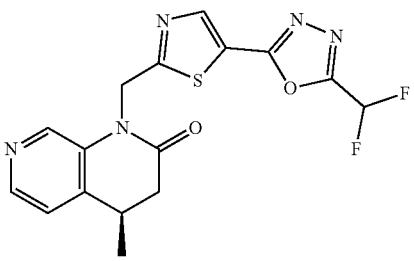 [SMILES: C[C@@H]1CC(=O)N(Cc2ncc(-c3nnc(C(F)F)o3)s2)c2cnccc21]
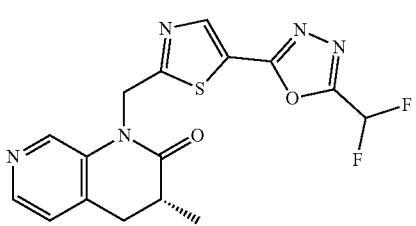 [SMILES: C[C@@H]1Cc2ccncc2N(Cc2ncc(-c3nnc(C(F)F)o3)s2)C1=O]
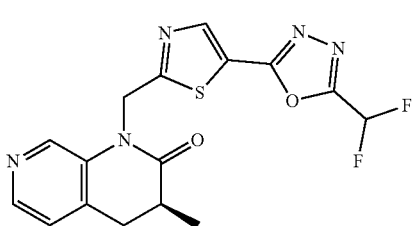
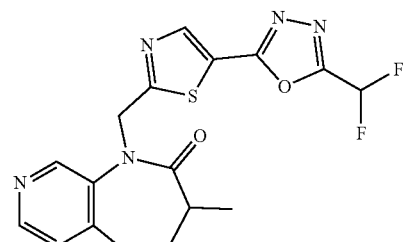
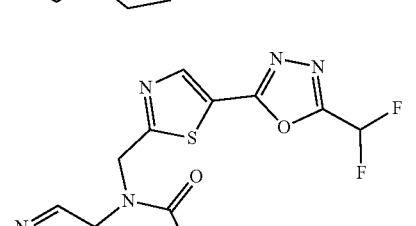
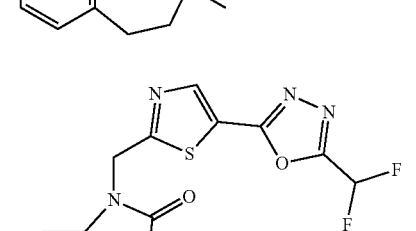

TABLE 1-continued
Compounds of Formula (I) of the Present Disclosure.
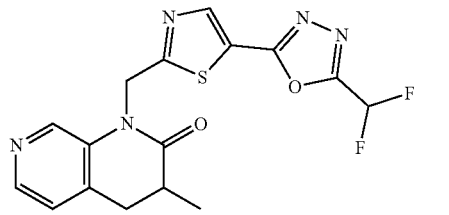 [SMILES: CC1Cc2ccncc2N(Cc2ncc(-c3nnc(C(F)F)o3)s2)C1=O]
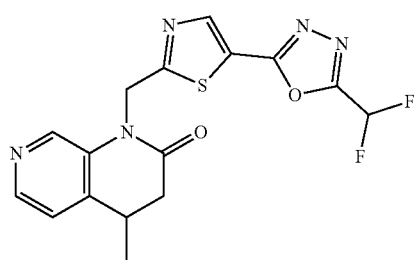 [SMILES: CC1CC(=O)N(Cc2ncc(-c3nnc(C(F)F)o3)s2)c2cnccc21]
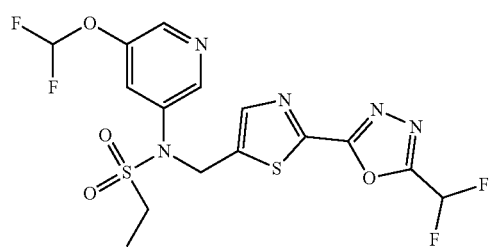 [SMILES: CCS(=O)(=O)N(Cc1cnc(-c2nnc(C(F)F)o2)s1)c1cncc(OC(F)F)c1]
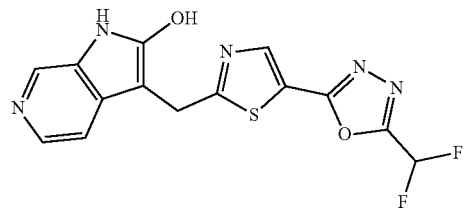 [SMILES: Oc1[nH]c2cnccc2c1Cc1ncc(-c2nnc(C(F)F)o2)s1]
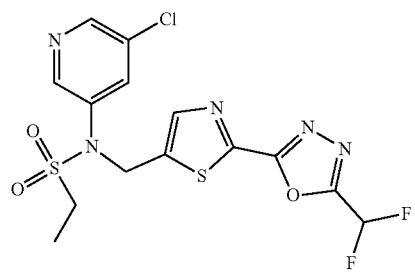
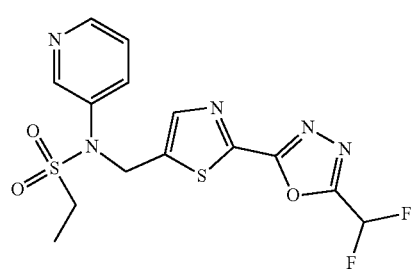 [SMILES: CCS(=O)(=O)N(Cc1cnc(-c2nnc(C(F)F)o2)s1)c1cccnc1]
TABLE 1-continued
Compounds of Formula (I) of the Present Disclosure.
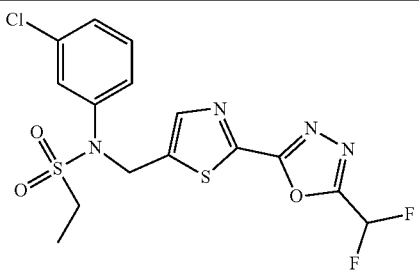
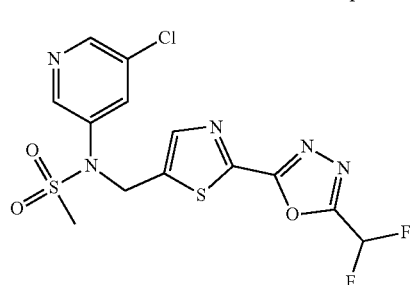
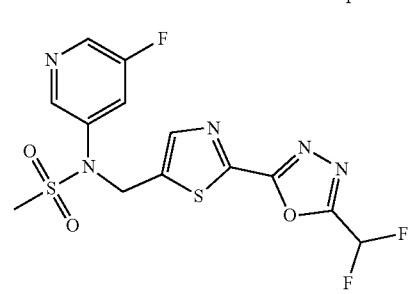
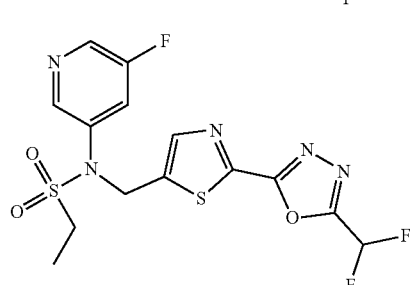
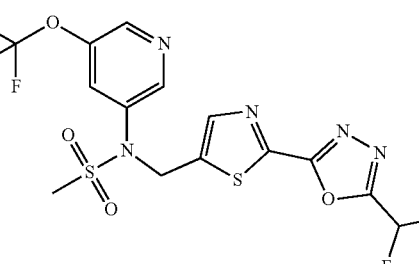
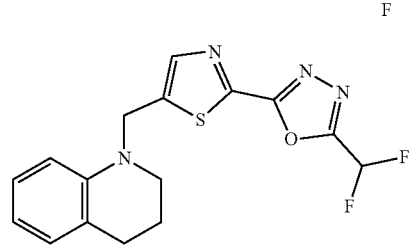

TABLE 1-continued

Compounds of Formula (I) of the Present Disclosure.

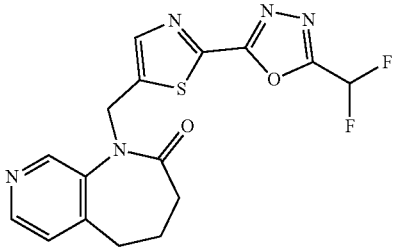 [SMILES: O=C1CCCc2ccncc2N1Cc1cnc(-c2nnc(C(F)F)o2)s1]

In some embodiments, the present disclosure provides a compound of Formula (Ic) or a pharmaceutically acceptable salt thereof:

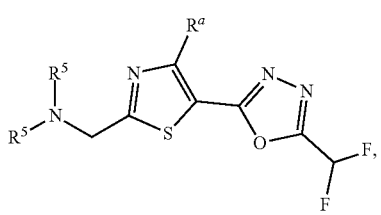
(Ic)

wherein:
$R^a$ is H, Me, or F; and
$R^4$ and $R^5$ are as defined above in Formula (I).

In some embodiments of Formula (Ic), $R^a$ is H. In some embodiments, $R^a$ is F. In some embodiments, $R^a$ is Me.

In some embodiments of Formula (Ic), $R^4$ is selected from the group consisting of alkylenealkoxy, alkyleneheterocyclyl, —S(O)$_2$alkyl, —S(O)$_2$cycloalkyl, —S(O)$_2$alkylenecycloalkyl, —S(O)$_2$alkyleneheterocyclyl, —S(O)$_2$N(H)alkyleneheterocyclyl, —C(O)alkyl, —C(O)cycloalkyl, —C(O)alkylenecycloalkyl, —C(O)alkyleneheterocyclyl, and —C(O)N(H)alkyleneheterocyclyl. In some embodiments, $R^4$ is selected from the group consisting of alkyleneheterocyclyl, —S(O)$_2$alkyl, —S(O)$_2$cycloalkyl, —S(O)$_2$alkyleneheterocyclyl, —C(O)alkyleneheterocyclyl, and —C(O)N(H)alkyleneheterocyclyl. In some embodiments, $R^4$ is selected from the group consisting of —S(O)$_2$alkyl, —S(O)$_2$cycloalkyl, and —S(O)$_2$alkyleneheterocyclyl. In some embodiments, $R^4$ is —S(O)$_2$alkyl. In some embodiments, $R^4$ is —S(O)$_2$cycloalkyl. In some embodiments, $R^4$ is —S(O)$_2$N(H)alkyleneheterocyclyl. In some embodiments, the alkylene is a $C_{1-5}$ alkylene and the heterocyclyl is an optionally substituted 4- to 10-membered heterocyclyl having 1, 2, or 3 heteroatoms selected from the group consisting of N, O, and S. In some embodiments, the alkylene is a $C_{1-5}$ alkylene and the heterocyclyl is an optionally substituted 4- to 7-membered heterocyclyl having 1, 2, or 3 heteroatoms selected from the group consisting of N, O, and S. In some embodiments, the alkylene is a $C_{2-4}$ alkylene and the heterocyclyl is an optionally substituted 6-membered heterocyclyl having 1, 2, or 3 heteroatoms selected from the group consisting of N, O, and S. In some embodiments, the heterocyclyl is selected from the group consisting of piperidine, morpholine, thiomorpholine, thiomorpholine 1-oxide, thiomorpholine 1,1-dioxide, and piperizine, each of which is optionally substituted. In some embodiments, the optional substituent is selected from the group consisting of alkyl, haloalkyl, alkoxy, acyl, sulfonyl, heteroaryl, and heterocyclyl.

In some embodiments of Formula (Ic), $R^5$ is selected from the group consisting of:

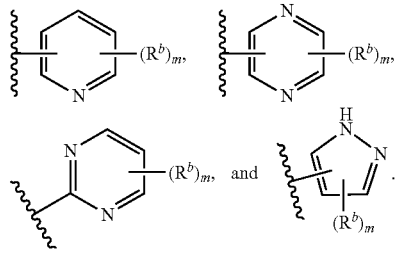

In some embodiments, $R^5$ is

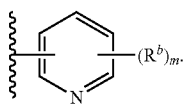

In some embodiments, $R^5$ is

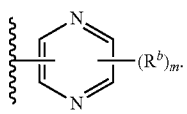

In some embodiments, $R^5$ is

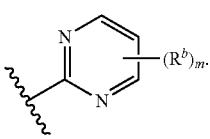

In some embodiments, $R^5$ is

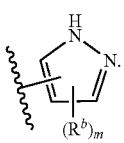

In some embodiments, $R^b$ is selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, $R^b$ is selected from the group consisting of halo, alkyl, haloalkyl, alkoxy, haloalkoxy, acyl, sulfonyl, cycloalkyl, heteroaryl, and heterocyclyl. In some embodiments, the haloalkyl is selected from $CF_3$, $CF_2CH_3$, $CHF_2$, or $CH_2F$. In some embodiments, the alkyl is a -$C_{1-5}$alkyl. In some embodiments, -$C_{1-5}$alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a $C_{3-6}$cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from $OCF_3$, $OCHF_2$, or $OCH_2F$. In some embodiments, the Oalkyl is O-methyl, O-ethyl, O-propyl, O-i-propyl, O-butyl, or O-t-butyl. In some embodiments, $R^b$ is selected from the group consisting of F, Cl, —$CH_3$, —$CH_2CH_3$, —$CF_3$, —$CHF_2$, —$CF_2CH_3$, —CN, —$OCH_3$, —$OCH_2CH_3$, —$OCH(CH_3)_2$, —$OCHF_2$, —$OCH_2CF_2H$, and cyclopropyl. In some embodiments, m is 0, 1, or 2. In some embodiments, m is 0 or 1. In some embodiments, m is 0. In some embodiments, m is 1. In some embodiments, m is 2.

In some embodiments, $R^1$ and $R^5$ together with the atom to which they are attached form a cycloalkyl or heterocyclyl.

In some embodiments, the present disclosure provides a compound of Formula (Id) or a pharmaceutically acceptable salt thereof:

(Id)

wherein:
U is $NR^d$, O, S, S(O), $S(O)_2$, $CH_2$, CHF, or $CF_2$;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, —$S(O_2)R^e$, cycloalkyl, heteroaryl, or heterocyclyl;
$R^e$ is each independently F, alkyl, haloalkyl, alkoxy, haloalkoxy, —$C(O)R^e$, —$C(O)OR^e$, —$C(O)N(R^e)(R^{e'})$, —$S(O_2)R^e$, heteroaryl, or heterocyclyl, and/or two $R^e$ groups taken together with the carbon atoms to which they are attached form a bridged or fused $C_{3-7}$ cycloalkyl, a bridged or fused 4- to 7-membered heterocyclyl; or a 5- or 6-membered heteroaryl, each of which is optionally substituted;
$R^d$ is H, alkyl, acyl, sulfonyl, cycloalkyl, aryl, or heteroaryl;
$R^e$ and $R^{e'}$ is each independently H, alkyl, cycloalkyl, heterocyclyl, aryl, heteroaryl, —$CH_2$cycloalkyl, —$CH_2$heterocyclyl, —$CH_2$aryl, or —$CH_2$heteroaryl;
m is 0, 1, 2, or 3;
p is 0, 1, 2, or 3;
q is 0, 1, or 2; and
r is 1, 2, 3, or 4.

In some embodiments, the present disclosure provides a compound of Formula (Ie) or a pharmaceutically acceptable salt thereof:

(Ie)

wherein:
U is $NR^d$, O, S, S(O), $S(O)_2$, $CH_2$, CHF, or $CF_2$;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, sulfonyl, cycloalkyl, heteroaryl, or heterocyclyl;
$R^c$ is each independently F, alkyl, haloalkyl, alkoxy, haloalkoxy, —$C(O)R^e$, —$C(O)OR^e$, —$C(O)N(R^e)(R^{e'})$, —$S(O_2)R^e$, heteroaryl, or heterocyclyl, and/or two $R^e$ groups taken together with the carbon atoms to which they are attached form a bridged or fused $C_{3-7}$ cycloalkyl, a bridged or fused 4- to 6-membered heterocyclyl; or a 5- or 6-membered heteroaryl, each of which is optionally substituted;
$R^d$ is H, alkyl, acyl, sulfonyl, cycloalkyl, aryl, or heteroaryl;
$R^e$ and $R^{e'}$ is each independently H, alkyl, cycloalkyl, heterocyclyl, aryl, heteroaryl, —$CH_2$cycloalkyl, —$CH_2$heterocyclyl, —$CH_2$aryl, or —$CH_2$heteroaryl;
m is 0, 1, 2, or 3;
p is 0, 1, 2, or 3;
q is 0, 1, or 2; and
r is 1, 2, 3, or 4.

In some embodiments, the present disclosure provides a compound of Formula (If) or a pharmaceutically acceptable salt thereof:

(If)

wherein:
U is $NR^d$, O, S, S(O), $S(O)_2$, $CH_2$, CHF, or $CF_2$;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, sulfonyl, cycloalkyl, heteroaryl, or heterocyclyl;
$R^c$ is each independently F, alkyl, haloalkyl, alkoxy, haloalkoxy, —$C(O)R^e$, —$C(O)OR^e$, —$C(O)N(R^e)(R^{e'})$, —$S(O_2)R^e$, heteroaryl, or heterocyclyl, and/or two $R^e$ groups taken together with the carbon atoms to which they are attached form a bridged or fused $C_{3-7}$ cycloalkyl, a bridged or fused 4- to 7-membered heterocyclyl; or a 5- or 6-membered heteroaryl, each of which is optionally substituted;

$R^d$ is H, alkyl, acyl, sulfonyl, cycloalkyl, aryl, or heteroaryl;

$R^e$ and $R^{e'}$ is each independently H, alkyl, cycloalkyl, heterocyclyl, aryl, heteroaryl, —CH$_2$cycloalkyl, —CH$_2$heterocyclyl, —CH$_2$aryl, or —CH$_2$heteroaryl;

m is 0, 1, 2, or 3;

p is 0, 1, 2, or 3;

q is 0, 1, or 2; and r is 1, 2, 3, or 4.

In some embodiments, the present disclosure provides a compound of Formula (Ig) or a pharmaceutically acceptable salt thereof:

(Ig)

wherein:

U is NR$^d$, O, S, S(O), S(O)$_2$, CH$_2$, CHF, or CF$_2$;

$R^a$ is H, Me, or F;

$R^b$ is each independently halo, alkyl, haloalkyl, alkoxy, haloalkoxy, —C(O)R$^e$, —C(O)OR$^e$, —C(O)N(R$^e$)(R$^{e'}$), sulfonyl, cycloalkyl, heteroaryl, or heterocyclyl;

$R^c$ is each independently F, alkyl, haloalkyl, alkoxy, haloalkoxy, —C(O)R$^e$, —C(O)OR$^e$, —C(O)N(R$^e$)(R$^{e'}$), —S(O$_2$)R$^e$, heteroaryl, or heterocyclyl, and/or two R$^c$ groups taken together with the carbon atoms to which they are attached form a bridged or fused C$_{3-7}$ cycloalkyl, a bridged or fused 4- to 7-membered heterocyclyl; or a 5- or 6-membered heteroaryl, each of which is optionally substituted;

$R^d$ is H, alkyl, acyl, sulfonyl, cycloalkyl, aryl, or heteroaryl;

$R^e$ and $R^{e'}$ is each independently H, alkyl, cycloalkyl, heterocyclyl, aryl, heteroaryl, —CH$_2$cycloalkyl, —CH$_2$heterocyclyl, —CH$_2$aryl, or —CH$_2$heteroaryl;

m is 0, 1, 2, or 3;

p is 0, 1, 2, or 3;

q is 0, 1, or 2; and r is 1, 2, 3, or 4.

In some embodiments, the present disclosure provides a compound of Formula (Id-1), (Ie-1), (If-1), or (Ig-1) or a pharmaceutically acceptable salt or stereoisomer thereof:

(Id-1)

(Ie-1)

(If-1)

(Ig-1)

wherein:

U, $R^a$, $R^b$, m, and r are as defined above in Formulas (Id), (Ie), (If), and (Ig); and V is O or NR$^d$.

In some embodiments, the present disclosure provides a compound of Formula (Id-2), (Id-3), (Id-4), or a pharmaceutically acceptable salt or stereoisomer thereof:

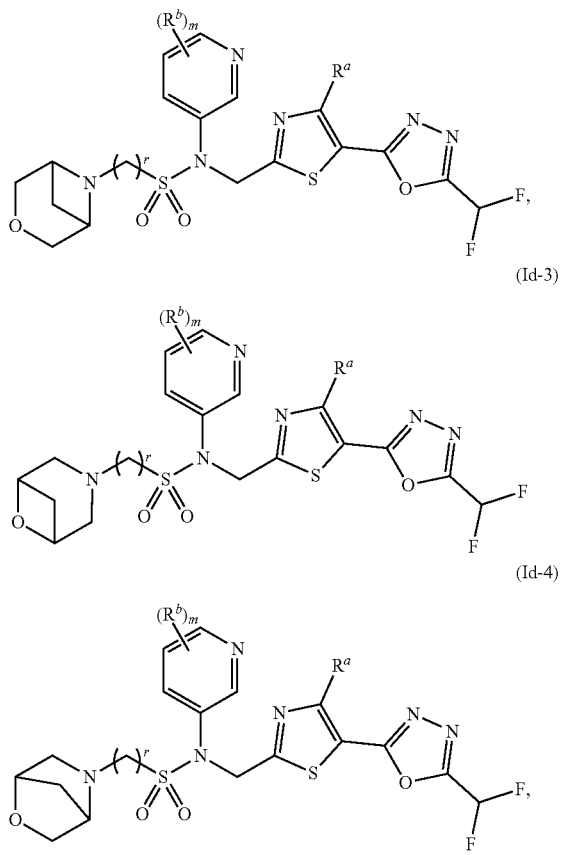

wherein:
U, $R^a$, $R^b$, m, and r are as defined above in Formulas (Id), (Ie), (If), and (Ig); and
V is O or $NR^d$.

In some embodiments of Formulas (Id)-(Ig) and (Id-1)-(Ig-1), U is $NR^d$, O, or S and V is O. In some embodiments, U is N, O, or S and V is $NR^d$. In some embodiments, U is $NR^d$ and V is $NR^d$. In some embodiments, U is O and V is $NR^d$. In some embodiments, U is S and V is $NR^d$. In some embodiments, U is $NR^d$ and V is O. In some embodiments, U is O and V is O. In some embodiments, U is S and V is O.

In some embodiments of Formulas (Id)-(Ig) and (Id-1)-(Ig-1), U is O, S, $S(O)_2$, $CH_2$, or $NR^d$. In some embodiments, U is O, S, $CH_2$, or $NR^d$. In some embodiments, U is O, S, or $NR^d$. In some embodiments, U is O or $CH_2$. In some embodiments, U is O. In some embodiments, U is S. In some embodiments, U is $NR^d$. In some embodiments, U is $S(O)_2$.

In some embodiments of Formulas (Id)-(Ig) and (Id-1)-(Ig-1), $R^a$ is H. In some embodiments, $R^a$ is F. In some embodiments, $R^d$ is Me.

In some embodiments of Formulas (Id)-(Ig) and (Id-1)-(Ig-1), $R^b$ is halo, alkyl, haloalkyl, alkyl, haloalkoxy, cycloalkyl, heterocyclyl, heteroaryl, or nitrile. In some embodiments, $R^b$ is halo, alkyl, haloalkyl, alkyl, haloalkoxy, cycloalkyl, or nitrile. In some embodiments, the haloalkyl is selected from $CF_3$, $CF_2CH_3$, $CHF_2$, or $CH_2F$. In some embodiments, the alkyl is a $-C_{1-5}$alkyl. In some embodiments, $-C_{1-5}$alkyl is methyl, ethyl, propyl, i-propyl, butyl, or t-butyl. In some embodiments, the cycloalkyl is a $C_{3-6}$cycloalkyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the haloalkoxy is selected from $OCF_3$, $OCHF_2$, or $OCH_2F$. In some embodiments, the alkoxy is O-methyl, O-ethyl, O-propyl, O-i-propyl, O-butyl, or O-t-butyl. In some embodiments, $R^b$ is $-C(O)R^e$, $-C(O)OR^e$, $-C(O)N(R^e)(R^{e'})$.

In some embodiments of Formulas (Id)-(Ig), $R^c$ is F, $C_{1-5}$ alkyl, haloalkyl, $C_{1-5}$ alkoxy, haloalkoxy, acyl, sulfonyl, 5- or 6-membered heteroaryl, or $C_{3-6}$ heterocyclyl. In some embodiments, $R^c$ is $-C(O)R^e$, $-C(O)OR^e$, $-C(O)N(R^e)(R^{e'})$. In some embodiments, two $R^c$ groups taken together with the carbon atoms to which they are attached form a bridged or fused $C_{3-7}$ cycloalkyl, a bridged or fused 5- or 6-membered heterocyclyl, or a 5- or 6-membered heteroaryl, each of which is optionally substituted. In some embodiments, two $R^c$ groups taken together with the carbon atoms to which they are attached form an optionally substituted bridged or fused $C_{3-7}$ cycloalkyl. In some embodiments, two $R^c$ groups taken together with the carbon atoms to which they are attached form an optionally substituted bridged or fused 5- or 6-membered heterocyclyl. In some embodiments, two $^c$ groups taken together with the carbon atoms to which they are attached form an alkoxy or aminoalkyl bridge. In some embodiments, the optional substituent is one or more $R^b$, as defined above. In some embodiments, the optional subsitutuent is selected from the group consisting of F, $C_{1-5}$ alkyl, $C_{1-5}$ alkoxy, $CF_3$, $CF_2H$, $CFH_2$, $-OCF_3$, $-OCF_2H$, $-OCFH_2$, $-C(O)R^e$, $-C(O)OR^e$, $-C(O)N(R^e)(R^{e'})$, and $-SO_2R^e$. In some embodiments, the optional subsitutuent is selected from the group consisting of F, $C_{1-5}$ alkyl, $C_{1-5}$ alkoxy, $CF_3$, $CF_2H$, $CFH_2$, $-OCF_3$, $-OCF_2H$, and $-OCFH_2$. In some embodiments, the optional subsitutuent is F or $C_{1-5}$ alkyl. In some embodiments, the optional subsitutuent is F. In some embodiments, the optional subsitutuent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl.

In some embodiments of Formulas (Id)-(Ig) and (Id-1)-(Ig-1), $R^e$ and $R^{e'}$ is each independently H, alkyl, cycloalkyl, or $-CH_2$cycloalkyl. In some embodiments, the alkyl is a $-C_{1-5}$alkyl. In some embodiments, $-C_{1-5}$alkyl is methyl, ethyl, propyl, i-propyl, butyl, or t-butyl. In some embodiments, the cycloalkyl is a $C_{3-6}$cycloalkyl. In some embodiments, the cycloalkyl is cyclopropyl. In some embodiments, $R^e$ and $R^{e'}$ are H.

In some embodiments of Formulas (Id)-(Ig) and (Id-1)-(Ig-1), m is 0, 1, or 2. In some embodiments, m is 0 or 1. In some embodiments, m is 0. In some embodiments, m is 1. In some embodiments, m is 2.

In some embodiments of Formulas (Id)-(Ig), p is 0, 1, or 2. In some embodiments, p is 0 or 1. In some embodiments, p is 1 or 2. In some embodiments, p is 0. In some embodiments, p is 1. In sonic embodiments, p is 2.

In some embodiments of Formulas (Id)-(Ig) and (Id-1)-(Ig-1), r is 1, 2, or 3. In some embodiments, r is 1 or 2. In some embodiments, r is 2 or 3. In some embodiments, r is 1. In some embodiments, r is 2. In some embodiments, r is 3. In some embodiments, r is 4.

In some embodiments of Formulas (Id)-(Ig), q is 0 or 1. In some embodiments, q is 0. In some embodiments, q is 1. In some embodiments, q is 2.

In some embodiments of Formulas (Id)-(Ig), r is 1 and p is 1. In some embodiments, r is 2 and p is 1. In some embodiments, r is 3 and p is 1.

In some embodiments, the present disclosure provides a compound of Formula (Ih) or a pharmaceutically acceptable salt thereof:

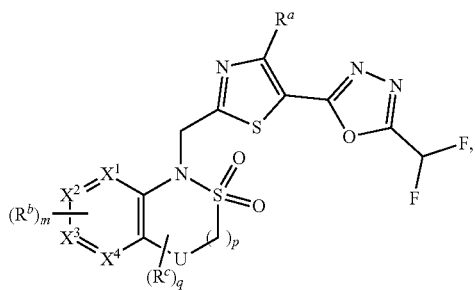

(Ih)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —C(O)$R^e$, —C(O)O$R^e$, —C(O)N($R^e$)($R^{e1}$), —$SO_2R^e$, cycloalkyl, heteroaryl, or heterocyclyl;
$R^c$ is each independently F, alkyl, haloalkyl, alkoxy, or haloalkoxy, and/or two $R^c$ groups taken together with the atoms to which they are attached form an optionally substituted $C_{3-7}$ cycloalkyl;
$R^d$ is H, alkyl, acyl, sulfonyl, cycloalkyl, aryl, or heteroaryl;
$R^e$ and $R^{e1}$ is each independently H, alkyl, cycloalkyl, heterocyclyl, aryl, heteroaryl, —$CH_2$cycloalkyl, —$CH_2$heterocyclyl, —$CH_2$aryl, or —$CH_2$heteroaryl;
m is 0, 1, 2, or 3;
p is 0, 1, 2, or 3; and
q is 0, 1, or 2.

In some embodiments, the present disclosure provides a compound of Formula (Ii) or a pharmaceutically acceptable salt thereof:

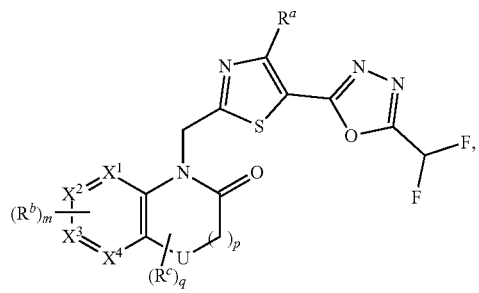

(Ii)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —C(O)$R^e$, —C(O)O$R^e$, —C(O)N($R^e$)($R^{e1}$), —$SO_2R^e$, cycloalkyl, heteroaryl, or heterocyclyl;
$R^c$ is each independently F, alkyl, haloalkyl, alkoxy, or haloalkoxy, and/or two $R^c$ groups taken together with the atoms to which they are attached form an optionally substituted $C_{3-7}$ cycloalkyl;
$R^d$ is H, alkyl, —C(O)$R^e$, sulfonyl, cycloalkyl, aryl, or heteroaryl;
$R^e$ and $R^{e1}$ is each independently H, alkyl, cycloalkyl, heterocyclyl, aryl, heteroaryl, —$CH_2$cycloalkyl, —$CH_2$heterocyclyl, —$CH_2$aryl, or —$CH_2$heteroaryl;
m is 0, 1, 2, or 3;
p is 0, 1, 2, or 3; and
q is 0, 1, or 2.

In some embodiments, the present disclosure provides a compound of Formula (Ij) or a pharmaceutically acceptable salt thereof:

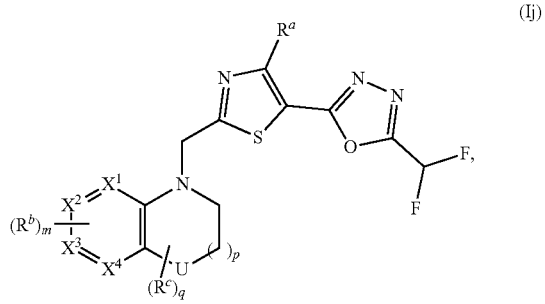

(Ij)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —C(O)$R^e$, —C(O)O$R^e$, —C(O)N($R^e$)($R^{e1}$), —$SO_2R^e$, cycloalkyl, heteroaryl, or heterocyclyl;
$R^c$ is each independently F, alkyl, haloalkyl, alkoxy, or haloalkoxy, and/or two $R^c$ groups taken together with the atoms to which they are attached form an optionally substituted $C_{3-7}$ cycloalkyl;
$R^d$ is H, alkyl, —C(O)$R^e$, sulfonyl, cycloalkyl, aryl, or heteroaryl;
$R^e$ and $R^{e1}$ is each independently H, alkyl, cycloalkyl, heterocyclyl, aryl, heteroaryl, —$CH_2$cycloalkyl, —$CH_2$heterocyclyl, —$CH_2$aryl, or —$CH_2$heteroaryl;
m is 0, 1, 2, or 3;
p is 0, 1, 2, or 3; and
q is 0, 1, or 2.

In some embodiments of Formulas (Ih)-(Ij), $NR^d$, O, S, $S(O)_2$, or $CH_2$. In some embodiments, U is $NR^d$, O, S, or $CH_2$. In some embodiments, U is O or $CH_2$. In some embodiments, U is O. In some embodiments, U is $CH_2$. In some embodiments, U is S. In some embodiments, U is $S(O)_2$. In some embodiments, U is $NR^d$.

In some embodiments of Formulas (Ih)-(Ij), each of $X^1$, $X^2$, $X^3$, and $X^4$ is CH. In some embodiments, one of $X^1$, $X^2$, $X^3$, and $X^4$ is N. In some embodiments, two of $X^1$, $X^2$, $X^3$, and $X^4$ are N. In some embodiments, $X^1$ is N and each of $X^2$, $X^3$, and $X^4$ is CH. In some embodiments, $X^2$ is N and each of $X^1$, $X^3$, and $X^4$ is CH. In some embodiments, $X^1$ is N and each of $X^1$, $X^2$, and $X^4$ is CH. In some embodiments, $X^4$ is N and each of $X^1$, $X^2$, and $X^3$ is CH.

In some embodiments of Formulas (Ih)-(Ij), U is $CH_2$ and one of $X^1$, $X^2$, $X^3$, and $X^4$ is N. In some embodiments, U is $CH_2$, $X^1$ is N and each of $X^2$, $X^3$, and $X^4$ is CH. In some embodiments, U is $CH_2$, $X^2$ is N and each of $X^1$, $X^3$, and $X^4$ is CH. In some embodiments, U is $CH_2$, $X^3$ is N and each of $X^1$, $X^2$, and $X^4$ is CH. In some embodiments, U is $CH_2$, $X^4$ is N and each of $X^1$, $X^2$, and $X^3$ is CH. In some embodiments, p is 0. In some embodiments, p is 1.

In some embodiments of Formulas (Ih)-(Ij), U is O and one of $X^1$, $X^2$, $X^3$, and $X^4$ is N. In some embodiments, U is O, $X^1$ is N and each of $X^2$, $X^3$, and $X^4$ is CH. In some embodiments, U is O, $X^2$ is N and each of $X^1$, $X^3$, and $X^4$ is CH. In some embodiments, U is O, $X^3$ is N and each of $X^1$, $X^2$, and $X^4$ is CH. In some embodiments, U is O, $X^4$ is N and each of $X^1$, $X^2$, and $X^3$ is CH.

In some embodiments of Formulas (Ih)-(Ij), $R^a$ is H. In some embodiments. $R^a$ is F. In some embodiments, $R^a$ is Me.

In some embodiments of Formulas (Ih)-(Ij), $R^b$ is halo, alkyl, haloalkyl, alkyl, haloalkoxy, cycloalkyl, heterocyclyl, heteroaryl, or nitrile. In some embodiments, $R^b$ is halo, alkyl, haloalkyl, alkyl, haloalkoxy, cycloalkyl, or nitrile. In some embodiments, the haloalkyl is selected from $CF_3$, $CF_2CH_3$, $CHF_2$, or $CH_2F$. In some embodiments, the alkyl is a $-C_{1-5}$alkyl. In some embodiments, $-C_{1-5}$alkyl is methyl, ethyl, propyl, i-propyl, butyl, or t-butyl. In some embodiments, the cycloalkyl is a $C_{3-6}$cycloalkyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the haloalkoxy is selected from $OCF_3$, $OCHF_2$, or $OCH_2F$. In some embodiments, the alkoxy is O-methyl, O-ethyl, O-propyl, O-i-propyl, O-butyl, or O-t-butyl.

In some embodiments of Formulas (Ih)-(Ij), $R^c$ is F, $C_{1-5}$ alkyl, haloalkyl, $C_{1-5}$ alkoxy, haloalkoxy, acyl, sulfonyl, 5- or 6-membered heteroaryl, or $C_{3-6}$ heterocyclyl. In some embodiments, $R^c$ is F, $C_{1-5}$ alkyl, haloalkyl, $C_{1-5}$ alkoxy, or haloalkoxy. In some embodiments, $R^c$ is F or $C_{1-5}$ alkyl. In some embodiments, $R^c$ is F or methyl. In some embodiments, $R^c$ is F. In some embodiments, $R^c$ is methyl. In some embodiments, the two $R^c$ groups are attached to the same carbon atom, which can also be referred to as germinal substitution. In some embodiments, two $R^c$ groups taken together with the atoms to which they are attached form an optionally substituted $C_{3-6}$ cycloalkyl. In some embodiments, two $R^c$ groups taken together with the atoms to which they are attached form an optionally substituted cyclopropyl. In some embodiments, the optional substituent is one or more $R^b$, as defined above. In some embodiments, the optional subsitutuent is selected from the group consisting of F, $C_{1-5}$ alkyl, $C_{1-5}$ alkoxy, $CF_3$, $CF_2H$, $CFH_2$, —$OCF_3$, —$OCF_2H$, —$OCFH_2$, —$C(O)R^e$, —$C(O)OR^e$, —$C(O)N(R^e)(R^{e1})$, and —$SO_2R^e$. In some embodiments, the optional subsitutuent is selected from the group consisting of F, $C_{1-5}$ alkyl, $C_{1-5}$ alkoxy, $CF_3$, $CF_2H$, $CFH_2$, —$OCF_3$, —$OCF_2H$, and —$OCFH_2$. In some embodiments, the optional subsitutuent is F or $C_{1-5}$ alkyl. In some embodiments, the optional subsitutuent is F. In some embodiments, the optional subsitutuent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl. In some embodiments, two optional substituents are attached to the same carbon, which is also referred to as germinal substitution.

In some embodiments of Formulas (Ih)-(Ij), when U is $NR^d$, an $R^d$ and $R^c$ taken together with the atoms to which they are attached form a 5- to 7-membered heterocyclyl. In some embodiments, an $R^d$ and $R^c$ taken together with the atoms to which they are attached form a 6-membered heterocyclyl. In some embodiments, the heterocyclyl comprises 1 or 2 heteroatoms selected from N, O, and S.

In some embodiments, the present disclosure provides a compound of Formula (Ih-1), Formula (Ii-1), or Formula (Ij-1):

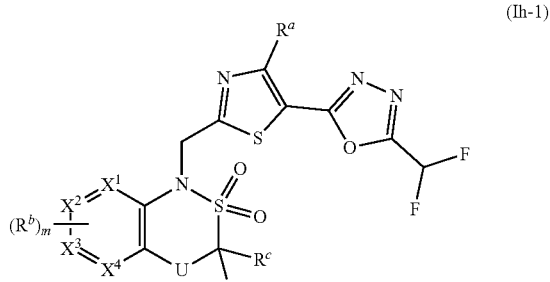

(Ih-1)

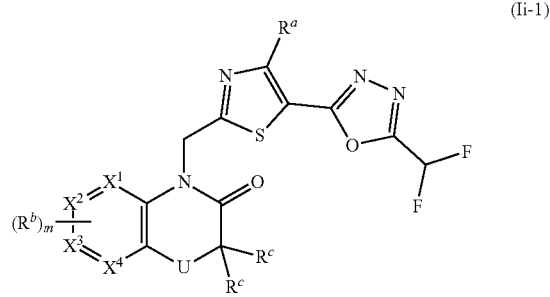

(Ii-1)

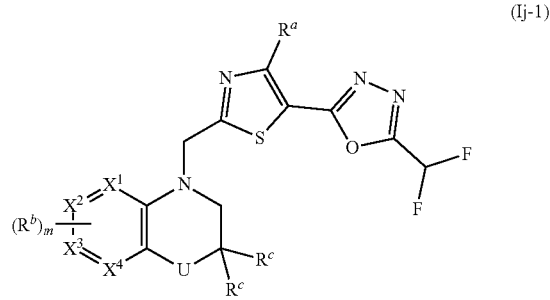

(Ij-1)

wherein $R^a$, $R^b$, $R^c$, $X^1$, $X^2$, $X^3$, $X^4$, U, and m are as defined above in Formula (Ih), Formula (Ii), and Formula (Ij).

In some embodiments of Formula (I-h-1), Formula (Ii-1), and Formula (Ij-1), each $R^c$ is F. In some embodiments, each $R^c$ is Me. In some embodiments, two $^c$ groups taken together with the carbon atoms to which they are attached form an optionally substituted $C_{3-6}$ cycloalkyl. In some embodiments, two $R^c$ groups taken together with the carbon atoms to which they are attached form a cyclopropyl or cyclobutyl, each of which is optionally substituted. In some embodiments, two $R^c$ groups taken together with the carbon atoms to which they are attached form an optionally substituted cyclopropyl. In some embodiments, the optional subsitutuent is F or $C_{1-5}$ alkyl. In some embodiments, the optional subsitutuent is F. In some embodiments, the optional subsitutuent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl. In some embodiments, two optional substituents are attached to the same carbon, which is also referred to as germinal substitution.

In some embodiments, $R^d$ is H, alkyl, or cycloalkyl. In some embodiments, $R^d$ is H. In some embodiments, $R^d$ is alkyl. In some embodiments, $R^d$ is cycloalkyl. In some embodiments, alkyl is methyl, ethyl, propyl, isopropyl, or t-butyl. In some embodiments, the cycloalkyl is cyclopropyl, cyclopentyl, or cyclohexyl.

In some embodiments, m is 0, 1, or 2. In some embodiments, m is 0 or 1. In some embodiments, m is 0. In some embodiments, m is 1. In some embodiments, m is 2.

In some embodiments, p is 0, 1, or 2. In some embodiments, p is 0 or 1. In some embodiments, p is 1 or 2. In some embodiments, p is 0. In some embodiments, p is 1. In some embodiments, p is 2.

In some embodiments, q is 0 or 1. In some embodiments, q is 0. In some embodiments, q is 1. In some embodiments, q is 2.

In some embodiments, the present disclosure provides a compound of Formula (Ik) or a pharmaceutically acceptable salt thereof:

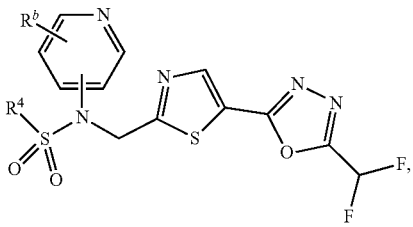

(Ik)

wherein:

$R^b$ is haloalkoxy; and $R^4$ is alkyl.

In some embodiments, the present disclosure provides a compound of Formula (Ik-1) or a pharmaceutically acceptable salt thereof:

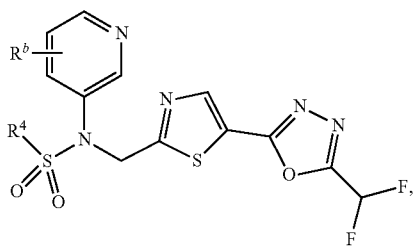

(Ik-1)

wherein:

$R^b$ is haloalkoxy; and $R^4$ is alkyl.

In some embodiments, the present disclosure provides a compound of Formula (Ik-2) or a pharmaceutically acceptable salt thereof:

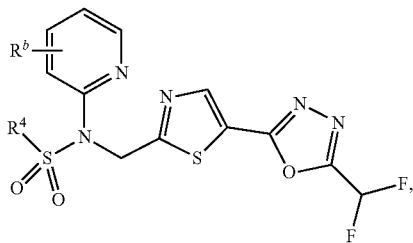

(Ik-2)

wherein:

$R^b$ is haloalkoxy; and $R^4$ is alkyl.

In some embodiments, the present disclosure provides a compound of Formula (Ik-3) or a pharmaceutically acceptable salt thereof:

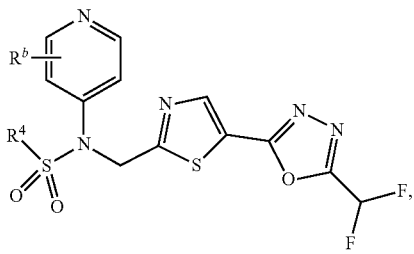

(Ik-3)

wherein:

$R^b$ is haloalkoxy; and $R^4$ is alkyl.

In some embodiments of Formulas (Ik)-(Ik-3), $R^b$ is H, —OCF$_3$, —OCHF$_2$, —OCH$_2$F, —OCH$_2$CF$_3$. In some embodiments, $R^b$ is H, or —OCHF$_2$. In some embodiments, $R^b$ is H or —OCH$_2$F. In some embodiments, $R^b$ is H or —OCF$_2$. In some embodiments, $R^b$ is H or —CHF$_2$. In some embodiments, $R^b$ is —OCF$_3$. In some embodiments, $R^b$ is —OCHF$_2$. In some embodiments, $R^b$ is —OCH$_2$F.

In some embodiments of Formulas (Ik)-(Ik-3), $R^4$ is a C$_{1-5}$ alkyl. In some embodiments, $R^4$ is methyl, ethyl, or propyl. In some embodiments, $R^4$ is methyl or ethyl. In some embodiments, $R^4$ is methyl. In some embodiments, $R^4$ is ethyl. In some embodiments, $R^4$ is propyl.

In some embodiments of Formulas (Ik)-(Ik-3), $R^b$ is H, —OCF$_3$, —OCHF$_2$ or —OCH$_2$F and $R^4$ is a C$_{1-5}$ alkyl. In some embodiments, $R^b$ is H or —OCHF$_2$ and $R^4$ is a C$_{1-5}$ alkyl. In some embodiments, $R^b$ is H or —OCH$_2$F and $R^4$ is a C$_{1-5}$ alkyl. In some embodiments, $R^b$ is H or —OCF$_3$ and $R^4$ is a C$_{1-5}$ alkyl. In some embodiments, $R^b$ is H or —OCH$_2$F and $R^4$ is a C$_{1-5}$ alkyl. In some embodiments, the C$_{1-5}$ alkyl is methyl, ethyl, or propyl. In some embodiments, the C$_{1-5}$ alkyl is methyl. In some embodiments, the C$_{1-5}$ alkyl is ethyl. In some embodiments, the C$_{1-5}$ alkyl is propyl.

Compounds of Formula (IL)

In one aspect, the present disclosure provides a compound of Formula (II) or pharmaceutically acceptable salt thereof:

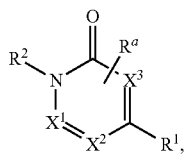

(II)

wherein
R¹ is selected from the group consisting of:

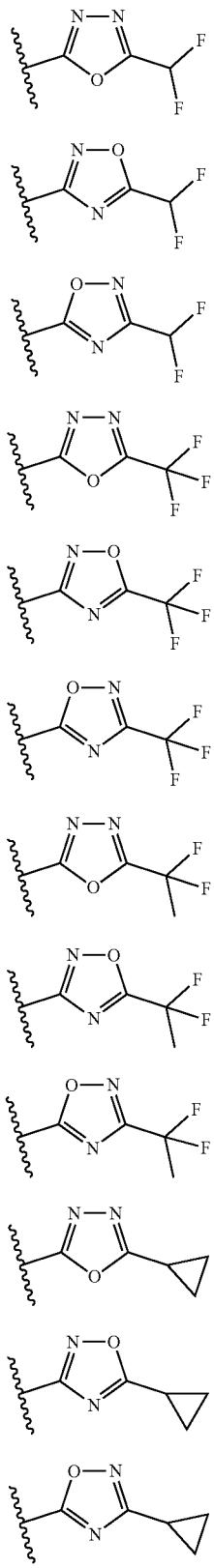
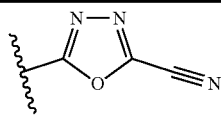
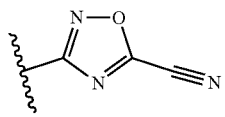 [SMILES: *c1noc(C#N)n1]
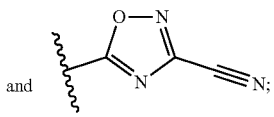 [SMILES: *c1nc(C#N)no1]

and

R$^a$ is selected from the group consisting of H, halo, C$_{1-3}$ alkyl, cycloalkyl, haloalkyl, and alkoxy;

R$^2$ is selected from the group consisting of H, aryl, heteroaryl, cycloalkyl, heterocyclyl, alkyl, haloalkyl, alkoxy, —(CH$_2$)$_m$aryl, —(CH$_2$)$_m$N(R$^3$)aryl, —(CH$_2$)$_m$Oaryl, —(CH$_2$)$_m$(SO$_2$)aryl, —(CH$_2$)$_m$heteroaryl, —(CH$_2$)$_m$N(R$^3$)heteroaryl, —(CH$_2$)$_m$Oheteroaryl, —(CH$_2$)$_m$cycloalkyl, —(CH$_2$)$_m$heterocyclyl, —(CH$_2$)$_m$(COOH), —(CH$_2$)$_m$(COOR$^3$), —(CH$_2$)$_m$(CONR$^3$R$^4$), —(CH$_2$)$_m$(NR$^3$SO$_2$NR$^3$R$^4$), and —(CH$_2$)$_m$(SO$_2$R$^3$), each of which is optionally substituted, wherein m is selected from 1, 2, or 3;

R$^3$ and R$^4$ are independently selected from the group consisting of H, aryl, heteroaryl, cycloalkyl, heterocyclyl, and alkyl, each of which is optionally substituted or R$^3$ and R$^4$ together with the atom to which they are attached form an optionally substituted heterocyclyl; and X$^1$, X$^2$ and X$^3$ are independently selected from C and N, with the proviso that X$^1$ and X$^2$ cannot both be N.

In some embodiments of Formula (II), X$^1$, X$^2$ and X$^3$ are C. In some embodiments, X$^1$ is N and X$^2$ and X$^3$ are C. In some embodiments, X$^1$ and X$^3$ are C and X$^2$ is N.

In some embodiments of Formula (II), R$^a$ is H, halo, C$_{1-3}$alkyl, or haloalkyl. In some embodiments, R$^a$ is H. In some embodiments, R$^a$ is C$_{1-3}$alkyl. In some embodiments, R$^a$ is haloalkyl. In some embodiments, halo is F. In some embodiments, the C$_{1-3}$alkyl alkyl is methyl, ethyl or isopropyl. In some embodiments, haloalkyl is CF$_3$, CHF$_2$, or CH$_2$F.

In some embodiments of Formula (II), R$^2$ is —(CH$_2$)$_m$cycloalkyl, —(CH$_2$)$_m$heterocyclyl, —(CH$_2$)$_m$aryl, —(CH$_2$)$_m$N(R$^3$)aryl, —(CH$_2$)$_m$Oaryl, —(CH$_2$)$_m$heteroaryl, —(CH$_2$)$_m$N(R$^3$)heteroaryl, or —(CH$_2$)$_m$Oheteroaryl, each of which is optionally substituted, wherein m is 1, 2, or 3.

In some embodiments of Formula (II), R$^2$ is optionally substituted —(CH$_2$)$_m$cycloalkyl, wherein m is 1, 2, or 3. In some embodiments, cycloalkyl is a C$_{3-6}$cycloalkyl. In some embodiments, the cycloalkyl is cyclopropyl. In some embodiments, the cycloalkyl is cyclobutyl. In some embodiments, the cycloalkyl is cyclopentyl. In some embodiments, the cycloalkyl is cyclohexyl.

In some embodiments, R$^2$ is heterocyclyl or —(CH$_2$)$_m$heterocyclyl, each of which is optionally substituted, wherein m is 1, 2, or 3. In some embodiments, heterocyclyl is selected from the group consisting of azetidinyl, tetrahydrofuranyl, morpholinyl, thiomorpholinyl, thiomorpholine-1,1-dioxide, tetrahydropyranyl, piperidinyl, or piperizinyl, each of which is optionally substituted. In some embodiments, the heterocyclyl is 2-oxa-5-azabicyclo[2.2.1]heptane, 8-azabicyclo[3.2.1]ooctane, or 9-azabicyclo[3.3.1]nonane.

In some embodiments, $R^2$ is —$(CH_2)_m$aryl, —$(CH_2)_m$N($R^3$)aryl, or —$(CH_2)_m$Oaryl, each of which is optionally substituted., wherein m is 1, 2, or 3. In some embodiments, aryl is an optionally substituted phenyl or naphthalenyl. In some embodiments, aryl is an optionally substituted phenyl.

In some embodiments, $R^2$ is —$(CH_2)_m$heteroaryl, —$(CH_2)_m$N($R^3$)aryl, or —$(CH_2)_m$Oaryl, each of which is optionally substituted, wherein m is 1, 2, or 3. In some embodiments, heteroaryl is an optionally substituted 5- to 14-membered heteroaryl. In some embodiments, heteroaryl is an optionally substituted 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzthiophenyl, imidazopyridinyl, imidazopyrazinyl, and benzimidazolyl. In some embodiments, the optionally substituted 5- to 14-membered heteroaryl is selected from the group consisting of pyrazolyl, pyridinyl, pyrimidinyl, pyrazinyl, pyridazinyl, benzoxazolyl, imidazopyridinyl, and imidazopyrazinyl. In some embodiments, the heteroaryl is quinolinyl, pyridinyl, pyrimidinyl, oxazolyl, imidazolyl, pyrazolyl, or pyrazinyl.

In some embodiments of Formula (II), $R^2$ is selected from the group consisting of H, $CH_3$, $CH_2$-$C_6H_5$, $CH_2CH_2$-$C_6H_5$, $CH_2$(COOt-Bu), $CH_2$(COOH), $CH_2$(CO—N-morpholine), and $CH_2$(CO—N-pyrrolidine). In some embodiments of Formula (II), $R^2$ is optionally substituted with one or more halogen atoms and/or one or more $C_{1-5}$alkyl groups.

In some embodiments of Formula (II), $R^2$ is unsubstituted $C_{1-6}$ alkyl. In some embodiments, $R^2$ is substituted $C_{1-6}$ alkyl. In some embodiments, the substituted $C_{1-6}$ alkyl is 2,2-dimethylpropylnitrile (i.e., —$CH_2C(CH_3)_2$—CN).

In some embodiments of Formula (II), $R^2$ is —C(H)($CH_3$)-$C_6H_5$. In some embodiments $R^2$ is alkylene-O-alkyl, or alkylene-O-aryl. In some embodiments, $R^2$ is alkylene-CN. In some embodiments of Formula (II), $R^2$ is —$(CH_2)_m$heteroaryl. In some embodiments of Formula (II), $R^2$ is —$(CH_2)_m$aryl. In some embodiments, $R^2$ is optionally substituted —$(CH_2)_m$cycloalkyl. In some embodiments, $R^2$ is optionally substituted cycloalkyl. In some embodiments, $R^2$ is —$(CH_2)_m$($COOR^3$). In some embodiments, $R^2$ is —$(CH_2)_m$($CONR^3R^4$). In some embodiments, m is selected from 1, 2, or 3. In some embodiments of Formula (II), $R^2$ is optionally substituted with one or more halogen atoms and/or one or more $C_{1-5}$alkyl groups. In some embodiments, $R^2$ is optionally substituted —$(CH_2)_m$heterocyclyl.

In some embodiments of Formula (II), the $R^2$ groups defined above are optionally substituted on an available carbon or heteroatom by one or more substituents independently selected from the group consisting of oxo, halo, $C_{1-6}$alkyl, haloalkyl, Ohaloalkyl, $C_{3-6}$cycloalkyl, 4- to 6-membered heteroaryl, phenyl, $SO_2$alkyl, $SO_2$aryl, C(O)alkyl, C(O)aryl, $CO_2$alkyl, $CO_2$aryl, and CN.

In some embodiments of Formula (II), alkyl, aryl, cycloalkyl, or heterocyclyl are each optionally substituted on an available carbon by one or more substituents independently selected from the group consisting of halo, —$OR^7$, alkyl, phenyl, heteroaryl, CN, $COOR^7$, C(O)$R^7$, $SO_2R^7$, and $CONR^7R^8$, wherein $R^7$, and $R^8$ are independently for each occurrence selected from the group consisting of H, alkyl and aryl, wherein the alkyl and aryl are optionally substituted with one or more halogens and/or one or more alkyl groups.

In some embodiments, m is 1. In some embodiments, m is 2. In some embodiments, m is 3. In some embodiments, in is 1 or 2. In some embodiments of Formula (II), $R^3$ and $R^4$ are independently selected from the group consisting of H, aryl, heteroaryl, cycloalkyl, heterocyclyl, and alkyl, each of which is optionally substituted. In some embodiments, the aryl, heteroaryl, cycloalkyl, heterocyclyl, and alkyl are optionally substituted with one or more halogen atoms and/or one or more $C_{1-5}$alkyl groups.

In some embodiments of Formula (II), $R^3$ and $R^4$ together with the atom to which they are attached form a heterocyclyl. In some embodiments the heterocyclyl is optionally substituted with one or more $C_{1-5}$alkyl groups.

In some embodiments of Formula (II), $R^1$ is

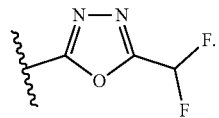 [SMILES: *c1nnc(C(F)F)o1]

In some embodiments, $R^1$ is

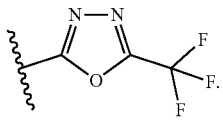 [SMILES: *c1nnc(C(F)(F)F)o1]

In some embodiments of Formula (II), $R^1$ is

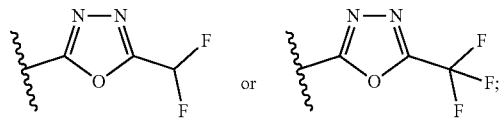 [SMILES: *c1nnc(C(F)F)o1 ; *c1nnc(C(F)(F)F)o1]

$X^1$, $X^2$ and $X^3$ are C; $R^2$ is selected from the group consisting of aryl, C-linked heteroaryl, cycloalkyl, C-linked heterocyclyl, alkyl, haloalkyl, —$(CH_2)_m$aryl, —$(CH_2)_m$heteroaryl, —$(CH_2)_m$cycloalkyl, —$(CH_2)_m$heterocyclyl, —$(CH_2)_m$(COOH), —$(CH_2)_m$($COOR^3$), —$(CH_2)_m$($CONR^3R^4$), —$(CH_2)_m$($NR^3SO_2NR^3R^4$), and —$(CH_2)_m$($SO_2R^3$), each of which is optionally substituted; wherein m is selected from 1, 2, or 3; and variables $R^a$, $R^3$ and $R^4$ are as defined above for Formula (II).

In some embodiments of Formula (II), $R^1$ is

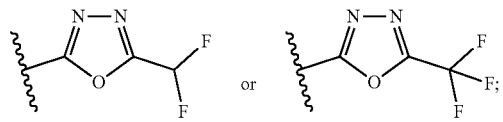 [SMILES: *c1nnc(C(F)F)o1 ; *c1nnc(C(F)(F)F)o1]

$X^1$, $X^2$ and $X^3$ are C; $R^2$ is selected from the group consisting of aryl, C-linked heteroaryl, cycloalkyl, C-linked heterocyclyl, alkyl, haloalkyl, —$(CH_2)_m$aryl, —$(CH_2)_m$($NR^3$)aryl, —$(CH_2)_m$Oaryl, —$(CH_2)_m$heteroaryl, —$(CH_2)_m$($NR^3$)heteroaryl, —$(CH_2)_m$Oheteroaryl, —$(CH_2)_m$cycloalkyl, —$(CH_2)_m$heterocyclyl, —$(CH_2)_m$(COOH), —$(CH_2)_m$($COOR^3$), —$(CH_2)_m$($CONR^3R^4$), —$(CH_2)_m$ (NR³SO₂NR³R⁴), and —(CH₂)ₘ(SO₂R³), each of which is optionally substituted; wherein m is selected from 1, 2, or 3; and variables Rᵃ, R³ and R⁴ are as defined above for Formula (II).

In some embodiments of Formula (II), R¹ is

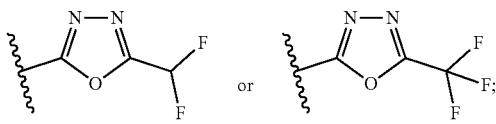 [SMILES: *c1nnc(C(F)F)o1 ; *c1nnc(C(F)(F)F)o1]

X¹ is N, X² and X³ are C; R² is selected from the group consisting of aryl, C-linked heteroaryl, cycloalkyl, C-linked heterocyclyl, alkyl, haloalkyl, —(CH₂)ₘaryl, —(CH₂)ₘ(NR³)aryl, —(CH₂)ₘOaryl, —(CH₂)ₘheteroaryl, —(CH₂)ₘ(NR³)heteroaryl, —(CH₂)ₘOheteroaryl, —(CH₂)ₘcycloalkyl, —(CH₂)ₘheterocyclyl, —(CH₂)ₘ(COOH), —(CH₂)ₘ(COOR³), —(CH₂)ₘ(CONR³R⁴), —(CH₂)ₘ(NR³SO₂NR³R⁴), and —(CH₂)ₘ(SO₂R³), each of which is optionally substituted; wherein m is selected from 1, 2, or 3; and variables Rᵃ, R³ and R⁴ are as defined above for Formula (II).

In some embodiments of Formula (II), each optionally substituted alkyl is independently an optionally substituted $C_{1-6}$ alkyl. In further embodiments, the $C_{1-6}$ alkyl is selected from the group consisting of methyl, ethyl, n-propyl, iso-propyl, n-butyl, isobutyl, tert-butyl, amyl, and isoamyl. In further embodiments, the $C_{1-6}$ alkyl is selected from the group consisting of methyl, ethyl, n-propyl, isopropyl, n-butyl, isobutyl, tert-butyl, amyl, and isoamyl. In some embodiments, the $C_{1-6}$ alkyl is Me or Et.

In some embodiments of Formula (II), each optionally substituted cycloalkyl is independently an optionally substituted $C_{3-12}$ cycloalkyl. In some embodiments, the cycloalkyl is a $C_{3-6}$ cycloalkyl. In some embodiments, the cycloalkyl is selected from the group consisting of cyclopropyl, cyclobutyl, cyclopentyl, and cyclohexyl.

In some embodiments of Formula (II), each optionally substituted heterocyclyl is independently an optionally substituted 3-12 membered heterocycloalkyl having 1 or 2 heteroatoms independently selected from N, O, and S. In some embodiments, each optionally substituted heterocyclyl is independently an optionally substituted 3-6 membered heterocycloalkyl having 1 or 2 heteroatoms independently selected from N, O, and S. In further embodiments, the heterocycloalkyl is an optionally substituted 5-membered or 6-membered heterocycle having 1 or 2 heteroatoms independently selected from N, O, and S. In some embodiments, the heterocyclyl is a saturated 4-7 membered heterocyclyl containing one or two heteroatoms independently selected from the group consisting of N, NR⁶O and SO₂. In some embodiments, R⁶ is selected from the group consisting of $C_1$-$C_6$ alkyl, —COO-alkyl, and C(O)-alkyl. In some embodiments, the heterocyclyl is selected from the group consisting of aziridinyl, azetidinyl, pyrrolidinyl, piperidinyl, morpholinyl, and thiomorpholinyl.

In some embodiments of Formula (II), each optionally substituted aryl is independently a $C_{6-12}$ aryl. In further embodiments, the $C_{6-12}$ aryl is an optionally substituted phenyl.

In some embodiments of Formula (II), each optionally substituted heteroaryl is independently a 5-12 membered heteroaryl having 1, 2, or 3 heteroatoms independently selected from N, O, and S. In some embodiments, each optionally substituted heteroaryl is independently a 5-12 membered heteroaryl having 3 heteroatoms independently selected from N, O, and S. In some embodiments, each optionally substituted heteroaryl is independently a 5-12 membered heteroaryl having 2 heteroatoms independently selected from N, O, and S. In some embodiments, each optionally substituted heteroaryl is independently a 5-12 membered heteroaryl having 1 heteroatom independently selected from N, O, and S. In further embodiments, each optionally substituted heteroaryl is an optionally substituted 5-membered or 6-membered heteroaryl having 1 heteroatom independently from N, O, and S. In further embodiments, each optionally substituted heteroaryl is an optionally substituted 5-membered or 6-membered heteroaryl having 1 or 2 N atoms. In some embodiments, each heteroaryl is independently selected from the group consisting of tetrazole, oxadiazole, thiadiazole, imidazole, pyrazole, thiazole, or oxazole, each of which is optionally substituted. In some embodiments, the heteroaryl is tetrazole. In some embodiments, the heteroaryl is oxadiazole.

In some embodiments, the compound of Formula (I) is a compound of Table 2.

TABLE 2

Compounds of Formula (II) of the Present Disclosure.

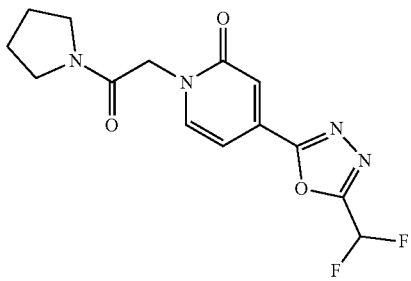 [SMILES: O=C(Cn1ccc(-c2nnc(C(F)F)o2)cc1=O)N1CCCC1]

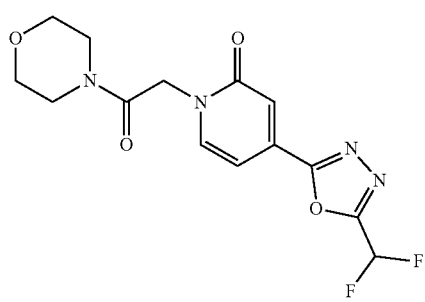 [SMILES: O=C(Cn1ccc(-c2nnc(C(F)F)o2)cc1=O)N1CCOCC1]

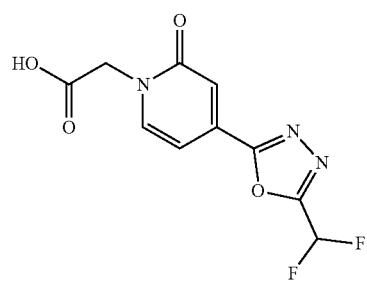 [SMILES: O=C(O)Cn1ccc(-c2nnc(C(F)F)o2)cc1=O]

TABLE 2-continued
Compounds of Formula (II) of the Present Disclosure.
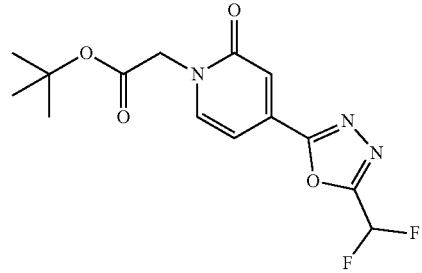 [SMILES: CC(C)(C)OC(=O)Cn1ccc(-c2nnc(C(F)F)o2)cc1=O]
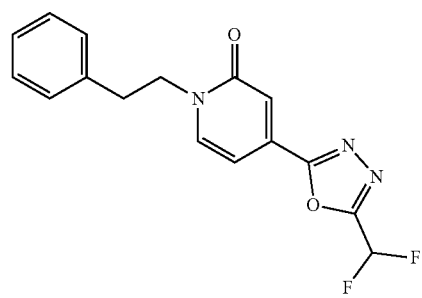 [SMILES: O=c1cc(-c2nnc(C(F)F)o2)ccn1CCc1ccccc1]
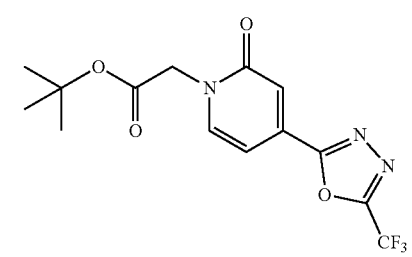 [SMILES: CC(C)(C)OC(=O)Cn1ccc(-c2nnc(C(F)(F)F)o2)cc1=O]
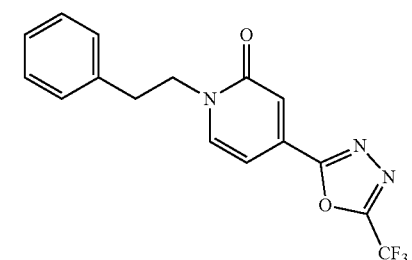
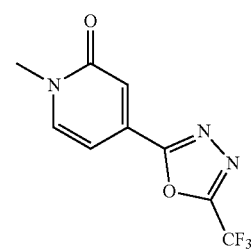 [SMILES: Cn1ccc(-c2nnc(C(F)(F)F)o2)cc1=O]
TABLE 2-continued
Compounds of Formula (II) of the Present Disclosure.
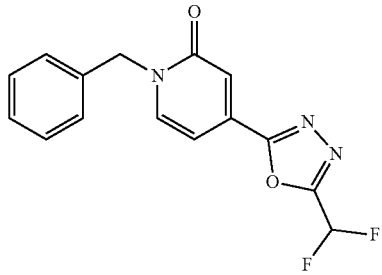 [SMILES: O=c1cc(-c2nnc(C(F)F)o2)ccn1Cc1ccccc1]
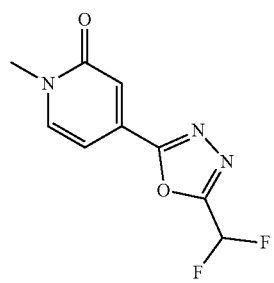 [SMILES: Cn1ccc(-c2nnc(C(F)F)o2)cc1=O]
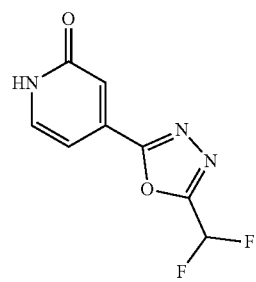 [SMILES: O=c1cc(-c2nnc(C(F)F)o2)cc[nH]1]
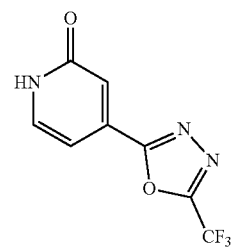 [SMILES: O=c1cc(-c2nnc(C(F)(F)F)o2)cc[nH]1]
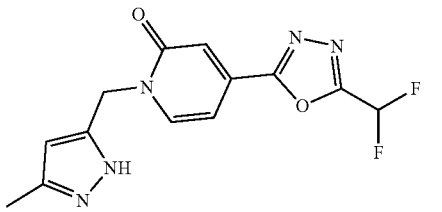 [SMILES: Cc1cc(Cn2ccc(-c3nnc(C(F)F)o3)cc2=O)[nH]n1]
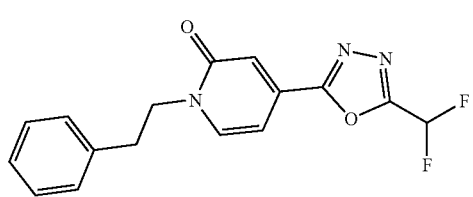 [SMILES: O=c1cc(-c2nnc(C(F)F)o2)ccn1CCc1ccccc1]

TABLE 2-continued
Compounds of Formula (II) of the Present Disclosure.
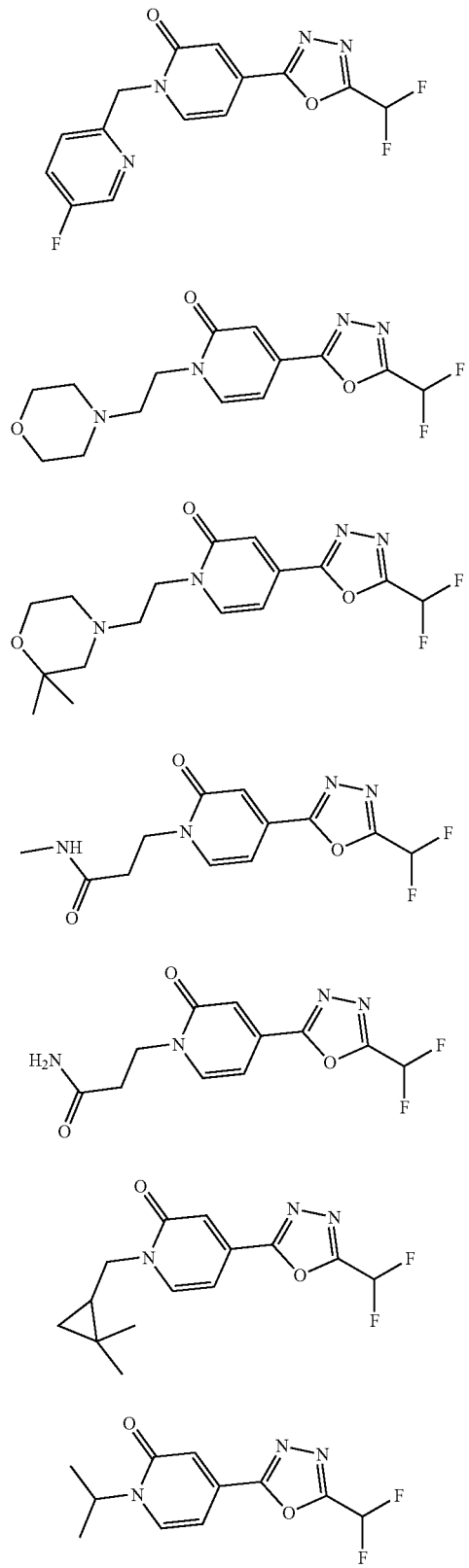
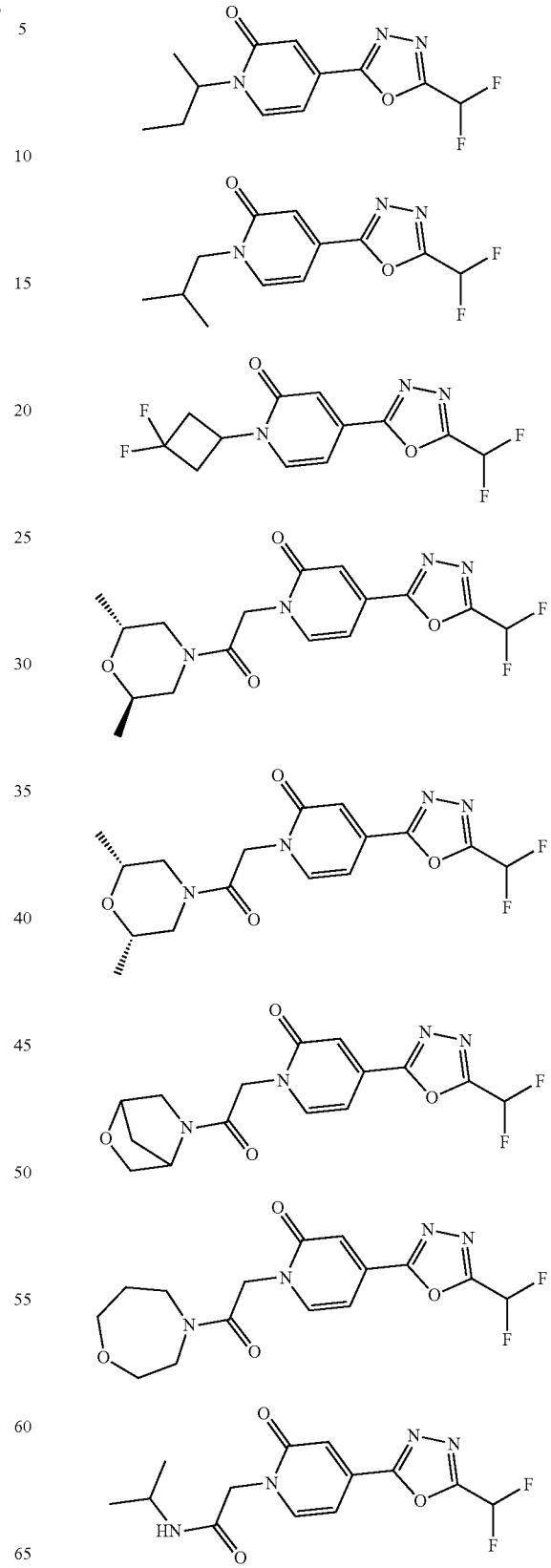

TABLE 2-continued
Compounds of Formula (II) of the Present Disclosure.
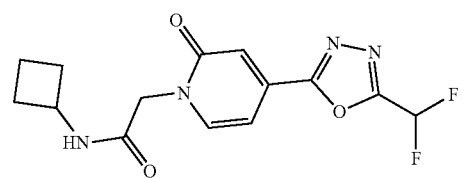 [SMILES: O=C(Cn1ccc(-c2nnc(C(F)F)o2)cc1=O)NC1CCC1]
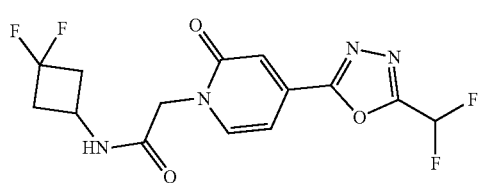 [SMILES: O=C(Cn1ccc(-c2nnc(C(F)F)o2)cc1=O)NC1CC(F)(F)C1]
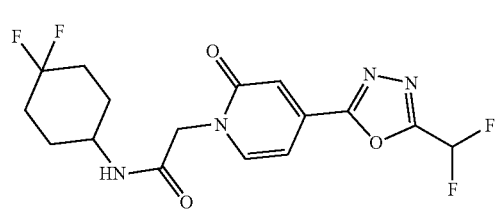 [SMILES: O=C(Cn1ccc(-c2nnc(C(F)F)o2)cc1=O)NC1CCC(F)(F)CC1]
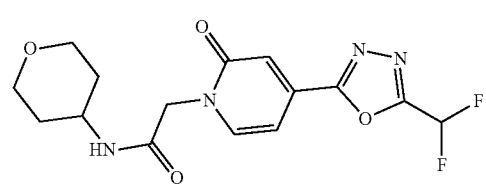 [SMILES: O=C(Cn1ccc(-c2nnc(C(F)F)o2)cc1=O)NC1CCOCC1]
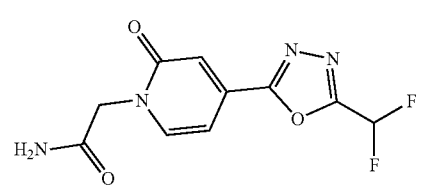 [SMILES: NC(=O)Cn1ccc(-c2nnc(C(F)F)o2)cc1=O]
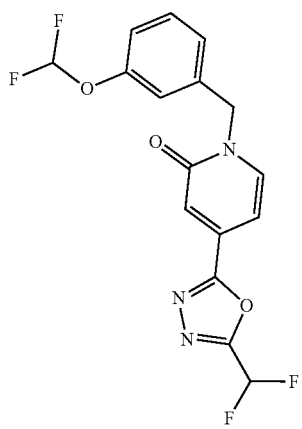 [SMILES: O=c1cc(-c2nnc(C(F)F)o2)ccn1Cc1cccc(OC(F)F)c1]
TABLE 2-continued
Compounds of Formula (II) of the Present Disclosure.
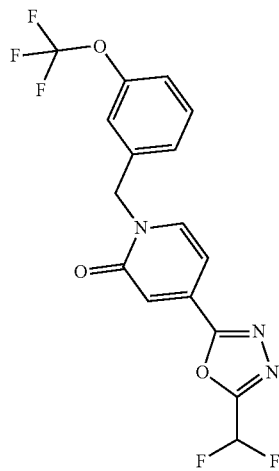 [SMILES: O=c1cc(-c2nnc(C(F)F)o2)ccn1Cc1cccc(OC(F)(F)F)c1]
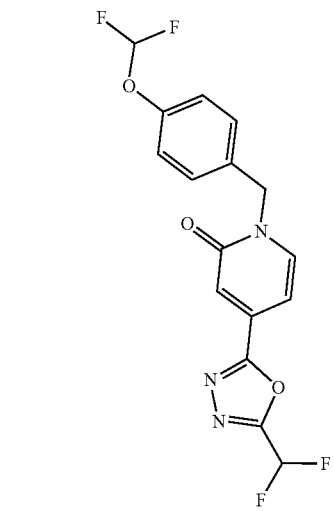 [SMILES: O=c1cc(-c2nnc(C(F)F)o2)ccn1Cc1ccc(OC(F)F)cc1]
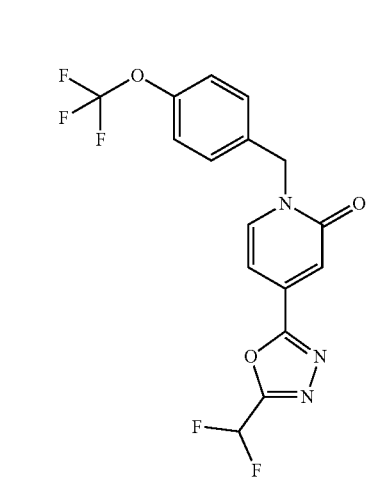 [SMILES: O=c1cc(-c2nnc(C(F)F)o2)ccn1Cc1ccc(OC(F)(F)F)cc1]

TABLE 2-continued
Compounds of Formula (II) of the Present Disclosure.
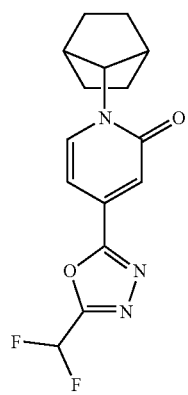 [SMILES: O=c1cc(-c2nnc(C(F)F)o2)ccn1C1C2CCC1CC2]
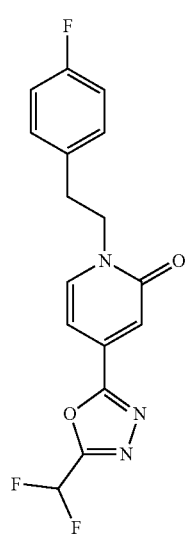
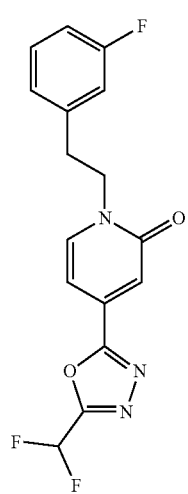
TABLE 2-continued
Compounds of Formula (II) of the Present Disclosure.
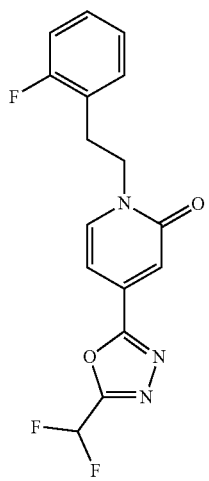 [SMILES: O=c1cc(-c2nnc(C(F)F)o2)ccn1CCc1ccccc1F]
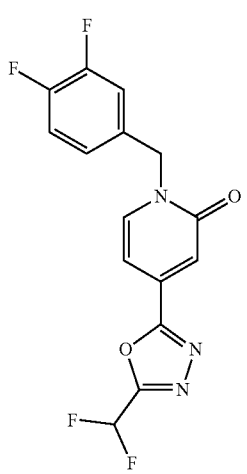 [SMILES: O=c1cc(-c2nnc(C(F)F)o2)ccn1Cc1ccc(F)c(F)c1]
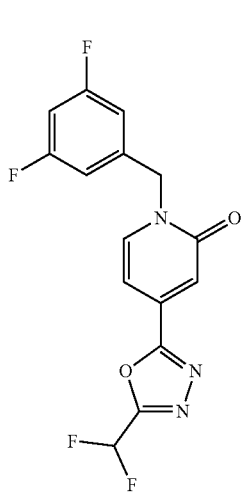

TABLE 2-continued
Compounds of Formula (II) of the Present Disclosure.
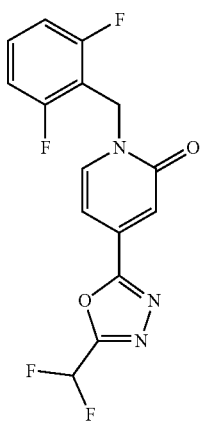 [SMILES: O=c1cc(-c2nnc(C(F)F)o2)ccn1Cc1c(F)cccc1F]
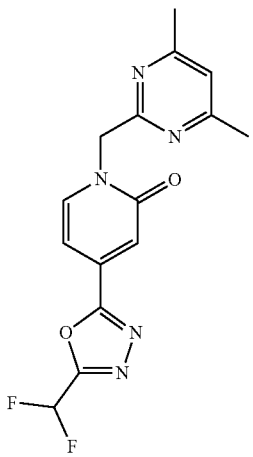
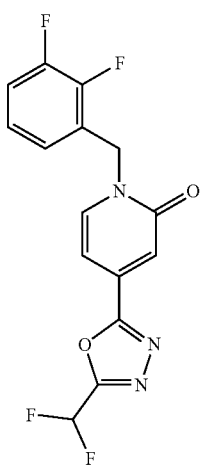 [SMILES: O=c1cc(-c2nnc(C(F)F)o2)ccn1Cc1cccc(F)c1F]
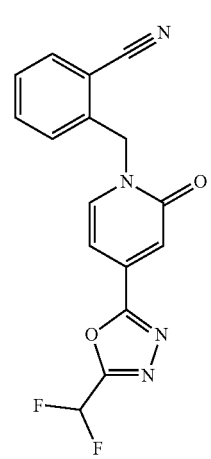 [SMILES: N#Cc1ccccc1Cn1ccc(-c2nnc(C(F)F)o2)cc1=O]
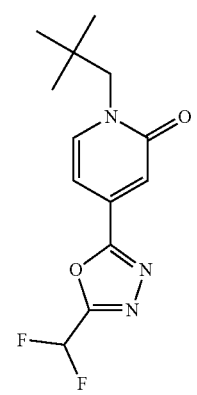
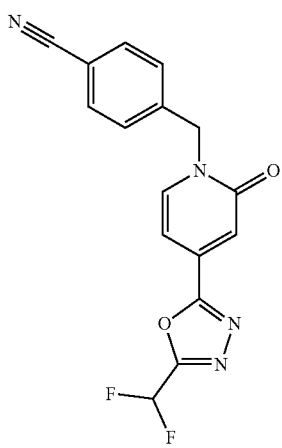 [SMILES: N#Cc1ccc(Cn2ccc(-c3nnc(C(F)F)o3)cc2=O)cc1]

TABLE 2-continued
Compounds of Formula (II) of the Present Disclosure.
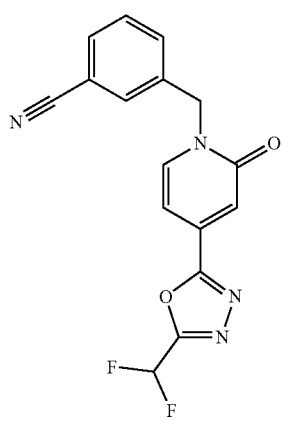 [SMILES: N#Cc1cccc(Cn2ccc(-c3nnc(C(F)F)o3)cc2=O)c1]
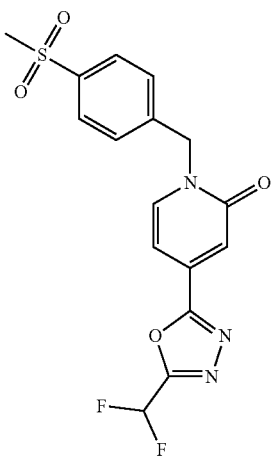
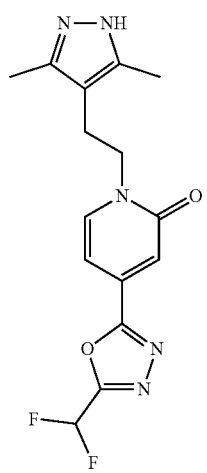 [SMILES: Cc1n[nH]c(C)c1CCn1ccc(-c2nnc(C(F)F)o2)cc1=O]
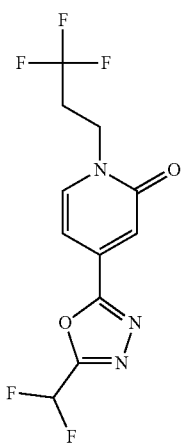
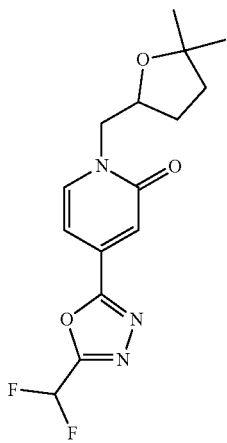 [SMILES: CC1(C)CCC(Cn2ccc(-c3nnc(C(F)F)o3)cc2=O)O1]
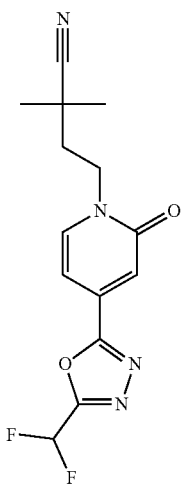

TABLE 2-continued
Compounds of Formula (II) of the Present Disclosure.
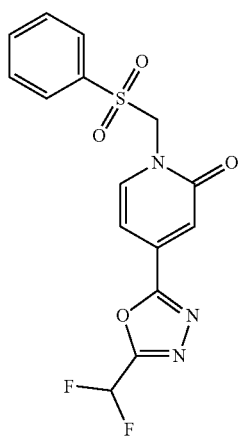 [SMILES: O=c1cc(-c2nnc(C(F)F)o2)ccn1CS(=O)(=O)c1ccccc1]
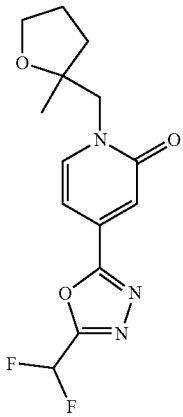
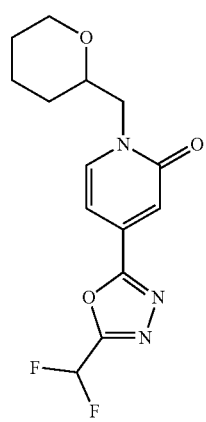 [SMILES: O=c1cc(-c2nnc(C(F)F)o2)ccn1CC1CCCCO1]
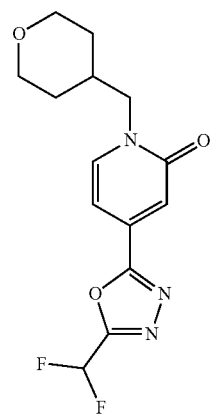
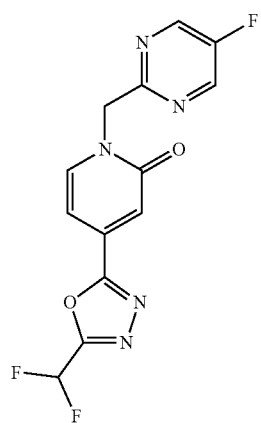 [SMILES: O=c1cc(-c2nnc(C(F)F)o2)ccn1Cc1ncc(F)cn1]
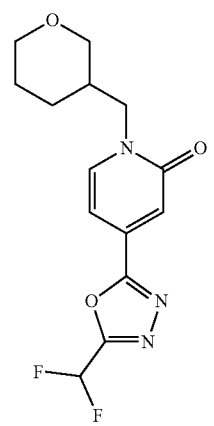 [SMILES: O=c1cc(-c2nnc(C(F)F)o2)ccn1CC1CCCOC1]

TABLE 2-continued
Compounds of Formula (II) of the Present Disclosure.
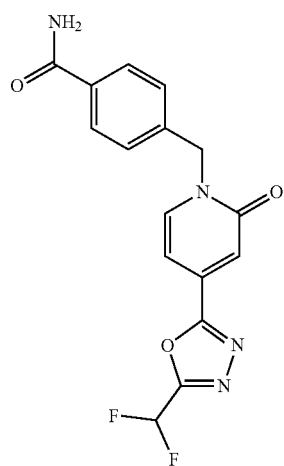 [SMILES: NC(=O)c1ccc(Cn2ccc(-c3nnc(C(F)F)o3)cc2=O)cc1]
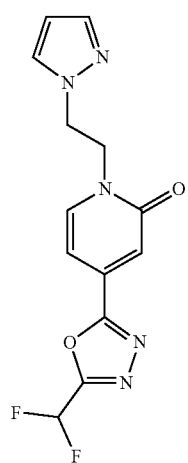 [SMILES: O=c1cc(-c2nnc(C(F)F)o2)ccn1CCn1cccn1]
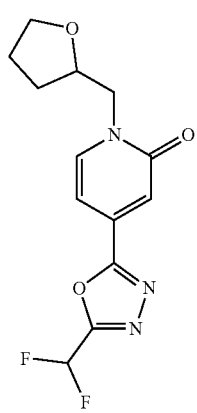 [SMILES: O=c1cc(-c2nnc(C(F)F)o2)ccn1CC1CCCO1]
TABLE 2-continued
Compounds of Formula (II) of the Present Disclosure.
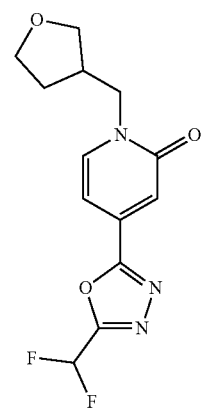 [SMILES: O=c1cc(-c2nnc(C(F)F)o2)ccn1CC1CCOC1]
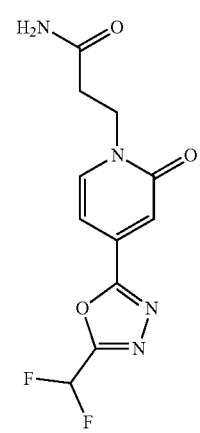 [SMILES: NC(=O)CCn1ccc(-c2nnc(C(F)F)o2)cc1=O]
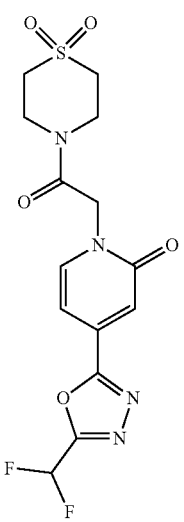 [SMILES: O=C(Cn1ccc(-c2nnc(C(F)F)o2)cc1=O)N1CCS(=O)(=O)CC1]

TABLE 2-continued
Compounds of Formula (II) of the Present Disclosure.
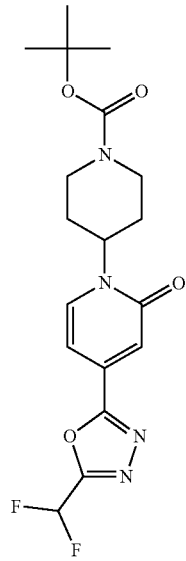 [SMILES: CC(C)(C)OC(=O)N1CCC(n2ccc(-c3nnc(C(F)F)o3)cc2=O)CC1]
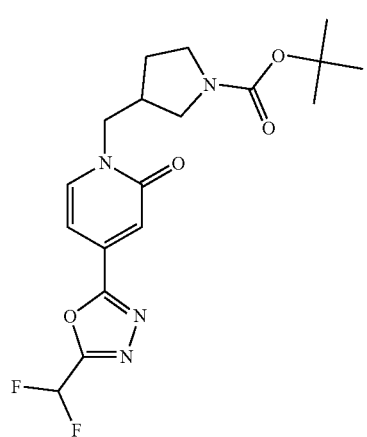 [SMILES: CC(C)(C)OC(=O)N1CCC(Cn2ccc(-c3nnc(C(F)F)o3)cc2=O)C1]
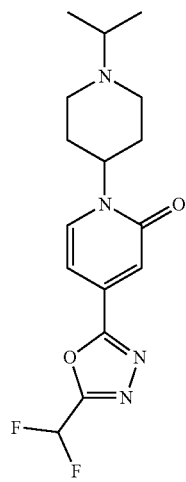 [SMILES: CC(C)N1CCC(n2ccc(-c3nnc(C(F)F)o3)cc2=O)CC1]
TABLE 2-continued
Compounds of Formula (II) of the Present Disclosure.
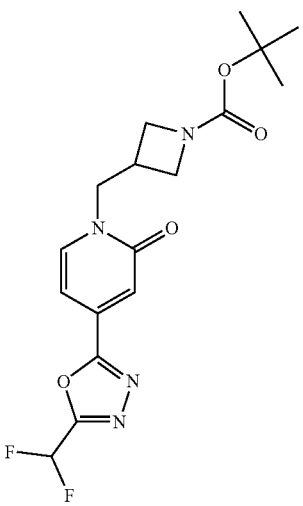 [SMILES: CC(C)(C)OC(=O)N1CC(Cn2ccc(-c3nnc(C(F)F)o3)cc2=O)C1]
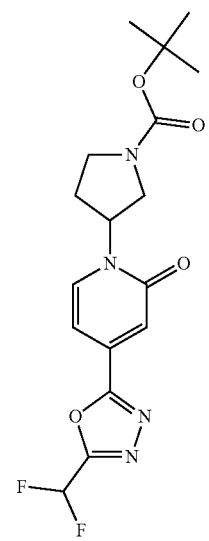 [SMILES: CC(C)(C)OC(=O)N1CCC(n2ccc(-c3nnc(C(F)F)o3)cc2=O)C1]
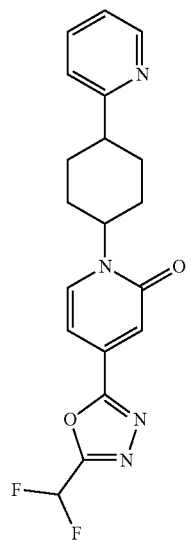

TABLE 2-continued
Compounds of Formula (II) of the Present Disclosure.
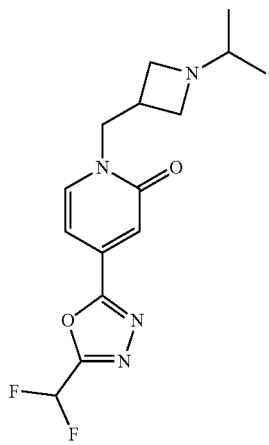 [SMILES: CC(C)N1CC(Cn2ccc(-c3nnc(C(F)F)o3)cc2=O)C1]
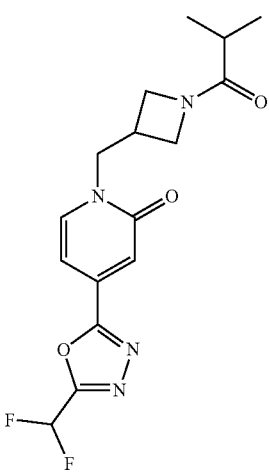
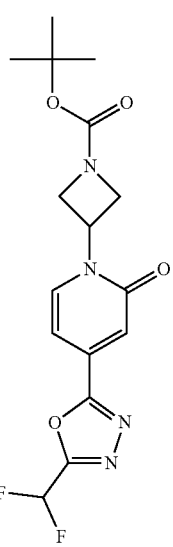
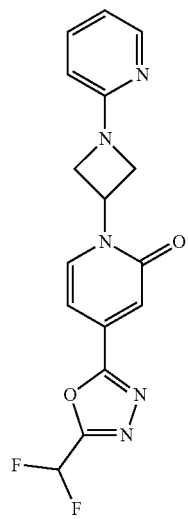
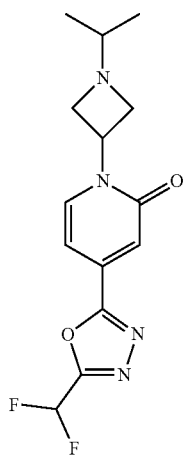 [SMILES: CC(C)N1CC(n2ccc(-c3nnc(C(F)F)o3)cc2=O)C1]
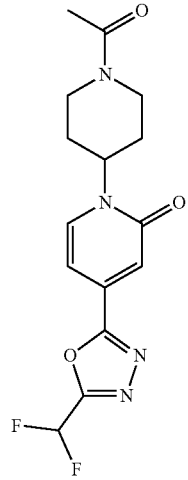

TABLE 2-continued
Compounds of Formula (II) of the Present Disclosure.
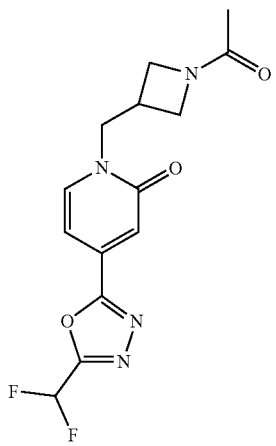 [SMILES: CC(=O)N1CC(Cn2ccc(-c3nnc(C(F)F)o3)cc2=O)C1]
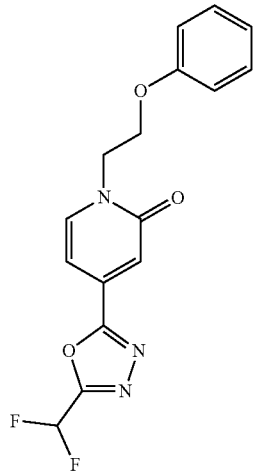
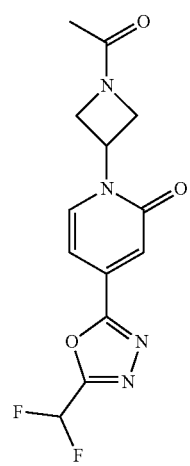 [SMILES: CC(=O)N1CC(n2ccc(-c3nnc(C(F)F)o3)cc2=O)C1]
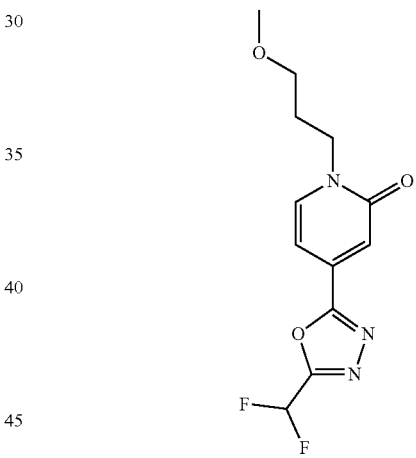
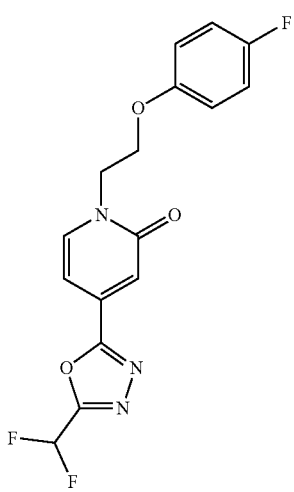 [SMILES: O=c1cc(-c2nnc(C(F)F)o2)ccn1CCOc1ccc(F)cc1]
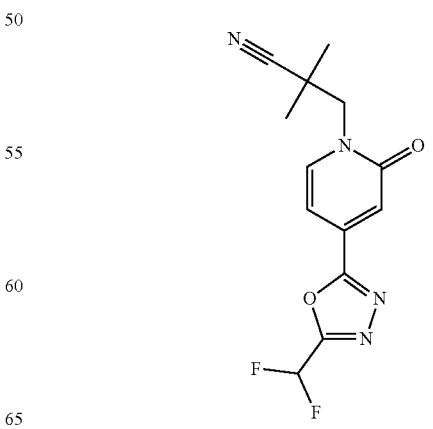

TABLE 2-continued
Compounds of Formula (II) of the Present Disclosure.
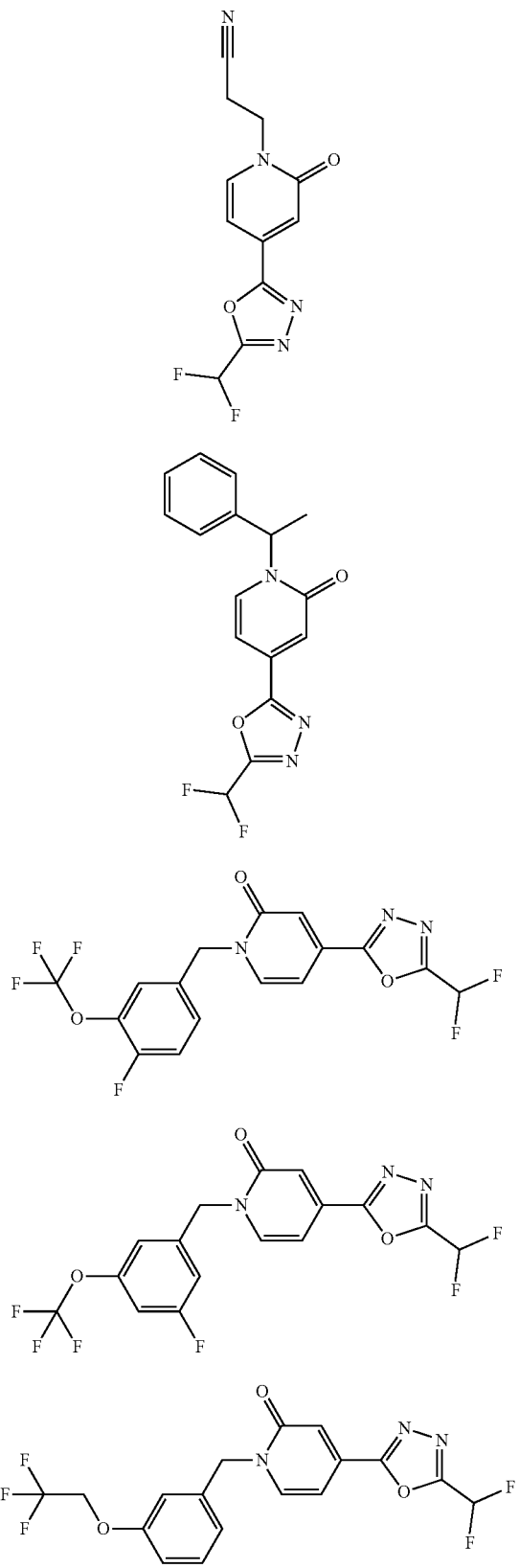
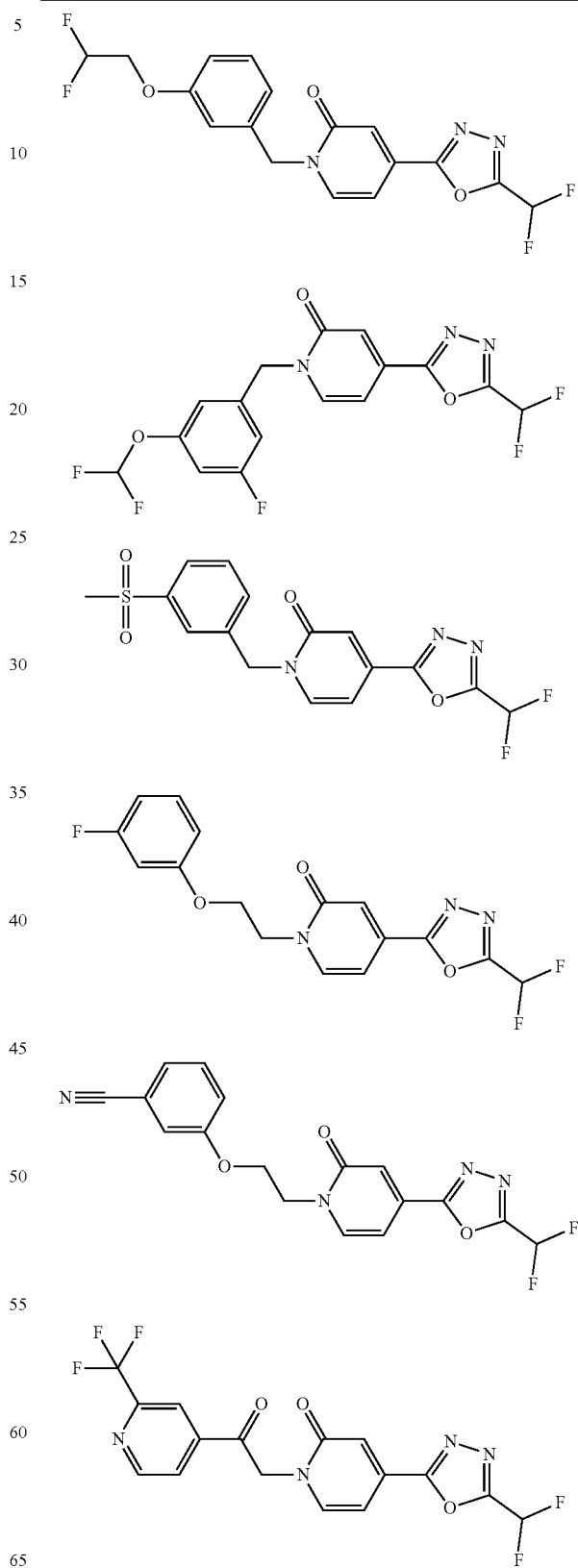

TABLE 2-continued
Compounds of Formula (II) of the Present Disclosure.
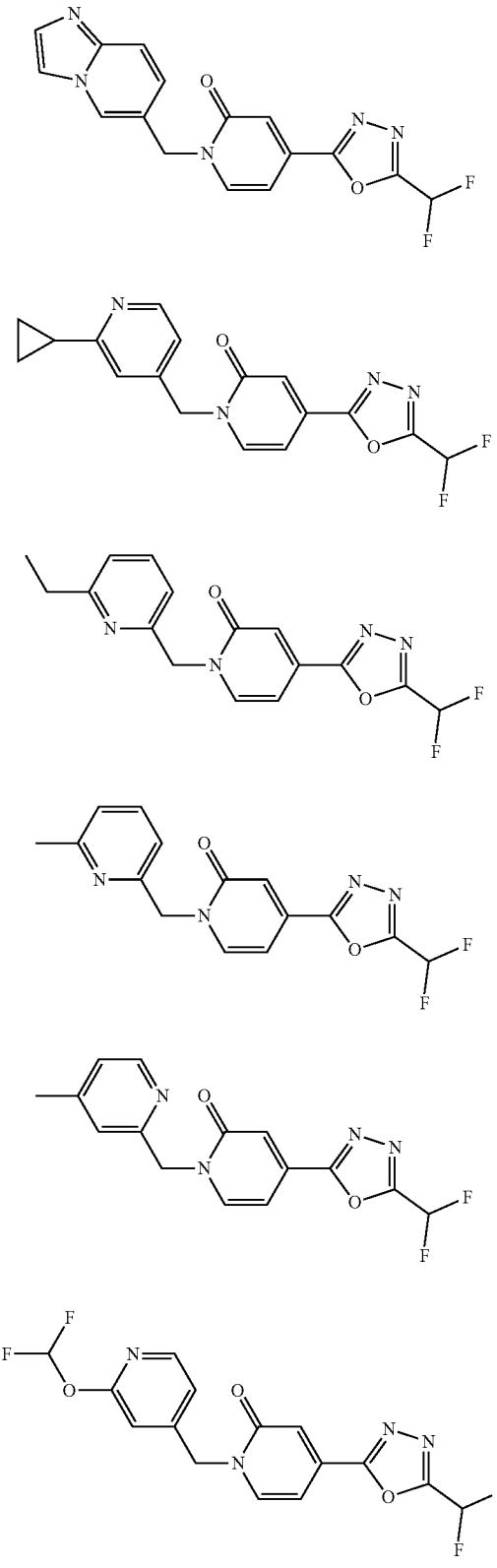
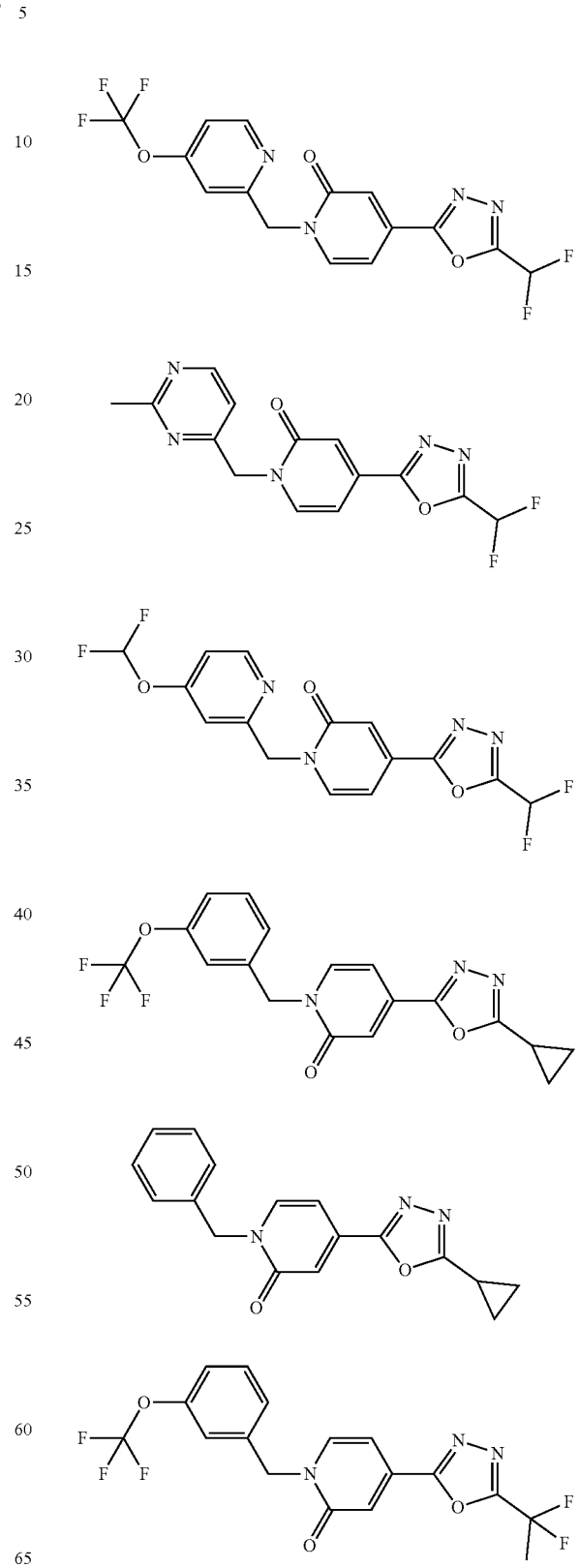

TABLE 2-continued
Compounds of Formula (II) of the Present Disclosure.
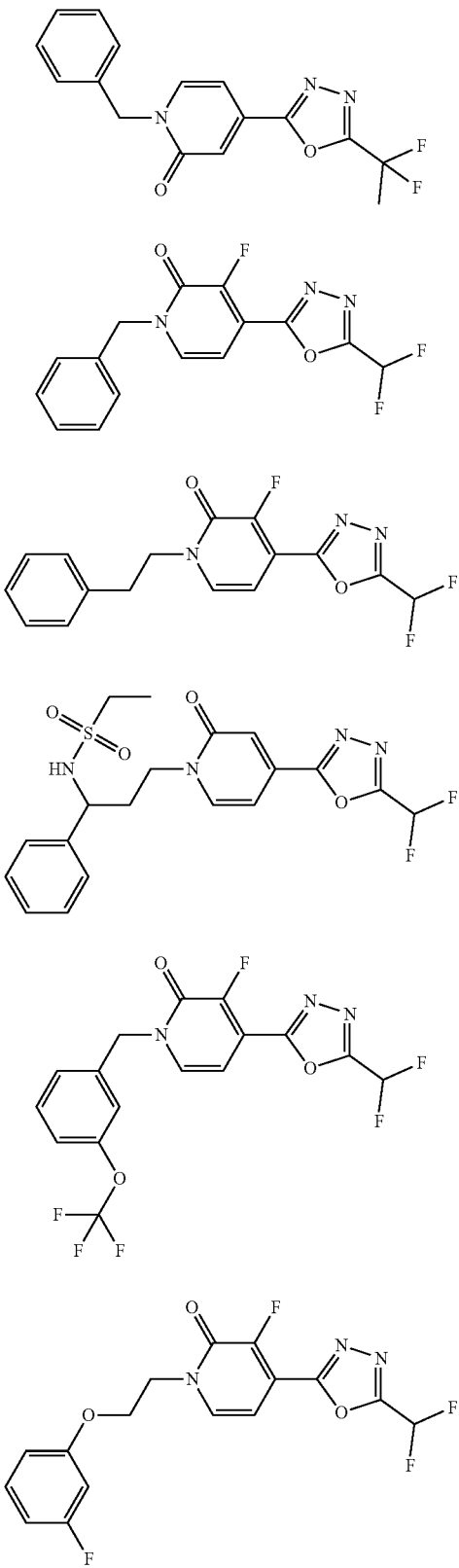

TABLE 2-continued
Compounds of Formula (II) of the Present Disclosure.
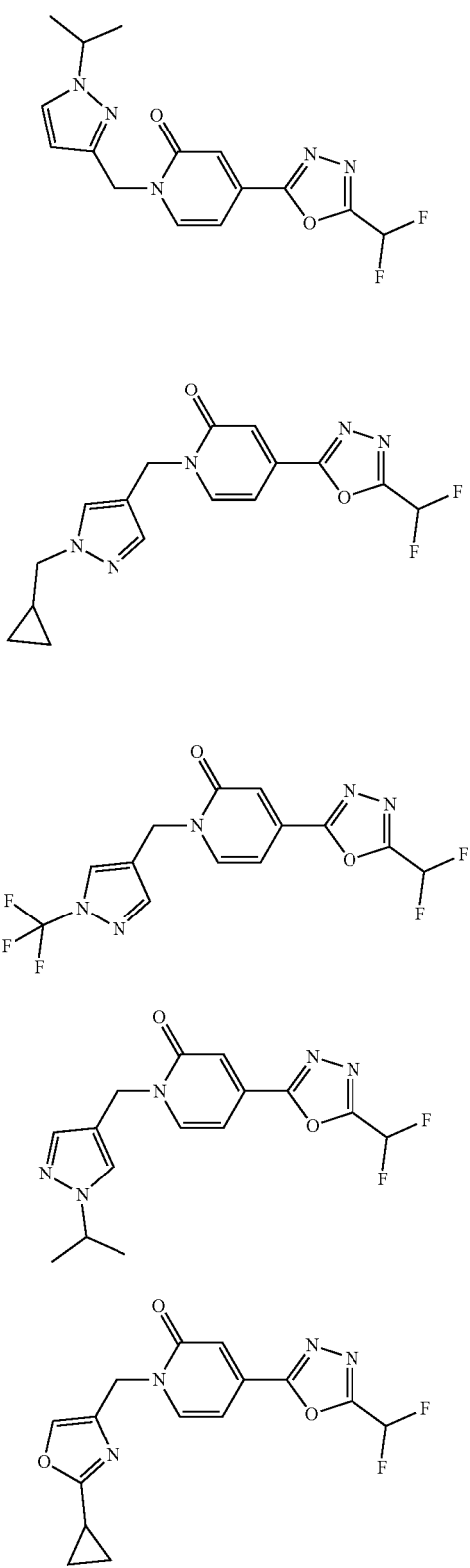
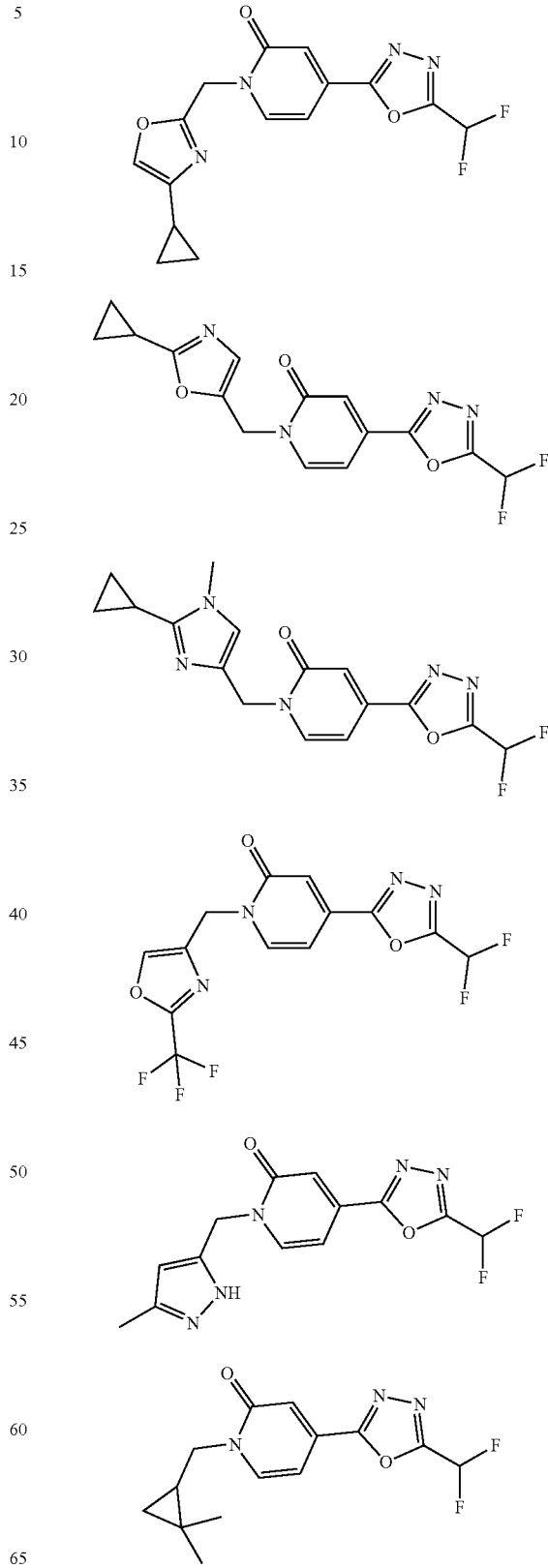

TABLE 2-continued
Compounds of Formula (II) of the Present Disclosure.
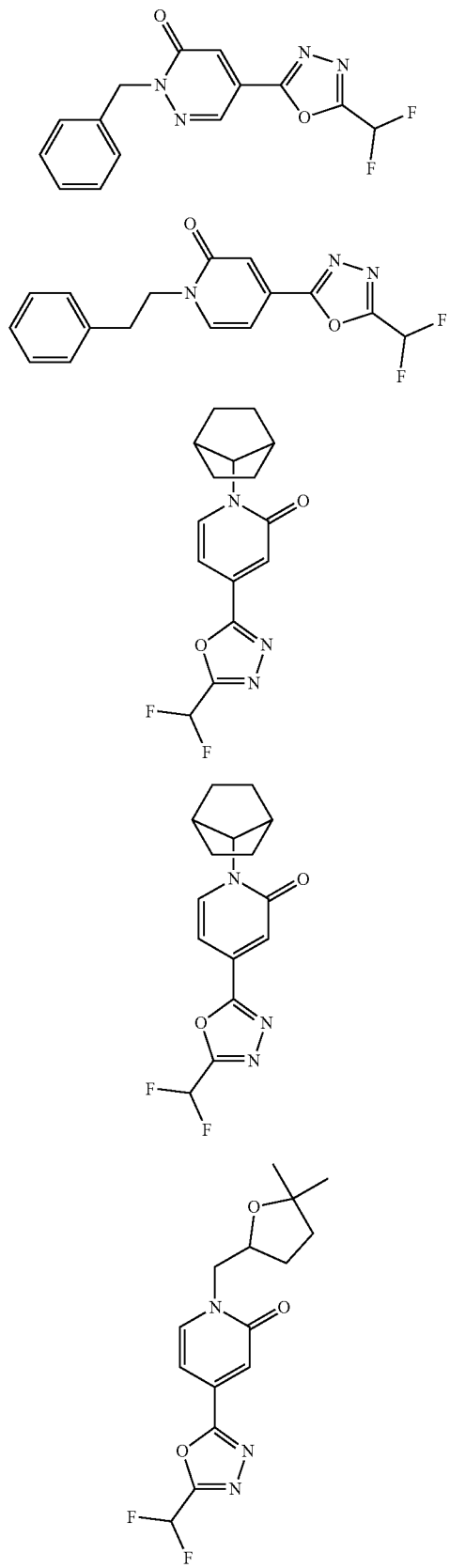
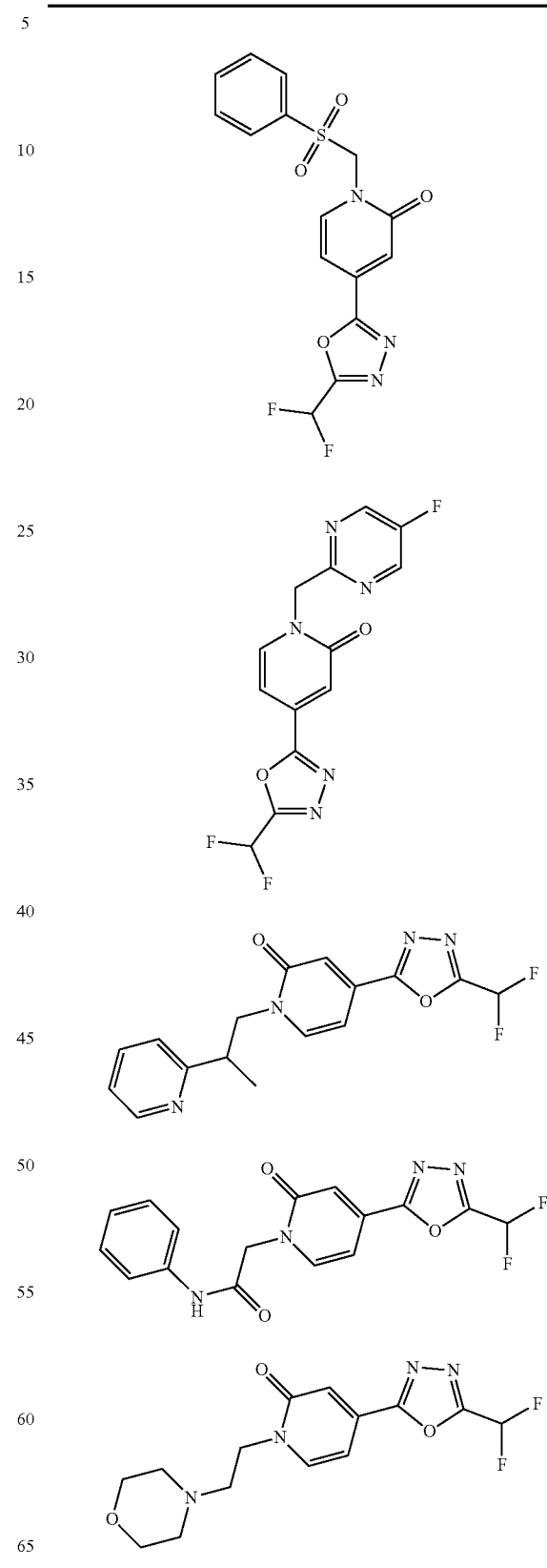

TABLE 2-continued
Compounds of Formula (II) of the Present Disclosure.
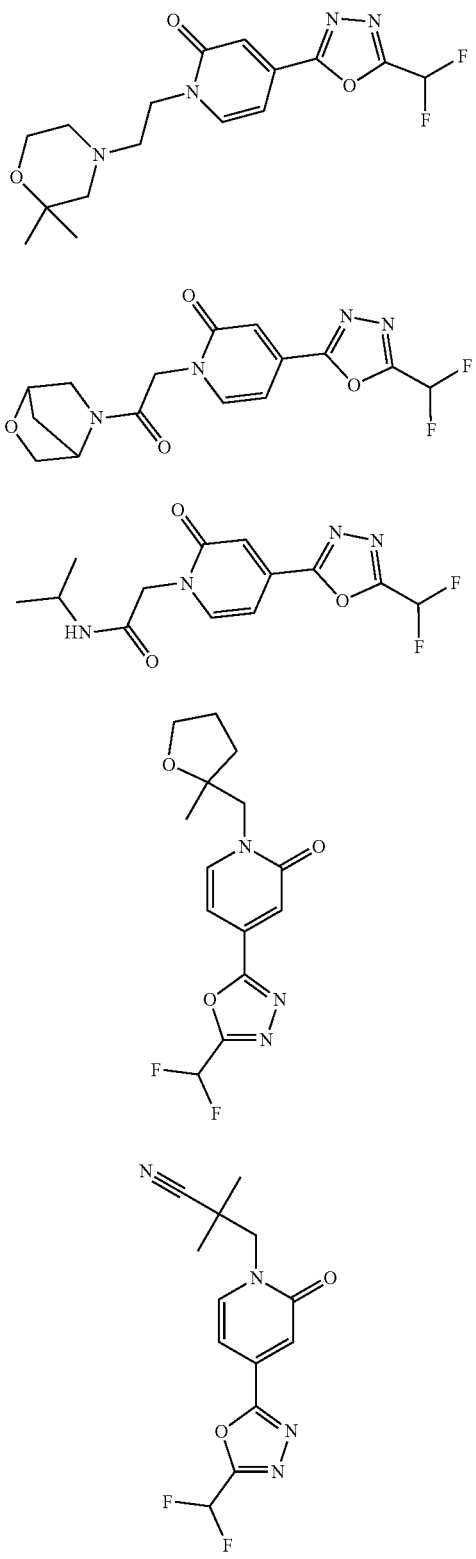
TABLE 2-continued
Compounds of Formula (II) of the Present Disclosure.
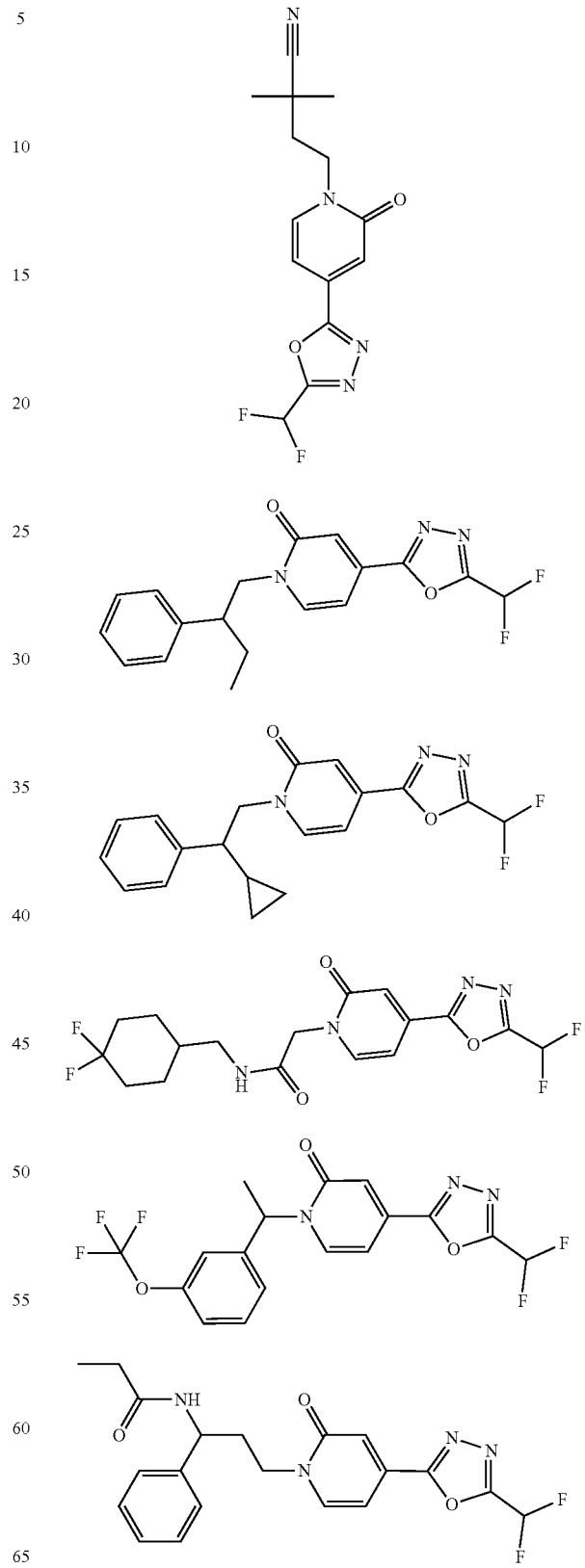

TABLE 2-continued
Compounds of Formula (II) of the Present Disclosure.
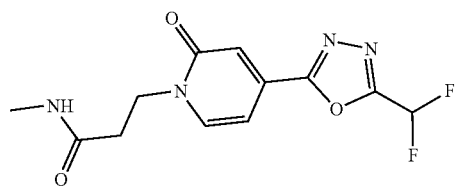 [SMILES: CNC(=O)CCn1ccc(-c2nnc(C(F)F)o2)cc1=O]
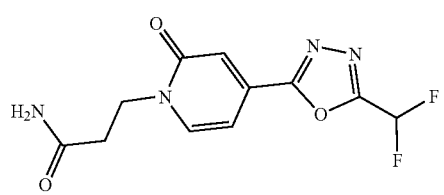 [SMILES: NC(=O)CCn1ccc(-c2nnc(C(F)F)o2)cc1=O]
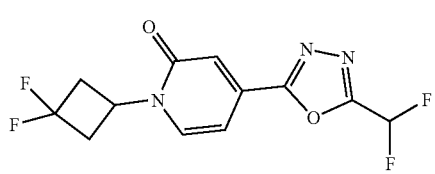 [SMILES: O=c1cc(-c2nnc(C(F)F)o2)ccn1C1CC(F)(F)C1]
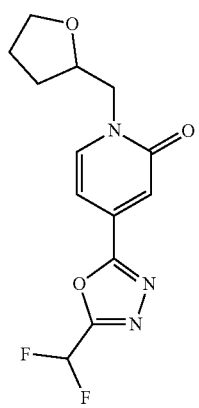 [SMILES: O=c1cc(-c2nnc(C(F)F)o2)ccn1CC1CCCO1]
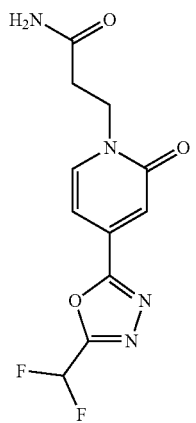
TABLE 2-continued
Compounds of Formula (II) of the Present Disclosure.
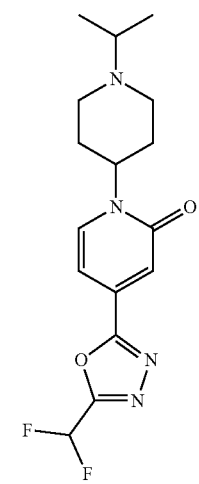
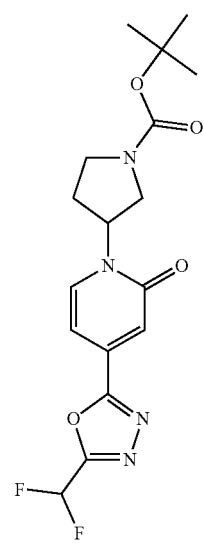 [SMILES: CC(C)(C)OC(=O)N1CCC(n2ccc(-c3nnc(C(F)F)o3)cc2=O)C1]
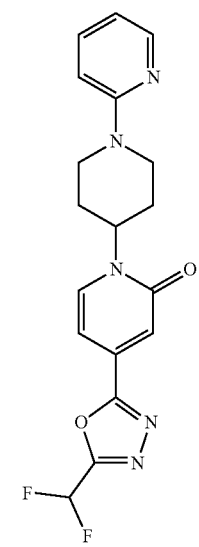

TABLE 2-continued
Compounds of Formula (II) of the Present Disclosure.
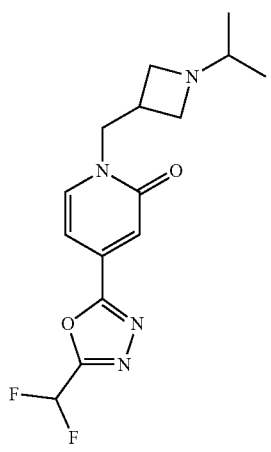
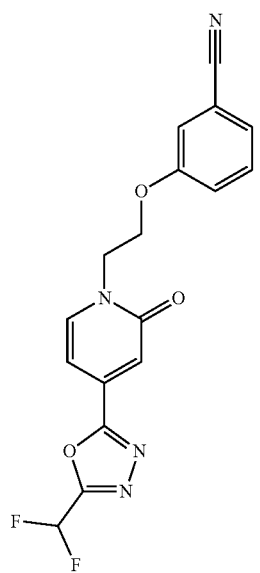 [SMILES: N#Cc1cccc(OCCn2ccc(-c3nnc(C(F)F)o3)cc2=O)c1]
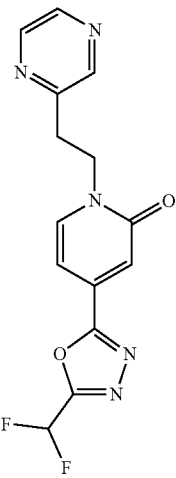
TABLE 2-continued
Compounds of Formula (II) of the Present Disclosure.
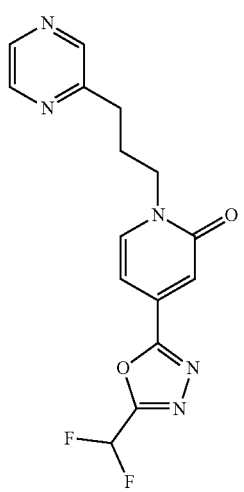 [SMILES: O=c1cc(-c2nnc(C(F)F)o2)ccn1CCCc1cnccn1]
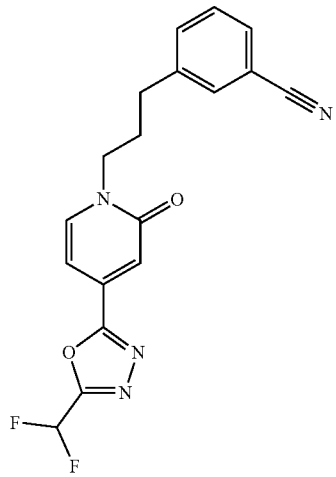 [SMILES: N#Cc1cccc(CCCn2ccc(-c3nnc(C(F)F)o3)cc2=O)c1]
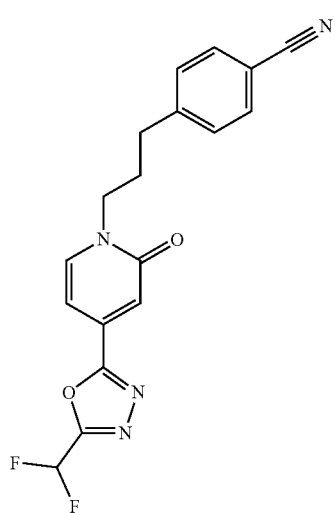 [SMILES: N#Cc1ccc(CCCn2ccc(-c3nnc(C(F)F)o3)cc2=O)cc1]

TABLE 2-continued
Compounds of Formula (II) of the Present Disclosure.
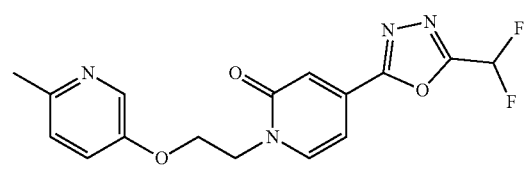 [SMILES: Cc1ccc(OCCn2ccc(-c3nnc(C(F)F)o3)cc2=O)cn1]
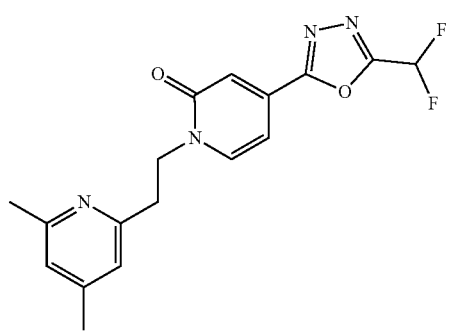 [SMILES: Cc1cc(C)nc(CCn2ccc(-c3nnc(C(F)F)o3)cc2=O)c1]
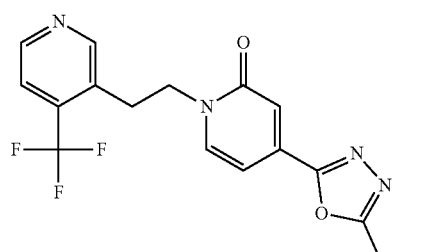
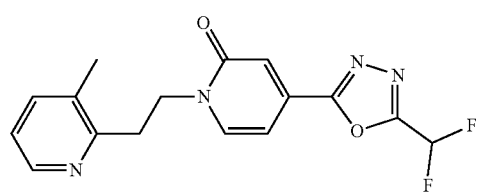 [SMILES: Cc1cccnc1CCn1ccc(-c2nnc(C(F)F)o2)cc1=O]
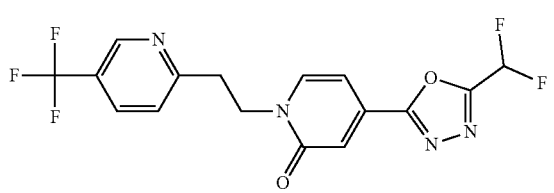 [SMILES: O=c1cc(-c2nnc(C(F)F)o2)ccn1CCc1ccc(C(F)(F)F)cn1]
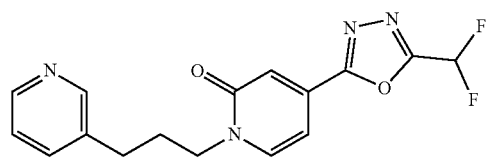 [SMILES: O=c1cc(-c2nnc(C(F)F)o2)ccn1CCCc1cccnc1]
TABLE 2-continued
Compounds of Formula (II) of the Present Disclosure.
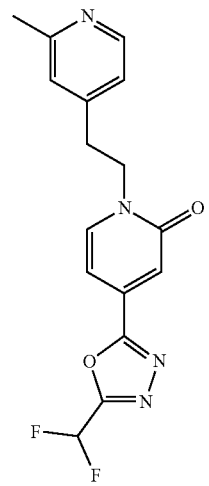 [SMILES: Cc1cc(CCn2ccc(-c3nnc(C(F)F)o3)cc2=O)ccn1]
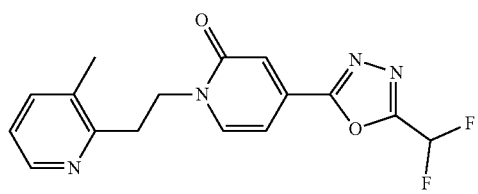 [SMILES: Cc1cccnc1CCn1ccc(-c2nnc(C(F)F)o2)cc1=O]
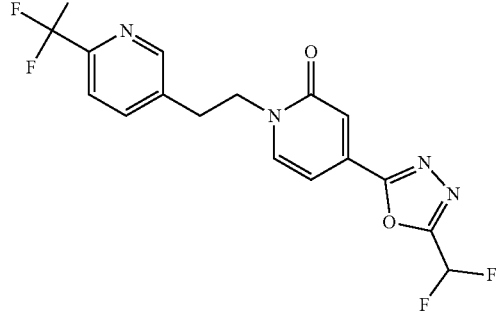
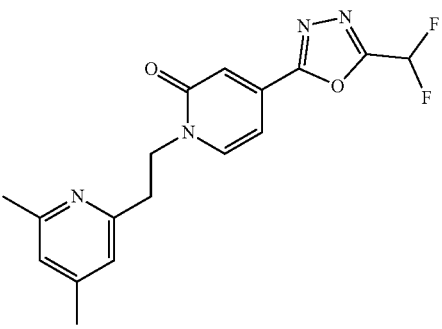 [SMILES: Cc1cc(C)nc(CCn2ccc(-c3nnc(C(F)F)o3)cc2=O)c1]

TABLE 2-continued
Compounds of Formula (II) of the Present Disclosure.
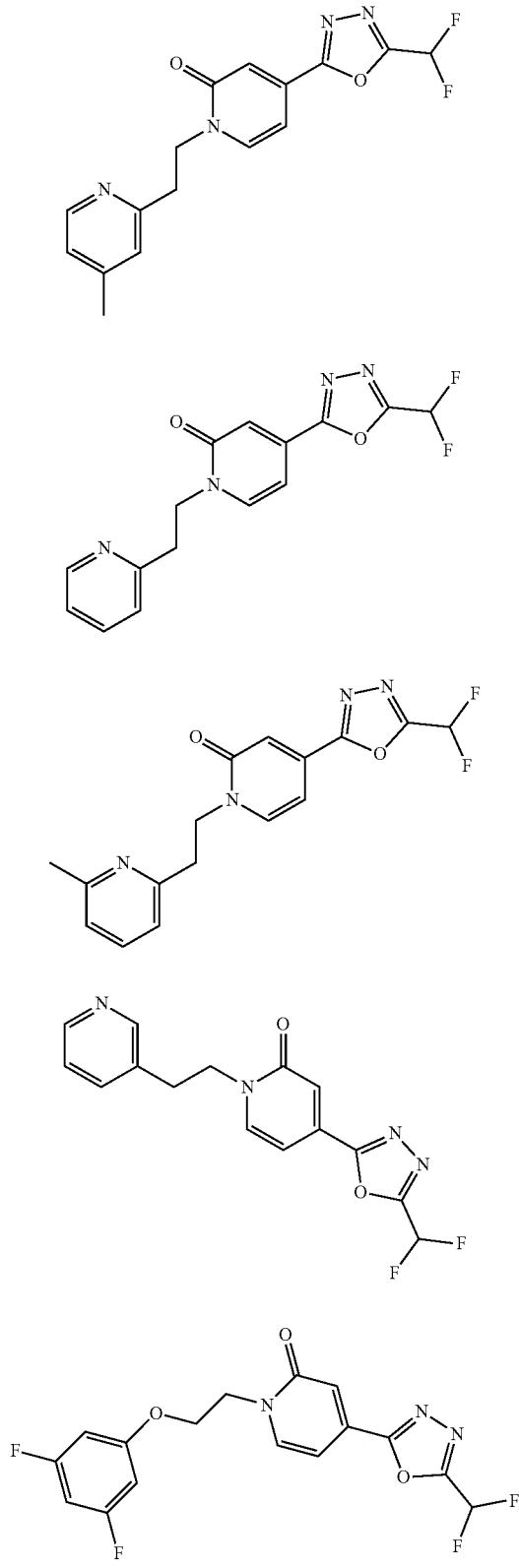
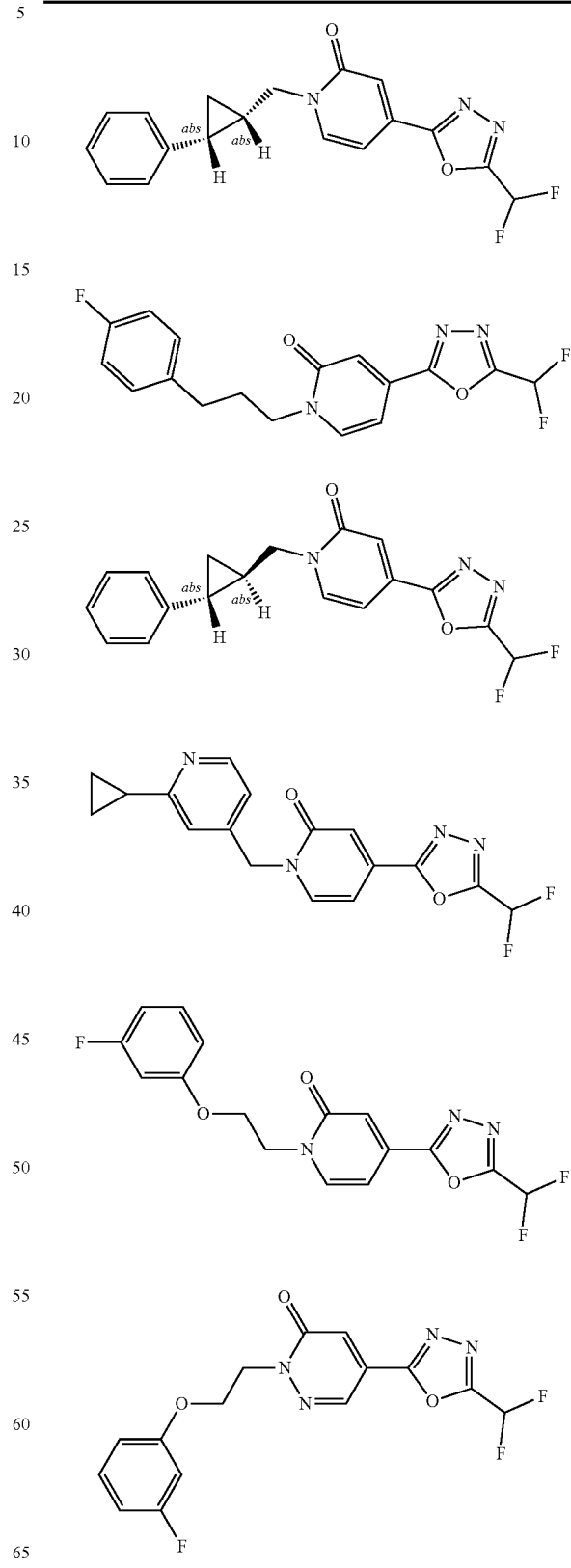

TABLE 2-continued

Compounds of Formula (II) of the Present Disclosure.

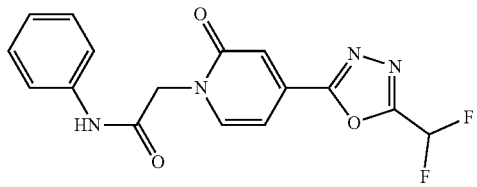 [SMILES: O=C(Cn1ccc(-c2nnc(C(F)F)o2)cc1=O)Nc1ccccc1]

Compounds of Formulas (III)

In another aspect, the present disclosure provides a compound of Formula (III) or pharmaceutically acceptable salt thereof:

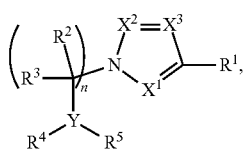
(III)

wherein
$R^1$ is selected from the group consisting of:

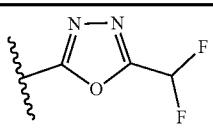

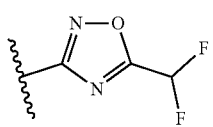

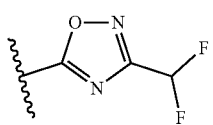 [SMILES: *c1nc(C(F)F)no1]

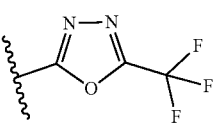 [SMILES: *c1nnc(C(F)(F)F)o1]

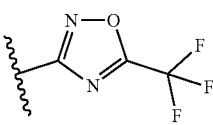 [SMILES: *c1noc(C(F)(F)F)n1]

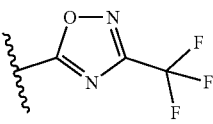 [SMILES: *c1nc(C(F)(F)F)no1]

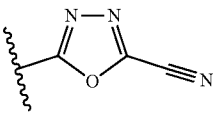 [SMILES: *c1nnc(C#N)o1]

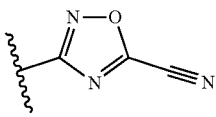 [SMILES: *c1noc(C#N)n1]

and

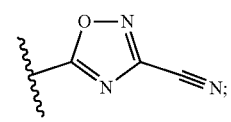

and

;

$R^a$ is selected from the group consisting of halo, $C_{1-3}$ alkyl, cycloalkyl, haloalkyl, and alkoxy;

$R^2$ and $R^3$ are independently selected from the group consisting of H, halogen, alkoxy, haloalkyl, aryl, heteroaryl, alkyl, and cycloalkyl, or $R^2$ and $R^3$ together with the atom to which they are attached form a cycloalkyl or heterocyclyl;

$R^4$ and $R^5$ are selected from the group consisting of H, —(SO$_2$)R$^2$, —(SO$_2$)NR$^2$R$^3$, —(CO)R$^2$, —(CONR$^2$R$^3$), aryl, arylheteroaryl, heteroaryl, cycloalkyl, heterocyclyl, alkyl, haloalkyl, and alkoxy, each of which is optionally substituted or $R^4$ and $R^5$ together with the atom to which they are attached form a cycloalkyl or heterocyclyl;

$X^1$, $X^2$, and $X^3$ are selected from the group consisting of: (1) $X^1$ is $CR^a$, $X^2$ is N, and $X^3$ is $CR^a$; (2) $X^1$ is N, $X^2$ is $CR^a$, and $X^3$ is $CR^a$; (3) $X^1$ is $CR^a$, $X^2$ is $CR^a$, and $X^3$ is N; (4) $X^1$ is N, $X^2$ is $CR^a$, and $X^3$ is (5) $X^1$ is $CR^a$, $X^2$ is N, and $X^3$ is N; and (6) $X^1$ is N, $X^2$ is N, and $X^3$ is $CR^a$;

Y is selected from the group consisting of $CR^2$, O, N, S, SO, and SO$_2$, wherein when Y is O, S, SO, or SO$_2$, $R^5$ is not present and when $R^4$ and $R^5$ together with the atom to which they are attached form a cycloalkyl or heterocyclyl, Y is $CR^2$ or N; and n is 1 or 2.

In some embodiments, n is 1. In some embodiments n is 2.

In some embodiments of Formula (III), wherein $X^1$ is $CR^a$, $X^2$ is N; and $X^3$ is $CR^a$. In some embodiments, $X^1$ is N, $X^2$ is $CR^a$; and $X^3$ is $CR^a$. In some embodiments, $R^a$ is H.

In some embodiments of Formula (III), $R^2$ and $R^3$ are H.

In some embodiments of Formula (III), Y is —CR$^2$ and $R^2$ is H.

In some embodiments of Formula (III), Y is N. In some embodiments of Formula (III), $R^4$ is —(SO$_2$)R$^2$ and $R^5$ is aryl. In some embodiments, $R^4$ is —(SO$_2$)R$^2$ and $R^5$ is heteroaryl. In some embodiments, $R^4$ is —(SO$_2$)R$^2$ and $R^5$ is cycloalkyl. In some embodiments, $R^4$ is —(CO)R$^2$ and $R^5$ is aryl.

In some embodiments Formula (III), $R^4$ is —(CO)R$^2$ and $R^5$ is H.

In some embodiments of Formula (III), $R^4$ is selected from the group consisting of ethyl sulfonyl, methyl sulfonyl and cyclopropyl sulfonyl. In some embodiments $R^4$ is ethyl sulfonyl. In some embodiments $R^4$ is methyl sulfonyl. In some embodiments, $R^4$ is selected from the group consisting of —(SO$_2$)-alkyl and —(CO)-aryl. In some embodiments, the alkyl or aryl are optionally substituted with one or more halogens.

In some embodiments of Formula (III), $R^5$ is selected from the group consisting of phenyl, 3-chlorophenyl, 3-chloro-4-fluorophenyl, 3-trifluoromethylphenyl, 3,4-difluorophenyl, and 2,6-difluorophenyl. In some embodiments, $R^5$ is cyclopropyl. In some embodiments, $R^5$ is selected from the group consisting of pyridin-3-yl and 1-methylindazole-6-yl. In some embodiments, $R^5$ is selected from the group consisting of H, pyridin-2-yl, 3-chlorophenyl, and phenyl.

In some embodiments of Formula (III), $R^1$ is

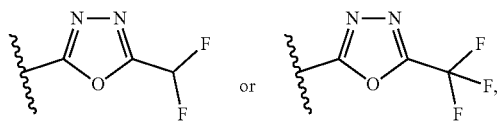 [SMILES: *c1nnc(C(F)F)o1 ; *c1nnc(C(F)(F)F)o1]

$X^1$ is CH, $X^2$ is N; and $X^3$ is CH; Y is $CR^2$ or N; $R^4$ and $R^5$ together with the atom to which they are attached form a cycloalkyl or heterocyclyl; and variables $R^2$, $R^3$, and n are as defined above for Formula (III).

In some embodiments of Formula (III), $R^1$ is

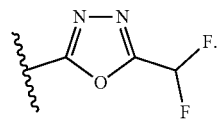 [SMILES: *c1nnc(C(F)F)o1]

In some embodiments, $R^1$ is

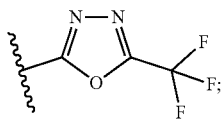 [SMILES: *c1nnc(C(F)(F)F)o1]

In some embodiments, $R^a$ is H, halo, $C_{1-3}$alkyl, or haloalkyl. In some embodiments, $R^a$ is H. In some embodiments, $R^a$ is $C_{1-3}$alkyl. In some embodiments, $R^a$ is haloalkyl. In some embodiments, halo is F. In some embodiments, the $C_{1-3}$alkyl alkyl is methyl, ethyl or isopropyl. In some embodiments, haloalkyl is $CF_3$, $CHF_2$, or $CH_2F$.

In some embodiments, the compounds of Formula (III) are selected from the group consisting of:

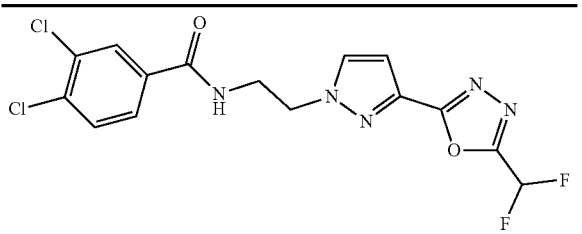

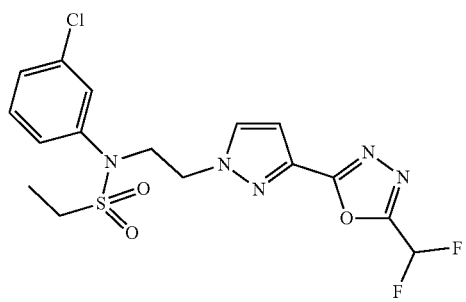 [SMILES: CCS(=O)(=O)N(CCn1ccc(-c2nnc(C(F)F)o2)n1)c1cccc(Cl)c1]

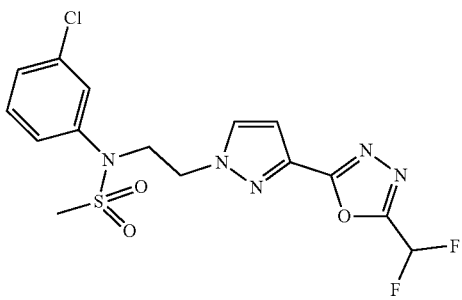 [SMILES: CS(=O)(=O)N(CCn1ccc(-c2nnc(C(F)F)o2)n1)c1cccc(Cl)c1]

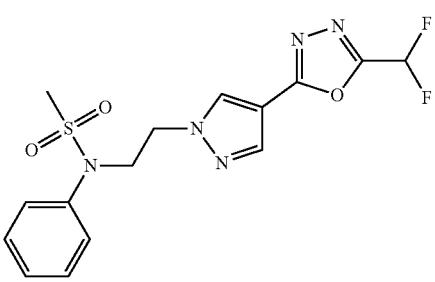 [SMILES: CS(=O)(=O)N(CCn1cc(-c2nnc(C(F)F)o2)cn1)c1ccccc1]

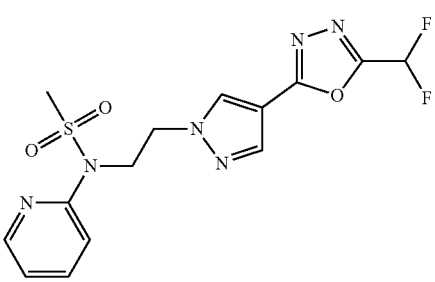 [SMILES: CS(=O)(=O)N(CCn1cc(-c2nnc(C(F)F)o2)cn1)c1ccccn1]

and

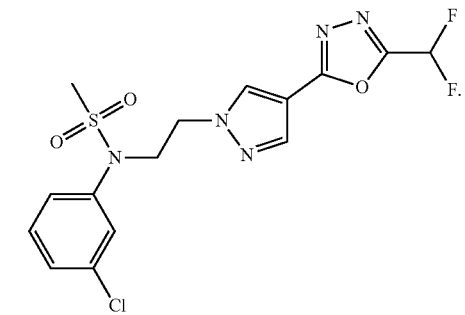

.

Compounds of Formula (IV)

In some embodiments, the present disclosure provides a compound of Formula (IV) or a pharmaceutically acceptable salt thereof:

(IVa)

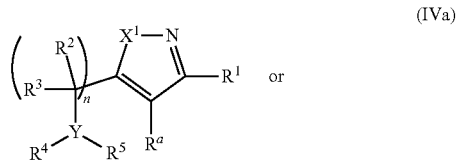

or

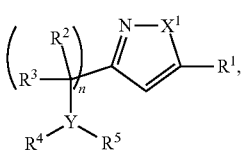

wherein
R¹ is selected from the group consisting of:

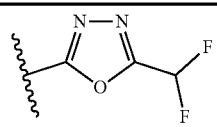

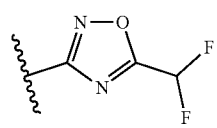 [SMILES: *c1noc(C(F)F)n1]

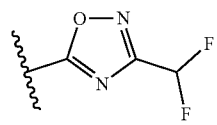 [SMILES: *c1nc(C(F)F)no1]

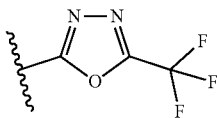 [SMILES: *c1nnc(C(F)(F)F)o1]

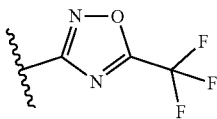 [SMILES: *c1noc(C(F)(F)F)n1]

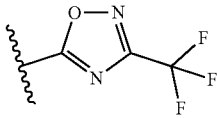

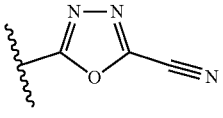 [SMILES: *c1nnc(C#N)o1]

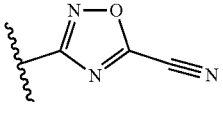 [SMILES: *c1noc(C#N)n1]

and

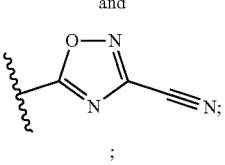

$R^a$ is selected from the group consisting of H, halo, $C_{1-3}$ alkyl, cycloalkyl, haloalkyl, and alkoxy;
$R^2$ and $R^3$ are independently selected from the group consisting of H, halogen, alkoxy, haloalkyl, aryl, heteroaryl, alkyl, and cycloalkyl each of which is optionally substituted, or $R^2$ and $R^3$ together with the atom to which they are attached form a cycloalkyl or heterocyclyl;
$R^4$ and $R^5$ are independently selected from the group consisting of H, $(SO_2)R^2$, $—(SO_2)NR^2R^3$, $—(CO)R^2$, $—(CONR^2R^3)$, aryl, arylheteroaryl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl;
$X^1$ is selected from the group consisting of O, S, NH, or $NR^6$, wherein $R^6$ is selected from the group consisting of $C_1$-$C_6$ alkyl, alkoxy, haloalkyl, cycloalkyl and heterocyclyl; and
Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and
n is selected from 0, 1, or 2.

In some embodiments of Formula (IVa) and (IVb), n is 0. In some embodiments, n is 1. In some embodiments n is 2. In some embodiments n is 1 or 2.

In some embodiments Formula (IVa) and (IVb), $X^1$ is O. In some embodiments, $X^1$ is NH. In some embodiments, $X^1$ is $NR^6$. In some embodiments, $X^1$ is $NCH_3$. In some embodiments $X^1$ is O or $NCH_3$.

In some embodiments of Formula (IVa) and (IVb), $R^2$ and $R^3$ are H.

In some embodiments of Formula (IVa) and (IVb), Y is N.

In some embodiments of Formula (IVa) and (IVb), $R^4$ is $—(SO_2)R^2$ and $R^5$ is aryl. In some embodiments, $R^4$ is $—(SO_2)R^2$ and $R^5$ is heteroaryl. In some embodiments, $R^4$ is $—(SO_2)R^2$ and $R^5$ is cycloalkyl. In some embodiments, $R^4$ is $—(CO)R^2$ and $R^5$ is aryl. In some embodiments, $R^4$ is $—(CO)R^2$ and $R^5$ is H.

In some embodiments of Formula (IVa) and (IVb), $R^4$ is selected from the group consisting of ethyl sulfonyl, methyl sulfonyl and cyclopropyl sulfonyl. In some embodiments, $R^a$ is selected from the group consisting of $—(SO_2)$-alkyl, $—(SO_2)$-cycloalkyl, $—(CO)$-alkyl, $—(CO)$-aryl and $—(CO)$-cycloalkyl. In some embodiments the alkyl, cycloalkyl and aryl are optionally substituted with one or more halogen atoms.

In some embodiments of Formula (IVa) and (IVb), $R^5$ is selected from the group consisting of phenyl, 3-chlorophenyl, 3-chloro-4-fluorophenyl, 3-trifluoromethylphenyl, 3,4-difluorophenyl, and 2,6-difluorophenyl. In some embodiments, $R^5$ is cyclopropyl. In some embodiments, $R^5$ selected from the group consisting of pyridin-3-yl and 1-methylindazole-6-yl. In some embodiments, $R^5$ is 3-chlorophenyl, In some embodiments of Formula (IVa) and (IVb), $R^1$ is

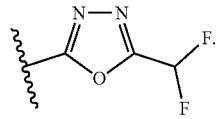 [SMILES: *c1nnc(C(F)F)o1]

In some embodiments of Formula (IVa) and (IVb), $R^a$ is H, halo, $C_{1-3}$alkyl, or haloalkyl. In some embodiments, $R^a$ is H. In some embodiments, $R^a$ is $C_{1-3}$alkyl. In some embodiments, $R^a$ is haloalkyl. In some embodiments, halo is F. In some embodiments, the $C_{1-3}$alkyl alkyl is methyl, ethyl or isopropyl. In some embodiments, haloalkyl is $CF_3$, $CHF_2$, or $CH_2F$.

In some embodiments, the compound of Formula (IVa) or Formula (IVb) is selected from the group consisting of:

173
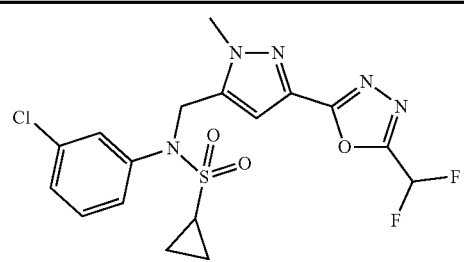
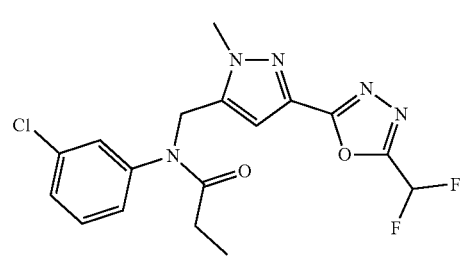 [SMILES: CCC(=O)N(Cc1cc(-c2nnc(C(F)F)o2)nn1C)c1cccc(Cl)c1]
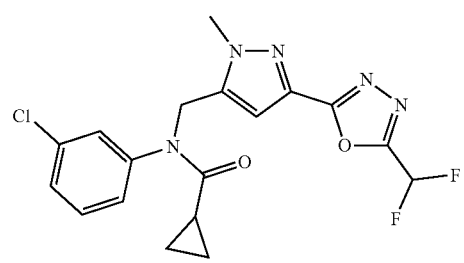 [SMILES: Cn1nc(-c2nnc(C(F)F)o2)cc1CN(C(=O)C1CC1)c1cccc(Cl)c1]
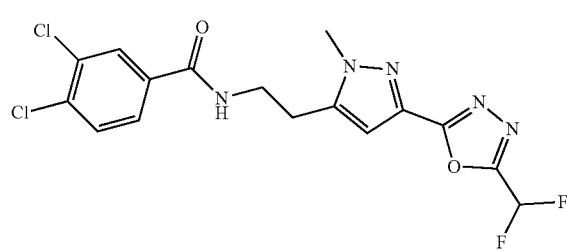 [SMILES: Cn1nc(-c2nnc(C(F)F)o2)cc1CCNC(=O)c1ccc(Cl)c(Cl)c1]
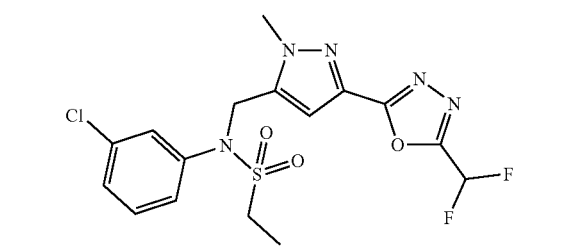 [SMILES: CCS(=O)(=O)N(Cc1cc(-c2nnc(C(F)F)o2)nn1C)c1cccc(Cl)c1]
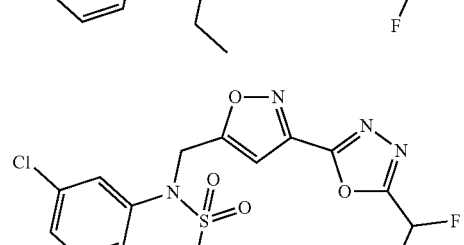
174
-continued
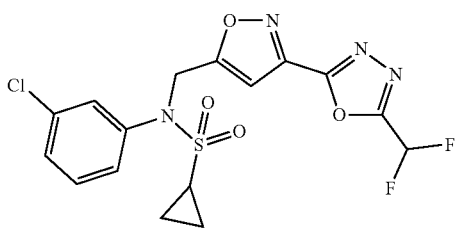 [SMILES: O=S(=O)(C1CC1)N(Cc1cc(-c2nnc(C(F)F)o2)no1)c1cccc(Cl)c1]
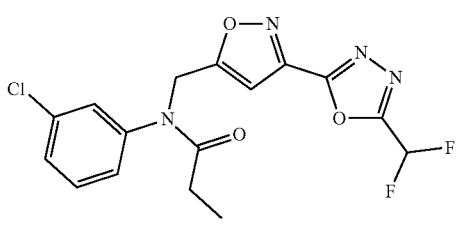 [SMILES: CCC(=O)N(Cc1cc(-c2nnc(C(F)F)o2)no1)c1cccc(Cl)c1]
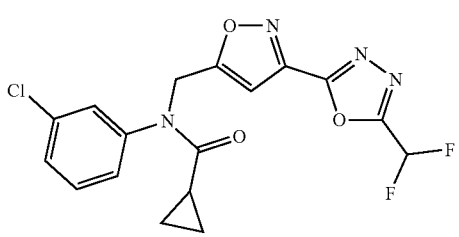 [SMILES: O=C(C1CC1)N(Cc1cc(-c2nnc(C(F)F)o2)no1)c1cccc(Cl)c1]
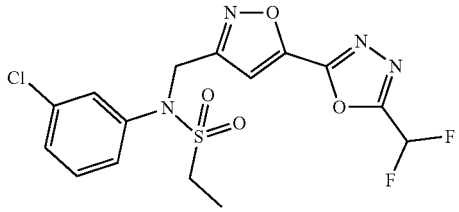 [SMILES: CCS(=O)(=O)N(Cc1cc(-c2nnc(C(F)F)o2)on1)c1cccc(Cl)c1]
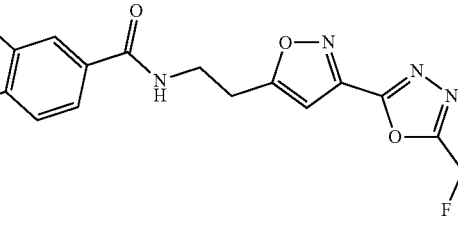
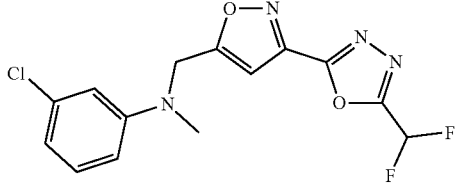 [SMILES: CN(Cc1cc(-c2nnc(C(F)F)o2)no1)c1cccc(Cl)c1]
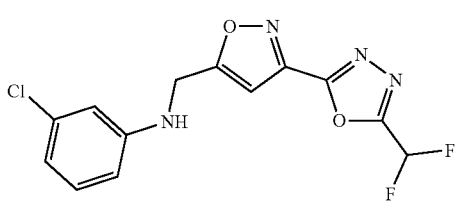 [SMILES: FC(F)c1nnc(-c2cc(CNc3cccc(Cl)c3)on2)o1]

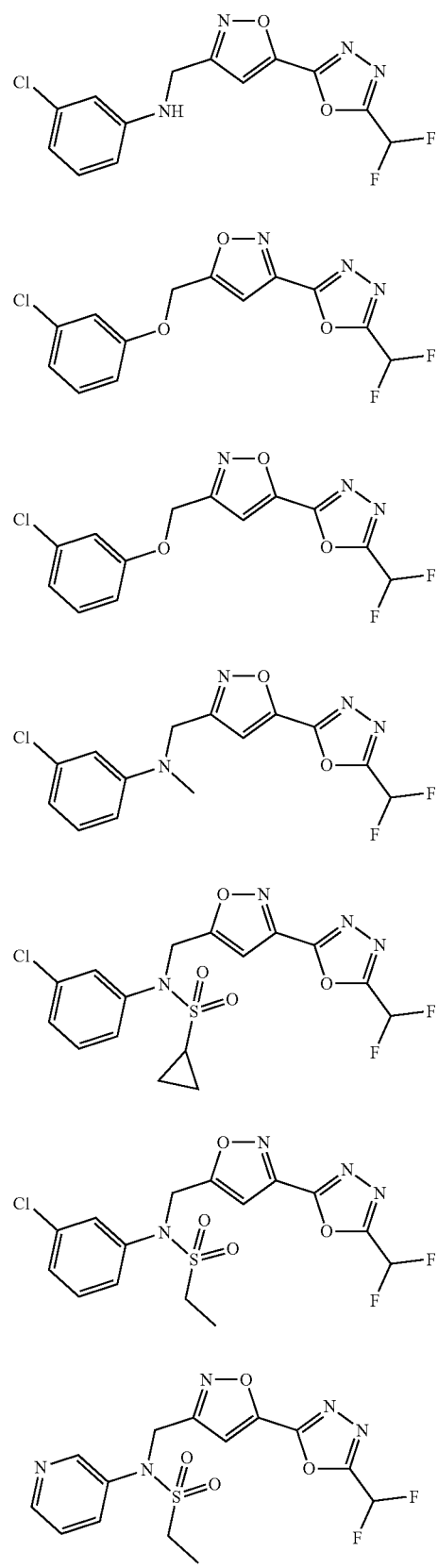
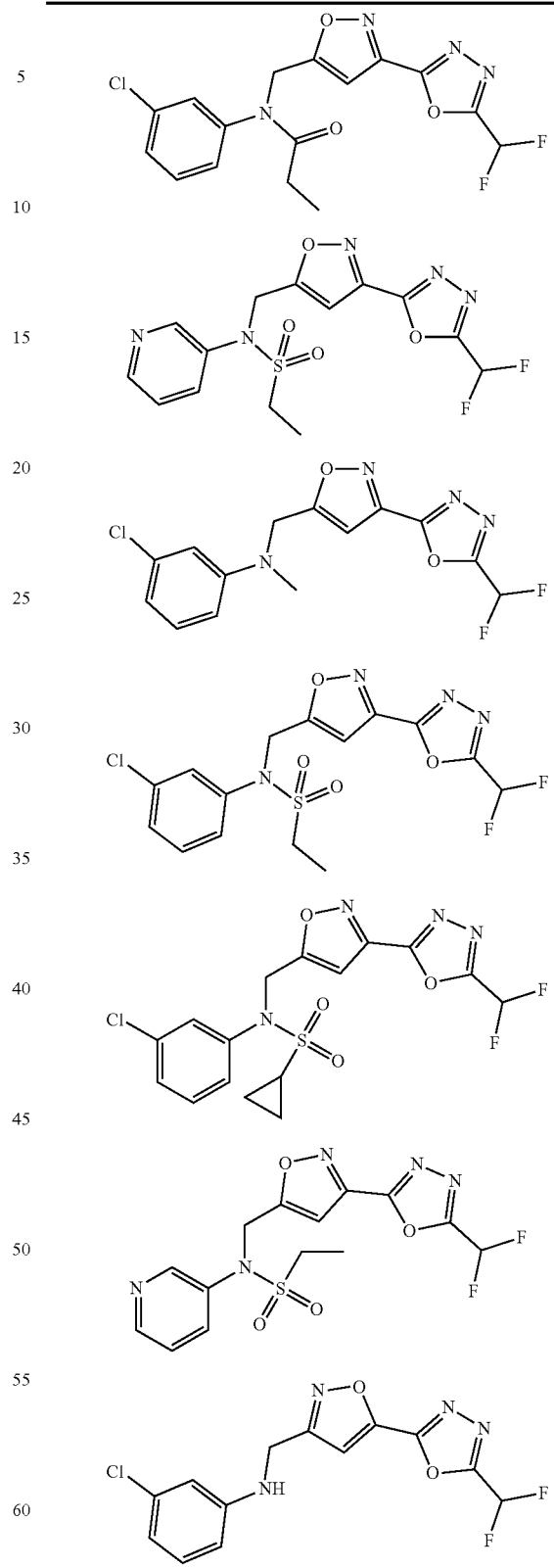
In some embodiments, the compound of the present disclosure is a compound of Table 3. In some embodiments, the compound of the present disclosure is a compound of Table 4.

In some embodiments, the compounds of the present disclosure encompass any isotopically-labeled (or "radio-labelled") derivatives of a compound described herein. Such a derivative is a derivative of a compound having a formula described herein wherein one or more atoms are replaced by an atom having an atomic mass or mass number different from the atomic mass or mass number typically found in nature. Examples of radionuclides that may be incorporated include $^2$H (also written as "D" for deuterium). As such, in one embodiment, a compound of Formula (I), Formula (Ia), Formula (Ib), Formula (Ic), Formula (Id), Formula (Id-1), Formula (Id-2), Formula (Id-3), Formula (Id-4), Formula (Ie), Formula (Ie-1), Formula (If), Formula (If-1), Formula (Ig), Formula (Ig-1), Formula (Ih), Formula (Ih-1), Formula (Ii), Formula (Ii-1), Formula (Ij), Formula (Ij-1), Formula (Ik), Formula (Ik-1), Formula (Ik-2), Formula (Ik-3), Formula (II), Formula (III), Formula (IVa), or Formula (IVb) is provided where one or more hydrogen atoms are replaced by one or more deuterium atoms.

Pharmaceutical Compositions

In various embodiments of the present disclosure, pharmaceutical compositions comprising one or more compounds disclosed herein, e.g., a compound of Formula (I), Formula (Ia), Formula (Ib), Formula (Ic), Formula (Id), Formula (Id-1), Formula (Id-2), Formula (Id-3), Formula (Id-4), Formula (Ie), Formula (Ie-1), Formula (If), Formula (If-1), Formula (Ig), Formula (Ig-1), Formula (Ih), Formula (Ih-1), Formula (Ii), Formula (Ii-1), Formula (Ij), Formula (Ij-1), Formula (Ik), Formula (Ik-1), Formula (Ik-2), Formula (Ik-3), Formula (II), Formula (III), Formula (IVa), or Formula (IVb) or a pharmaceutically acceptable solvate, hydrate, tautomer, N-oxide, or salt thereof, and a pharmaceutically acceptable excipient or adjuvant is provided. The pharmaceutically acceptable excipients and adjuvants are added to the composition or formulation for a variety of purposes. In some embodiments, a pharmaceutical compositions comprising one or more compounds disclosed herein, or a pharmaceutically acceptable solvate, hydrate, tautomer, N-oxide, or salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically, stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using e.g. prepacked silica gel cartridges, e.g. RediSep®R$_f$ and eluents such as gradients of 0-100% EtOAc in hexanes or 0-100% of 10% MeOH in $CH_2Cl_2$ Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art or be used as salts in subsequent biological assays. It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^1$H Nuclear magnetic resonance (NMR) spectroscopy was carried out using a Bruker Avance III instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification was performed by reverse phase HPLC using Agilent Technologies 1200 Infinity Series or an equivalent HPLC system such as Teledyne ISCO CombiFlash R$_f$.

Chemical names were generated using the ChemDraw naming software (Version 17.0.0.206) by PerkinElmer Informatics, Inc. In some cases, generally accepted names of commercially available reagents were used in place of names generated by the naming software.

Abbreviations

The following abbreviations are used in the examples, while other abbreviations have their customary meaning in the art:
AIBN Azobisisobutyronitrile
BOC: tert-butoxycarbonyl protecting group
DCM: Dichloromethane
DFAA: Difluoroacetic anhydride
DIPEA: Diisopropylethylamine
DMSO: Dimethylsulfoxide
EDCl: 1-ethyl-3-(3-dimethylaminopropyl)carbodiimide hydrochloride
EtOAc: Ethyl acetate
h: hour(s)
HATU 1-[Bis(dimethylamino)methylene]-1H-1,2,3-triazolo [4,5-b]pyridinium 3-oxid hexafluorophosphate
HCl: Hydrochloric acid
HOBt: Hydroxybenzotriazole
KO$^t$Bu: Potassium t-butoxide
L: Liter
LCMS: liquid chromatography-mass spectrometry
M: Molar
MeOH: Methanol min: Minute(s)
μL: Microliter
mL: Millliliter
N: Normal
NBS N-bromosuccinimide
NMR: nuclear magnetic resonance spectroscopy
ppm: parts per million
rt: Room temperature
tR: Retention time
sat.: Saturated
TEA: Triethylamine
TFA Trifluoroacetic acid
TFAA Trifluoroacetic anhydride
THF: Tetrahydrofuran
TSCl p-Toluenesulfonyl chloride Analytical LC-MS Methods Column: Eclipse Plus C18 4.6×3.5 μm; eluent A: 0.1% TEA in H$_2$O; eluent B: 0.1% TFA in CH$_3$CN; gradient: 20-100% over 4 minutes; flow: 1.5 mL/min; injection volume 1-5 μL; temperature: 23° C.; UV scan: 220 and 250 nm; signal settings—scan positive mode.

Analytical HPLC Methods

Column: Eclipse Plus C18 4.6×110 mm; eluent A: 0.1% TFA in H$_2$O; eluent B: 0.1% TFA in CH$_3$CN; gradient: 10-100% eluent B over 10 minutes; flow: 1 mL/min; injection volume 1-5 μL; temperature: 23° C.; UV scan: 220, 254 and 280 nm (method 1); 20-100% eluent B over 10 minutes; flow: 1 mL/min; injection volume 1-5 μL; temperature: 23° C.; UV scan: 220, 254 and 280 nm (method 2).

Preparative HPLC

Instrument: Agilent Technologies 1200 Infinity Series Column: Gemini 5 μm NX-C18 110 Å, 250×21.2 mm; eluent A: 0.1% TFA in H$_2$O, eluent B: 0.1% TFA in CH$_3$CN; gradient: 10-100%; flow: 20 mL/min; injection volume 0.5-2 mL; temperature: 23° C.; UV scan: 254 and 220 nm.

Synthesis of Compounds

Example 1: General Scheme for the Synthesis of Compounds of Formula (I) via Intermediate 4 and 6

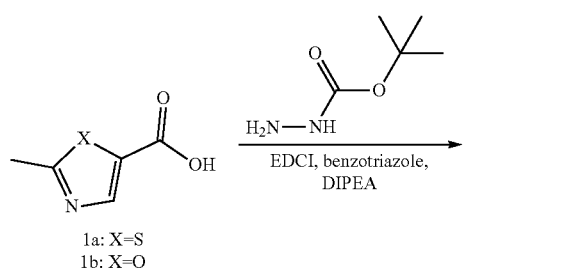

1a: X=S
1b: X=O

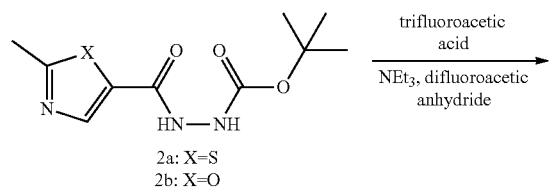

2a: X=S
2b: X=O

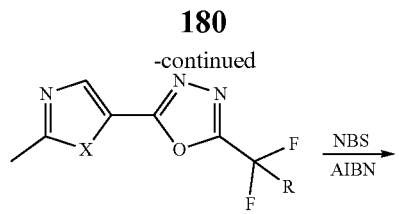

3a: R=H, X=S
3b: R=F, X=S
5a: R=H, X=O
5b: R=F, X=O

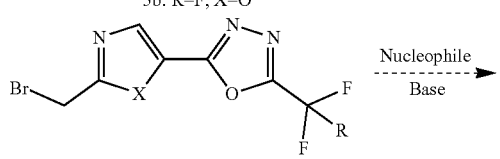

4a: R=H, X=S
4b: R=F, X=S
6a: R=H, X=O
6b: R=F, X=O

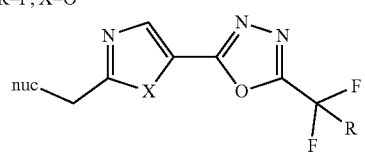

R=H or F

Compound of Formula (I)

Step 1: Preparation of tert-butyl 2-(2-methylthiazole-5-carbonyl)hydrazine-1-carboxylate (2a).

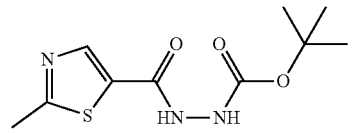 [SMILES: Cc1ncc(C(=O)NNC(=O)OC(C)(C)C)s1]

(Tert-butoxy)carbohydrazide (21 g, 161 mmol) was taken up in DMF (300 ml) and EDCI (31 g, 161 mmol) and benzotriazole (13 g, 94 mmol) were added. 2-Methyl-1,3-thiazole-5-carboxylic acid (1a, 20 g, 140 mmol) was then added and the resulting solution was cooled in an ice-bath. Diisopropylethylamine (53 ml, 307 mmol) was then added to the solution slowly and the reaction was stirred for 36 h. TLC indicated that the reaction was complete. The solution was quenched by adding water and then extracted with EtOAc (×2). The combined organic layers were filtered through MgSO$_4$ and concentrated. The residue was purified on Combiflash (DCM/methanol) to give the product as a yellow foam. $^1$H NMR (400 MHz, DMSO-d$_6$) δ 10.33 (s, 1H), 9.01 (s, 1H), 8.23 (s, 1H) 2.69 (s, 3H) 1.43 (s, 9H). LC-MS: tR (min) 3.15 (20-100% ACN with 0.1% TFA 6 min), m/z [M+H]+ C$_{10}$H$_{16}$N$_3$O$_3$S requires: 258.3; found 258.0

Step 2: Preparation of 2-(difluoromethyl)-5-(2-methylthiazol-5-yl)-1,3,4-oxadiazole (3a).

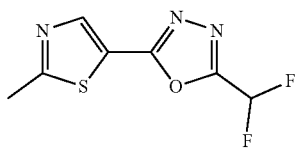

tert-Butyl 2-(2-methylthiazole-5-carbonyl)hydrazine-1-carboxylate (2.7 g, 10.5 mmol) was taken up in DCM (100 ml) and cooled in an ice-bath. Trifluoroacetic acid (8.0 ml, 105 mmol) was added dropwise to the solution and the reaction solution was stirred for 18 h at room temperature. TLC indicated that the reaction was complete. The solution was concentrated to give the hydrazide salt as a yellow oil. The resulting oil was dissolved in DMF (100 mL) and triethylamine (11.7 mL, 84 mmol) was added. Difluoroacetic anhydride (2.6 mL, 21 mmol) was then added and the solution was heated at 80° C. for 16 h. After cooling to room temperature, the solution was diluted with EtOAc and washed with water. The organic layer was filtered through MgSO$_4$ and concentrated. The resulting residue was purified on Combiflash (hexanes/EtOAc gradient) to afford the title compound (1.0 g, 44%) as an off-white solid. $^1$H NMR (400 MHz, CDCl$_3$) δ 8.35 (s, 1H) 6.90 (t, J=51.6 Hz, 1H) 2.83 (s, 3H). LC-MS: tR (min) 3.65 (20-100% ACN with 0.1% TFA 6 min), m/z C$_7$H$_6$N$_3$F$_2$OS requires: 217.2; found 218.0. HPLC Rt 5.35 min; 97.2% (10-100% ACN with 0.1% TFA 10 min.)

Step 3: Preparation of 2-[2-(bromomethyl)-1,3-thiazol-5-yl]-5-(difluoromethyl)-1,3,4-oxadiazole (4a)

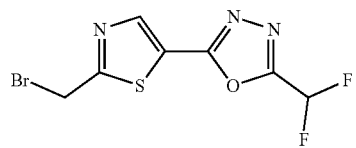 [SMILES: FC(F)c1nnc(-c2cnc(CBr)s2)o1]

2-(difluoromethyl)-5-(2-methylthiazol-5-yl)-1,3,4-oxadiazole (1.2 g, 5.5 mmol) was taken up in 1,2-dichloroethane (200 ml) with N-bromosuccinimide (1.7 g, 9.9 mmol) and 2-[(1E)-2-(1-cyano-1-methylethyl)diazen-1-yl]-2-methyl-propanenitrile (91 mg, 0.55 mmol) was added. The resulting solution was heated to reflux for 5 h. The solution was cooled to room temperature and concentrated. The residue was purified on Combiflash (hexanes/EtOAc) gradient to afford the title product (1.0 g, 63%) as a white solid. $^1$H NMR (400 MHz, CDCl$_3$) δ 8.43 (s, 1H) 6.20 (t, J=51.6 Hz, 1H) 4.78 (s, 2H). LC-MS: tR (min) 4.44 (20-100% ACN with 0.1% TFA 6 min), m/z [M+H]$^+$ C$_7$H$_5$BrF$_2$N$_3$OS requires: 296.1; found 295.9, 297.9.

Example 2. Synthesis of Amide Compounds of Formula (I)—Nucleophilic Substitution

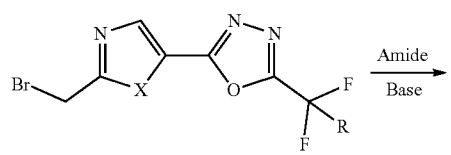

4a: R=H, X=S
4b: R=F, X=S
6a: R=H, X=O
6b: R=F, X=O

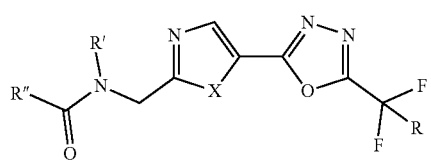

R=H or F

Compound of Formula (I)

Preparation of 4-((5-(5-(difluoromethyl)-1,3,4-oxadiazol-2-yl)thiazol-2-yl)methyl)-2,2-dimethyl-2H-pyrido[3,2-b][1,4]oxazin-3(4H)-one:

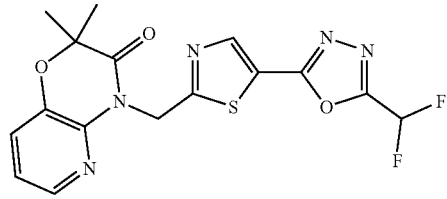

I-1

2,2-Dimethyl-2H,3H,4H-pyrido[3,2-b][1,4]oxazin-3-one (40 mg, 0.22 mmol) was taken up in DMF (0.7 ml) in an ice-bath. Sodium hydride (10 mg, 60 wt %, 0.22 mmol) was added and the solution was stirred for 20 min at 0° C. A solution of 2-[2-(bromomethyl)-1,3-thiazol-5-yl]-5-(difluoromethyl)-1,3,4-oxadiazole (4a, 50 mg, 0.17 mmol) in DMF (0.5 ml) was then added dropwise at 0° C. The solution was stirred at room temperature for 4 h. TLC indicted that the reaction was complete (all the bromide was consumed). The reaction was quenched by adding water and the separated aqueous phase was extracted with EtOAc. The organic layer was collected, washed with brine and then filtered through MgSO$_4$. The filtrate was concentrated, and the residue was purified on Combiflash (DCM/methanol gradient) to afford the title compound (42 mg, 63%) as a white powder.

Preparation of N-({5-[5-(difluoromethyl)-1,3,4-oxadiazol-2-yl]-1,3-thiazol-2-yl}methyl)-3-(morpholin-4-yl)-N-(pyridin-3-yl)propenamide (I-185)

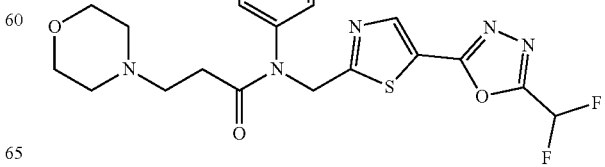

Step : 3-morpholino-N-(3-pyridyl)propanamide

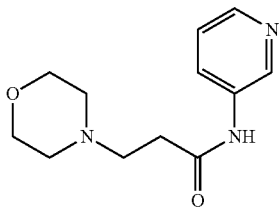 [SMILES: O=C(CCN1CCOCC1)Nc1cccnc1]

A mixture of 3-chloropyridine (359 mg, 3.16 mmol), 3-morpholinopropanamide (500 mg, 3.16 mmol), tris(dibenzylideneacetone)dipalladium(0) (145 mg, 0.16 mmol), ditert-butyl-[2,3,4,5-tetramethyl-6-(2,4,6-triisopropylphenyl)phenyl]phosphane (38 mg, 0.08 mmol) and potassium phosphate (1.0 g, 4.74 mmol) in tert-butanol (10 mL) was heated at 110° C. for 16 h under nitrogen and filtered. The filtrate was concentrated to dryness under reduced pressure. The residue was purified by flash column chromatography (silica gel, 100-200 mesh, 0-7% methanol in dichloromethane) to afford 3-morpholino-N-(3-pyridyl)propanamide (675 mg, 84%) as a brown oil.

Step 2: N-({5-[5-(difluoromethyl)-1,3,4-oxadiazol-2-yl]-1,3-thiazol-2-yl}methyl)-3-(morpholin-4-yl)-N-(pyridin-3-yl)propanamide

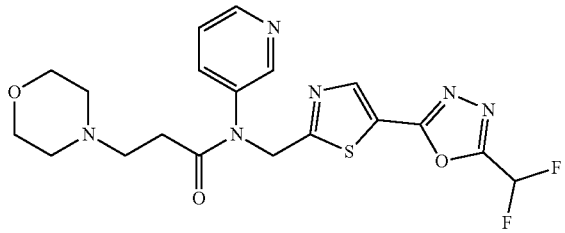 [SMILES: O=C(CCN1CCOCC1)N(Cc1ncc(-c2nnc(C(F)F)o2)s1)c1cccnc1]

To a solution of 3-morpholino-N-(3-pyridyl)propanamide (286 mg, 1.22 mmol) in tetrahydrofuran (5 mL) was added sodium hydride (60%, 41 mg, 1.01 mmol). After stirring at 0° C. for 30 minutes, 2-[2-(bromomethyl)thiazol-5-yl]-5-(difluoromethyl)-1,3,4-oxadiazole (4a, 300 mg, 1.01 mmol) was added. The mixture was stirred at 20° C. for 1 h and filtered. The filtrate was concentrated to dryness under reduced pressure. The residue was purified by RP-HPLC (0 to 20% acetonitrile in water and 0.225% formic acid) to afford N-({5-[5-(difluoromethyl)-1,3,4-oxadiazol-2-yl]-1,3-thiazol-2-yl}methyl)-3-(morpholin-4-yl)-N-(pyridin-3-yl)propanamide (3.4 mg, 3.7%) as a colorless oil.

Preparation of 1-({5-[5-(difluoromethyl)-1,3,4-oxadiazol-2-yl]-1,3-thiazol-2-yl}methyl)-1H,2H,3H,4H,5H-pyrido[4,3-b]azepin-2-one (I-200)

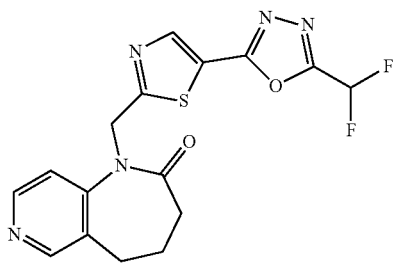 [SMILES: O=C1CCCc2cnccc2N1Cc1ncc(-c2nnc(C(F)F)o2)s1]

Step 1: tert-butyl (E)-4-(4-amino-3-pyridyl)but-3-enoate

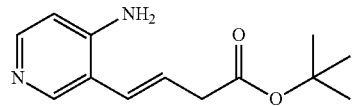 [SMILES: CC(C)(C)OC(=O)C/C=C/c1cnccc1N]

A mixture of 3-bromopyridin-4-amine (1.0 g, 5.78 mmol), tert-butyl but-3-enoate (3.3 g, 23.12 mmol), triethylamine (2.3 g, 23.12 mmol), palladium(II) acetate (130 mg, 0.58 mmol) and tris-o-tolylphosphane (352 mg, 1.16 mmol) in N,N-dimethylformamide (50 mL) was heated at 120° C. for 16 h and filtered. The filtrate was concentrated to dryness under reduced pressure. The residue was purified by flash column chromatography (silica gel, 100-200 mesh, 0-10% methanol in dichloromethane) to afford tert-butyl (E)-4-(4-amino-3-pyridyl)but-3-enoate (431 mg, 30%) as a brown oil.

Step 2: tert-butyl 4-(4-amino-3-pyridyl)butanoate

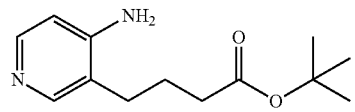

A mixture of tert-butyl (E)-4-(4-amino-3-pyridyl)but-3-enoate (331 mg, 1.41 mmol) and palladium (10% on carbon, 33 mg, 0.03 mmol) in methanol (30 mL) was hydrogenated (15 psi) at 20° C. for 16 h and filtered. The filtrate was concentrated to dryness under reduced pressure. The residue was purified by flash column chromatography (silica gel, 100-200 mesh, 0-7% methanol in dichloromethane) to afford tert-butyl 4-(4-amino-3-pyridyl)butanoate (354 mg, 78%) as a yellow oil.

Step 3: 1,3,4,5-tetrahydropyrido[4,3-b]azepin-2-one

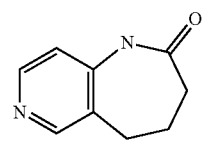

To a solution of tert-butyl 4-(4-amino-3-pyridyl)butanoate (284 mg, 1.20 mmol) in tetrahydrofuran (3 mL) was added potassium tert-butoxide (674 mg, 6.01 mmol). After stirring at 20° C. for 1 h, the reaction mixture was diluted with ethyl acetate (20 mL), washed with brine (20 mL), dried over sodium sulphate and concentrated to dryness under reduced pressure to afford crude 1,3,4,5-tetrahydropyrido[4,3-b]azepin-2-one (77 mg, crude) as a yellow solid, Step 4: 1-({5-[5-(difluoromethyl)-1,3,4-oxadiazol-2-yl]-1,3-thiazol-2-yl}methyl)-1H,2H,3H,4H,5H-pyrido[4,3-b]azepin-2-one

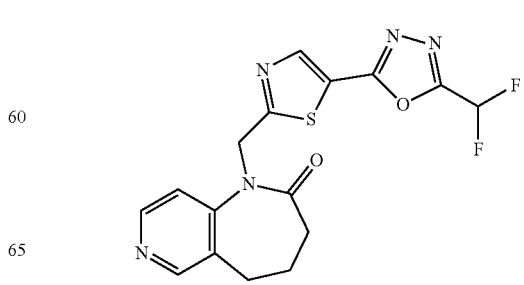

To a solution of 1,3,4,5-tetrahydropyrido[4,3-b]azepin-2-one (33 mg, 0.20 mmol) in N,N-dimethylformamide (1 mL) was added sodium hydride (60%, 7 mg, 0.19 mmol). After stirring at 0° C. for 0.5 hour, 2-[2-(bromomethyl)thiazol-5-yl]-5-(difluoromethyl)-1,3,4-oxadiazole (4a, 50 mg, 0.17 mmol) was added. The mixture was stirred at 20° C. for another 0.5 h and filtered. The filtrate was concentrated to dryness under reduced pressure. The residue was purified by RP-HPLC (0 to 40% acetonitrile in water and 0.225% formic acid) to afford 1-({5-[5-(difluoromethyl)-1,3,4-oxadiazol-2-yl]-1,3-thiazol-2-yl}methyl)-1H,2H,3H,4H,5H-pyrido[4,3-b]azepin-2-one (13.3 mg, 20%) as a yellow oil.

Preparation of 1-[[5-[5-(difluoromethyl)-1,3,4-oxadiazol-2-yl]thiazol-2-yl]methyl]-3,3-dimethyl-4,5-dihydropyrido[3,4-b]azepin-2-one (I-253)

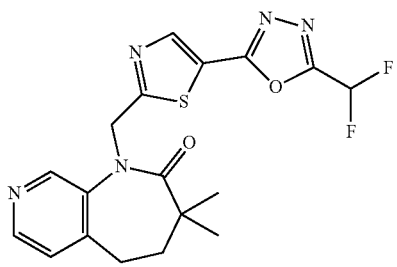 [SMILES: CC1(C)CCc2ccncc2N(Cc2ncc(-c3nnc(C(F)F)o3)s2)C1=O]

Step 1: benzyl 2,2-dimethylbut-3-enoate

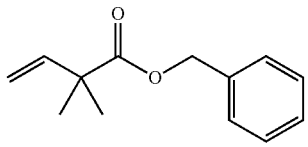

To a solution of 2,2-dimethylbut-3-enoic acid (1.0 g, 8.76 mmol) in N,N-dimethylformamide (20 mL) was added potassium carbonate (2.4 g, 17.52 mmol). The mixture was stirred at 20° C. for 5 minutes, then benzyl bromide (1.7 g, 9.64 mmol) was added. After stirring at 20° C. for 16 hours, the reaction mixture was filtered. The filtrate was diluted with ethyl acetate (100 mL) and washed with brine (3×100 mL). The separated organic layer was dried over anhydrous sodium sulfate and concentrated under reduced pressure. The residue was purified by column chromatography (silica gel, 100-200 mesh, 0-5% ethyl acetate in petroleum ether) to afford benzyl 2,2-dimethylbut-3-enoate (1.20 g, 67%) as colorless oil.

Step 2: benzyl (E)-4-(3-amino-4-pyridyl)-2,2-dimethyl-but-3-enoate

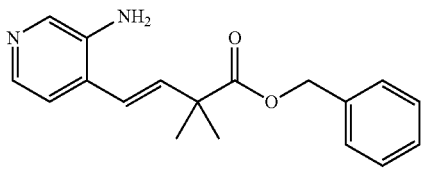 [SMILES: CC(C)(/C=C/c1ccncc1N)C(=O)OCc1ccccc1]

To a solution of benzyl 2,2-dimethylbut-3-enoate (1.1 g, 5.39 mmol) and 4-bromopyridin-3-amine (466 mg, 2.69 mmol) in 1,4-dioxane (15 mL) was added N-cyclohexyl-N-methyl-cyclohexanamine (1.47 g, 7.54 mmol), Pd$_2$(dba)$_3$ (123 mg, 0.13 mmol) and P(t-Bu)$_3$ (138 mg, 0.27 mmol). After stirring at 110° C. for 16 hours under nitrogen atmosphere, the reaction mixture was filtered. The filtrate was concentrated under reduced pressure. The residue was purified column chromatography (silica gel, 100-200 mesh, 0-70% ethyl acetate in petroleum ether) to afford benzyl (E)-4-(3-amino-4-pyridyl)-2,2-dimethyl-but-3-enoate (712 mg, 81%) as a light yellow oil.

Step 3: 4-(3-amino-4-pyridyl)-2,2-dimethyl-butanoic acid

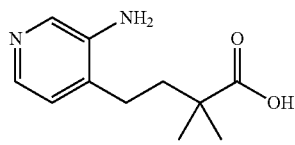

To a solution of benzyl (E)-4-(3-amino-4-pyridyl)-2,2-dimethyl-but-3-enoate (612 mg, 2.07 mmol) in methanol (30 mL) was added palladium (220 mg, 0.21 mmol, 10% on carbon). After stirring at 20° C. under hydrogen (15 psi) for 16 hours, the mixture was filtered. The filtrate was concentrated under reduced pressure. The residue was purified column chromatography (silica gel, 100-200 mesh, 0-10% methanol in dichloromethane) to afford 4-(3-amino-4-pyridyl)-2,2-dimethyl-butanoic acid (250 mg, 58%) as a light yellow solid.

Step 4: 3,3-dimethyl-4,5-dihydro-1H-pyrido[3,4-b]azepin-2-one

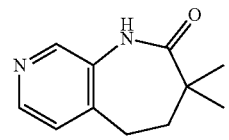

To a solution of 4-(3-amino-4-pyridyl)-2,2-dimethyl-butanoic acid (250 mg, 1.20 mmol) in N,N-dimethylformamide (3 mL) was added O-(7-azabenzotriazol-1-yl)-N,N,N,N-tetramethyluronium hexafluorophosphate (479 mg, 1.26 mmol) and N-ethyl-N-isopropylpropan-2-amine (310 mg, 2.40 mmol) at 0° C. After stirring at 20° C. for 2 hours, the reaction mixture was diluted with ethyl acetate (50 mL) and washed with brine (3×50 mL). The separated organic layer was dried over anhydrous sodium sulfate and concentrated under reduced pressure. The residue was purified by column chromatography (silica gel, 100-200 mesh, 0-10% methanol in dichloromethane) to afford 3,3-dimethyl-4,5-dihydro-1H-pyrido[3,4-b]azepin-2-one (340 mg, crude) as a light yellow solid.

Step 5: 1-[[5-[5-(difluoromethyl)-1,3,4-oxadiazol-2-yl]thiazol-2-yl]methyl]-3,3-dimethyl-4,5-dihydropyrido[3,4-b]azepin-2-one

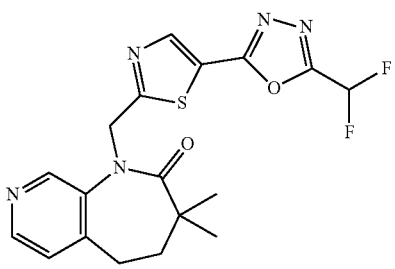 [SMILES: CC1(C)CCc2ccncc2N(Cc2ncc(-c3nnc(C(F)F)o3)s2)C1=O]

To a solution of 3,3-dimethyl-4,5-dihydro-1H-pyrido[3,4-b]azepin-2-one (50 mg, 0.26 mmol) in N,N-dimethylformamide (1 mL) was added sodium hydride (60%, 8 mg, 0.20 mmol). After stirring at 0° C. for 30 mins, the mixture was added 2-[2-(bromomethyl)thiazol-5-yl]-5-(difluoromethyl)-1,3,4-oxadiazole (60 mg, 0.20 mmol) and stirred for another 0.5 hour. The reaction mixture was filtered, and the filtrate was concentrated under reduced pressure. The residue was purified by RP-HPLC (25 to 55% acetonitrile in water and 0.225% formic acid) to afford 1-[[5-[5-(difluoromethyl)-1,3,4-oxadiazol-2-yl]thiazol-2-yl]methyl]-3,3-dimethyl-4,5-dihydropyrido[3,4-b]azepin-2-one (28 mg, 32%) as a light yellow solid.

Preparation of 1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one (I-252); (S)-1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one (I-246); (R)-1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one (I-245)

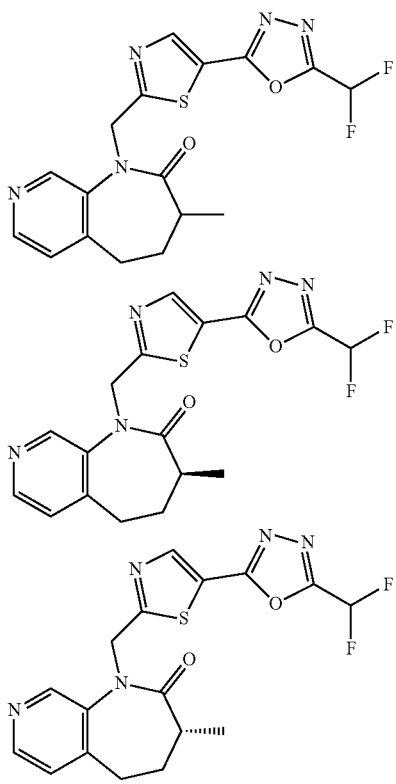

Step 1: benzyl 2-methylbut-3-enoate

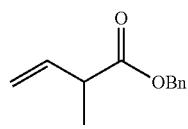

To a solution of 2-methylbut-3-enoic acid (1.0 g, 9.99 mmol) in dichloromethane (1 mL) was added benzyl alcohol (1.1 g, 9.99 mmol), N,N-dicyclohexylcarbodiimide (2.1 g, 9.99 mmol) and dimethylaminopyridine (122 mg, 1.00 mmol). After stirring at 20° C. for 16 hours, the reaction mixture was filtered. The filtrate was concentrated under reduced pressure. The residue was purified by column chromatography (silica gel, 100-200 mesh, 0-5% ethyl acetate in petroleum ether) to afford benzyl 2-methylbut-3-enoate (1.8 g, 95%) as colorless oil.

Step 2: benzyl 4-(3-aminopyridin-4-yl)-2-methylbut-3-enoate

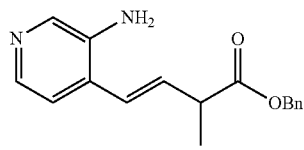 [SMILES: CC(/C=C/c1ccncc1N)C(=O)OCc1ccccc1]

To a solution of 4-bromopyridin-3-amine (1.1 g, 6.36 mmol) in 1,4-dioxane (20 mL) was added benzyl 2-methylbut-3-enoate (1.7 g, 8.90 mmol), Pd$_2$(dba)$_3$ (291 mg, 0.32 mmol), tritert-butylphosphane palladium (325 mg, 0.64 mmol) and N-cyclohexyl-N-methyl-cyclohexanamine (3.7 g, 19.07 mmol). After stirring at 110° C. under nitrogen atmosphere for 16 hours, the reaction mixture was filtered. The filtrate was concentrated under reduced pressure. The residue was purified by RP-HPLC (10 to 40% acetonitrile in water and 0.225% formic acid) to afford benzyl 4-(3-amino-4-pyridyl)-2-methyl-but-3-enoate (900 mg, 47%) as yellow oil.

Step 3: 4-(3-aminopyridin-4-yl)-2-methylbutanoic acid

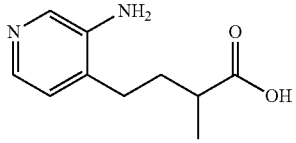

To a solution of benzyl 4-(3-amino-4-pyridyl)-2-methyl-but-3-enoate (800 mg, 2.83 mmol) in methanol (10 mL) was added palladium (302 mg, 0.28 mmol, 10% on carbon). After stirring at 20° C. under hydrogen atmosphere (15 psi) for 16 hours, the reaction mixture was filtered. The filtrate was concentrated to dryness under reduced pressure to afford crude 4-(3-amino-4-pyridyl)-2-methyl-butanoic acid (500 mg, 91%) as yellow oil.

Step 4: 3-methyl-4,5-dihydro-1H-pyrido[3,4-b]azepin-2(3H)-one

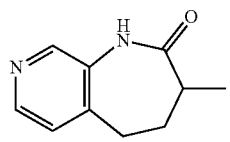

To a mixture of 4-(3-amino-4-pyridyl)-2-methyl-butanoic acid (500 mg, 2.57 mmol) in N,N-dimethylformamide (0.5 mL) was added 1-[bis(dimethylamino)methylene]-1H-1,2,3-triazolo[4,5-b]pyridinium-3-oxide hexafluorophosphate (979 mg, 2.57 mmol) and N-ethyl-N-isopropylpropan-2-amine (998 mg, 7.72 mmol). After stirring at 20° C. for 16 hours, the reaction mixture was diluted with ethyl acetate (60 mL) and washed with brine (3×30 mL). The separated organic layer was dried over anhydrous sodium sulfate and concentrated under reduced pressure. The residue was purified by column chromatography (silica gel, 100-200 mesh, 0-10% methanol in dichloromethane) to afford 3-methyl-1,3,4,5-tetrahydropyrido[3,4-b]azepin-2-one (800 mg, crude) as yellow oil.

Step 5: 1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one; (S)-1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one and (R)-1-((5-(5-(difluoromethyl)-1,3,4-oxadiazol-2-yl)thiazol-2-yl)methyl)-3-methyl-4,5-dihydro-1H-pyrido[3,4-b]azepin-2(3H)-one

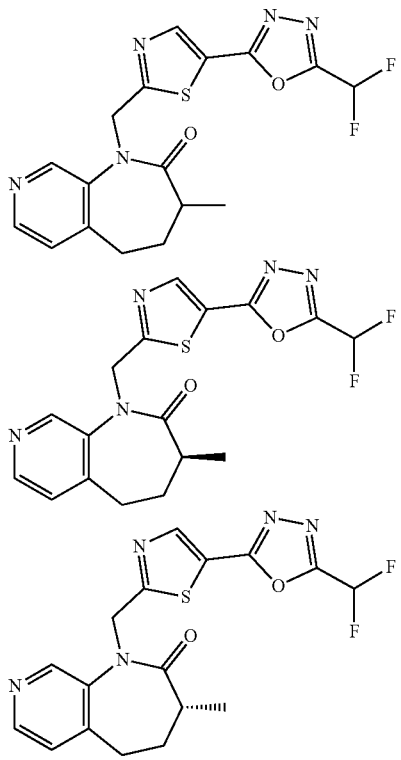

To a solution of 3-methyl-1,3,4,5-tetrahydropyrido[3,4-b]azepin-2-one (45 mg, 0.25 mmol) in N,N-dimethylformamide (1 mL) was added sodium hydride (60%, 7 mg, 0.17 mmol, 60%) at 0° C. After stirring at 0° C. for 30 min, the reaction was added 2-[2-(bromomethyl)thiazol-5-yl]-5-(difluoromethyl)-1,3,4-oxadiazole (50 mg, 0.17 mmol). After stirring at 20° C. for another 30 minutes, the reaction mixture was filtered. The filtrate was concentrated under reduced pressure, the residue was purified by RP-HPLC (15 to 45% acetonitrile in water and 0.225% formic acid) to afford 1-[[5-[5-(difluoromethyl)-1,3,4-oxadiazol-2-yl]thiazol-2-yl]methyl]-3-methyl-4,5-dihydro-3H-pyrido[3,4-b]azepin-2-one (3.5 mg, 5%) as a white solid.

Another batch of the racemic material (100 mg, 0.26 mmol) was further separated by SFC to afford arbitrarily assigned:

(3S)-1-[[5-[5-(difluoromethyl)-1,3,4-oxadiazol-2-yl]thiazol-2-yl]methyl]-3-methyl-4,5-dihydro-3H-pyrido[3,4-b]azepin-2-one (Peak 1, retention time=3.001 min) (49.5 mg, 49%) as a light yellow solid.

LCMS (0 to 60%, 0.018% TFA in acetonitrile 0.037% TFA in water over 4 min)

Retention time 1.251 min, ESI+found [M+H]$^+$=392.3.

(3R)-1-[[5-[5-(difluoromethy)-1,3,4-oxadiazol-2-yl]thiazol-2-yl]methyl]-3-methyl-4,5-dihydro-3H-pyrido[3,4-b]azepin-2-one (Peak 2, retention time=3.310 min) (49.8 mg, 49%) as a light yellow solid.

LCMS (0 to 60%, 0.018% TFA in acetonitrile+0.037% TFA in water over 4 min)

Retention time 1.250 min, ESI+found [M+H]$^+$=392.3.

SFC condition: Column: Chiral ND-3 100×4.6 mm I. D., 3 um, Mobile phase: A: CO$_2$ B: iso-propanol (0.05% DEA), Gradient: from 5% to 40% of B in 4.5 min and hold 40% for 2.5 min, then 5% of B for 1 min, Flow rate: 2.8 mL/min, Column temperature: 40° C.

Preparation of 1-((5-(5-(difluoromethyl)-1,3,4-oxadiazol-2-yl)thiazol-2-yl)methyl)-3-methyl-3,4-dihydro-1,7-naphthyridin-2(1H)-one (I-255); (R)-1-((5-(5-(difluoromethyl)-1,3,4-oxadiazol-2-yl)thiazol-2-yl)methyl)-3-methyl-3,4-dihydro-1,7-naphthyridin-2(1H)-one (I-250); and (S)-1-((5-(5-(difluoromethyl)-1,3,4-oxadiazol-2-yl)thiazol-2-yl)methyl)-3-methyl-3,4-dihydro-1,7-naphthyridin-2(1H)-one (I-251)

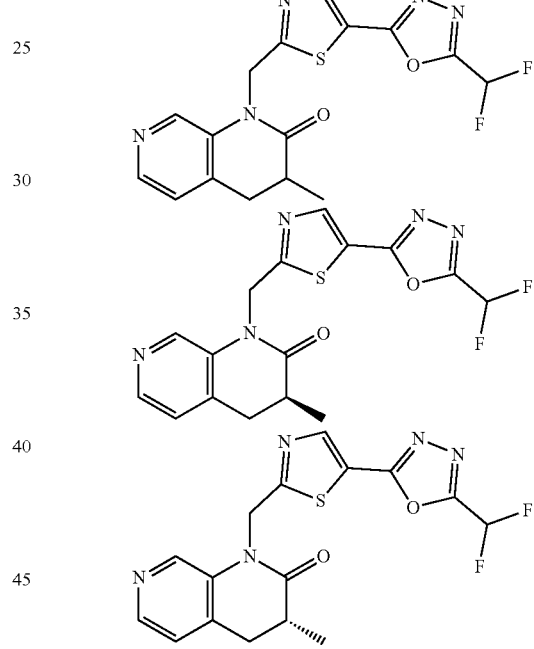

Step 1: methyl 3-(3-aminopyridin-4-yl)-2-methylacrylate

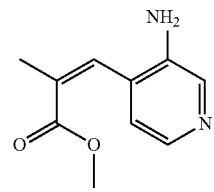

To a solution of 4-bromopyridin-3-amine (2.0 g, 11.56 mmol) in N,N-dimethylacetamide (2 mL) was added methyl 2-methylprop-2-enoate (2.3 g, 23.12 mmol), tetrabutyl ammonium chloride (321 mg, 1.16 mmol), N-cyclohexyl-N-methyl-cyclohexanamine (3.6 g, 18.50 mmol) and ditert-butyl(cyclopentyl)phosphane;dichloropalladium;iron (753 mg, 1.16 mmol). Ater stirring at 80° C. for 16 hours, the reaction mixture was filtered. The filtrate was concentrated under reduced pressure. The residue was diluted with ethyl acetate (100 mL) and washed with brine (3×100 mL). The separated organic extract was dried over anhydrous sodium sulphate and concentrated under reduced pressure. The residue was purified by column chromatography (silica gel, 100-200 mesh, 0-100% ethyl acetate in petroleum ether) to afford methyl 3-(3-aminopyridin-4-yl)-2-methylacrylate (1.8 g, 81%) as colorless oil.

Step 2: 3-methyl-3,4-dihydro-1,7-naphthyridin-2(1H)-one

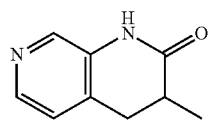

To a solution of methyl methyl 3-(3-aminopyridin-4-yl)-2-methylacrylate (1.5 g, 7.80 mmol) in methanol (2 mL) was added palladium (1.6 g, 1.56 mmol, 10% on carbon). After stirring at 50° C. under hydrogen (45 psi) for 16 hours, the reaction mixture was filtered. The filtrate was concentrated under reduced pressure. The residue was purified by preparative TLC (dichloromethane:methanol=10:1) to afford 3-methyl-3,4-dihydro-1,7-naphthyridin-2(1H)-one (300 mg, 23%) as a white solid.

Step 3: 1-((5-(5-(difluoromethyl)-1,3,4-oxadiazol-2-yl)thiazol-2-yl)methyl)-3-methyl-3,4-dihydro-1,7-naphthyridin-2(1H)-one; (R)-1-((5-(5-(difluoromethyl)-1,3,4-oxadiazol-2-yl)thiazol-2-yl)methyl)-3-methyl-3,4-dihydro-1,7-naphthyridin-2(1H)-one and (S)-1-((5-(5-(difluoromethyl)-1,3,4-oxadiazol-2-yl)thiazol-2-yl)methyl)-3-methyl-3,4-dihydro-1,7-naphthyridin-2(1H)-one To a solution of 3-methyl-3,4-dihydro-1H-1,7-naphthyridin-2-one (150 mg, 0.92 mmol) in N,N-dimethylformamide (5 mL) was added sodium hydride (60%, 33 mg, 0.84 mmol) at 0° C. After stirring at 0° C. for 0.5 hour, the reaction was added 2-[2-(bromomethyl)thiazol-5-yl]-5-(difluoromethyl)-1,3,4-oxadiazole (4a, 248 mg, 0.84 mmol). After stirring at 20° C. for another 0.5 hour, the reaction mixture was filtered. The filtrate was concentrated under reduced pressure. The residue was purified by RP-HPLC (8 to 48% acetonitrile in water and 0.225% formic acid) to afford 1-((5-(5 -(difluoromethyl)-1,3,4-oxadiazol-2-yl)thiazol-2-yl)methyl)-3-methyl-3,4-dihydro-1,7-naphthyridin-2(1H)-one (120 mg, 36%) as a white solid.

The above racemic material (100 mg, 0.26 mmol) was further separated by SFC to afford arbitrarily assigned:

(R)-1-((5-(5-(difluoromethyl)-1,3,4-oxadiazol-2-yl)thiazol-2-yl)methyl)-3-methyl-3,4-dihydro-1,7-naphthyridin-2(1H)-one (Peak 1, retention time=1.984 min) (24.7 mg, 24%) as colorless oil.

(S)-1-((5-(5-(difluoromethyl)-1,3,4-oxadiazol-2-yl)thiazol-2-yl)methyl)-3-methyl-3,4-dihydro-1,7-naphthyridin-2(1H)-one (Peak 2, retention time=2.744 min) (31.4 mg, 29%) as colorless oil.

SFC condition: Column: Chiral NS-3 100×4.6 mm I.D., 3 um Mobile phase: A: CO$_2$ B: ethanol (0.05% DEA), Gradient: from 5% to 40% of B in 4 min and hold 40% for 2.5 min, then 5% of B for 1.5 min, Flow rate: 2.8 mL/min, Column temperature: 40° C.

Preparation of 1'-[[5-[5-(difluoromethyl)-1,3,4-oxadiazol-2-yl]thiazol-2-yl]methyl]spiro[cyclopropane-1,3'-pyrrolo[2,3-c]pyridine]-2'-one (I-247)

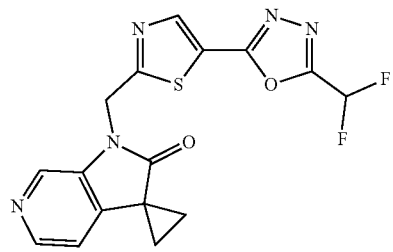 [SMILES: O=C1N(Cc2ncc(-c3nnc(C(F)F)o3)s2)c2cnccc2C12CC2]

Step 1: ethyl 2-(3-bromo-4-pyridyl)acetate

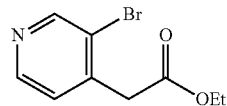 [SMILES: CCOC(=O)Cc1ccncc1Br]

To a mixture of 3-bromo-4-methyl-pyridine (5.0 g, 29.07 mmol) and diethyl carbonate (4.0 g, 34.30 mmol) in tetrahydrofuran (50 mL) was added lithium bis(trimethylsilyl)amide (1.0 M in tetrahydrofuran, 46.0 mL, 46.0 mmol) at 0° C. After stirring at 0° C. for 3 hours under nitrogen atmosphere, the mixture was poured into saturated aqueous ammonium chloride solution (100 mL) carefully and extracted with ethyl acetate (3×100 mL). The combined organic phases were dried over anhydrous sodium sulfate and concentrated under reduced pressure. The residue was purified by column chromatography (silica gel, 100-200 mesh, 0-6% ethyl acetate in petroleum ether) to afford ethyl 2-(3-bromo-4-pyridyl)acetate (5.68 g, 75%) as colorless oil.

Step 2: ethyl 1-(3-bromo-4-pyridyl)cyclopropanecarboxylate

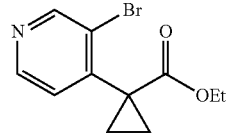 [SMILES: CCOC(=O)C1(c2ccncc2Br)CC1]

To a solution of ethyl 2-(3-bromo-4-pyridyl) acetate (500 mg, 2.05 mmol) in N,N-dimethylformamide (35 mL) was added sodium hydride (60%, 180 mg, 4.51 mmol) at 0° C. After stirring at 0° C. for 15 minutes, the reaction was added 1,2-dibromoethane (385 mg, 2.05 mmol). The mixture was stirred for 30 minutes at 30° C. and then added another batch of sodium hydride (60%, 41 mg, 1.02 mmol). Upon completion by monitoring by TLC, the reaction mixture was poured into water (50 mL) and extracted with ethyl acetate (3×50 mL). The combined organic extracts were dried over sodium sulfate and concentrated under reduced pressure. The residue was purified by column chromatography (silica gel, 100-200 mesh, 0-3% ethyl acetate in petroleum ether) to afford ethyl 1-(3-bromo-4-pyridyl)cyclopropanecarboxylate (390 mg, 47%) as a colorless oil.

Step 3: ethyl 1-[3-(benzhydrylideneamino)-4-pyridyl]cyclopropanecarboxylate

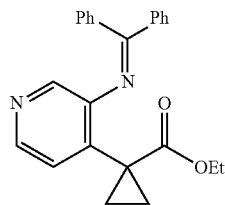 [SMILES: CCOC(=O)C1(c2ccncc2N=C(c2ccccc2)c2ccccc2)CC1]

A mixture of ethyl 1-(3-bromo-4-pyridyl)cyclopropanecarboxylate (1.1 g, 4.00 mmol), diphenylmethanimine (797 mg, 4.40 mmol), Pd$_2$(dba)$_3$ (183 mg, 0.2 mmol), BINAP (249 mg, 0.4 mmol) and sodium tert-butoxide (576 mg, 6.00 mmol) in toluene (10 mL) was stirring at 80° C. for 16 hours under nitrogen atmosphere. The reaction mixture was filtered, and the filtrate was concentrated under reduced pressure. The residue was purified by column chromatography (silica gel, 100-200 mesh, 0-10% ethyl acetate in petroleum ether) to afford ethyl 1-[3-(benzhydrylideneamino)-4-pyridyl]cyclopropanecarboxylate (836 mg, 50%) as a yellow solid.

Step 4: ethyl 1-(3-amino-4-pyridyl)cyclopropanecarboxylate

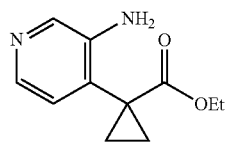 [SMILES: CCOC(=O)C1(c2ccncc2N)CC1]

To a solution of ethyl 1-[3-(benzhydrylideneamino)-4-pyridyl]cyclopropanecarboxylate (736 mg, 1.99 mmo) in tetrahydrofuran (7 mL) was added hydrochloric acid (1.0 M in water, 22.0 mL, 22.00 mmol). After stirring at 20° C. for 1 hour, the mixture was diluted with water (30 mL) and washed with ethyl acetate (2×20 mL). The water phase was adjusted to pH 8 with sodium carbonate and extracted with dichloromethane (3×20 mL). The combined organic extracts were dried over anhydrous sodium sulfate and concentrated under reduced pressure to afford crude ethyl 1-(3-amino-4-pyridyl)cyclopropanecarboxylate (300 mg) as yellow oil.

Step 5: spiro[1H-pyrrolo[2,3-c]pyridine-3,1'-cyclopropane]-2-one

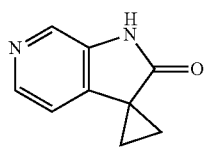

To a solution of ethyl 1-(3-amino-4-pyridyl)cyclopropanecarboxylate (250 mg, 1.21 mmol) in tetrahydrofuran (5 mL) was added potassium tert-butoxide (272 mg, 2.42 mmol). The mixture was stirring at 20° C. for 1 hour. The mixture was filtered, and the filtrate was concentrated under reduced pressure. The residue was purified by column chromatography (silica gel, 100-200 mesh, 0-10% methanol in dichloromethane) to afford spiro[1H-pyrrolo[2,3-c]pyridine-3,1'-cyclopropane]-2-one (185 mg, 64%) as a colorless oil.

Step 6: 1'-[[5-[5-(difluoromethyl)-1,3,4-oxadiazol-2-yl]thiazol-2-yl]methyl]spiro[cyclopropane-1,3'-pyrrolo[2,3-c]pyridine]-2'-one

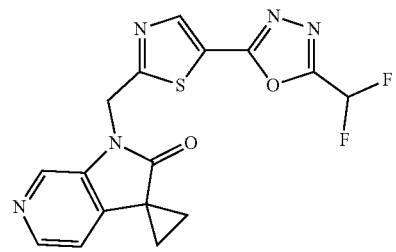 [SMILES: O=C1N(Cc2ncc(-c3nnc(C(F)F)o3)s2)c2cnccc2C12CC2]

To a solution of spiro[1H-pyrrolo[2,3-c]pyridine-3,1'-cyclopropane]-2-one (19 mg, 0.13 mmol) in N,N-dimethylformamide (1 mL) was added sodium hydride (60%, 4 mg, 0.11 mmol) at 0° C. After stirring at 0° C. for 30 minutes, the reaction was added 2-[2-(bromomethyl)thiazol-5-yl]-5-(difluoromethyl)-1,3,4-oxadiazole (4a, 30 mg, 0.11 mmol). After stirring at 20° C. for 1 hour, the mixture was filtered, and the filtrate was concentrated under reduced pressure. The residue was purified by RP-HPLC (0 to 30% acetonitrile in water and 0.225% formic acid) to afford 1'-[[5-[5-(difluoromethyl)-1,3,4-oxadiazol-2-yl]thiazol-2-yl]methyl]spiro[cyclopropane-1,3'-pyrrolo[2,3-c]pyridine]-2'-one (10.8 mg, 17%) as a yellow solid.

Preparation of 1-({5-[5-(difluoromethyl)-1,34-oxadiazol-2-yl]-1,3-thiazol-2-yl}methyl)-1H,2H,3H-pyrido[3,4-b][1,4]oxazin-2-one (I-176)

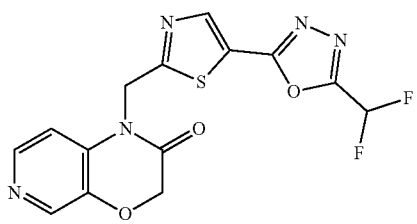 [SMILES: O=C1COc2cnccc2N1Cc1ncc(-c2nnc(C(F)F)o2)s1]

Step 1: 2-chloro-N-(3-hydroxy-4-pyridyl)acetamide

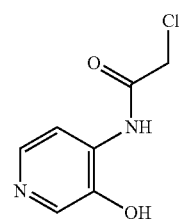 [SMILES: O=C(CCl)Nc1ccncc1O]

A mixture of 4-aminopyridin-3-ol (200 mg, 1.82 mmol) and 2-chloroacetyl chloride (2 mL) was stirred at 80° C. for 2 h and concentrated under reduced pressure. The residue was diluted with water (10 mL) and neutralized by addition of saturated aqueous sodium bicarbonate. The solid precipitate was collected by filtration and dried under reduced pressure to afford 2-chloro-N-(3-hydroxy-4-pyridyl)acetamide (324 mg, 93%) as a white solid.

Step 2: 1H-pyrido[3,4-b][1,4]oxazin-2-one

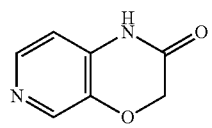 [SMILES: O=C1COc2cnccc2N1]

To a solution of 2-chloro-N-(3-hydroxy-4-pyridyl)acetamide (324 mg, 1.74 mmol) in water (8 mL) was added potassium carbonate (324 mg, 2.34 mmol). The mixture was stirred at 20° C. for 16 h and concentrated to dryness under reduced pressure. The residue was washed with methanol (2 mL) and hot ethyl acetate (2 mL). The solid was collected by filtration and dried under reduced pressure to afford crude 1H-pyrido[3,4-b][1,4]oxazin-2-one (370 mg) as a white solid.

Step 3: 1-({5-[5-(difluoromethyl)-1,3,4-oxadiazol-2-yl]-1,3-thiazol-2-yl}methyl)-1H,2H,3H-pyrido[3,4-b][1,4]oxazin-2-one

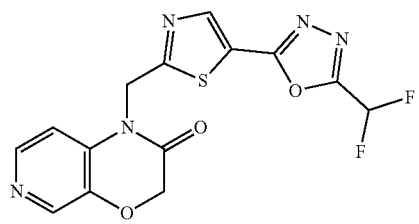

To a solution of 1H-pyrido[3,4-b][1,4]oxazin-2-one (101 mg, 0.68 mmol) in tetrahydrofuran (2 mL) was added sodium hydride (60%, 15 mg, 0.37 mmol, 60% purity) at 0° C. under nitrogen atmosphere. After stirring at 0° C. for 0.5 h, the mixture was added a solution of 2-[2-(bromomethyl)thiazol-5-yl]-5-(difluoromethyl)-1,3,4-oxadiazole (4a, 100 mg, 0.34 mmol) in tetrahydrofuran (1 mL). The mixture was stirred at 25° C. for 16 h and quenched by addition of saturated aqueous ammonium chloride (6 mL). The resulting solution was extracted with ethyl acetate (3×6 mL). The combined organic layers were dried over anhydrous sodium sulphate and concentrated under reduced pressure. The residue was purified by RP-HPLC (0 to 30% acetonitrile in water and 0.225% formic acid) to afford 1-({5-[5-(difluoromethyl)-1,3,4-oxadiazol-2-yl]-1,3-thiazol-2-yl}methyl)-1H,2H,3H-pyrido[3,4-b][1,4]oxazin-2-one (4.6 mg, 4%) as a light yellow oil.

The methods described in Example 2 were also used to prepare the following compounds: I-171, I-172, I-173, I-186, I-195, I-198, I-199, I-200, I-209, I-210, I-248, I-249, I-254, I-256, I-269, and I-270.

Example 3. Synthesis of Amide Compounds of Formula (I)—Via Pd Coupling

Preparation of (R)-3-(5-(5-(difluoromethyl)-1,3,4-oxadiazol-2-yl)thiazol-2-yl)-4-phenyloxazolidin-2-one (Compound I-43) and (S)-3-(5-(5-(difluoromethyl)-1,3,4-oxadiazol-2-yl)thiazol-2-yl)-4-phenyloxazolidin-2-one (Compound I-44).

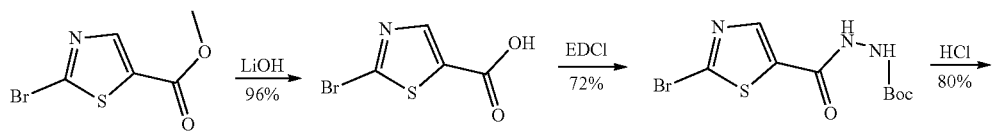

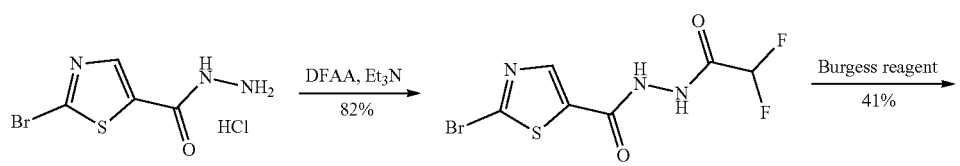

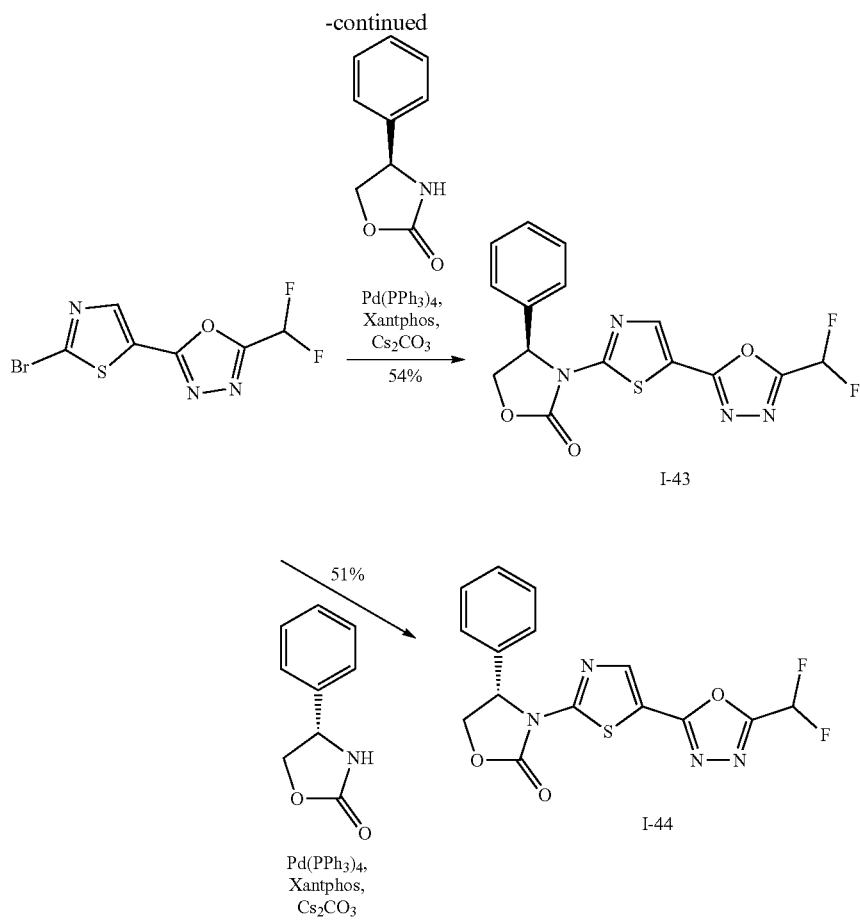

I-43

I-44

A solution of methyl 2-bronco-1,3-thiazole-5-carboxylate (2 g, 9.01 mmol) in THF/water/methanol 3:2:1 (24 mL:16 mL:8 mL) was treated with LiOH (2 eq, 431 mg, 18 mmol). After 5 min at rt LCMS showed complete conversion. The mixture was neutralized to pH 7 and concentrated. The residual aqueous layer was acidified with 6 N HCl to pH 1. The precipitate was filtered, washed with water and little amount of hexane (the desired product dissolved in hexane partially). The solid was dried in high vacuum for 2 hours, transferred to a pear-shaped flask, rinsed with toluene 3× (to remove moisture azeotropically) and dried again in high vacuum to yield 1.80 g (96%) of 2-bromothiazole-5-carboxylic acid as white solid.

To a cooled (0° C.) solution of amine (1.25 g, 6 mmol), ({[3-(dimethylamino)propyl]imino}-methylidene)(ethyl) amine hydrochloride (1.1 eq, 1.27 g, 6.61 mmol), (tert-butoxy)carbohydrazide (1.3 eq, 1.03 g, 7.81 mmol) and 1H-1,2,3-benzotriazol-1-ol (1.3 eq, 1.06 g, 7.81 mmol) in DMF (20 mL) was added dropwise DIPEA (4 eq, 3.11 g, 4.19 mmol, 24 mmol). After 90 min LCMS showed complete conversion. The mixture was poured into water and brine (1:1, 300 mL) and extracted with EtOAc (3×). The combined organics were washed with brine (3×), and dried (Na²SO4) and concentrated to give yellow oil 3.5 g. The crude material was purified by column chromatography (80g SiO$_2$, 0-50% EA in hexane). Yield: 1.39 g (72%) of 2-bromo-N'-[(tert-butoxy)carbonyl]-1,3-thiazole-5-carbohydrazide as white solid.

To a cooled (0° C.) solution of 2-bromo-N'-[(tert-butoxy)carbonyl]-1,3-thiazole-5-carbohydrazide (819 mg, 2.54 mmol) in anhydrous DCM (7 mL) was added 4 M HCl in dioxane (15 eq, 38.1 mmol, 9.53 mL) dropwise. The mixture was stirred at rt for 16 hours. LCMS showed complete conversion. The mixture was treated with a 1:3 mixture of MTBE:hexane (50 mL). The precipitate was filtered off, washed with hexane and dried in high vacuum. Yield: 529.7 mg (80%) of 2-bromothiazole-5-carbohydrazide hydrochloride as off-white solid.

A suspension of 2-bromo-1,3-thiazole-5-carbohydrazide HCl (250 mg, 0.968 mmol) in anhydrous THF (5 mL) was treated with triethylamine (6 eq, 588 mg, 0.81 mL, 5.81 mmol) followed by difluoroacetic anhydride (2 eq, 344 mg, 0.215 mL, 1.94 mmol). The mixture was stirred at 70° C. for 21 hours. LCMS indicated total consumption of the starting material but showed neither the desired mass, nor the distinctive bromide mass. However, a small sample was reacted with phenethylamine and the reaction gave the desired Sn—Ar product. This confirmed that the bromide was intact. The mixture was quenched with water (0.3 mL) and concentrated. The residue was rinsed with dichloromethane and evaporated. The process was repeated 4 times, 1.28 g residue was obtained and purified by column chromatography (40 g SiO2, 0-10% MeOH in dichloromethane). Yield: 238.3 mg (82%) of 2-bromo-N'-(2,2-difluoroacetyl)thiazole-5-carbohydrazide as yellow solid.

A mixture of 2-bromo-N'-(2,2-difluoroacetyl)-1,3-thiazole-5-carbohydrazide (154 mg, 0.513 mmol) and Burgess reagent (5 eq, 619 mg, 2.57 mmol) in anhydrous THF (5 mL) was heated in microwave at 150° C. for 90 min. LCMS showed complete conversion. The desired product didn't ionize well and [M+H]$^+$=282/284 was not observed (however, in the previous step it was proven that the bromide was intact). THF was removed in rotary evaporator. The residue was partitioned in water and ethyl acetate. The layers were separated and the aqueous layer was extracted with ethyl acetate (2×). The combined organics were washed with brine and dried (Na$_2$SO$_4$) and concentrated to give 146 mg crude material which was purified by column chromatography (12 g SiO$_2$, 0-15% EA in hexane). Yield: 59.9 mg (41%) of 2-(2-bromothiazol-5-yl)-5-(difluoromethyl)-1,3,4-oxadiazole as white solid.

A mixture of 2-(2-bromo-1,3-thiazol-5-yl)-5-(difluoromethyl)-1,3,4-oxadiazole (33.4 mg, 0.118 mmol), (4R)-4-phenyl-1,3-oxazolidin-2-one (1.3 eq, 25 mg, 0.149 mmol) and cesium carbonate (1.5 eq, 34.3 mg, 0.177 mmol) in dioxane (2 mL) was flushed with nitrogen for 5 min. Xantphos (0.09 eq, 6.14 mg, 0.01062 mmol) and Tetrakis (triphenylphosphine)-palladium (0.1 eq, 13.6 mg, 0.0118 mmol) were added. The mixture was flushed with nitrogen for 10 min, sealed and heated in microwave at 125° C. for 2 hours. LCMS showed complete conversion. The mixture was poured into water and extracted with ethyl acetate (3×). The combined organics were washed with water (3×), brine, dried (Na$_2$SO$_4$) and concentrated to give 101 mg yellow solid. The crude material was purified by column chromatography (4 g SiO$_2$, 0-50% EA in hexane). Yield: 15.6 mg (54%) of (R)-3-(5-(5-(difluoromethyl)-1,3,4-oxadiazol-2-yl)thiazol-2-yl)-4-phenyloxazolidin-2-one (I-43) as yellow solid.

A mixture of 2-(2-bromo-1,3-thiazol-5-yl)-5-(difluoromethyl)-1,3,4-oxadiazole (22.2 mg, 0.079 mmol), (4S)-4-phenyl-1,3-oxazolidin-2-one (1.3 eq, 15.4 mg, 0.0944 mmol) and cesium carbonate (1.5 eq, 22.9 mg, 0.118 mmol) in dioxane (2 mL) was flushed with nitrogen for 5 min. Xantphos (0.09 eq, 4.10 mg, 0.0071 mmol) and Tetrakis (triphenylphosphine)-palladium (0.1 eq, 9.10 mg, 0.0079 mmol) were added. The mixture was flushed with nitrogen for 10 min, sealed and heated in microwave at 125° C. for 2 hours. LCMS showed complete conversion. The mixture was poured into water and extracted with ethyl acetate (3×). The combined organics were washed with water (3×), brine, dried (Na$_2$SO$_4$) and concentrated to give 60 mg yellow solid. The crude material was purified by column chromatography (4 g SiO$_2$, 0-50% EA in hexane). Yield: 14.6 mg (51%) of (S)-3-(5-(5-(difluoromethyl)-1,3,4-oxadiazol-2-yl)thiazol-2-yl)-4-phenyloxazolidin-2-one (I-44) as yellow solid.

The methods described in Example 3 were also used to prepare compound I-101.

Example 4. Synthesis of Sulfonamide Compounds of Formula (I)

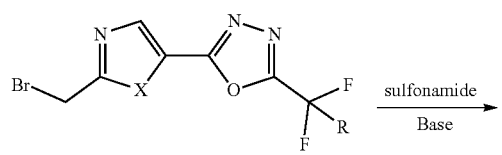

4a: R=H, X=S
4b: R=F, X=S
6a: R=H, X=O
6b: R=F, X=O

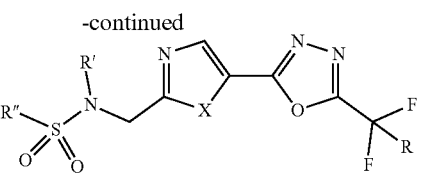

R=H or F

Compound of Formula (I)

Preparation of N-((5-(5-(difluoromethyl)-1,3,4-oxadiazol-2-yl)thiazol-2-yl)methyl)-N-(pyridin-3-yl)ethanesulfonamide (Compound I-6).

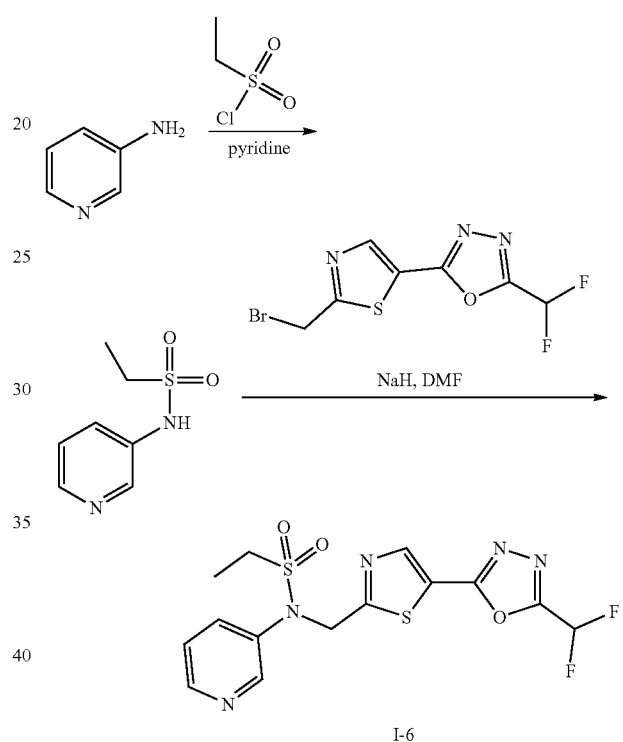

I-6

Step 1: Preparation of N-(pyridin-3-yl)ethanesulfonamide.

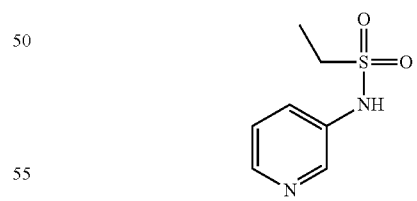

3-Aminopyridine (370 mg, 3.9 mmol) was taken up in DCM (15 mL) and cooled in an ice-bath. Pyridine (0.35 ml, 4.3 mmol) and ethanesulfonyl chloride (0.4 ml, 0.43 mmol) were added and the resulting solution stirred at room temperature for 16 h. The reaction was quenched by adding saturated brine and then extracted with DCM. The separated organic layer was filtered through MgSO$_4$ and then concentrated. The residue was purified on Combiflash (hexanes/EtOAc gradient) to afford the title compound (120 mg, 17%) as a white powder.

Step 2: Preparation of N-((5-(5-(difluoromethyl)-1,3,4-oxadiazol-2-yl)thiazol-2-yl)methyl)-N-(pyridin-3-yl)ethanesulfonamide.

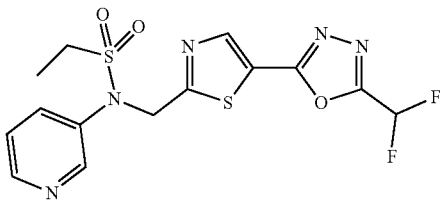

I-6

N-(Pyridin-3-yl)ethane-1-sulfonamide (31 mg, 0.17 mmol) was taken up in DMF (0.4 ml) in an ice bath. Sodium hydride (7 mg, 60% wt., 0.17 mmol) was then added and the solution stirred for 30 min in the ice-bath. A solution of 2-[2-(bromomethyl)-1,3-thiazol-5-yl]-5-(difluoromethyl)-1,3,4-oxadiazole (4a, 31 mg, 0.17 mmol) in DMF (0.5 ml) was then added and the reaction was stirred at room temperature 16 h. TLC indicated that the reaction was complete. The reaction was quenched by adding saturated NH₄Cl solution and then extracted with EtOAc. The organic layer was filtered through MgSO₄ and concentrated. The residue was purified on Combiflash (DCM/methanol gradient) to afford the title compound.

Preparation of N-[5-(difluoromethoxy)-3-pyridyl]-N-[[5-[5-(difluoromethyl)-1,3,4-oxadiazol-2-yl]thiazol-2-yl]methyl]ethanesulfonamide (Compound I-96).

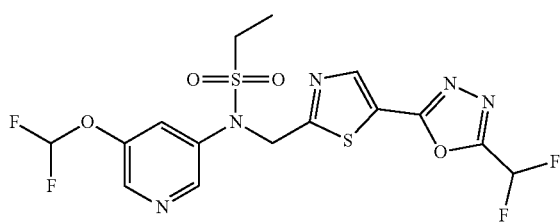 [SMILES: CCS(=O)(=O)N(Cc1ncc(-c2nnc(C(F)F)o2)s1)c1cncc(OC(F)F)c1]

Step 1: 3-(difluoromethoxy)-5-nitropyridine

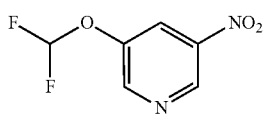

To a solution of 5-nitropyridin-3-ol (500 mg, 3.57 mmol) in N,N-dimethylformamide (5 mL) was added potassium carbonate (1.48 g, 10.71 mmol). The mixture was stirred at 20° C. for 30 minutes and then 2-chloro-2,2-difluoro-acetate (1.4 g, 8.92 mmol) was added. The reaction mixture was stirred at 100° C. for 4 hours and filtered. The filtrate was concentrated under reduced pressure. The residue was purified by column chromatography (silica gel, 100-200 mesh, 10-30% ethyl acetate in petroleum ether) to afford 3-(difluoromethoxy)-5-nitro-pyridine (200 mg, 29%) as yellow oil.

Step 2: 5-(difluoromethoxy)pyridin-3-amine

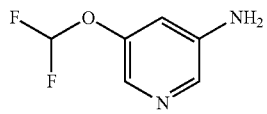 [SMILES: O=[N+]([O-])c1cncc(OC(F)F)c1]

To a solution of 3-(difluoromethoxy)-5-nitro-pyridine (150 mg, 0.80 mmol) in ethanol (2 mL) was added palladium (10% on carbon, 84 mg). The reaction mixture was stirred under hydrogen atmosphere at 15 psi for 2 hours and filtered. The filtrate was concentrated under reduced pressure to afford 5-(difluoromethoxy)pyridin-3-amine (150 mg, crude) as a yellow solid.

Step 3: N-(5-(difluoromethoxy)pyridin-3-yl)ethnesulfonamide

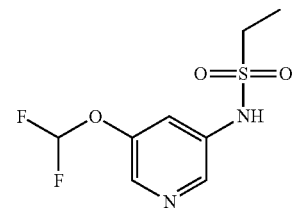 [SMILES: CCS(=O)(=O)Nc1cncc(OC(F)F)c1]

To a solution of 5-(difluoromethoxy)pyridin-3-amine (130 mg, 0.8 mmol) in pyridine (2 mL) was added ethanesulfonyl chloride (125 mg, 0.97 mmol). The reaction mixture was stirred at 20° C. for 16 hours and concentrated under reduced pressure. The residue was purified by RP-TLC (dichloromethane:methanol=10:1) to afford N-[5-(difluoromethoxy)-3-pyridyl]ethanesulfonamide (200 mg, 98%) as a white solid.

Step 4: N-[5-(difluoromethoxy)-3-pyridyl]-N-[[5-[5-(difluoromethyl)-1,3,4-oxadiazol-2-yl]thiazol-2-yl]methyl]ethanesulfonamide (Compound II-96)

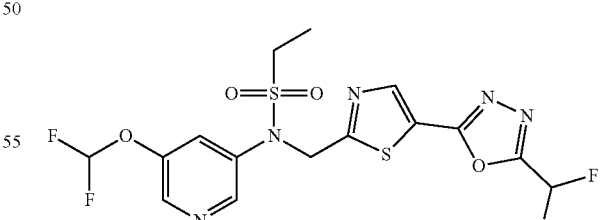

Prepared from 2-[2-(bromomethyl)thiazol-5-yl]-5-(difluoromethyl)-1,3,4-oxadiazole according to method described for I-6. The crude product was purified by RP-HPLC (50-80% acetonittile in water and 0.225% formic acid) to afford N-[5-(difluoromethoxy)-3-pyridyl]-N-[[5-[5-(difluoromethyl)-1,3,4-oxadiazol-2-yl]thiazol-2-yl]methyl] ethanesulfonamide (19.7 mg, 30%) as a white solid.

Preparation of N-[5-(difluoromethoxy)pyridin-3-yl]-N-({5-[5-(difluoromethyl)-1,3,4-oxadiazol-2-yl]-1,3-thiazol-2-yl}methyl)methanesulfonamide (I-147)

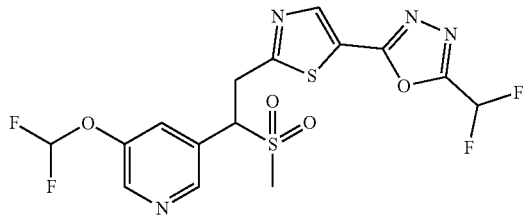 [SMILES: CS(=O)(=O)C(Cc1ncc(-c2nnc(C(F)F)o2)s1)c1cncc(OC(F)F)c1]

Prepared from 5-(difluoromethoxy)pyridin-3-amine and methanesulfonyl chloride according to method described for I-6. The crude product was purified by RP-HPLC (35 to 65% acetonitrile in water and 0.225% formic acid) to afford N-[5-(difluoromethoxy)pyridin-3-yl]-N-({5-[5-(difluoromethyl)-1,3,4-oxadiazol-2-yl]-1,3-thiazol-2-yl}methyl)methanesulfonamide (12 mg, 16%) as a light yellow solid.

Preparation of N-({5-[5-(difluoromethyl)-1,3,4-oxadiazol-2-yl]-1,3-thiazol-2-yl}methyl)-N-[5-(2,2-difluoropropoxy)pyridin-3-yl]methanesulfonamide (I-224)

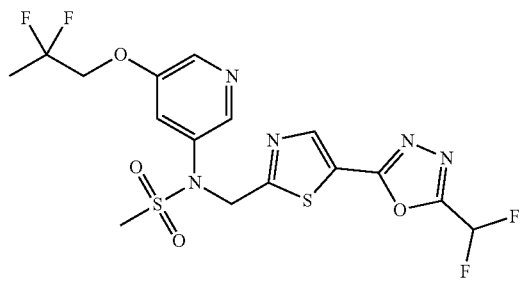 [SMILES: CC(F)(F)COc1cncc(N(Cc2ncc(-c3nnc(C(F)F)o3)s2)S(C)(=O)=O)c1]

Step 1: 1-((5-bromopyridin-3-yl)oxy)propan-2-one

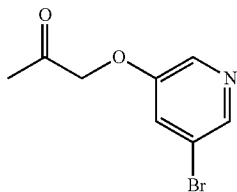

To a mixture of 5-bromopyridin-3-ol (2.0 g, 11.49 mmol) and 1-chloropropan-2-one (1.3 g, 13.79 mmol) in N,N-dimethylformamide (20 mL) was added potassium carbonate (1.8 g, 12.64 mmol). After stirring at 20° C. for 16 h, the reaction mixture was diluted with ethyl acetate (100 mL), washed with brine (3×50 mL), dried and concentrated under reduced pressure. The residue was purified by flash column chromatography (silica gel, 100-200 mesh, 0-15% ethyl acetate in petroleum ether) to afford 1-[(5-bromo-3-pyridyl)oxy]propan-2-one (2.6 g, 93%) as a brown solid.

Step 2: 3-bromo-5-(2,2-difluoropropoxy)pyridine

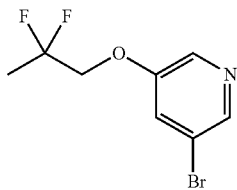

To a solution of 1-[(5-bromo-3-pyridyl)oxy]propan-2-one (2.4 g, 10.43 mmol) indichloromehtane (20 mL) was added diethylaminosulfur trifluoride (3.4 g, 20.86 mmol) at 0° C. The mixture was then stirred at 20° C. for 2 h and poured to ice water (100 mL) carefully. The solution was extracted with ethyl acetate (3×50 mL). The combined organic extracts were dried and concentrated under reduced pressure. The residue was purified by flash column chromatography (silica gel, 100-200 mesh, 0-13% ethyl acetate in petroleum ether) to afford 3-bromo-5-(2,2-difluoropropoxy)pyridine (1.85 g, 70%) as a yellow oil.

Step 3: 5-(2,2-difluoropropoxy)-N-(diphenylmethylene)pyridin-3-amine

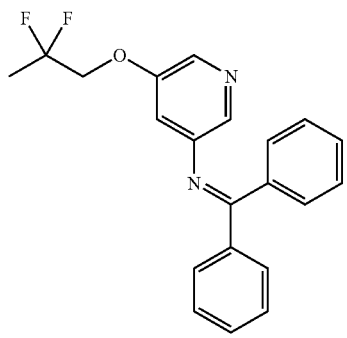 [SMILES: CC(F)(F)COc1cncc(N=C(c2ccccc2)c2ccccc2)c1]

To a solution of 3-bromo-5-(2,2-difluoropropoxy)pyridine (1.9 g, 7.34 mmol) and diphenylmethanimine (1.5 g, 8.07 mmol) in toluene (20 mL) was added sodium tert-butoxide (1.1 g), (R)-(+)-2,2-bis(diphenylphosphino)-1,1-binaphthalene (457 mg, 0.73 mmol) and tris(dibenzylideneacetone)dipalladium(0) (336 mg, 0.37 mmol). The mixture was heated at 80° C. under nitrogen atmosphere for 16 h and filtered. The filtrate was concentrated to dryness under reduced pressure. The residue was purified by flash column chromatography (silica gel, 100-200 mesh, 0-20% ethyl acetate in petroleum ether) to afford N-[5-(2,2-difluoropropoxy)-3-pyridyl]-1,1-diphenyl-methanimine (2.64 g, 77%) as a yellow oil.

Step 3: 5-(2,2-difluoropropoxy)pyridin-3-amine

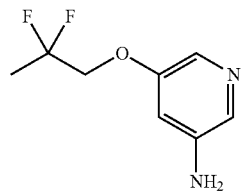

To a solution of N-[5-(2,2-difluoropropoxy)-3-pyridyl]-1,1-diphenyl-methanimine (2.3 g, 6.64 mmol) in tetrahydrofuran (2.3 mL) was added hydrochloric acid (2 M, 6.0 mL, 12.0 mmol). The mixture was stirred at 20° C. for 2 h and diluted with water (50 mL). The resulting solution was washed with ethyl acetate (3×50 mL). The separated aqueous layer was adjusted to pH=8 by addition of aqueous sodium hydroxide (1 M) and extracted with dichloromethane (3×20 mL). The combined organic extracts were dried and concentrated under reduced pressure to afford crude 5-(2,2-difluoropropoxy)pyridin-3-amine (1.32 g, crude) as a yellow solid.

Step 4: N-[5-(2,2-difluoropropoxy)-3-pyridyl]methanesulfonamide

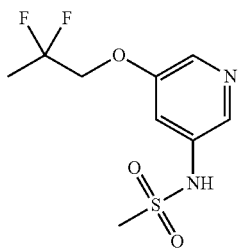 [SMILES: CC(F)(F)COc1cncc(NS(C)(=O)=O)c1]

To a solution of 5-(2,2-difloropropoxy)pyridin-3-amine (100 mg, 0.53 mmol) in pyridine (1 L) was added methanesulfonyl chloride (73 mg, 0.64 mmol). The mixture was stirred at 20° C. for 16 and filtered. The filtrate was concentrated to dryness under reduced pressure. The residue was purified by preparative TLC (dichloromethane:methanol=10:1) to afford N-[5-(2,2-difluoropropoxy)-3-pyridyl]methanesulfonamide (112 mg, 77%) as a yellow solid.

Step 5: N-({5-[5-(difluoromethyl)-1,3,4-oxadiazol-2-yl]-1,3-thiazol-2-yl}methyl)-N-[5-(2,2-difluoropropoxy)pyridin-3-yl]methanesulforamide

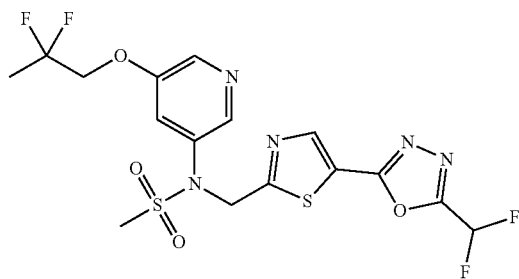 [SMILES: CC(F)(F)COc1cncc(N(Cc2ncc(-c3nnc(C(F)F)o3)s2)S(C)(=O)=O)c1]

To a solution of 2-[2-(bromomethyl)thiazol-5-yl]-5-(difluoromethyl)-1,3,4-oxadiazole (4a, 50 mg, 0.17 mmol) and N-[5-(2,2-difluoropropoxy)-3-pyridyl]methanesuffonamide (49 mg, 0.19 mmol) in N,N-dimethylformamide (1 mL) was added sodium bicarbonate (35 mg, 0.42 mmol). The mixture was stirred at 20° C. for 16 h and filtered. The filtrate was concentrated to dryness under reduced pressure. The residue was purified by RP-HPLC (35 to 65% acetonitrile in water and 0.225% formic acid) to afford N-({5-[5-(difluoromethyl)-1,3,4-oxadiazol-2-yl]-1,3-thiazol-2-yl}methyl)-N-[5-(2,2-difluoropropoxy)pyridin-3-yl]methanesulfonamide (26 mg, 32%) as a yellow oil.

Preparation of N-({5-[5-(difluoromethyl)-1,3,4-oxadiazol-2-yl]-1,3-thiazol-2-yl}methyl)-N-[5-(1-fluoroethyl)pyridin-3-yl]ethane-1-sulfonamide (I-227); N-({5-[5-(difluoromethyl)-1,3,4-oxadiazol-2-yl]-1,3-thiazol-2-yl}methyl)-N-{5-[(1S)-1-fluoroethyl]pyridin-3-yl}ethane-1-sulfonamide (I-207) and N-({5-[5-(difluoromethyl)-1,3,4-oxadiazol-2-yl]-1,3-thiazol-2-yl}methyl)-N-{5-[(1R)-1-fluoroethyl]pyridin-3-yl}ethane-1-sulfonamide (I-208)

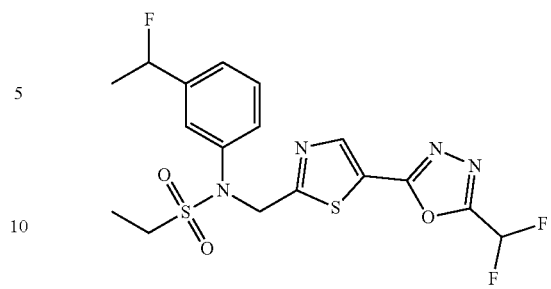

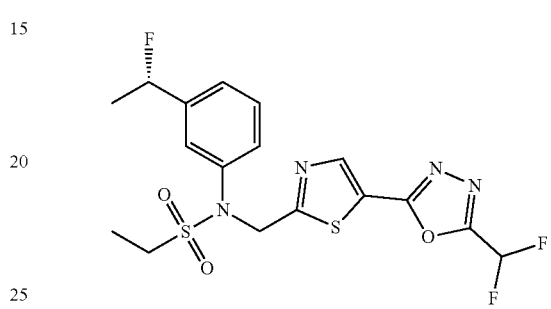

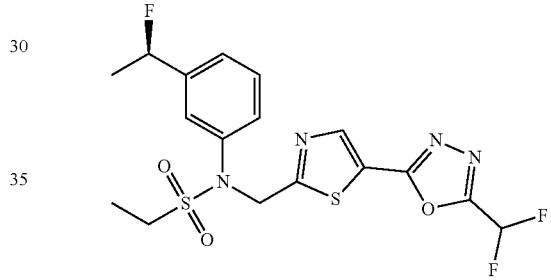

Step 1: 1-(5-bromo-3-pyridyl)ethanol

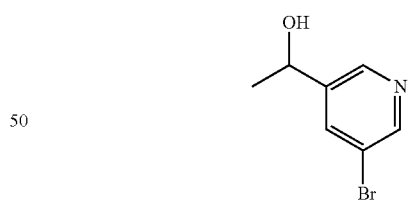

To a solution of 1-(5-bromo-3-pyridyl)ethanone (3.0 g, 15.00 mmol) in methanol (30 mL) was added sodium borohydride (1.1 g, 30.00 mmol) in small portions. The mixture was stirred at 20° C. for 16 h and concentrated under reduced pressure. The residue was diluted with saturated aqueous ammonium chloride (10 mL) and water (30 mL), and extracted with ethyl acetate (3×50 mL). The combined organic extracts were dried and concentrated. The residue was purified by flash column chromatography (silica gel, 100-200 mesh, 0-50% ethyl acetate in petroleum ether) to afford 1-(5-bromo-3-pyridyl)ethanol (2.80 g, 92%) as colorless oil.

Step 2: 3-bromo-5-(1-fluoroethyl)pyridine

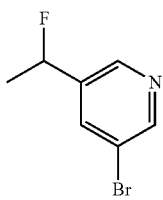

To a solution of 1-(5-bromo-3-pyridyl)ethanol (2.6 g, 12.87 mmol) in dichloromethane (2 mL) was added bis(2-methoxyethyl)aminosulfur trifluoride (2.9 g, 13.06 mmol) dropwise at 0° C. under nitrogen atmosphere. The mixture was stirred at 20° C. for 0.5 h and quenched by addition of saturated aqueous sodium bicarbonate (40 mL). The mixture was then extracted with ethyl acetate (3×40 mL). The combined organic extracts were dried and concentrated under reduced pressure. The residue was purified by flash column chromatography (silica gel, 100-200 mesh, 0-5% ethyl acetate in petroleum ether) to afford 3-bromo-5-(1-fluoroethyl)pyridine (1.78 g, 65%) as a light yellow oil.

Step 3: N-[5-(1-fluoroethyl)-3-pyridyl]-1,1-diphenyl-methanimine

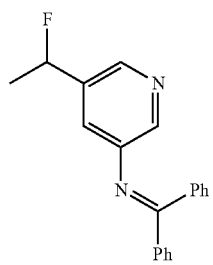 [SMILES: CC(F)c1cncc(N=C(c2ccccc2)c2ccccc2)c1]

To a solution of 3-bromo-5-(1-fluoroethyl)pyridine (1.8 g, 8.72 mmol) and diphenylmethanimine (1.7 g, 9.60 mmol) in toluene (30 mL) was added (R)-(+)-2,2-bis(diphenylphosphino)-1,1-binaphthalene (543 mg, 0.87 mmol), sodium tert-butoxide (838 mg, 8.72 mmol) and tris(dibenzylideneacetone)dipalladium (399 mg, 0.44 mmol) at 20° C. under nitrogen atmosphere. The mixture was stirred at 80° C. for 16 h and concentrated under reduced pressure. The residue was purified by flash column chromatography (silica gel, 100-200 mesh, 0-10% ethyl acetate in petroleum ether) to afford N-[5-(1-fluoroethyl)-3-pyridyl]-1,1-diphenyl-methanimine (2.19 g, 73%) as a light yellow oil.

Step 4: 5-(1-fluoroethyl)pyridin-3-amine

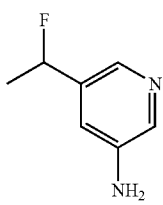

To a solution of N-[5-(1-fluoroethyl)-3-pyridyl]-1,1-diphenyl-methanimine (500 mg, 1.64 mmol) in tetrahydrofuran (6 mL) was added hydrochloric acid (1 M, 2.0 mL, 2.0 mmol) at 20° C. The mixture was stirred at 20° C. for 2 h and diluted with water (10 mL). The solution was washed with ethyl acetate (3×10 mL). The aqueous layer was adjusted to pH=8 by addition of aqueous sodium hydroxide (1 M) and extracted with dichloromethane (3×10 mL). The combined organic extracts were dried and concentrated under reduced pressure to afford crude 5-(1-fluoroethyl)pyridin-3-amine (200 mg, 86%) as light yellow oil.

Step 5: N-[5-(1-fluoroethyl)-3-pyridyl]ethanesufonamide

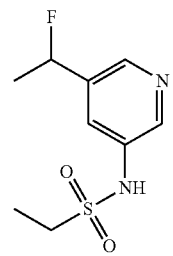

To a solution of 5-(1-fluoroethyl)pyridin-3-amine (200 mg, 1.43 mmol) in pyridine (5 mL) was added ethanesulfonyl chloride (22.0 mg, 1.71 mmol) at 20° C. The mixture was stirred at 20° C. for 16 h and concentrated under reduced pressure. The residue was purified by preparative TLC (dichloromethane:methanol=10:1) to afford N-[5-(1-fluoroethyl)-3-pyridyl]ethanesulfonamide (236 mg, 71%) as a white solid.

Step 6: N-({5-[5-(difluoromethyl)-1,3,4-oxadiazol-2-yl]-1,3-thiazol-2-yl}methyl)-N-[5-(1-fluoroethy)pyridin-3-yl] ethane-1-sulfonamide and N-({5-[5-(difluoromethyl)-1,3,4-oxadiazol-2-yl]-1,3-thiazol-2-yl}methyl)-N-{5-[(1S)-1-fluoroethyl]pyridin-3-yl}ethane-1-sulfonamide and N-({5-[5-(difluoromethyl)-1,3,4-oxadiazol-2-yl]-1,3-thiazol-2-yl}methyl)-N-{5-[(1R)-1-fluoroethyl]pyridin-3-yl}ethane-1-sulfonamide To a solution of N-[5-(1-fluoroethyl)-3-pyridyl]ethane-sulfonamide (206 mg, 0.89 mmol) in N,N-dimethylformamide (4.5 mL) was added 2-[2-(bromomethyl)thiazol-5-yl]-5-(difluoromethyl)-1,3,4-oxadiazole (263 mg, 0.89 mmol) and sodium bicarbonate (22.4 mg, 2.66 mmol) at 20° C. The mixture was stirred at 20° C. for 16 h and filtered. The filtrate was concentrated under reduced pressure. The residue was purified by RP-HPLC (0 to 40% acetonitrile in water and 0.225% formic acid) to afford N-({5-[5-(difluoromethyl)-1,3,4-oxadiazol-2-yl]-1,3-thiazol-2-yl}methyl)-N-[5-(1-fluoroethyl)pyridin-3-yl]ethane-1-sulfonamide (101.2 mg, 25%) as a brown oil.

The above racemate (98 mg, 0.22 mmol) was further separated by SFC to afford arbitrarily assigned:

N-({5-[5-(difluoromethyl)-1,3,4-oxadiazol-2-yl]-1,3-thiazol-2-yl}methyl)-N-{5-[(1R)-1-fluoroethyl]pyridin-3-yl}ethane-1-sulfonamide (Peak 1, retention time=2.597 min) (11.1 mg, 11%) as a light yellow oil.

N-({5-[5-(difluoromethyl)-1,3,4-oxadiazol-2-yl]-1,3-thiazol-2-yl}methyl)-N-{5-[(1S)-1-fluoroethyl]pyridin-3-yl}ethane-1-sulfonamide (Peak 2, retention time=2.689 min) (15.2 mg 15%) as a light yellow oil.

SFC condition: Column: (S,S)-Whelk-0-3 50iA4.6 mm I.D. 1.8 um, Mobile phase: A: $CO_2$ B: ethanol (0.05% DEA); Gradient: from 5% to 40% of B in 4.5 min and hold 40% for 2.5 min, then 5% of B for 1.5 min; Flow rate: 2.8 mL/min, Column temperature: 40° C.

Preparation of N-((5-(5-(difluoromethyl)-1,3,4-oxadiazol-2-yl)thiazol-2-yl)methyl)-N-(1-phenylcyclopropyl)ethanesulfoamide (Compound I-20).

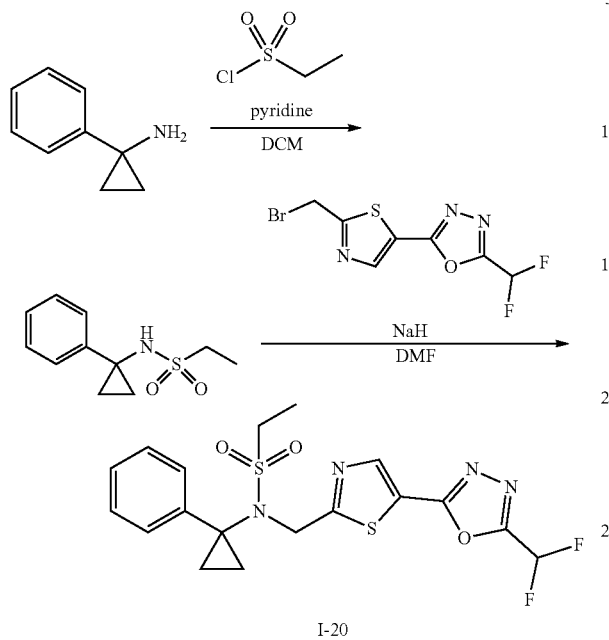

I-20

Step 1: Preparation of N-(1-phenylcyclopropyl)ethanesulfonamide.

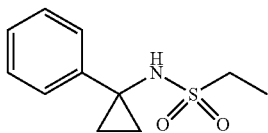

To a vial containing the commercially available 1-phenylcyclopropan-1-amine (200 mg, 1.50 mmol) in DCM (1 mL) at ambient temperature, was added pyridine (143 mg, 1.80 mmol) and then ethanesulfonyi chloride (232 mg, 1.80 mmol). The mixture was stirred at ambient temperature for 18 h. Quenched with 1 N HCl, the reaction mixture was extracted with EtOAc. The organic layer was washed with water, dried (Na$_2$SO$_4$), filtered and concentrated. The resulting residue was purified by chromatography (Silica gel, EtOAc/hexane, 0:1 to 1:1) to afford the title compound as an oil, 95 mg (28.1%).

Step 2: N-((5-(5-(difluoromethyl)-1,3,4-oxadiazol-2-yl)thiazol-2-yl)methyl)-N-(1-phenylcyclopropyl)ethanesulfonamide

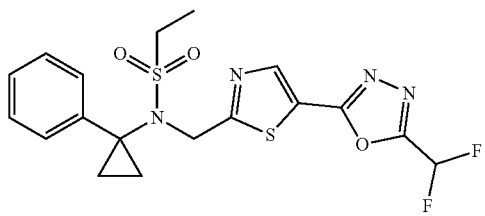

I-20

To a vial containing NaH (7.29 mg, 60 wt. % in mineral oil, 0.18 mmol) in DMF at 0° C. was added a solution of N-(1-phenylcyclopropyl)ethanesulfonamide from Step 1 in DMF (45 mg, 0.20 mmol) dropwise. After the reaction was stirred at ambient temperature for 10 min, the mixture was added dropwise to a cold solution of 2-[2-(bromomethyl)-1,3-thiazol-5-yl]-5-(difluoromethyl)1,3,4-oxadiazole (4a, 40 mg, 0.14 mmol) in DMF in an ice bath. The reaction mixture was then stirred and warmed up to ambient temperature for 4 h, then quenched with saturated aqueous NH$_4$Cl and added EtOAc, the organic layer was dried (Na$_2$SO$_4$), filtered and concentrated. The resulting residue was purified by chromatography (Silica gel, EtOAc/hexane, 0:1 to 3:2) to afford a light brow solid, 22 mg (37%).

Preparation of N-((5-(5-(difluoromethyl)-1,3,4-oxadiazol-2-yl)thiazol-2-yl)methyl)-N-(1-(difluoromethyl)-1H-pyrazol-4-yl)ethanesulfonamide (Compound I-48).

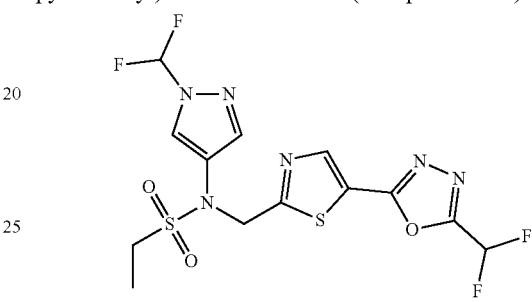

Step 1: N-[1-(difluoromethyl)pyrazol-4-yl]ethanesulfonamide

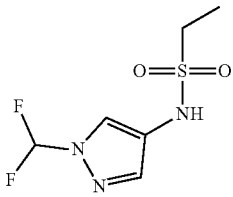

To a solution of 1-(difluoromethyl)pyrazol-4-amine (100 mg, 0.75 mmol) in pyridine (2 mL) was added ethanesulfonyl chloride (116 mg, 0.90 mmol). The mixture was stirred at 20° C. for 16 hours and concentrated under reduced pressure. The residue was purified by RP-TLC (dichloromethane:methanol=20:1) to afford N-[1-(difluoromethyl)pyrazol-4-yl]ethanesulfonamide (100 mg, 59%) as a red solid.

Step 2: N-((5-(5-(difluoromethyl)-1,3,4-oxadiazol-2-yl)thiazol-2-yl)methyl)-N-(1-(difluoromethyl)-1H-pyrazol-4-yl)ethanesulfonamide (Compound I-48)

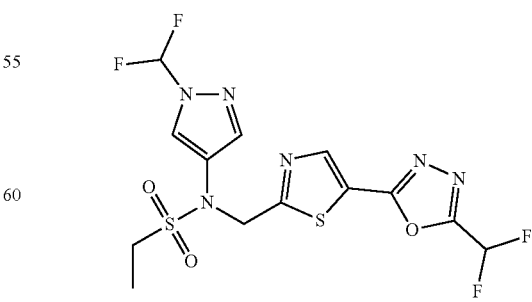

To a solution of 2-[2-(bromomethyl)thiazol-5-yl]-5-(difluoromethyl)-1,3,4-oxadiazole (4a, 17 mg, 0.06 mmol) in N,N-dimethylformamide (0.2 mL) was added sodium bicarbonate (15 mg, 0.17 mmol) and N-[1-(difluoromethyl)pyrazol-4-yl]ethanesulfonamide (19 mg, 0.08 mmol). The mixture was stirred at 20° C. for 16 hours and filtered. The filtrate was concentrated to dryness under reduced pressure. The residue was purified by RP-HPLC (22-55% acetonitrile in water and 0.225% formic acid) to afford N-[[5-[5-(difluoromethyl)-1,3,4-oxadiazol-2-yl]thiazol-2-yl]methyl]-N-[1-(difluoromethyl)pyrazol-4-yl]ethanesulfonamide (14.1 mg, 56%) as a yellow solid.

Preparation of N-({5-[5-(difluoromethyl)-1,3,4-oxadiazol-2-yl]-1,3-thiazol-2-yl}methyl)-N-(1H-imidazol-5-yl)ethane-1-sulfonamide (I-235)

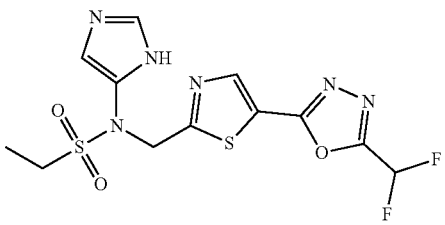 [SMILES: CCS(=O)(=O)N(Cc1ncc(-c2nnc(C(F)F)o2)s1)c1cnc[nH]1]

Step 1: trimethyl-[2-[(5-nitroimidazol-1-yl)methoxy]ethyl]silane

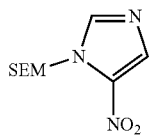 [SMILES: C[Si](C)(C)CCOCn1cncc1[N+](=O)[O-]]

To a solution of 5-nitro-1H-imidazole (2.0 g, 18 mmol) in tetrahydrofuran (20 mL) was added sodium hydride (60%, 1.1 g, 28 mmol) at 0° C. under nitrogen atmosphere. The mixture was stirred at 20° C. for 1 h and then 2-(chloromethoxy)ethyl-trimethyl-silane (3.5 g, 21 mmol) was added. The resulting mixture was stirred at 20° C. for 16 h and quenched by addition of water (5 mL). The solution was extracted with ethyl acetate (100 mL). The organic extract was washed with brine (100 mL), dried over sodium sulphate and concentrated to dryness under reduced pressure. The residue was purified by flash column chromatography (silica gel, 100-200 mesh, 0-30% ethyl acetate in petroleum ether) to afford trimethyl-[2-[(5-nitroimidazol-1-yl)methoxy]ethyl]silane (3.75 g, 83%) as a yellow solid.

Step 2.: 3-(2-trimethylsilylethoxymethyl)imidazol-4-amine

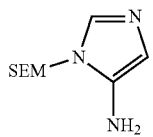

To a solution of trimethyl-[2-[(5-nitroimidazol-1-yl)methoxy]ethyl]silane (1.0 g, 4 mmol) in tetrahydrofuran (10 mL) was added palladium (10% on carbon, 437 mg, 0.41 mmol). The mixture was hydrogenated (15 psi) at 20° C. for 1 h and filtered. The filtrate was concentrated to dryness under reduced pressure to afford crude 3-(2-trimethylsilylethoxymethyl)imidazol-4-amine (800 mg, crude) as a black brown oil used as is in the next step.

Step 3: N-[3-(2-trimethylsilylethoxymethyl)imidazol-4-yl]ethanesulfonamide

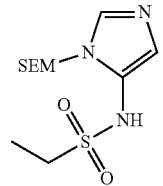 [SMILES: CCS(=O)(=O)Nc1cncn1COCC[Si](C)(C)C]

To a solution of 3-(2-trimethylsilylethoxymethyl)imidazol-4-amine (800 mg, 3.75 mmol) in tetrahydrofuran (15 mL) was added ethanesulfonyl chloride (579 mg, 4.50 mmol) and pyridine (890 mg, 11.25 mmol). The mixture was stirred at 20° C. for 2 h and concentrated to dryness under reduced pressure. The residue was purified by preparative TLC (dichloromethane:methanol=10:1) to afford N-[3-(2-trimethylsilylethoxymethyl)imidazol-4-yl]ethanesulfonamide (53 mg, 4%) as a light yellow solid.

Step 4: N-[[5-[5-(difluoromethyl)-1,3,4-oxadiazol-2-yl]ithiazol-2-yl]methyl]-N-[3-(2-trimethylsilylethoxymethyl)imidazol-4-yl]ethanesulfonamide

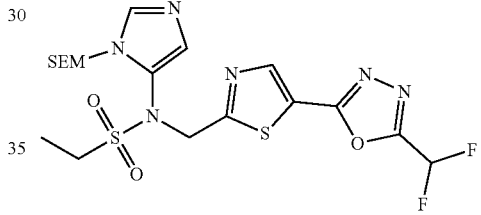

To a solution of N-[3-(2-trimetylsilylethoxymethyl)imidazol-4-yl]ethanesulfonamide (50 mg, 0.16 mmol) in N,N-dimethylformamide (2 mL) was added 2-[2-(bromomethyl)thiazol-5-yl]-5-(difluoromethyl)-1,3,4-oxadiazole (4a, 80 mg, 0.27 mmol) and sodium bicarbonate (34 mg, 0.41 mmol). The mixture was stirred at 20° C. for 2 h and filtered. The filtrate was concentrated to dryness under reduced pressure. The residue was purified by preparative TLC (dichloromethane:methanol=20:1) to afford N-[[5-[45-(difluoromethyl)-1,3,4-oxadiazol-2-yl]thiazol-2-yl]methyl]-N-[3-(2-trimethylsilylethoxymethyl)imidazol-4-yl]ethanesulfonamide (65 mg, 46%) as a yellow solid.

Step 5: N-({5-[5-(difluoromethyl)-1,3,4-oxadiazol-2-yl]-1,3-thiazol-2-yl}methyl)-N-(1H-imidazol-5-yl)ethane-1-sulfonamide

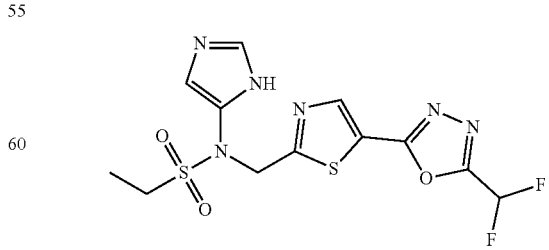

To a solution of N-[[5-[5-(difluoromethyl)-1,3,4-oxadiazol-2-yl]thiazol-2-yl]methyl]-N-[3-(2-trimethylsilylethoxymethyl)imidazol-4-yl]ethanesulfonamide (59 mg, 0.11 mmol) in 1,1,1,3,3,3-hexafluoropropan-2-ol (6 mL) was added trifluoroacetic acid (129 mg, 1.13 mmol). The mixture was stirred at 20° C. for 16 h and concentrated to dryness under reduced pressure. The residue was purified by RP-HPLC (20 to 50% acetonitrile in water and 0.225% formic acid) to afford N-({5-[5-(difluoromethyl)-1,3,4-oxadiazol-2-yl]-1,3-thiazol-2-yl}methyl)-N-(1H-imidazol-5-yl)ethane-1-sulfonamide (9.7 mg, 22%) as a light yellow solid Preparation of N-((5-(5-(difluoromethyl)-1,3,4-oxadiazol-2-yl)thiazol-2-yl)methyl)-N-(5-(difluoromethyl)pyridin-3-yl)ethanesulfonamide (Compound I-60).

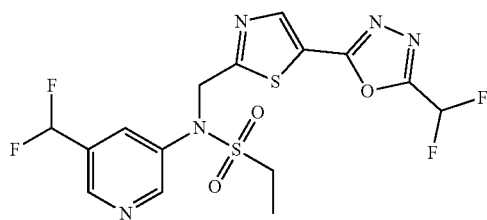 [SMILES: CCS(=O)(=O)N(Cc1ncc(-c2nnc(C(F)F)o2)s1)c1cncc(C(F)F)c1]

Step 1: 3-bromo-5-(difluoromethyl)pyridine

To a solution of 5-bromopyridine-3-carbaldehyde (500 mg, 2.7 mmol) in dichloromethane (4 mL) was added diethylaminosulphur trifluoride (867 mg, 5.38 mmol) at 0° C. under nitrogen atmosphere. Then the mixture was allowed to warm to 20° C. and stirred for 2 hours. After quenched by addition of water (50 mL) carefully, the reaction was extracted with ethyl acetate (50 mL×3). The combined organic layers were dried over sodium sulphate and concentrated to dryness under reduced pressure. The residue was purified by column chromatography (silica gel, 100-200 mesh, 0-50% ethyl acetate in petroleum ether) to give 3-bromo-5-(difluoromethyl)pyridine (370 mg, 66%) as a yellow solid.

Step 2: N-[5-(difluoromethyl)-3-pyridyl]-1,1-diphenyl-methanimine

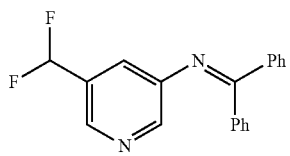 [SMILES: FC(F)c1cncc(N=C(c2ccccc2)c2ccccc2)c1]

A mixture of 3-bromo-5-(difluoromethyl)pyridine (300 mg, 1.44 mmol), diphenylmethanimine (262 mg, 1.44 mmol), BINAP (90 mg, 0.14 mmol), Pd₂(dba)₃ (66 mg, 0.07 mmol) and sodium tert-butoxide (139 mg, 1.44 mmol) in toluene (2 mL) was stirred at 80° C. for 16 hours under nitrogen protection. The reaction was quenched by addition of water (50 mL) and extracted with ethyl acetate (50 mL×3). The combined organic layers were dried over sodium sulphate and concentrated to dryness under reduced pressure. The residue was purified by column chromatography (silica gel, 100-200 mesh, 0-10% ethyl acetate in petroleum ether) to afford N-[5-(difluoromethyl)-3-pyridyl]-1,1-diphenyl-methanimine (300 mg, 68%) as a yellow solid.

Step 3: 5-(difluoromethyl)pyridin-3-amine

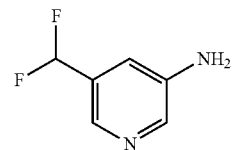

A solution of N-[5-(difluoromethyl)-3-pyridyl]-1,1-diphenyl-methanimine (300 mg, 0.97 mmol) in tetrahydrofuran (5 mL) and hydrochloric acid (1M in water, 2 mL) was stirred at 20° C. for 2 hours. The reaction mixture was diluted with water (50 mL) and then washed with ethyl acetate (50 mL×2). The aqueous layer was adjusted to pH=11 by addition of aqueous sodium hydroxide (1.0 M) and extracted with dichloromethane (50 mL×2). The combined organic layers were dried over sodium sulphate and concentrated to dryness under reduced pressure to afford crude 5-(difluoromethyl)pyridin-3-amine (112 mg, 80%) as a yellow solid.

Step 4: N-((5-(5-(difluoromethyl)-1,3,4-oxadiazol-2-yl)thiazol-2-yl)methyl)-N-(5-(difluoromethyl)pyridin-3-yl)ethanesulfonamide (Compound I-60)

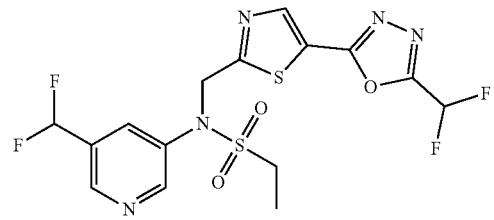 [SMILES: CCS(=O)(=O)N(Cc1ncc(-c2nnc(C(F)F)o2)s1)c1cncc(C(F)F)c1]

Prepared from the 2-[2-(bromomethyl)thiazol-5-yl]-5-(difluoromethyl)-1,3,4-oxadiazole as described above for I-6. The crude product was purified by RP-HPLC (30-60% acetonitrile in water and 0.05% ammonia hydroxide) to afford N-[[5-[5-(difluoromethyl)-1,3,4-oxadiazol-2-yl]thiazol-2-yl]methyl]-N-[5-(difluoromethyl)-3-pyridyl]ethanesulfonamide (4.9 mg, 16%) as a white solid.

Preparation of N-((5-(5-(difluoromethyl)-1,3,4-oxadiazol-2-yl)thiazol-2-yl)methyl)-N-(5-fluoropyrimidin-2-yl)ethanesulfonamide (Compound I-81).

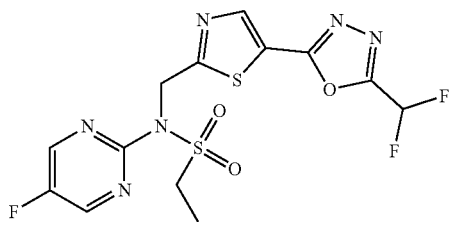 [SMILES: CCS(=O)(=O)N(Cc1ncc(-c2nnc(C(F)F)o2)s1)c1ncc(F)cn1]

215

Step 1: N-(5-fluoropyrimidin-2-yl)ethanesulfonamide

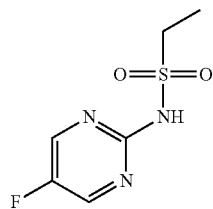

A mixture of 2-chloro-5-fluoro-pyrimidine (150 mg, 1.13 mmol), ethanesulfonamide (148 mg, 1.36 mmol) and cesium carbonate (922 mg, 2.83 mmol) in dimethyl sulfoxide (3 mL) was stirred at 100° C. for 16 hours and filtered. The filtrate was concentrated to dryness under reduced pressure. The residue was purified by RP-HPLC (10-40% acetonitrile in water and 0.225% formic acid) to afford N-(5-fluoropyrimidin-2-yl)ethanesulfonamide (63 mg, 27%) as a white solid.

Step 2: N-((5-(5-(difluoromethyl)-1,3,4-oxadiazol-2-yl)thiazol-2-yl)methyl)-N-(5-fluoropyrimidin-2-yl)ethanesulfonamide (Compound I-81)

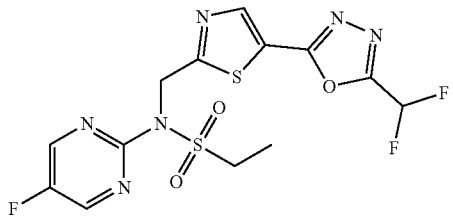 [SMILES: CCS(=O)(=O)N(Cc1ncc(-c2nnc(C(F)F)o2)s1)c1ncc(F)cn1]

A mixture of N-(5-fluoropyrimidin-2-yl)ethanesulfonamide (12 mg, 0.06 mmol), 2-[2-(bromomethyl)thiazol-5-yl]-5-(difluoromethyl)-1,3,4-oxadiazole (4a, 15 mg, 0.05 mmol) and potassium carbonate (21 mg, 0.15 mmol) in N,N-dimethylformamide (1 mL) was stirred at 20° C. for 1 hour and filtered. The filtrate was concentrated to dryness under reduced pressure. The residue was purified by RP-HPLC (44-74% acetonitrile in water and 0.225% formic acid) to afford N-[[5-[5-(difluoromethyl)-1,3,4-oxadiazol-2-yl]thiazol-2-yl]methyl]-N-(5-fluoropyrimidin-2-yl)ethanesulfonamide (9.9 mg, 46%) as a yellow solid.

Preparation of N-(pyridin-3-yl)-N-({5-[5-(trifluoromethyl)-1,3,4-oxadiazol-2-yl]-1,3-thiazol-2-yl}methyl)ethane-1-sulfonamide (I-119)

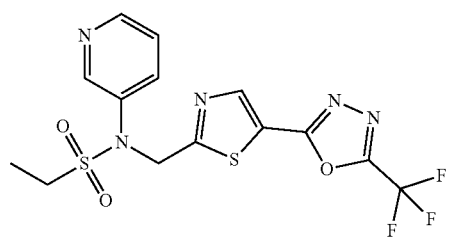 [SMILES: CCS(=O)(=O)N(Cc1ncc(-c2nnc(C(F)(F)F)o2)s1)c1cccnc1]

216

Step 1: 2-(2-metylthiazol-5-yl)-5-(trifluoromethyl)-1,3,4-oxadiazole

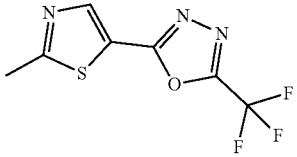

To a solution of 2-methylthiazole-5-carbohydrazide (3.5 g, 22.27 mmol) in N,N-dimethylformamide (50 mL) was added trifluoroacetic anhydride (18.7 g, 89.06 mmol) and triethylamine (22.5 g, 222.66 mmol). After stirring at 70° C. for 2 h, the reaction mixture was diluted with ethyl acetate (100 mL), washed with brine (3×50 mL), dried and concentrated to dryness under reduced pressure. The residue was purified by flash column chromatography (silica gel, 100-200 mesh, 0-15% ethyl acetate in petroleum ether) to afford 2-(2-methylthiazol-5-yl)-5-(trifluoromethyl)-1,3,4-oxadiazole (2.2 g, 39%) as a yellow solid.

Step 2: 2-(2-(bromomethyl)thiazol-5-yl)-5-(trifluoromethyl)-1,3,4-oxadiazole

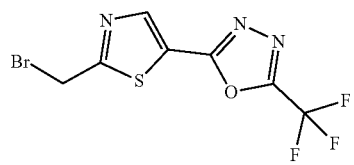 [SMILES: FC(F)(F)c1nnc(-c2cnc(CBr)s2)o1]

To a solution of 2-(2-methylthiazol-5-yl)-5-(trifluoromethyl)-1,3,4-oxadiazole (2.3 g, 9.78 mmol) in 1,2-dichloroethane (100 mL) was added N-bromosuccinimide (2.6 g, 14.67 mmol) and azodiisobutyronitrile;azobisisobutyronitrile (161 mg, 0.98 mmol). The mixture was stirred at 80° C. for 12 h and concentrated to dryness under reduced pressure. The residue was purified by flash column chromatography (silica gel, 100-200 mesh, 0-20% ethyl acetate in petroleum ether) to afford 2-[2-(bromomethyl)thiazol-5-yl]-5-(trifluoromethyl)-1,3,4-oxadiazole (1.11 g, 35%) as a yellow solid.

Step 3: N-(pyridin-3-yl)-N-({5-[5-(trifluoromethyl)-1,3,4-oxadiazol-2-yl]-1,3-thiazol-2-yl}methyl)ethane-1-sulfonamide

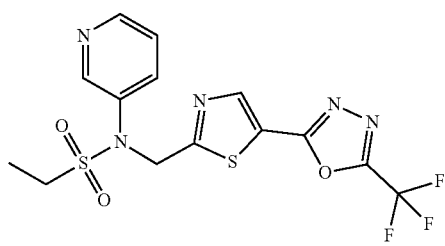 [SMILES: CCS(=O)(=O)N(Cc1ncc(-c2nnc(C(F)(F)F)o2)s1)c1cccnc1]

To a solution of N-(3-pyridyl)ethanesulfonamide (28 mg, 0.15 mmol) in N,N-dimethylformamide (1 mL) was added sodium bicarbonate (32 mg, 0.38 mmol) and 2-[2-(bromomethyl)thiazol-5-yl]-5-(trifluoromethyl)-1,3,4-oxadiazole (4b, 40 mg, 0,13 mmol). The mixture was stirred at 20° C. for 2 h and filtered. The filtrate was concentrated to dryness under reduced pressure. The residue was purified by RP-HPLC (45 to 75% acetonitrile in water and 0.225% formic acid) to afford N-(pyridin-3-yl)-N-({5-[5-(trifluoromethyl)-1,3,4-oxadiazol-2-yl]-1,3-thiazol-2-yl}methyl)ethane-1-sulfonamide (7.0 mg, 13%) as a yellow solid Preparation of N-((5-(5-(difluoromethyl)-1,3,4-oxadiazol-2-yl)thiazol-2-yl)methyl)-N-(5-(2-hydroxypropan-2-yl)pyridin-2-yl)ethanesulfonamide (Compound I-102)

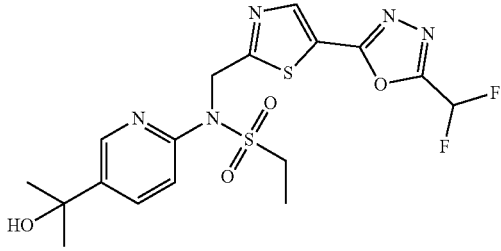 [SMILES: CCS(=O)(=O)N(Cc1ncc(-c2nnc(C(F)F)o2)s1)c1ccc(C(C)(C)O)cn1]

Step 1: [1-(6-bromo-3-pyridyl)-1-methyl-ethoxy]-tert-butyl-dimethyl-silane

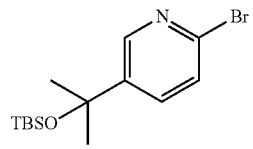 [SMILES: CC(C)(O[Si](C)(C)C(C)(C)C)c1ccc(Br)nc1]

To a solution of 2-(6-bromo-3-pyridyl)propan-2-ol (70 mg, 0.32 mmol) in dichloromethane (1 mL) was added 2,6-lutidine (69 mg, 0.65 mmol) and [tert-butyl (dimethyl) silyl]trifluoromethanesulfonate (128 mg, 0.49 mmol). After stirred at 20° C. for 2 hours, the reaction was quenched by addition of water (10 mL) and ethyl acetate (30 mL). The separated organic layer was dried over sodium sulphate and concentrated to dryness under reduced pressure. The residue was purified by column chromatography (silica gel, 100-200 mesh, 0-20% ethyl acetate in petroleum ether) to afford [1-(6-bromo-3-pyridyl)-1-methyl-ethoxy]-tert-butyl-dimethyl-silane (70 mg, 65%) as colorless oil.

Step 2: N-[5-[1-[tert-butyl(dimethyl)silyl]oxy-1-methyl-ethyl]-2-pyridyl]ethanesulfonamide

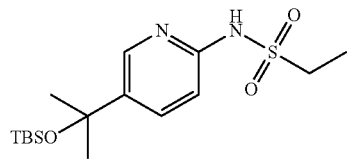 [SMILES: CCS(=O)(=O)Nc1ccc(C(C)(C)O[Si](C)(C)C(C)(C)C)cn1]

To a solution of [1-(6-bromo-3-pyridyl)-1-methyl-ethoxy]-tert-butyl-dimethyl-silane (160 mg, 0.48 mmol) in 1,4-dioxane (6 mL) was added ethanesulfonatnide (159 mg, 1.45 mmol), cesium carbonate (789 mg, 2.42 mmol), Xantphos (56 mg, 0.10 mmol) and Pd$_2$(dba)$_3$ (44 mg, 0.05 mmol). The reaction mixture was stirred at 110° C. for 16 hours under nitrogen atmosphere and filtered. The filtrate was concentrated to dryness under reduced pressure. The residue was purified by column chromatography (silica gel, 100-200 mesh, 0-10% methanol in dichloromethane) to afford N-[5-[1-[tert-butyl (dimethyl)silyl]oxy-1-methyl-ethyl]-2-pyridyl]ethanesulfonamide (71 mg, 38%) as a yellow solid.

Step 3: N-[5-[1-[tert-butyl(dimethyl)silyl]oxy-1-methyl-ethyl]-2-pyridyl]-N-[[5-[5-(difluoromethyl)-1,3,4-oxadiazol-2-yl]thiazol-2-yl]methyl]ethanesulfonamide

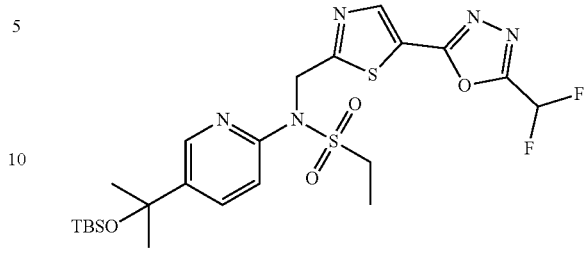

To a solution of N-[5-[1-[tert-butyl(dimethyl)silyl]oxy-1-methyl-ethyl]-2-pyridyl]ethanesulfonamide (68 mg, 0.19 mmol) in N,N-dimethylformamide (2 mL) was added 2-[2-(bromornethyl)thiazol-5-yl]-5-(difluoromethyl)-1,3,4-oxadiazole (4a, 73 mg, 0.25 mmol) and sodium bicarbonate (48 mg, 0.57 mmol). The reaction mixture was stirred at 20° C. for 6 hours and filtered. The filtrate was concentrated to dryness under reduced pressure. The residue was purified by column chromatography (silica gel, 100-200 mesh, 0-25% ethyl acetate in petroleum ether) to afford N-[5-[1-[tert-butyl (dimethyl)silyl]oxy-1-methyl-ethyl]-2-pyridyl]-N-[[5-[5-(difluoromethyl)-1,3,4-oxadiazol-2-yl]thiazol-2-yl]methyl]ethanesulfonamide (13 mg, 11%) as yellow oil.

Step 4: N-((5-(5-(difluoromethyl)-1,3,4-oxadiazol-2-yl)thiazol-2-yl)methyl)-N-(5-(2-hydroxypropan-2-yl)pyridin-2-yl)ethanesulfonamide (Compound I-102)

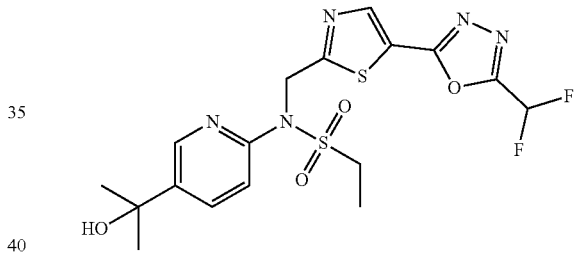

To a solution of N-[5-[1-[tert-butyl(dimethyl)silyl]oxy-1-methyl-ethyl]-2-pyridyl]-N-[[5-[5-(difluoromethyl)-1,3,4-oxadiazol-2-yl]thiazol-2-yl]methyl]ethanesulfonamide (10 mg, 0.02 mmol) in 1,1,1,3,3,3-hexafluoropropan-2-ol (2 mL) was added trifluoroacetic acid (154 mg, 1.35 mmol). The reaction mixture was stirred at 20° C. for 2 hours and concentrated under reduced pressure. The residue was purified by RP-HPLC (35-65% acetonitrile in water and 0.225% formic acid) to afford N-[[5-[5-(difluoromethyl)-1,3,4-oxadiazol-2-yl]thiazol-2-yl]methyl]-N-[5-(1-hydroxy-1-methyl-ethyl)-2-pyridyl]ethanesulfonamide (5.8 mg, 72%) as a white solid.

Preparation of 2-cyano-N-({5-[5-(difluoromethyl)-1,3,4-oxadiazol-2-yl]-1,3-thiazol-2-yl}methyl)-N-(5-methylpyridin-3-yl)ethane-1-sulfonamide (I-219)

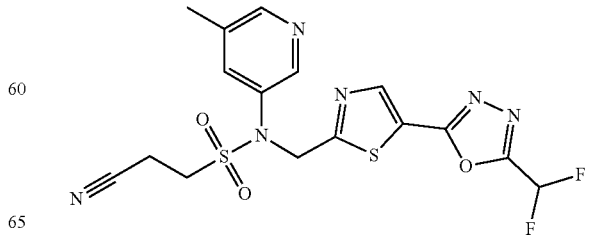

Step 1: methyl 3-[(5-methyl-3-pyridyl)sulfamoyl]propanoate

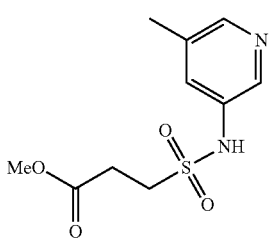 [SMILES: COC(=O)CCS(=O)(=O)Nc1cncc(C)c1]

To a solution of 5-methylpyridin-3-amine (400 mg, 3.70 mmol) in pyridine (6 mL) was added methyl 3-chlorosulfonylpropanoate (966 mg, 5.18 mmol). The mixture was stirred at 20° C. for 16 h and concentrated under reduced pressure. The residue was purified by preparative TLC (dichloromethane:methanol=10:1) to afford methyl 3-[(5-methyl-3-pyridyl)sulfamoyl]propanoate (440 mg, 40%) as a light yellow solid.

Step 2: 3-[(5-methyl-3-pyridyl)sulfamoyl]propanoic acid

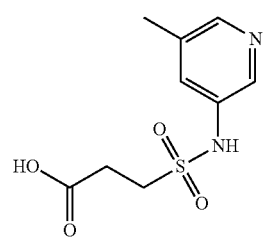 [SMILES: Cc1cncc(NS(=O)(=O)CCC(=O)O)c1]

To a solution of methyl 3-[(5-methyl-3-pyridyl)sulfamoyl]propanoate (390 mg, 1.51 mmol) in methanol (6 mL) was added sodium hydroxide (181 mg, 4.53 mmol) in water (2 mL). The mixture was stirred at 20° C. for 3 h and concentrated under reduced pressure. The residue was adjusted to pH=3 by addition of hydrochloric acid (1 M) and filtered to give crude 3-[(5-methyl-3-pyridyl)sulfamoyl]propanoic acid (213 mg, crude) as a light yellow solid.

Step 3: 3-[(5-methyl-3-pyridyl)sulfamoyl]propanamide

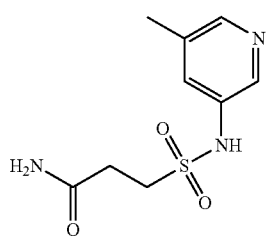 [SMILES: Cc1cncc(NS(=O)(=O)CCC(N)=O)c1]

To a solution of 3-[(5-methyl-3-pyridyl)sulfamoyl]propanoic acid (203 mg, 0.83 mmol) in N,N-dimethylformamide (6 mL) was added 2-(3H-[1,2,3]triazolo[4,5-b]pyridin-3-yl)-1,1,3,3-tetramethyluronium hexafluorophosphate(V) (632 mg, 1.66 mmol), ammonium chloride (178 mg, 3.32 mmol) and N-ethyl-N-isopropylpropan-2-amine (1.1 g, 8.31 mmol). The mixture was stirred at 20° C. for 16 h and concentrated under reduced pressure. The residue was purified by RP-HPLC (0 to 15% acetonitrile in water and 0.05% NH₃H₂O+10 mM NH₄HCO₃) to afford 3-[(5-methyl-3-pyridyl)sulfamoyl]propanoic acid (213 mg, crude) as a light yellow solid.

Step 4: 3-[[5-[5-(difluoromethyl)-1,3,4-oxadiazol-2-yl]thiazol-2-yl]methyl-(5-methyl-3-pyridyl)sulfamoyl]propanamide

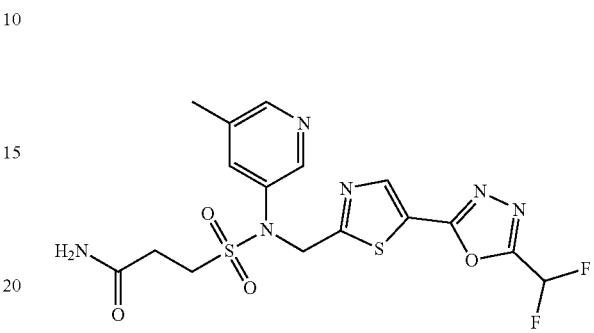

To a solution of 2-[2-(bromomethyl)thiazol-5-yl]-5-(difluoromethyl)-1,3,4-oxadiazole (4a, 43 mg, 0.14 mmol) in N,N-dimethylformamide (2 mL) was added 3-[(5-methyl-3-pyridyl)sulfamoyl]propanamide (42 mg, 0.17 mmol) and sodium bicarbonate (36 mg, 0.43 mmol). The mixture was stirred at 20° C. for 16 h and filtered. The filtrate was concentrated and the residue was purified by preparative TLC (dichloromethane:methanol=10:1) to afford 3-[[5-[5-(difluoromethyl)-1,3,4-oxadiazol-2-yl]thiazol-2-yl]methyl-(5-methyl-3-pyridyl)sulfamoyl]propanamide (12 mg, 15%) as a yellow solid.

Step 5: 2-cyano-N-({5-[5-(difluoromethyl)-1,3,4-oxadiazol-2-yl]-1,3-thiazol-2-yl}methyl)-N-(5-methylpyridin-3-yl)ethane-1-sulfonamide

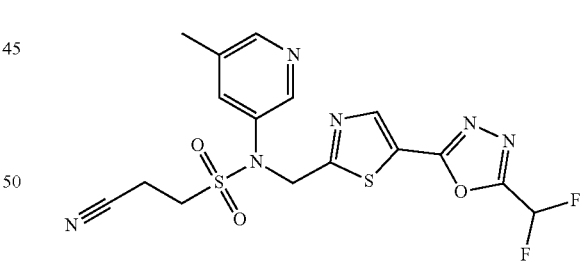

To a solution of 3-(N-((5-(5-(difluoromethyl)-1,3,4-oxadiazol-2-yl)thiazol-2-yl)methyl)-N-(5-methylpyridin-3-yl)sulfamoyl)propanamide (12 mg, 0.03 mmol) in dichloromethane (2 mL) was added Burgess reagent (37 mg, 0.16 mmol) at 0° C. The mixture was stirred at 20° C. for 2 h and filtered. The filtrate was concentrated under reduced pressure and the residue was purified by RP-HPLC (16 to 56% acetonitrile in water and 0.225% formic acid) to afford 2-cyano-N-({5-[5-(difluoromethyl)-1,3,4-oxadiazol-2-yl]-1,3-thiazol-2-yl}methyl)-N-(5-methylpyridin-3-yl)ethane-1-sulfonamide (1.4 mg, 12%) as a light yellow solid.

Preparation of N-((5-(5-(difluoromethyl)-1,3,4-oxadiazol-2-yl)thiazol-2-yl)methyl)-N-(pyridin-3-yl)-2-(tetrahydro-1H-furo[3,4-c]pyrrol-5(3H)-yl)ethane-1-sulfonamide (I-174)

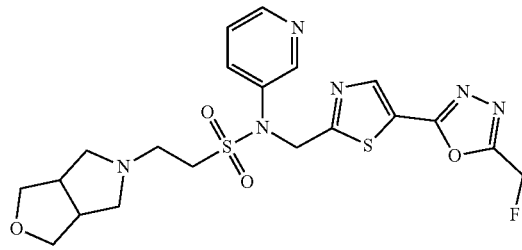

Step 1: N-(3-pyridyl)ethenesulfonamide

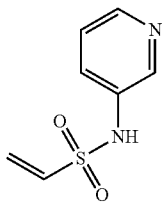

To a solution of ethenesulfonyl chloride (70 mg, 0.55 mmol) and pyridin-3-amine (52 mg, 0.55 mmol) in dichloromethane (2 mL) was added triethylamine (62 mg, 0.61 mmol) at −78° C. under nitrogen atmosphere. The mixture was stirred at −78° C. for 0.5 h and then at 0° C. for 2 h. The reaction mixture was to be used directly in next step without purification.

Step 2: 2-(1,3,3a,4,6,6a-hexahydrofuro[3,4-c]pyrrol-5-yl)-N-(3-pyridyl)ethanesulfonamide

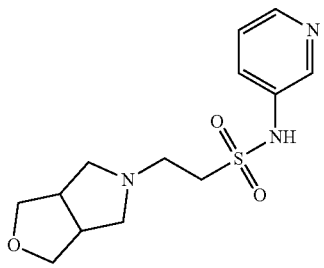 [SMILES: O=S(=O)(CCN1CC2COCC2C1)Nc1cccnc1]

To above solution of N-(3-pyridyl)ethenesulfonamide in dichloromethane (2 mL) was added 3,3a,4,5,6,6a-hexahydro-1H-furo[3,4-c]pyrrole hydrochloride (69 mg, 0.46 mmol) and triethylamine (71 mg, 0.71 mmol) at 25° C. under nitrogen atmosphere. The mixture was stirred at 25° C. for 16 h and then concentrated under reduced pressure. The residue was purified by preparative TLC (dichloromethane:methanol=10:1) to afford 2-(1,3,3a,4,6,6a-hexahydrofuro[3,4-c]pyrrol-5-yl)-N-(3-pyridyl)ethanesulfonamide (30 mg, 29%) as a light yellow oil.

Step 3: N-((5-(5-(difluoromethyl)-1,3,4-oxadiazol-2-yl)thiazol-2-yl)methy)-N-(pyridin-3-yl)-2-(tetrahydro-1H-furo[3,4-c]pyrrol-5(3H)-yl)ethane-1-sulfonamide

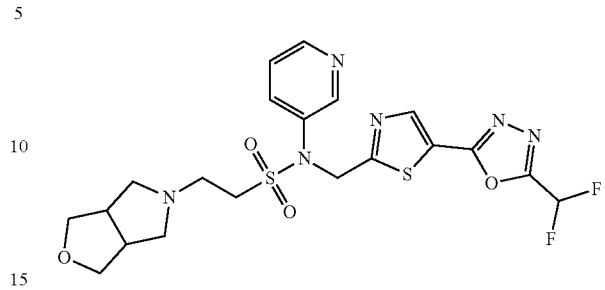

To a solution of 2-(1,3,3a,4,6,6a-hexahydrofuro[3,4-c]pyrrol-5-yl)-N-(3-pyridyl)ethanesulfonamide (25 mg, 0.08 mmol) and 2-[2-(bromomethyl)thiazol-5-yl]-5-(difluoromethyl)-1,3,4-oxadiazole (4a, 25 mg, 0.08 mmol) in N,N-dimethylformamide (0.3 mL) was added sodium bicarbonate (21 mg, 0.25 mmol). The mixture was stirred at 35° C. for 3 h and filtered. The filtrated was concentrated to dryness under reduced pressure. The residue was purified by RP-HPLC (0 to 40% acetonitrile in water and 0.225% formic acid) to afford N-((5-(5-(difluoromethyl)-1,3,4-oxadiazol-2-yl)thiazol-2-yl)methyl)-N-(pyridin-3-yl)-2-(tetrahydro-1H-furo[3,4-c]pyrrol-5(3H)-yl)ethane-1-sulfonamide (3.1 mg, 7%) as a light yellow oil.

Preparation of N-({5-[5-(difluoromethyl)-1,3,4-oxadiazol-2-yl]-1,3-thiazol-2-yl}methyl)-N-(5-fluoropyridin-3-yl)-2-(1,4-oxazepan-4-yl)ethane-1-sulfonamide (I-186)

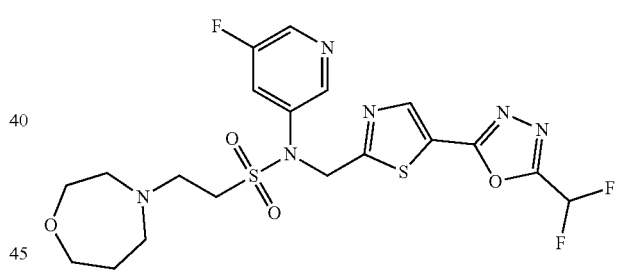

Step 1: N-(5-fluoro-3-pyridyl)ethenesulfonamide

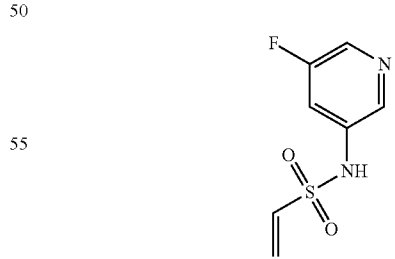

To a solution of ethenesulfonyl chloride (100 mg, 0.79 mmol) in dichloromethane (1 mL) was added 5-fluoropyridin-3-amine (88 mg, 0.79 mmol) and triethylamine (159 mg, 1.58 mmol) at −78° C. The mixture was warmed to 20° C. and stirred for 30 minutes. The reaction mixture was to be used directly in next step without further treatment.

Step 2: N-(5-fluoro-3-pyridyl)-2-(1,4-oxazepan-4-yl)ethanesulfonamide

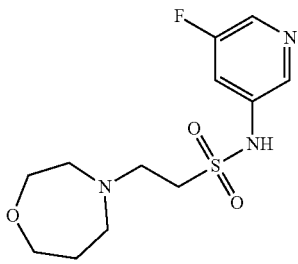 [SMILES: O=S(=O)(CCN1CCCOCC1)Nc1cncc(F)c1]

To the above solution was added 1,4-oxazepane (60 mg, 0.59 mmol) and triethyiamine (50 mg, 0.49 mmol) at 0° C. The mixture was stirred at 20° C. for 2 h and concentrated to dryness under reduced pressure. The residue was purified by preparative TLC (dichloromethane:methanol=20:1) to afford N-(5-fluoro-3-pyridyl)-2-(1,4-oxazepane-4-yl)ethanesulfonamide (57 mg, 37%) as a colorless oil.

Step 3: N-({5-[5-(difluoromethyl)-1,3,4-oxadiazol-2-yl]-1,3-thiazol-2-yl}methyl)-N-(5-fluoropyridin-3-yl)-2-(1,4-oxazepan-4-yl)ethane-1-sulfonamide

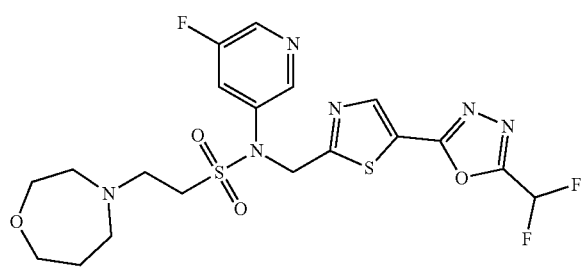 [SMILES: O=S(=O)(CCN1CCCOCC1)N(Cc1ncc(-c2nnc(C(F)F)o2)s1)c1cncc(F)c1]

To a solution of N-(5-fluoro-3-pyridyl)-2-(1,4-oxazepan-4-yl)ethanesulfonamide (57 mg, 0.18 mmol) in N,N-dimethylformamide (1 mL) was added 2-[2-(bromomethyl)thiazol-5-yl]-5-(difluoromethyl)-1,3,4-oxadiazole (4a, 55 mg, 0.19 mmol) and sodium bicarbonate (47 mg, 0.56 mmol). The mixture was stirred at 20° C. for 2 h and filtered. The filtrate was concentrated to dryness under reduced pressure and the residue was purified by RP-HPLC (0 to 40% acetonitrile in water and 0.225% formic acid) to afford N-({5-[5-(difluoromethyl)-1,3,4-oxadiazol-2-yl]-1,3-thiazol-2-yl}methyl)-N-(5-fluoropyridin-3-yl)-2-(1,4-oxazepan-4-yl)ethane-1-sulfonamide (12.6 mg, 12%) as a yellow oil.

Preparation of N-[5-(difluoromethoxy)pyridin-3-yl]-N-({5-[5-(difluoromethyl)-1,3,4-oxadiazol-2-yl]-1,3-thiazol-2-yl}methyl)butane-2-sulfonamide (I-177)

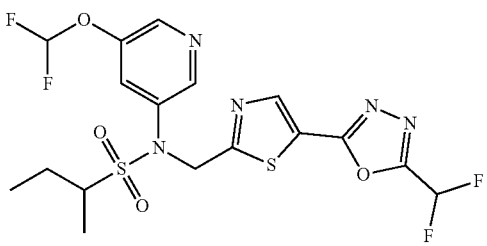 [SMILES: CCC(C)S(=O)(=O)N(Cc1ncc(-c2nnc(C(F)F)o2)s1)c1cncc(OC(F)F)c1]

Step 1: sec-butyl sulfonyloxysodium

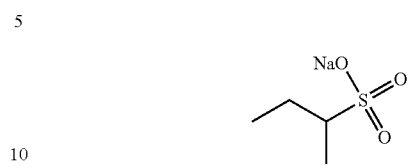

To a solution of 2-bromobutane (5.0 g, 36.49 mmol) in water (50 mL) was added sodium sulphate (5.1 g, 40.14 mmol). The mixture was stirred at 100° C. for 16 h and filtered. The filtrate was concentrated under reduced pressure. The residue was triturated with chloroform and filtered to give crude sec-butylsulfonyloxysodium (8.8 g, crude) as a white solid used in the next step as is.

Step 2: butane-2-sulfonyl chloride

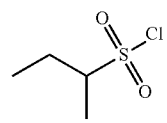

To a solution of sec-butylsulfonyloxysodium (8 g, 49.95 mmol) in thionyl chloride (25 mL) was added N,N-dimethylformamide (233 mg, 3.19 mmol). The mixture was heated at 100° C. for 3 h and concentrated under reduced pressure. The residue was triturated with chloroform and filtered. The filtrate was concentrated under reduced pressure to afford butane-2-sulfonyl chloride (3 g, crude) as a yellow oil used in the next step as is.

Step 3: N-[5-(difluoromethoxy)-3-pyridyl]butane-2-sulfonamide

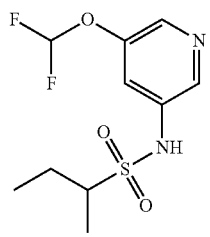 [SMILES: CCC(C)S(=O)(=O)Nc1cncc(OC(F)F)c1]

To a solution of 5-(difluoromethoxy)pyridin-3-amine (2 g, 12.49 mmol) in dichloromethane (20 mL) was added butane-2-sulfonyl chloride (2.74 g, 17.49 mmol) and pyridine (2.96 g, 37.47 mmol). After stirring at 25° C. for 3 h, the mixture was concentrated under reduced pressure. The residue was purified by RP-HPLC (25 to 70% acetonitrile in water and 0.225% formic acid) to afford N-[[5-[5-(difluoromethyl)-1,3,4-oxadiazol-2-yl]thiazol-2-yl]methyl]-N-[2-(trifluoromethyl)-4-pyridyl]ethanesulfonamide (790 mg, 20%) as a white solid.

Step 4: N-[5-(difluoromethoxy)pyridin-3-yl]-N-({5-[45-(difluoromethyl)-1,3,4-oxadiazol-2-yl]-1,3-thiazol-2-yl}methyl)butane-2-sulfonamide

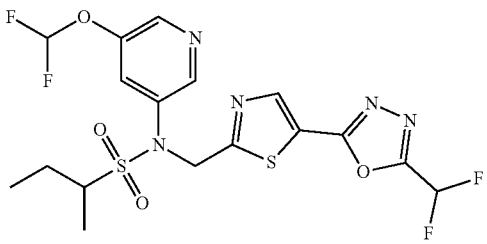 [SMILES: CCC(C)S(=O)(=O)N(Cc1ncc(-c2nnc(C(F)F)o2)s1)c1cncc(OC(F)F)c1]

To a solution of 2-[2-(bromomethyl)thiazol-5-yl]-5-(difluoromethyl)-1,3,4-oxadiazole (4a, 349 mg, 1.18 mmol) in acetone (3 mL) was added N-[5-(difluoromethoxy)-3-pyridyl]butane-2-sulfonamide (300 mg, 1.07 mmol) and potassium carbonate (444 mg, 3.21 mmol). The mixture was stirred at 25° C. for 1.5 h and filtered. The filtrate was concentrated under reduced pressure. The residue was purified by RP-HPLC (40 to 70% acetonitrile in water and 0.1% trifluoroacetic acid) to afford N-[5-(difluoromethoxy)pyridin-3-yl]-N-({5-[5-(difluoromethyl)-1,3,4-oxadiazol-2-yl]-1,3-thiazol-2-yl}methyl)butane-2-sulfonamide 318 (268.4 mg, 51%) as a yellow solid.

Preparation of N-[[5-[5-(difluoromethyl)-1,3,4-oxadiazol-2-yl]thiazol-2-yl]methyl]-N-[5-(trifluoromethoxy)-3-pyridyl]ethanesulfonamide (I-267)

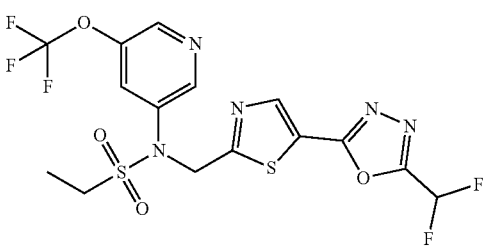 [SMILES: CCS(=O)(=O)N(Cc1ncc(-c2nnc(C(F)F)o2)s1)c1cncc(OC(F)(F)F)c1]

Step 1: 5-bromo-3-(trifluoromethoxy)pyridin-2-amine

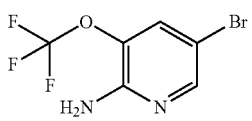 [SMILES: Nc1ncc(Br)cc1OC(F)(F)F]

To a solution of 3-(trifluoromethoxy)pyridin-2-amine (900 mg, 5.05 mmol) in dichloromethane (10 mL) was added N-bromosuccinimide (1.4 g, 7.58 mmol). After stirring at 25° C. for 0.5 hour, the reaction mixture was filtered. The filtrate was concentrated under reduced pressure. The residue was purified by column chromatography (silica gel, 100-200 mesh, 0-6% ethyl acetate in petroleum ether) to afford 5-bromo-3-(trifluoromethoxy)pyridin-2-amine (1.14 g, 84%) as a brown solid.

Step 2: 5-bromo-2-chloro-3-(trifluoromethoxy)pyridine

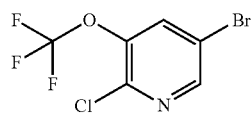

To a solution of 5-bromo-3-(trifluoromethoxy)pyridin-2-amine (1.1 g, 4.44 mmol) in dichloromethane (4 mL) was added chlorotrimethylsilane (4.3 g, 39.92 mmol). After stirring at 25° C. for 0.5 hour, isopentyl nitrite (1.6 g, 13.31 mmol) was added dropwise. After stirring at 25° C. for 2 hours, the reaction mixture was filtered. The filtrate was concentrated under reduced pressure. The residue was purified by column chromatography (silica gel, 100-200 mesh, 0-2%, ethyl acetate in petroleum ether) to afford 5-bromo-2-chloro-3-(trifluoromethoxy)pyridine (955 mg, 71%) as colorless oil.

Step 3: N-[6-chloro-5-(trifluoromethoxy)-3-pyridyl]ethanesulfonamide

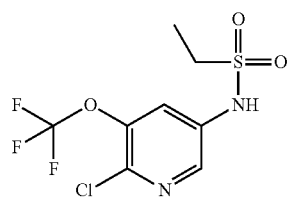 [SMILES: CCS(=O)(=O)Nc1cnc(Cl)c(OC(F)(F)F)c1]

To a solution of ethanesulfonamide (79 mg, 0.72 mmol) and 5-bromo-2-chloro-3-(trifluoromethoxy)pyridine (200 mg, 0.72 mmol) in 1,4-dioxane (5 mL) was added Xantphos Pd G3 (69 mg, 0.07 mmol) and cesium carbonate (589 mg, 1.81 mmol). After stirring at 110° C. for 16 hours under nitrogen atmosphere, the reaction mixture was filtered. The filtrate was concentrated under reduced pressure and the residue was purified by column chromatography (silica gel, 100-200 mesh, 0-15% methanol in dichloromethane) to afford N-[6-chloro-5-(trifluoromethoxy)-3-pyridyl]ethanesulfonamide (38 mg, 16%) as yellow oil.

Step 4: N-[5-(trifluoromethoxy)-3-pyridyl]ethanesulfonamide

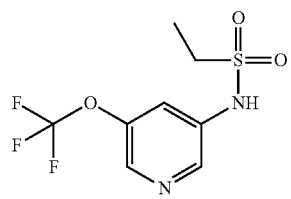 [SMILES: CCS(=O)(=O)Nc1cncc(OC(F)(F)F)c1]

To a solution of N-[6-chloro-5-(trifluoromethoxy)-3-pyridyl]ethanesulfonamide (38 mg, 0.12 mmol) in methanol (1 mL) was added palladium (13 mg, 0.01 mmol, 10% on carbon). After stirring at 25° C. under hydrogen atmosphere (15 psi) for 2 hours, the reaction mixture was filtered. The filtrate was concentrated under reduced pressure to afford crude N-[5-(trifluoromethoxy)-3-pyridyl]ethanesulfonamide (30 mg, crude) as a yellow solid.

Step 5: N-[[5-[5-(difluoromethyl)-1,3,4-oxadiazol-2-yl]thiazol-2-yl]methyl]-N-[5-(trifluoromethoxy)-3-pyridyl]ethanesulfonamide

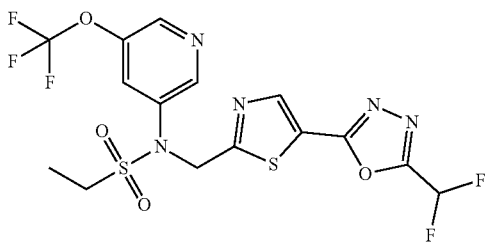 [SMILES: CCS(=O)(=O)N(Cc1ncc(-c2nnc(C(F)F)o2)s1)c1cncc(OC(F)(F)F)c1]

To a solution of N-[5-(trifluoromethoxy)-3-pyridyl]ethanesulfonamide (20 mg, 0.07 mmol) and 2-[2-(bromomethyl)thiazol-5-yl]-5-(difluoromethyl)-1,3,4-oxadiazole (4a, 20 mg, 0.07 mmol) in acetone (1 mL) was added potassium carbonate (28 mg, 0.20 mmol). After stirring at 25° C. for 1 hour, the reaction mixture was filtered. The filtrate was concentrated under reduced pressure. The residue was purified by RP-HPLC (35 to 65% acetonitrile in water and 0.225% formic acid) to afford N-[[5-[5-(difluoromethyl)-1,3,4-oxadiazol-2-yl]thiazol-2-yl]methyl]-N-[5-(trifluoromethoxy)-3-pyridyl]ethanesulfonamide (8.5 mg, 25%) as a yellow solid.

Preparation of N-({5-[5-(difluoromethyl)-1,3,4-oxadiazol-2-yl]-1,3-thiazol-2-yl}methyl)-N-{4H,6H,7H-pyrazolo[3,2-c][1,4]oxazin-2-yl}ethane-1-sulfonamide (I-231)

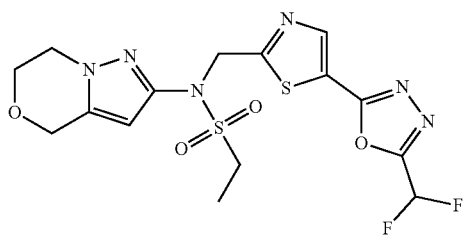 [SMILES: CCS(=O)(=O)N(Cc1ncc(-c2nnc(C(F)F)o2)s1)c1cc2n(n1)CCOC2]

Step 1: methyl 5-nitro-2-(2-tetrahydropyran-2-yloxyethyl)pyrazole-3-carboxylate

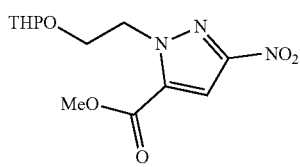

To a solution of methyl 3-nitro-1H-pyrazole-5-carboxylate (2.0 g, 11.69 mmol) in N-methyl-2-pyrrolidone (10 mL) was added 2-(2-bromoethoxy)tetrahydropyran (2.0 g, 9.35 mmol) and potassium carbonate (1.6 g, 11.69 mmol). After stirring at 80° C. for 16 h, the reaction mixture was diluted with water (30 mL) and ethyl acetate (50 mL). The separated organic layer was dried over sodium sulphate and concentrated to dryness under reduced pressure. The residue was purified by flash column chromatography (silica gel, 100-200 mesh, 0-25% ethyl acetate in petroleum ether) to afford methyl 5-nitro-2-(2-tetrahydropyran-2-yloxyethyl)pyrazole-3-carboxylate (2.2 g, 63%) as yellow oil.

Step 2: [5-nitro-2-(2-tetrahydropyran-2-yloxyethyl)pyrazol-3-yl]methanol

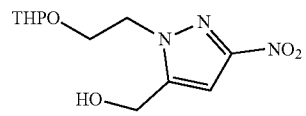

To a solution of methyl 5-nitro-2-(2-tetrahydropyran-2-yloxyethyl)pyrazole-3-carboxylate (2.2 g, 7.35 mmol) in tetrahydrofuran (30 mL) was added lithium borohydride (240 mg, 11.03 mmol) at 0° C. After stirring at 20° C. for 3 h, the reaction was quenched by addition of methanol (10 mL). The mixture was diluted with ethyl acetate (40 mL), washed with brine (40 mL), dried over sodium sulphate and concentrated to dryness under reduced pressure. The residue was purified by flash column chromatography (silica gel, 100-200 mesh, 0-50% ethyl acetate in petroleum ether) to afford [5-nitro-2-(2-tetrahydropyran-2-yloxyethyl)pyrazol-3-yl]methanol (1.4 g, 70%) as a yellow oil.

Step 3: 2-[5-(bromomethyl)-3-nitro-pyrazol-1-yl]ethanol

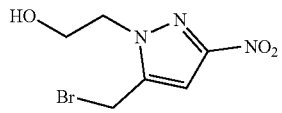 [SMILES: O=[N+]([O-])c1cc(CBr)n(CCO)n1]

To a solution of [5-nitro-2-(2-tetrahydropyran-2-yloxyethyl)pyrazol-3-yl]methanol (1.4 g, 5.16 mmol) in tetrahydrofuran (10 mL) was added pyridine (408 mg, 5.16 mmol), tetrabromomethane (3.4 g, 10.32 mmol) and triphenylphosphine (2.7 g, 10.32 mmol) at 0° C. The mixture was stirred at 20° C. for 17 h and filtered. The filtrate was concentrated to dryness under reduced pressure. The residue was purified by flash column chromatography (silica gel, 100-200 mesh, 0-10% ethyl acetate in petroleum ether), followed by preparative TLC (petroleum ether:ethyl acetate=1:1) to afford 2-[5-(bromomethyl)-3-nitro-pyrazol-1-yl]ethanol (180 mg, 14%) as a white solid.

Step 4: 2-nitro-6,7-dihydro-4H-pyrazolo[5,1-c][1,4]oxazine

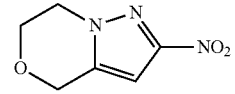 [SMILES: O=[N+]([O-])c1cc2n(n1)CCOC2]

To a solution of 2-[5-(bromomethyl)-3-nitro-pyrazol-1-yl]ethanol (140 mg, 0.56 mmol) in tetrahydrofuran (5 mL) was added sodium hydride (60%, 25 mg, 0.62 mmol) under nitrogen atmosphere. After stirring at 20° C. for 4 h, the reaction mixture was quenched by addition of water (10 mL) and extracted with ethyl acetate (30 mL). The organic extract was dried over sodium sulphate and concentrated to dryness under reduced pressure. The residue was purified by preparative TLC (petroleum ether:ethyl acetate=1:1) to afford 2-nitro-6,7-dihydro-4H-pyrazolo[5,1-c][1,4]oxazine (34 mg, 33%) as a white solid.

Step 5: 6,7-dihydro-4H-pyrazolo[5,1-c][1,4]oxazin-2-amine

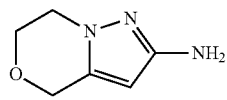

To a solution of 2-nitro-6,7-dihydro-4H-pyrazolo[5,1-c][1,4]oxazine (24 mg, 0.1 mmol) in ethanol (2.5 mL) and water (1 mL) was added iron (48 mg, 0.85 mmol) and ammonium chloride (91 mg, 1.70 mmol). The mixture was stirred at 80° C. for 4 h and filtered. The filtrate was concentrated to dryness under reduced pressure. The residue was diluted with dichloromethane (15 mL), washed with brine (20 mL), dried over sodium sulphate and concentrated to dryness under reduced pressure to afford 6,7-dihydro-4H-pyrazolo[5,1-c][1,4]oxazin-2-amine (13 mg, 66%) as a yellow solid.

Step 6: N-(6,7-dihydro-4H-pyrazolo[5,1-c][1,4]oxazin-2-yl)ethanesulfonamide

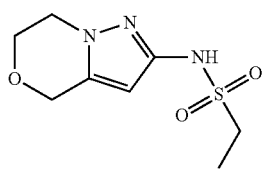

To a solution of 6,7-dihydro-4H-pyrazolo[5,1-c][1,4]oxazin-2-amine (22 mg, 0.16 mmol) in pyridine (0.5 mL) was added ethanesulfonyl chloride (24 mg, 0.19 mmol) at 0° C. The mixture was stirred at 20° C. for 2 h and filtered. The filtrate was concentrated to dryness under reduced pressure. The residue was purified by preparative TLC (dichloromethane:methanol=10:1) to afford N-(6,7-dihydro-4H-pyrazolo[5,1-c][1,4]oxazin-2-yl)ethanesulfonamide (24 mg, 53%) as a white solid.

Step 7: N-({5-[5-(difluoromethyl)-1,3,4-oxadiazol-2-yl]-1,3-thiazol-2-yl}methyl)-N-{4H,6H,7H-pyrazolo[3,2-c][1,4]oxazin-2-yl}ethane-1-sulfonamide

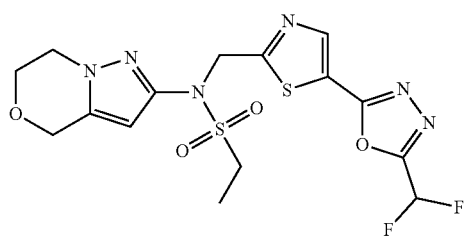 [SMILES: CCS(=O)(=O)N(Cc1ncc(-c2nnc(C(F)F)o2)s1)c1cc2n(n1)CCOC2]

To a solution of 2-[2-(bromomethyl)thiazol-5-yl]-5-(difluoromethyl)-1,3,4-oxadiazole (4a, 25 mg, 0.08 mmol) in N,N-dimethylformamide (0.5 mL) was added N-(6,7-dihydro-4H-pyrazolo[5,1-c][1,4]oxazin-2-yl)ethanesulfonamide (21 mg, 0.09 mmol) and sodium bicarbonate (21 mg, 0.25 mmol). The mixture was stirred at 25° C. for 2 h and filtered. The filtrate was concentrated to dryness under reduced pressure. The residue was purified by RP-HPLC (30 to 60% acetonitrile in water and 0.225% formic acid) to afford N-({5-[5-(difluoromethyl)-1,3,4-oxadiazol-2-yl]-1,3-thiazol-2-yl}methyl)-N-{4H,6H,7H-pyrazolo[3,2-c][1,4]oxazin-2-yl}ethane-1-sulfonamide (10.9 mg, 28%) as a yellow oil.

Preparation of N-((5-(5-(difluoromethyl)-1,3,4-oxadiazol-2-yl)thiazol-2-yl)methyl)-N-(5-fluoropyridin-3-yl)-1'-benzyl-1'-methylamino-sulfonamide (Compound I-29).

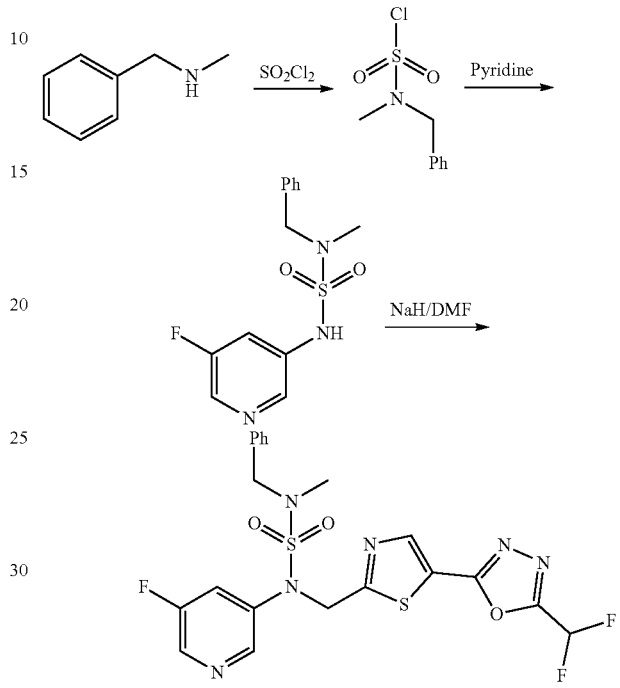

Step 1: N-Benzyl-N-methylsulfamoyl chloride

To a solution of sulfuryl chloride (1.11 g, 8.25 mmol) in dichloromethane (10 mL) at −10° C. is added N-methyl-N-benzylamine (1.00 g, 8.25 mmol). The cooling bath was removed after 30 min. and the reaction mixture was kept stirring for 5 h. Washed with water, the organic layer was dried (Na$_2$SO$_4$), filtered and concentrated. The resulting crude residue was directly used in the next step.

Step 2: N-Benzyl-N-methyl-[(5-fluoropyridin-3-yl)amino]sulfonamide

Half of the above crude material was mixed with 5-fluoro-3-pyridin-amine (196 mg, 0.89 mmol) and pyridine (106 mg, 1.34 mmol) in dichloromethane at ambient temperature. After stirred for 2 h, the reaction was quenched with sat. NH$_4$Cl. The organic residue was purified by chromatography (Silica gel, DCM/EtOAc, 1:0 to 1:1) to afford a white solid (25 mg, 9.5%). LC-MS: m/z [M+H]$^+$296.

Step 3: N-((5-(5-(Difluoromethyl)-1,3,4-oxadiazol-2-yl)thiazol-2-yl)methyl)-N-(5-fluoropyridin-3-yl)-1'-benzyl-1'-methylamino-sulfonamide The title compound was synthesized by following the same experimental procedure as described in the preparation of N-((5-(5-difluoromethyl)-1,3,4-oxadiazol-2-yl)thiazol-2-yl)methyl-N-(1-phenylcyclopropoyl)ethanesulfonamide (I-20), employing the above N-benzyl-N-methyl-[(5-fluoropyridin-3-yl)amino]sulfonamide instead (36% yield).

The methods disclosed above in Example 4 were also used to prepare the following compounds: I-2, I-3, I-4, I-5, I-9, I-10, I-13, I-14, I-15, I-16, I-17, I-22, I-23, I-24, I-25, I-27, I-30, I-31, I-32, I-33, I-34, I-35, I-36, I-37, I-38, I-39, I-40, I-46, I-47, I-49, I-50, I-51, I-52, I-53, I-54, I-55, I-56, I-57, I-58, I-59, I-61, I-62, I-63, I-64, I-65, I-66, I-67, I-68, I-69, I-70, I-74, I-75, I-76, I-77, I-78, I-79, I-80, I-87, I-88, I-89, I-90, I-91, I-92, I-93, I-94, I-95, I-97, I-98, I-99, I-100, I-103, I-104, I-405, I-406, I-107, I-108, I-109, I-110, I-111, I-112, I-113, I-114, I-115, I-116, I-117, I-118, I-120, I-121, I-122, I-123, I-125, I-126, I-127, I-128, I-129, I-130, I-131, I-132, I-133, I-134, I-136, I-137, I-138, I-139, I-140, I-141, I-145, I-146, I-148, I-149, I-150, I-151, I-152, I-153, I-155, I-156, I-157, I-158, I-159, I-160, I-161, I-162, I-163, I-164, I-165, I-166, I-167, I-168, I-169, I-170, I-178, I-179, I-180, I-181, I-182, I-183, I-184, I-187, I-188, I-189, I-190, I-191, I-191, I-192, I-193, I-194, I-196, I-197, I-201, I-202, I-203, I-204, I-205, I-206, I-211, I-212, I-213, I-214, I-215, I-216, I-217, I-218, I-220, I-221, I-222, I-223, I-225, I-226, I-228, I-229, I-230, I-232, I-233, I-234, I-236, I-237, I-238, I-239, I-240, I-241, I-242, I-243, I-244, I-265, I-266, and I-268.

Example 5. Synthesis of Amine/Aniline Compounds of Formula (I)

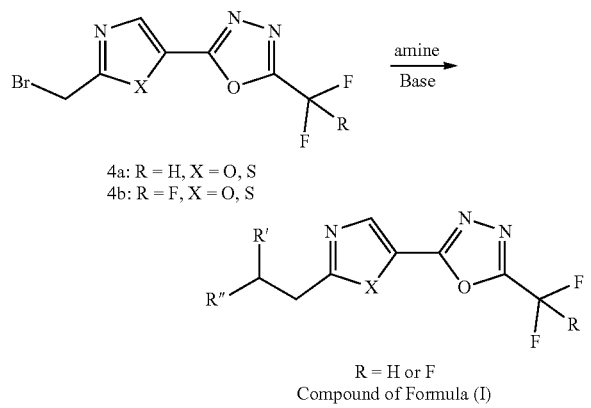

4a: R = H, X = O, S
4b: R = F, X = O, S

R = H or F
Compound of Formula (I)

Preparation of N-((5-(5-(difluoromethyl)-1,3,4-oxadiazol-2-yl)thiazol-2-yl)methyl)-3-(trifluoromethyl)aniline (Compound I-7).

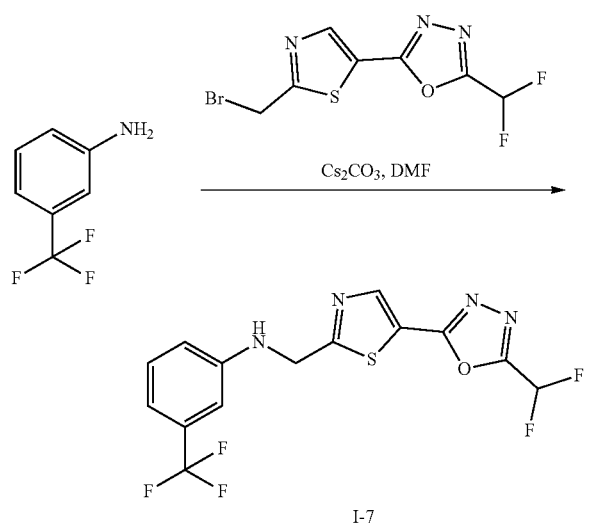

2-[2-(Bromomethyl)-1,3-thiazol-5-yl]-5-(difluoromethyl)-1,3,4-oxadiazole (4a, 150 mg, 0.51 mmol) was taken up in DMF (1 ml) with cesium carbonate (330 mg, 0.20 mmol) and then 3-trifluoromethylaniline (75 μL, 0.60 mmol) was added to it. The solution turned dark immediately and was stirred for 16 h at room temperature. TLC indicated that the reaction was complete. The solution was diluted with EtOAc and then washed with water. The organic layer was filtered through MgSO₄ and concentrated. The residue was purified on Combiflash (hexanes/EtOAc gradient) to afford the title compound (75 mg, 39%) as an oil.

Preparation of 3-chloro-N-({5-[5-(difluoromethyl)-1,3,4-oxadiazol-2-yl]-1,3-thiazol-2-yl}methyl)-N-(2-methoxyethyl)aniline (I-142)

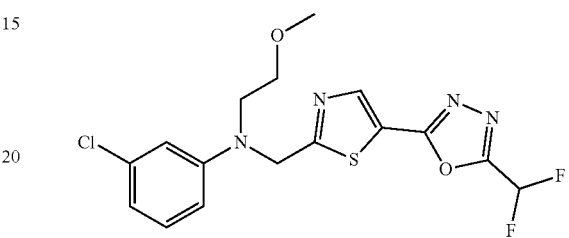

Step 1: 3-chloro-N-(2-methoxyethyl)aniline

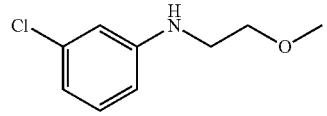

To a solution of 3-chloroaniline (500 mg, 3.92 mmol) in tetrahydrofuran (3 mL) was added sodium hydride (60%, 220 mg, 5.49 mmol) and 1-bromo-2-methoxy-ethane (817 mg, 5.88 mmol). The mixture was stirred at 70° C. for 2 h and quenched by addition of water (10 mL). The resulting solution was extracted with ethyl acetate (3×20 mL). The combined organic extracts were dried over sodium sulphate and concentrated under reduced pressure. The residue was purified by RP-HPLC (45 to 75% acetonitrile in water and 0.05% ammonium hydroxide+10 mM ammonium bicarbonate) to afford 3-chloro-N-(2-methoxyethyl)aniline (264 mg, 36%) as a colorless oil.

Step 2: 3-chloro-N-({5-[5-(difluoromethyl)-1,3,4-oxadiazol-2-yl]-1,3-thiazol-2-yl}methyl)-N-(2-methoxyethyl)aniline

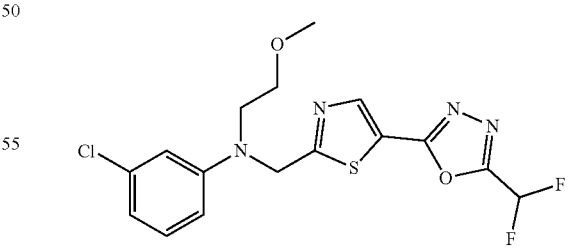

To a solution of 3-chloro-N-(2-methoxyethyl)aniline (19 mg, 0.1 mmol) in N,N-dimethylformamide (0.5 mL) was added 2-[2-(bromomethyl)thiazol-5-yl]-5-(difluoromethyl)-1,3,4-oxadiazole (4a, 60 mg, 0.2 mmol) and sodium bicarbonate (26 mg, 0.3 mmol). The mixture was stirred at 20° C. for 2 h and filtered. The filtrate was concentrated under reduced pressure. The residue was purified by RP-HPLC (20 to 70% acetonitrile in water and 10 mM ammonium bicarbonate) to afford 3-chloro-N-({5-[5-(difluoromethyl)-1,3,4-oxadiazol-2-yl]-1,3-thiazol-2-yl}methyl)-N-(2-methoxyethyl)aniline (13.7 mg, 33%) as a white solid.

The method disclosed in Example 5 was also used to prepare the following compounds: I-7, I-45, I-72, I-73, I-124, and I-135.

Preparation of N-(((5-(5-(difluoromethyl)-1,3,4-oxadiazol-2-yl)thiazol-2-yl)methyl)pyridin-3-amine (Compound I-28).

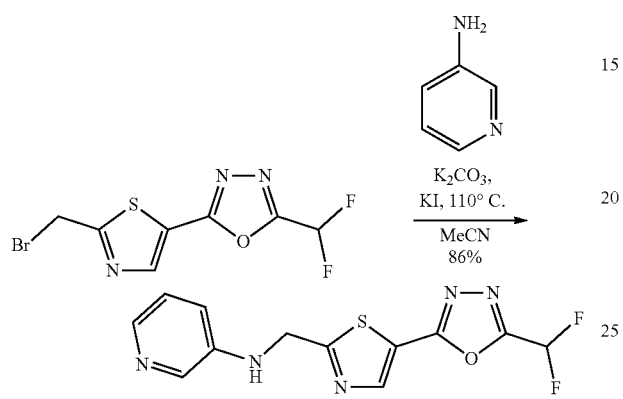

To a 5 mL microwave reaction vial was added 2-[2-(bromomethyl)-1,3-thiazol-5-yl]-5-(difluoromethyl)-1,3,4-oxadiazole (4a, 60 mg, 0.20 mmol), 3-aminopyridine (57 mg, 0.61 mmol), potassium iodide (3 mg, 0.02 mmol), potassium carbonate (31 mg, 0.22 mmol), and acetonitrile (0.68 mL). The reaction mixture was stirred at 110° C. for 15 min under microwave irradiation. The resulting crude reaction mixture was filtered through a plug of celite, the plug of celite was washed with acetonitrile, and the resulting filtrate was concentrated. The resulting residue was adsorbed onto silica with methanol and purified by column chromatography (0-20% MeOH/DCM) to afford the title compound as a light brown solid (54 mg, 86%).

Example 6. Synthesis of Tertiary Amide Compounds of Formula (I) from Amines of Example 5

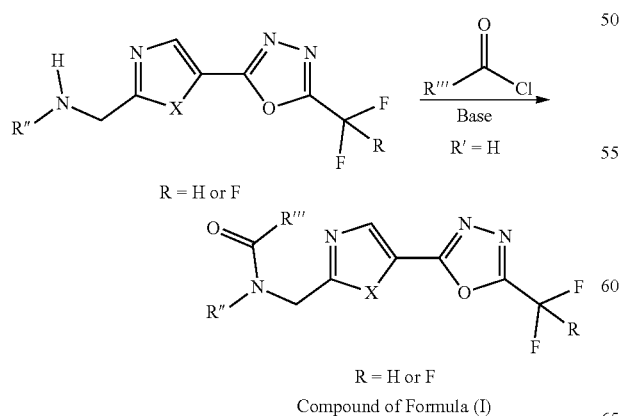

Preparation of N-((5-(5-(difluoromethyl)-1,3,4-oxadiazol-2-yl)thiazol-2-yl)methyl)-N-(3-(trifluoromethyl)phenyl)nicotinamide (Compound I-8).

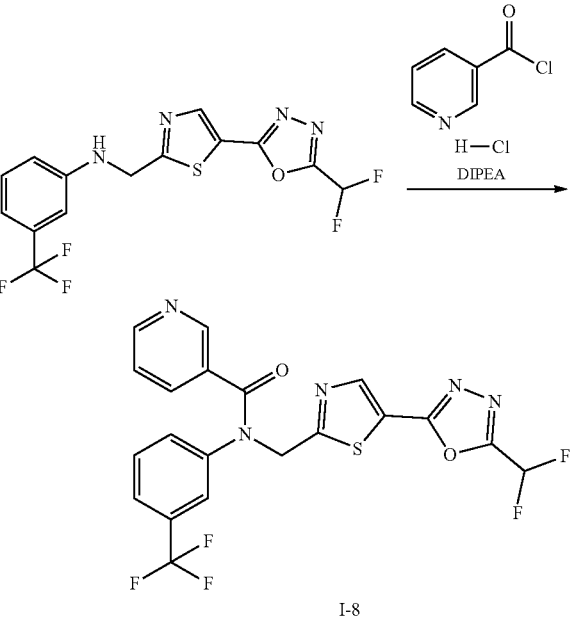

N-((5-(5-(difluoromethyl)-1,3,4-oxadiazol-2-yl)thiazol-2-yl)methyl)-3-(trifluoromethyl)aniline (I-7, 26 mg, 0.07 mmol) was taken in DMF (1 ml) with nicotinoyl chloride hydrochloride (15 mg, 0.80 mmol) and then diisopropylethylamine (0.04 mL, 0.21 mmol) was added to it. The solution was stirred at room temperature for 18 h and then at 40° C. for 16 h. TLC indicated that the reaction was completed. The reaction was cooled to room temperature, diluted with EtOAc and then washed with water. The organic layer was collected, filtered through MgSO$_4$ and concentrated. The residue was purified by Combiflash (DCM/methanol gradient) to afford the title compound (21 mg, 63%) as a white solid.

The method disclosed in Example 4 was also used to prepare compound I-175.

Preparation of 1-((5-(5-(difluoromethyl)-1,3,4-oxadiazol-2-yl)thiazol-2-yl)methyl)-3,3-dimethyl-1-(pyridin-3-yl)urea (Compound I-21).

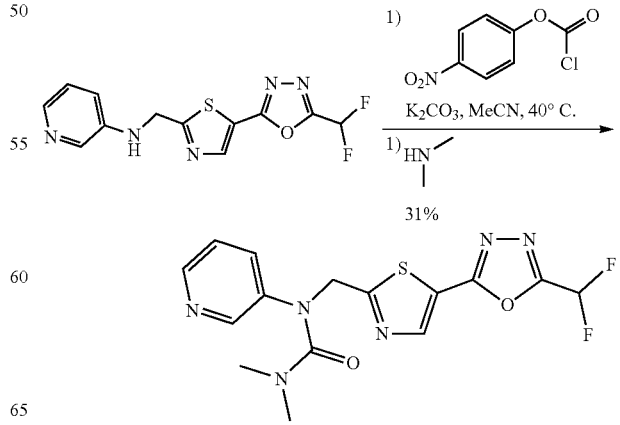

To a 2 dram vial was added N-({5-[5-(difluoromethyl)-1,3,4-oxadiazol-2-yl]-1,3-thiazol-2-yl}methyl)pyridin-3-amine (I-28, 30 mg, 0.097 mmol), potassium carbonate (40 mg, 0.15 mmol) and acetonitrile (1 mL). To the reaction mixture was added 4-nitrophenyl chloroformate (29.3 mg, 0.15 mmol). The reaction mixture was stirred at 45° C. for 4 h. To the crude reaction mixture was added a 2 M solution of dimethylamine in THF (0.24 mL, 0.49 mmol), and the reaction was stirred at 45° C. for 30 min. The reaction mixture was then filtered and concentrated under reduced pressure. The resulting residue was purified by column chromatography (0-20% MeOH/DCM) to yield the title compound as an amorphous brown solid (11.4 mg, 31%).

Preparation of Methyl ((5-(5-(difluoromethyl)-1,3,4-oxadiazol-2-yl)thiazol-2-yl)methyl)(pyridin-3-yl)carbamate (Compound I-26).

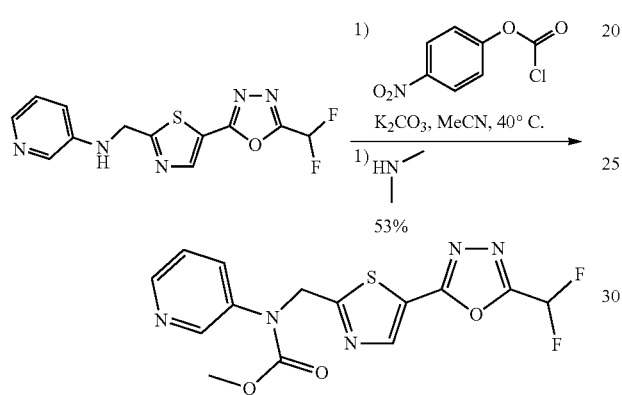

To a 2 dram vial was added N-({5-[5-(difluoromethyl)-1,3,4-oxadiazol-2-yl]-1,3-thiazol-2-yl}methyl)pyridin-3-amine (I-28, 20 mg, 0.065 mmol), potassium carbonate (18 mg, 0.13 mmol) and acetonitrile (0.6 mL). To the reaction mixture was added a 4-nitrophenyl chloroformate (19.6 mg, 0.097 mmol). The reaction mixture was stirred at 40° C. for 4 h. The reaction mixture was cooled to ambient temperature, and MeOH (1 mL) was added to the reaction mixture. After stirring the reaction mixture for 15 min, the crude reaction mixture was then filtered through celite and the celite was washed with MeOH. The combined filtrate was concentrated under reduced pressure, adsorbed onto silica and purified by column chromatography (0-20% EtOAc/hexane) to afford the title compound as an off-white solid (12.6 mg, 53%).

Example 7. Synthesis of Amine/Aniline Compounds of Formula (I)

Preparation of 5-(5-(difluoromethyl)-1,3,4-oxadiazol-2-yl)-N-(1-(2,6-difluorophenyl)cyclopropyl)thiazol-2-amine (Compound I-18).

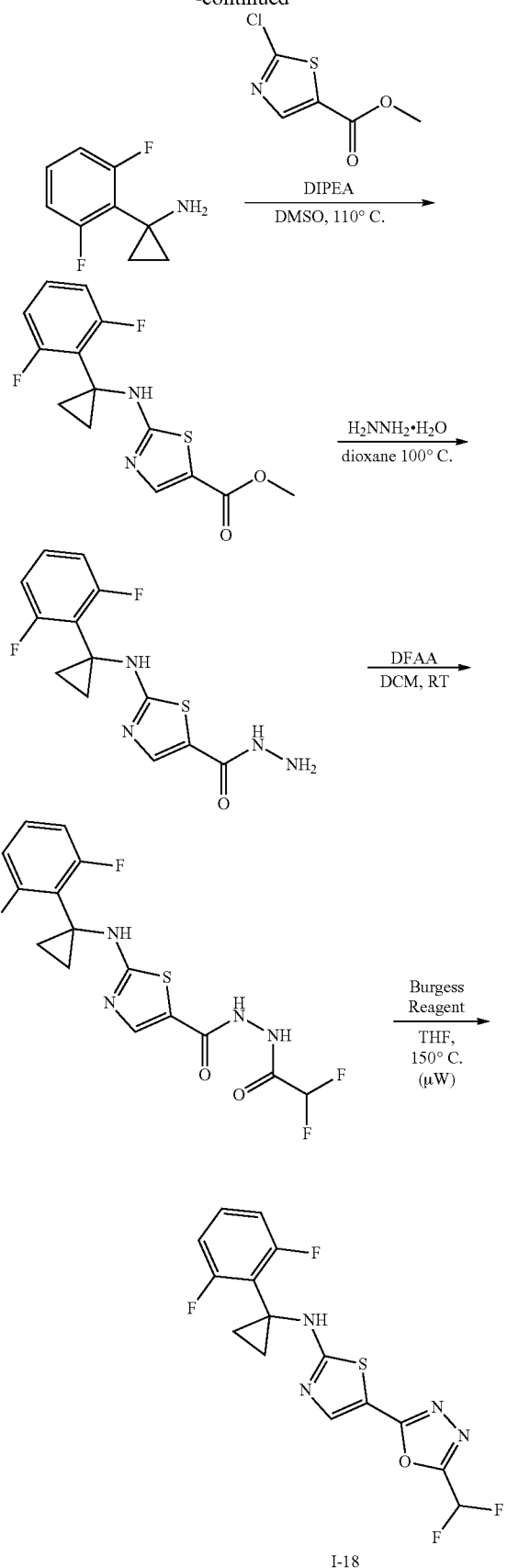

Step 1: Preparation of 1-(2,6-difluorophenyl)cyclopropan-1-amine.

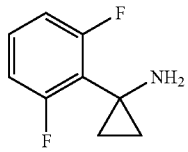 [SMILES: NC1(c2c(F)cccc2F)CC1]

To an oven-dried 200 mL round-bottom flask containing a 1,5-inch egg-shaped stirbar under N₂ atmosphere was added 2,6-difluorobenzonitrile (2.78 g, 20 mmol), followed by methyl tert-butyl ether (MTBE) (100 mL). The pale yellow solution was cooled to −78° C. and titanium tetraisopropoxide (7.3 mL, 24 mmol, 1.2 equiv.) was in one portion. Ethylmagnesium bromide (3M in ether, 16.7 mL, 50 mmol, 2.5 equiv.) was added dropwise over the course of 5 minutes with vigorous stirring, yielding a pale yellow homogeneous solution (caution: potential for exotherm and gas evolution). No gas evolution was observed in this case. The dry ice bath was left to expire slowly over the course of 4 hours with vigorous stirring (1500 RPM) of the solution. Upon warming to room temperature, a viscous opaque brown solution is formed. This solution was cooled to 0° C. in an ice bath. Then, BF₃·OEt₂ (4.9 mL, 40 mmol, 2 equiv.) was added dropwise over the course of 5 minutes (caution: exothermic, gas evolution). The ice bath was removed and the opaque brown suspension was allowed to warm to room temperature overnight. The following day, the reaction was quenched by adding 1M NaOH (100 mL, 5 equiv.) in small portions at first, followed by EtOAc (50 mL), and then stirred vigorously at room temperature for 2 hours to yield a biphasic mixture of a top colorless organic layer and a bottom dark blue aqueous emulsion. This biphasic mixture was filtered directly through water-wetted celite, washed once with water (50 mL) and once with EtOAc (50 mL). The filtrate was collected and the layers separated. The aqueous layer was extracted twice more with EtOAc (50 mL). The combined organic layers were washed twice with water (50 mL) and once with brine (25 mL), then dried over MgSO₄, filtered and concentrated by rotary evaporation. The crude product was purified by column chromatography (Silica gel, 0-50% EtOAc in hexanes) to afford the title compound.

Step 2.: Preparation of methyl 2-((1-(2,6-difluorophenyl)cyclopropyl)amino)-thiazole-5-carboxylate.

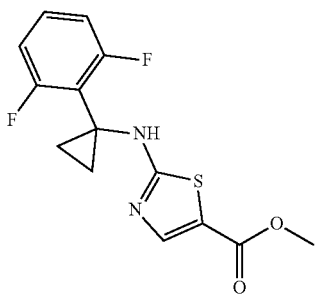 [SMILES: COC(=O)c1cnc(NC2(c3c(F)cccc3F)CC2)s1]

To a tail scintillation vial with a silicone cap under N₂ atmosphere (balloon) was added 1-(2,6-difluorophenyl)cyclopropan-1-amine (169 mg, 1.0 mmol, 1 equiv), methyl 2-chlorothiazole-5-carboxylate (195 mg, 1.1 mmol, 1.1 equiv), DIPEA (0.87 mL, 5 mmol, 5 equiv), and DMSO (3 mL). The orange biphasic clear mixture was heated to 110° C. overnight (12 hours), and it became a monophasic brown solution. The following day, LCMS and TLC analysis indicated complete conversion of the cyclopropylamine to a complex mixture of products. The reaction was allowed to cool to room temperature, then poured into water (50 mL) and extracted with EtOAc (3×50 mL). The combined organics were washed with water, then brine, then dried over MgSO₄, filtered and concentrated by rotary evaporation. The crude product, a dark brown oil, was dry loaded onto silica gel and purified by flash column chromatography (0-50% EtOAc in hexanes gradient) to provide the title compound as a brown oil, 47.9 mg (15% yield).

Step 3: Preparation of 2-((1-(2,6-difluorophenyl)cyclopropyl)amino)thiazole-5-carbohydrazide.

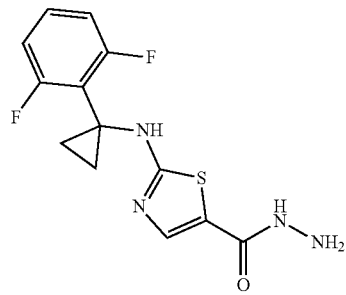 [SMILES: NNC(=O)c1cnc(NC2(c3c(F)cccc3F)CC2)s1]

To a tall scintillation vial with a red PTFE cap under N₂ atmosphere (balloon) was added methyl 2-((1-(2,6-difluorophenyl)cyclopropyl)amino)thiazole-5-carboxylate (30.0 mg, 0.97 mmol, 1 equiv.), 1,4-dioxane (1 mL), and lastly hydrazine monohydrate (0.05 mL, 1 mmol, 10 equiv.). The homogeneous orange solution was heated to 100° C. for 64 h, after which time LCMS analysis indicated complete conversion to the desired acyl hydrazide. The mixture was cooled to room temperature, then poured into water (50 mL) and extracted three times with EtOAc (50 mL). The combined organics were washed with water, then brine, then dried over MgSO₄, filtered and concentrated by rotary evaporation to provide the title compound as a brown oil of sufficient purity to take forward directly to the next step, 25.1 mg (84% yield).

Step 4: Preparation of N-(2,2-difluoroacetyl)-2-((1-(2,6-difluorophenyl)-cyclopropyl)amino)thiazole-5-carbohydrazide.

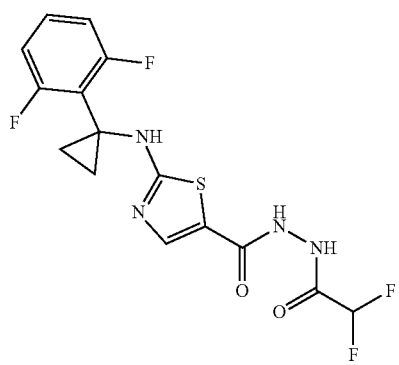 [SMILES: O=C(NNC(=O)C(F)F)c1cnc(NC2(c3c(F)cccc3F)CC2)s1]

To a vial was added 2-((1-(2,6-difluoropheny)cyclopropyl)amino)thiazole-5-carbohydrazide (25.1 mg, 0.081 mmol, 1 equiv.) and DCM (1 mL). The heterogeneous

239 orange suspension was cooled to 0° C. in an ice bath. Lastly, difluoroacetic anhydride (DFAA, 0.02 mL, 0.16 mmol, 2 equiv.) was added dropwise over 30 seconds. The resulting homogeneous orange solution was allowed to warm to room temperature. After 30 minutes, LCMS analysis indicated complete conversion to the desired diacyl hydrazide. The reaction was quenched by the addition of 1 mL saturated aqueous NaHCO$_3$ and 1 mL methanol, and was stirred at room temperature for 1 hour. Then, the reaction mixture was poured into 50 mL half-saturated NaHCO$_3$ and extracted three times with EtOAc (50 mL). The combined organics were washed with water, then brine, then dried over MgSO$_4$, filtered and concentrated by rotary evaporation to provide the title compound as a waxy orange solid, 22.9 mg (73% yield).

Step 5: Preparation of 5-(5-(difluoromethyl)-1,3,4-oxadiazol-2-yl)-N-(1-(2,6-difluorophenyl)cyclopropyl)thiazol-2-amine.

I-18

To a 0.5-2 mL microwave vial was added a stifling flea, N'-(2,2-difluoroacetyl)-2-((1-(2,6-difluorophenyl)cyclopropyl)amino)thiazole-5-carbohydrazide (22.9 mg, 0.06 mmol, 1 equiv) as a solution in THF (1 mL), and lastly Burgess reagent (70.6 mg, 0.3 mmol, 5 equiv). The mixture was pre-stirred for 2 minutes, then heated to 150° C. in a microwave for 2 hours at approximately 8 bar of pressure. After the reaction, the reaction was an orange natant with a sinking brown oil. LCMS analysis of the orange natant indicated complete conversion of the diacyl hydrazide to the desired oxadiazole. The reaction mixture was poured into water (50 mL) and extracted three times with EtOAc (50 mL). The combined organics were washed with water, then brine, then dried over MgSO$_4$, filtered and concentrated by rotary evaporation to provide the crude material as a yellow oil. The crude material was dry loaded onto silica gel and purified by flash column chromatography (0-50% EtOAc in hexanes gradient) to provide the title compound as a pale yellow solid, 16.6 mg, of still insufficient purity. The material was subjected to preparative HPLC purification (10-100% MeCN in water with 0.1% TFA), the product-containing fractions were frozen at −78° C. and lyophilized to provide the purified title compound as a fluffy white solid, 4.1 mg (19% yield).

240

Preparation of 5-(5-(difluoromethyl)-1,3,4-oxadiazol-2-yl)-N-phenethylthiazol-2-amine (Compound I-19).

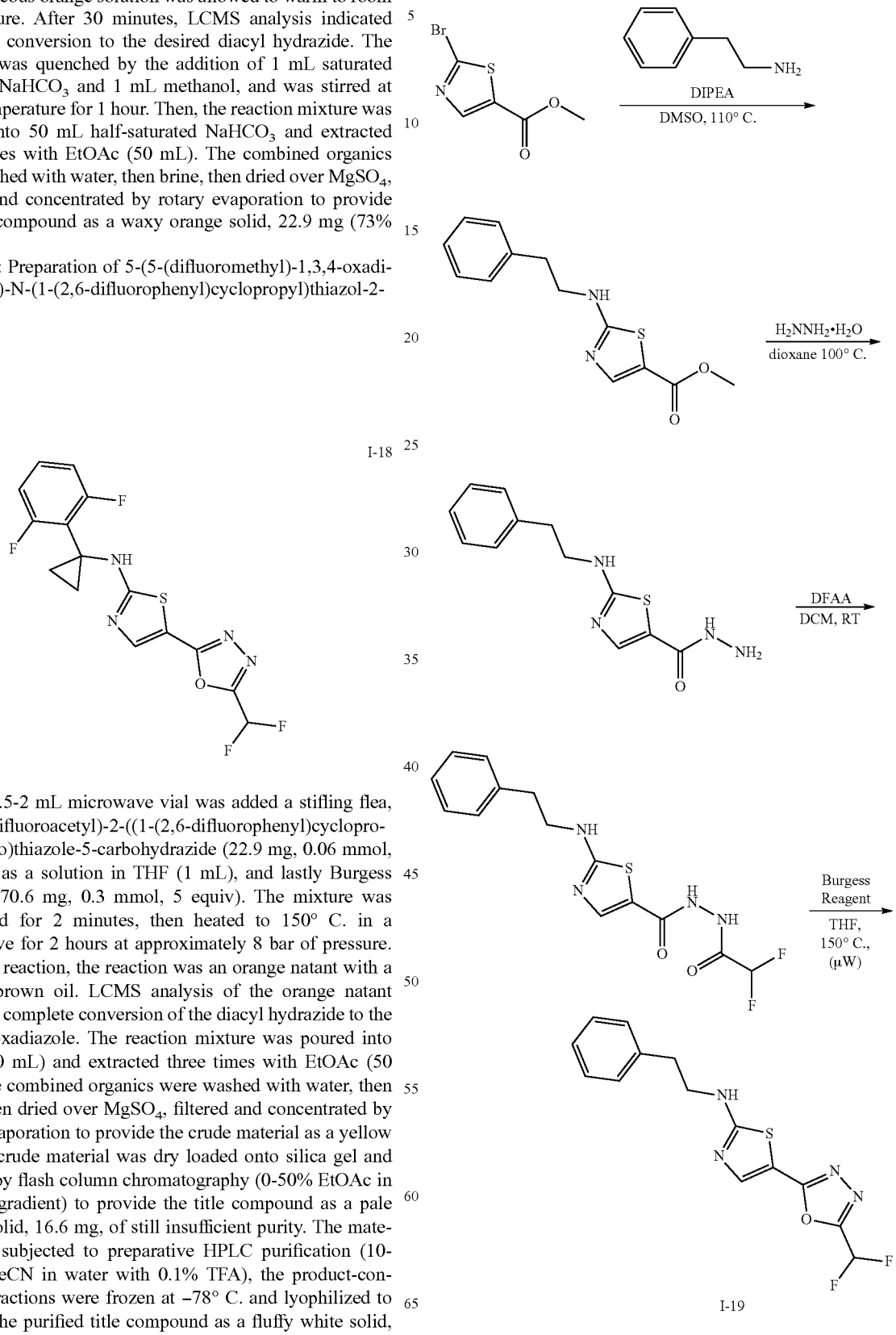

I-19

Step 1: Preparation of methyl 2-(phenethylamino)thiazole-5-carboxylate.

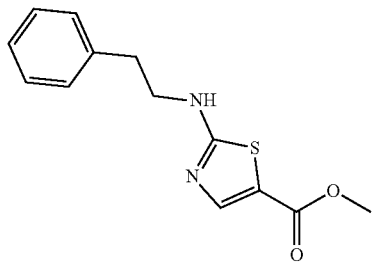 [SMILES: COC(=O)c1cnc(NCCc2ccccc2)s1]

To a tall scintillation vial with a PTFE cap under N₂ atmosphere (balloon) was added methyl 2-bromothiazole-5-carboxylate (444 mg, 2.0 mmol, 1 equiv.), 2-phenethylamine (0.30 mL, 2.4 mmol, 1.2 equiv.), DMSO (6 mL) and DIPEA (1.7 mL, 10 mmol, 5 equiv.). The pale yellow-orange biphasic clear mixture was heated to 110° C. for 2 hours, after which LCMS analysis indicated clean complete conversion to the desired product. The reaction was cooled to room temperature, then poured into half-saturated aqueous NH₄Cl (50 mL) and extracted with EtOAc (3×50 mL). The combined organics were washed with water, then brine, then dried over MgSO₄, filtered and concentrated by rotary evaporation to provide a crude red solid, which was dry loaded onto silica gel and purified by flash column chromatography (0-50% EtOAc in hexanes gradient) to provide the title compound as a light pink solid, 395.5 mg (75% yield).

Step 2: Preparation of 2-(phenethylamino)thiazole-5-carbohydrazide.

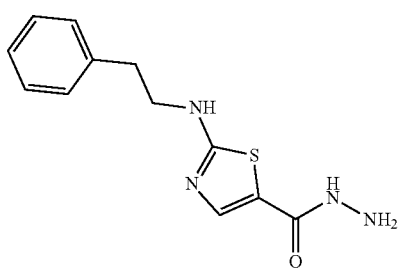 [SMILES: NNC(=O)c1cnc(NCCc2ccccc2)s1]

To a tall scintillation vial with a PTFE cap under N₂ atmosphere (balloon) was added methyl 2-(phenethylamino) thiazole-5-carboxylate (131 mg, 0.5 mmol, 1 equiv), followed by 1,4-dioxane (2 mL), and lastly hydrazine hydrate (0.24 mL, 5 mmol, 10 equiv). The light yellow biphasic clear mixture was heated to 100° C. overnight, after which LCMS analysis indicated complete conversion to the desired acyl hydrazide. The reaction was poured into water (50 mL), then extracted 3 times with EtOAc (50 mL). The combined organic layers were washed with water, then brine, then dried over MgSO₄, filtered and concentrated by rotary evaporation to provide the crude product as a light orange solid in sufficient purity to take forward directly, 105.1 mg (80% yield).

Step 3: Preparation of N'-(2,2-difluoroacetyl)-2-(phenethylamino)thiazole-5-carbohydrazide.

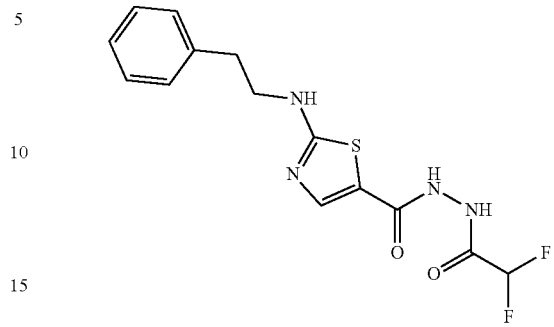

To a scintillation vial was added 2-(phenethylamino) thiazole-5-carbohydrazide (52.5 mg, 0.2 mmol), followed by DCM (1 mL). The heterogeneous white suspension was cooled to 0° C. in an ice bath. Then, difluoroacetic anhydride (DFAA, 0.05 mL, 0.4 mmol, 2 equiv) was added dropwise over 30 seconds. The now fully homogeneous pale yellow solution was allowed to warm to room temperature for 30 minutes, after which LCMS analysis indicated complete conversion to a mixture of the desired product and a side product in which the aminothiazole NH was also acylated, favoring the latter. The acylated aminothiazole was chemoselectively deprotected in situ by adding 1 mL methanol, followed by 1 mL saturated aqueous Na₂CO₃, and stirring the heterogeneous biphasic mixture at room temperature for 1 hour. Then, the mixture was poured into 50 mL water (50 mL), then extracted 3 times with EtOAc (50 mL). The combined organic layers were washed with water, then brine, then dried over MgSO₄, filtered and concentrated by rotary evaporation to provide the crude product as a pale yellow-orange solid in sufficient purity to take forward directly to the next step, 23.2 mg (34%).

Step 4: Preparation of 5-(5-(difluoromethyl)-1,3,4-oxadiazol-2-yl)-N-phenethylthiazol-2-amine.

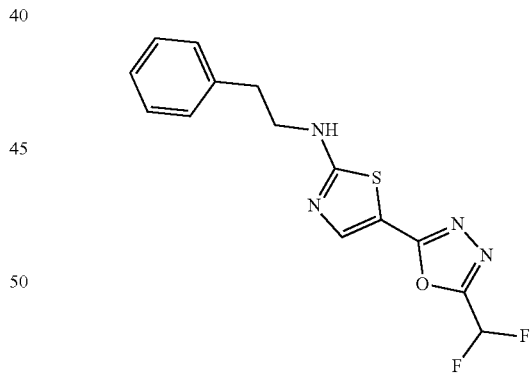

To a small microwave vial (0.5-2 mL) containing a magnetic stirring flea was added N'-(2,2-difluoroacetyl)-2-(phenethylamino)thiazole-5-carbohydrazide (23.2 mg, 0.068 mmol, 1 equiv) as a solution in THF (1 mL). Then, Burgess reagent (81.6 mg, 0.34 mmol, 5 equiv) was added, the vial crimped and microwaved for 2 hours at 150° C. at approximately 8 bar. After cooling to room temperature, the reaction contains a sinking brown oil with a clear yellow natant. LCMS analysis of the yellow natant indicated complete conversion of the diacylhydrazide starting material to the desired oxadiazole, along with multiple minor impurities. Then, the mixture was poured into 50 mL water (50 mL), then extracted 3 times with EtOAc (50 mL). The combined organic layers were washed with water, then brine, then dried over MgSO$_4$, filtered and concentrated by rotary evaporation to provide a crude pale yellow oil. The material was dry loaded onto silica gel and purified by flash column chromatography (0-50% EtOAc/hexanes gradient) to provide the title compound as a waxy white solid, 13.8 mg (63% yield).

Example 8. Preparation of 2-(2-((3-chlorophenoxy)methyl)thiazol-5-yl)-5-(difluoromethyl)-1,3,4-oxadiazole (Compound I-71)

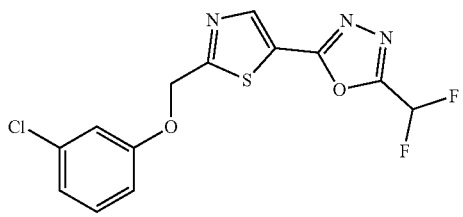 [SMILES: FC(F)c1nnc(-c2cnc(COc3cccc(Cl)c3)s2)o1]

To a solution of 2-[2-(bromomethyl)thiazol-5-yl]-5-(difluoromethyl)-1,3,4-oxadiazole (30 mg, 0.1 mmol) and 3-chlorophenol (16 mg, 0.12 mmol)) in N,N-dimethylformamide (1 mL) was added potassium carbonate (42 mg, 0.3 mmol). The mixture was stirred at 20° C. for 1 hour and filtered. The filtrate was concentrated to dryness under reduced pressure. The residue was purified by RP-HPLC (55-85% acetonitrile in water and 0.225% formic acid) to afford 2-[2-[(3-chlorophenoxy)methyl]thiazol-5-yl]-5-(difluoromethyl)-1,3,4-oxadiazole (9.7 mg, 28%) as a yellow solid.

Example 9. Synthesis of Regioisomeric Thiazole/Oxazole Compounds of Formula (I)—Amides Preparation of N-(3-chlorophenyl)-N-((4-(5-(difluoromethyl)-1,3,4-oxadiazol-2-yl)thiazol-2-yl)methyl)cyclopropanecarboxamide (Compound I-84).

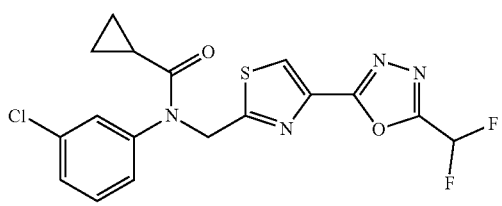 [SMILES: O=C(C1CC1)N(Cc1nc(-c2nnc(C(F)F)o2)cs1)c1cccc(Cl)c1]

N-(3-chlorophenyl)-N-((4-(5-(difluoromethyl)-1,3,4-oxadiazol-2-yl)thiazol-2-yl)methyl)cyclopropanecarboxamide
Step 1: 2-methylthiazole-4-carbohydrazide

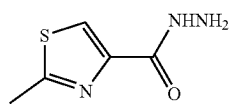

To a solution of ethyl 2-methylthiazole-4-carboxylate (5.0 g, 29.2 mmol) in ethanol (50 mL) was added hydrazine hydrate (16.5 g, 280.4 mmol) at 20° C. Then the reaction was stirred at 90° C. for 16 hours and concentrated to dryness under reduced pressure. The residue was purified by column chromatography (silica gel, 100-200 mesh, 0-10% methanol in dichloromethane) to afford 2-methylthiazole-4-carbohydrazide (2.2 g, 48%) as a yellow solid. LCMS R$_T$=0.483 min, m/z=158.2 [M+H]$^+$.

Step 2: N-(2,2-difluoroacetyl)-2-methyl-thiazole-4-carbohydrazide

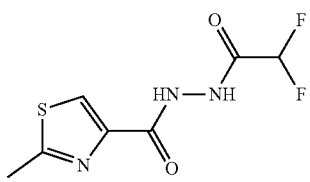

To a solution of 2-methtylthiazole-4-carbohydrazide (2.0 g, 12.7 mmol) and N,N-Diisopropylethylamine (1.6 g, 12.7 mmol) in tetrahydrofuran (20 mL) was added (2,2-difluoroacetyl) 2,2-difluoroacetate (2.7g, 15.3 mmol). The reaction was stirred at 20° C. for 16 hours and concentrated to dryness under reduced pressure. The residue was purified by column chromatography (silica gel, 100-200 mesh, 0-5% methanol in dichloromethane) to afford N'-(2,2-difluoroacetyl)-2-methyl-thiazole-4-carbohydrazide (2.8 g, 94%) as a white solid.

Step 3: 2-(difluoromethyl)-5-(2-methylthiazol-4-y)-1,3,4-oxadiazole

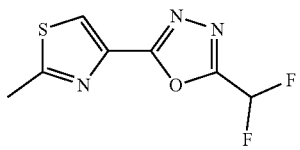

To a solution of N'-(2,2-difluoroacetyl)-2-methyl-thiazole-4-carbohydrazide (2.8 g, 11.9 mmol) in tetrahydrofuran (30 mL) was added Burgess reagent (7.1 g, 29.8 mmol). The mixture was stirred at 90° C. under microwave for 3 hours. The mixture was cooled and filtered. The filtrate was concentrated under reduced pressure and the residue was purified by column chromatography (silica gel, 100-200 mesh, 0-25% ethyl acetate in petroleum ether) to afford 2-(difluoromethyl)-5-(2-methylthiazol-4-yl)-1,3,4-oxadiazole (1.4 g, 54%) as a white solid.

Step 4: 2-[2-(bromomethyl)thiazol-4-yl]-5-(difluoromethyl)-1,3,4-oxadiazole

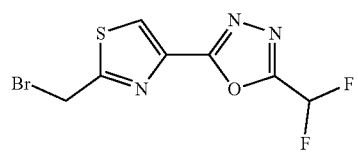

To a solution of 2-(difluoromethyl)-5-(2-methylthiazol-4-yl)-1,3,4-oxadiazole (150 mg, 0.69 mmol) in carbon tetrachloride (5 mL) were added N-bromosuccinimide (135 mg, 0.76 mmol) and azodiisobutyronitrile (11 mg, 0.07 mmol). The mixture was stirred at 80° C. for 16 hours and filtered. The filtrate was concentrated under reduced pressure. The residue was purified by RP-TLC (petrleum ether:ethyl acetate=3:1) to afford 2-[2-(bromomethyl)thiazol-4-yl]-5-(difluoromethyl)-1,3,4-oxadiazole (70 mg, 34%) as colorless oil. LCMS $R_T$=1.048 min, m/z=297.7 [M+H]$^+$.

Step 5: N-(3-chlorophenyl)cyclopropanecarboxamide

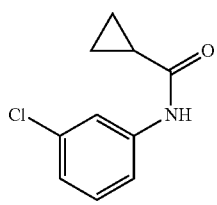 [SMILES: O=C(Nc1cccc(Cl)c1)C1CC1]

To a mixture of 3-chloroaniline (1.0 g, 7.84 mmol) and triethylamine (1.6 g, 15.68 mmol) in tetrahydrofuran (16 mL) was added cyclopropanecarbonyl chloride (901 mg, 8.62 mmol) at 0° C. After stirred at 20° C. for 16 hours, the reaction was quenched by addition of water (100 mL) and extracted with ethyl acetate (60 mL×3). The combined organic layers were dried over sodium sulphate and concentrated to dryness under reduced pressure. The residue was purified by column chromatography (silica gel, 100-200 mesh, 0-25% ethyl acetate in petroleum ether) to afford N-(3-chlorophenyl)cyclopropanecarboxamide (1.45 g, 95% yield) as a white solid.

Step 6: N-(3-chlorophenyl)-N-((4-(5-(difluoromethyl)-1,3,4-oxadiazol-2-yl)thiazol-2-yl)methyl)cyclopropanecarboxamide (I-84)

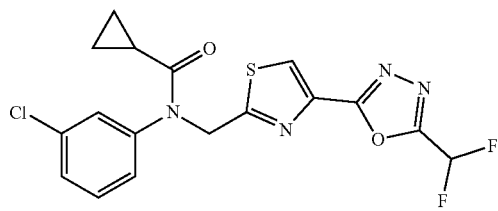 [SMILES: O=C(C1CC1)N(Cc1nc(-c2nnc(C(F)F)o2)cs1)c1cccc(Cl)c1]

To a solution of N-(3-chlorophenyl)cyclopropanecarboxamide (66 mg, 0.34 mmol) in tetrahydrofuran (3 mL) was added sodium hydride (12 mg, 0.30 mmol, 60% purity) at 0° C. under nitrogen atmosphere. After stirred for 30 mins at 0° C., the reaction mixture was added 2-[2-(bromomethyl)thiazol-4-yl]-5-(difluoromethyl)-1,3,4-oxadiazole (50 mg, 0.17 mmol) and stirred at 25° C. for 30 mins. The reaction was quenched by addition of water (50 mL) and extracted with ethyl acetate (50 mL×3). The combined organic layers were dried over sodium sulphate and concentrated to dryness under reduced pressure. The residue was purified by RP-HPLC (53 to 83% acetonitrile in water and 0.225% formic acid) to afford N-(3-chlorophenyl)-N-[[4-[5-(difluoromethyl)-1,3,4-oxadiazol-2-yl]thiazol-2-yl]methyl]cyclopropanecarboxamide (11.3 mg, 16%) as a white solid.

The methods used in Example 9 were also used to prepare compound I-82.

Example 10. Synthesis of Regioisomeric Thiazole/Oxazole Compounds of Formula (I)—Sulfonamides Preparation of N-(3-chlorophenyl)-N-((4-(5-(difloorom-ethyl)-1,3,4-oxadiazol-2-yl)thiazol-2-yl)methyl)cyclopropanesulfonamide (Compound I-83)

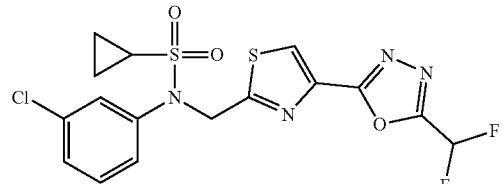

Step 1: N-(3-chlorophenyl)cyclopropanesulfonamide

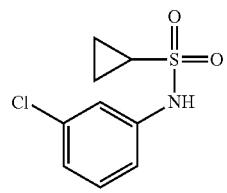 [SMILES: O=S(=O)(Nc1cccc(Cl)c1)C1CC1]

To a mixture of cyclopropanesulfonyl chloride (1.33 g, 9.43 mmol) and pyridine (930 mg, 11.76 mmol) in dichloromethane (10 mL) was added 3-chloroaniline (1.00 g, 7.84 mmol) at 0° C. After stirred at 20° C. for 16 hours, the reaction was quenched by addition of water (70 mL) and extracted with ethyl acetate (60 mL×3). The combined organic layers were dried over sodium sulphate and concentrated to dryness under reduced pressure. The residue was purified by column chromatography (silica gel, 100-200 mesh, 0-20% ethyl acetate in petroleum ether) to afford N-(3-chlorophenyl)cyclopropanesulfonamide (1.70 g, 94% yield) as a yellow solid.

Step 2: N-(3-chlorophenyl)-N-((4-(5-(difluoromethyl)-1,3,4-oxadiazol-2-yl)thiazol-2-yl)methyl)cyclopropanesulfonamide (Compound I-83)

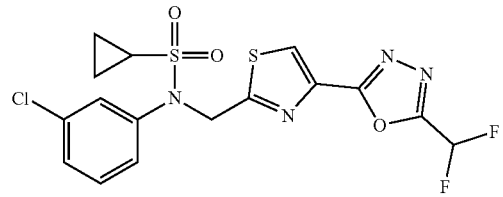 [SMILES: O=S(=O)(C1CC1)N(Cc1nc(-c2nnc(C(F)F)o2)cs1)c1cccc(Cl)c1]

A mixture of 2-[2-(bromomethyl)thiazol-4-yl]-5-(difluoromethyl)-1,3,4-oxadiazole (35.0 mg, 0.12 mmol), N-(3-chlorophenyl)cyclopropanesulfonamide (33.0 mg, 0.14 mmol) and potassium carbonate (49 mg, 0.35 mmol) in N,N-dimethylformamide (1 mL) was stirred at 30° C. for 1 hour and concentrated under reduced pressure. The residue was purified by RP-HPLC (45 to 75% acetonitrile in water and 0.225% formic acid) to afford N-(3-chlorophenyl)-N-[[4-[5-(difluoromethyl)-1,3,4-oxadiazol-2-yl]thiazol-2-yl]methyl]cyclopropanesulfonamide (25.2 mg, 47.2% yield) as a white solid.

Preparation of N-(3-chlorophenyl)-N-((4-(5-(difluoromethyl)-1,3,4-oxadiazol-2-yl)oxazol-2-yl)methyl)cyclopropanesulfonamide (Compound I-86).

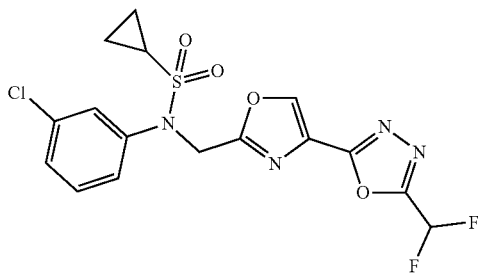 [SMILES: O=S(=O)(C1CC1)N(Cc1nc(-c2nnc(C(F)F)o2)co1)c1cccc(Cl)c1]

Step 1: 2-methyloxazole-4-carbohydrazide

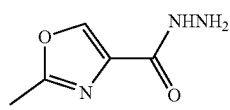

To a solution of ethyl 2-methyloxazole-4-carboxylate (4.5 g, 29.00 mmol) in ethyl alcohol (80 mL) was added hydrazine hydrate (15.8 g, 316.62 mmol). After stirred at 90° C. for 16 hours, the mixture was concentrated under reduced pressure. The residue was purified by column chromatography (silica gel, 100-200 mesh, 0-10% methanol in dichloromethane) to afford 2-methyloxazole-4-carbohydrazide (3.5 g, 86%) as an orange solid.

Step 2: N-(2,2-difluoroacetyl)-2-methyl-oxazole-4-carbohydrazide

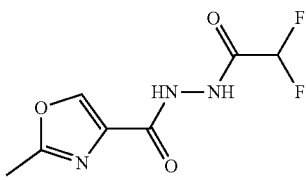

To a solution of 2-methyloxazole-4-carbohydrazide (3.5 g, 24.94 mmol) and N-ethyl-N-isopropylpropan-2-amine (3.87 g, 29.93 mmol) in tetrahydrofuran (38 mL) was added (2,2-difluoroacetyl) 2,2-difluoroacetate (5.21 g, 29.93 mmol). After stirred at 20° C. for 3 hours, the mixture was concentrated under reduced pressure. The residue was purified by column chromatography (silica gel, 100-200 mesh, 0-10% methanol in dichloromethane) to afford N'-(2,2-difluoroacetyl)-2-methyl-oxazole-4-carbohydrazide (5.0 g, 91%) as a yellow solid.

Step 3 : 2-(difluoromethyl)-5-(2-methyloxazol-4-yl)-1,3,4-oxadiazole

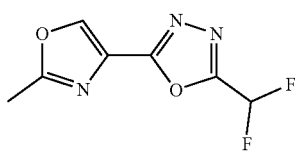

To a solution of N-(2,2-difluoroacetyl)-2-methyl-oxazole-4-carbohydrazide (3.0 g, 13.69 mmol) in tetrahydrofuran (8 mL) was added Burgess reagent (8.16 g, 34.22 mmol). The mixture was stirred at 90° C. for 3 hours under microwave and then quenched by addition of water (30 mL). The mixture was extracted with ethyl acetate (50 mL×3). The organic extracts were dried over sodium sulphate and concentrated to dryness under reduced pressure. The residue was purified by column chromatography (silica gel, 100-200 mesh, 0-80% ethyl acetate in petroleum ether) to afford 2-(difluoromethyl)-5-(2-methyloxazol-4-yl)-1,3,4-oxadiazole (1.14 g, 41%) as a yellow solid.

Step 4: 2-[2-(bromomethyl)oxazol-4-yl]-5-(difluoromethyl)-1,3,4-oxadiazole

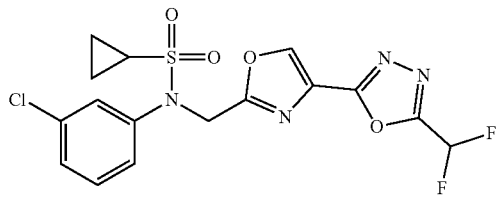 [SMILES: O=S(=O)(C1CC1)N(Cc1nc(-c2nnc(C(F)F)o2)co1)c1cccc(Cl)c1]

To a solution of 2-(difluoromethyl)-5-(2-methyloxazol-4-yl)-1,3,4-oxadiazole (1.14 g, 5.65 mmol) in tetrachloromethane (20 mL) was added 2-(2-cyanopropan-2-yldiazenyl)-2-methylpropanenitrile (93 mg, 0.56 mmol) and N-bromosuccinimide (2.52 g, 14.13 mmol). After stirred at 90° C. for 16 hours, the reaction mixture was concentrated under reduced pressure. The residue was purified by RP-TLC (petroleum ether:ethyl acetate=2:1) to afford 2-[2-(bromomethyl)oxazol-4-yl]-5-(difluoromethyl)-1,3,4-oxadiazole (200 mg, 10%) as a white solid. LCMS $R_T$=1.222 min, m/z=279.8 $[M+H]^+$.

Step 5: N-(3-chlorophenyl)-N-((4-(5-(difluoromethyl)-1,3,4-oxadiazol-2-yl)oxazol-2-yl)methyl)cyclopropanesulfonamide (Compound I-86)

A mixture of 2-[2-(bromomethyl)oxazol-4-yl]-5-(difluoromethyl)-1,3,4-oxadiazole (30 mg, 0.11 mmol), N-(3-chlorophenyl)cyclopropanesulfonamide (25 mg, 0.11 mmol) and potassium carbonate (30 mg, 0.22 mmol) in N,N-dimethylformamide (1 mL) was stirred at 20° C. for 1 hour and filtered.. The filtrate was concentrated under reduced pressure. The residue was purified by RP-HPLC (40-70% acetonitrile in water and 0.04% ammonium hydroxide and 10 mM ammonium bicarbonate) to afford N-(3-chlorophenyl)-N-[[4-[5-(difluoromethyl)-1,3,4-oxadiazol-2-yl]oxazol-2-yl]methyl]cyclopropanesulfonamide (17.2 mg, 37%) as a white solid.

The method described in Example 10 was also used to prepare compound I-85.

Example 11. Preparation of N-({5-[5-(difluoromethyl)-1,3,4-oxadiazol-2-yl]-1,3-thiazol-2-yl}methyl)-N-(1,5-dimethyl-1H-pyrazol-4-yl)ethane-1-sulfonamide (I-144)

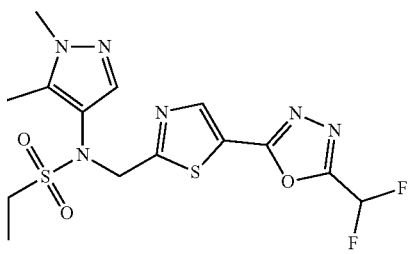 [SMILES: CCS(=O)(=O)N(Cc1ncc(-c2nnc(C(F)F)o2)s1)c1cnn(C)c1C]

Step 1: N-[[5-[5-(difluoromethyl)-1,3,4-oxadiazol-2-yl]thiazol-2-yl]methyl]-1,5-dimethyl-pyrazol-4-amine

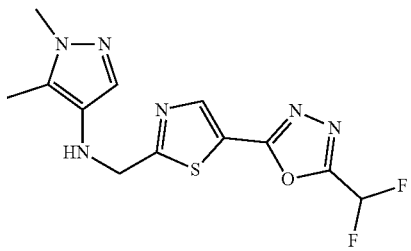 [SMILES: Cc1c(NCc2ncc(-c3nnc(C(F)F)o3)s2)cnn1C]

To a solution of 2-[2-(bromomethyl)thiazol-5-yl]-5-(difluoromethyl)-1,3,4-oxadiazole (30 mg, 0.1 mmol) in N,N-dimethylformamide (0.5 mL) was added sodium bicarbonate (26 mg, 0.3 mmol) and 1,5-dimethylpyrazol-4-amine (14 mg, 0.12 mmol). After stirring at 20° C. for 16 h, the mixture was concentrated to dryness under reduced pressure. The residue was purified by preparative TLC (petroleum ether: ethyl acetate=1:1) to afford N-[[5-[5-(difluoromethyl)-1,3,4-oxadiazol-2-yl]thiazol-2-yl]methyl]-1,5-dimethyl-pyrazol-4-amine (30 mg, 74%) as a yellow oil.

Step 2: N-({5-[5-(difluoromethyl)-1,3,4-oxadiazol-2-yl]-1,3-thiazol-2-yl}methyl)-N-(1,5-dimethyl-1H-pyrazol-4-yl)ethane-1-sulfonamide

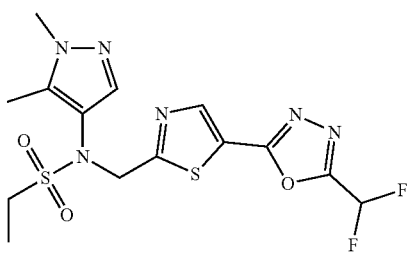 [SMILES: CCS(=O)(=O)N(Cc1ncc(-c2nnc(C(F)F)o2)s1)c1cnn(C)c1C]

To a solution of N-[[5-[5-(difluoromethyl)-1,3,4-oxadiazol-2-yl]thiazol-2-yl]methyl]-1,5-dimethyl-pyrazol-4-amine (27 mg, 0.08 mmol) in dichloromethane (0.5 mL) was added pyridine (20 mg, 0.25 umol) and ethanesulfonyl chloride (13 mg, 0.1 mmol). After stirring at 20° C. for 16 h, the mixture was concentrated to dryness under reduced pressure. The residue was purified by RP-HPLC (0 to 40% acetonitrile in water and 0.2% formic acid) to afford N-({5-[5-(difluoromethyl)-1,3,4-oxadiazol-2-yl]-1,3-thiazol-2-yl}methyl)-N-(1,5-dimethyl-1H-pyrazol-4-yl)ethane-1-sulfonamide (13 mg, 36%) as a white solid.

Example 12. Preparation of 3-(2-methylthiazol-5-yl)-5-(trifluoromethyl)-1,2,4-oxadiazole (Compound I-11)

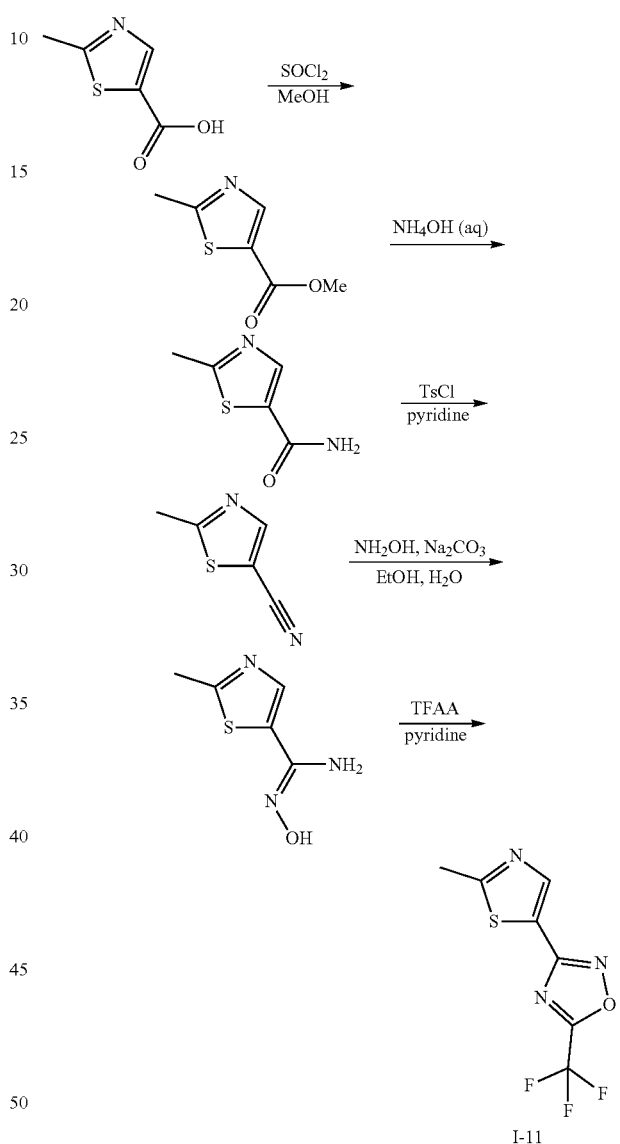

Step 1: preparation of methyl 2-methylthiazole-5-carboxylate.

To a 1 L round bottom flask was added 2-methyl-1,3-thiazole-5-carboxylic acid (10.0 g, 70 mmol) and MeOH (100 mL). The reaction mixture was then cooled to 0° C., and thionyl chloride (13 mL, 180 mmol) was added in a dropwise fashion. The reaction mixture was stirred at reflux for 16 h. The reaction mixture was partially concentrated then diluted with EtOAc. The organic layer was washed with water, brine, dried over MgSO$_4$, then concentrated to afford the title compound as a white solid, which was used without further purification (11.0 g, 100%).

Step 2: 2-methylthiazole-5-carboxamide.

To a 250 mL round bottom flask was added methyl 2-methyl-1,3-thiazole-5-carboxylate (11.0 g, 70 mmol) and an aqueous solution of ammonium hydroxide (28% NH₃ in H₂O, 140 mL). The reaction mixture was stirred for 3 h during which a white precipitate formed. The crude reaction mixture was diluted with water, and the product was extracted with EtOAc (15×). The combined organic layers were dried over MgSO₄, then concentrated to afford the title compound as a white solid (8.11 g, 81%).

Step 3: 2-methylthiazole-5-carbonitrile.

To a 100 mL round bottom flask was added 2-methyl-1,3-thiazole-5-carboxamide (4.00 g, 28.1 mmol), tosyl chloride (13.4 mg, 70.3 mmol), and pyridine (20 mL). The reaction mixture was stirred at 50° C. for 3 h. The reaction mixture was diluted with EtOAc, washed with ~1 M HCl (aq), water, sat. NaHCO₃ (aq), then brine. The organic layer was dried over MgSO₄, then concentrated to afford the title compound as a brown solid (2.30 g, 66%).

Step 4: N'-hydroxy-2-methylthiazole-5-carboximidamide.

To a 500 mL round bottom flask was added 2-methyl-1,3-thiazole-5-carbonitrile (2.30 g, 18.5 mmol), 8-hydroxyquinoline (13.4 mg, 0.093 mmol), and ethanol (180 mL). To the reaction mixture was added a solution of hydroxylamine hydrochloride (5.15 g, 74.1 mmol) in water (26 mL) and a solution of sodium carbonate (6.4 g, 59.3 mmol) in water (53 mL) in a sequential manner. The reaction mixture was then stirred at 78° C. for 16 h. The reaction mixture was then concentrated to remove ethanol, diluted with water, then acidified to pH 5 with 2M HCl (aq). The product was extracted with EtOAc (6×), dried over MgSO₄, then concentrated to afford the title compound as a brown solid (2.91 g, 89%).

Step 5: 3-(2-methylthiazol-5-yl)-5-(trifluoromethyl)-1,2,4-oxadiazole.

To a 20 mL vial was added (Z)-N'-hydroxy-2-methylthiazole-5-carboximidamide (247 mg, 0.54 mmol) and pyridine (3.8 mL). The reaction mixture was cooled to 0° C., and TFAA (0.66 mL, 4.7 mmol) was added in a dropwise fashion. The reaction mixture was stirred at 0° C. for 15 min, then stirred warming to ambient temperature for 45 min. The crude reaction mixture was diluted with EtOAc, then washed with 1 M HCl (aq), water, then brine. The organic layer was then dried over MgSO₄ and concentrated. The resulting residue was adsorbed onto celite then purified by column chromatography (0-15% EtOAc/hexanes) to afford the title compound as a yellow oil (369 mg, 58%). ¹H NMR (400 MHz, chloroform-d) δ ppm 8.38 (s, 1H) 2.82 (s, 3H). LCMS: tR (min): 4.90 (20-100% ACN with 0.1% TFA 6 min.); m/z [M+H]⁺ requires: 236.0; found: 236.0. HPLC tR (min) 6.34, 99% (10-100% ACN with 0.1% TFA 10 min).

Example 13. Preparation of N-(3-chlorophenyl)-N-((5-(5-(trifluoromethyl)-1,2,4-oxadiazol-3-yl)thiazol-2-yl)methyl)cyclopropanesulfonamide (Compound I-12)

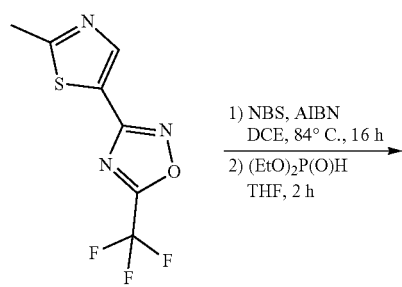

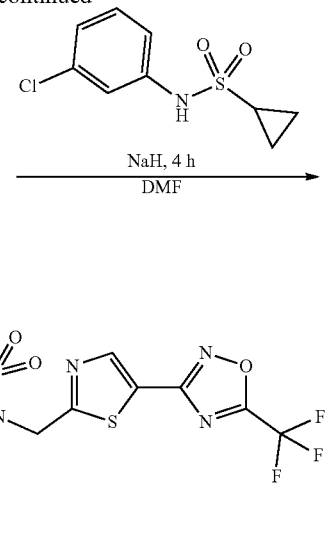

I-12

Step 1: 3-(2-(bromomethyl)thiazol-5-yl)-5-(trifluoromethyl)-1,2,4-oxadiazole.

To a 20 mL vial was added 3-(2-methylthiazol-5-yl)-5-(trifluoromethyl)-1,2,4-oxa.diazole (208 mg, 0.88 mmol), NBS (283 mg, 1.59 mmol), AIBN (7.3 mg, 0.044 mmol), and DCE (9.0 mL). The reaction mixture was stirred at 84° C. for 16 h. The crude reaction mixture was diluted with EtOAc, washed with water, washed with brine, dried over MgSO₄, then concentrated. To the resulting residue was added THF (9.0 mL). The reaction mixture was cooled to 0° C., then DIPEA (0.13 mL, 0.88 mmol) and diethyl phosphite (0.09 mL, 0.9 mmol) were added sequentially in a dropwise fashion. The reaction mixture was stirred warming to ambient temperature for 2 h. The reaction mixture was concentrated then diluted with EtOAc, washed with water, washed with brine, dried over MgSO₄, then concentrated. The crude product was adsorbed onto celite then purified by column chromatography (0-10% EtOAc/hexanes) to afford the title compound as a white solid (174 mg, 62%).

Step N-(3-chlorophenyl)-N-((5-(5-(trifluoromethyl)-1,2,4-oxadiazol-3-yl)thiazol-2-yl)methyl)cyclopropanesulfonamide.

To a 2 dram vial was added 60 wt % NaH in mineral oil (8.3 mg, 0.21 mmol) and DMF (0.5 mL). The reaction mixture was cooled to 0° C., then a solution of N-(3-chlorophenyl)cyclopropanesulfonamide (40.6 mg, 0.18 mmol) in DMF (0.5 mL) was added in a dropwise fashion. The reaction mixture was stirred warming to ambient temperature for 20 min. The reaction mixture was then cooled to 0° C., then a solution of 3-(2-(bromornethyl)thiazol-5-yl)-5-(trifluoromethyl)-1,2,4-oxadiazole (50.0 mg, 0.16 mmol) in DMF (1.0 mL) was added in a dropwise fashion. After 4 h, the reaction mixture was quenched with water and diluted with brine. The product was extracted with EtOAc (3×). The combined organic layers were washed with water (4×), washed with brine, dried over MgSO₄, then concentrated. The resulting residue was adsorbed onto celite and purified by column chromatography (0-70% EtOAc/hexanes) to yield the title compound as an orange solid (16.6 mg, 22%).

Example 14. Preparation of N-[[2-[5-(difluoromethyl)-1,3,4-oxadiazol-2-yl]thiazol-5-yl]methyl]-N-(5-fluoro-3-pyridyl)ethanesulfonamide (I-264)

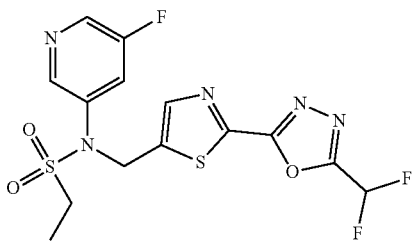 [SMILES: CCS(=O)(=O)N(Cc1cnc(-c2nnc(C(F)F)o2)s1)c1cncc(F)c1]

Step 1: tert-butyl N-[(5-methylthiazole-2-carbonyl)amino]carbamate

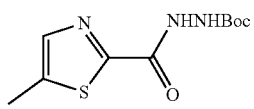

To a mixture of 5-methylthiazole-2-carboxylic acid (3.0 g, 20.95 mmol) in dichloromethane (50 mL) was added N-(3-dimethylaminopropyl)-n-ethylcarbodiimidehydrochloride (4.8 g, 25.15 mmol) and 1-hydroxybenzotriazole (1.42 g, 10.48 mmol). After stirring at 20° C. for 15 min, the reaction was added tert-butyl N-aminocarbamate (3.3 g, 25.15 mmol). After stirring at 20° C. for 16 hours, the reaction was quenched by addition of water (100 mL) and extracted with dichloromethane (2×100 mL). The combined organic extracts were dried over anhydrous sodium sulfate and concentrated under reduced pressure. The residue was purified by column chromatography (silica gel, 100-200 mesh, 0-20% ethyl acetate in petroleum ether) to afford tert-butyl N-[(5-methylthiazole-2-carbonyl)amino]carbamate (4.16 g, 75%) as a colorless oil.

Step 2: 5-methylthiazole-2-carbohydrazide

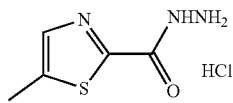

A solution of tert-butyl N-[(5-methylthiazole-2-carbonyl)amino]carbamate (4.07 g, 15.82 mmol) in hydrochloric acid (4.0 M in ethyl acetate, 40.0 mL, 160.00 mmol) was stirring at 20° C. for 2 hours and filtered. The collected solid was dried under reduced pressure to afford 5-methylthiazole-2-carbohydrazide hydrochloride (3.2 g, crude) as a white solid.

Step 3: N'-(2,2-difluoroacetyl)-5-methyl-thiazole-2-carbohydrazide

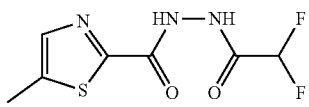

A solution of 5-methylthiazole-2-carbohydrazide hydrochloride (3.0 g, crude) in tetrahydrofuran (30 mL) was added N-ethyl-N-isopropylpropan-2-amine (4.0 g, 30.98 mmol) and (2,2-difluoroacetyl) 2,2-difluoroacetate (3.2 g, 18.59 mmol) at 0° C. After stirring at 20° C. for 1 hour, the reaction mixture was concentrated under reduced pressure. The residue was purified by column chromatography (silica gel, 100-200 mesh, 0-5% methanol in dichloromethane) to afford N'-(2,2-difluoroacetyl)-5-methyl-thiazole-2-carbohydrazide (2.0 g, 54%) as a white solid.

Step 4: 2-(difluoromethyl)-5-(5-methylthiazol-2-yl)-1,3,4-oxadiazole

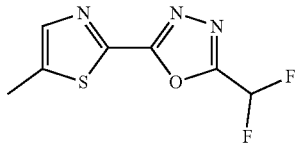

A mixture of N'-(2,2-difluoroacetyl)-5-methyl-thiazole-2-carbohydrazide (1.0 g, 4.25 mmol) and Burgess reagent (3.0 g, 12.75 mmol) in tetrahydrofuran (15 mL) was heated under microwave at 90° C. for 3 hours. The reaction mixture was concentrated under reduced pressure. The residue was purified by column chromatography (silica gel, 100-200 mesh, 0-15% ethyl acetate in petroleum ether)) to afford 2-(difluoromethyl)-5-(5-methylthiazol-2-yl)-1,3,4-oxadiazole (712 mg, 32%) as a white solid.

Step 5: 2-[5-(bromomethyl)thiazol-2-yl]-5-(difluoromethyl)-1,3,4-oxadiazole

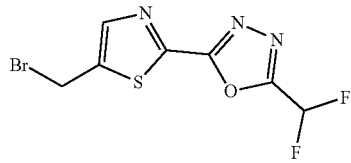 [SMILES: FC(F)c1nnc(-c2ncc(CBr)s2)o1]

To a solution of 2-(difluoromethyl)-5-(5-methylthiazol-2-yl)-1,3,4-oxadiazole (610 mg, 2.81 mmol) in 1,2-dichloroethane (20 mL) was added N-bromosuccinimide (550 mg, 3.09 mmol) and azodiisobutyronitrile;azobisisobutyronitrile (23 mg, 0.14 mmol). After stirring at 80° C. for 3 hours, the reaction mixture was concentrated under reduced pressure. The residue was purified by column chromatography (silica gel, 100-200 mesh, 0-20% ethyl acetate in petroleum ether) to afford 2-[5-(bromomethyl)thiazol-2-yl]-5-(difluoromethyl)-1,3,4-oxadiazole (743 mg, 73%) as a white solid.

Step 6: N-[[2-[5-(difluoromethyl)-1,3,4-oxadiazol-2-yl]thiazol-5-yl]methyl]-N-(5-fluoro-3-pyridyl)ethanesulfonamide

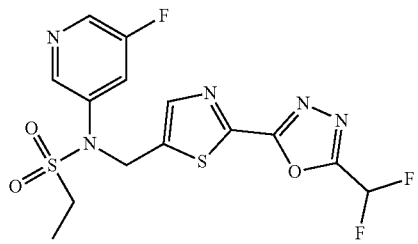 [SMILES: CCS(=O)(=O)N(Cc1cnc(-c2nnc(C(F)F)o2)s1)c1cncc(F)c1]

To a solution of 2-[5-(bromomethyl)thiazol-2-yl]-5-(difluoromethyl)-1,3,4-oxadiazole (50 mg, 0.7 mmol) in N,N-dimethylformamide (1 mL) was added sodium bicarbonate (43 mg, 0.51 mol) and N-(5-fluoro-3-pyridyl)ethanesulfonamide (41 mg, 0.2 mmol). After stirring at 20° C. for 1 hour, the mixture was filtered, and the filtrate was concentrated under reduced pressure. The residue was purified by RP-HPLC (35 to 65% acetonitrile in water and 0.225% formic acid) to afford N-[[2-[5-(difluoromethyl)-1,3,4-oxadiazol-2-yl]thiazol-5-yl]methyl]-N-(5-fluoro-3-pyridyl)ethanesulfonamide (37 mg, 51%) as colorless oil.

The methods described in Example 14 were also used to prepare the following compounds: I-257, I-259, I-260, I-261, I-262, and I-263.

Example 15. Preparation of 3-((5-(5-(difluoromethyl)-1,3,4-oxadiazol-2-yl)thiazol-2-yl)methyl)-1H-pyrrolo[2,3-c]pyridin-2-ol (I-258)

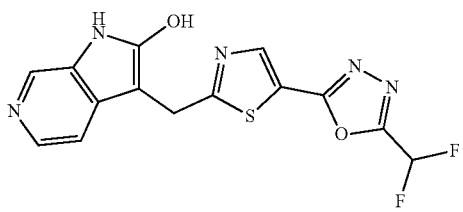 [SMILES: Oc1[nH]c2cnccc2c1Cc1ncc(-c2nnc(C(F)F)o2)s1]

To a solution of 1,3-dihydropyrrolo[2,3-c]pyridin-2-one (25 mg, 0.19 mmol) in N,N-dimethylformamide (0.5 mL) was added sodium hydride (60%, 7 mg, 0.17 mmol). After stirring at 0° C. for 0.5 hour, the reaction was added 2-[2-(bromomethyl)thiazol-5-yl]-5-(difluoromethyl)-1,3,4-oxadiazole (50 mg, 0.17 mmol). After stirring at 20° C. for another 0.5 hour, the mixture was filtered. The filtrate was concentrated under reduced pressure. The residue was purified by RP-HPLC (10 to 40% acetonitrile in water and 0.225% formic acid) to afford 3-[[5-[5-(difluoromethyl)-1,3,4-oxadiazol-2-yl]thiazol-2-yl]methyl]-1H-pyrrolo[2,3-c]pyridin-2-ol (10.3 mg, 17%) as a red solid.

Example 16. Synthesis of N-Alkyl Amide Pyridinone Compounds of Formula (I)

Preparation of 4-(5-(difluoromethyl)-1,3,4-oxadiazol-2-yl)pyridin-2(1H)-one (II-12), tert-butyl 2-(4-(5-(difluoromethyl)-1,3,4-oxadiazol-2-yl)-2-oxopyridin-1(2H)-yl)acetate (Compound II-11), 2-(4-(5-(difluoromethyl)-1,3,4-oxadiazol-2-yl)-2-oxopyridin-1(2H)-yl)acetic acid (Compound II-10) and 4-(5-(difluoromethyl)-1,3,4-oxadiazol-2-yl)-1-(2-morpholino-2-oxoethyl)pyridin-2(1H)-one (Compound II-1)

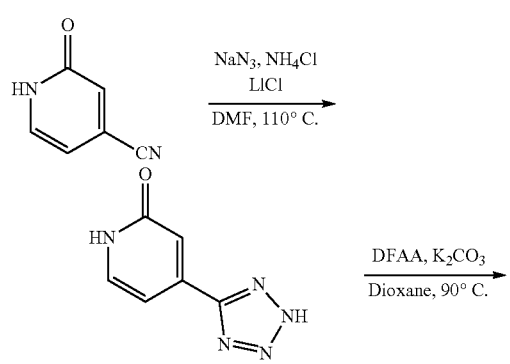

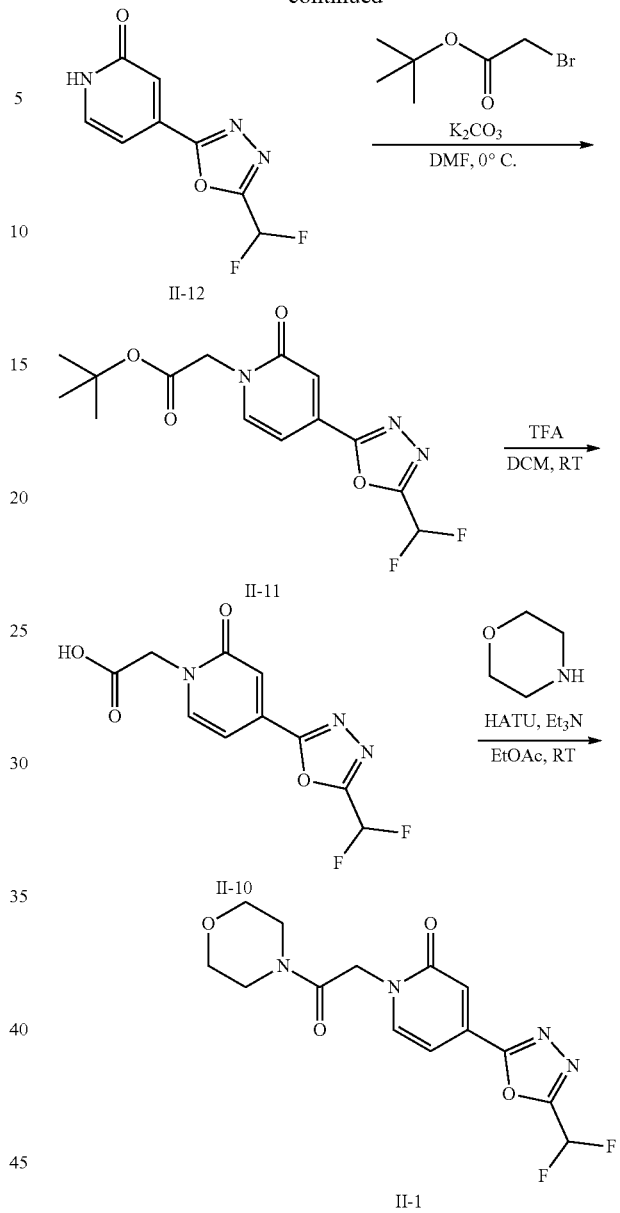

Step 1: Preparation of 4-(2H-tetrazol-5-yl)pyridin-2(1H)-one, HCl salt.

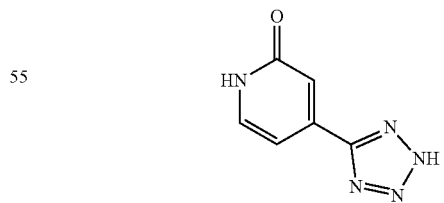

To a 100 mL round-bottom flask containing a 1-inch egg-shaped stirbar, fitted with an air condensor and under N₂ atmosphere (balloon), was added 2-oxo-1,2-dihydropyridine-4-carbonitrile (1.00 g, 8.33 mmol, 1 equiv), followed by sodium azide (1.62 g, 25.0 mmol, 3 equiv), ammonium chloride (1.34 g, 25.0 mmol, 3 equiv) and lithium chloride (529 mg, 12.5 mmol, 1.5 equiv). Lastly, DMF (20 mL) was added, and the pink heterogeneous suspension was vigorously stirred at 110° C. for 16 hours, after which LCMS analysis indicated clean, complete conversion to the desired tetrazole product. The reaction mixture was allowed to cool to room temperature, then 50 mL of water was added to form a pale orange homogeneous solution (pH=6). Concentrated aqueous HCl (approximately 2 mL) was added dropwise over 2 minutes with vigorous stirring until pH=1. Upon acidification, the desired tetrazole HCl salt precipitated out as a light beige solid. The suspension was filtered, and the light beige solid was washed with water (20 mL), followed by hexanes (20 mL), and then left to air-dry on the filter for 10 minutes. (Caution: the filtrate contains hydrazoic acid, which is volatile, toxic and explosive. Acidic aqueous solutions of hydrazoic acid can be safely quenched by the addition of sodium nitrite until spotting on starch-iodide paper gives a dark blue spot, indicating complete decomposition of hydrazoic acid). The wet solid obtained was dried on vacuum overnight to remove residual water to afford the title compound HCl salt as a free-flowing beige solid, 1.21 g (73%).

Step 2: Preparation of 4-(5-(difluoromethyl)-1,3,4-oxadiazol-2-yl)pyridin-2(1H)-one (Compound II-12).

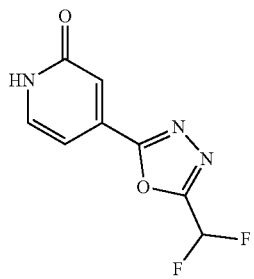

To a 100 mL round-bottom flask containing a 1-inch egg-shaped stirbar, fitted with an air condensor and under N$_2$ atmosphere (balloon), was added 4-(2H-tetrazol-5-yl)pyridin-2(1H)-one (HCl salt, 600 mg, 3.01 mmol, 1 equiv), followed by 1,4-dioxane (20 mL), and potassium carbonate (1.69 g, 12.0 mmol, 4 equiv). The beige heterogeneous suspension was stirred vigorously at room temperature for 5 minutes, after which time difluoroacetic anhydride (DFAA, 0.70 mL, 6.0 mmol, 2 equiv) was added dropwise over 2 minutes, with no immediate visible changes to the reaction. The reaction is heated to 90° C. overnight (16 hours) with vigorous stirring, after which LCMS analysis indicated approximately 80% clean conversion to the desired oxadiazole. Deemed sufficient, the reaction was allowed to cool to room temperature, then poured into 30 mL water, resulting in a dark yellow-orange homogeneous solution (pH=10). The basic aqueous layer was extracted three times with EtOAc (50 mL each), the organic layers washed with minimal saturated aqueous NaHCO$_3$ (10 mL), then brine (10 mL), then dried over MgSO$_4$, filtered and concentrated by rotary evaporation. The resulting yellow solid was taken up in MTBE (10 mL) and sonicated to make a fine suspension, then filtered to afford the title compound as a white solid, 477 mg (74% yield).

The method used to prepare compound II-12 was also used to prepare Compound II-6.

Step 3: Preparation of tert-butyl 2-(4-(5-(difluoromethyl)-1,3,4-oxadiazol-2-yl)-2-oxopyridin-1(2H)-yl)acetate (Compound II-11).

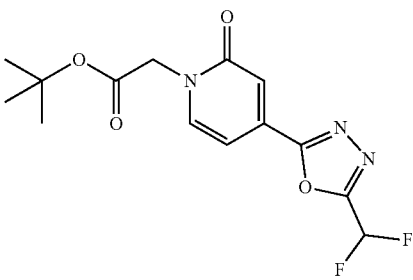 [SMILES: CC(C)(C)OC(=O)Cn1ccc(-c2nnc(C(F)F)o2)cc1=O]

To a scintillation vial containing a magnetic stirring flea was added 4-(5-(difluoromethyl)-1,3,4-oxadiazol-2-yl)pyridin-2(1H)-one (140 mg, 0.66 mmol, 1 equiv) and DMF (2 mL). The homogeneous orange solution was cooled to 0° C. in an ice bath. Potassium carbonate (461 mg, 3.3 mmol, 5 equiv) was added. Lastly, tert-butyl bromoacetate (0.29 mL, 2.0 mmol, 3 equiv) was added all at once. After 1 hour, LCMS analysis of the fine orange suspension indicated complete conversion to a >10:1 mixture of the N-alkylated to the O-alkylated pyridone. The N-alkylated pyridone is much more polar by both LCMS and TLC than the O-alkylated pyridone. Also, the N-alkylated pyridone exhibits bright blue fluorescence on TLC with 254 nm excitation. The reaction was worked up by pouring into 50 mL water, then extracting from the aqueous layer three times with EtOAc (50 mL). The combined organic layers were washed with water, then brine, then dried over MgSO$_4$, filtered and concentrated by rotary evaporation. The crude pale yellow oil was dry-loaded onto silica gel and purified by flash column chromatography (0-50% EtOAc in hexanes gradient) to provide the title compound as a white solid, 188.0 mg (87% yield). Connectivity was assigned by NOESY (NOE cross-peak is observed between the alpha CH$_2$ at 4.61 ppm and the most downfield pyridone doublet at 7.40 ppm).

The method used to prepare compound II-11 was also used to prepare Compound II-7.

Step 4: Preparation of 2-(4-(5-(difluoromethyl)-1,3,4-oxadiazol-2-yl)-2-oxopyridin-1(2H)-yl)acetic acid (Compound II-10).

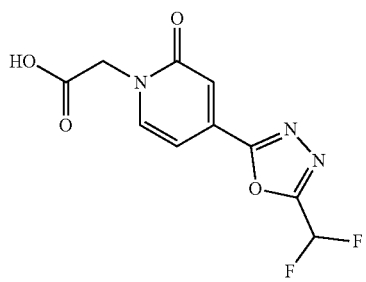 [SMILES: O=C(O)Cn1ccc(-c2nnc(C(F)F)o2)cc1=O]

To a scintillation vial containing a magnetic stirring flea was added tert-butyl 2-(4-(5-(difluoromethyl)-1,3,4-oxadiazol-2-yl)-2-oxopyridin-1(2H)-yl)acetate (188 mg, 0.57 mmol, 1 equiv), followed by DCM (2 mL) and lastly trifluoroacetic acid (TFA, 0.5 mL) dropwise over 1 minute at room temperature with stirring. The pale yellow homogeneous solution was stirred at room temperature for 6 hours open to air, after which LCMS analysis indicated about 96% clean conversion of the tert-butyl ester to the free carboxylic acid. Deemed sufficient, the reaction mixture was concentrated directly by rotary evaporation to provide the crude material as a colorless viscous oil containing residual TFA. The material was dissolved in 3 mL 1:1 acetonitrile:water, then frozen in a dry-ice acetone bath at −78° C., then lyophilized overnight to provide the title compound as a pale yellow brittle solid of sufficient purity, 165 mg (103% yield).

Step 5: Preparation of 4-(5-(difluoromethyl)-1,3,4-oxadiazol-2-yl)-1-(2-morpholino-2-oxoethyl)pyridin-2(1H)-one.

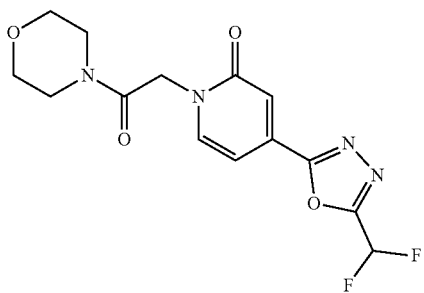

II-1

To a scintillation vial was added 2-(4-(5-(difluoromethyl)-1,3,4-oxadiazol-2-yl)-2-oxopyridin-1(2H)-yl)acetic acid (II-10, 27.1 mg, 0.10 mmol, 1 equiv.), followed by EtOAc (1 mL) and HATU (76.0 mg, 0.20 mmol, 2 equiv.). The heterogeneous white suspension was stirred at room temperature for 5 minutes, after which time morpholine (0.025 mL, 0.30 mmol, 3 equiv.) followed by triethylamine (0.07 mL, 0.5 mmol, 5 equiv.) were each added dropwise with vigorous stirring at room temperature. The heterogeneous white suspension was stirred at room temperature for 1 hour, after which LCMS analysis indicated complete conversion to the desired amide. The reaction was poured into water (50 mL), then extracting from the aqueous layer three times with EtOAc (50 mL). The combined organic layers were washed with minimal water, then brine, then dried over MgSO$_4$, filtered and concentrated by rotary evaporation to provide the crude product as a yellow oil. The material was dry loaded onto silica gel and purified by flash column chromatography (0-10% methanol in DCM gradient) to provide the title compound as a colorless oil, 7.8 mg (23% yield).

Any suitable amide coupling procedure known in the art can be used to prepare the disclosed compounds, including but not limited to: EDC/1-hydroxybenzotriazole (HOBT) and N-(3-dimethylaminopropyl)-N'-ethylcarbodiimide hydrochloride (EDAC)/HOBT/EtN(iPr$_2$)

The methods disclosed in Example 16 were also used to prepare the following compounds: II-2 and II-18.

Example 17. Synthesis of N-Alkyl Pyridinone Compounds of Formula (I)

Preparation of 1-benzyl-4-(5-(difluoromethyl)-1,3,4-oxadiazol-2-yl)pyridin-2(1H)-one (Compound II-4)

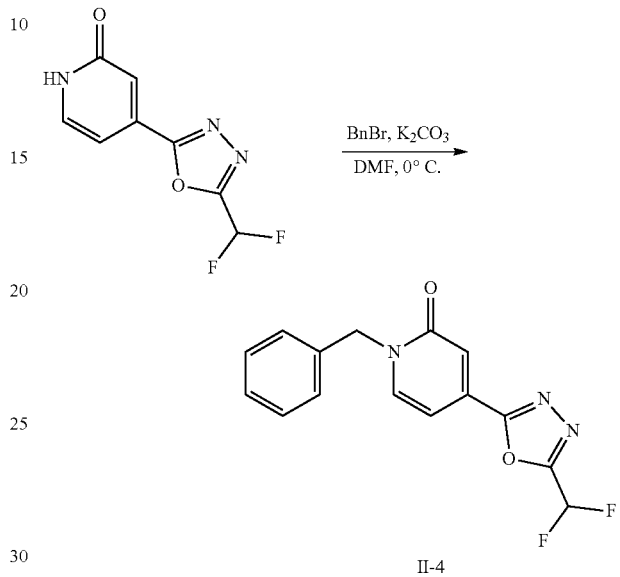

II-4

To a 1-dram vial containing a magnetic stirring flea was added 4-(5-(difluoromethyl)-1,3,4-oxadiazol-2-yl)pyridin-2 (1H)-one (II-12, 20.0 mg, 0.094 mmol, 1 equiv) and DMF (1 mL). The homogeneous orange solution was cooled to 0° C. in an ice bath. Potassium carbonate (69 mg, 0.5 mmol, 5 equiv) was added, followed by dropwise addition of benzyl bromide (0.05 mL, 0.5 mmol, 5 equiv). The reaction was allowed to warm to room temperature. After 2 hours, LCMS analysis indicated complete conversion to a >10:1 mixture of N-alkylated to O-alkylated pyridones. The reaction was worked up by pouring into 50 mL water, then extracting from the aqueous layer three times with EtOAc (50 mL). The combined organic layers were washed with water, then brine, then dried over MgSO$_4$, filtered and concentrated by rotary evaporation. The crude pale yellow film was dry-loaded onto silica gel and purified by flash column chromatography (0-50% EtOAc in hexanes gradient) to provide the title compound as a colorless oil which solidifies at room temperature into a waxy white solid, 25.3 mg (85% yield).

Preparation of 4-(5-(difluoromethyl)-1,3,4-oxadiazol-2-yl)-1-phenethylpyridin-2(1H)-one (Compound II-5)

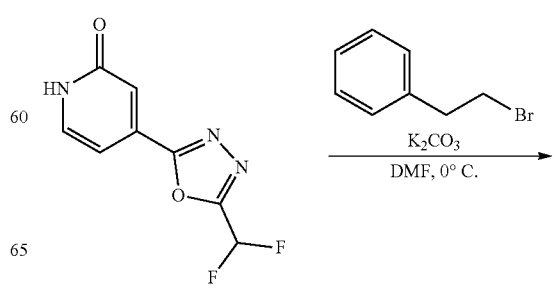

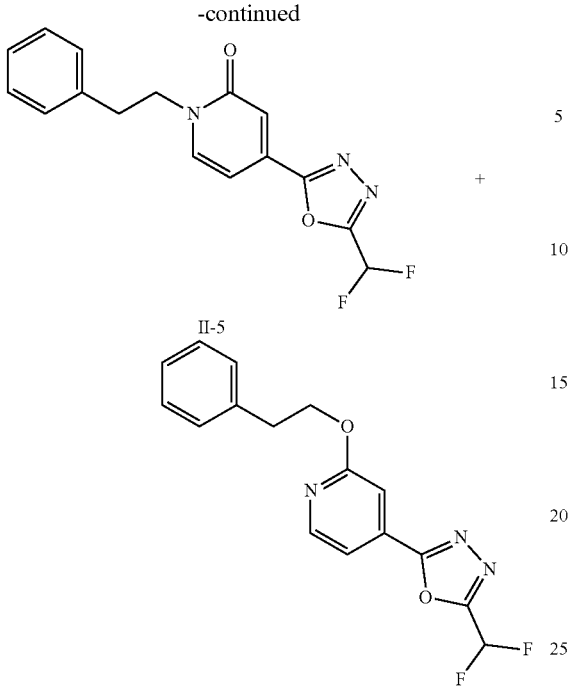

II-5

To a 1-dram vial containing a magnetic stirring flea was added 4-(5-(difluoromethyl)-1,3,4-oxadiazol-2-yl)pyridin-2(1H)-one (II-12, 21.0 mg, 0.099 mmol, 1 equiv.) and DMF (1 mL). The homogeneous orange solution was cooled to 0° C. in an ice bath. Potassium carbonate (69 mg, 0.5 mmol, 5 equiv.) was added, followed by dropwise addition of phenethyl bromide (0.07 mL, 0.5 mmol, 5 equiv.). The reaction was allowed to warm to room temperature. After 2 hours, LCMS analysis indicated complete conversion to an approximately 2:1 ratio of N-linked to O-linked pyridones (the selectivity is typically much greater for the N-linked pyridone than in this case). The reaction was worked up by pouring into 50 mL water, then extracting from the aqueous layer three times with EtOAc (50 mL). The combined organic layers were washed with water, then brine, then dried over MgSO$_4$, filtered and concentrated by rotary evaporation. The crude pale yellow oil was dry-loaded onto silica gel and purified by flash column chromatography (0-50% EtOAc in hexanes gradient) to provide each of the two isomeric title compounds in high purity (Connectivity was unambiguously verified by NOESY for both isomers).

N-linked 4-(5-(difluoromethyl)-1,3,4-oxadiazol-2-yl)-1-phenethylpyridin-2(1H)-one. White solid, 18.3 mg (58% yield). LC-MS: tR (min) 4.39 (20-100% ACN with 0.1%TFA 6 min), m/z [M+H]$^+$ CH$_{16}$H$_{13}$F$_2$N$_3$O$_2$ requires: 317.1, found: 318.1. HPLC tR (min) 5.89, 97.9% (10-100% ACN with 0.1% TFA 10 min.)

O-linked 2-(difluoromethyl)-5-(2-phenethoxypyridin-4-yl)-1,3,4-oxadiazole. Pale yellow oil which solidifies at room temperature into a waxy solid, 10.5 mg (33% yield). $^1$H NMR (400 MHz, chloroform-d) δ ppm 8.35 (br d, J=3.67 Hz, 1H) 7.18 -7.59 (m, 7H) 6.73 -7.12 (m, 1H) 4.60 (br t, J=6.85 Hz, 2H) 3.13 (br d, J=6.60 Hz, 2H), LC-MS: tR (min) 5.66 (20-100% ACN with 0.1% TFA 6 min), m/z [M+H]$^+$ C$_{16}$H$_{13}$F$_2$N$_3$O$_2$ requires: 317.1, found: 318.1. HPLC tR (min) 6.89, 98.1% (10-100% ACN with 0.1% TFA 10 min).

The methods described in Example 17 were also used to prepare II-3, II-8, and II-9.

Example 18. Preparation of 1-((2-cyclopropylpyridin-4-yl)methyl)-4-(5-(difluoromethyl)-1,3,4-oxadiazol-2-yl)pyridin-2(1H)-one (Compound II-15)

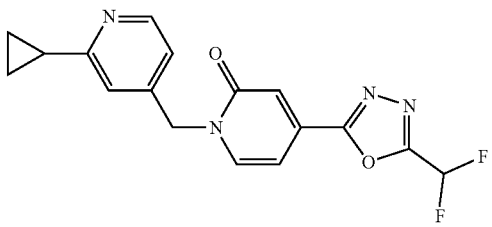 [SMILES: O=c1cc(-c2nnc(C(F)F)o2)ccn1Cc1ccnc(C2CC2)c1]

Step 1: methyl 2-cyclopropylpyridine-4-carboxylate

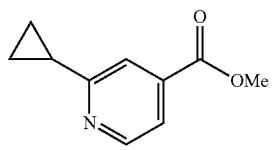 [SMILES: COC(=O)c1ccnc(C2CC2)c1]

A mixture of methyl 2-bromopyridine-4-carboxylate (5.0 g, 23.14 mmol), tricyclohexylphosphine (649 mg, 2.31 mmol), cyclopropylboronic acid (3.0 g, 34.72 mmol), potassium phosphate (17 g, 81.01 mmol) and palladium acetate (260 mg, 1.16 mmol) in toluene (140 mL) and water (28 mL) was stirred at 100° C. for 16 hours under nitrogen atmosphere. After cooled, the reaction mixture was diluted with water (100 mL) and ethyl acetate (100 mL). The separated organic layer was dried over anhydrous sodium sulfate and concentrated under reduced pressure. The residue was purified by column chromatography (silica gel, 100-200 mesh, 0-10% ethyl acetate in petroleum ether) to afford methyl 2-cyclopropylpyridine-4-carboxylate (1.33 g, 30%) as light yellow oil.

Step 2: (2-cyclopropyl-4-pyridyl)methanol

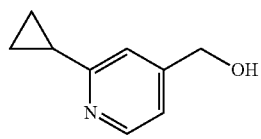 [SMILES: OCc1ccnc(C2CC2)c1]

To a solution of methyl 2-cyclopropylpyridine-4-carboxylase (1.3 g, 7.48 mmol) and sodium methoxide (20 mg, 0.37 mmol) in methanol (20 mL) was added sodium borohydride (851 mg, 22.49 mmol) at 0° C. After stirred at 80° C. for 16 hours, the reaction mixture was diluted with water (50 mL) and ethyl acetate (50 mL). The separated organic layer was dried over anhydrous sodium sulfate and concentrated under reduced pressure. The residue was purified by column chromatography (silica gel, 100-200 mesh, 0-50% ethyl acetate in petroleum ether) to afford (2-cyclopropyl-4-pyridyl)methanol (690 mg, 62%) as colorless oil.

Step 3: 1-((2-cyclopropylpyridin-4-yl)methyl)-4-(5-(difluoromethyl)-1,3,4-oxadiazol-2-yl)pyridin-2(1H)-one (Compound II-15)

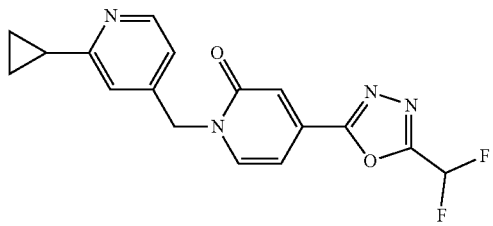 [SMILES: O=c1cc(-c2nnc(C(F)F)o2)ccn1Cc1ccnc(C2CC2)c1]

To a solution of (2-cyclopropyl-4-pyridyl)methanol (42 mg, 0.28 mmol), 4-[5-(difluoromethyl)-1,3,4-oxadiazol-2-yl]-1H-pyridin-2-one (II-12, 50 mg, 0.23 mmol), triphenylphosphine (123 mg, 0.47 mmol) in tetrahydrofuran (3 mL) was added diisopropylazodicarboxylate (95 mg, 0.47 mmol) at 0° C. After stirred at 20° C. for 16 hours, the reaction mixture was diluted with water (30 mL) and ethyl acetate (30 mL). The separated organic layer was dried over anhydrous sodium sulfate and concentrated under reduced pressure. The residue was purified by RP-HPLC (10-40% acetonitrile in water and 0.04% ammonium hydroxide and 10 mM ammonium bicarbonate) to afford 1-[(2-cyclopropyl-4-pyridyl)methyl]-4-[5-(difluoromethyl)-1,3,4-oxadiazol-2-yl]pyridin-2-one (11 mg, 13%) as a yellow solid.

Example 19. Synthesis of N-Alkyl Ether Pyridinone Compounds of Formula (I)

Preparation of 4-(5-(difluoromethyl)-1,3,4-oxadiazol-2-yl)-1-(2-(3,5-difluorophenoxy)ethyl)pyridin-2(1H)-one (Compound II-14)

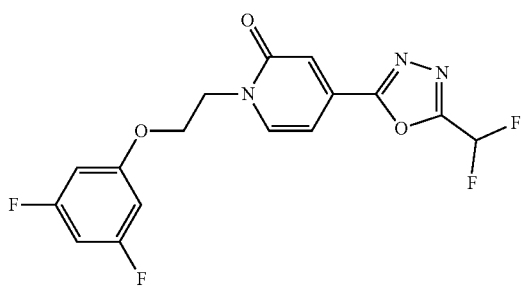 [SMILES: O=c1cc(-c2nnc(C(F)F)o2)ccn1CCOc1cc(F)cc(F)c1]

Step 1: 1-(2-bromoethoxy)-3,5-difluoro-benzene

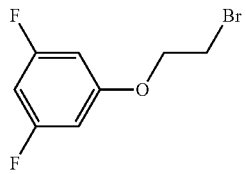

To a solution of 3,5-difluorophenol (500 mg, 3.84 mmol) and 1,2-dibromoethane (4.4 g, 23.54 mmol) in acetonitrile (10 mL) was added potassium carbonate (712 mg, 5.15 mmol). The mixture was stirred at 75° C. for 16 hours and filtered. The filtrate was concentrated under reduced pressure and the residue was purified by column chromatography (silica gel, 100-200 mesh, 0-5% ethyl acetate in petroleum ether) to afford 1-(2-bromoethoxy)-3,55-difluorobenzene (174 mg, 19%) as a colorless oil. $^1$H NMR (400 MHz, CDCl$_3$) δ 6.58-6.34 (m, 3 H), 4.26 (t, J=6.40 Hz, 2H), 3.64 (t, J=6.0 Hz, 2H).

Step 4-[5-(difluoromethyl)-1,3,4-oxadiazol-2-yl]-1-[2-(3,5-difluorophenoxy)ethyl]pyridin-2-one (Compound II-14)

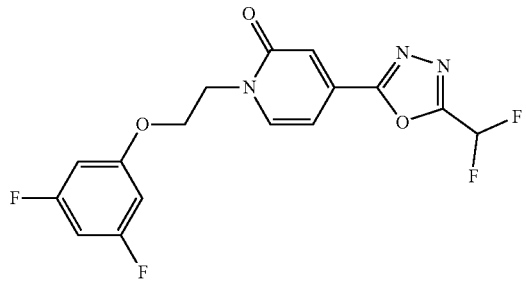 [SMILES: O=c1cc(-c2nnc(C(F)F)o2)ccn1CCOc1cc(F)cc(F)c1]

To a solution of 4-[5-(difluoromethyl)-1,3,4-oxadiazol-2-yl]-1H-pyridin-2-one (II-12, 40 mg, 0.19 mmol) and 1-(2-bromoethoxy)-3,5-difluoro-benzene (53 mg, 0.23 mmol) in N,N-dimethylformamide (1 mL) was added potassium carbonate (78 mg, 0.56 mmol). The mixture was stirred at 25° C. for 16 hours and filtered. The filtrate was concentrated under reduced pressure. The residue was purified by RP-HPLC (49-79% acetonitrile in water and 0.225% formic acid) to afford 4-[5-(difluoromethyl)-1,3,4-oxadiazol-2-yl]-1-[2-(3,5-difluorophenoxy)ethyl]pyridin-2-one (23.4 mg, 34%) as a white solid.

The methods disclosed in Example 19 were also used to prepare Compounds II-13 and II-16.

Example 20. Preparation of 5-(5-(difluoromethyl)-1,3,4-oxadiazol-2-yl)-2-(3-fluorophenoxy)ethyl)pyridazin-3(2H)-one (Compound II-17)

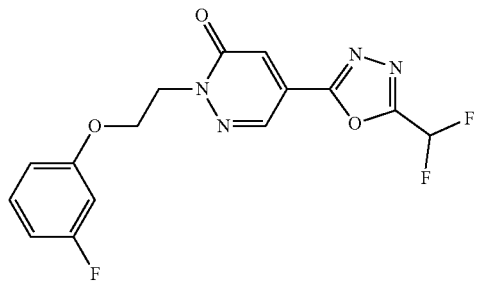 [SMILES: O=c1cc(-c2nnc(C(F)F)o2)cnn1CCOc1cccc(F)c1]

Step 1: ethyl 6-oxo-1H-pyridazine-4-carboxylate

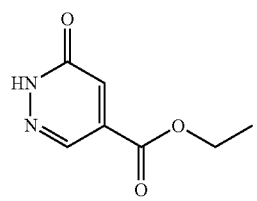

To a solution of 6-oxo-1H-pyridazine-4-carboxylic acid (5.5 g, 39.26 mmol) in ethyl alcohol (50 mL) was added concentrated sulfuric acid (98%, 10.1 g, 101.12 mmol). After stirred at 80° C. for 48 hours under nitrogen atmosphere, the mixture was concentrated under reduced pressure. The residue was adjusted to pH=8 by addition of saturated aqueous sodium carbonate and extracted with ethyl acetate (100 mL×3). The combined organic layers were dried over sodium sulphate and concentrated to dryness under reduced pressure to afford crude ethyl 6-oxo-1H-pyridazine-4-carboxylate (3 g, 45%) as a brown solid.

Step 2: ethyl 6-oxo-1-(2-trimethylsilylethoxymethyl)pyridazine-4-carboxylate

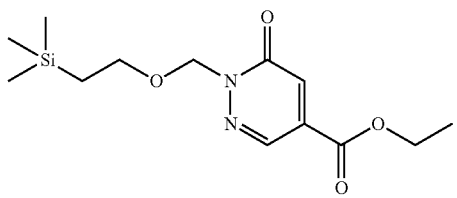 [SMILES: CCOC(=O)c1cnn(COCC[Si](C)(C)C)c(=O)c1]

To a solution of ethyl 6-oxo-1-(2-trimethylsilylethoxymethyl)pyridazine-4-carboxylate (3.0 g, 17.84 mmol) in N,N-dimethylformamide (20 ml,) was added N,N-diisopropylethylamine (3.7 g, 28.55 mmol) and (2-(chloromethoxy)ethyl)trimethylsilane (5.9 g, 35.68 mmol). After stirred at 20° C. for 32 hours, the reaction mixture was diluted with water (30 mL) and ethyl acetate (100 mL). The separated organic extract was washed with brine (50 mL×3), dried over sodium sulphate and concentrated to dryness under reduced pressure. The residue was purified by column chromatography (silica gel, 100-200 mesh, 0-20% ethyl acetate in petroleum ether) to afford ethyl 6-oxo-1-(2-trimethylsilylethoxymethyl)pyridazine-4-carboxylate (2.9 g, 42%) as yellow oil.

Step 3: 6-oxo-1-(2-trimethylsilylethoxymethyl)pyridazine-4-carbohydrazide

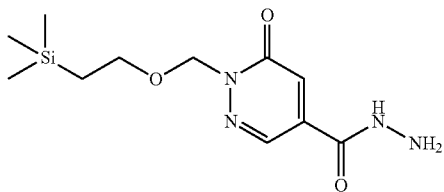 [SMILES: C[Si](C)(C)CCOCn1ncc(C(=O)NN)cc1=O]

To a solution of ethyl 6-oxo-1-(2-trimethylsilylethoxymethyl)pyridazine-4-carboxylate (2.9 g, 9.72 mmol) in ethyl alcohol (50 mL) was added hydrazine hydrate (85%, 6.2 g, 105.10 mmol). After stirred at 80° C. for 3 hours, the mixture was concentrated under reduced pressure. The residue was purified by column chromatography (silica gel, 100-200 mesh, 0-10% dichloromethane in methanol) to afford 6-oxo-1-(2-trimethylsilylethoxymethyl)pyridazine-4-carbohydrazide (2.5 g, 90%) as a yellow solid.

Step 4: 5-[5-(difluoromethyl)-1,3,4-oxadiazol-2-yl]-2-(2-trimethylsilylethoxymethyl)pyridazin-3-one

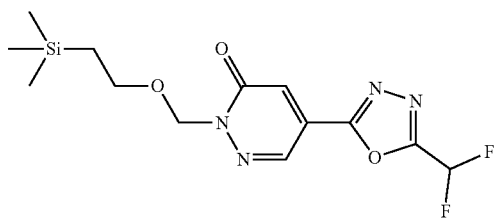 [SMILES: C[Si](C)(C)CCOCn1ncc(-c2nnc(C(F)F)o2)cc1=O]

To a solution of 6-oxo-1-(2-trimethylsilylethoxymethyl)pyridazine-4-carbohydrazide (2.5 g, 8.79 mmol) and N,N-diisopropylethylamine (9.1 g, 70.33 mmol) in tetrahydrofuran (30 mL) was added (2,2-difluoroacetyl) 2,2-difluoroacetate (6.1 g, 35.16 mmol) dropwise at 0° C. After stirred at 20° C. for 1 hour, the mixture was warm to 70° C. and stirred for 1 hour. The reaction mixture was diluted with water (150 mL) and extracted with ethyl acetate (150 mL×3). The combined organic layers were dried over sodium sulphate and concentrated to dryness under reduced pressure. The residue was purified by column chromatography (silica gel, 100-200 mesh, 0-5% methanol in dichloromethane) to afford 5-[5-(difluoromethyl)-1,3,4-oxadiazol-2-yl]-2-(2-trimethylsilylethoxymethyl)pyridazin-3-one (1.27 g, 40%) as a brown solid.

Step 5: 4-[5-(difluoromethyl)-1,3,4-oxadiazol-2-yl]-1H-pyridazin-6-one

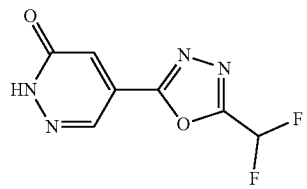 [SMILES: O=c1cc(-c2nnc(C(F)F)o2)cn[nH]1]

To a solution of 5-[5-(difluoromethyl)-1,3,4-oxadiazol-2-yl]-2-(2-trimethylsilylethoxymethyl)pyridazin-3-one (1.3 g, 3.69 mmol) in 1,1,1,3,3,3-hexafluoropropan-2-ol (10 mL) was added trifluoroacetic acid (4.2 g, 36.88 mmol.). After stirred at 20° C. for 1 h, the mixture was concentrated under reduced pressure. The residue was diluted with water (50 mL) and adjusted pH=8 by addition of aqueous saturated sodium bicarbonate. The mixture was extracted with dichloromethane (50 mL×3). The combined organic layers were dried over sodium sulphate and concentrated to dryness under reduced pressure. The residue was purified by column chromatography (silica gel, 100-200 mesh, 0-5% methanol in dichloromethane) to afford 4-[5-(difluoromethyl)-1,3,4-oxadiazol-2-yl]-1H-pyridazin-6-one (571 mg, 59%) as a yellow solid.

Step 6: 5-[5-(difluoromethyl)-1,3,4-oxadiazol-2-yl]-2-[2-(3-fluorophenoxy)ethyl]pyridazin-3-one (Compound II-17)

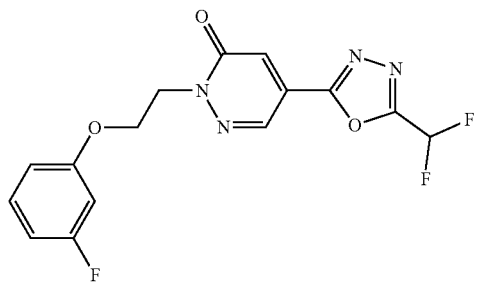 [SMILES: O=c1cc(-c2nnc(C(F)F)o2)cnn1CCOc1cccc(F)c1]

To a solution of 1-(2-bromoethoxy)-3-fluoro-benzene (56 mg, 0.26 mmol) in N,N-dimethylformamide (1 mL) was added sodium carbonate (49 mg, 0.47 mmol) and 4-[5-(difluoromethyl)-1,3,4-oxadiazol-2-yl]-1H-pyridazin-6-one (50 mg, 0.23 mmol). The mixture was stirred at 20° C. for 1 hour and filtered. The filtrate was concentrated under reduced pressure. The residue was purified by RP-HPLC (30-60% acetonitrile in water and 0.225% formic acid) to afford 5-[5-(difluoromethyl)-1,3,4-oxadiazol-2-yl]-2-[2-(3-fluorophenoxy)ethyl]pyridazin-3-one (19.2 mg, 23%) as a white solid.

Example 21. Preparation of 4-[5-(difluoromethyl)-1,3,4-oxadiazol-2-yl]-1-[[(1R,2R)-2-phenylcyclopropyl]methyl]pyridin-2-one (Compound II-19)

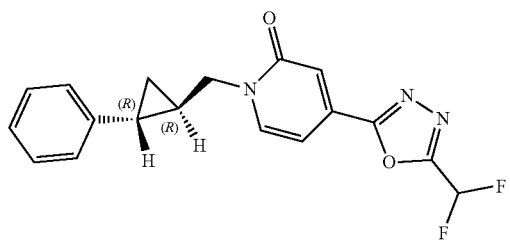

Step 1: [(1R,2R)-2-phenylcyclopropyl]methanol

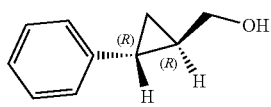

To a solution of ethyl (1R,2R)-2-phenylcyclopropanecarboxylate (500 mg, 2.63 mmol) in tetrahydrofuran (25 mL) was added diisobutylaluminium hydride (1 M in tetrahydrofuran, 5.3 mL, 5.3 mmol) at 0° C. After addition, the reaction mixture was warmed to 20° C. and stirred for 16 hours. The reaction was quenched by addition of saturated ammonium chloride solution (30 mL) and extracted with ethyl acetate (40 mL×3). The combined organic extracts were dried over sodium sulphate and concentrated to dryness under reduced pressure. The residue was purified by column chromatography (silica gel, 100-200 mesh, 0-100% ethyl acetate in petroleum ether) to afford [(1R,2R)-2-phenylcyclopropyl]methanol (301 mg, 77%) as colorless oil.

Step 2: [(1R,2R)-2-(iodomethyl)cyclopropyl]benzene

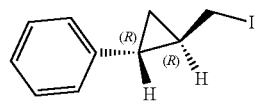

To a solution of [(1R,2R)-2-phenylcyclopropyl]methanol (160 mg, 1.08 mmol) in tetrahydrofuran (5 mL) was added iodine (411 mg, 1.62 mmol), imidazole (220 mg, 3.24 mmol) and triphenylphosphane (850 mg, 3.24 mmol). The reaction mixture was stirred at 25° C. for 0.5 hour and concentrated to dryness under reduced pressure. The residue was purified by RP-TLC (petroleum ether) to afford [(1R,2R)-2-(iodomethyl)cyclopropyl]benzene (54 mg, 19%) as a white solid.

Step 3: 4[5-(difluoromethyl)-1,3,4-oxadiazol-2-yl]-1-[[(1R,2R)-2-phenylcyclopropyl]methyl]pyridin-2-one (Compound II-19)

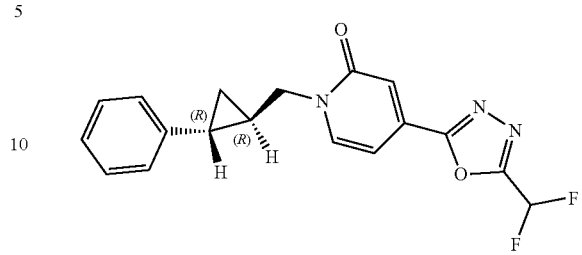

To a solution of [(1R,2R)-2-(iodomethyl)cyclopropyl]benzene (54 mg, 0.21 mmol) and 4-[5-(difluoromethyl)-1,3,4-oxadiazol-2-yl]-1H-pyridin-2-one (37 mg, 0.17 mmol) in N,N-dimethylformamide (1 mL) was added potassium phosphate (72 mg, 0.52 mmol). The mixture was stirred at 25° C. for 16 hours and filtered. The filtrate was concentrated to dryness under reduced pressure. The residue was purified by RP-HPLC (50-80% acetonitrile in water and 0.225% formic acid) to afford 4-[5-(difluoromethyl)-1,3,4-oxadiazol-2-yl]-1-[[(1R,2R)-2-phenylcyclopropyl]methyl]pyridin-2-one (5.6 mg, 9%) as a yellow solid.

Example 22. Preparation N-(3-chlorophenyl)-N-((5-(5-(difluoromethyl)-1,3,4-oxadiazol-2-yl)isoxazol-3-yl)methyl)ethanesulfonamide (Compound IVb-1)

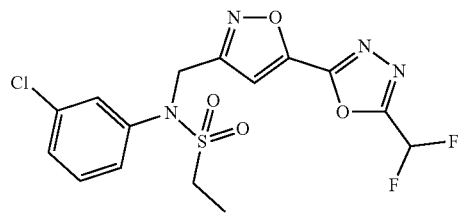 [SMILES: CCS(=O)(=O)N(Cc1cc(-c2nnc(C(F)F)o2)on1)c1cccc(Cl)c1]

Step 1:(1E)-2-chloroacetaldehyde oxime

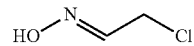

To a solution of 2-chloroacetaldehyde (14.5 g, 73.8 mmol, 40% purity) in water (50 mL) was added sodium acetate (7.3 g, 88.6 mmol) and hydroxylamine hydrochloride (6.2 g, 88.6 mmol). After stirred at 20° C. for 1 hour, the reaction was quenched by addition of saturated sodium bicarbonate (20 mL). The mixture was extracted with ethyl acetate (100 mL×2). The combined organic extracts were dried over sodium sulphate and concentrated to dryness under reduced pressure to afford (1E)-2-chloroacetaldehyde oxime (4.0 g, 58%) as a yellow solid which was used in next step without further purification.

Step 2: ethyl 3-(chloromethyl)isoxazole-5-carboxylate

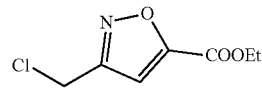 [SMILES: CCOC(=O)c1cc(CCl)no1]

To a solution of (1E)-2-chloroacetaldehyde oxime (4.0 g, 42.8 mmol) in tetrahydrofuran (15 mL) was added ethyl prop-2-ynoate (4.2 g, 42.8 mmol) and sodium hypochlorite (181.5 g, 243.8 mmol, 10% purity) at 0° C. After stirred at 20° C. for 18 hours, the reaction mixture was diluted with ethyl acetate (200 mL) and brine (200 mL). The separated organic layer was dried over sodium sulphate and concentrated to dryness under reduced pressure. The residue was purified by column chromatography (silica gel, 100-200 mesh, 0-10% ethyl acetate in petroleum ether) to afford ethyl 3-(chloromethyl)isoxazole-5-carboxylate (2.8 g, 35%) as a white solid.

Step 3: ethyl 3-[(3-chloro-N-ethylsulfonyl-anilino)methyl]isoxazole-5-carboxylate

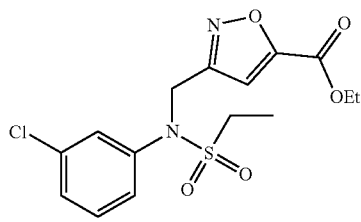 [SMILES: CCOC(=O)c1cc(CN(c2cccc(Cl)c2)S(=O)(=O)CC)no1]

To a solution of N-(3-chlorophenyl)ethanesulfonamide (461 mg, 2.10 mmol) in N,N-dimethylformamide (5 mL) was added ethyl 3-(chloromethyl)isoxazole-5-carboxylate (200 mg, 1.05 mmol) and sodium carbonate (334 mg, 3.15 mmol). After stirred at 30° C. for 16 hours, the mixture was diluted with ethyl acetate (50 mL) and washed with brine (50 mL×2). The separated organic layer was dried over sodium sulphate and concentrated to dryness under reduced pressure. The residue was purified by column chromatography (silica gel, 100-200 mesh, 0-10% ethyl acetate in petroleum ether) to afford ethyl 3-[(3-chloro-N-ethylsulfonyl-anilino)methyl]isoxazole-5-carboxylate (370 mg, 95%) as a white solid.

Step 4: N-(3-chlorophenyl)-N-[[5-(hydrazinecarbonyl)isoxazol-3-yl]methyl]ethanesulfonamide

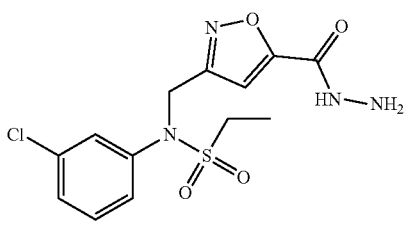 [SMILES: CCS(=O)(=O)N(Cc1cc(C(=O)NN)on1)c1cccc(Cl)c1]

To a solution of ethyl 3-[(3-chloro-N-ethylsulfonyl-anilino)methyl]isoxazole-5-carboxylate (170 mg, 0.46 mmol) in ethanol (2 mL) was added hydrazine hydrate (250 mg, 4.89 mmol). The mixture was stirred at 60° C. for 2 hours and concentrated under reduced pressure. The residue was purified by column chromatography (silica gel, 100-200 mesh, 0-10% methanol in dichloromethane) to afford N-(3-chlorophenyl)-N-[[5-(hydrazinecarbonyl)isoxazol-3-yl]methyl]ethanesulfonamide (100 mg, 61%) as a white solid.

Step 5: N-(3-chlorophenyl)-N-[[5-[[(-difluoroacetyl)amino]carbamoyl]-isoxazol-3-yl]methyl]ethanesulfonamide

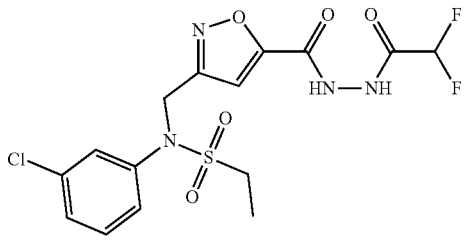 [SMILES: CCS(=O)(=O)N(Cc1cc(C(=O)NNC(=O)C(F)F)on1)c1cccc(Cl)c1]

To a solution of N-(3-chlorophenyl)-N-[[5-(hydrazinecarbonyl)isoxazol-3-yl]methyl]ethanesulfonamide (100 mg, 0.28 mmol) and N,N-diisopropylethylamine (36 mg, 0.28 mmol) in tetrahydrofuran (2 mL) was added (2,2-difluoroacetyl) 2,2-difluoroacetate (49 mg, 0.28 mmol) under nitrogen atmosphere. After stirred at 20° C. for 2 hours, the reaction was quenched by addition of water (50 mL) and extracted with ethyl acetate (30 mL×3). The combined organic layers were dried over sodium sulphate and concentrated to dryness under reduced pressure. The residue was purified by RP-TLC (petroleum ether:ethyl acetate=1:1) to afford N-(3-chlorophenyl)-N-[[5-[[(2,2-difluoroacetyl)amino]carbamotl]isoxazol-3-yl]methyl]ethane sulfonamide (110 mg, 90%) as a white solid.

Step 6: N-(3-chlorophenyl)-N-((5-(5-(difluoromethyl)-1,3,4-oxadiazol-2-yl)isoxazol-3-yl)methyl)ethanesulfonamide (Compound IVb-1)

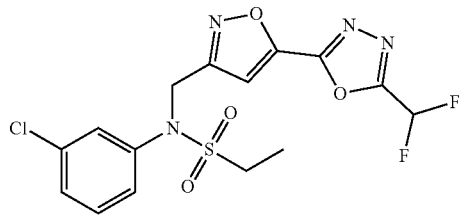 [SMILES: CCS(=O)(=O)N(Cc1cc(-c2nnc(C(F)F)o2)on1)c1cccc(Cl)c1]

To a solution of N-(3-chlorophenyl)-N-[[5-[[(2,2-difluoroacetyl)amino]carbamoyl]isoxazol-3-yl]methyl]ethanesulfonamide (100 mg, 0.23 mmol) in tetrahydrofuran (2 mL) was added. Burgess reagent (136 mg, 0.57 mmol). The mixture was stirred at 90° C. for 2 hours under nitrogen atmosphere and concentrated under reduced pressure. The residue was purified by RP-HPLC (35 to 65% acetonitrile in water and 0.1% trifluoroacetic acid) to afford N-(3-chlorophenyl)-N-[[5-[5-(difluoromethyl)-1,3,4-oxadiazol-2-yl]isoxazol-3-yl]methyl]ethanesulfonamide (13 mg, 13%) as a white solid.

Example 23. Preparation of N-({3-[5-(difluoromethyl)-1,3,4-oxadiazol-2-yl]-1,2-oxazol-5-yl}methyl)-N-(pyridin-3-yl)ethane-1-sulfonamide (IVa-2)

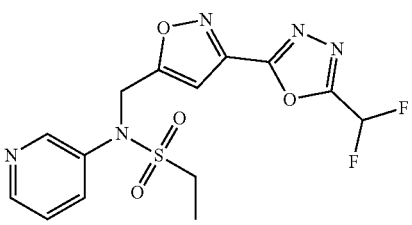 [SMILES: CCS(=O)(=O)N(Cc1cc(-c2nnc(C(F)F)o2)no1)c1cccnc1]

Step 1: ethyl 5-[[ethylsulfonyl(3-pyridyl)amino]methyl]isoxazole-3-carboxylate

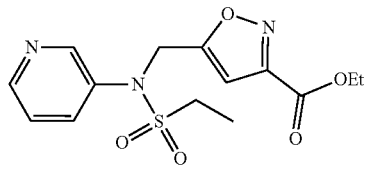 [SMILES: CCOC(=O)c1cc(CN(c2cccnc2)S(=O)(=O)CC)on1]

To a solution of ethyl 5-(p-tolylsulfonyloxymethyl)isoxazole-3-carboxylate (400 mg, 1.23 mmol) and N-(3-pyridyl)ethanesulfonamide (275 mg, 1.48 mmol) in N,N-dimethylformamide (8 mL) was added sodium carbonate (391 mg, 3.69 mmol) and potassium iodide (20 mg, 0.12 mmol) at 20° C. After stirring at 20° C. for 16 h, the residue was diluted with ethyl acetate (10 mL) and washed with brine (3×10 mL). The organic layer was dried over anhydrous sodium sulphate and concentrated under reduced pressure. The residue was purified by flash column chromatography (silica gel, 100-200 mesh, 0-6% methanol in dichloromethane) to afford ethyl 5-[[ethylsulfonyl(3-pyridyl)amino]methyl]isoxazole-3-carboxylate (323 mg, 75%) as a light yellow solid.

Step 2: N-[[3-(hydrazinecarbonyl)isoxazol-5-yl]methyl]-N-(3-pyridyl)ethanesulforamide

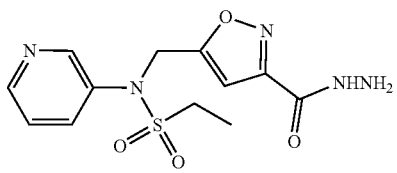 [SMILES: CCS(=O)(=O)N(Cc1cc(C(=O)NN)no1)c1cccnc1]

To a solution of ethyl 5-[[ethylsulfonyl(3-pyridyl)amino]methyl]isoxazole-3-carboxylate (273 mg, 0.80 mmol) in ethanol (3 mL) was added hydrazine hydrate (403 mg, 8.04 mmol). The mixture was stirred at 60° C. for 1 h and concentrated to dryness under reduced pressure. The residue was purified by flash column chromatography (silica gel, 100-200 mesh, 0-10% methanol in dichloromethane) to afford N-[[3-(hydrazinecarbonyl)isoxazol-5-yl]methyl]-N-(3-pyridyl)ethanesulfonamide (204 mg, 75%) as light yellow oil.

Step 3: N-[[3-[[(2,2-difluoroacetyl)amino]carbamoyl]isoxazol-5-yl]methyl]-N-(3-pyridyl)ethanesulfonamide

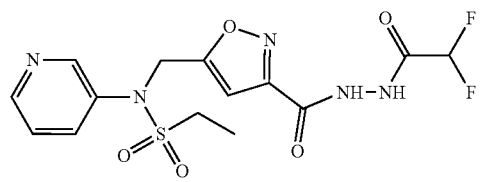 [SMILES: CCS(=O)(=O)N(Cc1cc(C(=O)NNC(=O)C(F)F)no1)c1cccnc1]

To a solution of N-[[3-(hydrazinecarbonyl)isoxazol-5-yl]methyl]-N-(3-pyridyl)ethanesulfonamide (184 mg, 0.56 mmol) in tetrahydrofuran (3 mL) was added N-ethyl-N-isopropylpropan-2-amine (80 mg, 0.62 mmol) and (2,2-difluoroacetyl) 2,2-difluoroacetate (118 mg, 0.69 mmol). After stirring at 20° C. for 1 h, the reaction mixture quenched by addition of water (5 mL) and extracted with ethyl acetate (2×10 mL). The combined organic extracts were dried over anhydrous sodium sulphate and concentrated to dryness under reduced pressure. The residue was purified by flash column chromatography (silica gel, 100-200 mesh, 0-10% methanol in dichloromethane) to afford N-[[3-[[(2,2-difluoroacetyl)amino]carbamoyl]isoxazol-5-yl]methyl]-N-(3-pyridyl)ethanesulfonamide (200 mg, 70%) as a colorless oil.

Step 4: N-({3-[5-(difluoromethyl)-1,3,4-oxadiazol-2-yl]-1,2-oxazol-5-yl}methyl)-N-(pyridin-3-yl)ethane-1-sulfonamide

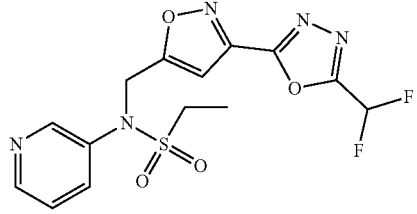 [SMILES: CCS(=O)(=O)N(Cc1cc(-c2nnc(C(F)F)o2)no1)c1cccnc1]

To a solution of N-[[3-[[(2,2-difluoroacetyl)amino]carbamoyl]isoxazol-5-yl]methyl]-N-(3-pyridyl)ethanesulfonamide (100 mg, 0.25 mmol) in tetrahydrofuran (2 mL) was added Burgess reagent (148 mg, 0.62 mmol). The mixture was stirred at 90° C. for 3 h and cooled. The solution was diluted with water (4 mL) and extracted with ethyl acetate (2×10 mL). The combined organic extracts were dried over anhydrous sodium sulphate and concentrated to dryness under reduced pressure. The residue was purified by preparative TLC (dichloromethane:methanol=20:1) to afford N-({3-[5-(difluoromethyl)-1,3,4-oxadiazol-2-yl]-1,2-oxazol-5-yl}methyl)-N-(pyridin-3-yl)ethane-1-sulfonamide (20.3 mg, 21%) as a white solid.

The method disclosed in Example 23 was also used to prepare Compounds IVa-3 and IVa-4.

Example 24. Preparation of 3-chloro-N-((5-(5-(difluoromethyl)-1,3,4-oxadiazol-2-yl)isoxazol-3-yl)methyl)-N-methylaniline (Compound IVb-2)

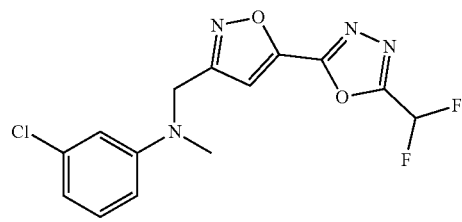 [SMILES: CN(Cc1cc(-c2nnc(C(F)F)o2)on1)c1cccc(Cl)c1]

Step 1: ethyl 3-[(3-chloro-N-methyl-anilino)methyl]isoxazole-5-carboxylate

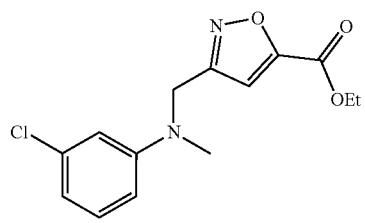 [SMILES: CCOC(=O)c1cc(CN(C)c2cccc(Cl)c2)no1]

To a solution of ethyl 3-(chloromethyl)isoxazole-5-carboxylate (300 mg, 1.58 mmol) in N,N-dimethylformamide (10 mL) was added 3-chloro-N-methyl-aniline (291 mg, 2.06 mmol), sodium carbonate (503 mg, 4.75 mmol) and potassium iodide (26 mg, 0.16 mmol). The reaction mixture was stirred at 25° C. for 2 hours and filtered. The filtrate was concentrated under reduced pressure. The residue was purified by column chromatography (silica gel, 100-200 mesh, 0-15% ethyl acetate in petroleum ether) to afford ethyl 3-[(3-chloro-N-methyl-anilino)methyl]isoxazole-5-carboxylate (270 mg, 54%).

Step 2: 3-[(3-chloro-N-methyl-anilino)methyl]isoxazole-5-carbohydrazide

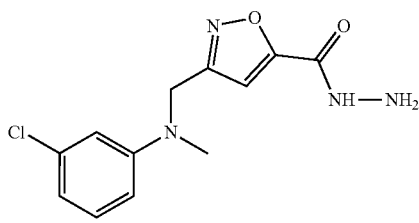 [SMILES: CN(Cc1cc(C(=O)NN)on1)c1cccc(Cl)c1]

To a solution of ethyl 3-[(3-chloro-N-methyl-anilino)methyl]isoxazole-5-carboxylate (220 mg, 0.75 mmol) in ethyl alcohol (4 mL) was added hydrazine hydrate (440 mg, 7.46 mmol, 85% purity). The reaction mixture was stirred at 60° C. for 2 hours and concentrated under reduced pressure. The residue was purified by column chromatography (silica gel, 100-200 mesh, 0-5% methanol in dichloromethane) to afford 3-[(3-chloro-N-methyl-anilino)methyl]isoxazole-5-carbohydrazide (150 mg, 68%) as yellow oil.

Step 3: 3-[(3-chloro-N-methyl-anilino)methyl]-N'-(2,2-difluoroacetyl)isoxazole-5-carbohydrazide

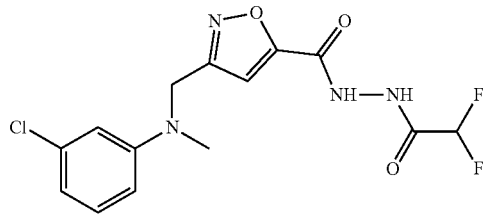 [SMILES: CN(Cc1cc(C(=O)NNC(=O)C(F)F)on1)c1cccc(Cl)c1]

To a solution of 3-[(3-chloro-N-methyl-anilino)methyl]isoxazole-5-carbohydrazide (150 mg, 0.53 mmol) in tetrahydrofuran (3 mL) was added N-ethyl-N-isopropylpropan-2-amine (69 mg, 0.53 mmol) and (2,2-difluoroacetyl) 2,2-difluoroacetate (112 mg, 0.64 mmol). The mixture was stirred at 20° C. for 2 hours and concentrated under reduced pressure. The residue was purified by column chromatography (silica gel, 100-200 mesh, 0-50% ethyl acetate in petroleum ether) to afford 3-[(3-chloro-N-methyl-anilino)methyl]-N'-(2,2-difluoroacetyl)isoxazole-5-carbohydrazide (150 mg, 74%) as a yellow solid.

Step 4: 3-chloro-N-[[5-[5-(difluoromethyl)-1,3,4-oxadisoxazol-2-yl]isoxazol-3-yl]methyl]-N-methyl-aniline (Compound IVb-2)

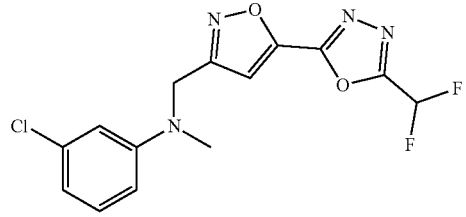 [SMILES: CN(Cc1cc(-c2nnc(C(F)F)o2)on1)c1cccc(Cl)c1]

To a solution of 3-[(3-chloro-N-methyl-anilino)methyl]-N'-(2,2-difluoroacetyl)isoxazole-5-carbohydrazide (50 mg, 0.14 mmol) in tetrahydrofuran (2 mL) was added Burgess reagent (83 mg, 0.35 mmol). The mixture was stirred at 90° C. for 3 hours in a microwave reactor and filtered. The filtrate was concentrated under reduced pressure. The residue was purified by RP-HPLC (40-70% acetonitrile in water and 0.04% ammonium hydroxide and 10 mM ammonium bicarbonate) to afford 3-chloro-N-[[5-[5-(difluoromethyl)-1,3,4-oxadiazol-2-tl]isoxazol-3-yl]methyl]-N-methyl-aniline (7.2 mg, 15%).

The method disclosed in Example 24 was also used to prepare Compound IVb-3.

Example 25. Preparation of 3-chloro-N-({3-[5-(difluoromethyl)-1,3,4-oxadiazol-2-yl]-1,2-oxazol-5-tl}methyl)-N-methylaniline (IVa-1)

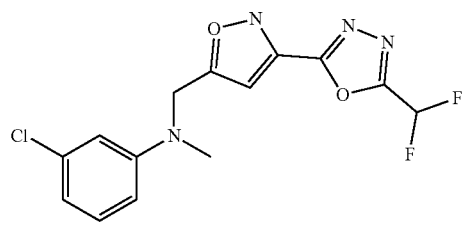

Step 1: ethyl 5-(p-tolylsulfonyloxymethyl)isoxazole-3-carboxylate

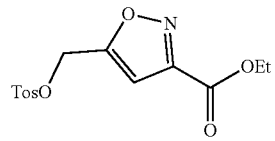

To a solution of ethyl 5-(hydroxymethyl)isoxazole-3-carboxylate (2.0 g, 11.69 mmol) in dichloromethane (50 mL) was added triethylamine (1.3 g, 12.85 mmol) and 4-methylbenzenesulfonyl chloride under nitrogen atmosphere. After stirring at 20° C. for 3 h, the reaction mixture was diluted with dichloromethane (30 mL) and washed with brine (50 mL). The organic layer was dried over anhydrous sodium sulphate and concentrated under reduced pressure. The residue was purified by flash column chromatography (silica gel, 100-200 mesh, 0-25% ethyl acetate in petroleum ether) to afford ethyl 5-(p-tolylsulfonyloxymethyl)isoxazole-3-carboxylate (2.54 g, 64%) as a white solid.

Step 2: ethyl 5-[(3-chloro-N-methyl-anilino)methyl]isoxazole-3-carboxylate

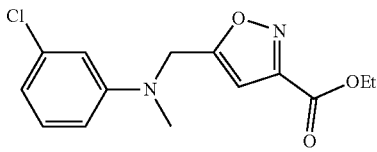 [SMILES: CCOC(=O)c1cc(CN(C)c2cccc(Cl)c2)on1]

To a solution of ethyl 5-(p-tolylsulfonyloxymethyl)isoxazole-3-carboxylate (400 mg, 1.23 mmol) and 3-chloro-N-methyl-aniline (209 mg, 1,48 mmol) in N,N-dimethylformamide (8 mL) was added sodium carbonate (391 mg, 3.69 mmol) and potassium iodide (20 mg, 0.12 mmol). After stirring at 20° C. for 16 h, the mixture was diluted with ethyl acetate (10 mL) and washed with brine (3×10 mL). The organic layer was dried over anhydrous sodium sulphate and concentrated under reduced pressure. The residue was purified by flash column chromatography (silica gel, 100-200 mesh, 0-25% ethyl acetate in petroleum ether) to afford ethyl 5-[(3-chloro-N-methyl-anilino)methyl]isoxazole-3-carboxylate (230 mg, 59%) as a white solid.

Step 3: 5-[(3-chloro-N-methyl-anilino)methyl]isoxazole-3-carbohydrazide

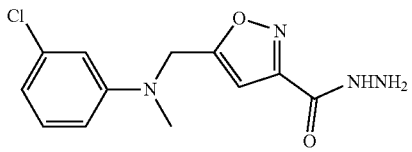 [SMILES: CN(Cc1cc(C(=O)NN)no1)c1cccc(Cl)c1]

To a solution of ethyl 5-[(3-chloro-N-methyl-anilino)methyl]isoxazole-3-carboxylate (180 mg, 0.61 mmol) in ethanol (3 mL) was added hydrazine hydrate (360 mg, 6.11 mmol). The mixture was stirred at 60° C. for 1 h and concentrated to dryness under reduced pressure. The residue was purified by flash column chromatography (silica gel, 100-200 mesh, 0-5% methanol in dichloromethane) to afford 5-[(3-chloro-N-methyl-anilino)methyl]isoxazole-3-carbohydrazide (181 mg, 88%) as a light yellow oil.

Step 4: 5-[(3-chloro-N-methyl-anilino)methyl]-N-(2,2-difluoroacetyl)isoxazole-3-carbohydrazide

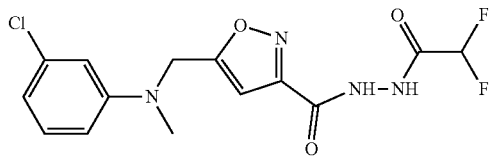 [SMILES: CN(Cc1cc(C(=O)NNC(=O)C(F)F)no1)c1cccc(Cl)c1]

To a solution of 5-[(3-chloro-N-methyl-anilino)methyl]isoxazole-3-carbohydrazide (181 mg, 0.64 mmol) in tetrahydrofuran (3 mL) was added N-ethyl-N-isopropylpropan-2-amine (92 mg, 0.71 mmol) and (2,2-difluoroacetyl) 2,2-difluoroacetate (135 mg, 0.77 mmol) under nitrogen atmosphere. After stirring at 20° C. for 1 hour, the reaction mixture was quenched by addition of water (5 mL) and extracted with ethyl acetate (2×10 mL). The combined organic extracts were dried over anhydrous sodium sulphate and concentrated to dryness under reduced pressure. The residue was purified by flash column chromatography (silica gel, 100-200 mesh, 0-50% ethyl acetate in petroleum ether) to afford 5-[(3-chloro-N-methyl-anilino)methyl]-N'-(2,2-difluoroacetyl)isoxazole-3-carbohydrazide (148 mg, 62%) as a white solid.

Step 5: 3-chloro-N-({3-[5-(difluoromethyl)-1,3,4-oxadiazol-2-yl]-1,2-oxazol-5-yl}methyl)-N-methylaniline

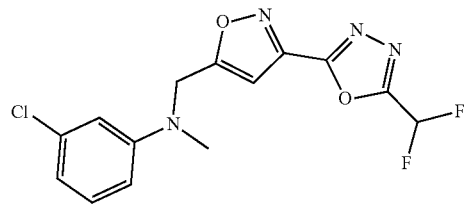 [SMILES: CN(Cc1cc(-c2nnc(C(F)F)o2)no1)c1cccc(Cl)c1]

To a solution of 5-[(3-chloro-N-methyl-anilino)methyl]-N'-(2,2-difluoroacetyl)isoxazole-3-carbohydrazide (72 mg, 0.20 mmol) in tetrahydrofuran (2 mL) was added Burgess reagent (120 mg, 0.50 mmol). The mixture was stirred at 90° C. for 3 h and cooled. The solution was diluted with water (4 mL) and extracted with ethyl acetate (2×10 mL). The combined organic extracts were dried over anhydrous sodium sulphate and concentrated to dryness under reduced pressure. The residue was purified by preparative TLC (petroleum ether:ethyl acetate=3 1) to afford 3-chloro-N-({3-[5-(difluoromethyl)-1,3,4-oxadiazol-2-yl]-1,2-oxazol-5-yl}methyl)-N-methylaniline (22.2 mg, 27%) as a light yellow oil.

Example 26. Preparation of 5-(6-((1-(2,6-difluorophenyl)cyclopropyl)amino)-5-fluoropyridin-3-yl)-1,3,4-oxadiazole-2-carbonitrile (A-1)

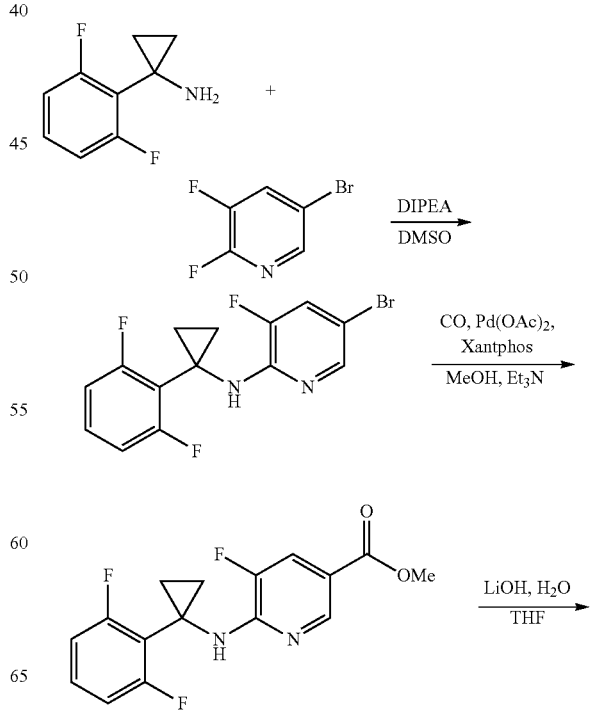

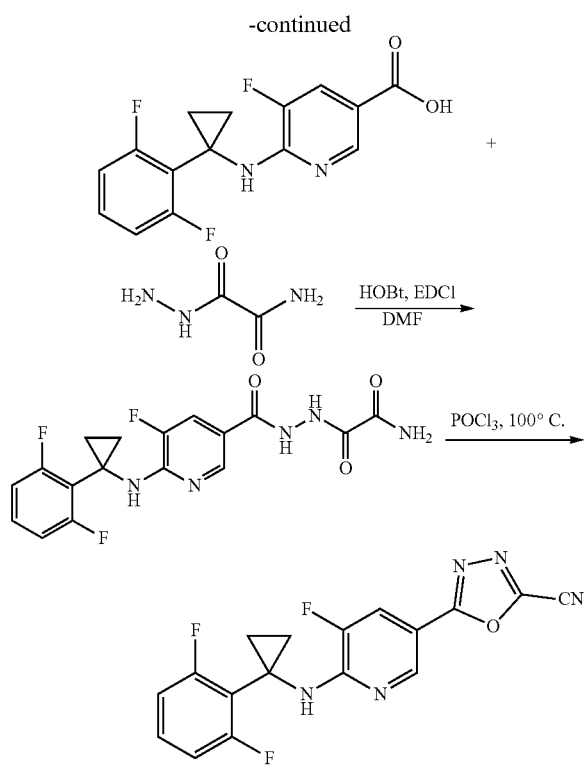

Step 1: 5-bromo-N-(1-(2,6-difluorophenyl)cyclopropyl)-3-fluoropyridin-2-amine

To a vial was added 1-(2,6-difluorophenyl)cyclopropan-1-amine (304 mg, 1.80 mmol),,DMSO (3 mL), DIPEA (1.57 mL, 9.0 mmol, 5 equiv), and 5-bronco-2,3-difluoropyridine (0.29 mL, 2.2 mmol, 1.2 equiv). The biphasic homogeneous mixture was heated to 120° C. overnight under $N_2$ atmosphere (balloon). Upon reaching 120° C., the reaction becomes monophasic. The following day, LCMS analysis of the dark brown mixture reveals full conversion of the amine partner. The reaction was worked up by pouring into water (50 mL) and extracting three times with EtOAc (30 mL each). The combined organic layers were washed twice with water and once with brine, then dried over $MgSO_4$, filtered and concentrated by rotary evaporation. The crude product, a brown oil, was dry-loaded onto silica gel and purified by column chromatography (Silica gel, 0-25% EtOAc/hexanes) to afford the title compound as a pale-yellow oil, 400 mg (65%).

Step 2: methyl 6-((1-(2,6-difluorophenyl)cyclopropyl)amino)-5-fluoronicotinate

5-Bromo-N-(1-(2,6-difluorophenypcyclopropyl)-3-fluoropyridin-2-amine (686 mg, 2 mmol), $Pd(OAc)_2$ (22 mg, 0.1 mmol) and Xantphos (115 mg, 0.2 mmol) were dissolved in MeOH (6.5 mL) and $Et_3N$ (35 mL) mixture. A balloon with carbon monoxide was attached and the gas was bubbled through the solution for 1 minute. The reaction mixture with attached carbon monoxide balloon was heated at 70° C. overnight. The reaction mixture was cooled to rt, evaporated, diluted with MeOH, preadsorbed on silica gel and purified by column chromatography (silica gel; hex/EtOAc 1:0 gradient to 4:1) to give 525 mg (81%) of product.

Step 3: 6-((1-(2,6-difluorophenyl)cyclopropyl)amino)-5-fluoronicotinic acid

A LiOH solution (1.5 mmol, 1.5 mL, 1M in water) was added to a stirred solution of methyl 6-((1-(2,6-difluorophenyl)cyclopropyl)amino)-5-fluoronicotinate (161 mg, 0.5 mmol) in THF (2 mL). The reaction mixture was stirred at 70° C. for 3 hours, cooled to rt and acidified with HCl solution (1M in water). The reaction mixture was diluted with EtOAc and washed with water (2×) and brine. Organic fraction was dried with anhydrous $Na_2SO_4$ and evaporated to give 170 mg (quantitative yield) of product.

Step 4: 2-(2-(6-((1-(2,6-difluorophenyl)cyclopropyl)amino)-5-fluoronicotinoyl)hydrazineyl)-2-oxoacetamide HOBt (4 mg, 0.025 mmol) was added to a solution of 6-((1-(2,6-difluorophenyl)cyclopropyl)amino)-5-fluoronicotinic acid (154 mg, 0.5 mmol) and 2-hydrazineyl-2-oxoacetamide (77 mg, 0.75 mmol) in DMF (5 mL) and the reaction mixture was stirred at rt for 15 min. 1-Ethyl-3-(3-dimethylaminopropyl)carbodiimide hydrochloride (144 mg, 0.75 mmol) was added in one portion and the reaction mixture was heated at 50° C. for 3 hours. The reaction mixture was cooled to rt, diluted with water and extracted with EtOAc (3×). Combined organic fractions were dried with anhydrous $Na_2SO_4$. The solvent was evaporated, and the crude product was purified by column chromatography (silica gel; $CH_2Cl_2$/MeOH; 19:1 gradient to 3:1) to give 149 mg of product that was contaminated with DMF. Trituration from $CHCl_3$ gave 81 mg (41%) of pure material.

Step 5: 5-(6-((1-(2,6-difluorophenyl)cyclopropyl)amino)-5-fluoropyridin-3-yl)-1,3,4-oxadiazole-2-carbonitrile A solution of 2-(2-(6-((1-(2,6-difluorophenyl)cyclopropyl)amino)-5-fluoronicotinoyl)hydrazineyl)-2-oxoacetamide (61 mg, 0.16 mmol) in $POCl_3$ (3 mL) was stirred at 100° C. for 6 hours. The reaction mixture was cooled to rt, $POCl_3$ was evaporated and the residue was dissolved in EtOAc. This solution was poured into saturated $NaHCO_3$ solution and layers were separated. Organic fraction was dried with anhydrous $Na_2SO_4$. The solvent was evaporated, and the crude product was purified by column chromatography (silica gel; hexane/EtOAc 1:0 gradient to 7:3) to give 18 mg (33%) of product.

Example 27. Preparation of 1-(5-(5-(difluoromethyl)-1,3,4-oxadiazol-2-yl)thiazol-2-yl)-5-phenylpyrrolidin-2-one (Compound A-2)

Step 1: ethyl 2-benzylpyrazolo[1,5-a]pydmidine-6-carboxylate

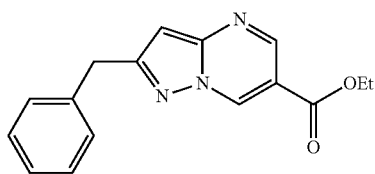 [SMILES: CCOC(=O)c1cnc2cc(Cc3ccccc3)nn2c1]

To a solution of ethyl 2-formyl-3-oxo-propanoate (247 mg, 1.71 mmol) in ethanol (5 mL) was added 3-benzyl-1H-pyrazol-5-amine (300 mg, 1.73 mmol). The mixture was stirred at 80° C. for 2 hours. The reaction was quenched by addition of saturated sodium bicarbonate (50 mL) and extracted with ethyl acetate (50 mL×2). The combined organic layers were dried over sodium sulphate and concentrated to dryness under reduced pressure. The residue was purified by column chromatography (silica gel, 100-200 mesh, 0-20% ethyl acetate in petroleum ether) to afford ethyl 2-benzylpyrazolo[1,5-a]pyrimidine-6-carboxylate (205 mg, 42%) as a white solid.

Step 2: 2-benzylpyrazolo[1,5-a]pyrimidine-6-carboxylic acid

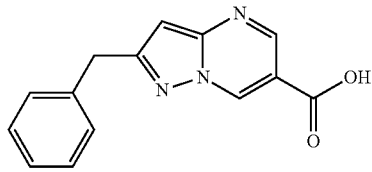 [SMILES: O=C(O)c1cnc2cc(Cc3ccccc3)nn2c1]

To a solution of ethyl 2-benzylpyrazolo[1,5-a]pyrimidine-6-carboxylate (200 mg, 0.71 mmol) in tetrahydrofuran (1 mL) and water (1 mL) was added lithium hydroxide monohydrate (60 mg, 1.42 mmol). The mixture was stirred at 20° C. for 2 hours and adjusted to pH=4 by addition of hydrochloric acid (1 M). The resulting mixture was extracted with ethyl acetate (30 mL×3). The combined organic extracts were dried over sodium sulphate and concentrated to dryness under reduced pressure to afford crude 2-benzylpyrazolo[1,5-a]pyrimidine-6-carboxylic acid (180 mg, crude) as a white solid.

Step 3: tert-butyl N-[(2-benzylpyrazolo[1,5-a]pyrimidine-6-carbonyl)-amino]carbamate

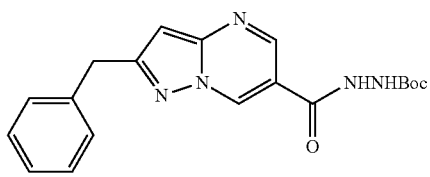

To a solution of 2-benzylpyrazolo[1,5-a]pyrimidine-6-carboxylic acid (130 mg, 0.51 mmol) in dichloromethane (5 mL) was added HATU (234 mg, 0.61 mmol) and N-ethyl-N-isopropylpropan-2-amine (100 mg, 0.77 mmol). After stirred at 0° C. for 15 minutes, tert-butyl N-aminocarbamate (75 mg, 0.56 mmol) was added. After stirred at 20° C. for 16 hours, the reaction mixture was diluted with ethyl acetate (50 mL) and brine (50 mL). The separated organic extract was dried over sodium sulphate and concentrated to dryness under reduced pressure. The residue was purified by column chromatography (silica gel, 100-200 mesh, 0-20% ethyl acetate in petroleum ether) to afford tert-butyl N-[(2-benzylpyrazolo[1,5-a]pyrimidine-6-carbonyl)amino]carbamate (185 mg, 98%) as a white solid.

Step 4: 2-benzylpyrazolo[1,5-a]pyrimidine-6-carbohydrazide

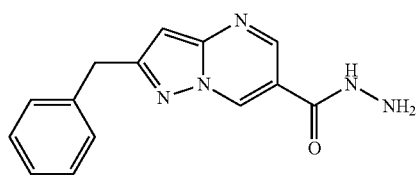 [SMILES: NNC(=O)c1cnc2cc(Cc3ccccc3)nn2c1]

A solution of tert-butyl N-[(2-benzylpyrazolo[1,5-a]pyrimidine-6-carbonyl)amino]carbamate (150 mg, 0.48 mmol) in hydrochloric acid (4 M in methanol, 5 mL) was stirred at 20° C. for 2 hours and concentrated to dryness under reduced pressure. The residue was diluted with ethyl acetate (50 mL) and added sodium bicarbonate (200 mg). The resulting mixture was stirred for 30 minutes and filtered. The filtrate was concentrated to dryness under reduced pressure. The residue was purified by RP-TLC (dichloromethane:methanol=10:1) to afford 2-benzylpyrazolo[1,5-a]pyrimidine-6-carbohydrazide (35 mg, 32%) as a white solid.

Step 5: 2-benzyl-N'-(2,2-difluoroacetyl)pyrazolo[1,5-a]pyrimidine-6-carbohydrazide

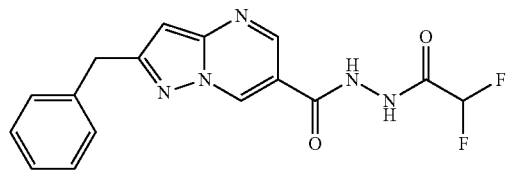 [SMILES: O=C(NNC(=O)C(F)F)c1cnc2cc(Cc3ccccc3)nn2c1]

To a solution of 2-benzylpyrazolo[1,5-a]pyrimidine-6-carbohydrazide (35 mg, 0.13 mmol) in tetrahydrofuran (5 mL) was added N-ethyl-N-isopropylpropan-2-amine (17 mg, 0.13 mmol) and (2,2-difluoroacetyl) 2,2-difluoroacetate (27 mg, 0.16 mmol). After stirred at 20° C. for 1 hour, the reaction mixture was concentrated to dryness under reduced pressure. The residue was purified by RP-TLC (petroleum ether:ethyl acetate=1:1) to afford 2-benzyl-N'-(2,2-difluoroacetyl)pyrazolo[1,5-a]pyrimidine-6-carbohydrazide (35 mg, 77%) as a white solid.

Step 6: 2-(2-benzylpyrazolo[1,5-a]pyrimid n-6-yl)-5-(difluoromethyl)-1,3,4-oxadiazole (Compound A-2)

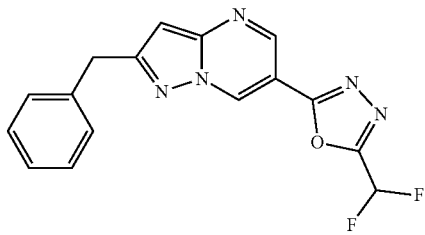 [SMILES: FC(F)c1nnc(-c2cnc3cc(Cc4ccccc4)nn3c2)o1]

To a solution of 2-benzyl-N'-(2,2-difluoroacetyl)pyrazolo[1,5-a]pyrimidine-6-carbohydrazide (35 mg, 0.10 mmol) in tetrahydrofuran (2 mL) was added Burgess reagent (109 mg, 0.46 mmol). The mixture was stirred at 90° C. for 3 hours in a microwave reactor under nitrogen atmosphere. The mixture was filtered and the filtrate was concentrated to dryness under reduced pressure. The residue was purified by RP-HPLC (30-60% acetonitrile in water and 0.225% formic acid) to afford 2-(2-benzylpyrazolo[1,5-a]pyrimidin-6-yl)-5-(difluoromethyl)-1,3,4-oxadiazole (2.7 mg, 8%) as a white solid.

Biochemical Assay The compounds disclosed herein were tested for potency against HDAC6 and selectivity against HDAC1 in a biochemical assay. A biochemical assay was adopted using a luminescent HDAC-Glo I/II assay (Promega) and measured the relative activity of HDAC6 and HDAC1 recombinant proteins. Compounds were first incubated in the presence of HDAC6 or HDAC1 separately, followed by addition of the luminescent substrate. The data was acquired using a plate reader and the biochemical $IC_{50}$ were calculated from the data accordingly. Data is tabulated in Table 3 and Table 4. From these studies, it was determined that the compounds of the present disclosure are selective inhibitors of HDAC6 over HDAC1, providing selectivity ratios from about 5 to about 30,0000.

TABLE 3

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-1 Example 2 | 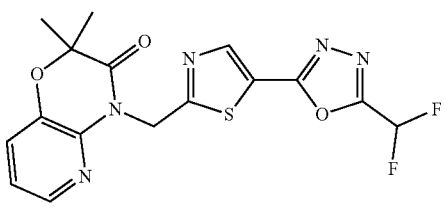 [SMILES: CC1(C)Oc2cccnc2N(Cc2ncc(-c3nnc(C(F)F)o3)s2)C1=O]<br>4-((5-(5-(difluoromethyl)-1,3,4-oxadiazol-2-yl)thiazol-2-yl)methyl)-2,2-dimethyl-2H-pyrido[3,2-b][1,4]oxazin-3(4H)-one | $^1$H NMR (400 MHz, CDCl$_3$) δ 8.39 (s, 1 H), 8.01-8.05 (m, 1 H), 7.29 (dd, J = 8.1, 1.5 Hz, 1 H),7.01 (dd, J = 8.1 1.5 Hz, 1H), 6.89 (t, J = 51.6 Hz, 1 H), 5.70 (s, 2 H)<br>LCMS: RT = 5.00 min, m/z = 394.0 | 0.107 |
| I-2 Example 4 | 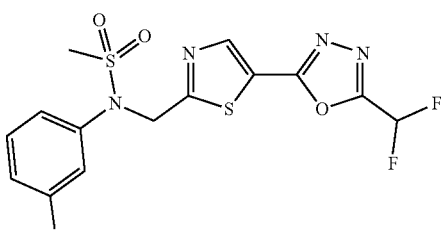<br>N-(3-chlorophenyl)-N-((5-(5-(difluoromethyl)-1,3,4-oxadiazol-2-yl)thiazol-2-yl)methyl)methanesulfonamide | $^1$H NMR (400 MHz, CDCl$_3$) δ 8.39 (s, 1 H), 7.48 (s, 1 H), 7.32-7.40 (m, 3 H), 6.91 (t, J = 51.6 Hz, 1 H), 5.25 (s, 2 H) 3.07 (s, 3 H)<br>LCMS: RT = 4.83 min, m/z = 421.0 | 0.021 |
| I-3 Example 4 | 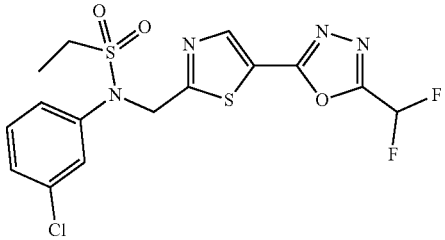 [SMILES: CCS(=O)(=O)N(Cc1ncc(-c2nnc(C(F)F)o2)s1)c1cccc(Cl)c1]<br>N-(3-chlorophenyl-N-((5-(5-(difluoromethyl)-1,3,4-oxadiazol-2-yl)thiazol-2-yl)methyl)ethanesulfonamide | $^1$H NMR (400 MHz, CDCl$_3$) δ 8.37 (s, 1 H), 7.48 (s, 1 H), 7.25-7.40 (m, 3 H), 6.19 (t, J = 51.6 Hz, 1 H), 5.28 (s, 2 H), 3.18 (q, J = 7.6 Hz, 2 H), 1.44 (t, J = 7.2 Hz, 3 H)<br>LCMS: RT = 4.90 min, m/z = 435.0 | 0.0044 |
| I-4 Example 4 | 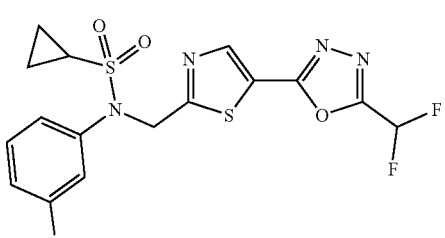<br>N-(3-chlorophenyl)-N-((5-(5-(difluoromethyl)-1,3,4-oxadiazol-2-yl)thiazol-2-yl)methyl)cyclopropanesulfonamide | $^1$H NMR (400 MHz, DMSO-d$_6$) δ 8.53 (s, 1 H), 7.40-7.70 (m, 5 H), 5.43 (s, 2 H), 2.95-3.00 (m, 1 H), 1.00-1.05 (m, 2 H), 0.90-0.95 (m, 2 H)<br>LCMS: RT = 5.10 min, m/z = 447.0 | 0.0042 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-5 Example 4 | 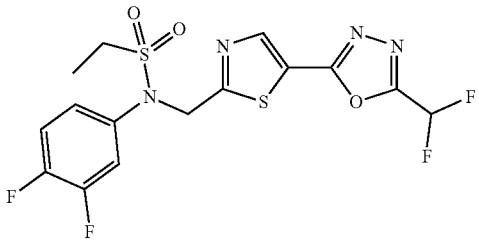 [SMILES: CCS(=O)(=O)N(Cc1ncc(-c2nnc(C(F)F)o2)s1)c1ccc(F)c(F)c1]<br>N-((5-(5-(difluoromethyl)-1,3,4-oxadiazol-2-yl)thiazol-2-yl)methyl)-N-(3,4-difluorophenyl)ethanesulfonamide | ¹H NMR (400 MHz, DMSO-d$_6$) δ 8.38 (s, 1 H), 7.30-7.40 (m, 1 H), 7.15-7.25 (m, 2 H), 6.91 (t, J = 51.2 Hz, 1 H), 5.24 (s, 2 H), 3.17 (q, J = 7.6 Hz, 2 H), 1.44 (t, J = 5.7 Hz, 3 H)<br>LCMS: RT = 4.92 min, m/z = 437.0 | 0.016 |
| I-6 Example 4 | 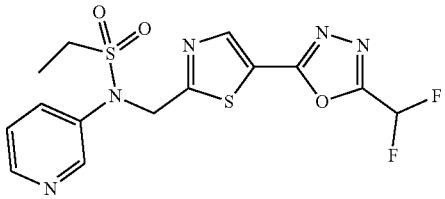 [SMILES: CCS(=O)(=O)N(Cc1ncc(-c2nnc(C(F)F)o2)s1)c1cccnc1]<br>N-((5-(5-(difluoromethyl)-1,3,4-oxadiazol-2-yl)thiazol-2-yl)methyl)-N-(pyridin-3-yl)ethanesulfonamide | ¹H NMR (400 MHz, CDCl$_3$) δ 8.71 (br s, 1 H) 8.58 (br s, 1 H), 8.38 (s, 1 H) 7.80-7.85 (m, 1 H), 7.31-7.35 (m, 1 H), 6.91 (t, J = 51.6 Hz, 1 H), 5.30 (s, 2 H), 3.21 (q, J = 7.2 Hz, 2 H), 1.46 (t, J = 7.6 Hz, 1 H)<br>LCMS: RT = 3.39 min, m/z = 402.0 | 0.029 |
| I-7 Example 5 | 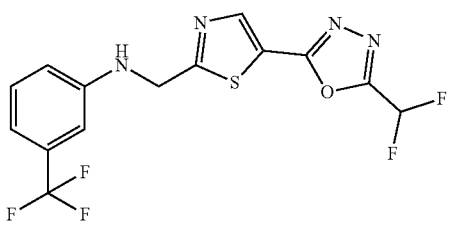 [SMILES: FC(F)c1nnc(-c2cnc(CNc3cccc(C(F)(F)F)c3)s2)o1]<br>N-((5-(5-(difluoromethyl-1,3,4-oxadiazol-2-yl)thiazol-2-yl)methyl)-3-(trifluoromethyl)aniline | ¹H NMR (400 MHz, CDCl$_3$) δ 8.58 (s, 1 H) 7.52 (t, J = 51.2 Hz, 1 H) 7.22-7.35 (m, 2 H) 6.89-6.87 (m, 3 H) 4.80 (d, J = 6.1 Hz, 2 H)<br>LCMS: RT 5.20 min, m/z = 377.0 | 0.222 |
| I-8 Example 6 | 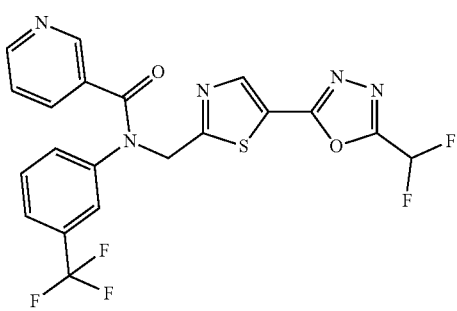 [SMILES: O=C(c1cccnc1)N(Cc1ncc(-c2nnc(C(F)F)o2)s1)c1cccc(C(F)(F)F)c1]<br>N-((5-(5-(difluoromethyl-1,3,4-oxadiazol-2-yl)thiazol-2-yl)methyl)-N-(3-(trifluoromethyl)phenyl)nicotinamide | ¹H NMR (400 MHz, CDCl$_3$) δ 8.50-8.60 (m, 1 H) 8.41 (s, 1 H) 7.71 (d, J = 7.8 Hz, 1 H), 7.50 (d, J = 7.8 Hz, 1 H), 7.35-7.45 (m, 2 H), 7.25-7.30 (m, 1 H) 7.20-7.25 (m, 1 H) 6.91 (t, J = 51.6 Hz, 1 H) 5.46 (s, 2 H)<br>LCMS: RT = 4.22 min, m/z = 482.0 | 0.088 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-9 Example 4 | N-((5-(5-(difluoromethyl)-1,3,4-oxadiazol-2-yl)thiazol-2-yl)methyl)-N-phenylmethanesulfonamide | ¹H NMR (400 MHz, CDCl$_3$) δ = 8.37 (s, 1 H), 7.33-7.49 (m, 5 H), 6.90 (t, 1 H, J = 51.6 Hz) 5.27 (s, 2 H), 3.05 (s, 3 H) ppm<br>LCMS: RT = 4.42 min, m/z = 387.0 | 0.051 |
| I-10 Example 4 | N-((5-(5-(difluoromethyl)-1,3,4-oxadiazol-2-yl)thiazol-2-yl)methyl)-N-phenylethanesulfonamide | ¹H NMR (400 MHz, CDCl$_3$) δ 8.35 (s, 1 H), 7.29-7.53 (m, 5 H), 6.90 (t, 1 H, J = 51.5 Hz), 5.30 (s, 2 H), 3.17 (q, J = 7.34 Hz, 2 H), 1.45 (t, J = 7.46 Hz, 4 H) ppm<br>LCMS: RT = 4.65 min, m/z = 401.0 | 0.026 |
| I-12 Example 4 | N-(3-chlorophenyl-N-((5-(5-(trifluoromethyl)-1,2,4-oxadiazol-3-yl)thiazol-2-yl)methyl)cyclopropanesulfonamide | ¹H NMR (400 MHz, chloroform-d) δ ppm 8.39 (s, 1 H) 7.51 (s, 1 H) 7.41 (br s, 1 H) 7.32 (br d, J = 3.91 Hz, 2 H) 5.27 (s, 2 H) 2.48-2.59 (m, 1H) 1.10-1.17 (m, 2 H) 0.99-1.09 (m, 2 H)<br>LCMS: RT = 5.84 min, m/z = 465 | 0.869 |
| I-13 Example 4 | N-(3-chloro-4-fluorophenyl)-N-((5-(5-(difluoromethyl)-1,3,4-oxadiazol-2-yl)thiazol-2-yl)methylmethanesulfonamide | ¹H NMR (400 MHz, CDCl$_3$) δ 8.40 (s, 1 H) 7.56 (dd, J = 6.36, 2.69 Hz, 1 H) 7.32-7.41 (m, 1 H) 7.18 (t, J = 8.56 Hz, 1 H) 6.76-7.08 (m, 1 H) 5.22 (s, 2 H) 3.07 (s, 3 H)<br>LCMS: RT = 4.93 min, m/z = 438.9 | 0.021 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-14 Example 4 | N-(3-chloro-4-fluorophenyl)-N-((5-(5-(difluoromethyl)-1,3,4-oxadiazol-2-yl)thiazol-2-yl)methyl)ethanesulfonamide | ¹H NMR (400 MHz, CDCl₃) δ 8.38 (s, 1 H) 7.54 (dd, 1 = 6.24, 2.32 Hz, 1 H) 7.33-7.40 (m, 1 H) 7.16 (t, J 8.68 Hz, 1 H) 6.76-7.06 (m, 1 H) 5.23 (s, 2 H) 3.18 (q, J = 7.34 Hz, 2 H) 1.45 (t, J = 7.34 Hz, 3 H) LCMS: RT = 5.11 min m/z = 453 | 0.014 |
| I-15 Example 4 | N-((5-(5-(difluoromethyl)-1,3,4-oxadiazol-2-yl)thazol-2-yl)methyl)-N-(1-methyl-1H-indazol-6-yl)ethanesulfonamide | ¹H NMR (400 MHz, CDCl₃) δ 8.36 (s, 1 H) 7.98 (d, J = 0.98 Hz, 1 H) 7.75 (d, J = 8.56 Hz, 1 H) 7.60 (s, 1 H) 7.18 (d, J = 8.31 Hz, 1H) 6.75-7.05 (m, 1 H) 5.39 (s, 2 H) 4.09 (s, 3 H) 3.19 (q, J = 7.17 Hz, 2 H) 1.46 (t, J = 7.46 Hz, 3 H) LCMS: RT = 4.43 min, m/z = 455.0. | 0.014 |
| I-16 Example 4 | [(3-chlorophenyl)({5-[5-(difluoromethyl)-1,3,4-oxadiazol-2-yl]-1,3-thiazol-2-yl}methyl)sulfamoyl]dimethylamine | ¹H NMR (400 MHz, CDCl₃) δ 8.36 (s, 1 H) 7.49 (s, 1 H) 7.28-7.42 (m, 3 H) 6.76-6.06 (m, 1 H) 5.17 (s, 2 H) 2.82 (s, 6 H) LCMS: RT = 5.18 min, m/z = 450.0 | 0.012 |
| I-17 Example 4 | N-cyclopropyl-N-((5-(5-(difluoromethyl)-1,3,4-oxadiazol-2-yl)thiazol-2-yl)methyl)ethanesulfonamide | ¹H NMR (400 MHz, chloroform-d) δ ppm 8.42 (s, 1 H) 6.74-7.07 (m, 1 H) 4.83 (s, 2 H) 3.21 (q, J = 7.50 Hz, 2 H) 2.70 (br s, 1 H) 1.41 (t, J = 7.46 Hz, 3 H) 0.83-0.95 (m, 4 H) LCMS: RT = 4.34 min, m/z = 365.0 | 1.23 |

TABLE 3-continued

Characterization Data and HDAC6 Activity for Compounds of Formula (I).

| Cmpd ID/Prep | Structure/Name | $^{1}$H NMR MS (m/z) (RT) | HDAC6 IC$_{50}$ (μM) |
|---|---|---|---|
| I-18 Example 7 | 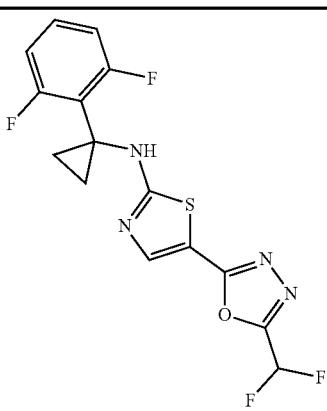<br>5-(5-(difluoromethyl)-1,3,4-oxadiazol-2-yl)-N-(1-(2,6-difluorophenyl)cyclopropyl)thiazol-2-amine | $^{1}$H NMR (400 MHz, DMSO-d$_6$) δ ppm 9.62 (br s, 1 H) 7.95 (br s, 1 H) 7.29-7.67 (overlapping m, 2 H) 7.02-7.18 (m, 2 H) 1.35 (d, J = 26.80 Hz, 4 H) LCMS: RT = 4.87 min, m/z 371.1 | 1.95 |
| I-19 Example 7 | 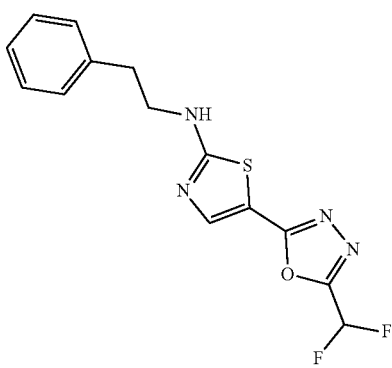 [SMILES: FC(F)c1nnc(-c2cnc(NCCc3ccccc3)s2)o1]<br>5-(5-(difluoromethyl)-1,3,4-oxadiazol-2-yl)-N-phenethylthiazol-2-amine | $^{1}$H NMR (400 MHz, chloroform-d) δ ppm 7.86 (s, 1 H) 7.16-7.46 (m, 5 H) 6.68-7.03 (m, 1H) 5.75 (brs, 1 H) 3.64 (br d, .7 = 6.11 Hz, 2 H) 3.02 (br t, J = 6.85 Hz, 2 H) LCMS: RT = 4.73 min, m/z = 323.0. | 13.6 |
| I-20 Example 4 | 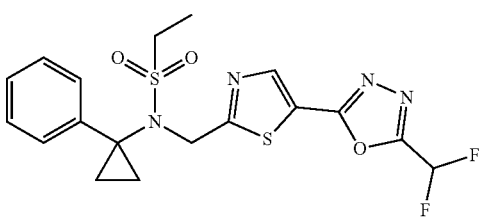 [SMILES: CCS(=O)(=O)N(Cc1ncc(-c2nnc(C(F)F)o2)s1)C1(c2ccccc2)CC1]<br>N-((5-(5-(difluoromethyl)-1,3,4-oxadiazol-2-yl)thiazol-2-yl)methyl)-N-(1-phenylcyclopropyl)ethanesulfonamide | $^{1}$H NMR (400 MHz, CDCl$_3$-d$_3$) δ 8.78 (s, 1 H), 8.40 (s, 1 H), 7.50 (d, J = 7.34 Hz, 2 H), 7.26-7.38 (m, 4 H), 7.04 (s, 0.25 H), 6.91 (s, 0.5 H), 6.78 (s, 0.25 H), 4.94 (s, 2 H), 2.81 (q, J = 7.58 Hz, 2 H), 1.47 (m, 2H), 1.31-1.22 (m, 5 H). LCMS: RT = 6.12, m/z = 441.1 | 4.14 |
| I-21 Example 6 | 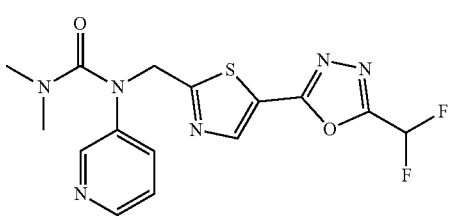 [SMILES: CN(C)C(=O)N(Cc1ncc(-c2nnc(C(F)F)o2)s1)c1cccnc1]<br>1-((5-(5-(difluoromethyl)-1,3,4-oxadiazol-2-yl)thiazol-2-yl)methyl)-3,3-dimethyl-1-(pyridin-3-yl)urea | $^{1}$H NMR (400 MHz, METHANOL-d4) δ ppm 9.55 (s, 1 H), 8.78 (br d, J = 5.62 Hz, 1 H) 8.52-8.59 (m, 2 H) 8.06 (br d, J = 7.83 Hz, 1 H) 7.26 (t, J = 51.2 Hz, 1 H) 6.33 (s, 2 H) 3.09 (s, 6 H). LCMS RT = 2.85 min, m/z = 381.1 | 1.2 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-22 Example 4 | 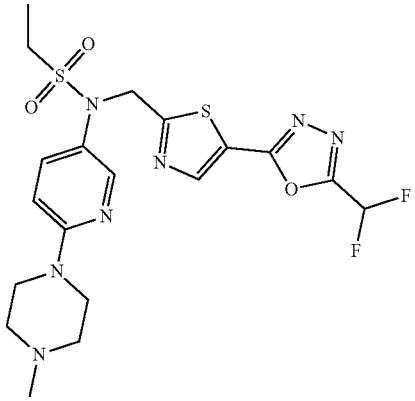 [SMILES: CCS(=O)(=O)N(Cc1ncc(-c2nnc(C(F)F)o2)s1)c1ccc(N2CCN(C)CC2)nc1]<br>N-((5-(5-(difluoromethyl)-1,3,4-oxadiazol-2-yl)thiazol-2-yl)methyl)-N-(6-(4-methylpiperazin-1-yl)pyridin-3-yl)ethanesulfonamide | 1H NMR (400 MHz, CD3OD) δ 8.40 (s, 1 H), 8.15 (s, 1 H), 7.63 (m, 1 H), 7.21 (t, J = 51.2 Hz, 1H), 6.79 (m, 1 H), 5.24 (s, 2 H), 3.56 (m, 4 H), 3.25 (q, J = 7.2 Hz, 2 H), 2.51 (m, 4 H), 2.32 (s, 3 H), 1.40 (t, J = 7.2 Hz, 3 H).<br>m/z = 500,1 | 0.143 |
| I-23 Example 4 | 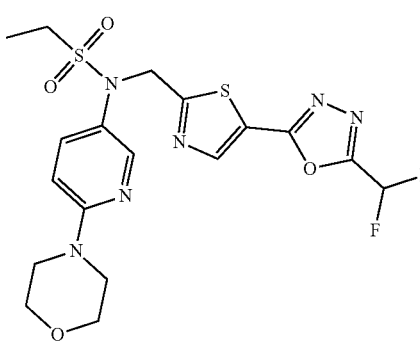<br>N-((5-(5-(difluoromethyl)-1,3,4-oxadiazol-2-yl)thiazol-2-yl)methyl)-N-(6-morpholinopyridin-3-yl)ethanesulfonamide | ¹H NMR (400 MHz, DMSO-d6) δ 8.51 (s, 1 H), 8.18 (s, 1 H), 7.69 (m, 1 H), 7.54 (t, J = 51.2 Hz, 1 H), 6.83 (m, 1 H), 5.28 (s, 1 H), 3.66 (m, 4 H), 3.44 (m, 4 H), 3.30 (q, J = 6.8 Hz, 2 H), 1.29 (t, J = 6.8 Hz, 3 H).<br>m/z = 487.1 | 0.417 |
| I-24 Example 4 | 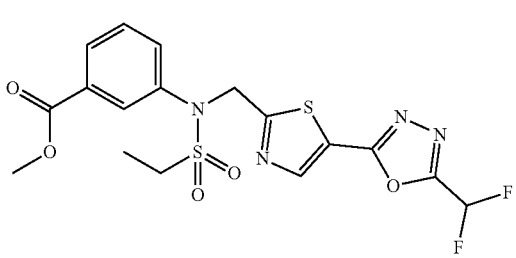 [SMILES: CCS(=O)(=O)N(Cc1ncc(-c2nnc(C(F)F)o2)s1)c1cccc(C(=O)OC)c1]<br>methyl 3-(N-((5-(5-(difluoromethyl)-1,3,4-oxadiazol-2-yl)thiazol-2-yl)methyl)ethylsulfonamido)benzoate | ¹H NMR (400 MHz, DMSO-d$_6$) δ 8.50 (s, 1 H), 8.08 (s, 1 H), 7.95-7.83 (m, 2 H), 7.67-7.39 (m, 2 H), 5.43 (s, 2 H), 3.86 (s, 3 H), 3.45-3.33 (m, 2), 1.28 (t, J = 7.21 Hz, 3 H).<br>LCMS RT = 4.73 min, m/z = 459.1 | 0.031 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-25 Example 4 | tert-butyl 4-(N-((5-(5-(difluoromethyl)-1,3,4-oxadiazol-2-yl)thiazol-2-yl)methyl)ethylsulfonamido)benzoate | ¹H NMR (400 MHz, CDCl$_3$) δ 8.36 (s, 1 H), 8.01 (m, 2 H), 7.53 (m, 2 H), 6.91 (t J = 51.6 Hz, 1H), 5.34 (s, 2 H), 3.21 (q, J = 7.2 Hz, 2 H), 1,57 (s, 9 H), 1.43 (t, J = 7.2 Hz, 3 H). m/z = 501.1 | 0.101 |
| I-26 Example 6 | methyl ((5-(5-(difluoromethyl)-1,3,4-oxadiazol-2-yl)thiazol-2-yl)methyl)(pyridin-3-yl)carbamate | ¹H NMR (400 MHz, METHANOL-d4) δ ppm 9.55 (s, 1 H) 8.85 (br d, J = 5.87 Hz, 1 H) 8.57 (s, 1 H) 8.45 (br d, J = 8.80 Hz, 1 H) 8.06-8.13 (m, 1 H) 7.26 (t, J = 51.2 Hz, 1 H) 3.86 (s, 3 H). LCMS RT = 2.97 min, m/z = 368.0 | 2.5 |
| I-27 Example 4 | N-((5-(5-(difluoromethyl)-1,3,4-oxadiazol-2-yl)thiazol-2-yl)methyl)-N-(pyrimidin-5-yl)ethanesulfonamide | ¹H NMR (400 MHz, DMSO-d$_6$) δ 9.12 (s, 1 H), 9.00 (s, 2 H), 8.53 (s, 1 H), 7.70-7.30 (m, 1 H), 5.50 (s, 2 H), 3.55-3.40 (m, 2 H), 1.31 (t, −7.34 Hz, 3 H). LCMS RT = 3.84 min, m/z = 403.0 | 0.050 |
| I-28 Example 4 | N-((5-(5-(difluoromethyl)-1,3,4-oxadiazol-2-yl)thiazol-2-yl)methyl)pyridin-3-amine | ¹H NMR (400 MHz, METHANOL-d4) δ ppm 8.58 (s, 1 H) 8.22-8.32 (m, 2 H) 7.69-7.78 (m, 2 H) 7.26 (t, J = 51.2 Hz, 1H) 6.17 (s, 2 H). LCMS RT = 1.24 min, m/z = 310.1 | 1.5 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-29 Example 4 | | $^1$H NMR (400 MHz, CDCl$_3$-d$_3$) δ 8.55 (s, 1 H), 8.47 (s, 1 H), 8.39 (s, 1 H), 7.67 (d, J = 9.05 Hz, 1 H), 7.36-7.28 (m, 2 H), 7.19 (d, J = 6.60 Hz, 2 H), 7.04-6.77 (m, 1 H) 5.22 (s, 2H), 4.25 (s, 2 H), 2.74 (s, 3 H). LCMS RT = 5.23 min, m/z = 511.1 | 0.041 |
| I-30 Example 4 | N-((5-(5-(difluoromethyl)-1,3,4-oxadiazol-2-yl)thiazol-2-yl)methyl-N-(6-fluoropyridin-3-yl)ethanesulfonamide | $^1$H NMR (400 MHz, CDCl$_3$) δ 8.39 (s, 1 H), 8.31 (s, 1 H), 7.94 (m, 1 H), 7.02 (m, 1 H), 6.91 (t, J = 51.6 Hz, 1 H), 5.25 (s, 2 H), 3.21 (q, J = 7.2 Hz, 2 H), 1.21 (t, J = 7.2 Hz, 3 H). m/z = 420.0 | 0.011 |
| I-31 Example 4 | N-((5-(5-(difluoromethyl)-1,3,4-oxadiazol-2-yl)thiazol-2-yl)methyl)-N-(pyridin-3-yl)propane-2-sulfonamide | $^1$H NMR (400 MHz, DMSO-d6) δ 8.72 (s, 1 H), 8.50 (m, 2 H), 8.02 (m, 1 H), 7.40-7.66 (m, 2 H), 5.46 (s, 2 H), 3.60 (m, 1 H), 1.34 (d, J = 6.8 Hz, 6 H). m/z = 416.1 | 0.042 |
| I-32 Example 4 | N-((5-(5-(difluoromethyl)-1,3,4-oxadiazol-2-yl)thiazol-2-yl)methyl)-N-(1-methyl-6-oxo-1,6-dihydropyridin-3-yl)ethanesulfonamide | $^1$H NMR (400 MHz, Methanol-d$_4$) δ 8.47 (s, 1 H), 7.96 (s, 1 H), 7.66 (d, 1 = 9.54, 1 H), 7.35 (s, 0.25 H), 7.22 (s, 0.5 H), 7.09 (s, 0.25 H), 6.53 (d, J = 9.54 Hz, 1 H), 5.22 (s, 2 H), 3.56 (s, 3 H), 3.35-3.30 (m, 2 H), 1.43 (t, J = 7.34 Hz, 3 H). LCMS RT = 3.53 min, m/z = 432.1 | 0.411 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-33 Example 4 | N-(3-chloro-4-fluorophenyl)-N-((5-(5-(difluoromethyl)-1,3,4-oxadiazol-2-yl)thiazol-2-yl)methyl)morpholine-4-sulfonamide | ¹H NMR (400 MHz, DMSO-d6) δ 8.52 (s, 1 H), 7.86-7.95 (m, 1 H), 7.35-7.69 (m, 3 H), 5.36 (s, 2 H), 3.58 (m, 4 H), 3.20 (m, 4H). m/z = 510.0 | 0.047 |
| I-34 Example 4 | N-(3-chlorophenyl)-N-((5-(5-(difluoromethyl)-1,3,4-oxadiazol-2-yl)thiazol-2-yl)methyl)thiomorpholine-4-sulfonamide 1,1-dioxide | ¹H NMR (400 MHz, CHLOROFORM-d) δ ppm 8.41 (s, 1 H) 7.48 (s, 1 H) 7.30-7.40 (m, 3 H) 6.91 (t, J = 52.4 Hz, 1 H) 5.15 (s, 2 H) 3.73-3.82 (m, 4H) 3.05-3.13 (m, 4H). LCMS RT = 4.83 min, m/z = 540.0 | 0.022 |
| I-35 Example 4 | N-(4-(1H-imidazol-1-yl)phenyl)-N-((5-(5-(difluoromethyl)-1,3,4-oxadiazol-2-yl)thiazol-2-yl)methyl)ethanesulfonamide | ¹H NMR (400 MHz, DMSO-d6) δ 8.51 (s, 1 H), 8.27 (s, 1 H), 7.69-7.76 (m, 5 H), 7.3 (t, J = 51.2 Hz, 1 H), 7.10 (s, 1 H), 5.41 (s, 2 H), 3.37 (q, J = 6.8 Hz, 2 H), 1.30 (t, J = 6.8 Hz, 3 H). m/z = 467.0 | 0.008 |
| I-36 Example 4 | N-(3-chlorophenyl)-N-((5-(5-(difluoromethyl)-1,3,4-oxadiazol-2-yl)thiazol-2-yl)methyl)morpholine-4-sulfonamide | ¹H NMR (400 MHz, DMSO-d6) δ 8.52 (s, 1 H), 7.73 (m, 1 H), 7.54-7.58 (m, 2 H), 7.36-7.44 (m, 2 H), 5.38 (s, 2 H), 3.59 (m, 4 H), 3.18 (m, 4 H). m/z = 492.1 | 0.005 |

TABLE 3-continued

Characterization Data and HDAC6 Activity for Compounds of Formula (I).

| Cmpd ID/Prep | Stracture/Name | $^1$H NMR MS (m/z) (RT) | HDAC6 IC$_{50}$ (μM) |
|---|---|---|---|
| I-37 Example 4 | 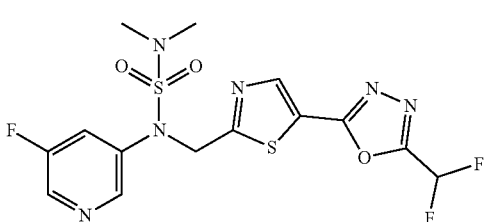 | $^1$H NMR (400 MHz, DMSO-d$_6$) δ 8.63 (s, 1 H), 8.54 (d, J = 9. Hz, 2 H), 8.10 (d, J = 10.0 Hz, 1 H), 7.65-7.39 (m, 1 H), 5.41 (s, 2H), 2.83 (s, 6 H). LCMS RT = 4.39 min, m/z = 435.1 | 0.013 |
| I-38 Example 4 | 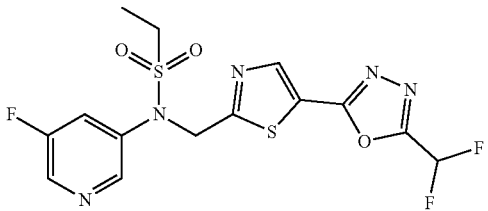 [SMILES: CCS(=O)(=O)N(Cc1ncc(-c2nnc(C(F)F)o2)s1)c1cncc(F)c1]<br>N-((5-(5-(difluoromethyl)-1,3,4-oxadiazol-2-yl)thiazol-2-yl)methyl)-N-(5-fluoropyridin-3-yl)ethanesulfonamide | $^1$H NMR (400 MHz, DMSO-d$_6$) δ 8.62-8.52 (m, H), 8.13-8.09 (m, 1 H), 7.65-7.39 (m, 1 H), 5.46 (s, 2 H), 3.55-3.45 (m, 2 H), 1.30 (t, J = 7.34 Hz, 3 H). LCMS RT = 4.32 min, m/z = 420.0 | 0.019 |
| I-39 Example 4 | 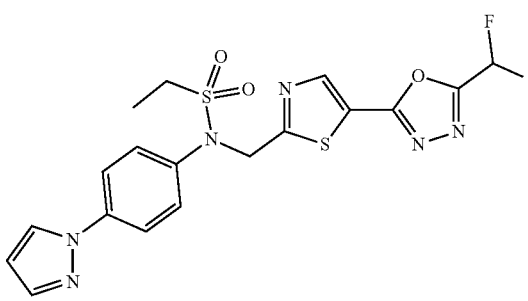<br>N-(4-(1H-pyrazol-1-yl)phenyl)-N-((5-(5-(difluoromethyl)-1,3,4-oxadiazol-2-yl)thiazol-2-yl)methyl)ethanesulfonamide | $^1$H NMR (400 MHz, CHLOROFORM-d) δ ppm 8.36 (s, 1 H) 7.90 (s, 1 H) 7.69-7.77 (m, 3 H) 7.55 (d, J = 8.31 Hz, 2 H) 6.90 (t, J = 52.0 Hz, 1 H) 6.48 (s, 1 H) 5.31 (s, 2 H) 3.19 (d, 7 = 7.34 Hz, 2 H) 1.46 (t, J = 7.46 Hz, 3 H). LCMS RT = 4.67 min, m/z = 467.0 | 0.010 |
| I-40 Example 4 | 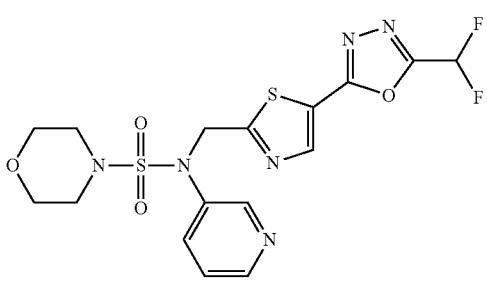 [SMILES: O=S(=O)(N1CCOCC1)N(Cc1ncc(-c2nnc(C(F)F)o2)s1)c1cccnc1]<br>N-((5-(5-(difluoromethyl)-1,3,4-oxadiazol-2-yl)thiazol-2-yl)methyl)-N-(pyridin-3-yl)morpholine-4-sulfonamide | $^1$H NMR (400 MHz, CD3OD) δ 8.57 (s, 1 H), 8.45 (s, 1 H), 8.27 (m, 1 H), 7.97 (m, 1 H), 7.73 (m, 1 H), 7.22 (t, J = 51.6 Hz, 1 H), 4.88 (s, 2 H), 3.36 (m, 4 H), 3.10 (m, 4 H) m/z = 459.1 | 4.22 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-43 Example 3 | (R)-3-(5-(5-(difluoromethyl)-1,3,4-oxadiazol-2-yl)thiazol-2-yl)-4-phenyloxazolidin-2-one | ¹H NMR (400 MHz, METHANOL-d4) δ = 8.07 (s, 1 H) 7.40 (s, 5 H) 7.19 (t, 1 H, J = 51.6 Hz) 5.84 (dd, J = 8.80, 3.67 Hz, 1 H) 5.03 (t, J = 8.80 Hz, 1 H) 4.48 (dd, J = 8.93, 4.03 Hz, 1 H) ppm LCMS: RT = 4.67 min, m/z = 365.1 | 0.085 |
| I-44 Example 3 | (S)-3-(5-(5-(difluoromethyl)-1,3,4-oxadiazol-2-yl)thiazol-2-yl)-4-phenyloxazolidin-2-one | 1H NMR (400 MHz, METHANOL-d4) δ = 8.07 (s, 1 H), 7.40 (s, 4 H), 7.33-7.38 (m, 1 H), 7.19 (t, 1 H, J = 5.6 Hz), 5.84 (dd, J = 8.56, 3.91 Hz, 1 H), 5.03 (t, J = 8.93 Hz, 1 H), 4.43-4.51 (m, 1 H) ppm LCMS: RT = 4.95 min, m/z = 365.1 | 8.97 |
| I-45 Example 5 | N-(1-(cyclopropylmethyl)-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CD3OD) δ ppm 8.55 (s, 1 H), 8.27-8.24 (m, 2 H), 7.78-7.67 (m, 2 H), 7.23 (t, J = 51.6 Hz, 1 H), 6.15 (s, 2 H), 2.90 (s, 3 H). LCMS RT = 2.431 min, m/z = 324.0 | 1.3 |
| I-46 Example 4 | N-(1-(cyclopropylmethyl)-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.40 (s, 1 H), 7.69 (s, 1 H), 7.49 (s, 1 H), 6.91 (t, J = 51.6 Hz, 1 H), 5.17 (s, 2 H), 3.93 (d, J = 7.2 Hz, 2 H), 3.18 (q, J = 7.6 Hz, 2 H), 1.42 (t, J = 7.6 Hz, 3 H), 1.31-1.22 (m, 1 H), 0.70-0.62 (m, 2 H), 0.38-0.32 (m, 2 H). LCMS RT = 2.417 min, m/z = 444.9 | 0.077 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-47 Example 4 | N-(1-cyclopropyl-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.40 (s, 1 H), 7.65 (s, 1 H), 7.46 (s, 1 H), 6.91 (t, J = 51.6 Hz, 1 H), 5.14 (s, 2 H), 3.58-3.52 (m, 1 H), 3.16 (q, J = 8.0 Hz, 2 H), 1.42 (t, J = 8.0 Hz, 3 H), 1.13-1.00 (m, 4 H). LCMS RT = 1.223 mm, m/z = 430.9 | 0.070 |
| I-48 Example 4 | N-((5-(5-(difluoromethyl)-1,3,4-oxadiazol-2-yl)thiazol-2-yl)methyl)-N-(1-(difluoromethyl)-1H-pyrazol-4-yl)ethanesulfonamide | 1H NMR (400 MHz, CDCl3) δ ppm 8.35 (s, 1 H), 7.92 (s, 1 H), 7.66 (s, 1 H), 6.96 (t, J = 60.4 Hz, 1 H), 6.84 (t, J = 45.2 Hz, 1 H), 5.11 (s, 2 H), 3.10 (q, J = 7.2 Hz, 2 H), 1.33 (t, J = 7.6 Hz, 3 H). LCMS RT = 3.543 min, m/z = 441.1 | 0.262 |
| I-49 Example 4 | N-((5-(5-(difluoromethyl)-1,3,4-oxadiazol-2-yl)thiazol-2-yl)methyl)-N-(1-(2-methoxyethyl)-1H-pyrazol-4-yl)ethanesulfonamide | 1H NMR (400 MHz, CDCl3) δ ppm 8.40 (s, 1 H), 7.65 (s, 1 H), 7.51 (s, 1 H), 6.91 (t, J = 51.6 Hz, 1 H), 5.15 (s, 2 H), 4.22 (t, J = 4.8 Hz, 2 H), 3.70 (t, J = 5.2 Hz, 2 H), 3.30 (s, 3 H), 3.17 (q, J = 7.6 Hz, 2 H), 1.41 (t, J = 7.2 Hz, 3 H). LCMS RT = 3.093 min, m/z = 448.9 | 0.134 |
| I-50 Example 4 | N-((5-(5-(difluoromethyl)-1,3,4-oxadiazol-2-yl)thiazol-2-yl)methyl)-N-(pyridin-3-yl)cyclopropanesulfonamide | 1H NMR (400 MHz, CDCl3) δ ppm 8.69 (d, J = 2.0 Hz, 1 H), 8.53-8.50 (m, 1 H), 8.30 (s, 1 H), 7.79-7.76 (m, 1 H), 7.30-7.26 (m, 1 H), 6.83 (t, J = 51.6 Hz, 1 H), 5.23 (s, 2 H), 2.53-2.46 (m, 1 H), 1.06-0.95 (m, 4 H). LCMS RT = 2.897 mm, m/z = 414.1 | 0.036 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-51 Example 4 | N-((5-(5-(difluoromethyl)-1,3,4-oxadiazol-2-yl)thiazol-2-yl)methyl)-N-(pyridin-3-yl)methanesulfonamide | 1H NMR (400 MHz, CDCl3) δ ppm 8.54 (s, 1 H), 8.50 (s, 1 H), 7.93-7.90 (m, 1 H), 7.68 (d, J = 8.0 Hz, 1 H), 7.49-7.44 (m, 1 H), 6.92 (t, J = 51.6 Hz, 1 H), 5.84 (s, 2 H), 3.00 (s, 3 H). LCMS RT = 1.096 min, m/z = 387.9 | 0.676 |
| I-52 Example 4 | N-(5-cyanopyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.96 (d, 1 = 2.8 Hz, 1 H), 8.82 (s, 1 H), 8.42 (s, 1 H), 8.18-8.17 (m, 1 H), 6.92 (t, J = 51.6 Hz, 1 H), 5.30 (s, 2 H), 3.21 (q, J = 7.6 Hz, 2 H), 1.44 (t 1 = 7.6 Hz, 3H). LCMS RT = 0.752 min, m/z = 427.1 | 0.022 |
| I-53 Example 4 | N-(6-(2-cyanopropan-2-yl)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.70 (d, J = 2.8 Hz, 1 H), 8.40 (s, 1 H), 7.86 (d, J = 8.4 Hz, 1 H), 7.63 (d, J = 8.4 Hz, 1 H), 6.91 (t, J = 51.6 Hz, 1 H), 5.29 (s, 2 H), 3.22 (q, J = 7.6 Hz, 2 H), 1.75 (s, 6 H), 1.47 (t, J = 7.2 Hz, 3 H). LCMS RT = 0.828 min, m/z = 469.2 | 0.317 |
| I-54 Example 4 | N-((5-(5-(difluoromethyl)-1,3,4-oxadiazol-2-yl)thiazol-2-yl)methyl)-N-(5-fluorobenzo[d]oxazol-2-yl)ethanesulfonamide | 1H NMR (400 MHz, CDCl$_3$) δ ppm 8.45 (s, 1 H), 7.40-7.38 (m, 1 H), 7.10-6.91 (m, 3 H), 5.40 (s, 2 H), 3.29 (q, J = 7.2 Hz, 2 H), 1.52 (t, J = 7.2 Hz, 3 H). LCMS RT = 3.800 min, m/z = 460.0 | 0.104 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (μM) |
|---|---|---|---|
| I-55 Example 4 | N-((5-(5-(difluoromethyl)-1,3,4-oxadiazol-2-yl)thiazol-2-yl)methyl)-N-(6-fluorobenzo[d]oxazol-2-yl)ethanesulfonamide | 1H NMR (400 MHz, CDCl3) δ ppm 8.44 (s, 1 H), 7.29-7.21 (m, 2 H), 7.10-7.04 (m, 1 H), 6.91 (t, J = 51.6 Hz, 1 H), 5.42 (s, 2 H), 3.29 (q, J = 7.2 Hz, 2 H), 1.52 (t, J = 7.2 Hz, 3 H). LCMS RT = 0.863 min, m/z = 459.7 | 0.124 |
| I-56 Example 4 | N-(6-(difluoromethoxy)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.39 (s, 1 H), 8.28 (d, J = 2.8 Hz, 1 H), 7.85 (d, J = 8.8 Hz, 1 H), 7.41 (t, J = 51.6 Hz, 1 H), 7.06-6.76 (m, 2 H), 5.24 (s, 2 H), 3.20 (q, J = 7.2 Hz, 2 H), 1.47 (t, J = 7.6 Hz, 3 H). LCMS RT = 0.886 mm, m/z = 468.1 | 0.050 |
| I-57 Example 4 | N-((5-(5-(difluoromethyl)-1,3,4-oxadiazol-2-yl)thiazol-2-yl)methyl)-N-(1,5-dimethyl-1H-pyrazol-3-yl)ethanesulfonamide | 1H NMR (400 MHz, CDCl$_3$) δ ppm 8.40 (s, 1 H), 6.91 (t, J = 51.6 Hz, 1 H), 6.13 (s, 1 H), 5.37 (s, 2 H), 3.70 (s, 3 H), 3.27 (q, J = 7.6 Hz, 2 H), 2.24 (s, 3 H), 1.42 (t, J = 7.2 Hz, 3 H). LCMS RT = 3.486 min, m/z = 418.9 | 0.117 |
| I-58 Example 4 | N-(5-cyclopropylpyridin-3-yl)-N-((5-5-(difluoromethyl)-1,3,4-oxadiazol-2-yl)thiazol-2-yl)methyl)ethanesulfonamide | ¹H NMR (400 MHz, CDCl3) δ ppm 8.45 (s, 1 H), 8.41 (s, 1 H), 8.35 (s, 1 H), 7.46 (s, 1 H), 6.91 (t, J = 51.6 Hz, 1 H), 5.27 (s, 2 H), 3.19 (q, J = 8.0 Hz, 2 H), 1.92-1.89 (m, 1 H), 1.45 (t, J = 7.2 Hz, 3 H), 1.11-1.05 (m, 2 H), 0.76-0.74 (m, 2 H). LCMS RT = 0.992 min, m/z = 442.3 | 0.025 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-59 Example 4 | N-((5-5-(difluoromethyl)-1,3,4-oxadiazol-2-yl)thiazol-2-yl)methyl)-N-(5-(trifluoromethyl)pyridin-3-yl)ethanesulfonamide | $^1$H NMR (400 MHz, CDCl3) δ ppm 8.93 (d, J = 2.0 Hz, 1 H), 8.83 (s, 1 H), 8.41 (s, 1 H), 8.10 (s, 1 H), 6.91 (t, J = 51.6 Hz, 1 H), 5.31 (s, 2 H), 3.22 (q, J = 7.6 Hz, 2 H), 1.45 (t, J = 7.6 Hz, 3 H). LCMS RT = 1.190 mm, m/z = 469.8 | 0.030 |
| I-60 Example 4 | N-((5-(5-(difluoromethyl)-1,3,4-oxadiazol-2-yl)thiazol-2-yl)methyl)-N-(5-(difluoromethyl)pyridin-3-yl)ethanesalfonamide | 1H NMR (400 MHz, CDCl3) δ ppm 8.85 (s, 1 H), 8.73 (s, 1 H), 8.40 (s, 1 H), 7.99 (s, 1 H), 6.91 (t, J = 52.0 Hz, 1 H), 6.74 (t, J = 56.0 Hz, 1 H), 5.31 (s, 2 H), 3.22 (q, J = 4.0 Hz, 2 H), 1.46 (t, J = 8.0 Hz, 3 H). LCMS RT = 2.508 mm, m/z = 452.1 | 0.070 |
| I-61 Example 4 | N-((5-(5-(difluoromethyl-1,3,4-oxadiazol-2-yl)thiazol-2-yl)methyl)-N-(6-isopropylpyridin-3-yl)ethanesulfonamide | 1H NMR (400 MHz, CDCl3) δ ppm 8.59 (d, J = 2.4 Hz, 1 H), 8.38 (s, 1 H), 7.75-7.71 (m, 1 H), 7.22 (d, J = 8.0 Hz, 1H), 6.91 (t, J = 51.6 Hz, 1 H), 5.27 (s, 2 H), 3.20 (q, J = 7.2 Hz, 2 H), 3.11-3.03 (m, 1 H), 1.47 (t, J = 7.2 Hz, 3 H), 1.29 (d, J = 7.2 Hz, 6 H). LCMS RT = 0.757 mm, m/z = 444.2 | 0.073 |
| I-62 Example 4 | N-((5-(5-(difluoromethyl)-1,3,4-oxadiazol-2-yl)thiazol-2-yl)methyl)-N-(6-(difluoromethyl)pyridin-2-yl)ethanesulfonamide | 1H NMR (400 MHz, CDCl3) δ ppm 8.30 (s, 1 H), 7.85-7.69 (m, 2 H), 7.39 (d, J = 7.6 Hz, 1 H), 6.81 (t, J = 51.6 Hz, 1 H), 6.47 (t, J = 79.2 Hz, 1 H), 5.54 (s, 2 H), 3.29 (q, J = 7.6 Hz, 2 H), 1.33 (t, J = 7.6 Hz, 3 H). LCMS RT = 2.238 min, m/z = 452.1 | 0.0206 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-63 Example 4 | 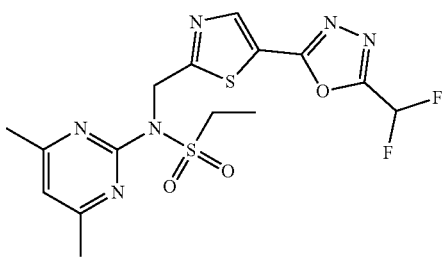 [SMILES: CCS(=O)(=O)N(Cc1ncc(-c2nnc(C(F)F)o2)s1)c1nc(C)cc(C)n1]<br>N-((5-(5-(difluoromethyl)-1,3,4-oxadiazol-2-yl)thiazol-2-yl)methyl)-N-(4,6-dimethylpyrimidin-2-yl)ethanesulfonamide | 1H NMR (400 MHz, CDCl3) δ ppm 8.40 (s, 1 H), 6.89 (t, J = 51.6 Hz, 1 H), 6.77 (s, 1 H), 5.65 (s, 2 H), 3.95 (q, J = 7.6 Hz, 2 H), 2.44 (s, 6 H), 1.39 (t, 1 = 7.6 Hz, 3 H). LCMS RT = 3.758 min, m/z = 431.2 | 0.018 |
| I-64 Example 4 | 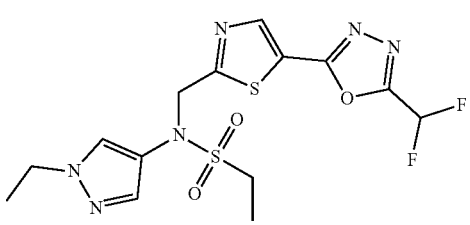 [SMILES: CCn1cc(N(Cc2ncc(-c3nnc(C(F)F)o3)s2)S(=O)(=O)CC)cn1]<br>N-((5-(5-(difluoromethyl-1,3,4-oxadiazol-2-yl)thiazol-2-yl)methyl)-N-(1-ethyl-1H-pyrazol-4-yl)ethanesulfonamide | 1H NMR (400 MHz, CDCl3) δ ppm 8.40 (s, 1 H), 7.60 (s, 1 H), 7.49 (s, 1 H), 6.91 (t, J = 51.6 Hz, 1 H), 5.16 (s, 2 H), 4.12 (q, J = 7.2 Hz, 2 H), 3.17 (q, J = 7.6 Hz, 2 H), 1.50-1.40 (m, 6 H). LCMS RT = 1.418 min, m/z = 418.9 | 0.065 |
| I-65 Example 4 | 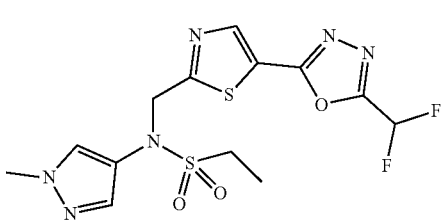 [SMILES: CCS(=O)(=O)N(Cc1ncc(-c2nnc(C(F)F)o2)s1)c1cnn(C)c1]<br>N-((5-(5-(difluoromethyl)-1,3,4-oxadiazol-2-yl)thiazol-2-yl)methyl)-N-(1-methyl-1H-pyrazol-4-yl)ethanesulfonamide | 1H NMR (400 MHz, CD3OD) δ ppm 8.33 (s, 1 H), 7.71 (s, 1 H), 7.48 (s, 1 H), 7.11 (t, J = 51.6 Hz, 1 H), 5.10 (s, 2 H), 3.74 (s, 3 H), 3.14 (q, J = 7.2 Hz, 2 H), 1.28 (t, J = 7.2 Hz, 3 H). LCMS RT = 2.950 min, m/z = 404.9 | 0.022 |
| I-66 Example 4 | 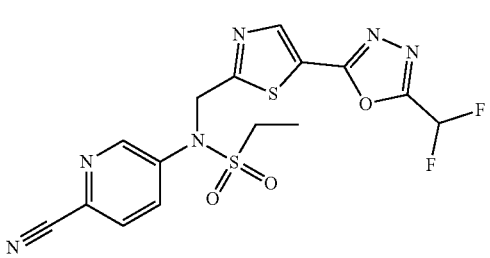 [SMILES: CCS(=O)(=O)N(Cc1ncc(-c2nnc(C(F)F)o2)s1)c1ccc(C#N)nc1]<br>N-(6-cyanopyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.87 (s, 1 H), 8.40 (s, 1 H), 8.04 (d, J = 8.4 Hz, 1 H), 7.74 (d, J = 8.4 Hz, 1 H), 6.91 (t, J = 51.6 Hz, 1 H), 5.35 (s, 2 H), 3.23 (q, J = 7.2 Hz, 2 H), 1.43 (t, J = 7.2 Hz, 3 H). LCMS RT = 1.030 mm, m/z = 426.8 | 0.029 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (µM) |
|---|---|---|---|
| I-67 Example 4 | N-(5-cyanopyridin-2-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.66 (s, 1 H), 8.39 (s, 1 H), 7.96-7.78 (m, 2 H), 6.90 (t, J = 51.6 Hz, 1 H), 5.63 (s, 2 H), 3.48 (q, J = 7.6 Hz, 2 H), 1.43 (t, J = 7.6 Hz, 3 H). LCMS RT = 2.180 min, m/z = 427.1 | 0.037 |
| I-68 Example 4 | N-((5-(5-(difluoromethyl-1,3,4-oxadiazol-2-yl)thiazol-2-yl)methyl)-N-(6-methylpyrazin-2-yl)ethanesulfonamide | 1H NMR (400 MHz, CDCl3) δ ppm 8.80 (s, 1 H), 8.39 (s, 1 H), 8.29 (s, 1 H), 6.90 (t, J = 51.6 Hz, 1 H), 5.58 (s, 2 H), 3.38 (q, J = 7.2 Hz, 2 H), 2.55 (s, 3 H), 1.42 (t, J = 7.6 Hz, 3 H). LCMS RT = 1.657 min, m/z = 417.1 | 0.100 |
| I-69 Example 4 | N-((5-(5-(difluoromethyl)-1,3,4-oxadiazol-2-yl)thiazol-2-yl)methyl)-N-(4,6-dimethylpyridin-2-yl)ethanesulfonamide | 1H NMR (400 MHz, CDCl3) δ ppm 8.38 (s, 1 H), 7.27 (s, 1 H), 7.02-6.72 (m, 2 H), 5.58 (s, 2 H), 3.24 (q, J = 7.6 Hz, 2 H), 2.47 (s, 3 H), 2.33 (s, 3 H), 1.36 (t, J = 7.4 Hz, 3 H). LCMS RT = 3.082 min, m/z = 429.9 | 0.071 |
| I-70 Example 4 | N-((5-(5-(difluoromethyl)-1,3,4-oxadiazol-2-yl)thiazol-2-yl)methyl)-N-(6-(trifluoromethyl)pyridin-2-yl)ethanesulfonamide | 1H NMR (400 MHz, CD3OD) δ ppm 8.42 (s, 1 H), 8.07-8.02 (m, 1 H), 7.92-7.89 (m, 1 H), 7.61-7.58 (m, 1 H), 7.19 (t, J = 51.6 Hz, 1 H), 5.62 (s, 2 H), 3.57 (q, J = 7.2 Hz, 2 H), 1.38 (t, J = 7.2 Hz, 3 H). LCMS RT = 2.965 min, m/z = 470.1 | 0.0281 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (μM) |
|---|---|---|---|
| I-71 Example 8 | 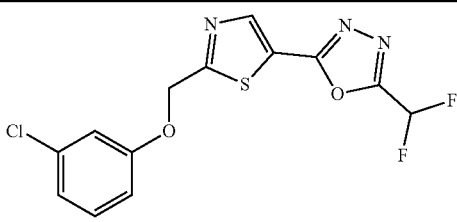<br>2-(2-((3-chlorophenoxy)methyl)thiazol-5-yl)-5-(difluoromethyl)-1,3,4-oxadiazole | 1H NMR (400 MHz, CDCl3) δ ppm 8.49 (s, 1 H), 7.29-7.24 (m, 1 H), 7.06-7.04 (m, 2 H), 6.94-6.78 (m, 2 H), 5.43 (s, 2 H).<br>LCMS RT = 1.840 min, m/z = 344.1 | 0.251 |
| I-72 Example 5 | 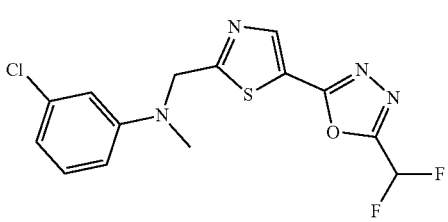 [SMILES: CN(Cc1ncc(-c2nnc(C(F)F)o2)s1)c1cccc(Cl)c1]<br>3-chlor-N-((5-(5-(difluoromethyl)-1,3,4-oxadiazol-2-yl)thiazol-2-yl)methyl)-N-methylaniline | 1H NMR (400 MHz, CDCl3) δ ppm 8.55 (s, 1 H), 7.43-6.70 (m, 5 H), 4.93 (s, 2 H), 3.26 (s, 3 H).<br>LCMS RT = 3.547 min, m/z = 356.8 | 0.034 |
| I-73 Example 5 | 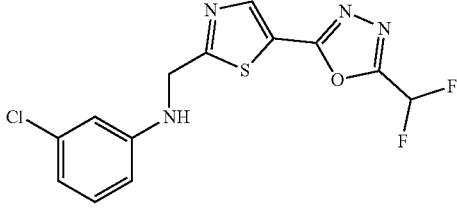<br>3-chloro-N-((5-(5-(difluoromethyl)-1,3,4-oxadiazol-2-yl)thiazol-2-yl)methyl)aniline | 1H NMR (400 MHz, CDCl3) δ ppm 8.37 (s, 1 H), 7.06-6.44 (m, 5 H), 4.66 (s, 3 H).<br>LCMS RT = 2.368 min, m/z = 343.1 | 0.046 |
| I-74 Example 4 | 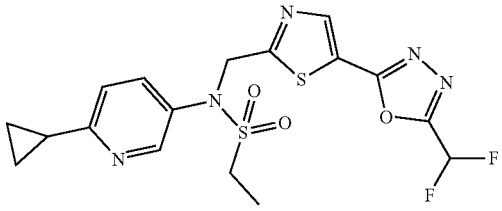 [SMILES: CCS(=O)(=O)N(Cc1ncc(-c2nnc(C(F)F)o2)s1)c1ccc(C2CC2)nc1]<br>N-(6-cyclopropylpyridin-3-yl)-N-((5-(5-(difluoromethyl)-1,3,4-oxadiazol-2-yl)thiazol-2-yl)methyl)ethanesulfonamide | 1H NMR (400 MHz, CD3OD) δ ppm 8.46 (d, J = 2.4 Hz, 1 H), 8.41 (s, 1 H), 7.80 (dd, J = 8.4, 2.8 Hz, 1 H), 7.33-7.07 (m, 2 H), 5.33 (s, 2 H), 3.31-3.27 (m, 2 H), 2.11-2.08 (m, 1 H), 1.40 (t, J = 7.2 Hz, 3 H), 1.04-0.94 (m, 4 H).<br>LCMS RT = 5.273 min, m/z = 441.9 | 0.016 |
| I-75 Example 4 | 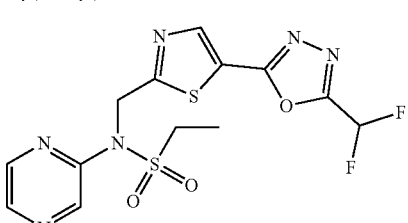<br>N-((5-(5-(difluoromethyl)-1,3,4-oxadiazol-2-yl)thiazol-2-yl)methyl)-N-(pyrazin-2-yl)ethanesalfonamide | 1H NMR (400 MHz, CDCl3) δ ppm 9.00 (s, 1 H), 8.43 (d, J = 2.8 Hz, 1 H), 8.39-8.35 (m, 2 H), 6.89 (t, J = 51.6 Hz, 1 H), 5.58 (s, 2 H), 3.41 (q, J = 7.6 Hz, 2 H), 1.43 (t, J = 7.2 Hz, 3 H).<br>LCMS RT = 2.823 mm, m/z = 403.1 | 0.023 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-76 Example 4 | N-((5-(5-(difluoromethyl)-1,3,4-oxadiazol-2-yl)thiazol-2-yl)methyl)-N-(pyridazin-4-yl)ethanesulfonamide | 1H NMR (400 MHz, CD3OD) δ ppm 8.57 (d, J = 7.6 Hz, 1 H), 8.53 (s, 1 H), 8.23 (s, 1 H), 7.42-7.40 (m, 1 H), 7.22 (t, J = 51.6 Hz, 1 H), 5.85 (s, 2 H), 3.10 (q, J = 7.6 Hz, 2 H), 1.36 (t, J = 7.2 Hz, 3H). LCMS RT = 3.671 mm, m/z = 402.9 | 0.097 |
| I-77 Example 4 | N-((5-(5-(difluoromethyl)-1,3,4-oxadiazol-2-yl)thiazol-2-yl)methyl)-N-(2-(trifluoromethyl)pyrimidin-5-yl)ethanesulfonamide | 1H NMR (400 MHz, CDCl3) δ ppm 9.10 (s, 2 H), 8.43 (s, 1 H), 6.92 (t, J = 51.6 Hz, 1 H), 5.32 (d, J = 12 Hz, 2 H) 3.25 (q, J = 7.2 Hz, 2 H), 1.44 (t, J = 7.2 Hz, 3 H). LCMS RT = 2.594 min, m/z = 471.1 | 0.155 |
| I-78 Example 4 | N-((5-(5-(difluoromethyl)-1,3,4-oxadiazol-2-yl)thiazol-2-yl)methyl)-N-(6-(trifluoromethyl)pyridin-3-yl)ethanesulfonamide | 1H NMR (400 MHz, CDCl3) δ ppm 8.86 (s, 1 H), 8.40 (s, 1 H), 8.10 (d, J = 8.4 Hz, 1 H), 7.74 (d, J = 8.4 Hz, 1 H), 6.91 (t, J = 51.6 Hz, 1 H), 5.34 (s, 2 H), 3.23 (q, J = 7.2 Hz, 2 H), 1.45 (t, J = 7.2 Hz, 3 H). LCMS RT = 0.882 min, m/z = 470.1 | 0.059 |
| I-79 Example 4 | N-((5-(5-(difluoromethyl)-1,3,4-oxadiazol-2-yl)thiazol-2-yl)methyl)-N-(6-methylpyridin-3-yl)ethanesulfonamide | 1H NMR (400 MHz, CDCl3) δ ppm 8.55 (s, 1 H), 8.37 (s, 1 H), 7.73-7.68 (m, 1 H), 7.20 (d, J = 7.6 Hz, 1 H), 6.91 (t, J = 51.6 Hz, 1 H), 5.27 (s, 2 H), 3.20 (q, J = 7.2 Hz, 2 H), 2.56 (s, 3 H), 1.46 (t, J = 7.2 Hz, 3 H). LCMS RT = 0.616 min, m/z = 416.2 | 0.073 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-80 Example 4 | N-((5-(5-(difluoromethyl-1,3,4-oxadiazol-2-yl)thiazol-2-yl)methyl)-N-(5-fluoropyridin-2-yl)ethanesulfonamide | 1H NMR (400 MHz, CDCl3) δ ppm 8.37 (s, 1 H), 8.28 (s, 1 H), 7.70-7.60 (m, 1 H), 7.50-7.40 (m, 1 H), 6.89 (t, J = 51.6 Hz, 1 H), 5.54 (s, 2 H), 3.25 (q, J = 7.2 Hz, 2 H), 1.40 (t, J = 7.6 Hz, 3 H). LCMS RT = 2.661 min, m/z = 419.9 | 0.0265 |
| I-81 Example 4 | N-((5-(5-(difluoromethyl)-1,3,4-oxadiazol-2-yl)thiazol-2-yl)methyl)-N-(5-fluoropyrimidin-2-yl)ethanesulfonamide | 1H NMR (400 MHz, CDCl3) δ ppm 8.49 (s, 2 H), 8.40 (s, 1 H), 6.90 (t, J = 51.6 Hz, 1 H), 5.65 (s, 2 H), 3.91 (q, J = 7.6 Hz, 2 H), 1.45 (t, J = 7.6 Hz, 3 H). LCMS RT = 1.977 min, m/z = 421.1 | 0.116 |
| I-82 Example 9 | N-(3-chloropheny)-N-((4-(5-(difluoromethyl)-1,3,4-oxadiazol-2-yl)thiazol-2-yl)methyl)propionamide | 1H NMR (400 MHz, CDCl3) δ ppm 8.28 (s, 1 H), 7.37-7.32 (m, 2 H), 7.25-7.23 (m, 1 H), 7.10-7.07 (m, 1 H), 6.91 (t, J = 51.6 Hz, 1 H), 5.22 (s, 2 H), 2.19 (q, J = 7.2 Hz, 2 H), 1.21 (t, J = 7.2 Hz, 3 H). LCMS RT = 0.931 min, m/z = 399.1 | 4.1 |
| I-83 Example 10 | N-(3-chlorophenyl)-N-((4-(5-(difluoromethyl)-1,3,4-oxadiazol-2-yl)thiazol-2-yl)methyl)cyclopropanesulfonamide | 1H NMR (400 MHz, CDCl3) δ ppm 8.26 (s, 1 H), 7.51 (s, 1 H), 7.41-7.30 (m, 3 H), 6.91 (t, J = 51.6 Hz, 1 H), 5.32 (s, 2 H), 2.59-2.52 (m, 1 H), 1.18-1.13 (m, 2 H), 1.08-1.04 (m, 2 H). LCMS RT = 0.944 min, m/z = 447.1 | 0.759 |
| I-84 Example 9 | N-(3-chlorophenyl)-N-((4-(5-(difluoromethyl)-1,3,4-oxadiazol-2-yl)thiazol-2-yl)methyl)cyclopropanecarboxamide | 1H NMR (400 MHz, CDCl3) δ ppm 8.27 (s, 1 H), 7.40-7.20 (m, 4 H), 6.91 (t, J = 51.6 Hz, 1 H), 5.25 (s, 2 H), 1.50-1.40 (m, 1 H), 1.18-1.09 (m, 2 H), 0.83-0.74 (m, 2 H). LCMS RT = 1.163 min, m/z = 410.8 | 7.5 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-85 Example 10 | 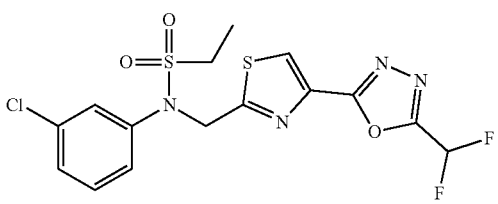 [SMILES: CCS(=O)(=O)N(Cc1nc(-c2nnc(C(F)F)o2)cs1)c1cccc(Cl)c1]<br>N-(3-chlorophenyl)-N-((4-(5-(difluoromethyl)-1,3,4-oxadiazol-2-yl)thiazol-2-yl)methyl)ethanesulfonamide | 1H NMR (400 MHz, CDCl3) δ ppm 8.26 (s, 1 H), 7.48 (s, 1 H), 7.37-7.31 (m, 3 H), 6.91 (t, J = 51.6 Hz, 1 H), 5.32 (s, 2 H), 3.19 (q, J = 7.2 Hz, 2 H), 1.46 (t, J = 7.2 Hz, 3 H). LCMS RT = 0.922 min, m/z = 435.0 | 0.584 |
| I-86 Example 10 | 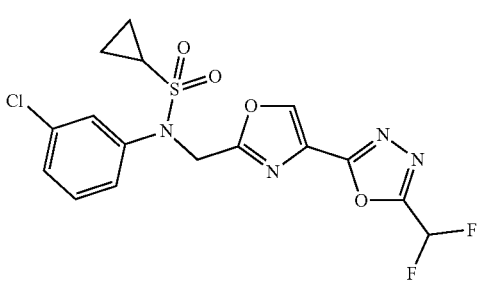 [SMILES: O=S(=O)(C1CC1)N(Cc1nc(-c2nnc(C(F)F)o2)co1)c1cccc(Cl)c1]<br>N-(3-chlorophenyl)-N-((4-(5-(difluoromethyl)-1,3,4-oxadiazol-2-yl)oxazol-2-yl)methyl)cyclopropanesulfonamide | 1H NMR (400 MHz, CDCl3) δ ppm 8.36 (s, 1 H), 7.50 (s, 1 H), 7.39-7.37 (m, 1 H), 7.33-7.30 (m, 2 H), 6.91 (t, J = 51.6 Hz, 1 H), 5.03 (s, 2 H), 2.69-2.65 (m, 1 H), 1.09-0.90 (m, 4 H). LCMS RT = 3.210 mm, m/z = 431.1 | 8.0 |
| I-87 Example 4 | 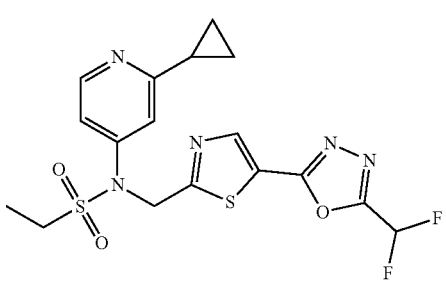 [SMILES: CCS(=O)(=O)N(Cc1ncc(-c2nnc(C(F)F)o2)s1)c1ccnc(C2CC2)c1]<br>N-(2-cyclopropylpyridin-4-yl)-N-((5-(5-(difluoromethyl)-1,3,4-oxadiazol-2-yl)thiazol-2-yl)methyl)ethanesulfonamide | 1H NMR (400 MHz, CDCl3) δ 8.42-8.36 (m, 2 H), 7.31 (s, 1 H), 7.18-7.14 (m, 1 H), 6.90 (t, J = 51.6 Hz, 1 H), 5.37 (s, 2 H), 3.26 (q, J = 7.6 Hz, 2 H), 2.04-1.95 (m, 1 H), 1.42 (t, J = 7.2 Hz, 3 H), 1.05-1.00 (m, 4 H). LCMS RT = 1.094 min, m/z = 441.9 | 0.039 |
| I-88 Example 4 | 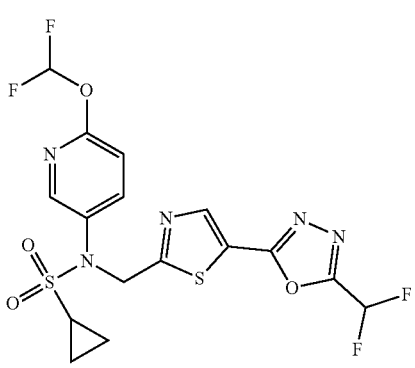 [SMILES: O=S(=O)(C1CC1)N(Cc1ncc(-c2nnc(C(F)F)o2)s1)c1ccc(OC(F)F)nc1]<br>N-(6-(difluoromethoxy)pyridin-3-yl)-N-((5-(5-(difluoromethyl)-1,3,4-oxadiazol-2-yl)thiazol-2-yl)methyl)cyclopropanesulfonamide | 1H NMR (400 MHz, CDCl3) δ 8.39 (s, 1 H), 8.33 (d, J = 2.8 Hz, 1 H), 7.87 (dd, J = 2.8, 8.8 Hz, 1 H), 7.42 (t, J = 72.0 Hz, 1 H), 7.06-6.77 (m, 2 H), 5.26 (s, 2 H), 2.64-2.48 (m, 1 H), 1.21-0.98 (m, 4H). LCMS RT = 0.957 min, m/z = 479.9 | 0.048 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-89 Example 4 | N-((5-(5-(difluoromethyl)-1,3,4-oxadiazol-2-yl)thiazol-2-yl)methyl)-N-(5-(trifluoromethyl)pyridin-3-yl)methanesulfonamide | 1H NMR (400 MHz, CDCl3) δ 8.95 (d, J = 2.4 Hz, 1 H), 8.87 (d, 4-2.4 Hz, 1 H), 8.44 (s, 1 H), 8.13 (s, 1 H), 6.92 (t, J = 51.6 Hz, 1 H), 5.31 (s, 2 H), 3.12 (s, 3 H). LCMS RT = 0.878 min, m/z = 455.9 | 0.049 |
| I-90 Example 4 | N-((5-(5-(difluoromethyl)-1,3,4-oxadiazol-2-yl)thiazol-2-yl)methyl)-N-(pyrazin-2-yl)methanesulfonamide | 1H NMR (400 MHz, CDCl3) δ 9.00 (s, 1 H), 8.47-8.36 (m, 3 H), 6.91 (t, J = 51.2 Hz, 1 H), 5.58 (s, 2 H), 3.27 (s, 3 H). LCMS RT = 0.943 min, m/z = 389.1 | 0.041 |
| I-91 Example 4 | N-((5-(5-(difluoromethyl)-1,3,4-oxadiazol-2-yl)thiazol-2-yl)methyl)-N-(pyrazin-2-yl)cyclopropanesulfonamide | 1H NMR (400 MHz, CDCl3) δ 9.02 (d, J = 1.2 Hz, 1 H), 8.46-8.35 (m, 3 H), 6.91 (t, J = 51.6 Hz, 1 H), 5.58 (s, 2 H), 2.72-2.61 (m, 1 H), 1.27-1.21 (m, 2 H), 1.11-1.01 (m, 2H). LCMS RT = 1.031 min, m/z = 415.1 | 0.018 |
| I-92 Example 4 | N-((5-(5-(difluoromethyl)-1,3,4-oxadiazol-2-yl)thiazol-2-yl)methyl)-N-(5-fluoropyridin-3-yl)cyclopropanesulfonamide | 1H NMR (400 MHz, CDCl3) δ 8.61 (s, 1 H), 8.47 (d, J = 4.0 Hz, 1 H), 8.40 (s, 1 H), 7.68-7.62 (m, H), 6.91 (t, J = 51.6 Hz, 1 H), 5.31 (s, 2 H), 2.63-2.52 (m, 1 H), 1.17-1.02 (m, 4 H). LCMS RT = 2.295 min, m/z = 431.9 | 0.014 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-93 Example 4 | N-((5-(5-(difluoromethyl)-1,3,4-oxadiazol-2-yl)thiazol-2-yl)methyl)-N-(5-methylpyridin-3-yl)methanesulfonamide | 1H NMR (400 MHz, CDCl3) δ 8.52-8.43 (m, 2 H), 8.40 (s, 1 H), 7.65 (s, 1 H), 6.91 (t, J = 51.6 Hz, 1 H), 5.27 (s, 2 H), 3.10 (s, 3 H), 2.39 (s, 3 H). LCMS RT = 0.828 min, m/z = 401.9 | 0.055 |
| I-94 Example 4 | N-((5-(5-(difluoromethyl)-1,3,4-oxadiazol-2-yl)thiazol-2-yl)methyl)-N-(5-fluoropyridin-3-yl)methanesulfonamide | 1H NMR (400 MHz, CDCl3) δ 8.58 (s, 1 H), 8.49 (s, 1 H), 8.43 (s, 1 H), 7.68-7.65 (m, 1 H), 6.92 (t, J = 51.6 Hz, 1 H), 5.29 (s, 2 H), 3.12 (s, 3 H). LCMS RT = 1.877 min, m/z = 406.1 | 0.025 |
| I-95 Example 4 | N-(5-chloropyridin-3-yl)-N-((5-(5-(difluoromethyl)-1,3,4-oxadiazol-2-yl)thiazol-2-yl)methyl)methanesulfonamide | 1H NMR (400 MHz, CDCl3) δ 8.62 (d, J = 2.4 Hz, 1 H), 8.57 (d, J = 2.4 Hz, 1 H), 8.43 (s, 1 H), 7.90 (s, 1 H), 6.92 (t, J = 51.6 Hz, 1 H), 5.27 (s, 2 H), 3.11 (s, 3 H). LCMS RT = 2.188 min, m/z = 421.8 | 0.0235 |
| I-96 Example 4 | N-(5-(difluoromethoxy)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ 8.63 (s, 1 H), 8.46 (s, 1 H), 8.39 (s, 1 H), 7.68 (s, 1 H), 6.91 (t, J = 51.6 Hz, 1 H), 6.58 (t, J = 51.6 Hz, 1 H), 5.29 (s, 2 H), 3.22 (q, J = 7.2 Hz, 2 H), 1.44 (t, 1 = 7.6 Hz, 3 H). LCMS RT = 0.907 min, m/z = 467.8 | 0.010 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-97 Example 4 | 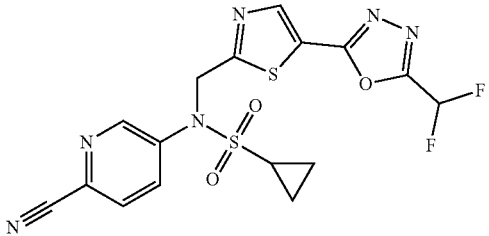 [SMILES: N#Cc1ccc(N(Cc2ncc(-c3nnc(C(F)F)o3)s2)S(=O)(=O)C2CC2)cn1]<br>N-(6-cyanopyridin-3-yl)-N-((5-(5-(difluoromethyl)-1,3,4-oxadiazol-2-yl)thiazol-2-yl)methyl)cyclopropanesulfonamide | 1H NMR (400 MHz, CDCl3) δ 8.89 (d, J = 2.4 Hz, 1 H), 8.39 (s, 1 H), 8.05 (d, J = 8.4 Hz, 1 H), 7.74 (d, J = 8.8 Hz, 1 H), 6.91 (t, J = 51.6 Hz, 1 H), 5.35 (s, 2 H), 2.59-2.53 (m, 1 H), 1.16-1.07 (m, 4 H).<br>LCMS RT = 0.859 min, m/z = 439.0 | 0.010 |
| I-98 Example 4 | 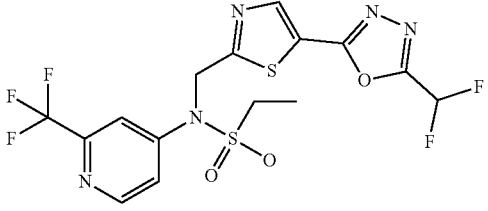<br>N-((5-(5-(difluoromethyl)-1,3,4-oxadiazol-2-yl)thiazol-2-yl)methyl)-N-(2-(trifluoromethyl)pyridin-4-yl)ethanesulfonamide | 1H NMR (400 MHz, CDCl3) δ 8.59 (d, J = 5.6 Hz, 1 H), 8.39 (s, 1 H), 7.81 (s, 1 H), 7.61-7.53 (m, 1 H), 6.83 (t, J = 51.6 Hz, 1 H), 5.35 (s, 2 H), 3.24 (q, J = 7.2 Hz, 2 H), 1.35 (t, J = 7.2 Hz, 3 H).<br>LCMS RT = 0.956 min, m/z = 469.9 | 0.069 |
| I-99 Example 4 | 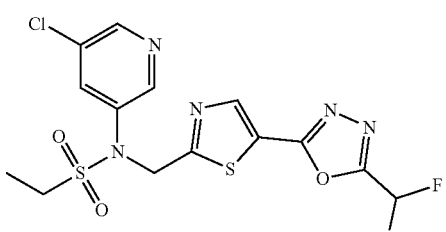<br>N-(5-chloropyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ 8.61 (d, J = 2.0 Hz, 1 H), 8.55 (d, J = 2.0 Hz, 1 H), 8.41 (s, 1 H), 7.89 (t, J = 2.2 Hz, 1 H), 6.92 (t, J = 51.6 Hz, 1 H), 5.28 (s, 2 H) 3.22 (q, J = 7.2 Hz, 2 H), 1.46 (t, 1 = 7.6 Hz, 3 H).<br>LCMS RT = 2.461 min, m/z = 435.9 | 0.0189 |
| I-100 Example 4 | 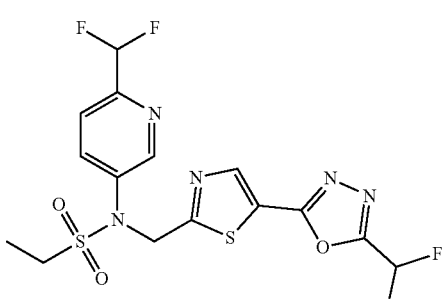<br>N-((5-(5-(difluoromethyl-1,3,4-oxadiazol-2-yl)thiazol-2-yl)methyl)-N-(6-(difluoromethyl)pyridin-3-yl)ethanesulfonamide | 1H NMR (400 MHz, CDCl3) δ 8.77 (d, J = 2.4 Hz, 1 H), 8.47 (s, 1 H), 8.01 (dd, J = 2.4, 8.4 Hz, 1 H), 7.69 (d, 1 = 8.4 Hz, 1 H), 6.91 (t, J = 51.6 Hz, 1 H), 6.63 (t, J = 55.2 Hz, 1 H), 5.32 (s, 2 H), 3.21 (q, J = 7.2 Hz, 2 H), 1.45 (t, J = 7.6 Hz, 3 H).<br>LCMS RT = 2.547 min, m/z = 452.1 | 0.065 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-101 Example 3 | 1-(5-(5-(difluoromethyl)-1,3,4-oxadiazol-2-yl)thiazol-2-yl)-5-phenylpyrrolidin-2-one | 1H NMR (400 MHz, CDCl3) δ 8.08 (s, 1 H), 7.38-7.30 (m, 3 H), 7.18 (d, J = 7.2 Hz, 2 H), 6.88 (t, J = 51.6 Hz, 1 H), 5.80 (d, 1 = 7.6 Hz, 1 H), 2.93-2.74 (m, 3 H), 2.25-2.20 (m, 1 H). LCMS RT = 2.937 min, m/z = 362.9 | 0.171 |
| I-102 Example 4 | N-((5-(5-(difluoromethyl)-1,3,4-oxadiazol-2-yl)thiazol-2-yl)methyl)-N-(5-(2-hydroxypropan-2-yl)pyridin-2-yl)ethanesulfonamide | 1H NMR (400 MHz, CDCl3) δ 8.55 (d, J = 2.0 Hz, 1 H), 8.38 (s, 1 H), 7.86 (d, J = 6.8 Hz, 1 H), 7.60 (d, J = 8.8 Hz, 1 H), 6.89 (t, J = 51.6 Hz, 1 H) 5.58 (s, 2 H), 3.29 (q, J = 7.6 Hz , 2 H), 1.61 (s, 6 H), 1.39 (t, J = 7.6 Hz, 3 H). LCMS RT = 1.017 min, m/z = 459.9 | 0.137 |
| I-103 Example 4 | N-((5-(5-(difluoromethyl)-1,3,4-oxadiazol-2-yl)thiazol-2-yl)methyl)-1-methyl-N-(pyridin-3-yl)cyclopropane-1-sulfonamide | 1H NMR (400 MHz, CDCl3) δ 8.74 (d, J = 2.4 Hz, 1 H), 8.58 (d, J = 3.6 Hz, 1 H), 8.35 (s, 1 H), 7.87-7.81 (m, 1 H), 7.38-7.31 (m, I H), 6.90 (t, J = 51.6 Hz, 1 H), 5.35 (s, 2 H), 1.59 (s, 3 H), 1.22-1.15 (m, 2 H), 0.79-0.72 (m, 2 H). LCMS RT = 0.956 mm, m/z = 427.9 | 0.013 |
| I-104 Example 4 | N-((5-(5-(difluoromethyl)-1,3,4-oxadiazol-2-yl)thiazol-2-yl)methyl)-N-(6-(methoxymethyl)pyridin-3-yl)ethanesulfonamide | 1H NMR (400 MHz, CDCl3) δ 8.63 (d, J = 2.4 Hz, 1 H), 8.38 (s, 1 H), 7.83 (dd, J = 2.4, 8.0 Hz, 1 H) 7.48 (d, J = 8.4 Hz, 1 H), 6.91 (t, J = 51.6 Hz, 1 H), 5.29 (s, 2 H), 4.57 (s, 2 H), 3.49 (s, 3 H), 3.20 (q, J = 7.6 Hz, 2 H), 1.46 (t, J = 7.6 Hz, 3 H). LCMS RT = 0.789 min, m/z = 446.2 | 0.051 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-105 Example 4 | 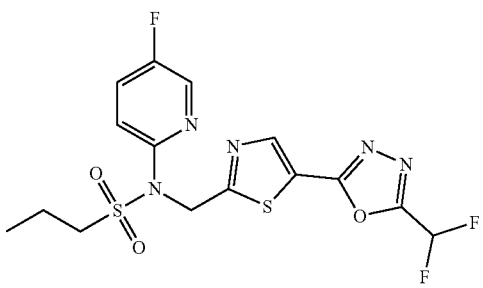 [SMILES: CCCS(=O)(=O)N(Cc1ncc(-c2nnc(C(F)F)o2)s1)c1ccc(F)cn1] N-({5-[5-(difluoromethyl)-1,3,4-oxadiazol-2-yl]-1,3-thiazol-2-yl}methyl)-N-(5-fluoropyridin-2-yl)propane-1-sulfonamide | ¹H NMR (400 MHz, CDCl$_3$) δ 8.37 (s, 1 H), 8.28 (d, J = 3.2 Hz, 1 H) 7.69-7.63 (m, 1 H), 7.51-7.43 (m, 1 H), 6.89 (t, J = 51.6 Hz, 1 H), 5.52 (s, 2 H), 3.20-3.14 (m, 2 H), 1.91-1.83 (m, 2 H), 1.05 (t, J = 7.6 Hz, 3 H). LCMS Rt = 0.684 min, m/z = 433.9 | 0.0268 |
| I-106 Example 4 | 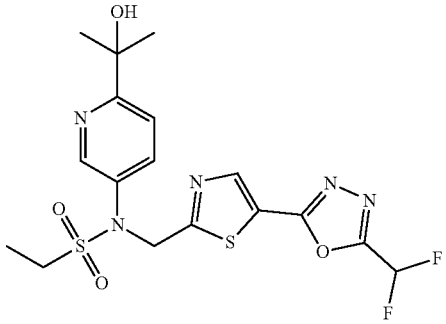 [SMILES: CCS(=O)(=O)N(Cc1ncc(-c2nnc(C(F)F)o2)s1)c1ccc(C(C)(C)O)nc1] N-({5-[5-(difluoromethyl)-1,3,4-oxadiazol-2-yl]-1,3-thiazol-2-yl}methyl)-N-[6-(2-hydroxyropan-2-yl)pyridin-3-yl]ethane-1-sulfonamide | ¹H NMR (400 MHz, CDCl$_3$) δ 8.55 (s, 1 H), 8.38 (s, 1 H), 7.85 (d, J = 8.8 Hz, 1 H), 7.60 (d, J = 8.4 Hz, 1 H), 6.89 (t, J = 52.0 Hz, 1 H), 5.58 (s, 2 H), 3.30 (q, J = 7.2 Hz, 2 H), 2.63 (s, 1 H), 1.39 (t, J = 7.6 Hz, 3 H), 1.30-1.23 co 6 H), LCMS R$_T$ = 1.467 min, m/z = 460.2 | 0.480 |
| I-107 Example 4 | 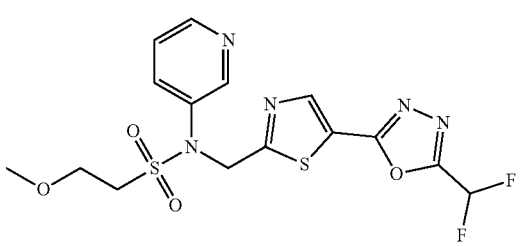 [SMILES: COCCS(=O)(=O)N(Cc1ncc(-c2nnc(C(F)F)o2)s1)c1cccnc1] N-({5-[5-(difluoromethyl)-1,3,4-oxadiazol-2-yl]-1,3-thiazol-2-yl}methyl)-2-methoxy-N-(pyridin-3-yl)ethane-1-sulfonamide | ¹H NMR (400 MHz, CDCl$_3$) δ 8.40 (s, 1 H), 8.57 (d, J = 3.6 Hz, 1 H), 8.34 (s, 1 H), 7.91-7.88 (m, 1 H), 7.36-7.33 (m, 1 H), 6.90 (t, J = 51.6 Hz, 1 H), 5.24 (s, 2 H), 3.87 (t, J = 5.2 Hz, 2 H), 3.51 (s, 3 H), 3.35 (t, J = 5.2 Hz, 2 H). LCMS R$_T$ = 1.284 min, m/z = 431.9 | 0.0212 |
| I-108 Example 4 | 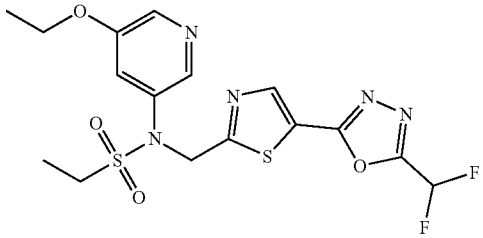 [SMILES: CCOc1cncc(N(Cc2ncc(-c3nnc(C(F)F)o3)s2)S(=O)(=O)CC)c1] N-({5-[5-(difluoromethyl)-1,3,4-oxadiazol-2-yl]-1,3-thiazol-2-yl}methyl)-N-(5-ethoxypyridin-3-yl)ethane-1-sulfonamide | ¹H NMR (400 MHz, CDCl$_3$) δ 8.40 (s, 1 H), 8.32-8.27 (m, 2 H), 7.42-7.38 (m, 1 H), 6.92 (t, J = 51.6 Hz, 1 H), 5.31 (s, 2 H), 4.10 (q, J = 6.8 Hz, 2 H), 3.22 (q, J = 7.2 Hz, 2 H), 1.49-1.43 (m, 6 H). LCMS R$_T$ = 0.604 min, m/z = 446.0 | 0.0138 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-109 Example 4 | N-(5-chloropyridin-3-yl)-N-({5-[5-(difluoromethyl)-1,3,4-oxadiazol-2-yl]-1,3-thiazol-2-yl}methyl)propane-1-sulfonamide | ¹H NMR (400 MHz, CDCl$_3$) δ 8.60 (d, J = 2.0 Hz, 1 H), 8.54 (s, 1 H), 8.40 (s, 1 H), 7.88 (t, J = 2.4 Hz, 1 H), 6.91 (t, J = 51.6 Hz, 1 H), 5.27 (s, 2 H), 3.22-3.00 (m, 2 H), 1.99-1.70 (m, 2 H), 1.09 (t, J = 7.6 Hz, 3 H). LCMS R$_T$ = 0.668 min, m/z = 449.9 | 0.00392 |
| I-110 Example 4 | N-({5-[5-(difluoromethyl)-1,3,4-oxadiazol-2-yl]-1,3-thiazol-2-yl}methyl)-N-(5-fluoropyridin-3-yl)propane-]-sulfonamide | ¹H NMR (400 MHz, CDCl$_3$) δ 8.56 (s, 1 H), 8.46 (d, J = 2.4 Hz, 1 H), 8.40 (s, 1 H), 7.67-7.61 (m, 1 H), 6.91 (t, J = 51.6 Hz, 1 H) 5.29 (s, 2 H), 3.19-3.09 (m, 2 H), 1.97-1.85 (m, 2 H), 1.08 (t, J = 7.2 Hz, 3 H). LCMS R$_T$ = 2.144 min, m/z = 434.2 | 0.0104 |
| I-111 Example 4 | N-(5-cyanopyridin-3-yl)-N-({5-[5-(difluoromethyl)-1,3,4-oxadiazol-2-yl]-1,3-thiazol-2-yl}methyl)methanesulfonamide | ¹H NMR (400 MHz, CDCl$_3$) δ 8.98 (d, J = 2.4 Hz, 1 H), 8.84 (s, 1 H), 8.45 (s, 1 H), 8.20 (s, 1 H), 6.93 (t, J = 51.2 Hz, 1 H), 5.29 (s, H), 3.11 (s, 3 H). LCMS R$_T$ = 1.456 min, m/z = 412.8 | 0.0374 |
| I-112 Example 4 | N-[5-(1,1-difluoroethyl)pyridin-3-yl]-N-({5-[5-(difluoromethyl)-1,3,4-oxadiazol-2-yl]-1,3-thiazol-2-yl}methyl)ethane-1-sulfonamide | ¹H NMR (400 MHz, CDCl$_3$) δ 8.79 (s, 1 H), 8.72 (s, 1 H), 8.40 (s, 1 H), 7.96 (s, 1 H) 6.91 (t, J = 52.0 Hz, 1 H), 5.30 (s, 2 H), 3.21 (q, J = 7.2 Hz, 2 H), 1.97 (t, J = 18.4 Hz, 3 H), 1.46 (t, J = 7.6 Hz, 3 H). LCMS R$_T$ = 1.138 min, m/z = 466.2 | 0.0101 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-113 Example 4 | N-(5-cyanopyridin-3-yl)-N-({5-[5-(difluoromethyl)-1,3,4-oxadiazol-2-yl]-1,3-thiazol-2-yl}methyl)propane-1-sulfonamide | $^1$H NMR (400 MHz, CDCl$_3$) δ 8.95 (d, J = 2.4 Hz, 1 H), 8.82 (d, J = 2.0 Hz, 1 H), 8.42 (s, 1 H), 8.20-8.12 (m, 1 H), 6.92 (t, J = 51.6 Hz, 1 H), 5.29 (s, 2 H), 3.19-3.08 (m, 2 H), 1.98-1.85 (m, 2 H), 1.09 (t, J = 7.6 Hz, 3 H). LCMS R$_T$ = 1.560 min, m/z = 441.2. | 0.0429 |
| I-114 Example 4 | N-phenyl-N-({5-[5-(trifluoromethyl)-1,3,4-oxadiazol-2-yl]-1,3-thiazol-2-yl}methyl)methanesulfonamide | 1H NMR (400 MHz, CDCl$_3$) δ 8.39 (s, 1 H), 7.48-7.38 (m, 5 H), 5.28 (s, 2 H), 3.06 (s, 3 H). LCMS R$_T$ = 2.568 min, m/z = 404.8 | 0.354 |
| I-115 Example 4 | N-(5-fluoropyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.57 (s, 1 H), 8.47 (d, J = 2.4 Hz, 1 H), 8.42 (s, 1 H), 7.68-7.63 (m, 1 H), 5.31 (s, 2 H), 3.22 (q, J = 7.2 Hz, 2 H), 1.46 (t, J = 7.2 Hz, 3 H). LCMS R$_T$ = 0.904 min, m/z = 437.9 | 0.022 |
| I-116 Example 4 | N-[6-(1,1-difluoroethyl)pyridin-3-yl]-N-({5-[5-(difluoromethyl)-1,3,4-oxadiazol-2-yl]-1,3-thiazol-2-yl}methyl)ethane-1-sulfonamide | $^1$H NMR (400 MHz, CDCl$_3$) δ 8.74 (d, J = 2.4 Hz, 1 H), 8.39 (s, 1 H), 7.98-7.92 (m, 1 H), 7.70 (d, J = 8.4 Hz, 1 H), 6.91 (t, J = 51.6 Hz, 1 H), 5.32 (s, 2 H), 3.22 (q, J = 7.6 Hz, 2 H), 2.01 (t, J = 18.8 Hz, 3 H), 1.46 (t, J = 7.6 Hz, 3 H). LCMS R$_T$ = 0.908 min, m/z = 465.9 | 0.0514 |

TABLE 3-continued

Characterization Data and HDAC6 Activity for Compounds of Formula (I).

| Cmpd ID/Prep | Stracture/Name | $^1$H NMR MS (m/z) (RT) | HDAC6 IC$_{50}$ (μM) |
|---|---|---|---|
| I-117 Example 4 | N-(5-chloropyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.61 (d, J = 2.4 Hz, 1 H), 8.55 (d, J = 2.4 Hz, 1 H), 8.42 (s, 1 H), 7.88 (t, J = 2.0 Hz, 1 H), 5.29 (s, 2 H), 3.21 (q, J = 4.0 Hz, 2 H), 1.46 (t, J = 8.0 Hz, 3H). LCMS R$_T$ = 2.591 min, m/z = 453.8 | 0.0245 |
| I-118 Example 4 | N-(pyrazin-2-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 9.00 (s, 1 H) 8.44-8.37 (m, 3 H), 5.58 (s, 2 H), 3.41 (d, J = 6.8 Hz, 2 H), 1.43 (t, J = 6.8 Hz, 3 H). LCMS R$_T$ = 0.895 min, m/z = 420.9 | 0.0278 |
| I-119 Example 4 | N-(pyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.73 (s, 1 H), 8.62-8.60 (m, 1 H), 8.41 (s, 1 H), 7.86 (d, J = 8.0 Hz, 1 H), 7.40-7.35 (m, 1 H), 5.32 (s, 2 H), 3.22 (q, J = 6.8 Hz, 2 H), 1.48 (t, J = 7.2 Hz, 3H). LCMS R$_T$ = 1.897 min, m/z = 420.1 | 0.042 |
| I-120 Example 4 | N-(5-cyanopyridin-3-yl)-N-({5-[5-(trifluoromethyl)-1,3,4-oxadiazol-2-yl]-1,3-thiazol-2-yl}methyl)methanesulfonamide | $^1$H NMR (400 MHz, CDCl$_3$) δ 8.98 (d, J = 2.8 Hz, 1 H), 8.85 (s, 1 H), 8.46 (s, 1 H), 8.20 (t, J = 2.0 Hz, 1 H) 5.30 (s, 2 H), 3.11 (s, 3 H). LCMS R$_T$ = 2.105 min, m/z = 431.1 | 0.111 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-121 Example 4 | N-(3-fluorophenyl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.40 (s, 1 H), 7.41-7.36 (m, 1 H), 7.28 (s, 1 H), 7.25-7.22 (m, 1 H), 7.09-7.04 (m, 1 H) 5.30 (s, 2 H), 3.19 (q, J = 7.6 Hz, 2 H) 1.45 (t, J = 7.2 Hz, 3 H). LCMS R$_T$ = 1.978 min, m/z = 437.1 | 0.0839 |
| I-122 Example 4 | N-phenyl-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.38 (s, 1 H), 7.50-7.30 (m, 5 H), 5.31 (s, 2 H), 3.17 (q, J = 7.2 Hz, 2 H), 1.45 (t, J = 7.2 Hz, 3 H). LCMS R$_T$ = 0.973 min, m/z = 419.0 | 0.0249 |
| I-123 Example 4 | N-({5-[5-(difluoromethyl)-1,3,4-oxadiazol-2-yl]-1,3-thiazol-2-yl}methyl)-N-(1-methyl-1H-pyrazol-4-yl)methanesulfonamide | $^1$H NMR (400 MHz, CDCl$_3$) δ 8.42 (s, 1 H), 7.57 (s, 1 H), 7.48 (s, 1 H), 6.91 (t, J = 51.6 Hz, 1 H), 5.14 (s, 2 H), 3.88 (s, 3 H), 3.03 (s, 3 H). LCMS R$_T$ = 1.057 min, m/z = 390.9 | 0.0388 |
| I-124 Example 5 | 5-[({5-[5-(difluoromethyl)-1,3,4-oxadiazol-2-yl]-1,3-thiazol-2-yl}methyl(methyl)amino]pyridine-3-carbonitrile | 1H NMR (400 MHz, CDCl$_3$) δ 8.46 (s, 1 H), 8.41 (s, 1 H), 8.33 (s, 1 H), 7.25 (s, 1 H) 6.90 (t, J = 51.6 Hz, 1 H), 4.92 (s, 2 H), 3.27 (s, 3 H). LCMS R$_T$ = 0.971 min, m/z = 349.0 | 0.0636 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-125 Example 4 | N-({5-[5-(difluoromethyl)-1,3,4-oxadiazol-2-yl]-1,3-thiazol-2-yl}methyl)-N-(pyridin-3-yl)propane-1-sulfonamide | $^1$H NMR (400 MHz, CDCl$_3$) δ 8.71 (d, J = 2.4 Hz, 1 H), 8.60-8.56 (m, 1 H), 8.38 (s, 1 H), 7.85-7.82 (m, 1 H), 7.39-7.32 (m, 1 H), 6.91 (t, J = 51.6 Hz, 1 H), 5.29 (s, 2 H), 3.18-3.11 (m, 2 H), 1.98-1.89 (m, 2 H), 1.09 (t, J = 7.2 Hz, 3H). LCMS R$_T$ = 0.776 min, m/z = 416.1 | 0.0599 |
| I-126 Example 4 | N-({5-[5-(difluoromethyl)-1,3,4-oxadiazol-2-yl]-1,3-thiazol-2-yl}methyl)-N-{1-[2-(trifluoromethoxy)ethyl]-1H-pyrazol-4-yl}ethane-1-sulfonamide | $^1$H NMR (400 MHz, CDCl$_3$) δ 8.39 (s, 1 H), 7.64 (s, 1 H), 7.57 (s, 1 H), 6.91 (t, J = 51.6 Hz, 1 H), 5.16 (s, 2 H) 4.36-4.33 (m, 2 H), 4.30-4.23 (m, 2 H), 3.15 (q, J = 7.6 Hz, 2 H), 1.40 (t, J = 7.2 Hz, 3 H). LCMS R$_T$ = 1.043 min, m/z = 502.9 | 0.134 |
| I-127 Example 4 | N-({5-[5-(difluoromethyl)-1,3,4-oxadiazol-2-yl]-1,3-thiazol-2-yl}methyl)-N-(5-fluoropyridin-2-yl)methanesulfonamide | $^1$H NMR (400 MHz, CDCl$_3$) δ 8.37 (s, 1 H), 8.29 (d, J = 3.2 Hz, 1 H), 7.67-7.61 (m, 1 H), 7.53-7.46 (m, 1 H), 6.90 (t, J = 51.6 Hz, 1 H), 5.50 (s, 2 H), 3.10 (s, 3 H). LCMS R$_T$ = 0.854 min, m/z = 406.1 | 0.0215 |
| I-128 Example 4 | N-({5-[5-(difluoromethyl)-1,3,4-oxadiazol-2-yl]-1,3-thiazol-2-yl}methyl)-1,1-difluoro-N-(1-propyl-1H-pyrazol-4-yl)methanesulfonamide | $^1$H NMR (400 MHz, CDCl$_3$) δ 8.42 (s, 1 H), 7.49 (d, J = 4.4 Hz, 2 H), 6.92. (t, J = 51.6 Hz, 1 H) 6.44 (t, J = 53.2 Hz, 1 H), 5.21 (s, 2 H), 4.02 (t, J = 7.2 Hz, 2 H), 1.94-1.78 (m, 2 H) 0.88 (t, 7 = 7.6 Hz, 3H). LCMS R$_T$ = 0.901 min, m/z = 455.1 | 0.2.51 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (μM) |
|---|---|---|---|
| I-129 Example 4 | N-({5-[5-(difluoromethyl)-1,3,4-oxadiazol-2-yl]-1,3-thiazol-2-yl}methyl)-N-(1-propyl-1H-pyrazol-4-yl)methanesulfonamide | ¹H NMR (400 MHz, CDCl$_3$) δ 8.41 (s, 1 H), 7.58 (s, 1 H), 7.49 (s, 1 H), 6.91 (t, J = 51.6 Hz, 1 H), 5.14 (s, 2 H), 4.03 (1, J = 7.2 Hz, 2 H), 3.03 (s, 3 H), 1.92-1.81 (m, 2 H), 0.90 (t, J = 7.2 Hz, 3 H). LCMS R$_T$ = 0.795 min, m/z = 418.9 | 0.118 |
| I-130 Example 4 | N-({5-[5-(difluoroinethyl)-1,3,4-oxadiazol-2-yl]-1,3-thiazol-2-yl}methyl)-N-(1-methyl-1H-pyrazol-4-yl)cyclopropanesulfonamide | ¹H NMR (400 MHz, CDCl$_3$) δ 8.39 (s, 1 H), 7.56 (s, 1 H), 7.52 (s, 1 H), 6.91 (t, J = 51.6 Hz, 1 H), 5.15 (s, 2 H), 3.87 (s, 3 H), 2.58-2.50 (m, 1 H), 1.20-1.15 (m, 2 H), 1.07-1.01 (m, 2H). LCMS R$_T$ = 1.320 min, m/z = 416.8 | 0.0348 |
| I-131 Example 4 | N-({5-[5-(difluoromethyl)-1,3,4-oxadiazol-2-yl]-1,3-thiazol-2-yl}methyl)-N-(5-methylpyridin-3-yl)ethane-1-sulfonamide | ¹H NMR (400 MHz, CDCl$_3$) δ 8.50 (d, J = 2.4 Hz, 1 H), 8.41 (s, 1 H), 8.38 (s, 1 H), 7.65 (s, 1 H), 6.91 (t, J = 51.6 Hz, 1 H), 5.29 (s, 2 H), 3.20 (q, J = 7.6 Hz, 2 H), 2.37 (s, 3 H), 1.47 (t, J = 7.6 Hz, 3 H). LCMS R$_T$ = 0.714 min, m/z = 416.2 | 0.013 |
| I-132 Example 4 | N-[5-(2,2-difluoroethoxy)pyridin-3-yl]-N-({5-[5-(difluoromethyl)-1,3,4-oxadiazol-2-yl]-1,3-thiazol-2-yl}methyl)ethane-1-sulfonamide | ¹H NMR (400 MHz, CDCl$_3$) δ 8.40 (s, 2 H), 8.32 (d, J = 2.4 Hz, 1 H), 7.45 (t, J = 2.4 Hz, 1 H), 6.91 (t, J = 51.6 Hz, 1 H), 6.25-5.96 (m, 1 H), 5.30 (s, 2 H), 4.30-4.20 (m, 2 H), 3.21 (q, J = 7.2 Hz, 2 H), 1.46 (t, J = 7.6 Hz, 3 H). LCMS R$_T$ = 0.857 min, m/z = 482.2 | 0.00964 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (µM) |
|---|---|---|---|
| I-133 Example 4 | N-({5-[5-(difluoromethyl)-1,3,4-oxadiazol-2-yl]-1,3-thiazol-2-yl}methyl-1,1-difluoro-N-(5-fluoropyridin-2-yl)methanesulfonamide | $^1$H NMR (400 MHz, CDCl$_3$) δ 8.39 (s, 1 H), 8.30 (d, J = 2.8 Hz, 1 H), 7.58-7.55 (m, 1 H), 7.54-7.48 (m, 1 H), 7.03 (t, J = 51.6 Hz, 1 H), 6.33 (t, J 53.6 Hz, 1 H), 5.55 (s, 2 H). LCMS R$_T$ = 0.954 min, m/z = 441.9 | 0.0857 |
| I-134 Example 4 | N-[1-(1-cyano-1-methylethyl)-1H-pyrazol-4-yl]-N-({5-[5-(difluoromethyl)-1,3,4-oxadiazol-2-yl]-1,3-thiazol-2-yl}methyl)ethane-1-sulfonamide | $^1$H NMR (400 MHz, CDCl$_3$) δ 8.42 (s, 1 H), 7.83 (s, 1 H), 7.63 (s, 1 H), 6.91 (t, J = 51.6 Hz, 1 H), 5.17 (s, 2 H), 3.17 (q, J = 7.2 Hz, 2 H), 1.99 (s, 6 H), 1.42 (t, J = 7.2 Hz, 3 H). LCMS R$_T$ = 1.012 min, m/z = 458.1 | 0.121 |
| I-135 Example 5 | 3-chloro-N-({5-[5-(difluoromethyl)-1,3,4-oxadiazol-2-yl]-1,3-thiazol-2-yl}methyl)-N-ethylaniline | $^1$H NMR (400 MHz, CDCl$_3$) δ 8.45 (s, 1 H), 7.14 (t, J = 8.0 Hz, 1 H), 6.88 (t, J = 51.6 Hz, 1 H), 6.76-6.74 (m, 2 H), 6.64-6.60 (m, 1 H), 4.79 (s, 2 H), 3.58 (q, J = 7.2 Hz, 2 H), 1.30 (t, J = 7.2 Hz, 3 H). LCMS R$_T$ = 1.098 min, m/z = 370.9 | 0.0531 |
| I-136 Example 4 | N-(5-cyclopropylpyridin-3-yl)-N-({5-[5-(difluoromethyl)-1,3,4-oxadiazol-2-yl]-1,3-thiazol-2-yl}methyl)methanesulfonamide | $^1$H NMR (400 MHz, CDCl$_3$) δ 8.46 (s, 1 H), 8.41 (s, 1 H), 8.37 (s, 1 H), 7.46 (s, 1 H), 6.91 (t, J = 51.6 Hz, 1 H), 5.25 (s, 2 H), 3.09 (s, 3 H), 1.96-1.89 (m, 1 H), 1.14-1.06 (m, 2 H), 0.79-0.71 (m, 2 H). LCMS R$_T$ = 0.743 min, m/z = 427.9 | 0.013 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-137 Example 4 | N-({5-[5-(difluoromethyl)-1,3,4-oxadiazol-2-yl]-1,3-thiazol-2-yl}methyl)-N-[6-(difluoromethyl)pyridin-2-yl]methanesulfonamide | ¹H NMR (400 MHz, CDCl$_3$) δ 8.38 (s, 1 H), 7.90 (t, J = 8.0 Hz, 1 H), 7.77 (d, J = 8.4 Hz, 1 H), 7.48 (d, J = 7.6 Hz, 1 H), 6.89 (t, J = 51.6 Hz, 1 H), 6.54 (t, J = 55.2 Hz, 1 H), 5.59 (s, 2 H), 3.23 (s, 3 H). LCMS R$_T$ = 0.899 min, m/z = 437.9 | 0.0107 |
| I-138 Example 4 | N-({5-[5-(difluoromethyl)-1,3,4-oxadiazol-2-yl]-1,3-thiazol-2-yl}methyl-N-[1-(propan-2-yl)-1H-pyrazol-4-yl]ethane-1-sulfonamide | ¹H NMR (400 MHz, CDCl$_3$) δ 8.37 (s, 1 H), 7.57 (s, 1 H), 7.46 (s, 1 H), 6.87 (t, J = 51.2 Hz, 1 H), 5.12 (s, 2 H), 4.44-4.34 (m, 1 H), 3.13 (q, J = 7.2 Hz, 2 H), 1.45 (d, J = 6.8 Hz, 6 H), 1.39 (t, J = 7.2 Hz, 3 H). LCMS R$_T$ = 1.141 min, m/z = 433.2 | 0.043 |
| I-139 Example 4 | N-({5-[5-(difluoromethyl)-1,3,4-oxadiazol-2-yl]-1,3-thiazol-2-yl}methyl)-N-[1-(propan-2-yl)-1H-pyrazol-4-yl]methanesulfonamide | ¹H NMR (400 MHz, CDCl$_3$) δ 8.39 (s, 1 H), 7.58 (s, 1 H), 7.46 (s, 1 H), 6.88 (t, J = 51.6 Hz, 1 H), 5.11 (s, 2 H), 4.45-4.35 (m, 1 H), 3.00 (s, 3 H), 1.46 (d, J = 6.8 Hz, 6 H). LCMS R$_T$ = 0.997 min, m/z = 419.2 | 0.118 |
| I-140 Example 4 | N-({5-[5-(difluoromethyl)-1,3,4-oxadiazol-2-yl]-1,3-thiazol-2-yl}methyl)-N-[6-(trifluoromethyl)pyridin-2-yl]methanesulfonamide | ¹H NMR (400 MHz, CDCl$_3$) δ 8.37 (s, 1 H), 7.95-7.85 (m, 2 H), 7.51 (d, J = 7.2 Hz, 1 H), 6.90 (t, J = 51.6 Hz, 1 H), 5.61 (s, 2 H), 3.29 (s, 3 H). LCMS R$_T$ = 1.112 min, m/z = 455.8 | 0.0576 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-141 Example 4 | N-({5-[5-(difluoromethyl)-1,3,4-oxadiazol-2-yl]-1,3-thiazol-2-yl}methyl)-1,1-difluoro-N-(pyridin-3-yl)methanesulfonamide | ¹H NMR (400 MHZ, CDCl$_3$) δ 8.70-8.60 (m, 2 H), 8.39 (s, 1 H), 7.75 (d, J = 6.8 Hz, 1 H), 7.39-7.36 (m, 1 H), 6.92 (t, J = 51.6 Hz, 1 H), 6.49 (t, J = 53.2 Hz, 1 H), 5.35 (s, 2 H). LCMS R$_T$ = 0.965 min, m/z = 423.8 | 0.0655 |
| I-142 Example 5 | 3-chloro-N-({5-[5-(difluoromethyl)-1,3,4-oxadiazol-2-yl]-1,3-thiazol-2-yl}methyl)-N-(2-methoxyethyl)aniline | ¹H NMR (400 MHz, CDCl$_3$) δ 8.44 (s, 1 H), 7.13 (t, J = 8.0 Hz, 1 H), 6.88 (t, J = 89.2 Hz, 1 H), 6.80-6.70 (m, 2 H), 6.68-6.55 (m, 1H), 4.94 (s, 2 H), 3.74-3.71 (m, 2 H), 3.70-3.65 (m, 2 H), 3.38 (s, 3 H). LCMS R$_T$ = 1.055 min, m/z = 400.9 | 0.0245 |
| I-143 Example 4 | N-(5-cyanopyridin-3-yl)-N-({5-[5-(difluoromethyl)-1,3,4-oxadiazol-2-yl]-1,3-thiazol-2-yl}methyl)cyclopropanesulfonamide | ¹H NMR (400 MHz, CDCl$_3$) δ 8.99 (d, J = 2.0 Hz, 1 H), 8.83 (s, 1 H), 8.41 (s, 1 H), 8.18 (t, J = 2.0 Hz, 1 H), 6.92 (t, J = 51.6 Hz, 1H), 5.31 (s, 2 H), 2.59-2.50 (m, 1 H), 1.13-1.08 (m, 4 H). LCMS R$_T$ = 0.834 min, m/z = 439.1 | 0.0153 |
| I-144 Example 11 | N-({5-[5-(difluoromethyl)-1,3,4-oxadiazol-2-yl]-1,3-thiazol-2-yl}methyl)-N-(1,5-dimethyl-1H-pyrazol-4-yl)ethane-1-sulfonamide | ¹H NMR (400 MHz, CDCl$_3$) δ 8.39 (s, 1 H), 7.38 (s, 1 H), 6.91 (t, J = 51.6 Hz, 1 H), 5.11 (s, 2 H), 3.76 (s, 3 H), 3.20 (q, J = 7.2 Hz, 2 H), 2.25 (s, 3 H), 1.47 (t, J = 7.4 Hz, 3 H). LCMS R$_T$ = 0.751 min, m/z = 419.0 | 0.102 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC₅₀ (μM) |
|---|---|---|---|
| I-145 Example 4 | N-[5-(difluoromethoxy)pyridin-3-yl]-N-({5-[5-(difluoromethyl)-1,3,4-oxadiazol-2-yl]-1,3-thiazol-2-yl}methyl)propane-2-sulfonamide | 1H NMR (400 MHz, CDCl3) δ 8.61 (d, J = 2.0 Hz, 1 H), 8.45 (d, 1 = 2.4 Hz, 1 H), 8.38 (s, 1 H), 7.68 (t, J = 2.0 Hz, 1 H), 6.91 (t, J = 51.6 Hz, 1 H), 6.58 (t, J = 72.0 Hz, 1 H), 5.31 (s, 2 H), 3.40-3.29 (m, 1 H), 1.45 (d, J = 6.8 Hz, 6 H). LCMS RT = 1.625 min, m/z = 482.2. | 0.0102 |
| I-146 Example 4 | N-({5-[5-(difluoromethyl)-1,3,4-oxadiazol-2-yl]-1,3-thiazol-2-yl}methyl)-N-(5-ethylpyridin-3-yl)ethane-1-sulfonamide | 1H NMR (400 MHz, CD3OD) δ 8.59 (s, 1 H), 8.40 (s, 2 H), 8.02 (s, 1 H), 7.19 (t, J = 51.2 Hz, 1 H), 5.40 (s, 2 H), 3.40-3.30 (m, 2 H), 2.73 (q, J = 7.6 Hz, 2 H) 1.39 (t, J = 7.6 Hz, 3 H), 1.25 (t, J = 7.6 Hz, 3 H). LCMS RT = 1.215 min, m/z = 430.2 | 0.0162 |
| I-147 Example 4 | N-[5-(difluoromethoxy)pyridin-3-yl]-N-({5-[5-(difluoromethyl)-1,3,4-oxadiazol-2-yl]-1,3-thiazol-2-yl}methyl)methanesulfonamide | 1H NMR (400 MHz, CDCl3) δ 8.62 (s, 1 H), 8.49 (s, 1 H), 8.43 (s, 1 H), 7.69 (s, 1 H), 6.92 (t, J = 51.6 Hz, 1 H), 6.59 (t, J = 72.0 Hz, 1 H), 5.28 (s, 2 H), 3.12 (s, 3 H). LCMS RT = 1.512 min, m/z = 453.8 | 0.019 |
| I-148 Example 4 | N-({5-[5-(difluoromethyl)-1,3,4-oxadiazol-2-yl]-1,3-thiazol-2-yl}methyl)-N-(5-methoxypyridin-3-yl)ethane-1-sulfonamide | 1H NMR (400 MHz, CDCl3) δ ppm 8.39 (s, 1 H), 8.30-8.28 (m, 2 H), 7.38 (s, 1 H), 6.91 (t, J = 51.6 Hz, 1 H), 5.30 (s, 2 H), 3.87 (s, 3 H), 3.21 (q, J = 7.6 Hz, 2 H), 1.46 (t, J = 7.6 Hz, 3 H). LCMS RT = 1.360 min, m/z = 431.9 [M + H]+ | 0.0192 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-149 Example 4 | 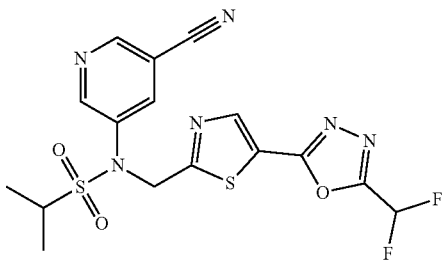 [SMILES: CC(C)S(=O)(=O)N(Cc1ncc(-c2nnc(C(F)F)o2)s1)c1cncc(C#N)c1]<br>N-(5-cyanopyridin-3-yl)-N-({5-[5-(difluoromethyl)-1,3,4-oxadiazol-2-yl]-1,3-thiazol-2-yl}methyl)propane-2-sulfonamide | 1H NMR (400 MHz, CDCl3) δ 8.95 (d, J = 2.8 Hz, 1 H), 8.80 (s, 1 H), 8.39 (s, 1 H), 8.16 (s, 1 H), 6.92 (t, J = 51.6 Hz, 1 H), 5.30 (s, 2 H), 3.39-3.25 (m, 1 H), 1.45 (d, J = 6.8 Hz, 6 H).<br>LCMS RT = 1.584 min, m/z = 440.9 | 0.0231 |
| I-150 Example 4 | 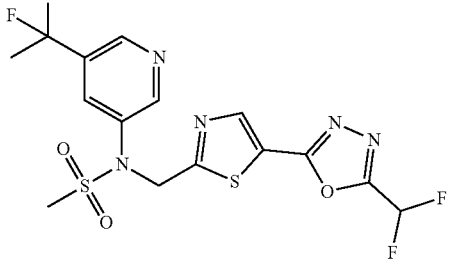<br>N-[5-(1,1-difluorethyl)pyridin-3-yl]-N-({5-[5-(difluoromethyl)-1,3,4-oxadiazol-2-yl]-1,3-thiazol-2-yl}methyl)methanesulfonamide | 1H NMR (400 MHz, CDCl3) δ 8.80 (s, 1 H), 8.75 (s, 1 H), 8.43 (s, 1 H), 7.98 (s, 1 H), 6.92 (t, J = 51.6 Hz, 1 H), 5.29 (s, 2 H), 3.12 (s, 3 H), 1.98 (t, J = 18.0 Hz, 3 H).<br>LCMS RT = 1.554 mm, m/z = 451.8 | 0.0255 |
| I-151 Example 4 | 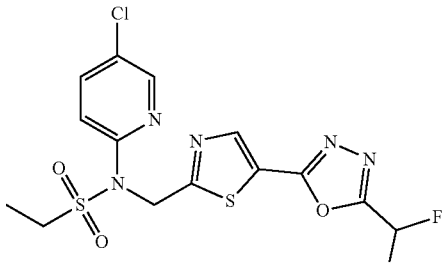<br>N-(5-chloropyridin-2-yl)-N-({5-[5-(difluoromethyl)-1,3,4-oxadiazol-2-yl]-1,3-thiazol-2-yl}methyl)ethane-1-sulfonamide | 1H NMR (400 MHz, CDCl3) δ 8.37 (d, J = 4.0 Hz, 2 H), 7.74-7.67 (m, 2 H), 6.90 (t, J = 51.6 Hz, 1 H), 5.56 (s, 2 H), 3.29 (q, J = 7.2 Hz, 2 H), 1.39 (t, 1 = 7.2 Hz, 3 H).<br>LCMS RT = 1.826 min, m/z = 436.1 | 0.0315 |
| I-152 Example 4 | 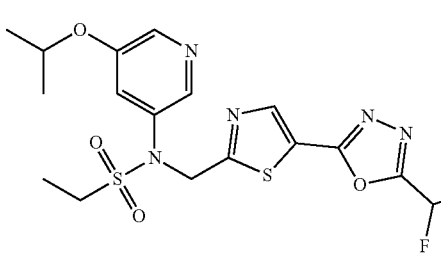<br>N-({5-[5-(difluoromethyl)-1,3,4-oxadiazol-2-yl]-1,3-thiazol-2-yl}methyl)-N-[5-(propan-2-yloxy)pyridin-3-yl]ethane-1-sulfonamide | 1H NMR (400 MHz, CDCl3) δ 8.39 (s, 1 H), 8.25 (s, 2 H), 7.35 (s, 1 H), 6.91 (t, J = 51.6 Hz, 1 H), 5.29 (s, 2 H), 4.61-4.55 (m, 1 H), 3.25-3.18 (m, 2 H), 1.61 (s, 3 H), 1.36 (d, J = 4.4 Hz, 6 H).<br>LCMS RT = 1.666 min, m/z = 459.9 | 0.0429 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-153 Example 4 | N-({5-[5-(difluoromethyl)-1,3,4-oxadiazol-2-yl]-1,3-thiazol-2-yl}methyl)-N-(5-methylpyridin-2-yl)ethane-1-sulfonamide | 1H NMR (400 MHz, CDCl3) δ 8.22 (s, 1 H), 8.10 (s, 1 H), 7.40 (s, 2 H), 6.75 (t, J = 51.6 Hz, 1 H), 5.42 (s, 2 H), 3.09 (q, J = 7.6 Hz, 2 H), 2.18 (s, 3 H), 1.23 (t, J = 7.2 Hz, 3 H). LCMS RT = 1.666 mm, m/z = 416.2 | 0.043 |
| I-155 Example 4 | N-({5-[5-(difluoromethyl)-1,3,4-oxadiazol-2-yl]-1,3-thiazol-2-yl)methyl)-N-(4-methylpyridin-2-yl)ethane-1-sulfonamide | 1H NMR (400 MHz, CDCl3) δ 8.39 (s, 1 H), 8.29 (d, J = 4.8 Hz, 1 H), 7.47 (s, 1 H), 7.01 (d, J = 4.8 Hz, 1 H), 6.90 (t, J = 51.6 Hz, 1 H), 5.60 (s, 2 H), 3.28 (q, J = 7.6 Hz, 2 H), 2.40 (s, 3 H), 1.39 (t, J = 7.2 Hz, 3 H). LCMS RT = 1.635 min m/z = 416.2 | 0.0528 |
| I-156 Example 4 | N-(5-chloropyridin-3-yl)-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CD3OD) δ ppm 8.68 (d, J = 2.4 Hz, 1 H), 8.52 (d, J = 2.0 Hz, 1 H), 8.44 (s, 1 H), 8.17 (t, J = 2.0 Hz, 1 H), 7.22 (t, J = 52.0 Hz, 1 H), 5.45 (s, 2 H), 3.73-3.70 (m, 4 H), 3.58 (t, J = 7.6 Hz, 2 H), 2.89 (t, J = 6.8 Hz, 2 H) 2.58-2.51 (m, 4 H). LCMS RT = 0.992 min, m/z = 521.2 | 0.00253 |
| I-157 Example 4 | N-[5-(difluoromethoxy)pyridin-3-yl]-N-({5-[5-(difluoromethyl)-1,3,4-oxadiazol-2-yl]-1,3-thiazol-2-yl}methyl)-2-methylpropane-1-sulfonamide | 1H NMR (400 MHz, CDCl3) δ 8.59 (d, J = 2.0 Hz, 1 H), 8.47 (d, J = 2.0 Hz, 1 H), 8.40 (s, 1 H), 7.67 (t, J = 2.4 Hz, 1 H), 6.91 (t, J = 51.6 Hz, 1 H), 6.59 (t, J = 72.0 Hz, 1 H), 5.28 (s, 2 H), 3.05 (d, J = 8.0 Hz, 2 H), 2.40-2.30 (m, 1 H), 1.12 (d, J = 6.8 Hz, 6 H). LCMS RT = 0.644 min, m/z = 496.1 | 0.00693 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (μM) |
|---|---|---|---|
| I-158 Example 4 | N-(5-chloropyridin-3-yl)-2-cyano-N-({5-[5-(difluoromethyl)-1,3,4-oxadiazol-2-yl]-1,3-thiazol-2-yl}methyl)ethane-1-sulfonamide | 1H NMR (400 MHz, CDCl3) δ ppm 8.63 (d, J = 2.4 Hz, 1 H), 8.60 (d, J = 2.0 Hz, 1 H), 8.46 (s, 1 H), 7.91 (t, J = 2.4 Hz, 1 H), 6.93 (T, J = 51.6 Hz, 1 H), 5.30 (s, 2 H), 3.54 (t, J = 7.2 Hz, 2 H), 2.98 (t, J = 7.2 Hz, 2 H). LCMS RT = 0.576 min, m/z = 461.1 | 0.00722 |
| I-159 Example 4 | N-[5-(1,1-difluoroethyl)pyridin-3-yl]-N-({5-[5-(difluoromethyl)-1,3,4-oxadiazol-2-yl]-1,3-thiazol-2-yl}methyl)-2-methoxyethane-1-sulfonamide | 1H NMR (400 MHz, CDCl3) δ 8.85 (s, 1 H), 8.56 (s, 1 H), 8.72 (s, 1 H), 8.35 (s, 1 H), 8.01 (s, 1 H), 6.91 (t, J = 51.6 Hz, 1 H), 5.26 (s, 2 H), 3.87 (t, J = 5.2 Hz, 2 H), 3.50 (s, 3 H), 3.36 (t, J = 5.2 Hz, 2 H), 1.97 (t, J = 18.4 Hz, 3 H). LCMS RT = 1.701 min, m/z = 495.9 | 0.00994 |
| I-160 Example 4 | N-({5-[5-(difluoromethyl)-1,3,4-oxadiazol-2-yl]-1,3-thiazol-2-yl}methyl)-N-(5-methylpyridin-3-yl)propane-1-sulfonamide | 1H NMR (400 MHz, CDCl3) δ 8.49 (d, J = 2.4 Hz, 1 H), 8.41 (s, 1 H), 8.38 (s, 1 H), 7.65 (s, 1 H), 6.91 (t, J = 51.6 Hz, 1 H), 5.27 (s, 2 H), 3.16-3.08 (m, 2 H), 2.37 (s, 3 H), 1.99-1.85 (m, 2 H), 1.09 (t, J = 7.2 Hz, 3 H). LCMS RT = 1.815 min, m/z = 430.2 | 0.0109 |
| I-161 Example 4 | N-(5-chloropyridin-3-yl)-N-({5-[5-(difluoromethyl)-1,3,4-oxadiazol-2-yl]-1,3-thiazol-2-yl}methyl)-2-methoxyethane-1-sulfonamide | 1H NMR (400 MHz, CDCl3) δ 8.67 (s, 1 H), 8.53 (s, 1 H), 8.35 (s, 1 H), 7.90 (t, J = 2.0 Hz, 1 H), 6.90 (t, J = 51.6 Hz, 1 H), 5.22 (s, 2 H), 3.86 (t, J = 5.6 Hz, 2 H) 3.49 (s, 3 H), 3.36 (t, J = 5.6 Hz, 2 H). LCMS RT = 1.529 min, m/z = 466.1 | 0.012 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC₅₀ (μM) |
|---|---|---|---|
| I-162 Example 4 | N-[5-(difluoromethoxy)pyridin-3-yl]-N-({5-[5-(difluoromethyl)-1,3,4-oxadiazol-2-yl]-1,3-thiazol-2-yl}methyl)propane-1-sulfonamide | 1H NMR (400 MHz, CDCl3) δ 8.60 (s, 1 H), 8.47 (s, 1 H), 8.40 (s, 1 H), 7.67 (s, 1 H), 6.91 (t, J = 51.6 Hz, 1 H), 6.59 (t, J = 72.0 Hz, 1 H), 5.29 (s, 2 H) 3.19-3.11 (m, 2 H), 1.99-1.86 (m, 2 H), 1.09 (t, J = 7.2 Hz, 3 H). LCMS RT = 1.794 min, m/z = 481.9 | 0.0144 |
| I-163 Example 4 | N-({5-[5-(difluoromethyl)-1,3,4-oxadiazol-2-yl]-1,3-thiazol-2-yl}methyl)-2-methyl-N-(pyridin-3-yl)propane-1-sulfonamide | 1H NMR (400 MHz, CDCl3) δ 8.70 (d, J = 2.4 Hz, 1 H), 8.60-8.55 (m, 1 H), 8.41 (s, 1 H), 8.07-8.01 (m, 1 H), 7.53-7.47 (m, 1 H), 7.20 (t, J = 51.6 Hz, 1 H), 5.37 (s, 2 H), 3.20 (d, J = 6.4 Hz, 2 H), 2.34-2.22 (m, 1 H), 1.10 (d, J = 6.4 Hz, 6 H). LCMS RT = 1.423 min, m/z = 430.2 | 0.0161 |
| I-164 Example 4 | N-({5-[5-(difluoromethyl)-1,3,4-oxadiazol-2-yl]-1,3-thiazol-2-yl}methyl)-2-(morpholin-4-yl)-N-(pyridin-3-yl)ethane-1-sulfonamide | 1H NMR (400 MHz, CDCl3) δ ppm 8.73 (d, J = 2.4 Hz, 1 H), 8.60-8.55 (m, 1 H), 8.38 (s, 1 H), 7.87-7.81 (m, 1 H), 7.38-7.33 (m, 1 H), 6.91 (t, J = 51.6 Hz, 1 H), 5.32 (s, 2 H), 3.76-3.72 (m, 4 H), 3.37 (t, J = 7.2 Hz, 2 H), 2.90 (t, J = 6.8 Hz, 2 H), 2.52-2.50 (m, 4 H). LCMS RT = 0.430 min, m/z = 487.2 | 0.0173 |
| I-165 Example 4 | N-[5-(difluoromethoxy)pyridin-3-yl]-N-({5-[5-(difluoromethyl)-1,3,4-oxadiazol-2-yl]-1,3-thiazol-2-yl}methyl)-2-methoxyethane-1-sulfonamide | 1H NMR (400 MHz, CD3OD) δ 8.59 (s, 1 H), 8.40 (s, 2 H), 7.87 (d, J = 2.4 Hz, 1 H), 7.19 (t, J = 51.6 Hz, 1 H), 6.97 (t, J = 72.8 Hz, 1 H), 5.34 (s, 2 H), 3.83 (t, J = 5.2 Hz, 2 H), 3.52 (t, 1 = 5.6 Hz, 2 H). 3.30 (t, J = 1.6 Hz, 3 H). LCMS RT = 1.533 mm, m/z = 498.2 | 0.0196 |

TABLE 3-continued

Characterization Data and HDAC6 Activity for Compounds of Formula (I).

| Cmpd ID/Prep | Stracture/Name | $^1$H NMR MS (m/z) (RT) | HDAC6 IC$_{50}$ (µM) |
|---|---|---|---|
| I-166 Example 4 | N-({5-[5-(difluoromethyl)-1,3,4-oxadiazol-2-yl]-1,3-thiazol-2-yl}methyl)-2-methoxy-N-(5-methylpyridin-3-yl)ethane-1-sulfonamide | 1H NMR (400 MHz, CD3OD) δ 8.49 (s, 1 H), 8.39 (s, 1 H), 8.34 (s, 1 H), 7.87 (s, 1 H), 7.20 (t, J = 51.6 Hz, 1 H), 5.31 (s, 2 H), 3.83 (t, J = 5.2 Hz, 2 H), 3.49 (t, 1 = 5.6 Hz, 2 H), 3.43 (s, 3 H), 2.38 (s, 3 H). LCMS RT = 2.329 min, m/z = 446.5 | 0.0266 |
| I-167 Example 4 | N-(5-chloropyridin-2-yl)-N-({5-[5-(difluoromethyl)-1,3,4-oxadiazol-2-yl]-1,3-thiazol-2-yl}methyl)propane-1-sulfonamide | 1H NMR (400 MHz, CDCl3) δ 8.40-8.35 (m, 2 H), 7.73-7.68 (m, 1 H), 7.66-7.60 (m, 1 H), 6.89 (t, J = 51.6 Hz, 1 H), 5.55 (s, 2 H), 3.26-3.17 (m, 2 H), 1.93-1.81 (m, 2 H), 1.05 (t, J = 7.4 Hz. 3H). LCMS RT = 2.072 min, m/z = 449.8 | 0.0266 |
| I-168 Example 4 | N-(5-cyanopyridin-3-yl)-N-({5-[5-(difluoromethyl)-1,3,4-oxadiazol-2-yl]-1,3-thiazol-2-yl}methyl)-2-methylpropane-1-sulfonamide | 1H NMR (400 MHz, CDCl3) δ 8.95 (d, J = 2.4 Hz, 1 H), 8.82 (s, 1 H), 8.42 (s, 1 H), 8.16 (s, 1 H), 6.92 (t, J = 52.0 Hz, 1 H) 5.28 (s, 2 H), 3.03 (d, J = 6.4 Hz, 2 H), 2.42-2.28 (m, 1 H), 1.12 (d, J = 6.8 Hz, 6 H). LCMS RT = 1.690 min, m/z = 455.2 | 0.0305 |
| I-169 Example 4 | N-({5-[5-(difluoromethyl)-1,3,4-oxadiazol-2-yl]-1,3-thiazol-2-yl}methyl)-N-(6-methylpyridin-2-yl)propane-1-sulfonamide | 1H NMR (400 MHz, CDCl3) δ 8.38 (s, 1 H), 7.61 (t, J = 7.6 Hz, 1 H), 7.45 (d, J = 8.4 Hz, 1 H), 7.02-6.75 (m, 2 H), 5.59 (s, 2 H), 3.22-3.15 (m, 2 H), 2.52 (s, 3 H), 1.93-1.80 (m, 2 H), 1.03 (t, J = 7.6 Hz, 3 H). LCMS RT = 1.942 min, m/z = 429.9 | 0.0309 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (µM) |
|---|---|---|---|
| I-170 Example 4 | N-({5-[5-(difluoromethyl)-1,3,4-oxadiazol-2-yl]-1,3-thiazol-2-yl}methyl)-N-(pyridin-3-yl)butane-1-sulfonamide | 1H NMR (400 MHz, CDCl3) δ 8.70 (s, 1 H), 8.58 (d, J = 4.8 Hz, 1 H), 8.38 (s, 1 H), 7.90-7.80 (m, 1 H), 7.45-7.31 (m, 1 H), 6.91 (t, J = 51.2 Hz, 1 H), 5.29 (s, 2 H), 3.21-3.06 (m, 2 H), 1.92-1.83 (m, 2 H), 1.52-1.43 (m, 2 H), 0.96 (t, J = 7.2 Hz, 3 H). LCMS RT = 0.623 min, m/z = 429.9 | 0.0264 |
| I-171 Example 2 | 1-({5-[5-(difluoromethyl)-1,3,4-oxadiazol-2-yl]-1,3-thiazol-2-yl}methyl)-1,2,3,4-tetrahydro-1,7-naphtbyridin-2-one | 1H NMR (400 MHz, CDCl3) δ 8.55 (s, 1 H), 8.42 (s, 1 H), 8.31 (d, J = 3.6 Hz, 1 H), 7.16 (d, J = 4.4 Hz, 1 H), 6.89 (t, J = 51.6 Hz, 1 H), 5.52 (s, 2 H), 3.04 (t, J = 6.8 Hz, 2 H), 2.81 (t, J = 8.0 Hz, 2 H). LCMS RT = 1.398 min, m/z = 363.9 | 0.0215 |
| I-172 Example 2 | 4-({5-[5-(difluoromethyl)-1,3,4-oxadiazol-2-yl]-1,3-thiazol-2-yl}methyl)-2H,3H,4H-pyrido[4,3-b][1,4]oxazin-3-one | 1H NMR (400 MHz, CDCl3) δ 8.52 (s, 1 H), 8.43 (s, 1 H), 8.27 (d, J = 5.6 Hz, 1 H), 6.96 (d, 1 = 5.2 Hz, 1 H), 6.90 (t, J = 51.6 Hz, 1 H), 5.52 (s, 2 H), 4.85 (s, 2 H). LCMS RT = 0.418 min, m/z = 366.0 | 0.025 |
| I-173 Example 2 | 4-((5-(5-(difluoromethyl)-1,3,4-oxadiazol-2-yl)thiazol-2-yl)methyl)-2,2-dimethyl-2H-pyrido[3,2-b][1,4]oxazin-3(4H)-one | $^1$H NMR (400 MHz, CDCl$_3$) δ 8.39 (s, 1 H), 8.01-8.05 (m, 1H), 7.29 (dd, J = 8.1, 1.5 Hz, 1 H), 7.01 (dd, J = 8.1, 1.5 Hz, 1H), 6.89 (t, J = 51.6 Hz, 1 H), 5.70 (s, 2 H) LCMS: RT = 5.00 min, m/z = 394.0 | 0.108 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-174 Example 4 | N-((5-(5-(difluoromethyl)-1,3,4-oxadiazol-2-yl)thiazol-2-yl)methyl)-N-(pyridin-3-yl)-2-(tetrahydro-1H-furo[3,4-c]pyrrol-5(3H)-yl)ethane-1-sulfonamide | 1H NMR (400 MHz, CDCl3) δ 8.76 (s, 1 H), 8.58 (d, J = 4.4 Hz, 1 H), 8.39 (s, 1 H), 7.89 (d, J = 8.4 Hz, 1 H), 7.40-7.35 (m, 1 H), 6.91 (t, J = 51.6 Hz, 1 H), 5.33 (s, 2 H), 3.75-3.70 (m, 4 H), 3.49 (t, J = 6.8 Hz, 2 H), 3.07 (t, 1 = 6.8 Hz, 2 H), 2.99-2.96 (m, 4 H), 2.49 (d, J = 6.0 Hz. 2H). LCMS RT = 1.435 min, m/z = 513.0 | 0.022 |
| I-175 Example 6 | N-({5-[5-(difluoromethyl)-1,3,4-oxadiazol-2-yl]-1,3-thiazol-2-yl}methyl)-N-(5-fluoropyridin-3-yl)-3-(morpholin-4-yl)propanamide | 1H NMR (400 MHz, CDCl3) δ 8.55 (d, J = 2.0 Hz, 1 H), 8.43-8.36 (m, 2 H), 7.50-7.44 (m, 1 H), 6.92 (t, J = 51.6 Hz, 1 H), 5.20 (s, 2 H), 3.71-3.66 (m, 4 H), 2.81 (t, J = 6.8 Hz, 2 H), 2.50-2.22 (m, 6 H). LCMS RT = 0.400 min, m/z = 469.2 | 0.496 |
| I-176 Example 2 | 1-({5-[5-(difluoromethyl)-1,3,4-oxadiazol-2-yl]-1,3-thiazol-2-yl}methyl)-1H,2H,3H-pyrido[3,4-b][1,4]oxazin-2-one | 1H NMR (400 MHz, CD3OD) δ 8.54-8.53 (m, 1 H), 8.13-8.10 (m, 1 H), 7.22 (t, J = 51.6 Hz, 1 H), 6.97-6.89 (m, 1 H), 5.84-5.78 (m, 1 H), 4.72-4.45 (m, 4 H). LCMS RT = 1.091 min, m/z = 365.8 | 2.52 |
| I-177 Example 4 | N-[5-(difluoromethoxy)pyridin-3-yl]-N-({5-[5-(difluoromethyl)-1,3,4-oxadiazol-2-yl]-1,3-thiazol-2-yl}methyl)butane-2-sulfonamide | 1H NMR (400 MHz, CDCl3) δ 8.59 (d, J = 2.0 Hz, 1 H), 8.45 (d, J = 2.4 Hz, 1 H), 8.37 (s, 1 H), 7.67 (t, J = 2.4 Hz, 1 H), 6.91 (t, J = 51.6 Hz, 1 H), 6.58 (t, J = 72.0 Hz, 1 H), 5.38-5.20 (m, 2 H), 3.15-3.07 (m, 1 H), 2.13-2.02 (m, 1 H), 1.73-1.60 (m, I H), 1.43 (d, J = 6.8 Hz, 3H), 1.05 (t, J = 7.2 Hz, 3 H). LCMS RT = 1.580 min, m/z = 496.2 | 0.006 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (μM) |
|---|---|---|---|
| I-178 Example 4 | N-({5-[5-(difluoromethyl)-1,3,4-oxadiazol-2-yl]-1,3-thiazol-2-yl}methyl)-N-[(pyridin-3-yl)methyl]ethane-1-sulfonamide | 1H NMR (400 MHz, CDCl3) δ 8.62-8.55 (m, 2 H), 8.42 (s, 1 H), 7.88-7.82 (m, 1 H), 7.38-7.34 (m, 1 H), 6.88 (t, J = 51.6 Hz, 1 H), 4.71 (s, 2 H), 4.60 (s, 2 H), 3.19 (q, J = 7.6 Hz, 2 H), 1.44 (t, J = 7.2 Hz, 3 H). LCMS RT = 1.031 min, m/z = 416 2 | 4.35 |
| I-179 Example 4 | N-({5-[5-(difluoromethyl)-1,3,4-oxadiazol-2-yl]-1,3-thiazol-2-yl}methyl)-2-{3-oxa-6-azabicyclo[3.1.1]heptan-6-yl}-N-(pyridin-3-yl)ethane-1-sulfonamide | 1H NMR (400 MHz, CDCl3) δ 8.76 (d, J = 2.4 Hz, 1 H), 8.58 (d, 1 = 3.2 Hz, 1 H), 8.38 (s, 1 H), 7.89-7.86 (m, 1 H), 7.39-7.35 (m, 1 H), 6.91 (t, J = 51.6 Hz, 1 H), 5.34 (s, 2 H), 4.22 (d, J = 11.2 Hz, 2 H), 3.81 (d, J = 11.6 Hz, 2 H), 3.64 (d, 1 = 6.4 Hz, 2 H), 3.36-3.20 (m, 4 H), 2.74-2.69 (m, 1 H), 1.91 (d, J = 8.8 Hz, 1 H). LCMS RT = 1.438 min, m/z = 499.0 | 0.013 |
| I-180 Example 4 | N-({5-[5-(difluoromethyl)-1,3,4-oxadiazol-2-yl]-1,3-thiazol-2-yl}methyl)-N-(5-fluoropyridin-3-yl)-2-{hexahydro-1H-furo[3,4-c]pyrrol-5-yl}ethane-1-sulfonamide | 1H NMR (400 MHz, CDCl3) δ 8.62 (s, 1 H), 8.45 (d, J = 2.4 Hz, 1 H), 8.38 (s, 1 H), 7.75-7.70 (m, 1 H), 6.91 (t, J = 51.6 Hz, 1 H), 5.35 (s, 2 H), 3.78-3.69 (m, 4 H), 3.34 (t, J = 6.8 Hz, 2 H), 2.94 (t, J = 6.4 Hz, 2 H), 2.87-2.86 (m, 2 H), 2.72-2.68 (m, 2 H), 2.49-2.46 (m, 2 H). LCMS RT = 0.417 min, m/z = 531.2 | 0.010 |
| I-181 Example 4 | N-({5-[5-(difluoromethyl)-1,3,4-oxadiazol-2-yl]-1,3-thiazol-2-yl}methyl)-N-[(5-fluoropyridin-2-yl)methyl]ethane-1-sulfonamide | 1H NMR (400 MHz, CDCl3) δ 8.44 (t, J = 2.0 Hz, 1 H), 8.41 (s, 1 H), 7.44 (d, J = 2.4 Hz, 1 H), 7.42 (s, 1 H), 6.92 (t, J = 51.6 Hz, 1 H), 4.86 (s, 2 H), 4.65 (s, 2 H), 3.23 (q, J = 7.2 Hz, 2 H), 1.42 (t, J = 7.2 Hz, 3 H). LCMS RT = 1.338 min, m/z = 434.2 | 3.46 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-182 Example 4 | N-({5-[5-(difluoromethyl)-1,3,4-oxadiazol-2-yl]-1,3-thiazol-2-yl}methyl)-N-(5-fluoropyridin-3-yl)-2-{3-oxa-6-azabicyclo[3.1.1]heptan-6-yl}ethane-1-sulfonamide | 1H NMR (400 MHz, CDCl3) δ 8.61 (s, 1 H), 8.46 (d, J = 2.4 Hz, 1 H), 8.39 (s, 1 H), 7.72-7.65 (m, 1 H), 6.91 (t, J = 51.6 Hz, 1 H), 5.35 (s, 2 H), 4.19 (d, J = 11.2 Hz, 2 H), 3.78 (d, J = 11.2 Hz, 2 H) 3.56 (d, J = 6.4 Hz, 2 H), 3.29-3.25 (m, 2 H), 3.21-3.18 (m, 2 H), 2.70-2.65 (m, 1 H), 1.89 (d, J = 8.4 Hz, 1 H) LCMS RT = 0.844 min, m/z = 517.3 | 0.018 |
| I-183 Example 4 | N-({5-[5-(difluoromethyl)-1,3,4-oxadiazol-2-yl]-1,3-thiazol-2-yl}methyl)-N-[(pyridin-2-yl)methyl]ethane-1-sulfonamide | 1H NMR (400 MHz, CDCl3) δ 8.59 (d, J = 4.4 Hz, 1 H), 8.40 (s, 1 H), 7.76-7.69 (m, 1 H), 7.39 (d, J = 7.6 Hz, 1 H), 7.25 (s, 1 H), 6.92 (t, J = 51.6 Hz, 1 H), 4.89 (s, 2 H), 4.68 (s, 2 H), 3.25 (q, J = 7.2 Hz, 2 H), 1.42 (t, J = 7.2 Hz, 3 H). LCMS RT = 0.932 min, m/z = 416.2 | 2.54 |
| I-184 Example 4 | N-({5-[5-(difluoromethyl)-1,3,4-oxadiazol-2-yl]-1,3-thiazol-2-yl}methyl)-2-{6-oxa-3-azabicyclo[3.1.1]heptan-3-yl]-N-(pyridin-3-yl)ethane-1-sulfonamide | 1H NMR (400 MHz, CDCl3) δ 8.73 (d, J = 2.4 Hz, 1 H), 8.60 (d, J = 3.2 Hz, 1 H), 8.39 (s, 1 H), 7.89-7.82 (m, 1 H), 7.40-7.33 (m, 1 H), 6.91 (t, J = 51.6 Hz, 1 H), 5.31 (s, 2 H), 4.53 (d, J = 6.4 Hz, 2 H), 3.46-3.42 (m, 2 H), 3.21-3.02 (m, 5 H), 2.86 (d, J = 11.2 Hz, 2 H), 2.29 (d, J = 8.4 Hz, 1 H). LCMS RT = 1.352 min, m/z = 498.9 | 0.014 |
| I-185 Example 2 | N-({5-[5-(difluoromethyl)-1,3,4-oxadiazol-2-yl]-1,3-thiazol-2-yl}methyl)-3-(morpholin-4-yl)-N-(pyridin-3-yl)propanamide | 1H NMR (400 MHz, CDCl3) δ 8.65 (d, J = 4.4 Hz, 1 H), 8.55 (d, J = 2.4 Hz, 1 H), 8.38 (s, 1 H), 7.63 (d, J = 8.0 Hz, 1 H), 7.43-7.39 (m, 1 H), 6.92 (t, J = 51.6 Hz, 1 H), 5.21 (s, 2 H), 3.65 (t, J = 4.4 Hz, 4 H), 2.73 (t, J = 7.2 Hz, 2 H), 2.38-2.33 (m, 6 H). LCMS RT = 0.411 min, m/z = 451.2 | 0.516 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-186 Example 4 | N-({5-[5-(difluoromethyl)-1,3,4-oxadiazol-2-yl]-1,3-thiazol-2-yl}methyl)-N-(5-fluoropyridin-3-yl)-2-(1,4-oxazepan-4-yl)ethane-1-sulfonamide | 1H NMR (400 MHz, CDCl3) δ 8.58 (s, 1 H), 8.47 (d, J = 2.4 Hz, 1 H), 8.40 (s, 1 H), 7.70-7.67 (m, 1 H), 6.91 (t, J = 51.6 Hz, 1 H), 5.32 (s, 2 H), 3.81 (t, J = 6.4 Hz, 2 H), 3.75 (t, J = 4.8 Hz, 2 H), 3.41 (t, J = 7.2 Hz, 2 H), 3.12 (t, J = 7.6 Hz, 2 H) 2.84-2.76 (m, 4 H), 1.97-1.92 (m, 2 H). LCMS RT = 0.414 min, m/z = 519.2 | 0.0276 |
| I-187 Example 4 | N-({5-[5-(difluoromethyl)-1,3,4-oxadiazol-2-yl]-1,3-thiazol-2-yl}methyl)-2-[(1S,4S)-2-oxa-5-azabicyclo[2.2.1]heptan-5-yl]-N-(pyridin-3-yl)ethane-1-sulfonamide | 1H NMR (400 MHz, CDCl3) δ 8.74 (d, J = 2.4 Hz, 1 H), 8.60-8.57 (m, 1 H), 8.38 (s, 1 H), 7.88-7.85 (m, 1 H), 7.40-7.26 (m, 1 H), 6.91 (t, J = 51.6 Hz, 1 H), 5.37-5.25 (m, 2 H), 4.47 (s, 1 H), 4.02 (d, J = 8.4 Hz, 1 H), 3.70-3.55 (m, 1 H), 3.58 (s, 1 H), 3.36 (t, J = 6.8 Hz, 2 H), 3.22-3.09 (m, 2 H), 3.00-2.92 (m, 1 H), 2.60 (d, J = 9.6 Hz, 1 H), 1.86-1.80 (m, 2 H). LCMS RT = 0.429 min, m/z = 499.2 | 0.0247 |
| I-188 Example 4 | N-({5-[5-(difluoromethyl)-1,3,4-oxadiazol-2-yl]-1,3-thiazol-2-yl)methyl)-N-(5-fluoropyridin-3-yl)-2-[(1R,4R)-2-oxa-5-azabicyclo[2.2.1]heptan-5-yl]ethane-1-sulfonamide | 1H NMR (400 MHz, CDCl3) δ 8.58 (s, 1 H), 8.47 (d, J = 2.4 Hz, 1 H), 8.39 (s, 1 H), 7.69-7.66 (m, 1 H), 6.91 (t, J = 51.6 Hz, 1 H), 5.37-5.27 (m, 2 H), 4.47 (s, 1 H), 4.02 (d, J = 8.0 Hz, 1 H), 3.68 (dd, J = 8.4, 1.6 Hz, 1 H), 3.58 (s, 1 H), 3.38 (t, J = 6.8 Hz, 2 H), 3.22-3.09 (m, 2 H), 2.98-2.96 (m, 1 H), 2.60 (d, J = 10.0 Hz, 1 H), 1.85-1.83 (m, 2 H). LCMS RT = 0.457 min, m/z = 517.2 | 0.0151 |
| I-189 Example 4 | N-({5-[5-(difluoromethyl)-1,3,4-oxadiazol-2-yl]-1,3-thiazol-2-yl)methyl)-2-[(2S)-2-methylmorpholin-4-yl]-N-(pyridin-3-yl)ethane-1-sulfonamide | 1H NMR (400 MHz, CDCl3) δ 8.73 (d, J = 2.4 Hz, 1 H), 8.59 (d, J = 3.6 Hz, 1 H), 8.38 (s, 1 H), 7.88-7.85 (m, 1 H), 7.39-7.35 (m, 1 H), 6.91 (t, J = 51.6 Hz, 1 H), 5.32 (s, 2 H), 3.91-3.88 (m, 1 H), 3.71-3.62 (m, 2 H), 3.38 (t, J = 6.8 Hz, 2 H), 2.90 (t, J = 7.2 Hz, 2 H), 2.76-2.69 (m, 2 H), 2.28-2.21 (m, 1 H), 1.93 (t, J = 10.8 Hz, 1 H), 1.17 (d, J = 6.0 Hz, 3 H). LCMS RT = 1.427 min, m/z = 500.9 | 0.0363 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-190 Example 4 | 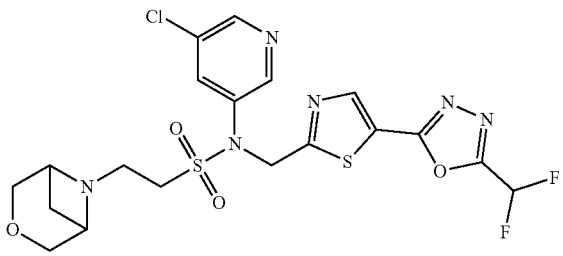 [SMILES: O=S(=O)(CCN1C2COCC1C2)N(Cc1ncc(-c2nnc(C(F)F)o2)s1)c1cncc(Cl)c1]<br>N-(5-chloropyridin-3-yl)-N-({5-[5-(difluoromethyl)-1,3,4-oxadiazol-2-yl]-1,3-thiazol-2-yl}methyl)-2-{3-oxa-6-azabicyclo[3.1.1]heptan-6-yl}ethane-1-sulfonamide | 1H NMR (400 MHz, CDCl3) δ 8.65 (d, J = 2.4 Hz, 1 H), 8.54 (d, J = 2.4 Hz, 1 H), 8.39 (s, 1 H), 7.95 (t, J = 2.4 Hz, 1 H), 6.91 (t, J = 51.6 Hz, 1 H), 5.34 (s, 2 H), 4.21 (d, J = 11.6 Hz, 2 H), 3.80 (d, J = 11.2 Hz, 2 H), 3.60 (d, J = 6.0 Hz, 2 H), 3.32-3.25 (m, 2 H), 3.24-3.17 (m, 2 H), 2.77-2.63 (m, 1 H), 1.91 (d, J = 8.4 Hz, 1 H).<br>LCMS RT = 0.968 min, m/z = 533.2 | 0.016 |
| I-191 Example 4 | 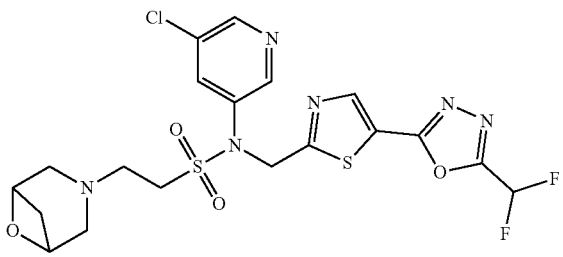 [SMILES: O=S(=O)(CCN1CC2CC(C1)O2)N(Cc1ncc(-c2nnc(C(F)F)o2)s1)c1cncc(Cl)c1]<br>N-(5-chloropyridin-3-yl)-N-({5-[5-(difluoromethyl)-1,3,4-oxadiazol-2-yl]-1,3-thiazol-2-yl}methyl)-2-{6-oxa-3-azabicyclo[3.1.1]heptan-3-yl}ethane-1-sulfonamide | 1H NMR (400 MHz, CDCl3) δ 8.62 (d, J = 2.0 Hz, 1 H), 8.55 (d, J = 2.0 Hz, 1 H), 8.41 (s, 1 H), 7.90 (t, J = 2.4 Hz, 1 H), 6.91 (t, 1 = 51.2 Hz, 1 H), 5.29 (s, 2 H), 4.52 (d, 1 = 6.4 Hz, 2 H), 3.43 (t, J = 6.8 Hz, 2 H), 3.18 (t, J = 7.2 Hz, 2 H), 3.10 (d, 1 = 10.8 Hz, 2 H), 3.06-2.80 (m, 3 H), 2.28 (d, J = 8.0 Hz, 1 H).<br>LCMS RT = 0.482 mm, m/z = 533.2 | 0.0124 |
| I-192 Example 4 | 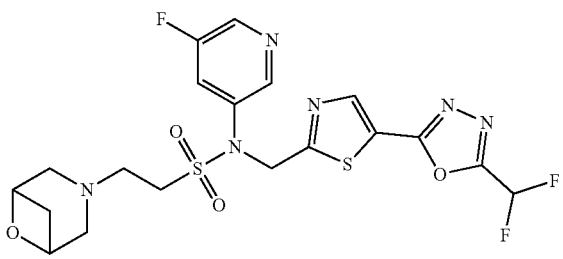 [SMILES: O=S(=O)(CCN1CC2CC(C1)O2)N(Cc1ncc(-c2nnc(C(F)F)o2)s1)c1cncc(F)c1]<br>N-({5-[5-(difluoromethyl)-1,3,4-oxadiazol-2-yl]-1,3-thiazol-2-yl}methyl)-N-(5-fluoropyridin-3-yl)-2-{6-oxa-3-azabicyclo[3.1.1]heptan-3-yl}ethane-1-sulfonamide | 1H NMR (400 MHz, CDCl3) δ 8.57 (s, 1 H), 8.46 (d, J = 2.4 Hz, 1 H), 8.40 (s, 1 H), 7.73-7.61 (m, 1 H), 6.92 (t, J = 51.2 Hz, 1 H), 5.31 (s, 2 H), 4.52 (d, J = 6.0 Hz, 2 H), 3.46 (t, J = 6.8 Hz, 2 H), 3.18 (t, J = 7.6 Hz, 2 H), 3.12 (d, J = 11.0 Hz, 2 H), 3.08-3.01 (m, 1 H), 2.86 (d, J = 11.2 Hz, 2 H), 2.27 (d, J = 8.0 Hz, 1 H).<br>LCMS RT = 1.368 min, m/z = 517.2 | 0.0168 |
| I-193 Example 4 | 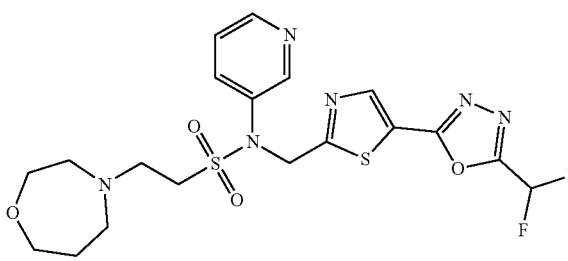<br>N-({5-[5-(difluoromethyl)-1,3,4-oxadiazol-2-yl]-1,3-thiazol-2-yl}methyl)-2-(1,4-oxazepan-4-yl)-N-(pyridin-3-yl)ethane-1-sulfonamide | 1H NMR (400 MHz, CDCl3) δ ppm 8.73 (d, J = 2.4 Hz, 1 H), 8.58 (d, J = 4.0 Hz, 1 H), 8.38 (s, 1 H), 7.86 (d, J = 8.0 Hz, 1 H), 7.39-7.35 (m, 1 H), 6.92 (t, J = 51.6 Hz, 1 H), 5.32 (s, 2 H), 3.80 (t, J = 6.0 Hz, 2 H), 3.75-3.73 (m, 2 H), 3.37 (t, J = 7.6 Hz, 2 H), 3.10 (t, J = 6.4 Hz, 2 H), 2.79-2.75 (m, 4 H), 1.95-1.91 (m, 2 H).<br>LCMS RT = 0.429 min, m/z = 501.2 | 0.0203 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-194 Example 4 | N-({5-[5-(difluoromethyl)-1,3,4-oxadiazol-2-yl]-1,3-thiazol-2-yl}methyl)-2-[(2R)-2-methylmorpholin-4-yl]-N-(pyridin-3-yl)ethane-1-sulfonamide | 1H NMR (400 MHz, CDCl3) δ ppm 8.73 (s, 1 H), 8.59 (d, J = 4.4 Hz, 1 H), 8.38 (s, 1 H), 7.86-7.83 (m, 1 H), 7.38-7.35 (m, 1 H), 6.91 (t, J = 51.2 Hz, 1 H), 5.31 (s, 2 H), 3.87-3.67 (m, 1 H), 3.66-3.64 (m, 2 H), 3.64 (t, 1 = 6.8 Hz, 2 H), 2.89 (t, J = 6.8 Hz, 2 H), 2.74-2.67 (m, 2 H) 2.24-2.23 (m, 1 H), 1.92 (t, J = 6.8 Hz, 1 H), 1.17 (d, J = 6.8 Hz, 3H). LCMS RT = 0.748 mm. m/z = 501.2 | 0.0267 |
| I-195 Example 2 | N-(5-chloropyridin-3-yl)-N-({5-[5-(difluoromethyl)-1,3,4-oxadiazol-2-yl]-1,3-thiazol-2-yl}methyl)-3-(morpholin-4-yl)propanamide | 1H NMR (400 MHz, CDCl3) δ ppm 8.62 (s, 1 H), 8.44 (s, 1 H), 8.39 (s, 1 H), 7.72 (s, 1 H), 6.92 (t, J = 51.6 Hz, 1 H), 5.18 (s, 2 H), 3.17-3.69 (m, 8 H), 2.86-2.83 (m, 2 H), 2.44-2.41 (m, 2 H). LCMS RT = 1.381 min, m/z = 485.3 | 0.312 |
| I-196 Example 4 | N-({5-[5-(difluoromethyl)-1,3,4-oxadiazol-2-yl]-1,3-thiazol-2-yl)methyl)-2-[(1R,4R)-2-oxa-5-azabicyclo[2.2.1]heptan-5-yl]-N-(pyridin-3-yl)ethane-1-sulfonamide | 1H NMR (400 MHz, CDCl3) δ 8.74 (s, 1 H), 8.59 (d, J = 4.0 Hz, 1 H), 8.39 (s, 1 H), 7.87 (d, J = 8.4Hz, 1 H), 7.39-7.35 (m, 1 H), 6.91 (t, J = 51.6 Hz, 1 H), 5.36-5.27 (m, 2 H), 4.48 (s, 1 H), 4.05 (d, J = 8.4 Hz, 1 H), 3.70-3.66 (m, 2 H), 3.43 (t, J = 6.8 Hz, 2 H), 3.26-3.13 (m, 2 H), 3.03 (d, J = 10.0 Hz, 1 H), 2.66 (d, 1 = 10.4 Hz, 1 H), 1.95-1.85 (m, 2 H). LCMS RT = 1.117 min, m/z = 499.2 | 0.0497 |
| I-197 Example 4 | N-(5-chloropyridin-3-yl)-N-({5-[5-(difluoromethyl)-1,3,4-oxadiazol-2-yl]-1,3-thiazol-2-yl}methyl)-2-[(2R)-2-methylmorpholin-4-yl]ethane-1-sulfonamide | 1H NMR (400 MHz, CDCl3) δ 8.63 (d, J = 2.0 Hz, 1 H), 8.54 (d, J = 2.0 Hz, 1 H), 8.39 (s, 1 H), 7.91 (t, J = 2.0 Hz, 1 H), 6.91 (t, J = 51.6 Hz, 1 H), 5.30 (s, 2 H), 3.93-3.85 (m, 1 H), 3.72-3.60 (m, 2 H), 3.36 (t, J = 6.8 Hz, 2 H), 2.88 (t, J = 6.8 Hz, 2 H), 2.75-2.65 (m, 2 H), 2.28-2.17 (m, 1 H), 1.91 (t, J = 10.8 Hz, 1 H), 1.17 (d, J = 6.4 Hz, 3 H). LCMS RT = 1.558 min, m/z = 535.2 | 0.0472 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-198 Example 2 | 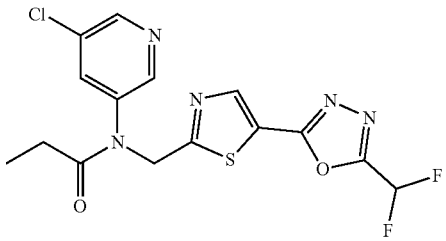<br>N-(5-chloropyridin-3-yl)-N-({5-[5-(difluoromethyl)-1,3,4-oxadiazol-2-yl]-1,3-thiazol-2-yl}methyl)propanamide | 1H NMR (400 MHz, CDCl3) δ 8.62 (s, 1 H), 8.44-8.35 (m, 2 H), 7.67 (t, J = 2.0 Hz, 1 H), 6.92 (t, J = 51.6 Hz, 1 H), 5.18 (s, 2 H), 2.18 (q, J = 7.2Hz, 2 H), 1.13(t, J = 7.6 Hz, 3 H).<br>LCMS RT = 1.929 min, m/z = 400.2 | 0.299 |
| I-199 Example 2 | 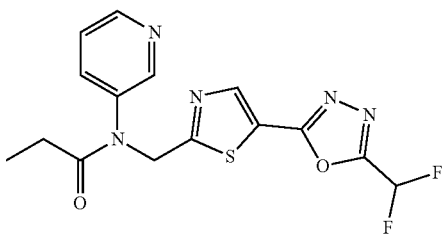 [SMILES: CCC(=O)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-N-(pyridin-3-yl)propanamide | 1H NMR (400 MHz, CDCl3) δ 8.64 (d, J = 4.0 Hz, 1 H), 8.53 (s, 1 H), 8.37 (s, 1 H), 7.61 (d, J = 8.0 Hz, 1 H), 7.42-7.36 (m, 1 H), 6.91 (t, J = 51.6 Hz, 1 H), 5.20 (s, 2 H), 2.15 (q, J = 7.2 Hz, 2 H), 1.12 (t, J = 7.2 Hz, 3 H).<br>LCMS RT = 1.372 min, m/z = 366.2 | 0.355 |
| I-200 Example 2 | 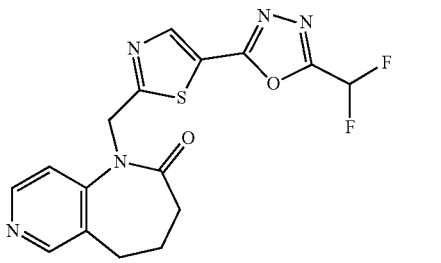 [SMILES: O=C1CCCc2cnccc2N1Cc1ncc(-c2nnc(C(F)F)o2)s1]<br>1-({5-[5-(difluoromethyl)-1,3,4-oxadiazol-2-yl]-1,3-thiazol-2-yl}methyl)-1H,2H,3H,4H,5H-pyrido[4,3-b]azepin-2-one | 1H NMR (400 MHz, CDCl3) δ 8.56 (d, J = 5.2 Hz, 1 H), 8.46 (s, 1 H), 8.39 (s, 1 H), 7.36 (d, J = 5.6 Hz, 1 H), 6.91 (t, J = 51.6 Hz, 1 H), 5.33 (s, 2 H), 2.80 (t, J = 7.2 Hz, 2 H), 2.44 (t, J = 7.2 Hz, 2 H), 2.36-2.24 (m, 2 H).<br>LCMS RT = 0.993 min, m/z = 378.2 | 0.125 |
| I-201 Example 4 | 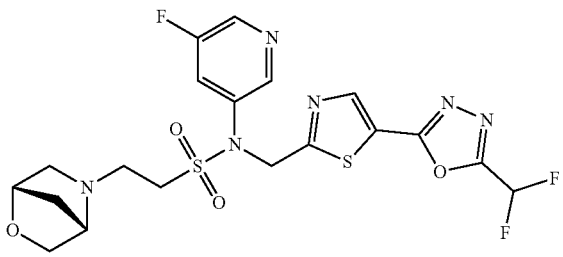 [SMILES: O=S(=O)(CCN1C[C@@H]2C[C@H]1CO2)N(Cc1ncc(-c2nnc(C(F)F)o2)s1)c1cncc(F)c1]<br>N-({5-[5-(difluoromethyl)-1,3,4-oxadiazol-2-yl]-1,3-thiazol-2-yl)methyl)-N-(5-fluoropyridin-3-yl)-2-[(1S,4S)-2-oxa-5-azabicyclo[2.2.1]heptan-5-yl]ethane-1-sulfonamide | 1H NMR (400 MHz, CDCl3) δ 8.57 (s, 1 H), 8.46 (d, J = 2.4 Hz, 1 H), 8.39 (s, 1 H), 7.70-7.62 (m, 1 H), 6.91 (t, J = 51.6 Hz, 1 H), 5.39-5.25 (m, 2 H), 4.46 (s, 1 H), 4.00 (d, J = 8.0 Hz, 1 H), 3.69-3.64 (m, 1 H), 3.52 (s, 1 H), 3.34 (t, J = 6.8 Hz, 2 H), 3.19-3.07 (m, 2 H), 2.94 (d, J = 10.0 Hz, 1 H), 2.56 (d, 1 = 10.0 Hz, 1H), 1.89-1.79 (m, 2 H).<br>LCMS RT = 0.459 min, m/z = 517.2 | 0.0207 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-202 Example 4 | 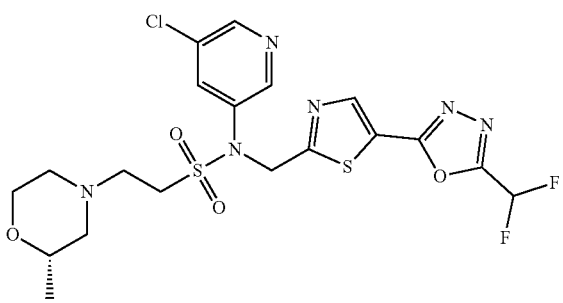<br>N-(5-chloropyridin-3-yl)-N-({5-[5-(difluoromethyl)-1,3,4-oxadiazol-2-yl]-1,3-thiazol-2-yl}methyl)-2-[(2S)-2-methylmorpholin-4-yl]ethane-1-sulfonamide | 1H NMR (400 MHz, CDCl3) δ 8.63 (s, 1 H), 8.54 (s, 1 H), 8.39 (s, 1 H), 7.91 (s, 1 H), 6.91 (t, J = 51.2 Hz, 1 H), 5.30 (s, 2 H), 3.94-3.85 (m, 1 H), 3.74-3.62 (m, 2 H), 3.43 (t, J = 6.8 Hz, 2 H), 2.88 (t, J = 6.8 Hz, 2 H), 2.72 (t, J = 12.8 Hz, 2 H), 2.28-2.17 (m, 1 H), 1.92 (t, J = 9.6 Hz, 1 H), 1.17 (d, J = 6.0 Hz, 3 H). LCMS RT = 1.561 min, m/z = 535.2 | 0.0127 |
| I-203 Example 4 | 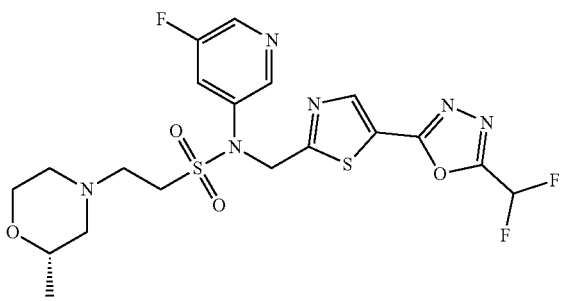 [SMILES: C[C@H]1CN(CCS(=O)(=O)N(Cc2ncc(-c3nnc(C(F)F)o3)s2)c2cncc(F)c2)CCO1]<br>N-({5-[5-(difluoromethyl)-1,3,4-oxadiazol-2-yl]-1,3-thiazol-2-yl}methyl)-N-(5-fluoropyridin-3-yl)-2-[(2S)-2-methylmorpholin-4-yl]ethane-1-sulfonamide | 1H NMR (400 MHz, CDCl3) δ 8.58 (s, 1 H), 8.47 (d, 1 = 2.4 Hz, 1 H), 8.40 (s, 1 H), 7.68 (d, J = 9.2 Hz, 1 H), 6.92 (t, J = 51.2 Hz, 1 H), 5.32 (s, 2 H), 3.91-3.71 (m, 1 H), 3.72-3.64 (m, 2 H), 3.41 (t, J = 6.8 Hz, 2 H), 2.91 (t, J = 7.2 Hz, 2 H), 2.73 (t, J = 12.8 Hz, 2 H), 2.29-2.22 (m, 1 H), 1.96-1.94 (m, 1 H), 1.17 (d, J = 6.4 Hz, 3 H). LCMS RT = 1.660 mm, m/z = 519.0 | 0.0254 |
| I-204 Example 4 | 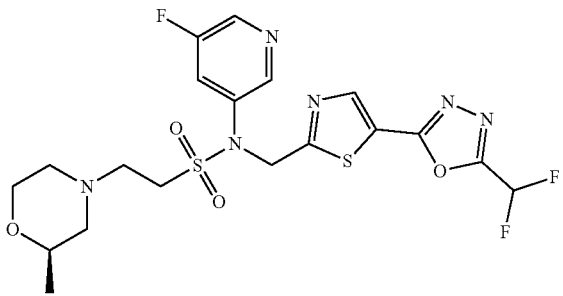<br>N-({5-[5-(difluoromethyl)-1,3,4-oxadiazol-2-yl]-1,3-thiazol-2-yl)methyl)-N-(5-fluoropyridin-3-yl)-2-[(2R)-2-methylmorpholin-4-yl]ethane-1-sulfonamide | 1H NMR (400 MHz, CDCl3) δ 8.58 (s, 1 H), 8.47 (s, 1 H), 8.40 (s, 1 H), 7.70-7.66 (m, 1 H), 6.91 (t, J = 51.6 Hz, 1 H), 5.32 (s, 2 H), 3.89 (d, J = 9.6 Hz, 1 H), 3.70-3.60 (m, 2 H), 3.37 (t, J = 6.8 Hz, 2 H), 2.88 (t, J = 6.8 Hz, 2 H), 2.72-2.65 (m, 2 H), 2.26-2.20 (m, 1 H), 1.91 (t, J = 10.4 Hz, 1 H), 1.17 (d, J = 6.0 Hz, 3 H). LCMS RT = 1.664 min, m/z = 518.9 | 0.0336 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-205 Example 4 | N-(5-chloropyridin-3-yl)-N-({5-[5-(difluoromethyl)-1,3,4-oxadiazol-2-yl]-1,3-thiazol-2-yl}methyl)-2-[(1R,4R)-2-oxa-5-azabicyclo[2.2.1]heptan-5-yl]ethane-1-sulfonamide | 1H NMR (400 MHz, CDCl3) δ 8.62 (d, J = 2.0 Hz, 1 H), 8.54 (d, J = 2.0 Hz, 1 H), 8.40 (s, 1 H), 7.91 (t, J = 2.0 Hz, 1 H), 6.91 (t, J = 51.6 Hz, 1 H), 5.40-5.21 (m, 2 H), 4.47 (s, 1 H), 4.02 (d, J = 8.0 Hz, 1 H), 3.68-3.63 (m, 1 H), 3.56 (s, 1 H), 3.35 (t, J = 6.8 Hz, 2 H), 3.25-3.05 (m, 2 H), 3.01-2.90 (m, 1 H), 2.59 (d, J = 10.0 Hz, 1 H), 1.93-1.80 (m, 2 H). LCMS RT = 0.919 min, m/z = 533.2 | 0.0159 |
| I-206 Example 4 | N-(5-chloropyridin-3-yl)-N-({5-[5-(difluoromethyl)-1,3,4-oxadiazol-2-yl]-1,3-thiazol-2-yl}methyl)-2-[(1S,4S)-2-oxa-5-azabicyclo[2.2.1]heptan-5-yl]ethane-1-sulfonamide | 1H NMR (400 MHz, CDCl3) δ 8.62 (d, J = 2.0 Hz, 1 H), 8.54 (d, J = 2.0 Hz, 1 H), 8.39 (s, 1 H), 7.91 (t, J = 2.0 Hz, 1 H), 6.91 (t, J = 51.6 Hz, 1 H), 5.37-5.25 (m, 2 H), 4.46 (s, 1 H), 4.01 (d, J = 8.4 Hz, 1 H), 3.69-3.62 (m, 1 H), 3.51 (s, 1 H), 3.31 (t, J = 6.8 Hz, 2 H), 3.18-3.07 (m, 2 H), 2.93 (d, J = 10.0 Hz, 1 H), 2.56 (d, J = 9.6 Hz, 1 H), 1.89-1.84 (q, J = 7.2 Hz, 2 H). LCMS RT = 0.472 min, m/z = 533.2. | 0.0162 |
| I-207 Example 4 | N-({5-[5-(difluoromethyl)-1,3,4-oxadiazol-2-yl]-1,3-thiazol-2-yl}methyl)-N-{5-[(1S)-1-fluoroethyl]pyridin-3-yl}ethane-1-sulfonamide | 1H NMR (400 MHz, CDCl3) δ 8.67 (d, J = 2.4 Hz, 1 H), 8.56 (s, 1 H), 8.39 (s, 1 H), 7.83 (s, 1 H), 6.91 (t, J = 51.6 Hz, 1 H), 5.79-5.60 (m, 1 H), 5.30 (s, 2 H), 3.21 (q, J = 7.2 Hz, 2 H), 1.69-1.55 (m, 3 H), 1.46 (t, J = 7.6 Hz, 3 H). LCMS RT = 1.500 min, m/z = 447.8 | 0.0137 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (µM) |
|---|---|---|---|
| I-208 Example 4 | N-({5-[5-(difluoromethyl)-1,3,4-oxadiazol-2-yl]-1,3-thiazol-2-yl}methyl)-N-{5-[(1R)-1-fluoroethyl]pyridin-3-yl}ethane-1-sulfonamide | 1H NMR (400 MHz, CDCl3) δ 8.67 (d, J = 2.0 Hz, 1 H), 8.56 (s, 1 H), 8.39 (s, 1 H), 7.83 (s, 1 H), 6.91 (t, J = 52.0 Hz, 1 H), 5.78-5.62 (m, 1 H), 5.30 (s, 2 H), 3.21 (q, J = 7.2 Hz, 2 H), 1.74-1.62 (m, 3 H), 1.46 (t, J = 7.6 Hz, 3 H). LCMS RT = 1.503 min, m/z = 447.8 | 0.027 |
| I-209 Example 2 | N-({5-[5-(difluoromethyl)-1,3,4-oxadiazol-2-yl]-1,3-thiazol-2-yl}methyl)-N-(5-fluoropyridin-3-yl)propanamide | 1H NMR (400 MHz, CDCl3) δ 8.54 (d, J = 2.4 Hz, 1 H), 8.39-8.35 (m, 2 H), 7.44-7.40 (m, 1 H), 6.92 (t, J = 51.6 Hz, 1 H) 5.19 (s, 2 H), 2.19 (q, J = 6.8 Hz, 2 H), 1.13 (t, J = 7.6 Hz, 3 H). LCMS RT = 1.755 min, m/z = 384.2 | 0.284 |
| I-210 Example 2 | 1-({5-[5-(difluoromethyl)-1,3,4-oxadiazol-2-yl]-1,3-thiazol-2-yl}methyl)-1,2,3,4-tetrahydro-1,6-naphthyridin-2-one | 1H NMR (400 MHz, CDCl$_3$) δ 8.49-8.37 (m, 3 H), 7.19 (d, J = 5.6 Hz, 1 H), 6.89 (t, J = 51.6 Hz, 1 H), 5.46 (s, 2 H), 3.10-3.01 (m, 2 H), 2.91-2.80 (m, 2 H). LCMS RT = 0.971 min, m/z = 364.2 | 0.0487 |
| I-211 Example 4 | (2R)-N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.70 (s, 1 H), 8.57-8.55 (m, 1 H), 8.35 (s, 1 H), 7.87-7.82 (m, 1 H), 7.38-7.32 (m, 1 H), 6.91 (t, J = 51.6 Hz, 1 H), 5.38-5.20 (m, 2 H), 3.14-3.06 (m, 1 H), 2.13-2.05 (m, 1 H), 1.72-1.65 (m, 1 H), 1.45 (d, J = 6.8 Hz, 3 H), 1.04 (t, J = 7.6 Hz, 3 H). LCMS RT = 0.563 min, m/z = 430.1 | 0.0137 |

TABLE 3-continued

Characterization Data and HDAC6 Activity for Compounds of Formula (I).

| Cmpd ID/Prep | Structure/Name | ¹H NMR<br>MS (m/z) (RT) | HDAC6 IC$_{50}$ (μM) |
|---|---|---|---|
| I-212<br>Example 4 | (2S)-N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.70 (s, 1 H), 8.58-8.55 (m, 1 H), 8.35 (s, 1 H), 7.89-7.86 (m, 1 H), 7.34 (q, J = 4.8 Hz, 1 H), 6.91 (t, J = 51.6 Hz, 1 H), 5.39-5.23 (m, 2 H), 3.14-3.06 (m, 1 H), 2.14-2.04 (m, 1 H), 1.74-1.65 (m, 1 H), 1.45 (d, J = 6.8 Hz, 3 H), 1.04 (t, 1 = 7.6 Hz, 3 H).<br>LCMS RT = 0.563 min, m/z = 430.1 | 0.0105 |
| I-213<br>Example 4 | N-(5-cyanopyridin-3-yl)-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CDCl3) δ 8.96 (d, J = 2.4 Hz, 1 H), 8.82 (s, 1 H), 8.41 (s, 1 H), 8.19 (s, 1 H), 6.92 (t, J = 51.6 Hz, 1 H), 5.33 (s, 2 H), 3.74 (t, J = 4.8 Hz, 4 H), 3.38 (t, J = 6.8 Hz, 2 H), 2.89 (t, J = 7.2 Hz, 2 H), 2.50 (t, J = 4.8 Hz, 4 H).<br>LCMS RT = 1.295 min, m/z = 512.2 | 0.0902 |
| I-214<br>Example 4 | N-({5-[5-(difluoromethyl)-1,3,4-oxadiazol-2-yl]-1,3-thiazol-2-yl}methyl)-N-(5-fluoropyridin-3-yl)-2-(morpholin-4-yl)ethane-1-sulfonamide | 1H NMR (400 MHz, CDCl3) δ ppm 8.59 (s, 1 H), 8.47 (d, J = 2.4 Hz, 1 H), 8.40 (s, 1 H), 7.71-7.67 (m, 1 H), 6.93 (t, J = 51.6 Hz, 1 H), 5.33 (s, 2 H), 3.78-3.72 (m, 4 H), 3.40 (t, J = 6.8 Hz, 2 H), 2.91 (t, J = 6.8 Hz, 2 H), 2.53-2.51 (m, 4 H).<br>LCMS RT = 0.908 min, m/z = 505.2 | 0.0154 |
| I-215<br>Example 4 | N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.72 (d, J = 2.8 Hz, 1 H), 8.58-8.56 (m, 1 H), 8.35 (s, 1 H), 7.89-7.86 (m, 1 H), 7.36 (q, J = 4.8 Hz, 1 H), 6.91 (t, J = 51.6 Hz, 1 H), 5.37-5.26 (m, 2 H), 3.14-3.05 (m, 1 H), 2.12-2.06 (m, 1 H), 1.75-1.69 (m, 1 H), 1.45 (d, J = 6.8 Hz, 3 H), 1.04 (t, J = 7.6 Hz, 3 H).<br>LCMS RT = 0.560 min, m/z = 430.1 | 0.00675 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-216 Example 4 | 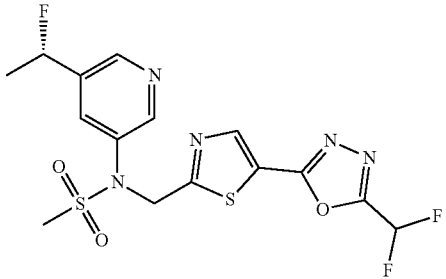 [SMILES: C[C@H](F)c1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-{5-[(1S)-1-fluoroethyl]pyridin-3-yl}methanesulfonamide | 1H NMR (400 MHz, CDCl3) δ 8.68 (s, 1 H), 8.58 (s, 1 H), 8.42 (s, 1 H), 7.84 (s, 1 H), 6.92 (t, J = 51.6 Hz, 1 H), 5.80-5.61 (m, 1 H), 5.29 (s, 2 H), 3.11 (s, 3 H), 1.75-1.55 (m, 3 H).<br>LCMS RT = 0.550 min, m/z = 434.1 | 0.0119 |
| I-217 Example 4 | 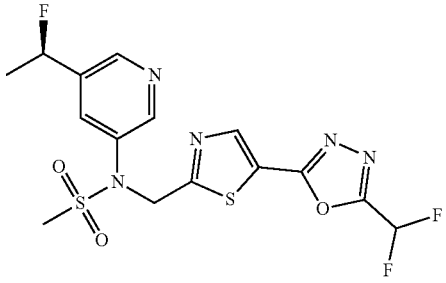 [SMILES: C[C@@H](F)c1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-{5-[(1R)-1-fluoroethyl]pyridin-3-yl}methanesulfonamide | 1H NMR (400 MHz, CDCl3) δ 8.70 (s, 1 H), 8.58 (s, 1 H), 8.42 (s, 1 H), 7.86 (s, 1 H), 6.92 (t, J = 51.6 Hz, 1 H), 5.81-5.60 (m, 1 H), 5.29 (s, 2 H), 3.11 (s, 3 H), 1.75-1.55 (m, 3 H).<br>LCMS RT = 0.551 min, m/z = 434.1 | 0.0236 |
| I-218 Example 4 | 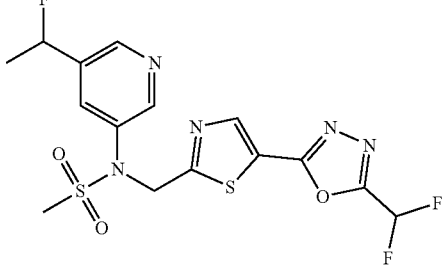<br>N-({5-[5-(difluoromethyl)-1,3,4-oxadiazol-2-yl]-1,3-thiazol-2-yl}methyl)-N-[5-(1-fluoroethyl)pyridin-3-yl]methanesulfonamide | 1H NMR (400 MHz, CDCl3) δ 8.68 (d, J = 2.4 Hz, 1 H), 8.57 (s, 1 H), 8.41 (s, 1 H), 7.84 (s, 1 H), 6.91 (t, J = 51.2 Hz, 1 H), 5.79-5.62 (m, 1 H), 5.28 (s, 2 H), 3.11 (s, 3 H), 1.75-1.55 (m, 3 H).<br>LCMS RT = 0.545 min, m/z = 434.1 | 0.0369 |
| I-219 Example 4 | 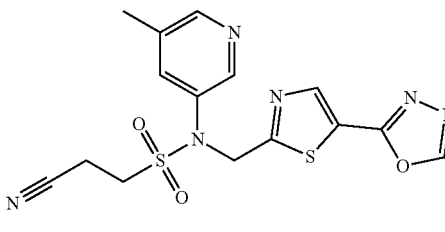<br>2-cyano-N-({5-[5-(difluoromethyl)-1,3,4-oxadiazol-2-yl]-1,3-thiazol-2-yl}methyl)-N-(5-methylpyridin-3-yl)ethane-1-sulfonamide | 1H NMR (400 MHz, CDCl3) δ 8.52 (d, J = 2.0 Hz, 1 H), 8.47 (s, 1 H), 8.45 (s, 1 H), 7.65 (s, 1 H), 6.92 (t, J = 51.6 Hz, 1 H), 5.28 (s, 2 H), 3.53 (t, J = 7.6 Hz, 2 H), 2.98 (t, J = 7.2 Hz, 2 H), 2.39 (s, 3 H).<br>LCMS RT = 0.507 min, m/z = 441.1 | 0.0202 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-220 Example 4 | N-[5-(difluoromethoxy)pyridin-3-yl]-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CDCl3) δ 8.61 (s, 1 H), 8.46 (s, 1 H), 8.39 (s, 1 H), 7.70 (s, 1 H), 6.91 (t, J = 51.6 Hz, 1 H), 6.59 (t, J = 72.0 Hz, 1 H), 5.31 (s, 2 H), 3.77-3.69 (m, 4 H), 3.38 (t, J = 6.8 Hz, 2 H), 2.89 (t, J = 7.2 Hz, 2 H), 2.54-2.46 (m, 4 H). LCMS RT = 1.504 min, m/z = 553.2 | 0.0184 |
| I-221 Example 4 | N-({5-[5-(difluoromethyl)-1,3,4-oxadiazol-2-yl]-1,3-thiazol-2-yl}methyl)-N-(6-ethylpyridin-3-yl)ethane-1-sulfonamide | 1H NMR (400 MHz, CDCl3) δ 8.58 (d, J = 2.4 Hz, 1 H), 8.37 (s, 1 H), 7.75-7.70 (m, 1 H), 7.22 (d, J = 8.4 Hz, 1 H), 6.91 (t, J = 51.6 Hz, 1 H), 5.7 (s, 2 H), 3.20 (q, J = 7.6 Hz, 2 H), 2.83 (q, J = 7.6 Hz, 2 H), 1.46 (t, J = 7.2 Hz, 3 H), 1.30 (t, J = 7.6 Hz, 3 H). LCMS RT = 1.134 min, m/z = 430.2 | 0.033 |
| I-222 Example 4 | N-({5-[5-(difluoromethyl)-1,3,4-oxadiazol-2-yl]-1,3-thiazol-2-yl}methyl)-N-[5-(2-fluoropropan-2-yl)pyridin-3-yl]methanesulfonamide | 1H NMR (400 MHz, CDCl3) δ 8.64 (d, J = 2.0 Hz, 1 H), 8.60 (s, 1 H), 8.42 (s, 1 H), 7.86 (t, J = 2.0 Hz, 1 H), 6.92 (t, J = 51.6 Hz, 1 H), 5.28 (s, 2 H), 3.11 (s, 3 H), 1.75 (s, 3 H), 1.69 (s, 3H). LCMS RT = 1.499 min, m/z = 447.9 | 0.0376 |
| I-223 Example 4 | N-({5-[5-(difluoromethyl)-1,3,4-oxadiazol-2-yl]-1,3-thiazol-2-yl}methyl)-N-(5-fluoropyridin-3-yl)-2-methylpropane-1-sulfonamide | 1H NMR (400 MHz, CDCl3) δ 8.58 (s, 1 H), 8.47 (d, J = 2.8 Hz, 1 H), 8.40 (s, 1 H), 7.68-7.62 (m, 1 H), 6.91 (t, J = 51.6 Hz, 1 H), 5.29 (s, 2 H), 3.05 (d, J = 2.0 Hz, 2 H), 2.40-2.30 (m, 1 H), 1.12 (d, J = 6.8 Hz, 6 H). LCMS RT = 1.790 min, m/z = 447.9 | 0.00563 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-224 Example 4 | N-({5-[5-(difluoromethyl)-1,3,4-oxadiazol-2-yl]-1,3-thiazol-2-yl}methyl)-N-[5-(2,2-difluoropropoxy)pyridin-3-yl]methanesulfonamide | 1H NMR (400 MHz, CDCl3) δ 8.42 (s, 1 H), 8.39-8.33 (m, 2 H), 7.48-7.41 (m, 1 H), 6.92 (t, J = 51.6 Hz, 1 H), 5.28 (s, 2 H), 4.18 (t, J = 11.2 Hz, 2 H), 3.11 (s, 3 H), 1.79 (t, J = 18.8 Hz, 3 H). LCMS RT = 1.492 min, m/z = 482.2 | 0.0204 |
| I-225 Example 4 | N-({5-[5-(difluoromethyl)-1,3,4-oxadiazol-2-yl]-1,3-thiazol-2-yl}methyl)-N-[5-(2,2-difluoropropoxy)pyridin-3-yl]ethane-1-sulfonamide | 1H NMR (400 MHz, CDCl3) δ 8.42-8.36 (m, 2 H), 8.33 (s, 1 H), 7.45 (s, 1 H) 6.91 (t, J = 51.6 Hz, 1 H), 5.30 (s, 2 H), 4.17 (t, J = 11.2 Hz, 2 H), 3.21 (q, J = 7.6 Hz, 2 H), 1.79 (t, 1 = 18.8 Hz, 3 H), 1.46 (t, J = 7.6 Hz, 3 H). LCMS RT = 1.559 min, m/z = 496.2 | 0.00601 |
| I-226 Example 4 | N-({5-[5-(difluoromethyl)-1,3,4-oxadiazol-2-yl]-1,3-thiazol-2-yl}methyl)-N-[5-(2-fluoropropan-2-yl)pyridin-3-yl]ethane-1-sulfonamide | 1H NMR (400 MHz, CDCl3) δ 8.66 (d, J = 2.4 Hz, 1 H), 8.59 (d, J = 1.2 Hz, 1 H) 8.40 (s, 1 H), 7.91-7.86 (m, 1 H), 6.91 (t, J = 5 1.6 Hz, 1 H), 5.30 (s, 2 H), 3.21 (q, J = 6.8 Hz, 2 H), 1.75 (s, 3 H), 1.69 (s, 3 H), 1.47 (E, J = 6.4 Hz, 3 H). LCMS RT = 1.510 min, m/z = 462.2 | 0.0319 |
| I-227 Example 4 | N-({5-[5-(difluoromethyl)-1,3,4-oxadiazol-2-yl]-1,3-thiazol-2-yl}methyl)-N-[5-(1-fluoroethyl)pyridin-3-yl]ethane-1-sulfonamide | 1H NMR (400 MHz, CDCl3) δ 8.67 (d, J = 2.4 Hz, 1 H), 8.56 (s, 1 H), 8.39 (s, 1 H), 7.83 (s, 1 H), 6.91 (t, J = 51.6 Hz, 1 H), 5.79-5.62 (m, 1 H), 5.30 (s, 2 H), 3.21 (q, J = 7.2 Hz, 2 H), 1.74-1.56 (m, 3 H), 1.47 (t, J = 7.2 Hz, 3 H). LCMS RT = 1.518 min, m/z = 447.9 | 0.0123 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-228 Example 4 | N-({5-[5-(difluoromethyl)-1,3,4-oxadiazol-2-yl]-1,3-thiazol-2-yl}methyl)-N-(6-ethylpyridin-3-yl)methanesulfonamide | 1H NMR (400 MHz, CD3OD) δ 8.54 (d, J = 2.4 Hz, 1 H), 8.39 (s, 1 H), 7.93-7.88 (m, 1 H), 7.35 (d, J = 8.4 Hz, 1 H), 7.17 (t, J = 51.6 Hz, 1 H), 5.31 (s, 2 H), 3.12 (s, 3 H), 2.78 (q, J = 7.6 Hz, 2 H) 1.24 (t, J = 7.6 Hz, 3 H). LCMS RT = 0.981 min, m/z = 416.2 | 0.0435 |
| I-229 Example 4 | N-({5-[5-(difluoromethyl)-1,3,4-oxadiazol-2-yl]-1,3-thiazol-2-yl}methyl)-N-(5-ethylpyridin-3-yl)methanesulfonamide | 1H NMR (400 MHz, CD3OD) δ 8.51 (s, 1 H), 8.42 (s, 1 H), 8.40 (s, 1 H), 7.89 (s, 1 H), 7.18 (t, J = 51.6 Hz, 1 H), 5.35 (s, 2 H), 3.14 (s, 3 H), 2.69 (q, J = 7.2 Hz, 2 H), 1.25 (t, J = 7.6 Hz, 3 H). LCMS RT = 1.099 min, m/z = 416.2 | 0.0248 |
| I-230 Example 4 | N-({5-[5-(difluoromethyl)-1,3,4-oxadiazol-2-yl]-1,3-thiazol-2-yl}methyl)-N-(5-ethylpyridin-3-yl)-2-methoxyethane-1-sulfonamide | 1H NMR (400 MHz, CD3OD) δ 8.50 (d, J = 2.4 Hz, 1 H), 8.38 (s, 1 H), 8.35 (s, 1 H), 7.88 (s, 1 H), 7.18 (t, J = 51.6 Hz, 1 H), 5.31 (s, 2 H), 3.82 (t, J = 5.6 Hz, 2 H), 3.48 (t, J = 5.2 Hz, 2 H), 3.43 (s, 3 H), 2.69 (q, J = 5.2 Hz, 2 H), 1.24 (t, J = 7.6 Hz, 3 H). LCMS RT = 1.752 min, m/z = 460.2 | 0.033 |
| I-231 Example 4 | N-({5-[5-(difluoromethyl)-1,3,4-oxadiazol-2-yl]-1,3-thiazol-2-yl}methyl)-N-{4H,6H,7H-pyrazolo[3,2-c][1,4]oxazin-2-yl}ethane-1-sulfonamide | 1H NMR (400 MHz, CDCl3) δ 8.39 (s, 1 H), 6.90 (t, J = 51.6 Hz, 1 H), 6.12 (s, 1 H), 5.38 (s, 2 H), 4.77 (s, 2 H), 4.12-1.06 (m, 4 H), 3.27 (q, J = 7.2 Hz, 2 H), 1.42 (t, J = 7.6 Hz, 3H). LCMS RT = 0.552 min, m/z = 447.1 | 0.0924 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-232 Example 4 | N-[5-(difluoromethoxy)pyridin-3-yl]-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.63 (d, J = 2.0 Hz, 1 H), 8.51 (d, J = 2.4 Hz, 1 H), 8.46 (s, 1 H), 7.70 (s, 1 H), 6.61 (t, J = 71.6 Hz, 1 H), 5.30 (s, 2 H) 3.13 (s, 3 H). LCMS RT = 1.766 min, m/z = 471.8 | 0.0342 |
| I-233 Example 4 | N-[5-(difluoromethoxy)pyridin-3-yl]-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.59 (d, J = 2.0 Hz, 1 H), 8.47 (d, J = 2.4 Hz, 1 H), 8.42 (s, 1 H), 7.67 (t, J = 2.4 Hz, 1 H), 6.59 (t, J = 72.0 Hz, 1 H), 5.29 (s, 2 H), 3.19-3.11 (m, 2H), 1.97-1.88 (m, 2 H), 1.08 (t, J = 7.6 Hz, 3 H). LCMS RT = 2.013 min, m/z = 499.9 | 0.0606 |
| I-234 Example 4 | N-(5-cyanopyridin-3-yl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.95 (d, J = 2.4 Hz, 1 H), 8.82 (s, 1 H), 8.44 (s, 1 H), 8.16 (d, J = 2.4 Hz, 1 H), 5.29 (s, 2 H), 3.18-3.11 (m, 2 H), 2.00-1.80 (m, 2 H), 1.09 (t, J = 7.2 Hz, 3 H). LCMS RT = 1.811 min, m/z = 459.2 | 0.184 |
| I-235 Example 4 | N-({5-[5-(difluoromethyl)-1,3,4-oxadiazol-2-yl]-1,3-thiazol-2-yl}methyl)-N-(1H-imidazol-5-yl)ethane-1-sulfonamide | 1H NMR (400 MHz, CD3OD) δ 8.43 (s, 1 H), 7.99 (s, 1 H), 7.39-7.03 (m, 2 H), 5.30 (s, 2 H), 3.39-3.28 (m, 2 H), 1.40 (t, J = 7.2 Hz, 3 H). LCMS RT = 1.848 mm, m/z = 390.8 | 0.323 |

TABLE 3-continued

Characterization Data and HDAC6 Activity for Compounds of Formula (I).

| Cmpd ID/Prep | Stracture/Name | ¹H NMR MS (m/z) (RT) | HDAC6 IC$_{50}$ (µM) |
|---|---|---|---|
| I-236 Example 4 | N-({5-[5-(difluoromethyl)-1,3,4-oxadiazol-2-yl]-1,3-thiazol-2-yl}methyl)-N-(6-methylpyridin-2-yl)ethane-1-sulfonamide | 1H NMR (400 MHz, CDCl3) δ 8.39 (s, 1 H), 7.61 (t, J = 8.0 Hz, 1 H), 7.45 (d, J = 8.4 Hz, 1 H), 7.01 (s, 1 H), 6.89 (t, J = 51.6 Hz, 1 H) 5.60 (s, 2 H), 3.27 (q, J = 7.6 Hz, 2 H), 2.52 (s, 3 H), 1.37 (t, J = 7.4 Hz, 3 H). LCMS RT = 1.704 min, m/z = 416.2 | 0.0592 |
| I-237 Example 4 | N-(3-fluorophenyl)-N-({5-[5-(trifluorornethyl)-1,3,4-oxadiazol-2-yl]-1,3-thiazol-2-yl}methyl)methanesulfonamide | 1H NMR (400 MHz, CDCl3) δ 8.41 (s, 1 H), 7.44-7.36 (m, 1 H), 7.30-7.27 (m, 1 H), 7.24-7.20 (m, 1 H), 7.12-7.05 (m, 1 H), 5.27 (s, 2 H), 3.07 (s, 3 H). LCMS RT = 1.912 min, m/z = 422.8 | 0.0992 |
| I-238 Example 4 | N-({5-[5-(trifluoromethyl)-1,3,4-oxadiazol-2-yl]-1,3-thiazol-2-yl}methyl)-N-[5-(trifluoromethyl)pyridin-3-yl]methanesulfonamide | 1H NMR (400 MHz, CDCl3) δ 8.95 (d, J = 2.0 Hz, 1 H), 8.87 (s, 1 H), 8.46 (s, 1 H), 8.12 (t, J = 2.0 Hz, 1 H), 5.31 (s, 2 H), 3.12 (s, 3 H). LCMS RT = 1.905 min, m/z = 473.8 | 0.256 |
| I-239 Example 4 | N-(5-cyclopropylpyridin-3-yl)-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.46 (s, 1 H), 8.42 (s, 1 H), 8.37 (s, 1 H), 7.45 (t, J = 2.4 Hz, 1 H), 5.26 (s, 2 H), 3.09 (s, 3 H), 2.00 1.90 (m, 1 H), 1.11-1.08 (m, 2 H), 0.78-0.75 (m, 2 H). LCMS RT = 1.621 min, m/z = 445.9 | 0.085 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-240 Example 4 | N-(5-chloropyridin-3-yl)-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.62 (s, 1 H), 8.57 (s, 1 H), 7.89 (s, 1 H), 5.28 (s, 2 H), 3.11 (s, 3 H). LCMS RT = 2.259 min, m/z = 440.1 | 0.062 |
| I-241 Example 4 | N-({5-[5-(difluoromethyl)-1,3,4-oxadiazol-2-yl]-1,3-thiazol-2-yl}methyl)-N-[5-(2-methoxyethyl)pyridin-3-yl]ethane-1-sulfonamide | 1H NMR (400 MHz, CDCl3) δ 8.50 (s, 1 H), 8.48 (s, 1 H), 7.80 (s, 1 H), 7.65 (s, 1 H), 6.92 (t, J = 51.6 Hz, 1 H), 5.80 (s, 2 H), 3.60 (t, J = 6.0 Hz, 2 H), 3.33 (s, 3 H), 3.08 (q, J = 7.2 Hz, 2 H), 2.85 (t, J = 6.0 Hz, 2 H), 1.40 (t, J = 7.6 Hz, 3 H). LCMS RT = 0.718 min, m/z = 460.2 | 0.994 |
| I-242 Example 4 | N-(3-fluorophenyl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.41 (s, 1 H), 7.43-7.37 (m, 1 H), 7.27-7.26 (m, 1 H), 7.25-7.22 (m, 1 H), 7.10-7.05 (m, 1 H), 5.30 (s, 2 H), 3.15-3.10 (m, 2 H), 1.97-1.89 (m, 2 H), 1.09 (t, J = 7.2 Hz, 3 H). LCMS RT = 2.207 min, m/z = 450.8 | 0.053 |
| I-243 Example 4 | N-(5-cyanopyridin-3-yl)-N-({5-[5-(trifluoromethyl)-1,3,4-oxadiazol-2-yl]-1,3-thiazol-2-yl}methyl)ethane-1-sulfonamide | 1H NMR (400 MHz, CDCl3) δ 8.96 (d, J = 2.4 Hz, 1 H), 8.82 (d, J = 2.0 Hz, 1 H), 8.44 (s, 1 H), 8.17 (t, J = 2.0 Hz, 1 H), 5.30 (s, 2 H), 3.21 (q, J = 7.2 Hz, 2 H), 1.45 (t, J = 7.2 Hz, 3 H). LCMS RT = 1.718 min, m/z = 444.8 | 0.129 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-244 Example 4 | N-(5-chloropyridin-3-yl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.61 (d, J = 2.4 Hz, 1 H), 8.55 (d, J = 2.4 Hz, 1 H), 8.42 (s, 1 H), 7.88 (t, J = 2.0 Hz, 1 H), 5.28 (s, 2 H), 3.19-3.11 (m, 2 H), 1.97-1.82 (m, 2 H), 1.09 (t, J = 7.6 Hz, 3 H). LCMS RT = 2.027 min, m/z = 467.8 | 0.0872 |
| I-245 Example 2 | (3R)-1-{(5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.96 (s, 1 H), 8.52 (d, J = 5.2 Hz, 1 H), 8.38 (s, 1 H), 7.52 (d, J = 5.2 Hz, 1 H), 6.91 (t, J = 51.6 Hz, 1 H) 5.47-5.27 (m, 2 H), 3.09-3.04 (m, 1 H), 2.83-2.78 (m, 1 H), 2.51-2.47 (m, 1 H), 2.26-2.21 (m, 1 H), 2.18-2.11 (m, 1 H), 1.16 (d, J = 6.4 Hz, 3 H) LCMS RT = 1.250 min, m/z = 392.3. | 1.42 |
| I-246 Example 2 | (3S)-1-({5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.91 (s, 1 H), 8.50 (d, J = 5.2 Hz, 1 H), 8.37 (s, 1 H), 7.47 (d, J = 5.2 Hz, 1 H), 6.91 (t, J = 51.6 Hz, 1 H), 5.46-5.28 (m, 2 H), 3.11-2.85 (m, 1 H), 2.84-2.71 (m, 1 H), 2.548-2.45 (m, 1 H), 2.29-2.14 (m, 1 H), 2.18-2.07 (m, 1 H), 1.16 (d, J = 6.4 Hz, 3 H) LCMS RT = 1.251 min, m/z = 392.3. | 0.039 |
| I-247 Example 2 | 1-(5-[5-(difluoromethyl)-1,3,4-oxadiazol-2-yl]-1,3-thiazol-2-yl}methyl)-1',2'-dihydrospiro[cyclopropane-1,3'-pyrrolo[2,3-c]pyridin]-2'-one | 1H NMR (400 MHz, CDCl3) δ 8.47 (s, 1 H), 8.44-8.40 (m, 2 H) 7.07 (d, J = 5.2 Hz, 1 H), 6.90 (t, J = 51.6 Hz, 1 H), 5.43 (s, 2 H), 2.17-2.10 (m, 2 H), 1.93-1.86 (m, 2 H) LCMS RT = 0.970 min, m/z = 376.2. | 0.158 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-248 Example 2 | (4S)-1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.54 (s, 1 H), 8.41 (s, 1 H), 8.35 (d, J = 4.8 Hz, 1 H), 7.19 (d, J = 4.8 Hz, 1 H), 6.89 (t, J = 51.6 Hz, 1 H), 5.62-5.46 (m, 2 H), 3.23-3.16 (m, 1 H), 2.92-2.84 (m, 1 H). 2.66-2.55 (m, 1 H), 1.38 (d, J = 6.8 Hz, 3H) LCMS RT = 1.098 min, m/z = 378.3. | 0.034 |
| I-249 Example 2 | (4R)-1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.53 (s, 1 H), 8.40 (s, 1 H), 8.34 (d, J = 4.8 Hz, 1 H), 7.18 (d, J = 4.8 Hz, 1 H), 6.90 (t, J = 51.6 Hz, 1 H), 5.60-5.46 (m, 2 H), 3.23-3.15 (m, 1 H), 2.90-2.81 (m, 1 H), 2.64-2.55 (m, 1 H), 1.38 (d, J = 6.8 Hz, 3H) LCMS RT = 1.028 min, m/z = 378.2. | 0.089 |
| I-250 Example 2 | (3R)-1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.54 (s, 1 H), 8.41 (s, 1 H), 8.31 (d, J = 3.6 Hz, 1 H) 7.18 (d, J = 4.4 Hz, 1 H), 6.89 (t, J = 51.6 Hz, 1 H), 5.62-5.36 (m, 2 H), 3.09-3.02 (m, 1 H), 2.89-2.79 (m, 2 H), 1.35 (d, J = 6.8 Hz, 3H) LCMS RT = 0.684 min, m/z = 378.2. | 0.041 |
| I-251 Example 2 | (3S)-1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.52 (s, 1 H), 8.41 (s, 1 H), 8.30 (d, J = 4.4 Hz, 1 H), 7.17 (d, J = 4.8 Hz, 1 H), 6.89 (t, J = 51.6 Hz, 1 H), 5.62-5.36 (m, 2 H), 3.09-3.02 (m, 1 H), 2.89-2.79 (m, 2 H), 1.34 (d, J = 6.8 Hz, 3 H). LCMS RT = 0.521 min, m/z = 378.2. | 0.034 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-252 Example 2 | 1-({5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.77 (s, 1 H), 8.46 (d, J = 4.8 Hz, 1 H), 8.37 (s, 1 H), 7.30 (d, J = 4.4 Hz, 1 H), 6.90 (t, J = 51.6 Hz, 1 H), 5.37 (s, 2 H), 2.99-2.90 (m, 1 H), 2.70-2.66 (m, 1 H), 2.55-2.49 (m, 1 H), 2.23-2.14 (m, 1 H), 2.18-2.04 (m, 1 H), 1.16 (d, J = 6.4 Hz, 3 H). LCMS RT = 1.229 min, m/z = 392.3. | 0.073 |
| I-253 Example 2 | 1-({5-[5-(difluoromethyl)-1,3,4-oxadiazol-2-yl]-1,3-thiazol-2-yl}methyl)-3,3-dimethyl-1H,2H,3H,4H,5H-pyrido[3,4-b]azepin-2-one | 1H NMR (400 MHz, CDCl3) δ 8.84 (s, 1 H), 8.47 (s, 1 H), 8.40 (s, 1 H), 7.42 (s, 1 H), 6.91 (t, J = 51.6 Hz, 1 H), 5.37 (s, 2H), 2.91 (t, J = 6.0 Hz, 2 H), 2.18 (t, J = 6.4 Hz, 2 H), 1.04 (s, 6 H) LCMS RT = 1.946 min, m/z = 405.9. | 0.035 |
| I-254 Example 2 | 1-({5-[5-(difluoromethyl)-1,3,4-oxadiazol-2-yl]-1,3-thiazol-2-yl)methyl)-3,3-dimethyl-1H,2H,3H-pyrrolo[2,3-c]pyridin-2-one | 1H NMR (400 MHz, CDCl3) δ 8.45-8.43 (m, 2 H), 8.29 (s, 1 H), 7.24 (d, J = 4.8 Hz, 1 H), 6.89 (t, J = 51.6 Hz, 1 H). 5.33 (s, 2 H), 1.49 (s, 6 H) LCMS RT = 0.408 min, m/z = 378.1. | 0.149 |
| I-255 Example 2 | 1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.59 (s, 1 H), 8.42 (s, 1 H), 8.34 (d, J = 4.8 Hz, 1 H), 7.26 (d, J = 4.8 Hz, 1 H), 6.90 (t, J = 51.6 Hz, 1 H), 5.63-5.37 (m, 2 H), 3.13-3.06 (m, 1 H), 2.92-2.80 (m, 2 H), 1.36 (d, J = 6.4 Hz, 3 H) LCMS RT = 0.583 min, m/z = 378.2. | 0.036 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-256 Example 2 | 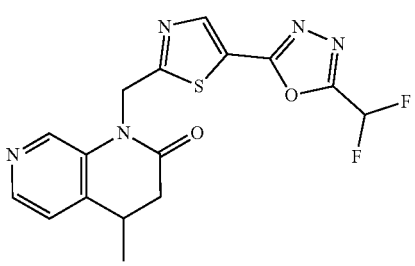 [SMILES: CC1CC(=O)N(Cc2ncc(-c3nnc(C(F)F)o3)s2)c2cnccc21]<br>1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.58 (s, 1 H), 8.45-8.34 (m, 2 H), 7.25 (d, J = 4.8 Hz, 1 H), 6.89 (t, J = 51.6 Hz, 1 H), 5.62-5.47 (m, 2 H), 3.27-3.20 (m, 1 H), 2.94-2.82 (m, 1 H), 2.67-2.56 (m, 1 H), 1.40 (d, J = 6.8 Hz, 3 H)<br>LCMS RT = 0.580 min, m/z = 378.2. | 0.057 |
| I-257 Example 14 | 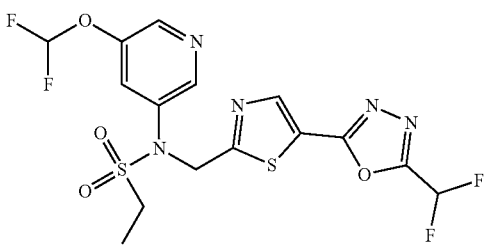 [SMILES: CCS(=O)(=O)N(Cc1ncc(-c2nnc(C(F)F)o2)s1)c1cncc(OC(F)F)c1]<br>N-[5-(difluoromethoxy)pyridin-3-yl]-N-({2-[5-(difluoromethyl)-1,3,4-oxadiazol-2-yl]-1,3-thiazol-5-yl}methyl)ethane-1-sulfonamide | 1H NMR (400 MHz, CD3OD) δ 8.48 (d, J = 2.4 Hz, 1 H), 8.40 (d, J = 2.4 Hz, 1 H), 7.90 (s, 1 H), 7.77 (t, J = 2.4 Hz, 1 H), 7.23 (t, J = 51.6 Hz, 1 H), 6.97 (t, J = 72.8 Hz, 1 H), 5.35 (s, 2 H), 3.31 (q, J = 7.6 Hz, 2 H), 1.41 (t, J = 7.6 Hz, 3 H)<br>LCMS RT = 1.251 min, m/z = 468.2. | 0.231 |
| I-258 Example 15 | 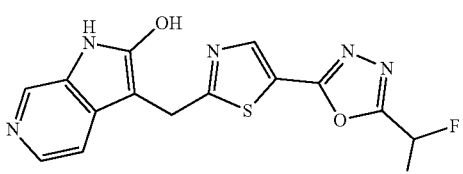<br>3-({5-[5-(difluormethyl)-1,3,4-oxadiazol-2-yl]-1,3-thiazol-2-yl}methyl)-1H-pyrrolo[2,3-c]pyridin-2-ol | 1H NMR (400 MHz, CD3OD) δ 8.40 (s, 1 H), 7.65 (s, 1 H), 7.50 (d, J = 6.8 Hz, 1 H), 7.17 (t, J = 51.6 Hz, 1 H), 6.94 (d, J = 6.8 Hz, 1 H), 4.27 (s, 2 H)<br>LCMS RT = 0.778 min, m/z = 350.2. | 0.069 |
| I-259 Example 14 | 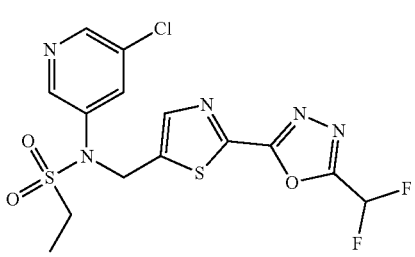 [SMILES: CCS(=O)(=O)N(Cc1cnc(-c2nnc(C(F)F)o2)s1)c1cncc(Cl)c1]<br>N-(5-chloropyridin-3-yl)-N-((2-[5-(difluoromethyl)-1,3,4-oxadiazol-2-yl]-1,3-thiazol-5-yl]methyl)ethane-1-sulfonamide | 1H NMR (400 MHz, CD3OD) δ 8.55-8.51 (m, 2 H), 8.05 (t, J = 2.4 Hz, 1 H), 7.92 (s, 1 H), 7.25 (t, J = 51.6 Hz, 1 H), 5.36 (s, 2 H), 3.34 (q, J = 7.2Hz, 2 H), 1.42 (t, 1 = 7.6 Hz, 3 H)<br>LCMS RT = 1.273 min, m/z = 436.2. | 0.121 |

TABLE 3-continued

Characterization Data and HDAC6 Activity for Compounds of Formula (I).

| Cmpd ID/Prep | Structure/Name | ¹H NMR MS (m/z) (RT) | HDAC6 IC$_{50}$ (μM) |
|---|---|---|---|
| I-260 Example 14 | N-({2-[5-(difluorometiiyl)-1,3,4-oxadiazol-2-yl]-1,3-thiazol-5-yl}methyl)-N-(pyridin-3-yl)ethane-1-sulfonamide | 1H NMR (400 MHz, CDCl3) δ 8.58 (d, J = 2.4 Hz, 1 H), 8.52-8.48 (m, 1 H), 7.98 (s, 1 H), 7.87-7.66 (m, 1 H), 7.56 (t, J = 51.2 Hz, 1 H), 7.45-7.42 (m, 1 H), 5.34 (s, 2 H), 3.37 (q, J = 7.2 Hz, 2 H), 1.30 (t, J = 7.2 Hz, 3 H) LCMS RT = 0.821 min, m/z = 402.2. | 0.333 |
| I-261 Example 14 | N-(3-chlorophenyl)-N-({2-[5-(difluoromethyl)-1,3,4-oxadiazol-2-yl]-1,3-thiazol-5-yl}methyl)ethane-1-sulfonamide | 1H NMR (400 MHz, CDCl3) δ 8.00 (s, 1 H), 7.56 (t, J = 51.2 Hz, 1 H), 7.41-7.36 (m, 4 H), 5.32 (s, 2 H), 3.36 (q, J = 7.2 Hz, 2 H), 1.29 (t, J = 8.0 Hz, 3 H) LCMS RT = 1.554 min, m/z = 435.1. | 0.089 |
| I-262 Example 14 | N-(5-chloropyridin-3-yl)-N-({2-[5-(difluoromethyl)-1,3,4-oxadiazol-2-yl]-1,3-thiazol-5-yl}methylmethanesulfonamide | 1H NMR (400 MHz, CD3OD) δ 8.61-8.47 (m, 2 H), 8.05 (t, J = 2.4 Hz, 1 H), 7.93 (s, 1 H), 7.23 (t, J = 51.6 Hz, 1 H), 5.32 (s, 2H), 3.16 (s, 3H) LCMS RT = 1.643 min, m/z = 422.1. | 0.110 |
| I-263 Example 14 | N-({2-[5-(difluoromethyl)-1,3,4-oxadiazol-2-yl]-1,3-thiazol-5-yl}methyl)-N-(5-fluoropyridin-3-yl)methanesulfonamide | 1H NMR (400 MHz, CD3OD) δ 8.48 (s, 1 H), 8.46 (d, J = 2.4 Hz, 1 H), 7.93 (s, 1 H), 7.88-7.82 (m, 1 H), 7.23 (t, J = 51.6 Hz, 1 H), 5.33 (s, 2 H), 3.16 (s, 3 H) LCMS RT = 1.478 min, m/z = 406.1. | 0.108 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (µM) |
|---|---|---|---|
| I-264 Example 14 | N-({2-[5-(difluoromethyl)-1,3,4-oxadiazol-2-yl]-1,3-thiazol-5-yl}methyl)-N-(5-fluoropyridin-3-yl)ethane-1-sulfonamide | 1H NMR (400 MHz, CD3OD) δ 8.48 (s, 1 H), 8.45 (d, J = 2.8 Hz, 1 H), 7.91 (s, 1 H), 7.86-7.80 (m, 1 H), 7.24 (t, J = 51.6 Hz, 1 H), 5.35 (s, 2 H), 3.31 (q, J = 7.2 Hz, 2 H), 1.41 (t, J = 7.6 Hz, 3 H). LCMS RT = 1.618 min, m/z = 420.2. | 0.087 |
| I-265 Example 4 | N-({5-[5-(difluoromethyl)-1,3,4-oxadiazol-2-yl]-1,3-thiazol-2-yl}methyl)-N-[5-(trifluoromethoxy)pyridin-3-yl]methanesulfonamide | 1H NMR (400 MHz, CDCl3) δ 8.72 (d, J = 2.0 Hz, 1 H), 8.56 (s, 1 H), 8.44 (s, 1 H), 7.80 (s, 1 H), 6.92 (t, J = 51.6 Hz, 1 H), 5.30 (s, 2 H), 3.11 (s, 3 H) LCMS RT = 1.950 min, m/z = 472.1. | 0.048 |
| I-266 Example 4 | 2-cyano-N-({5-[5-(difluoromethyl)-1,3,4-oxadiazol-2-yl]-1,3-thiazol-2-yl}methyl)-N-(pyridin-3-yl)ethane-1-sulfonamide | 1H NMR (400 MHz, CD3OD) δ 8.70 (d, J = 2.8 Hz, 1 H), 8.52 (d, J = 3.6 Hz, 1 H), 8.44 (s, 1 H), 8.07-8.01 (m, 1 H), 7.54-7.49 (m, 1 H), 7.21 (t, J = 51.6 Hz, 1 H), 5.41 (s, 2 H), 3.72 (t, J = 7.2 Hz, 2 H), 3.05 (t, 1 = 7.2 Hz, 2 H). LCMS RT = 1.287 min, m/z = 426.8. | 0.042 |
| I-267 Example 4 | N-({5-[5-(difluoromethyl)-1,3,4-oxadiazol-2-yl]-1,3-thiazol-2-yl)methyl)-N-[5-(trifluoromethoxy)pyridin-3-yl]ethane-1-sulfonamide | 1H NMR (400 MHz, CDCl3) δ 8.71 (s, 1 H), 8.54 (s, 1 H), 8.41 (s, 1 H), 7.79 (s, 1 H), 6.92 (t, J = 51.6 Hz, 1 H), 5.30 (s, 2 H), 3.22 (q, J = 7.6 Hz, 2 H), 1.45 (t, J = 7.6 Hz, 3 H) LCMS RT = 0.328 min, m/z = 486.1 | 0.044 |

TABLE 3-continued

Characterization Data and HDAC6 Activity for Compounds of Formula (I).

| Cmpd ID/Prep | Structure/Name | $^1$H NMR MS (m/z) (RT) | HDAC6 IC$_{50}$ (μM) |
|---|---|---|---|
| I-268 Example 4 | 3-[({5-[5-(difluoromethyl)-1,3,4-oxadiazol-2-yl]-1,3-thiazol-2-yl}methyl)(pyridin-3-yl)sulfamoyl]propanamide | 1H NMR (400 MHz, CDCl3) δ 8.75 (d, J = 2.4 Hz, 1 H), 8.62-8.55 (m, 1 H) 8.39 (s, 1 H), 7.90-7.84 (m, 1 H), 7.40-7.33 (m, 1 H), 6.91 (t, J = 52.0 Hz, 1 H), 5.27 (s, 2 H), 3.58 (t, J = 7.2 Hz, 2 H), 2.81 (t, J = 7.2 Hz, 2 H). LCMS RT = 0.783 min, m/z = 444.9. | 0.013 |
| I-269 Example 2 | 1-({5-[5-(difluoromethyl)-1,3,4-oxadiazol-2-yl]-1,3-thiazol-2-yl]methyl)-1H,2H,3H,4H,5H-pyrido[3,4-b]azepin-2-one | 1H NMR (400 MHz, CDCl3) δ 8.77 (s, 1 H), 8.46 (s, 1 H), 8.38 (s, 1 H), 7.28 (s, 1 H), 6.91 (t, J = 51.6 Hz, 1 H), 5.36 (s, 2 H), 2.84 (t, J = 6.8 Hz, 2 H), 2.49-2.37 (m, 2 H), 2.37-2.23 (m, 2 H). LCMS RT = 1.043 min, m/z = 378.2 | 0.018 |
| I-270 Example 2 | 1-({5-[5-(difluoromethyl)-1,3,4-oxadiazol-2-yl]-1,3-thiazol-2-yl}methyl)-1,2,3,4-tetrahydroquinoline | 1H NMR (400 MHz, DMSO-d6) δ 8.57 (s, 1 H), 7.51 (t, J = 51.2 Hz, 1 H), 7.00-6.90 (m, 2 H), 6.60-6.55 (m, 2 H), 4.86 (s, 2 H), 3.47 (t, J = 5.6 Hz, 2 H) 2.75 (t, J = 6.0 Hz, 2 H), 2.02-1.92 (m, 2 H) LCMS RT = 1.769 min, m/z = 349.2 | 0.539 |

TABLE 4

Characterization Data and HDAC6 Activity for Compounds of Formula (II), Formula (III), Formula (IV), and Formula (A).

| Cmpd ID | Structure/Name | $^1$H NMR MS (m/z) (RT) | HDAC6 IC$_{50}$ (μM) |
|---|---|---|---|
| II-1 Example 16 | 4-(5-(difluoromethyl)-1,3,4-oxadiazol-2-yl)-1-(2-morpholino-2-oxoethyl)pyridin-2(1H)-one | $^1$H NMR (400 MHz, DMSO-d$_6$) δ ppm 7.83 (br d, J = 7.09 Hz. 1 H) 7.37-7.73 (m, 1 H) 6.99 (s, 1 H) 6.81 (br d. J = 6.85 Hz, 1 H) 4.92 (s, 2 H) 3.42-3.71 (m 8 H, overlaps with water peak). LCMS: RT = 2.29 min, m/z = 341.1 | 0.592 |

TABLE 4-continued

Characterization Data and HDAC6 Activity for Compounds of Formula (II), Formula (III), Formula (IV), and Formula (A).

| Cmpd ID | Structure/Name | ¹H NMR MS (m/z) (RT) | HDAC6 IC$_{50}$ (μM) |
|---|---|---|---|
| II-2 Example 16 | 4-(5-(difluoromethyl)-1,3,4-oxadiazol-2-yl)-1-(2-oxo-2-(pyrrolidin-1-yl)ethyl)pyridin-2(1H)-one | ¹H NMR (400 MHz, DMSO-d$_6$) δ ppm 7.83 (br d, J = 7.09 Hz, 1 H) 7.38-7.74 (m, 1 H) 6.99 (s, 1 H) 6.80 (br d, .7 = 6.60 Hz, 1 H) 4.80 (s, 2 H) 3.53 (br t, .7 = 6.60 Hz, 2 H) 3.28-3.36 (m, 2 H, overlaps with water peak) 1.89-2.00 (m, 2 H) 1.74-1.88 (m, 2 H) LCMS: RT = 2.82 min, mz = 325.1 | 0.987 |
| II-3 Example 17 | 4-(5-(difluoromethyl)-1,3,4-oxadiazol-2-yl)-1-methylpyridin-2(1H)-one | ¹H NMR (400 MHz, chloroform-d) δ ppm 7.48 (br d, J = 6.60 Hz, 1 H) 7.27 (s, 1 H, overlaps with CHCl$_3$) 6.73-7.11 (overlapping m, 2 H) 3.62 (br s, 3 H) LCMS: RT = 2.66 min, m/z = 228.1 | 0.158 |
| II-4 Example 17 | 1-benzyl-4-(5-(difluoromethyl)-1,3,4-oxadiazol-2-yl)pyridin-2(1H)-one | ¹H NMR (400 MHz, chloroform-d) δ ppm 7.19-7.50 (overlapping m, 7 H) 6.74-7.10 (overlapping m, 2 H) 5.19 (s, 2 H) LCMS: RT = 4.21 min, m/z = 304.1 | 0.337 |
| II-5 Example 17 | 4-(5-(difluoromethyl)-1,3,4-oxadiazol-2-yl)-1-phenethylpyridin-2(1H)-one | ¹H NMR (400 MHz, chloroform-d) δ ppm 7.21-7.38 (m, 5 H) 7.14 (br d, J = 7.09 Hz, 1 H) 6.75-7.07 (overlapping m, 2 H) 6.65 (br d, J = 6.85 Hz, 1 H) 4.21 (br t, J = 6.85 Hz, 2 H) 3.10 (br t, J = 6.85 Hz, 2 H) LCMS: RT = 4.39 min. m/z = 318.1 | 0.245 |

TABLE 4-continued

Characterization Data and HDAC6 Activity for Compounds of Formula (II), Formula (III), Formula (IV), and Formula (A).

| Cmpd ID | Structure/Name | $^1$H NMR MS (m/z) (RT) | HDAC6 IC$_{50}$ (μM) |
|---|---|---|---|
| II-6 Example 16 | 4-(5-(trifluoromethyl)-1,3,4-oxadiazol-2-yl)pyridin-2(1H)-one | $^1$H NMR (400 MHz, DMSO-d$_6$) δ ppm 12.17 (br s, 1H) 7.67 (br d, J = 6.11 Hz, 1 H) 6.96 (br s, 1 H) 6.73 (br d, J = 5.14 Hz, 1 H) LCMS: RT = 2.93 min m/z = 232.0 | 1.1 |
| II-7 Example 16 | tert-butyl 2-(2-oxo-4-(5-(trifluoromethyl)-1,3,4-oxadiazol-2-yl)pyridin-1(2H)-yl)acetate | $^1$H NMR (400 MHz, chloroform-d) δ ppm 7.42 (br d, J = 7.09 Hz, 1 H) 7.27 (br s, 1 H, overlaps with (HCl) 6.83-6.93 (m, 1 H) 4.61 (s, 2 H) 1.50 (s, 9 H) LCMS: RT = 4.66 min, m/z = 368.1 | 0.742 |
| II-8 Example 17 | 1-methyl-4-(5-(trifluoromethyl)-1,3,4-oxadiazol-2-yl)pyridin-2(1H)-one | $^1$H NMR (400 MHz, chloroform-d) δ ppm 7.50 (br d, J = 6.85 Hz. 1 H) 7,26 (s, 1 H, overlaps with CHCl$_3$) 6.85 (br d, J = 6.36 Hz, 1 H) 3.63 (s, 3 H) LCMS: RT = 3.43 min, m/z = 246.0 | 4 |
| II-9 Example 17 | | $^1$H NMR (400 MHz, chloroform-d) δ ppm 7.07-7.40 (overlapping m, 7 H) 6.60-6.73 (m, 1 H) 4.21 (brt, J = 6.85 Hz, 2 H) 3.10 (br t J = 6.60 Hz, 2 H) LCMS: RT = 4.88 min. m/z = 336.1 | 4.3 |
| II-10 Example 16 | 2-(4-(5-(difluoromethyl)-1,3,4-oxadiazol-2-y))-2-oxopyridin-1(2H)-yl)acetic acid | $^1$H NMR (400 MHz, DMSO-d$_6$) δ ppm 7.94 (br d, J = 7.09 Hz, 1 H) 7.39-7.74 (m, 1 H) 7.02 (s, 1 H) 6.83 (brd, J = 7.09 Hz, 1 H) 4.71 (s, 2 H) LCMS: RT = 2.52 min, m/z = 272.0 | 3.2 |

TABLE 4-continued

Characterization Data and HDAC6 Activity for Compounds of Formula (II), Formula (III), Formula (IV), and Formula (A).

| Cmpd ID | Structure/Name | ¹H NMR MS (m/z) (RT) | HDAC6 IC$_{50}$ (μM) |
|---|---|---|---|
| II-11 Example 16 | 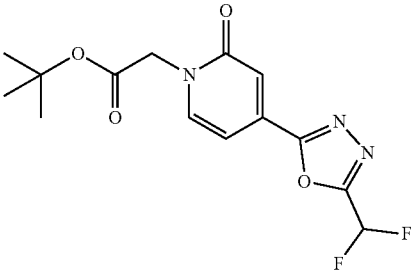 [SMILES: CC(C)(C)OC(=O)Cn1ccc(-c2nnc(C(F)F)o2)cc1=O]<br>tert-butyl 2-(4-(5-(difluoromethyl)-1,3,4-oxadiazol-2-yl)-2-oxopyridin-1(2H)-yl)acetate | ¹H NMR (400 MHz, chloroform-d) δ ppm 7.40 (d, J = 7.09 Hz, 1 H) 7.29 (s, 1 H) 6.76-7.10 (overlapping m, 2 H) 4.61 (s, 2 H) 1.49 (s, 9 H)<br>LCMS: RT 4.20 mm, m/z = 350.1 | 0.145 |
| II-12 Example 16 | 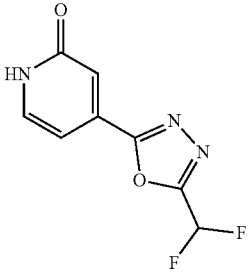 [SMILES: O=c1cc(-c2nnc(C(F)F)o2)cc[nH]1]<br>4-(5-(difluoromethyl)-1,3,4-oxadiazol-2-yl)pyridin-2(1H)-one | ¹H NMR (400 MHz, DMSO-d$_6$) δ ppm 12.13 (br s, 1 H) 7.38-7.73 (overlapping m, 2 H) 6.92 (s, 1 H) 6.72 (br d, J = 6.36 Hz, 1 H).<br>LCMS: RT = 1.15 min, m/z = 214.0 | 0.810 |
| II-13 Example 19 | 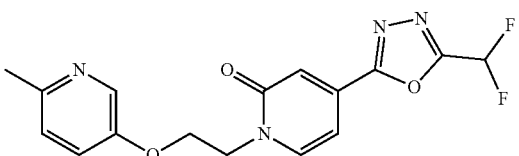<br>4-(5-(difluoromethyl)-1,3,4-oxadiazol-2-yl)-1-(2-((6-methylpyridin-3-yl)oxy)ethyl)pyridin-2(1H)-one | ¹H NMR (400 MHz CDCl$_3$) δ 8.16 (s. 1 H), 7.64 (d, J = 7.2 Hz, 1 H), 7.29 (s, 1 H), 7.08-7.05 (m, 2 H), 6.93-6.86 (m, 2 H), 4.43-4.38 (m. 2 H). 4.36-4.32 (m, 2 H), 2.48 (s, 3 H).<br>LCMS RT = 1.256 min, m/z = 349.2. | 0.024 |
| II-14 Example 19 | 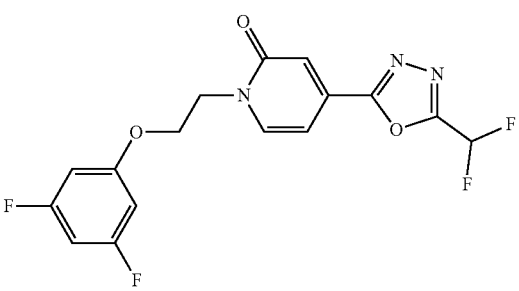 [SMILES: O=c1cc(-c2nnc(C(F)F)o2)ccn1CCOc1cc(F)cc(F)c1]<br>4-(5-(difluoromethyl)-1,3,4-oxadiazol-2-yl)-1-(2-(3,5-difluorophenoxy)ethyl)pyridin-2(1H)-one | ¹H NMR (400 MHz, CDCl$_3$) δ 7.59 (d, J = 7.2 Hz. 1 H), 7.29 (s, 1 H), 7.08-6.88 (m, 2 H), 6.43-6.38 (m, 3 H), 4.41-4.37 (m, 2 H), 4.34-4.27 (m, 2 H). LCMS R$_T$ = 0.861 min, m/z = 370.2. [M + H]⁺<br>LCMS RT = 0.861 min, m/z = 370.2. | 0.003 |

TABLE 4-continued

Characterization Data and HDAC6 Activity for Compounds of Formula (II), Formula (III), Formula (IV), and Formula (A).

| Cmpd ID | Structure/Name | ¹H NMR MS (m/z) (RT) | HDAC6 IC$_{50}$ (μM) |
|---|---|---|---|
| II-15 Example 18 | 1-((2-cyclopropylpyridin-4-yl)methyl)-4-(5-(difluoromethy))-1,3,4-oxadiazol-2-yl)pyridin-2(1H)-one | ¹H NMR (400 MHz, CDCl$_3$) δ ppm 8.42 (d, J = 5.2 Hz, 1 H), 7.46 (d, J = 12 Hz, 1 H), 7.35 (s, 1 H), 7.07-6.75 (m, 4 H), 5.15 (s, 2 H), 2.03-1.94 (m. 1 H). 1.07-0.96 (m, 4 H) LCMS RT = 0.358 min, m/z = 345.2 | 0.103 |
| II-16 Example 19 | 4-(5-(difluoromethyl)-1,3,4-oxadiazol-2-yl)-1-(2-(3-fluorophenoxy)ethyl)pyridin-2(1H)-one | ¹H NMR (400 MHz, CDl$_3$) δ ppm 7.64 (d, J = 7.2 Hz, 1 H), 7.30-7.22 (m 2 H), 6.92-6.80 (m, 2 H), 6.71-6.66 (m 3 H), 4.43-4.38 (m, 2 H), 4.35-4.31 (m, 2 H) LCMS RT = 0,837 min, m/z = 352.2 | 0.002 |
| II-17 Example 20 | 5-(5-(difluoromethyl)-1,3,4-oxadiazol-2-yl)-2-(2-(3-fluorophenoxy)ethyl)pyridazin-3(2H)-one | ¹H NMR (400 MHz, CDCl$_3$) δ ppm 8.48 (d, J = 2.4 Hz, 1 H), 7.56 (d, J = 2.4 Hz, 1 H), 7.24-7.18 (m, 1 H), 6.96 (t J = 51.6 Hz, 1 H), 6.69-6.59 (m, 3 H), 4.64 (t, J- 5.2 Hz, 2 H), 4.41 (t. J = 5.2 Hz, 2 H) LCMS RT = 0.846 min, m/z = 353.2 | 0.009 |
| II-18 Example 16 | 2-(4-(5-(difluoromethyl)-1,3,4-oxadiazol-2-yl)-2-oxopyridin-1(2H)-yl)-N-phenylacetamide | ¹H NMR (400 MHz, DMSO - d$_6$) δ ppm 10.4 (s, 1 H), 7.95 (d, J = 7.2 Hz, 1 H), 7.70-7.45 (m, 3 H), 7.32 (t, J= 8.0 Hz, 2 H), 7.10-7.02 (m, 1 H), 7.00 (s, 1 H), 6.86-6.82 (m, 1 H), 4.84 (s, 2 H) LCMS R$_T$ = 0.931 min, m/z = 346.9 | 0.218 |

TABLE 4-continued

Characterization Data and HDAC6 Activity for Compounds of Formula (II), Formula (III), Formula (IV), and Formula (A).

| Cmpd ID | Structure/Name | $^1$H NMR MS (m/z) (RT) | HDAC6 IC$_{50}$ (µM) |
|---|---|---|---|
| II-19 Example 21 | 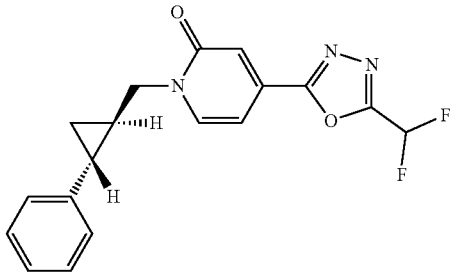 [SMILES: O=c1cc(-c2nnc(C(F)F)o2)ccn1C[C@@H]1C[C@H]1c1ccccc1]<br>4-(5-(difluoromethyl)-1,3,4-oxadiazol-2-yl)-1-(((1R,2R)-2-phenylcyclopropyl)methyl)pyridin-2(1H)-one | $^1$H NMR (400 MHz, CDCl$_3$) δ 7.58 (d, J = 6.8 Hz 1 H), 7.32-7.27 (m, 2 H), 7.24 (s, 1 H), 7.21-7.15 (m, 1 H), 7.09-7.03 (m, 2 H), 7.02-6.77 (m, 2 H), 4.14-3.97 (m, 2 H), 2.12-1.99 (m, 1 H), 1.65-1.60 (m, 1 H), 1.13 (t. J = 7.6 Hz, 2H).<br>LCMS R$_T$ = 0.929 min, m/z = 344.2 | 0.023 |
| IVa-1 Example 25 | 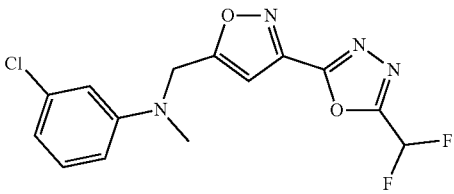 [SMILES: CN(Cc1cc(-c2nnc(C(F)F)o2)no1)c1cccc(Cl)c1]<br>3-chloro-N-({3-[5-(difluoromethyl)-1,3,4-oxadiazol-2-yl]-1,2-oxazol-5-yl}methyl)-N-methylaniline | $^1$H NMR (400 MHz, CDCl$_3$) δ 7.17 (t, J = 8.4 Hz. 1 H). 7.06-6.93 (m, 1 H), 6.80-6.61 (m, 4 H), 4.74 (s. 2 H). 3.31 (s, 3 H).<br>LCMS RT = 1.331 min, m/z = 341.1 | 0.255 |
| IVa-2 Example 23 | 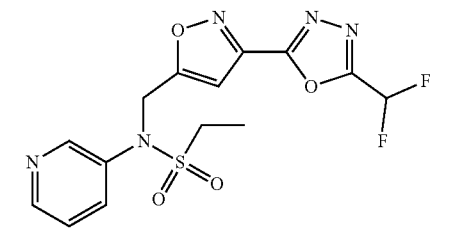 [SMILES: CCS(=O)(=O)N(Cc1cc(-c2nnc(C(F)F)o2)no1)c1cccnc1]<br>N-({3-[5-(difluoromethyl)-1,3,4-oxadiazol-2-yl]-1,2-oxazol-5-yl}methyl)-N-(pyridin-3-yl)ethane-1-sulfonamide | $^1$H NMR (400 MHz, CDCl$_3$) δ 8.64-8.62 (m, 2 H), 7.77-7.74 (m, 1 H), 7.40-7.37 (m, 1 H), 7.08-6.82 (m, 2 H), 5.14 (s, 2 H), 3.17 (q, J = 7.2 Hz, 2 H), 1.45(1, J = 7.6 Hz, 3 H).<br>RT = 1.119 mm, m/z = 386.1. | 0.0821 |
| IVa-3 Example 23 | 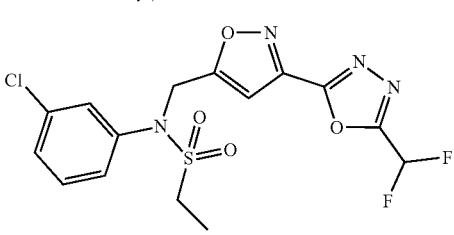<br>N-(3-chlorophenyl)-N-({3-[5-(difluoromethyl)-1,3,4-oxadiazol-2-yl]-1,2-oxazol-5-yl}methyl)ethane-1-sulfonamide | $^1$H NMR (400 MHz, CDCl$_3$) δ 7.45-7.23 (m 4 H), 7.09-6.80 (m, 2 H), 5.11 (s, 2 H), 3.14 (q, J = 7.6 Hz, 2 H), 1.43 (t, J = 8.0 Hz, 3 H).<br>RT = 1.954 min, m/z = 418.8 | 0.012 |
| IVa-4 Example 23 | 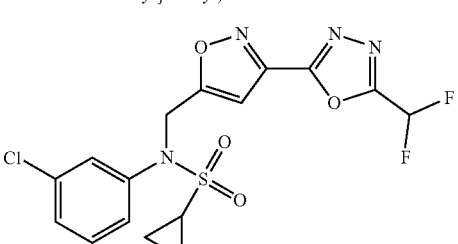<br>N-(3-chlorophenyl)-N-({3-[5-(difluoromethyl)-1,3,4-oxadiazol-2-yl]-1,2-oxazol-5-yl}methyl)cyclopropanesulfonamide | $^1$H NMR (400 MHz, CDCl$_3$) δ 7.36 (s, 1 H). 7.35-7.30 (m, 3 H), 6.94 (t, J = 51.6 Hz, 1 H), 6.93 (s, 1 H), 5.11 (s, 2 H), 2.51-2.43 (m, 1 H), 1.13-1.10 (m, 2 H), 1.06-1.01 (m, 2 H).<br>RT = 1.921 min. m/z = 431.1. | 0.022 |

TABLE 4-continued

Characterization Data and HDAC6 Activity for Compounds of Formula (II), Formula (III), Formula (IV), and Formula (A).

| Cmpd ID | Structure/Name | $^1$H NMR MS (m/z) (RT) | HDAC6 IC$_{50}$ (μM) |
|---|---|---|---|
| IVb-1 Example 22 | N-(3-chlorophenyl)-N-((5-(5-(difluoromethyl)-1,3,4-oxadiazol-2-yl)isoxazol-3-yl)methyl)ethanesulfonamide | $^1$H NMR (400 MHz, CDCl$_3$) δ ppm 7.34 (s, 1 H), 7.29-7.21 (m. 4 H), 6.91 (t, J = 51.6 Hz, 1 H), 5.02 (s, 2 H), 3.12 (q, J = 7.6 Hz. 2 H). 1.40 (t, J = 7.6 Hz, 3 H) LCMS: RT = 3.179 min, m/z = 419.1 | 0.037 |
| IVb-2 Example 24 | 3-chloro-N-({5-(5-(difluoromethyl)-1,3,4-oxadiazol-2-yl)isoxazol-3-yl)methyl)-N-methylaniline | $^1$H NMR (400 MHz, DMSO - d$_6$) δ 7.57 (t, J = 51.2 Hz, 1 H), 7.42 (s, 1 H), 7.18 (t, J = 8.0 Hz, 1 H), 6.83-6.63 (m, 3 H), 4.80 (s, 2H). 3.07 (s, 3 H). LCMS: RT = 2.277 min, m/z = 341.0 | 0.518 |
| IVb-3 Example 24 | 3-chloro-N-({5-[5-(difluoromethyl)-1,3,4-oxadiazol-2-yl]-1,2-oxazol-3-yl}methyl)aniline | $^1$H NMR (400 MHz, CD$_3$OD) δ 7.19-7.12 (m, 2 H), 7.01-6.94 (m, 1 H), 6.53-6.50 (m, 3 H), 4.41 (s, 2 H). RT = 0.983 min, m/z = 327.0. | 1.4 |
| A-1 Example 26 | 5-(6-((1-(2,6difluorophenyl)cyclopropyl)amino)-5-fluoropyridin-3-yl)-1,3,4-oxadiazole-2-carbonitrile | $^1$H NMR (400 MHz, CDCl$_3$) δ = 8.68 (s, 1H), 7.73 (d, J = 11.2 Hz, 1H), 7.19 (m, 1H), 6.84 (m, 2H), 6.08 (br s, 1H), 1.40 (m, 4H) m/z = 358.0 | |
| A-2 Example 27 | 2-(2-benzylpyrazolo[1,5-a]pyrimidin-6-yl-5-(difluoromethyl)-1,3,4-oxadiazole | $^1$H NMR (400 MHz, CDCl$_3$) δ 9.33 (s, 1 H) 9.06 (s. 1 H). 7.40-7.10 (m, 5 H), 6.96 (t, J = 51.6 Hz, 1 H), 6.21 (s, 1 H), 4.25 (s, 2 H) LCMS RT = 4.160 min, m/z = 328.2 | 0.346 |

What is claimed is:

1. A compound having the formula:

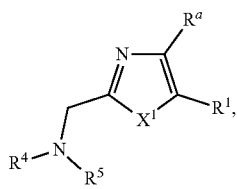

or a pharmaceutically acceptable salt thereof,
wherein:
X¹ is S;
R^a is selected from the group consisting of H, halogen, and C$_{1-3}$ alkyl;
R¹ is

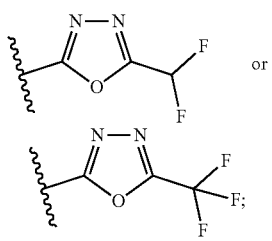

R² is selected from the group consisting of alkyl, alkoxy, and cycloalkyl, each of which is optionally substituted;
R³ is H or alkyl;
R⁴ is selected from the group consisting of alkyl, —(SO₂)R², —(SO₂)NR²R³, and —(CO)R²; and
R⁵ is heteroaryl.

2. The compound of claim 1, wherein R^a is H.

3. The compound of claim 1, wherein R¹ is

[structure]

4. The compound of claim 1, wherein R⁴ is —(SO₂)R².

5. The compound of claim 4, wherein —(SO₂)R² is —(SO₂)alkyl, —(SO₂)alkyleneheterocyclyl, —(SO₂)haloalkyl, —(SO₂)haloalkoxy, or —(SO₂)cycloalkyl.

6. The compound of claim 1, wherein the heteroaryl is a 5- to 6-membered heteroaryl.

7. The compound of claim 6, wherein the 5- to 6-membered heteroaryl is selected from the group consisting of

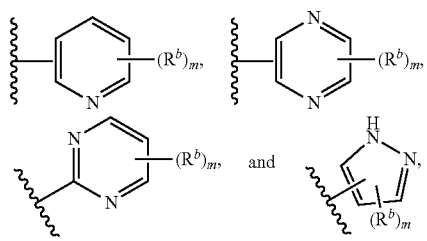

wherein R^b is halogen, alkyl, alkoxy, cycloalkyl, —CN, haloalkyl, or haloalkoxy; and m is 0 or 1.

8. The compound of claim 7, wherein R^b is F, Cl, —CH₃, —CH₂CH₃, —CF₃, —CHF₂, —CF₂CH₃, —CN, —OCH₃, —OCH₂CH₃, —OCH(CH₃)₂, —OCF₃, —OCHF₂, —OCH₂CF₂H, and cyclopropyl.

9. A compound of Formula (Ik):

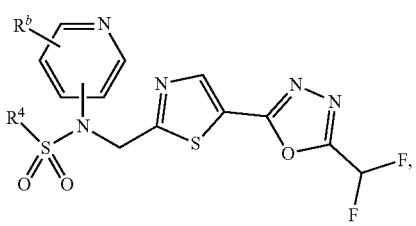

or a pharmaceutically acceptable salt thereof,
wherein:
R^b is H, halogen, alkyl, cycloalkyl, —CN, haloalkyl, or haloalkoxy; and
R⁴ is alkyl, alkoxy, haloalkyl, or cycloalkyl, each of which is optionally substituted.

10. The compound of claim 9, wherein R^b is H, halogen, haloalkyl, or haloalkoxy.

11. The compound of claim 9, wherein R⁴ is optionally substituted alkyl or cycloalkyl.

12. The compound of claim 9, having the structure:

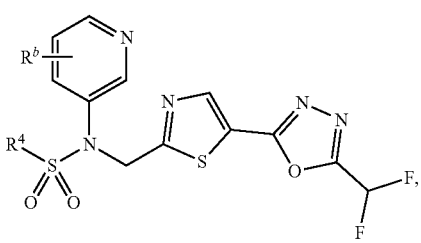

or a pharmaceutically acceptable salt thereof,
wherein:
R^b is H, halogen, alkyl, cycloalkyl, —CN, haloalkyl, or haloalkoxy; and
R⁴ is alkyl, alkoxy, haloalkyl, or cycloalkyl, each of which is optionally substituted.

13. The compound of claim 12, wherein R^b is H, halogen, haloalkyl, or haloalkoxy.

14. The compound of claim 12, wherein R⁴ is optionally substituted alkyl or cycloalkyl.

15. The compound of claim 14, wherein R⁴ is alkyl.

16. The compound of claim 9, having the structure:

(Ik-2)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

17. The compound of claim 16, wherein $R^b$ is H, halogen, haloalkyl, or haloalkoxy.

18. The compound of claim 16, wherein $R^4$ is optionally substituted alkyl.

19. The compound of claim 1 of formula:

or a pharmaceutically acceptable salt thereof.

20. The compound of claim 1 of formula:

or a pharmaceutically acceptable salt thereof.

21. The compound of claim 1 of formula:

or a pharmaceutically acceptable salt thereof.

22. The compound of claim 1 of formula:

or a pharmaceutically acceptable salt thereof.

23. The compound of claim 1 of formula:

or a pharmaceutically acceptable salt thereof.

24. The compound of claim 1 of formula:

or a pharmaceutically acceptable salt thereof.

25. The compound of claim 1 of formula:
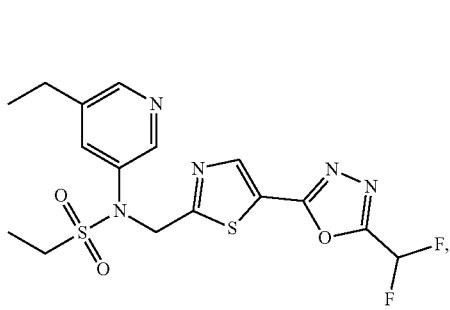 [SMILES: CCc1cncc(N(Cc2ncc(-c3nnc(C(F)F)o3)s2)S(=O)(=O)CC)c1]
or a pharmaceutically acceptable salt thereof.
26. The compound of claim 1 of formula:
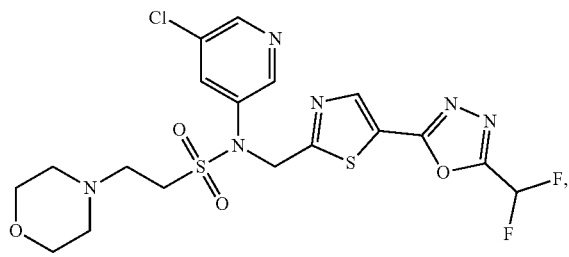 [SMILES: O=S(=O)(CCN1CCOCC1)N(Cc1ncc(-c2nnc(C(F)F)o2)s1)c1cncc(Cl)c1]
or a pharmaceutically acceptable salt thereof.
27. The compound of claim 1 of formula:
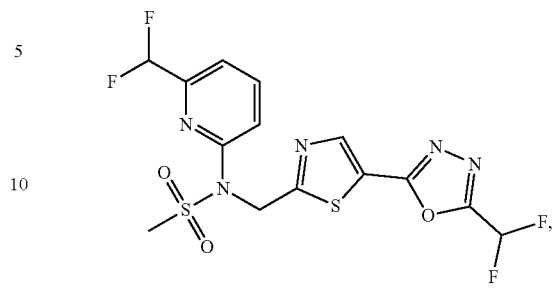
or a pharmaceutically acceptable salt thereof.
28. The compound of claim 1 of formula:
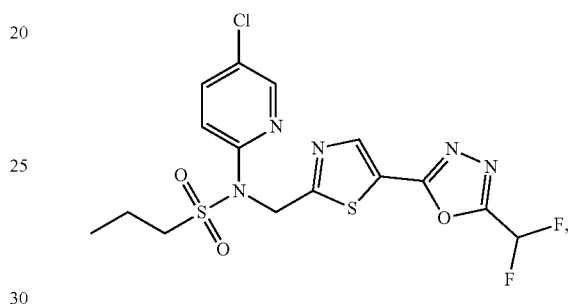
or a pharmaceutically acceptable salt thereof.
* * * * *